(12) United States Patent  
Halsall et al.

(10) Patent No.: US 7,709,471 B2
(45) Date of Patent: May 4, 2010

(54) COMPOUNDS

(75) Inventors: Christopher Thomas Halsall, Macclesfield (GB); David Alan Rudge, Macclesfield (GB); Iain Simpson, Macclesfield (GB); Richard Andrew Ward, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 294 days.

(21) Appl. No.: 11/773,674

(22) Filed: Jul. 5, 2007

(65) Prior Publication Data

US 2008/0009482 A1  Jan. 10, 2008

Related U.S. Application Data

(60) Provisional application No. 60/818,878, filed on Jul. 6, 2006.

(51) Int. Cl.  
*C07D 401/12* (2006.01)  
*A61K 31/4545* (2006.01)

(52) U.S. Cl. .................. 514/220; 514/221; 540/495; 540/502; 540/522; 540/523

(58) Field of Classification Search ............... 540/495, 540/502, 522, 523; 514/220, 221  
See application file for complete search history.

(56) References Cited

U.S. PATENT DOCUMENTS

| | | | |
|---|---|---|---|
| 6,806,272 B2 | 10/2004 | Bauer et al. | |
| 6,861,422 B2 | 3/2005 | Hoffmann et al. | |
| 7,241,889 B2 | 7/2007 | Hoffmann et al. | |
| 2004/0147524 A1 | 7/2004 | Bauer et al. | |
| 2005/0014760 A1 | 1/2005 | Hoffmann et al. | |
| 2005/0014761 A1 | 1/2005 | Hoffmann et al. | |
| 2006/0004014 A1 | 1/2006 | Hoffmann et al. | |
| 2006/0025411 A1 | 2/2006 | Hoffmann et al. | |
| 2006/0035902 A1 | 2/2006 | Linz et al. | |
| 2006/0035903 A1 | 2/2006 | Mohr et al. | |
| 2006/0046989 A1 | 3/2006 | Grauert et al. | |
| 2006/0046990 A1 | 3/2006 | Stadtmueller et al. | |
| 2006/0047118 A1 | 3/2006 | Stadtmueller et al. | |
| 2006/0052383 A1 | 3/2006 | Grauert et al. | |
| 2006/0058311 A1 | 3/2006 | Munzert et al. | |
| 2006/0074088 A1 | 4/2006 | Munzert et al. | |

FOREIGN PATENT DOCUMENTS

| | | |
|---|---|---|
| CA | 2517020 A1 | 9/2004 |
| CA | 2458699 A1 | 3/2008 |
| WO | 2006018220 A2 | 2/2006 |
| WO | 2007090844 A1 | 8/2007 |
| WO | 2007095188 A2 | 8/2007 |
| WO | 03020722 A1 | 3/2008 |

OTHER PUBLICATIONS

Steegmaler et al; BI 2536, a Potent and Selective Inhibitor of Polo-like Kinase 1, Inhibits Tumor Growth In Vivo; Current Biology, 17, 2007, 316-322.

Lenart et al; The Small Molecule Inhibitor BI 2536 reveals Novel Insights into Mitotic Roles of Polo-like Kinase 1; Current Biology, 17, 2007, 304-315.

*Primary Examiner*—Bruck Kifle

(57) ABSTRACT

There is provided a compound of formula (I):

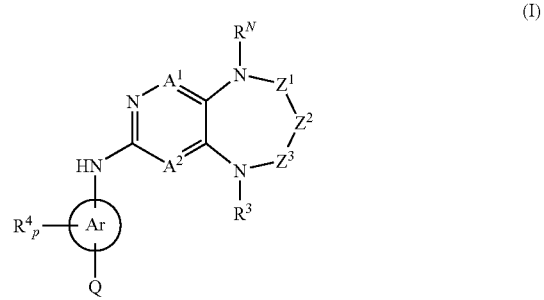

processes for the manufacture thereof, pharmaceutical compositions thereof and uses in therapy.

6 Claims, No Drawings

COMPOUNDS

This application claims the benefit under 35 U.S.C. §119(e) of Application No U.S. 60/818,878 filed on 6 Jul. 2006.

The present invention relates to pyrimidine derivatives, a process for their preparation, pharmaceutical compositions containing them, a process for preparing the pharmaceutical compositions, and their use in therapy and the treating of conditions mediated by polo-like kinases.

Many of the current treatment regimes for cell proliferation diseases such as cancer and psoriasis utilise compounds that inhibit DNA synthesis. Compounds that inhibit DNA synthesis may often prove to be toxic to many types of cells. However, the marked toxic effect on rapidly dividing cells such as tumour cells is often seen to offer a benefit in light of the general toxic nature of such compounds. Therefore, alternative antiproliferative agents that act by mechanisms other than the inhibition of DNA synthesis may offer the potential for selective targeting of the proliferating cells.

The Cyclin dependent kinase family (Cdks) have long been considered the master regulators of the cell cycle but an increasing number of diverse protein kinases are emerging as critical components of cell cycle progression. Among these are the polo-like kinase family (Plks), serine/threonine kinases that play multiple roles in regulating progress through cell cycle. In man, four distinct family members have been identified. These are Plk1, Plk2 (Snk), Plk3 (Fnk, Prk) and Plk4 (Sak).

The best characterized family member is Plk1 which is conserved from yeast to man and has been implicated in numerous mitotic processes including activation of Cdc25C and Cdk1/Cyclin B at the G2-M transition, centrosome maturation, spindle formation and assembly (Glover et al. 1998, Genes Dev. 12:3777-87; Barr et al 2004, Nat. Rev. Mol. Cell Biol 5:429-441). In the later stages of mitosis Plk1 is involved in separation of sister chromatids, activation of components of the anaphase-promoting complex and septin regulation during cytokinesis (van Vugt & Medema 2005, Oncogene 24:2844-2859).

Plk1 is overexpressed in a broad spectrum of cancer types including breast, colorectal, endometrial, oesophageal, ovarian, prostate, pancreatic, non small cell lung cancers and melanomas (Wolf et al. 1997, Oncogene 14:543-549; Knecht et al. 1999, Cancer Res. 59:2794-2797; Wolf et al. 2000, Pathol. Res. Pract. 196:753-759; Takahashi et al. 2003, Cancer Sci. 94:148-152). The expression of Plk1 often correlates with poor patient prognosis. The conclusion that Plk1 elevation is a cause and not a consequence of oncogenesis resulted from a study demonstrating that overexpression or constitutive expression of Plk1 induces malignant transformation of mammalian cells, causing tumour formation in nude mice (Smith et al 1997, Biochem. Biophys. Res. Commun 234:397-405)

Therapeutic potential for Plk1 inhibition has been demonstrated in studies employing both antisense oligonucleotides (ASO) and small molecule RNA (siRNA). Reduction in the level of Plk1 results in the inhibition of proliferation of tumour cells and loss of cell viability both in vivo and in vitro but does not inhibit proliferation of primary cells (Spankuch-Schmitt et al 2002, Oncogene 21: 3162-3171; Elez et al 2003, Oncogene 22:69-80). Microinjection of anti-Plk1 antibodies induced mitotic catastrophe in HeLa tumour cells. These cells displayed abnormal distribution of chromatin and monoastral microtubules while normal fibroblast cells arrested transiently in G2 phase of cell cycle as single mononucleated cells (Lane & Nigg 1996 J. Cell Biol. 135:1701-1713). These results suggest that Plk1 inhibition specifically targets cancer cells with checkpoint defects while cells with intact checkpoint pathways are less affected.

Although the exact functions of the other family members remains largely unknown, silencing of Plk2 in the presence of taxol or nocodazole significantly increases apoptosis suggesting Plk2 may prevent mitotic catastrophe following spindle damage (Burns et al. 2003, Mol Cell Biol 23: 5556-5571). Likewise silencing of Plk4 in mammalian cells induces apoptosis (Li et al. 2005, Neoplasia 7: 312-323) and plk4 null mouse embryos arrest with an increase in mitotic and apoptotic cells (Hudson et al. 2001, Curr Biol 11: 441-446).

Plk3 also appears to play roles in mitosis, like Plk1 it has been reported to phosphorylate Cdc25C, regulate microtubule dynamics and is involved in centrosome function. Overexpression of Plk3 has been observed in both breast and ovarian carcinomas, with little or no expression in adjacent normal tissue. Increased protein level was associated with enhanced mitosis and was significantly linked to reduced median survival time of patients (Weichert et al. 2005, Virchows Arch 446: 442-450; Weichert et al. 2004 Br. J. Cancer 90:815-821).

These findings suggest that pharmacological inhibitors of Plk family members should be of therapeutic value for treatment of proliferative disease including solid tumours such as carcinomas and sarcomas and the leukaemias and lymphoid malignancies. In addition Plk inhibitors should be useful in the treatment of other disorders associated with uncontrolled cellular proliferation.

Pteridinone derivatives are known from the prior art as active substances with an antiproliferative activity. WO 01/019825 and WO 03/020722 describe the use of pteridinone derivatives for the treatment of tumoural diseases.

The resistance of many types of tumours calls for the development of new pharmaceutical compositions for combating tumours.

The aim of the present invention is to provide new compounds having an antiproliferative activity.

According to a first aspect of the present invention there is provided a compound of formula (I):

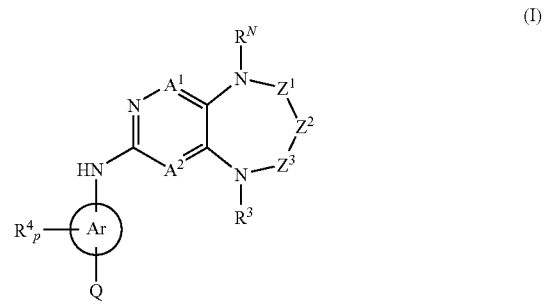

wherein
R$^3$ represents hydrogen, an optionally substituted C$_{1-12}$alkyl group, an optionally substituted C$_{2-12}$alkenyl group, an optionally substituted C$_{2-12}$alkynyl group, an optionally substituted C$_{6-14}$aryl group, an optionally substituted C$_{3-12}$cycloalkyl group, an optionally substituted C$_{3-12}$cycloalkenyl group, an optionally substituted C$_{7-12}$polycycloalkyl group, an optionally substituted C$_{7-12}$polycycloalkenyl group, an optionally substituted C$_{5-12}$spirocycloalkyl group, an optionally substituted 3- to 12-membered heterocycloalkyl group comprising 1 or 2 heteroatoms, an optionally substituted 4- to 12-membered heterocycloalkenyl group comprising 1 or 2 heteroatoms, or an optionally substituted heteroaryl ring comprising 1, 2 or 3 heteroatoms each independently selected from nitrogen, oxygen or sulphur;

$R^4$ each independently represent —CN, hydroxy, —$NR^6R^7$, —$NR^6SO_2R^7$, halogen, an optionally substituted $C_{1-6}$alkyl group, an optionally substituted $C_{3-7}$cycloalkyl group, an optionally substituted $C_{2-6}$alkenyl group, an optionally substituted $C_{2-6}$alkynyl group, an optionally substituted $C_{1-5}$alkyloxy group, an optionally substituted $C_{3-6}$cycloalkyloxy group, an optionally substituted $C_{2-5}$alkenyloxy group, an optionally substituted $C_{2-5}$alkynyloxy group, an optionally substituted $C_{1-6}$alkylthio group, an optionally substituted $C_{1-6}$alkylsulphoxo group or an optionally substituted $C_{1-6}$alkylsulphonyl group, an optionally substituted 3- to 12-membered heterocycloalkyl group comprising 1 or 2 heteroatoms, or an optionally substituted 3- to 12-membered heterocycloalkoxy group comprising 1 or 2 heteroatoms;

$R^N$ represents hydrogen, —$NH_2$, —OH, —CN, —C≡CH, —C(=O)$NH_2$, $C_{1-3}$alkyl, $C_{1-3}$alkylamino, $C_{1-3}$alkylthio, $C_{1-3}$alkyloxy, $C_{1-3}$alkylcarbonyl, —CHO, or —$SO_2Me$ p is 0, 1 or 2;

Q is —C(=$X^1$)—$NR^aR^b$, —S(O)$_2$—$NR^{a2}R^{b2}$, -(optionally substituted $C_{1-3}$alkyl)$_g$-$NR^{a3}R^{b3}$, —S(O)$_k$—$R^{a8}$, —C(=$X^2$)—$OR^{a9}$, —$OR^{a10}$ or -(5- or 6-membered aromatic or heteroaromatic ring optionally comprising at least one ring heteroatom selected from nitrogen, oxygen and sulphur)-$L_n$-$R^5_m$;

g is 0 or 1;

k is 0, 1 or 2;

$R^a$ represents H or an optionally substituted $C_{1-6}$alkyl group, and $R^b$ represents -$L_n$-$R^5_m$, or $R^a$ and $R^b$ together with the nitrogen atom to which they are attached form a 3- to 7-membered saturated or unsaturated heterocyclic ring optionally comprising 1 to 2 additional heteroatoms;

$R^{a2}$ represents H or an optionally substituted $C_{1-6}$alkyl group, and $R^{b2}$ represents -$L_n$-$R^5_m$, or $R^{a2}$ and $R^{b2}$ together with the nitrogen atom to which they are attached form a 3- to 7-membered saturated or unsaturated heterocyclic ring optionally comprising 1 to 2 additional heteroatoms;

$R^{a3}$ represents H or an optionally substituted $C_{1-6}$alkyl group, and $R^{b3}$ represents -$L_n$-$R^5_m$, —$SO_2NR^{a4}R^{b4}$, —C(=O)$NR^{a5}R^{b5}$, —$SO_2R^{a6}$, —C(=O)$OR^{a7}$, or $R^{a3}$ and $R^{b3}$ together with the nitrogen atom to which they are attached form a 3- to 7-membered saturated or unsaturated heterocyclic ring optionally comprising 1 to 2 additional heteroatoms;

$R^{a4}$ represents H or an optionally substituted $C_{1-6}$alkyl group, and $R^{b4}$ represents -$L_n$-$R^5_m$, or $R^{a4}$ and $R^{b4}$ together with the nitrogen atom to which they are attached form a 3- to 7-membered saturated or unsaturated heterocyclic ring optionally comprising 1 to 2 additional heteroatoms;

$R^{a5}$ represents H or an optionally substituted $C_{1-6}$alkyl group, and $R^{b5}$ represents -$L_n$-$R^5_m$, or $R^{a5}$ and $R^{b5}$ together with the nitrogen atom to which they are attached form a 3- to 7-membered saturated or unsaturated heterocyclic ring optionally comprising 1 to 2 additional heteroatoms;

$R^{a6}$ represents -$L_n$-$R^5_m$;
$R^{a7}$ represents -$L_n$-$R^5_m$;
$R^{a8}$ represents -$L_n$-$R^5_m$;
$R^{a9}$ represents -$L_n$-$R^5_m$;
$R^{a10}$ represents -$L_n$-$R^5_m$;

L represents a linker selected from optionally substituted $C_{2-10}$alkyl, optionally substituted $C_{2-10}$alkenyl, optionally substituted $C_{6-14}$aryl, optionally substituted —$C_{2-4}$alkyl-$C_{6-14}$aryl, optionally substituted —$C_{6-14}$aryl-$C_{1-4}$alkyl, optionally substituted $C_{3-12}$cycloalkyl, optionally substituted $C_{7-12}$polycycloalkyl group, optionally substituted $C_{7-12}$polycycloalkenyl group, optionally substituted $C_{5-12}$-spirocycloalkyl group and optionally substituted heteroaryl comprising 1 or 2 nitrogen atoms;

n is 0 or 1 m is 1 or 2

$R^5$ represents a group selected from among hydrogen, optionally substituted morpholinyl, optionally substituted piperidinyl, optionally substituted piperazinyl, optionally substituted piperazinylcarbonyl, optionally substituted pyrrolidinyl, optionally substituted tropenyl, optionally substituted diketomethylpiperazinyl, optionally substituted sulphoxomorpholinyl, optionally substituted sulphonylmorpholinyl, optionally substituted thiomorpholinyl, optionally substituted azacycloheptyl, optionally substituted granatane, optionally substituted oxogranatane and —$NR^8R^9$;

$R^6$, $R^7$ each independently represents hydrogen or an optionally substituted $C_{1-4}$alkyl group;

$R^8$, $R^9$ each independently represents hydrogen, optionally substituted $C_{1-6}$alkyl, optionally substituted —$C_{1-4}$alkyl-$C_{3-10}$cycloalkyl, optionally substituted $C_{3-10}$cycloalkyl, optionally substituted $C_{6-14}$aryl, optionally substituted —$C_{1-4}$alkyl-$C_{6-14}$aryl, optionally substituted pyranyl, optionally substituted pyridinyl, optionally substituted pyrimidinyl, optionally substituted $C_{1-4}$alkyloxycarbonyl, optionally substituted optionally substituted $C_{6-14}$arylcarbonyl, optionally substituted $C_{1-4}$alkylcarbonyl, optionally substituted $C_{6-14}$arylmethyloxycarbonyl, optionally substituted $C_{6-14}$arylsulphonyl, optionally substituted $C_{1-4}$alkylsulphonyl, optionally substituted $C_{6-14}$aryl-$C_{1-4}$alkylsulphonyl, or $R^8$ and $R^9$ together with the nitrogen atom to which they are attached form a 3- to 7-membered bridged or unbridged, saturated or unsaturated heterocyclic ring optionally comprising 1 to 2 additional heteroatoms;

$X^1$ is O or S;

X is O, S or $H_2$;

Ar represents a 5- or 6-membered aromatic or heteroaromatic ring optionally comprising at least one ring heteroatom selected from nitrogen, oxygen and sulphur; and $A^1$, $A^2$ each independently represents N or CH;

and wherein when $Z^1$ is C=O, $Z^2$ is $CR^cR^d$ or $NR^e$ and $Z^3$ is $CR^1R^2$;

$R^1$, $R^2$ each independently represents hydrogen, an optionally substituted $C_{1-6}$alkyl group or an optionally substituted $C_{3-6}$cycloalkyl group, or $R^1$ and $R^2$ together with the carbon atom to which they are attached form a 3- to 6-membered saturated or unsaturated ring optionally comprising 1 to 2 heteroatoms;

$R^c$, $R^d$ each independently represents hydrogen, an optionally substituted $C_{1-6}$alkyl group or an optionally substituted $C_{3-6}$cycloalkyl group, or $R^c$ and $R^d$ together with the carbon atom to which they are attached form a 3- to 6-membered saturated or unsaturated ring optionally comprising 1 to 2 heteroatoms;

$R^e$ represents hydrogen, an optionally substituted $C_{1-6}$alkyl group or an optionally substituted $C_{3-6}$cycloalkyl group; or optionally one of $R^1$ and $R^3$ or $R^2$ and $R^3$, or $R^1$ and $R^c$, or $R^2$ and $R^d$, or $R^1$ and $R^e$ together represent a saturated or unsaturated $C_{1-4}$alkyl bridge optionally comprising 1 heteroatom;

or when $Z^2$ is C=O, $Z^1$ is $CR^{f2}R^{g2}$ and $Z^3$ is $CR^1R^2$;

$R^1$, $R^2$ each independently represents hydrogen, an optionally substituted $C_{1-6}$alkyl group or an optionally substituted $C_{3-6}$cycloalkyl group, or $R^1$ and $R^2$ together with the carbon atom to which they are attached form a 3- to 6-membered saturated or unsaturated ring optionally comprising 1 to 2 heteroatoms;

$R^{f2}$, $R^{g2}$ each independently represents hydrogen, an optionally substituted $C_{1-6}$alkyl group or an optionally substituted $C_{3-6}$cycloalkyl group, or $R^{f2}$ and $R^{g2}$ together with the carbon atom to which they are attached form a 3- to 6-membered saturated or unsaturated ring optionally comprising 1 to 2 heteroatoms; or optionally one of $R^1$ and $R^3$ or $R^2$ and $R^3$ together represent a saturated or unsaturated $C_{1-4}$alkyl bridge optionally comprising 1 heteroatom;

or when $Z^3$ is C=O, $Z^2$ is $CR^{c3}R^{d3}$ or $NR^{e3}$ and $Z^1$ is $CR^{f3}R^{g3}$;

$R^{c3}$, $R^{d3}$ each independently represents hydrogen, an optionally substituted $C_{1-6}$alkyl group or an optionally substituted $C_{3-6}$cycloalkyl group, or $R^{c3}$ and $R^{d3}$ together with the carbon atom to which they are attached form a 3- to 6-membered saturated or unsaturated ring optionally comprising 1 to 2 heteroatoms;

$R^{e3}$ represents hydrogen, an optionally substituted $C_{1-6}$alkyl group or an optionally substituted $C_{3-6}$cycloalkyl group;

$R^{f3}$, $R^{g3}$ each independently represents hydrogen, an optionally substituted $C_{1-6}$alkyl group or an optionally substituted $C_{3-6}$cycloalkyl group, or $R^{f3}$ and $R^{g3}$ together with the carbon atom to which they are attached form a 3- to 6-membered saturated or unsaturated ring optionally comprising 1 to 2 heteroatoms; or optionally one of $R^{c3}$ and $R^{f3}$, or $R^{d3}$ and $R^{g3}$ or $R^{e3}$ and $R^{f3}$ together represent a saturated or unsaturated $C_{1-4}$alkyl bridge optionally comprising 1 heteroatom or when $Z^1$ is $CR^fR^g$, $Z^2$ is $CR^cR^d$ or $NR^e$ and $Z^3$ is $CR^1R^2$;

$R^1$, $R^2$ each independently represents hydrogen, an optionally substituted $C_{1-6}$alkyl group or an optionally substituted $C_{3-6}$cycloalkyl group, or $R^1$ and $R^2$ together with the carbon atom to which they are attached form a 3- to 6-membered saturated or unsaturated ring optionally comprising 1 to 2 heteroatoms;

$R^c$, $R^d$ each independently represents hydrogen, an optionally substituted $C_{1-6}$alkyl group or an optionally substituted $C_{3-6}$cycloalkyl group, or $R^c$ and $R^d$ together with the carbon atom to which they are attached form a 3- to 6-membered saturated or unsaturated ring optionally comprising 1 to 2 heteroatoms;

$R^e$ represents hydrogen, an optionally substituted $C_{1-6}$alkyl group or an optionally substituted $C_{3-6}$cycloalkyl group;

$R^f$, $R^g$ each independently represents hydrogen, an optionally substituted $C_{1-6}$alkyl group or an optionally substituted $C_{3-6}$cycloalkyl group, or $R^f$ and $R^g$ together with the carbon atom to which they are attached form a 3- to 6-membered saturated or unsaturated ring optionally comprising 1 to 2 heteroatoms; or optionally one of $R^1$ and $R^3$, or $R^2$ and $R^3$, or $R^1$ and $R^c$, or $R^2$ and $R^d$, or $R^1$ and $R^{e3}$ together represent a saturated or unsaturated $C_{1-4}$alkyl bridge optionally comprising 1 heteroatom, or pharmacologically acceptable salts thereof.

The term alkyl group, including alkyl groups which are a part of other groups, unless otherwise stated, includes branched and unbranched alkyl groups with 1 to 12 carbon atoms. Examples of $C_{1-12}$alkyl groups include methyl, ethyl, propyl, butyl, pentyl, hexyl, heptyl, octyl, nonyl, decyl and dodecyl groups. Unless otherwise stated, the terms propyl, butyl, pentyl, hexyl, heptyl, octyl, nonyl, decyl and dodecyl include all the possible isomeric forms. For example, the term propyl includes the two isomeric groups n-propyl and iso-propyl, the term butyl includes n-butyl, iso-butyl, sec-butyl and tert-butyl, the term pentyl includes iso-pentyl, neopentyl, etc.

In the above mentioned alkyl groups, one or more hydrogen atoms may optionally be replaced by other substituent groups. For example, alkyl groups may be substituted by the following substituents groups: =O; OH; $NO_2$; CN; —$NH_2$; halogen, for example fluorine or chlorine; optionally substituted $C_{1-10}$alkyl, for example methyl, ethyl, propyl, trifluoromethyl; optionally substituted —$OC_{1-3}$alkyl, for example OMe, OEt, —$OCHF_2$, —$OCF_3$; —COOH; —COO—$C_{1-4}$alkyl, for example —COOMe or —COOEt; or —$CONH_2$. "=O" denotes an oxygen atom linked via a double bond. All the hydrogen atoms of the alkyl group may optionally be replaced by substituent groups, for example a trifluoromethyl group is a methyl group wherein all the hydrogen atoms have been replaced with fluorine atoms.

The term alkyl bridge, unless otherwise stated, includes branched and unbranched alkyl bridging groups with 1 to 5 carbon atoms, for example methylene, ethylene, propylene, butylene and pentylene bridges. Unless otherwise stated, the terms propylene, butylene and pentylene include all the possible isomeric forms. In the aforementioned alkyl bridges, 1 or 2 C-atoms may optionally be replaced by one or more heteroatoms selected from among oxygen, nitrogen or sulphur.

The term alkenyl groups (including those which are a part of other groups), unless otherwise stated, includes branched and unbranched alkylene groups with 2 to 10 carbon atoms comprising at least one carbon-carbon double bond. Examples of $C_{2-10}$alkenyl groups include ethenyl, propenyl, butenyl, pentenyl, hexenyl, heptenyl, octenyl nonenyl and decenyl groups. Unless otherwise stated, the abovementioned terms propenyl, butenyl, pentenyl, hexenyl, heptenyl, octenyl, nonenyl and decenyl also include all the possible isomeric forms. For example, the term butenyl includes 1-butenyl, 2-butenyl, 3-butenyl, 1-methyl-1-propenyl, 1-methyl-2-propenyl, 2-methyl-1-propenyl, 2-methyl-2-propenyl and 1-ethyl-1-ethenyl.

In the above mentioned alkenyl groups, unless otherwise stated, one or more hydrogen atoms may optionally be replaced by other substituent groups. For example, alkenyl groups may be substituted by the following substituents groups: =O; OH; $NO_2$; CN; —$NH_2$; halogen, for example fluorine or chlorine; optionally substituted $C_{1-10}$alkyl, for example methyl, ethyl, propyl, trifluoromethyl; optionally substituted —$OC_{1-3}$alkyl, for example OMe, OEt, —$OCHF_2$, —$OCF_3$; —COOH; —COO—$C_{1-4}$alkyl, for example —COOMe or —COOEt; or —$CONH_2$. "=O" denotes an oxygen atom linked via a double bond. All the hydrogen atoms of the alkenyl group may optionally be replaced, for example a trifluoroethylene group is an ethylene group wherein all the hydrogen atoms have been replaced with fluorine atoms.

The term alkynyl groups (including those which are a part of other groups), unless otherwise stated, includes branched and unbranched alkynyl groups with 2 to 10 carbon atoms comprising at least one triple bond. Examples of $C_{2-10}$alkynyl groups include ethynyl, propynyl, butynyl, pentynyl, hexynyl, heptynyl, octynyl, nonynyl and decynyl groups. Unless otherwise stated, the terms propynyl, butynyl, pentynyl, hexynyl, heptynyl, octynyl, nonynyl and decynyl also include all the possible isomeric forms. For example, the term butynyl includes 1-butynyl, 2-butynyl, 3-butynyl and 1-methyl-2-propynyl.

In the above mentioned alkynyl groups, unless otherwise stated, one or more hydrogen atoms may optionally be replaced by other substituent groups. For example, alkynyl groups may be substituted by the following substituents groups: =O; OH; $NO_2$; CN; —$NH_2$; halogen, for example fluorine or chlorine; optionally substituted $C_{1-10}$alkyl, for example methyl, ethyl, propyl, trifluoromethyl; optionally substituted —$OC_{1-3}$alkyl, for example OMe, OEt, —$OCHF_2$, —$OCF_3$; —COOH; —COO—$C_{1-4}$alkyl, for example —COOMe or —COOEt; or —$CONH_2$. "=O" denotes an oxygen atom linked via a double bond. All the hydrogen atoms of the alkynyl group may optionally also be replaced.

The term aryl includes aromatic ring systems with 6 to 14 carbon atoms, said aromatic ring systems comprising one or more rings having from 6 to 14 ring atoms wherein at least one ring is aromatic. Examples of $C_{6-14}$aryl groups include phenyl ($C_6$), indenyl ($C_9$), naphthyl ($C_{10}$), fluorenyl ($C_{13}$), anthracyl ($C_{14}$), and phenanthryl ($C_{14}$). In the above mentioned aryl groups, unless otherwise stated, one or more hydrogen atoms may optionally be replaced by other substituent groups. For example, aryl groups may be substituted by the following substituents groups: OH; $NO_2$; CN; $NH_2$; halogen, for example fluorine or chlorine; optionally substituted $C_{1-10}$alkyl, for example methyl, ethyl, propyl or $CF_3$; optionally substituted —$OC_{1-3}$alkyl, for example —OMe, —OEt, $OCHF_2$, or $OCF_3$; —COOH, —COO—$C_{1-4}$alkyl, for example —COOMe or —COOEt, or —$CONH_2$.

The term heteroaryl comprising 1 or 2 nitrogen atoms includes heteroaromatic ring systems with 5 to 14 ring atoms, said heteroaromatic ring systems comprising one or more rings having from 5 to 14 ring atoms wherein at least one ring is aromatic and wherein one or two of the ring atoms are replaced by nitrogen atoms the remaining ring atoms being carbon atoms. Examples of heteroaryl groups wherein up to two carbon atoms are replaced by one or two nitrogen atoms comprising one ring include pyrrolyl, pyrazolyl, imidazolyl, triazolyl, pyridinyl and pyrimidinyl groups. Each of the aforementioned examples of heteroaryl rings may optionally also be anellated by a further ring, for example a benzene ring. Examples of heteroaryl groups wherein up to two carbon atoms are replaced by one or two nitrogen atoms comprising two rings include indolyl, benzimidazolyl, quinolinyl, isoquinolinyl and quinazolinyl. In the above mentioned heteroaryl groups, unless otherwise stated, one or more hydrogen atoms may optionally be replaced by other substituent groups. For example, heteroaryl groups may be substituted by the following substituents groups: F; Cl; Br; OH; OMe; Me; Et; CN; $NH_2$; $CONH_2$; optionally substituted phenyl; and optionally substituted heteroaryl, for example optionally substituted pyridyl.

The term optionally substituted heteroaryl ring comprising 1, 2 or 3 heteroatoms each independently selected from nitrogen, oxygen or sulphur includes heteroaromatic ring systems with 5 to 14 ring atoms, said heteroaromatic ring systems comprising one or more rings having from 5 to 14 ring atoms wherein at least one ring is aromatic and wherein one, two or three of the ring atoms are replaced by nitrogen, oxygen or sulphur atoms the remaining ring atoms being carbon atoms. Examples of heteroaryl rings wherein up to three carbon atoms are replaced by nitrogen, oxygen or sulphur comprising one ring include furyl, imidazolyl, isothiazolyl, isoxazolyl, oxazolyl, pyrazinyl, pyrazolyl, pyridazinyl, pyridyl, pyrimidinyl, pyrrolyl, thiazolyl, thienyl and triazolyl groups. Each of the aforementioned examples of heteroaryl rings may optionally also be anellated by a further ring, for example a benzene ring. Examples of heteroaryl rings wherein up to three carbon atoms are replaced by nitrogen, oxygen or sulphur atoms comprising two rings include indolyl, benzimidazolyl, benzoxazoyl, benzioxazoyl, quinolinyl, isoquinolinyl and quinazolinyl. In the above mentioned heteroaryl rings, unless otherwise stated, one or more hydrogen atoms may optionally be replaced by other substituent groups. For example, heteroaryl groups may be substituted by the following substituents groups: F; Cl; Br; OH; OMe; Me; Et; CN; $NH_2$; $CONH_2$; optionally substituted phenyl; and optionally substituted heteroaryl, for example optionally substituted pyridyl.

The term cycloalkyl groups, unless otherwise stated, includes cycloalkyl groups comprising 1 ring with 3-12 carbon atoms. Examples of $C_{3-12}$cycloalkyl groups include cyclopropyl, cyclobutyl, cyclopentyl, cyclohexyl, cycloheptyl, cyclooctyl, cyclononyl, cyclodecyl, cycloundecyl and cyclododecyl groups. In the abovementioned cycloalkyl groups, unless otherwise stated, one or more hydrogen atoms may optionally be replaced by other substituent groups. For example, cycloalkyl groups may be substituted by the following substituents groups: =O; OH; $NO_2$; CN; —$NH_2$; halogen, for example fluorine or chlorine; optionally substituted $C_{1-10}$alkyl, for example methyl, ethyl, propyl, trifluoromethyl; optionally substituted —$OC_{1-3}$alkyl, for example OMe, OEt, —$OCHF_2$, —$OCF_3$; —COOH; —COO—$C_{1-4}$alkyl, for example —COOMe or —COOEt; or —$CONH_2$. "=O" denotes an oxygen atom linked via a double bond.

The term cycloalkenyl, unless otherwise stated, includes cycloalkenyl groups with 3-12 carbon atoms comprising one ring, said ring comprising at least one carbon-carbon double bond. Examples of $C_{3-12}$cycloakenyl groups include cyclopropenyl, cyclobutenyl, cyclopentenyl, cyclohexenyl, cycloheptenyl, cyclooctenyl, cyclononenyl, cyclodecenyl, cycloundecenyl and cyclododecenyl groups. In the abovementioned cycloalkenyl groups, unless otherwise stated, one or more hydrogen atoms may optionally be replaced by other substituent groups. For example, cycloalkenyl groups may be substituted by the following substituent groups: =O; OH; $NO_2$; CN; —$NH_2$; halogen, for example fluorine or chlorine; optionally substituted $C_{1-10}$alkyl, for example methyl, ethyl, propyl, trifluoromethyl; optionally substituted —$OC_{1-3}$alkyl, for example OMe, OEt, —$OCHF_2$, —$OCF_3$; —COOH; —COO—$C_{1-4}$alkyl, for example —COOMe or —COOEt; or —$CONH_2$. "=O" denotes an oxygen atom linked via a double bond.

The terms heterocycloalkyl and heterocycloakenyl, unless otherwise described in the definitions, includes 3- to 12-membered, for example 5-, 6- or 7-membered, heterocycles which may contain 1 to 4 heteroatoms selected from nitrogen, oxygen or sulphur. Heterocycloalkyl denotes a saturated heterocycle, and heterocycloakenyl denotes an unsaturated heterocycle. Examples of heterocycloalkyl or heterocycloakenyl groups include tetrahydrofuran, tetrahydrofuranone, gamma-butyrolactone, alpha-pyran, gamma-pyran, dioxolane, tetrahydropyran, dioxane, dihydrothiophene, thiolan, dithiolan, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole, and pyrazolidine. In the abovementioned heterocycloalkyl or heterocycloakenyl groups, unless otherwise stated, one or more hydrogen atoms may optionally be replaced by other substituent groups. For example, heterocycloalkyl or heterocycloakenyl groups may be substituted by the following substituents groups: =O; OH; CN; —NH$_2$; halogen, for example fluorine or chlorine; optionally substituted C$_{1-4}$alkyl, for example methyl, ethyl, propyl, trifluoromethyl; optionally substituted —OC$_{1-3}$alkyl, for example OMe, OEt, —OCHF$_2$, —OCF$_3$; —COOH; —COO—C$_{1-4}$ alkyl, for example —COOMe or —COOEt; or —CONH$_2$. "=O" denotes an oxygen atom linked via a double bond.

The term polycycloalkyl, unless otherwise stated, includes cycloalkyl groups comprising 3 to 12 carbon atoms and comprising 2 or more rings. Examples of polycycloalkyl groups include optionally substituted, bi-, tri-, tetra- or pentacyclic cycloalkyl groups, for example pinane, 2,2,2-octane, 2,2,1-heptane or adamantane.

The term polycycloalkenyl, unless otherwise stated, includes cycloalkenyl groups comprising 7 to 12 carbon atoms and comprising 2 or more rings wherein at least one ring comprises a carbon-carbon double bond. Examples of polycycloalkenyl groups are optionally bridged and/or substituted bi-, tri-, tetra- or pentacyclic cycloalkenyl groups, for example bicycloalkenyl or tricycloalkenyl groups having at least one double bond, such as norbornene.

The term spirocycloalkyl unless otherwise stated, includes spirocycloalkyl groups comprising 5 to 12 carbon atoms and comprising 2 or more rings wherein two rings are joined at a spiro carbon centre. Examples of spirocycloalkyl groups include spiro[4,4]nonyl and spiro[3,4]octyl.

The term 5- or 6-membered aromatic or heteroaromatic ring optionally comprising at least one ring heteroatom selected from nitrogen, oxygen and sulphur is a fully unsaturated, aromatic monocyclic ring containing 5 or 6 atoms of which one or more ring atoms is optionally a heteroatom selected from nitrogen, oxygen or sulphur, with the remaining ring atoms being carbon. Examples of a 5- or 6-membered aromatic or heteroaromatic ring optionally comprising at least one ring heteroatom selected from nitrogen, oxygen and sulphur include furyl, imidazolyl, isothiazolyl, isoxazolyl, oxazolyl, phenyl, pyrazinyl, pyrazolyl, pyridazinyl, pyridyl, pyrimidinyl, pyrrolyl thiazolyl, thienyl and triazolyl rings.

The term 3- to 6-membered saturated or unsaturated ring optionally comprising 1 to 2 heteroatoms includes optionally substituted C$_{3-6}$cylcoalkyl and optionally substituted C$_{3-6}$cylcoalkenyl groups, and optionally substituted 3- to 6-membered heterocylcoalkyl and optionally substituted 3- to 6-membered heterocylcoalkenyl groups each with 1 or 2 heteroatoms.

The term halogen includes fluorine, chlorine, bromine or iodine.

The terms alkyloxy (—OR wherein R is an alkyl), alkenyloxy (—OR wherein R is an alkenyl), alkynyloxy (—OR wherein R is an alkynyl), cycloalkyloxy (—OR wherein R is a cycloalkyl) and heterocycloalkoxy (—OR wherein R is a heterocycloalkyl) denote an —OR group wherein the respective alkyl, alkenyl, alkynyl, cycloalkyl or heterocycloalkyl group is as hereinbefore described above.

The terms alkylthio, alkylsulphoxo and alkylsulphono denotes an —S(O)$_x$R group wherein x=0, 1 or 2 respectively and R is an alkyl group as hereinbefore described above.

The term -alkyl-aryl refers to an alkyl group with an aryl substituent. The term -alkyl-cycloalkyl refers to an alkyl group with a cycloakyl substituent. The term -aryl-alkyl refers to an aryl group with an alkyl substituent. The terms alkoxycarbonyl (—(C=O)OR), alkylcarbonyl (—COR) and arylcarbonyl (—COR) refer to a carbonyl group with an alkoxy, alkyl or aryl substituent.

When R$^5$ represents a substituted morpholinyl, piperidinyl, homopiperidinyl, piperazinyl, piperazinylcarbonyl, pyrrolidinyl, tropenyl, diketomethylpiperazinyl, sulphoxomorpholinyl, sulphonylmorpholinyl, thiomorpholinyl, granatanyl, oxogranatanyl or azacycloheptyl, one or more substituents may be present and are as defined above for R$^8$.

All the groups mentioned in the definition of R$^1$ to R$^9$ may optionally be branched and/or substituted.

According to a second aspect of the present invention there is provided a compound of formula (II):

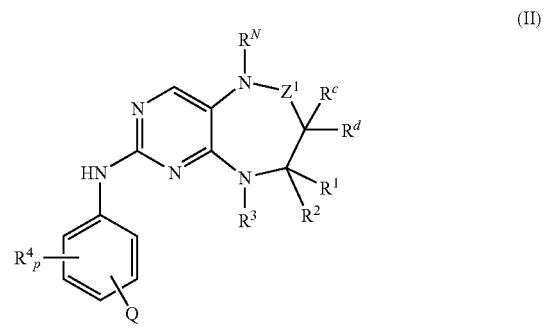

wherein
R$^1$, R$^2$ each independently represents hydrogen, an optionally substituted C$_{1-6}$alkyl group or an optionally substituted C$_{3-6}$cycloalkyl group, or R$^1$ and R$^2$ together with the carbon atom to which they are attached form a 3- to 6-membered saturated or unsaturated ring optionally comprising 1 to 2 heteroatoms;
R$^c$, R$^d$ each independently represents hydrogen, an optionally substituted C$_{1-6}$alkyl group or an optionally substituted C$_{3-6}$cycloalkyl group, or R$^c$ and R$^d$ together with the carbon atom to which they are attached form a 3- to 6-membered saturated or unsaturated ring optionally comprising 1 to 2 heteroatoms;
R$^3$ represents hydrogen, an optionally substituted C$_{1-12}$alkyl group, an optionally substituted C$_{2-12}$alkenyl group, an optionally substituted C$_{2-12}$alkynyl group, an optionally substituted C$_{6-14}$aryl group, an optionally substituted C$_{3-12}$cycloalkyl group, an optionally substituted C$_{3-12}$cycloalkenyl group, an optionally substituted C$_{7-12}$polycycloalkyl group, an optionally substituted C$_{7-12}$polycycloalkenyl group, an optionally substituted C$_{5-12}$-spirocycloalkyl group, an optionally substituted 3- to 12-membered heterocycloalkyl group comprising 1 or 2 heteroatoms, or an optionally substituted 4- to 12-membered heterocycloalkenyl group comprising 1 or 2 heteroatoms, or
optionally one of R$^1$ and R$^3$, or R$^2$ and R$^3$, or R$^1$ and R$^c$, or R$^2$ and R$^d$ together represent a saturated or unsaturated C$_{1-4}$alkyl bridge optionally comprising 1 heteroatom;
R$^4$ each independently represent —CN, hydroxy, —NR$^6$R$^7$, —NR$^6$SO$_2$R$^7$, halogen, an optionally substituted C$_{1-6}$alkyl group, an optionally substituted C$_{3-7}$cycloalkyl group, an optionally substituted C$_{2-6}$alkenyl group, an optionally substituted C$_{2-6}$alkynyl group, an optionally substituted C$_{1-5}$alkyloxy group, an optionally substituted C$_{3-6}$cycloalkyloxy group, an optionally substituted C$_{2-5}$alkenyloxy group, an optionally substituted C$_{2-5}$alkynyloxy group, an optionally substituted C$_{1-6}$alkylthio group, an optionally substituted C$_{1-6}$alkylsulphoxo group or an optionally substituted $C_{1-6}$alkyl-sulphonyl group, an optionally substituted 3- to 12-membered heterocycloalkyl group comprising 1 or 2 heteroatoms, or an optionally substituted 3- to 12-membered heterocycloalkoxy group comprising 1 or 2 heteroatoms;

$R^N$ represents hydrogen, —$NH_2$, —OH, —CN, —C≡CH, —C(=O)$NH_2$, $C_{1-3}$alkyl, $C_{1-3}$alkylamino, $C_{1-3}$alkylthio, $C_{1-3}$alkyloxy, $C_{1-3}$alkylcarbonyl, —CHO, or —$SO_2$Me;

p is 0, 1 or 2;

Q is —C(=$X^1$)—$NR^aR^b$, —S(O)$_2$—$NR^{a2}R^{b2}$, -(optionally substituted $C_{1-3}$alkyl)$_g$-$NR^{a3}R^{b3}$, —S(O)$_k$—$R^{a8}$, —C(=$X^2$)—$OR^{a9}$, —$OR^{a10}$ or -(5- or 6-membered aromatic or heteroaromatic ring optionally comprising at least one ring heteroatom selected from nitrogen, oxygen and sulphur)-$L_n$-$R^5_m$;

g is 0 or 1;

k is 0, 1 or 2;

$R^a$ represents H or an optionally substituted $C_{1-6}$alkyl group, and $R^b$ represents -$L_n$-$R^5_m$, or $R^a$ and $R^b$ together with the nitrogen atom to which they are attached form a 3- to 7-membered saturated or unsaturated heterocyclic ring optionally comprising 1 to 2 additional heteroatoms;

$R^{a2}$ represents H or an optionally substituted $C_{1-6}$alkyl group, and $R^{b2}$ represents -$L_n$-$R^5_m$, or $R^{a2}$ and $R^{b2}$ together with the nitrogen atom to which they are attached form a 3- to 7-membered saturated or unsaturated heterocyclic ring optionally comprising 1 to 2 additional heteroatoms;

$R^{a3}$ represents H or an optionally substituted $C_{1-6}$alkyl group, and $R^{b3}$ represents -$L_n$-$R^5_m$, —$SO_2NR^{a4}R^{b4}$, —C(=O)$NR^{a5}R^{b5}$, —$SO_2R^{a6}$, —C(=O)$OR^{a7}$, or $R^{a3}$ and $R^{b3}$ together with the nitrogen atom to which they are attached form a 3- to 7-membered saturated or unsaturated heterocyclic ring optionally comprising 1 to 2 additional heteroatoms;

$R^{a4}$ represents H or an optionally substituted $C_{1-6}$alkyl group, and $R^{b4}$ represents -$L_n$-$R^5_m$, or $R^{a4}$ and $R^{b4}$ together with the nitrogen atom to which they are attached form a 3- to 7-membered saturated or unsaturated heterocyclic ring optionally comprising 1 to 2 additional heteroatoms;

$R^{a5}$ represents H or an optionally substituted $C_{1-6}$alkyl group, and $R^{b5}$ represents -$L_n$-$R^5_m$, or $R^{a5}$ and $R^{b5}$ together with the nitrogen atom to which they are attached form a 3- to 7-membered saturated or unsaturated heterocyclic ring optionally comprising 1 to 2 additional heteroatoms;

$R^{a6}$ represents -$L_n$-$R^5_m$;
$R^{a7}$ represents -$L_n$-$R^5_m$;
$R^{a8}$ represents -$L_n$-$R^5_m$;
$R^{a9}$ represents -$L_n$-$R^5_m$;
$R^{a10}$ represents -$L_n$-$R^5_m$;

L represents a linker selected from optionally substituted $C_{2-10}$alkyl, optionally substituted $C_{2-10}$alkenyl, optionally substituted $C_{6-14}$aryl, optionally substituted —$C_{2-4}$alkyl-$C_{6-14}$aryl, optionally substituted —$C_{6-14}$aryl-$C_{1-4}$alkyl, optionally substituted $C_{3-12}$cycloalkyl and optionally substituted heteroaryl comprising 1 or 2 nitrogen atoms;

n is 0 or 1 m is 1 or 2

$R^5$ represents a group selected from among hydrogen, optionally substituted morpholinyl, optionally substituted piperidinyl, optionally substituted piperazinyl, optionally substituted piperazinylcarbonyl, optionally substituted pyrrolidinyl, optionally substituted tropenyl, optionally substituted diketomethylpiperazinyl, optionally substituted sulphoxomorpholinyl, optionally substituted sulphonylmorpholinyl, optionally substituted thiomorpholinyl, optionally substituted azacycloheptyl, optionally substituted granatanyl, optionally substituted oxogranatanyl and —$NR^8R^9$;

$R^6$, $R^7$ each independently represents hydrogen or an optionally substituted $C_{1-4}$alkyl group;

$R^8$, $R^9$ each independently represents hydrogen, optionally substituted $C_{1-6}$alkyl, optionally substituted —$C_{1-4}$alkyl-$C_{3-10}$cycloalkyl, optionally substituted $C_{3-10}$cycloalkyl, optionally substituted $C_{6-14}$aryl, optionally substituted —$C_{1-4}$alkyl-$C_{6-14}$aryl, optionally substituted pyranyl, optionally substituted pyridinyl, optionally substituted pyrimidinyl, optionally substituted $C_{1-4}$alkyloxycarbonyl, optionally substituted optionally substituted $C_{6-14}$arylcarbonyl, optionally substituted $C_{1-4}$alkylcarbonyl, optionally substituted $C_{6-14}$arylmethyloxycarbonyl, optionally substituted $C_{6-14}$arylsulphonyl, optionally substituted $C_{1-4}$alkylsulphonyl, optionally substituted $C_{6-14}$aryl-$C_{1-4}$alkylsulphonyl, or $R^8$ and $R^9$ together with the nitrogen atom to which they are attached form a 3- to 7-membered bridged or unbridged, saturated or unsaturated heterocyclic ring optionally comprising 1 to 2 additional heteroatoms; and $Z^1$ is C=O or $CR^fR^g$ wherein $R^f$, $R^g$ each independently represents hydrogen, an optionally substituted $C_{1-6}$alkyl group or an optionally substituted $C_{3-6}$cycloalkyl group, or $R^f$ and $R^g$ together with the carbon atom to which they are attached form a 3- to 6-membered saturated or unsaturated ring optionally comprising 1 to 2 heteroatoms, or pharmacologically acceptable salts thereof.

According to a third aspect of the present invention there is provided a compound of formula (IIa):

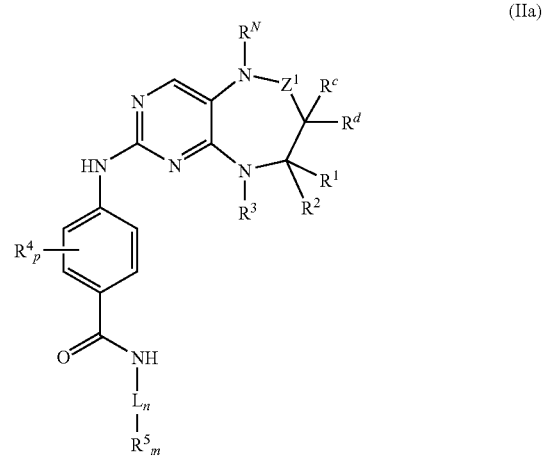

(IIa)

wherein
$R^1$, $R^2$ each independently represents hydrogen, an optionally substituted $C_{1-6}$alkyl group or an optionally substituted $C_{3-6}$cycloalkyl group, or $R^1$ and $R^2$ together with the carbon atom to which they are attached form a 3- to 6-membered saturated or unsaturated ring optionally comprising 1 to 2 heteroatoms;

$R^c$, $R^d$ each independently represents hydrogen, an optionally substituted $C_{1-6}$alkyl group or an optionally substituted $C_{3-6}$cycloalkyl group, or $R^c$ and $R^d$ together with the carbon atom to which they are attached form a 3- to 6-membered saturated or unsaturated ring optionally comprising 1 to 2 heteroatoms;

$R^3$ represents hydrogen, an optionally substituted $C_{1-12}$alkyl group, an optionally substituted $C_{2-12}$alkenyl group, an optionally substituted $C_{2-12}$alkynyl group, an optionally substituted $C_{6-14}$aryl group, an optionally substituted $C_{3-12}$cycloalkyl group, an optionally substituted $C_{3-12}$cycloalkenyl group, an optionally substituted $C_{7-12}$polycycloalkyl group, an optionally substituted $C_{7-12}$polycycloalkenyl group, an optionally substituted $C_{5-12}$spirocycloalkyl group, an optionally substituted 3- to 12-membered heterocycloalkyl group comprising 1 or 2 heteroatoms, or an optionally substituted 4- to 12-membered heterocycloalkenyl group comprising 1 or 2 heteroatoms, or optionally one of $R^1$ and $R^3$, or $R^2$ and $R^3$, or $R^1$ and $R^c$, or $R^2$ and $R^d$ together represent a saturated or unsaturated $C_{1-4}$alkyl bridge optionally comprising 1 heteroatom;

$R^4$ each independently represent —CN, hydroxy, —$NR^6R^7$, —$NR^6SO_2R^7$, halogen, an optionally substituted $C_{1-6}$alkyl group, an optionally substituted $C_{3-7}$cycloalkyl group, an optionally substituted $C_{2-6}$alkenyl group, an optionally substituted $C_{2-6}$alkynyl group, an optionally substituted $C_{1-5}$alkyloxy group, an optionally substituted $C_{3-6}$cycloalkyloxy group, an optionally substituted $C_{2-5}$alkenyloxy group, an optionally substituted $C_{2-5}$alkynyloxy group, an optionally substituted $C_{1-6}$alkylthio group, an optionally substituted $C_{1-6}$alkylsulphoxo group or an optionally substituted $C_{1-6}$alkylsulphonyl group, an optionally substituted 3- to 12-membered heterocycloalkyl group comprising 1 or 2 heteroatoms, or an optionally substituted 3- to 12-membered heterocycloalkoxy group comprising 1 or 2 heteroatoms;

$R^N$ represents hydrogen, —$NH_2$, —OH, —CN, —C≡CH, —C(=O)$NH_2$, $C_{1-3}$alkyl, $C_{1-3}$alkylamino, $C_{1-3}$alkylthio, $C_{1-3}$alkyloxy, $C_{1-3}$alkylcarbonyl, —CHO, or —$SO_2Me$;

p is 0, 1 or 2;

L represents a linker selected from optionally substituted $C_{2-10}$alkyl, optionally substituted $C_{2-10}$alkenyl, optionally substituted $C_{6-14}$aryl, optionally substituted —$C_{2-4}$alkyl-$C_{6-14}$aryl, optionally substituted —$C_{6-14}$aryl-$C_{1-4}$alkyl, optionally substituted $C_{3-12}$cycloalkyl and optionally substituted heteroaryl comprising 1 or 2 nitrogen atoms;

n is 0 or 1 m is 1 or 2

$R^5$ represents a group selected from among hydrogen, optionally substituted morpholinyl, optionally substituted piperidinyl, optionally substituted piperazinyl, optionally substituted piperazinylcarbonyl, optionally substituted pyrrolidinyl, optionally substituted tropenyl, optionally substituted diketomethylpiperazinyl, optionally substituted sulphoxomorpholinyl, optionally substituted sulphonylmorpholinyl, optionally substituted thiomorpholinyl, optionally substituted azacycloheptyl, optionally substituted granatanyl, optionally substituted oxogranatanyl and —$NR^8R^9$;

$R^6$, $R^7$ each independently represents hydrogen or an optionally substituted $C_{1-4}$alkyl group;

$R^8$, $R^9$ each independently represents hydrogen, optionally substituted $C_{1-6}$alkyl, optionally substituted —$C_{1-4}$alkyl-$C_{3-10}$cycloalkyl, optionally substituted $C_{3-10}$cycloalkyl, optionally substituted $C_{6-14}$aryl, optionally substituted —$C_{1-4}$alkyl-$C_{6-14}$aryl, optionally substituted pyranyl, optionally substituted pyridinyl, optionally substituted pyrimidinyl, optionally substituted $C_{1-4}$alkyloxycarbonyl, optionally substituted optionally substituted $C_{6-14}$arylcarbonyl, optionally substituted $C_{1-4}$alkylcarbonyl, optionally substituted $C_{6-14}$arylmethyloxycarbonyl, optionally substituted $C_{6-14}$arylsulphonyl, optionally substituted $C_{1-4}$alkylsulphonyl, optionally substituted $C_{6-14}$aryl-$C_{1-4}$alkylsulphonyl, or $R^8$ and $R^9$ together with the nitrogen atom to which they are attached form a 3- to 7-membered bridged or unbridged, saturated or unsaturated heterocyclic ring optionally comprising 1 to 2 additional heteroatoms; and $Z^1$ is C=O or $CR^fR^g$ wherein $R^f$, $R^g$ each independently represents hydrogen, an optionally substituted $C_{1-6}$alkyl group or an optionally substituted $C_{3-6}$cycloalkyl group, or $R^f$ and $R^g$ together with the carbon atom to which they are attached form a 3- to 6-membered saturated or unsaturated ring optionally comprising 1 to 2 heteroatoms, or pharmacologically acceptable salts thereof.

In one embodiment of the second aspect of the invention, $Z^1$ is C=O or $CH_2$.

According to a fourth aspect of the present invention there is provided a compound of formula (III):

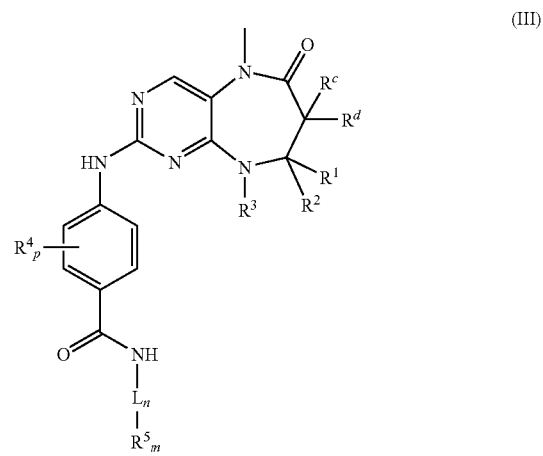

(III)

wherein $R^1$, $R^2$ each independently represents hydrogen or an optionally substituted $C_{1-6}$alkyl group, or $R^1$ and $R^2$ together with the carbon atom to which they are attached form a 3- to 6-membered saturated or unsaturated ring optionally comprising 1 to 2 heteroatoms;

$R^c$, $R^d$ each independently represents hydrogen, an optionally substituted $C_{1-6}$alkyl group or an optionally substituted $C_{3-6}$cycloalkyl group, or $R^c$ and $R^d$ together with the carbon atom to which they are attached form a 3- to 6-membered saturated or unsaturated ring optionally comprising 1 to 2 heteroatoms;

$R^3$ represents hydrogen, an optionally substituted $C_{1-12}$alkyl group, an optionally substituted $C_{2-12}$alkenyl group, an optionally substituted $C_{2-12}$alkynyl group, an optionally substituted $C_{6-14}$aryl group, an optionally substituted $C_{3-12}$cycloalkyl group, an optionally substituted $C_{3-12}$cycloalkenyl group, an optionally substituted $C_{7-12}$polycycloalkyl group, an optionally substituted $C_{7-12}$polycycloalkenyl group, an optionally substituted $C_{5-12}$spirocycloalkyl group, an optionally substituted 3- to 12-membered heterocycloalkyl group comprising 1 or 2 heteroatoms, or an optionally substituted 4- to 12-membered heterocycloalkenyl group comprising 1 or 2 heteroatoms, or optionally one of $R^1$ and $R^3$, or $R^2$ and $R^3$, or $R^1$ and $R^c$, or $R^2$ and $R^d$ together represent a saturated or unsaturated $C_{1-4}$alkyl bridge optionally comprising 1 heteroatom;

$R^4$ each independently represent —CN, hydroxy, —$NR^6R^7$, —$NR^6SO_2R^7$, halogen, an optionally substituted $C_{1-6}$alkyl group, an optionally substituted $C_{3-7}$cycloalkyl group, an optionally substituted $C_{2-6}$alkenyl group, an optionally substituted $C_{2-6}$alkynyl group, an optionally substituted $C_{1-5}$alkyloxy group, an optionally substituted $C_{3-6}$cycloalkyloxy group, an optionally substituted $C_{2-5}$alkenyloxy group, an optionally substituted $C_{2-5}$alkynyloxy group, an optionally substituted $C_{1-6}$alkylthio group, an optionally substituted $C_{1-6}$alkylsulphoxo group or an optionally substituted $C_{1-6}$alkylsulphonyl group, an optionally substituted 3- to 12-membered heterocycloalkyl group comprising 1 or 2 heteroatoms, or an optionally substituted 3- to 12-membered heterocycloalkoxy group comprising 1 or 2 heteroatoms;

p is 0, 1 or 2;

L represents a linker selected from optionally substituted $C_{2-10}$alkyl, optionally substituted $C_{2-10}$alkenyl, optionally substituted $C_{6-14}$aryl, optionally substituted —$C_{2-4}$alkyl-$C_{6-14}$aryl, optionally substituted —$C_{6-14}$aryl-$C_{1-4}$alkyl, optionally substituted $C_{3-12}$cycloalkyl and optionally substituted heteroaryl comprising 1 or 2 nitrogen atoms;

n is 0 or 1;

m is 1 or 2;

$R^5$ represents a group selected from among hydrogen, optionally substituted morpholinyl, optionally substituted piperidinyl, optionally substituted piperazinyl, optionally substituted piperazinylcarbonyl, optionally substituted pyrrolidinyl, optionally substituted tropenyl, optionally substituted diketomethylpiperazinyl, optionally substituted sulphoxomorpholinyl, optionally substituted sulphonylmorpholinyl, optionally substituted thiomorpholinyl, optionally substituted azacycloheptyl, optionally substituted granatanyl, optionally substituted oxogranatanyl and —$NR^8R^9$;

$R^6$, $R^7$ each independently represents hydrogen or an optionally substituted $C_{1-4}$alkyl group; and $R^8$, $R^9$ each independently represents hydrogen, optionally substituted $C_{1-6}$alkyl, optionally substituted —$C_{1-4}$alkyl-$C_{3-10}$cycloalkyl, optionally substituted $C_{3-10}$cycloalkyl, optionally substituted $C_{6-14}$aryl, optionally substituted —$C_{1-4}$alkyl-$C_{6-14}$aryl, optionally substituted pyranyl, optionally substituted pyridinyl, optionally substituted pyrimidinyl, optionally substituted $C_{1-4}$alkyloxycarbonyl, optionally substituted optionally substituted $C_{6-14}$arylcarbonyl, optionally substituted $C_{1-4}$alkylcarbonyl, optionally substituted $C_{6-14}$arylmethyloxycarbonyl, optionally substituted $C_{6-14}$arylsulphonyl, optionally substituted $C_{1-4}$alkylsulphonyl, optionally substituted $C_{6-14}$aryl-$C_{1-4}$alkylsulphonyl, or $R^8$ and $R^9$ together with the nitrogen atom to which they are attached form a 3- to 7-membered bridged or unbridged, saturated or unsaturated heterocyclic ring optionally comprising 1 to 2 additional heteroatoms, or pharmacologically acceptable salt thereof.

According to a fifth aspect of the present invention there is provided a compound of formula (IIIa):

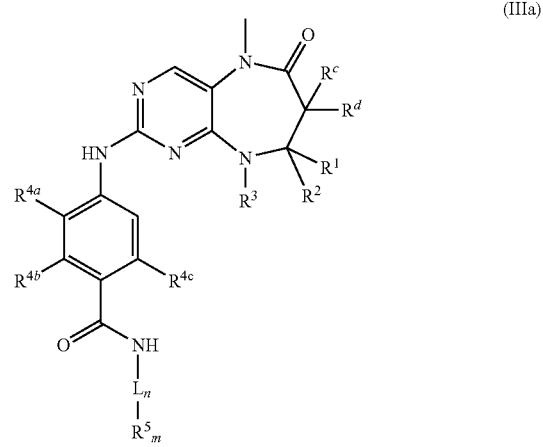

(IIIa)

wherein
$R^1$, $R^2$ each independently represents hydrogen or an optionally substituted $C_{1-6}$alkyl group, or $R^1$ and $R^2$ together with the carbon atom to which they are attached form a 3- to 6-membered saturated or unsaturated ring optionally comprising 1 to 2 heteroatoms;

$R^c$, $R^d$ each independently represents hydrogen, an optionally substituted $C_{1-6}$alkyl group or an optionally substituted $C_{3-6}$cycloalkyl group, or $R^c$ and $R^d$ together with the carbon atom to which they are attached form a 3- to 6-membered saturated or unsaturated ring optionally comprising 1 to 2 heteroatoms;

$R^3$ represents hydrogen, an optionally substituted $C_{1-12}$alkyl group, an optionally substituted $C_{2-12}$alkenyl group, an optionally substituted $C_{2-12}$alkynyl group, an optionally substituted $C_{6-14}$aryl group, an optionally substituted $C_{3-12}$cycloalkyl group, an optionally substituted $C_{3-12}$cycloalkenyl group, an optionally substituted $C_{7-12}$polycycloalkyl group, an optionally substituted $C_{7-12}$polycycloalkenyl group, an optionally substituted $C_{5-12}$spirocycloalkyl group, an optionally substituted 3- to 12-membered heterocycloalkyl group comprising 1 or 2 heteroatoms, or an optionally substituted 4- to 12-membered heterocycloalkenyl group comprising 1 or 2 heteroatoms, or optionally one of $R^1$ and $R^3$, or $R^2$ and $R^3$, or $R^1$ and $R^c$, or $R^2$ and $R^d$ together represent a saturated or unsaturated $C_{1-4}$alkyl bridge optionally comprising 1 heteroatom;

$R^{4a}$, $R^{4b}$, $R^{4c}$ each independently represent —CN, hydroxy, —$NR^6R^7$, —$NR^6SO_2R^7$, halogen, an optionally substituted $C_{1-6}$alkyl group, an optionally substituted $C_{3-7}$cycloalkyl group, an optionally substituted $C_{2-6}$alkenyl group, an optionally substituted $C_{2-6}$alkynyl group, an optionally substituted $C_{1-5}$alkyloxy group, an optionally substituted $C_{3-6}$cycloalkyloxy group, an optionally substituted $C_{2-5}$alkenyloxy group, an optionally substituted $C_{2-5}$alkynyloxy group, an optionally substituted $C_{1-6}$alkylthio group, an optionally substituted $C_{1-6}$alkylsulphoxo group or an optionally substituted $C_{1-6}$alkylsulphonyl group, an optionally substituted 3- to 12-membered heterocycloalkyl group comprising 1 or 2 heteroatoms, or an optionally substituted 3- to 12-membered heterocycloalkoxy group comprising 1 or 2 heteroatoms;

p is the number of $R^{4a, 4b, 4c}$ groups that are not hydrogen and is selected from 0, 1 or 2;

L represents a linker selected from optionally substituted $C_{2-10}$alkyl, optionally substituted $C_{2-10}$alkenyl, optionally substituted $C_{6-14}$aryl, optionally substituted —$C_{2-4}$alkyl-$C_{6-14}$aryl, optionally substituted —$C_{6-14}$aryl-$C_{1-4}$alkyl, optionally substituted $C_{3-12}$cycloalkyl and optionally substituted heteroaryl comprising 1 or 2 nitrogen atoms;

n is 0 or 1;

m is 1 or 2;

$R^5$ represents a group selected from among hydrogen, optionally substituted morpholinyl, optionally substituted piperidinyl, optionally substituted piperazinyl, optionally substituted piperazinylcarbonyl, optionally substituted pyrrolidinyl, optionally substituted tropenyl, optionally substituted diketomethylpiperazinyl, optionally substituted sulphoxomorpholinyl, optionally substituted sulphonylmorpholinyl, optionally substituted thiomorpholinyl, optionally substituted azacycloheptyl, optionally substituted granatanyl, optionally substituted oxogranatanyl and —$NR^8R^9$;

$R^6$, $R^7$ each independently represents hydrogen or an optionally substituted $C_{1-4}$alkyl group; and $R^8$, $R^9$ each independently represents hydrogen, optionally substituted $C_{1-6}$alkyl, optionally substituted —$C_{1-4}$alkyl-$C_{3-10}$cycloalkyl, optionally substituted $C_{3-10}$cycloalkyl, optionally substituted $C_{6-14}$aryl, optionally substituted —$C_{1-4}$alkyl-$C_{6-14}$aryl, optionally substituted pyranyl, optionally substituted pyridinyl, optionally substituted pyrimidinyl, optionally substituted $C_{1-4}$alkyloxycarbonyl, optionally substituted optionally substituted $C_{6-14}$arylcarbonyl, optionally substituted $C_{1-4}$alkylcarbonyl, optionally substituted $C_{6-14}$arylmethyloxycarbonyl, optionally substituted $C_{6-14}$arylsulphonyl, optionally substituted $C_{1-4}$alkylsulphonyl, optionally substituted $C_{6-14}$aryl-$C_{1-4}$alkylsulphonyl, or $R^8$ and $R^9$ together with the nitrogen atom to which they are attached form a 3- to 7-membered bridged or unbridged, saturated or unsaturated heterocyclic ring optionally comprising 1 to 2 additional heteroatoms, or pharmacologically acceptable salt thereof.

In one embodiment, for compounds of the first, second, third, fourth and fifth aspects, the groups $R^1$ and $R^2$ may be identical or different and represent hydrogen or a $C_1$-$C_6$alkyl group optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino.

In another embodiment, for compounds of the first, second, third, fourth and fifth aspects, the groups $R^1$ and $R^2$ may be identical or different and represent hydrogen or a methyl or ethyl group.

In another embodiment, for compounds of the first, second, third, fourth and fifth aspects, the groups $R^1$ and $R^2$ are different wherein one of $R^1$ or $R^2$ represents hydrogen and the other represents a methyl or ethyl group.

In another embodiment, for compounds of the first, second, third, fourth and fifth aspects, $R^1$ and $R^2$ together represent a 2- to 5-membered alkyl bridge optionally comprising 1 to 2 heteroatoms selected from oxygen or nitrogen and optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino.

In another embodiment, for compounds of the first, second, third, fourth and fifth aspects, $R^1$ and $R^2$ together represent an ethylene or propylene bridge.

In another embodiment, for compounds of the first, second, third, fourth and fifth aspects, the groups $R^c$ and $R^d$ may be identical or different and represent hydrogen or a $C_1$-$C_6$alkyl group optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino.

In another embodiment, for compounds of the first, second, third, fourth and fifth aspects, the groups $R^c$ and $R^d$ may be identical or different and represent hydrogen or a methyl or ethyl group.

In another embodiment, for compounds of the first, second, third, fourth and fifth aspects, the groups $R^c$ and $R^d$ are different wherein one of $R^c$ or $R^d$ represents hydrogen and the other represents a methyl or ethyl group.

In another embodiment, for compounds of the first, second, third, fourth and fifth aspects, $R^c$ and $R^d$ together represent a 2- to 5-membered alkyl bridge optionally comprising 1 to 2 heteroatoms selected from oxygen or nitrogen and optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino.

In another embodiment, for compounds of the first, second, third, fourth and fifth aspects, $R^c$ and $R^d$ together represent an ethylene, propylene or butylene bridge.

In another embodiment, for compounds of the first, second, third, fourth and fifth aspects, at least one of $R^1$, $R^2$, $R^c$, or $R^d$ is hydrogen.

In another embodiment, for compounds of the first, second, third, fourth and fifth aspects, at least two of $R^1$, $R^2$, $R^c$, or $R^d$ are hydrogen.

In another embodiment, for compounds of the first, second, third, fourth and fifth aspects, $R^1$ and $R^2$ are hydrogen.

In another embodiment, for compounds of the first, second, third, fourth and fifth aspects, $R^1$ and $R^2$ are hydrogen, and one of $R^c$ or $R^d$ is hydrogen.

In another embodiment, for compounds of the first, second, third, fourth and fifth aspects, $R^1$ and $R^2$ are hydrogen, and one of $R^c$ or $R^d$ is hydrogen and the other is methyl.

In another embodiment, for compounds of the first, second, third, fourth and fifth aspects, $R^1$ and $R^2$ are hydrogen, and $R^c$ and $R^d$ are methyl.

In another embodiment, for compounds of the first, second, third, fourth and fifth aspects, $R^1$ and $R^2$ are hydrogen, and $R^c$ and $R^d$ together represent an ethylene bridge.

In another embodiment, for compounds of the first, second, third, fourth and fifth aspects, $R^3$ represents hydrogen; a $C_1$-$C_{12}$alkyl, for example ethyl, propyl, butyl, pentyl or hexyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; a $C_2$-$C_{12}$alkenyl, for example $C_5$-$C_7$alkenyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_2$-$C_{12}$alkynyl, for example $C_5$-$C_7$alkynyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; a $C_6$-$C_{14}$aryl, for example phenyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; a $C_3$-$C_{12}$cycloalkyl, for example cyclopentyl or cyclohexyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; a $C_3$-$C_{12}$cycloalkenyl, for example $C_5$-$C_7$cycloalkenyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_7$-$C_{12}$polycycloalkyl optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_7$-$C_{12}$polycycloalkenyl optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_5$-$C_{12}$spirocycloalkyl optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_3$-$C_{12}$heterocycloalkyl which contains 1 to 2 heteroatoms selected from oxygen, nitrogen or sulphur, for example pyranyl or piperizyl, pyrrolidinyl, pyrazinyl or morpholinyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; and $C_3$-$C_{12}$heterocycloalkenyl which contains 1 to 2 heteroatoms selected from oxygen, nitrogen or sulphur, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino.

In another embodiment, for compounds of the first, second, third, fourth and fifth aspects, $R^3$ represents isopropyl, isobutyl, isopentyl, cyclopentyl, phenyl or cyclohexyl.

In another embodiment, for compounds of the first, second, third, fourth and fifth aspects, $R^3$ represents cyclopentyl, or cyclohexyl.

In another embodiment, for compounds of the first, second, third, fourth and fifth aspects, $R^1$ and $R^3$ or $R^2$ and $R^3$ together represent a saturated or unsaturated $C_3$-$C_4$alkyl bridge optionally comprising 1 heteroatom selected from oxygen or nitrogen.

In another embodiment, for compounds of the first, second, third, fourth and fifth aspects, when p is 1 or 2, $R^4$ represents a group selected from among —CN; hydroxyl; —NR$^6$R$^7$; halogen, for example chlorine or fluorine; $C_1$-$C_6$alkyl, for example methyl, ethyl or propyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_2$-$C_6$alkenyl, for example ethenyl or propenyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_2$-$C_6$alkynyl, for example ethynyl, propynyl or butynyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_1$-$C_5$alkyloxy, for example methoxy, ethoxy or propargyloxy, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_2$-$C_5$alkenyloxy optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_2$-$C_5$alkynyloxy optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_1$-$C_6$alkylthio optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_1$-$C_6$alkylsulphoxo optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino and $C_1$-$C_6$alkylsulphonyl optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino.

In another embodiment, for compounds of the first, second, third and fourth aspects, when p is 1, $R^4$ represents methoxy, methyl, ethoxy, chlorine or fluorine.

In another embodiment, for compounds of the first, second, third, and fourth aspects, when p is 2, each $R^4$ may be the same or different and selected from methoxy, methyl, ethoxy, ethyl, propargyloxy, chlorine or fluorine.

In another embodiment, for compounds of the first, second, third, and fourth aspects, when p is 2 and when each $R^4$ is adjacent, both $R^4$ together with the aromatic ring atoms to which they are attached form a 4- to 7-member unsaturated ring optionally comprising 1 to 2 heteroatoms.

In another embodiment, for compounds of the fifth aspect, when p is 1, $R^{4b}$ and $R^{4c}$ are hydrogen and $R^{4a}$ represents methoxy, methyl, ethoxy, chlorine or fluorine.

In another embodiment, for compounds of the fifth aspect, when p is 2, $R^{4b}$ is hydrogen and $R^{4a}$ and $R^{4c}$ may be the same or different and selected from methoxy, methyl, ethoxy, chlorine or fluorine.

In another embodiment, for compounds of the fifth aspect, when p is 2, $R^{4c}$ is hydrogen and $R^{4a}$ and $R^{4b}$ together form a OCH$_2$O bridge.

In another embodiment, for compounds of the first, second, third, fourth and fifth aspects, L represents a linker selected from among $C_2$-$C_{10}$alkyl, for example ethyl, propyl, butyl or pentyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_2$-$C_{10}$alkenyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_6$-$C_{14}$aryl, for example phenyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; —$C_2$-$C_4$alkyl-$C_6$-$C_{14}$aryl optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; —$C_6$-$C_{14}$aryl-$C_1$-$C_4$alkyl optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; $C_3$-$C_{12}$cycloalkyl, for example cyclohexyl, optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino; and heteroaryl which contains 1 or 2 nitrogen atoms optionally substituted by one or more substituents selected from $C_{1-3}$alkyloxy, $C_{1-3}$alkylthio, $C_{1-3}$alkyl-S(O)$_2$, $C_{1-3}$alkylamino and di-($C_{1-3}$alkyl)amino.

In another embodiment, for compounds of the first, second, third, fourth and fifth aspects, when n is 1, L represents an optionally substituted a $C_{2-10}$alkyl or an optionally substituted $C_{3-12}$cycloalkyl linker.

In another embodiment, for compounds of the first, second, third, fourth and fifth aspects, when n is 1, L represents cyclohexyl, —C(CH$_3$)$_2$—CH$_2$— or —CH$_2$—C(CH$_3$)$_2$—CH$_2$—.

In another embodiment, for compounds of the first, second, third, fourth and fifth aspects, n is 0.

In another embodiment, for compounds of the first, second, third, fourth and fifth aspects, m is 1.

In another embodiment, for compounds of the first, second, third, fourth and fifth aspects, $R^5$ represents a group selected from among hydrogen, optionally substituted morpholinyl, optionally substituted piperidinyl, optionally substituted piperazinyl, optionally substituted piperazinylcarbonyl, optionally substituted pyrrolidinyl, optionally substituted tropenyl, optionally substituted diketomethylpiperazinyl, optionally substituted sulphoxomorpholinyl, sulphonylmorpholinyl, optionally substituted thiomorpholinyl, optionally substituted granatanyl, optionally substituted oxogranatanyl —NR$^8$R$^9$ and optionally substituted azacycloheptyl wherein each morpholinyl, piperidinyl, piperazinyl, piperazinylcarbonyl, pyrrolidinyl, tropenyl, diketomethylpiperazinyl, sulphoxomorpholinyl, sulphonylmorpholinyl, thiomorpholinyl, —NR$^8$R$^9$ and azacycloheptyl is optionally substituted by one or more groups as defined for R$^8$.

In another embodiment, for compounds of the first, second, third, fourth and fifth aspects, R$^5$ represents hydrogen, —NR$^8$R$^9$ or a piperidinyl, morpholinyl, pyrrolidinyl, sulphoxomorpholiny, piperazinyl, thiomorpholinyl, tropenyl, granatanyl, oxogranatanyl or azacycloheptyl each optionally substituted by one or more groups as defined for R$^8$.

In another embodiment, for compounds of the first, second, third, fourth and fifth aspects, R$^5$ represents piperidinyl optionally substituted by one or more groups as defined for R$^8$.

In another embodiment, for compounds of the first, second, third, fourth and fifth aspects, R$^5$ represents pyrrolidinyl optionally substituted by one or more groups as defined for R$^8$.

In another embodiment, for compounds of the first, second, third, fourth and fifth aspects, R$^5$ represents granatanyl optionally substituted by one or more groups as defined for R$^8$.

In another embodiment, for compounds of the first, second, third, fourth and fifth aspects, the groups R$^6$ and R$^7$ may be identical or different and represent hydrogen or C$_1$-C$_4$alkyl, for example methyl or ethyl.

In another embodiment, for compounds of the first, second, third, fourth and fifth aspects, the groups R$^8$ and R$^9$ may be identical or different and represent hydrogen; a C$_1$-C$_6$alkyl, for example methyl, ethyl or propyl, optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; —C$_1$-C$_4$alkyl-C$_3$-C$_{10}$cycloalkyl, for example —CH$_2$-cyclopropyl, optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; C$_3$-C$_{10}$cycloalkyl optionally substituted by one or more substituents selected from C$_{1-3}$alkyloxy, C$_{1-3}$alkylthio, C$_{1-3}$alkyl-S(O)$_2$, C$_{1-3}$alkylamino and d-(C$_{1-3}$alkyl)amino; C$_6$-C$_{14}$aryl, for example phenyl, optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; —C$_1$-C$_4$alkyl-C$_6$-C$_{14}$aryl, for example benzyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; pyranyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; pyridinyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; pyrimidinyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; pyranyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; C$_1$-C$_4$alkyloxycarbonyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; C$_6$-C$_{14}$arylcarbonyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; C$_1$-C$_4$alkylcarbonyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; C$_6$-C$_{14}$ arylmethyloxycarbonyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; C$_6$-C$_{14}$arylsulphonyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino; C$_1$-C$_4$alkylsulphonyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino and C$_6$-C$_{14}$aryl-C$_1$-C$_4$alkylsulphonyl optionally substituted by one or more substituents selected from C$_{1-3}$alkyloxy, C$_{1-3}$alkylthio, C$_{1-3}$alkyl-S(O)$_2$, C$_{1-3}$alkylamino and di-(C$_{1-3}$alkyl)amino.

In another embodiment, for compounds of the first, second, third, fourth and fifth aspects, R$^5$ represents methyl, ethyl or propyl.

In another embodiment, for compounds of the first, second, third, fourth and fifth aspects, R$^9$ represents methyl, ethyl or propyl.

In another embodiment, for the compound of formula (I), R$^N$ represents C$_{1-3}$alkyl.

In another embodiment, for the compound of formula (I), R$^N$ represents methyl or ethyl.

In another embodiment, for the compound of formula (I), Z$^1$ represents C=O or CR$^f$R$^g$.

In another embodiment, for the compound of formula (I), Z$^1$ represents C=O or CR$^f$R$^g$, and Z$^2$ represents CR$^c$R$^d$.

In another embodiment, for the compound of formula (I), Z$^1$ represents C=O or CH$_2$.

In another embodiment, for the compound of formula (I), Q represents —CH$_2$—NR$^{a3}$R$^{b3}$ or —C(=X$^1$)—NR$^a$R$^b$, wherein X$^1$ is O.

In another embodiment, for the compounds of formula (I), (II), (IIa), (III) or (IIIa), n is 1 and L is an optionally substituted C$_{2-10}$alkyl linker.

In another embodiment, for the compounds of formula (I), (II), (IIa), (III) or (IIIa), n is 0.

In a further embodiment of the invention there is provided a subset of compounds of formula (III) or (IIIa) wherein R$^1$ to R$^4$, R$^{4a}$, R$^{4b}$, R$^{4c}$, R$^c$, R$^d$, R$^6$ and R$^7$ are as hereinbefore defined; and L represents a linker selected from among optionally substituted C$_{2-10}$alkyl, optionally substituted C$_{2-10}$alkenyl, optionally substituted C$_{6-14}$aryl, optionally substituted —C$_{2-4}$alkyl-C$_{6-14}$aryl, optionally substituted —C$_{6-14}$aryl-C$_{1-4}$alkyl, optionally substituted C$_{3-12}$cycloalkyl and optionally substituted heteroaryl comprising 1 or 2 nitrogen ring atoms; n denotes 1; m denotes 1 or 2; R$^5$ denotes hydrogen or a group which is bound to L via a nitrogen atom, selected from optionally substituted morpholinyl, optionally substituted piperidinyl, optionally substituted piperazinyl, optionally substituted pyrrolidinyl, optionally substituted tropenyl, optionally substituted diketomethylpiperazinyl, optionally substituted sulphoxomorpholinyl, optionally substituted sulphonylmorpholinyl, optionally substituted thiomorpholinyl, —NR$^8$R$^9$ and optionally substituted azacycloheptyl; R$^8$, R$^9$ independently represent hydrogen, C$_{1-6}$alkyl, —C$_{1-4}$alkyl-C$_{3-10}$cycloalkyl, C$_{3-10}$cycloalkyl, C$_{6-14}$aryl, —C$_{1-4}$alkyl-C$_{6-14}$aryl, pyranyl, pyridinyl, pyrimidinyl, C$_{1-4}$alkyloxycarbonyl, C$_{6-14}$arylcarbonyl, C$_{1-4}$alkylcarbonyl, C$_{6-14}$arylmethyloxycarbonyl, C$_{6-14}$arylsulphonyl, C$_{1-4}$alkylsulphonyl or C$_{6-14}$aryl-C$_{1-4}$alkylsulphonyl, or pharmacologically acceptable salts thereof.

In a still further embodiment of the invention there is provided another subset of compounds of formula (III) or (IIIa) wherein p, R$^1$ to R$^4$, R$^{4a}$, R$^{4b}$, R$^{4c}$, R$^c$, R$^d$, R$^6$ and R$^7$ are as hereinbefore defined; L represents a linker selected from optionally substituted C$_{2-10}$alkyl, optionally substituted C$_{2-10}$alkenyl, optionally substituted C$_{6-14}$aryl, optionally substituted —C$_{2-4}$alkyl-C$_{6-14}$aryl, optionally substituted —$C_{6-14}$aryl-$C_{1-4}$alkyl, optionally substituted $C_{3-12}$cycloalkyl and optionally substituted heteroaryl comprising 1 or 2 nitrogen ring atoms; n denotes 0 or 1; m denotes 1 or 2; $R^5$ denotes hydrogen or a group which is bound to L via a carbon atom, selected from among piperidinyl, piperazinyl, pyrrolidinyl, piperazinylcarbonyl, tropenyl, morpholinyl, granatanyl, oxogranatanyl and azacycloheptyl each optionally substituted by one or more groups as defined for $R^5$; and $R^5$ independently represent hydrogen, $C_{1-6}$alkyl, —$C_{1-4}$alkyl-$C_{3-10}$cycloalkyl, $C_{3-10}$cycloalkyl, $C_{6-14}$aryl, —$C_{1-4}$alkyl-$C_{6-14}$aryl, pyranyl, pyridinyl, pyrimidinyl, $C_{1-4}$alkyloxycarbonyl, $C_{6-14}$arylcarbonyl, $C_{1-4}$alkylcarbonyl, $C_{6-14}$arylmethyloxycarbonyl, $C_{6-14}$arylsulphonyl, $C_{1-4}$alkylsulphonyl or $C_{6-14}$aryl-$C_{1-4}$alkylsulphonyl, or pharmacologically acceptable salts thereof.

In an additional embodiment of the invention there is provided an additional subset of compounds of formula (III) or (IIIa) wherein L, m, n, p, $R^3$ to $R^9$, $R^c$ and $R^d$ are as hereinbefore defined; and $R^1$, $R^2$ each independently represents hydrogen, Me, Et, Pr, or $R^1$ and $R^2$ together with the carbon atom to which they are attached form a 3- to 5-membered cycloalkyl ring, or pharmacologically acceptable salts thereof.

In an additional embodiment of the invention there is provided an additional subset of compounds of formula (III) or (IIIa) wherein L, m, n, p and $R^1$ to $R^9$ are as hereinbefore defined; and $R^c$, $R^d$ each independently represents hydrogen, Me, Et, Pr, or $R^c$ and $R^d$ together with the carbon atom to which they are attached form a 3- to 5-membered cycloalkyl ring, or pharmacologically acceptable salts thereof.

In an additional embodiment of the invention there is provided an additional subset of compounds of formula (III) or (IIIa) wherein L, m, n, p and $R^3$ to $R^9$ are as hereinbefore defined; and at least two of $R^1$, $R^2$, $R^c$ or $R^d$ are hydrogen.

In an additional embodiment of the invention there is provided an additional subset of compounds of formula (III) or (IIIa) wherein L, m, n, p and $R^3$ to $R^9$ are as hereinbefore defined; $R^1$ and $R^2$ are hydrogen, and one of $R^c$ or $R^d$ is hydrogen.

In a further additional embodiment of the invention there is provided an additional subset of compounds of formula (III) or (IIIa) wherein $R^1$, $R^2$, $R^c$, $R^d$, m, n and $R^5$ to $R^8$ are as hereinbefore defined; and $R^3$ represents an optionally substituted $C_{1-10}$alkyl, optionally substituted $C_{3-7}$cycloalkyl, optionally substituted $C_{3-6}$heterocycloalkyl or optionally substituted $C_{6-14}$aryl group or $R^1$ and $R^3$ or $R^2$ and $R^3$ together represent a saturated or unsaturated $C_{3-4}$alkyl bridge optionally comprising 1 or 2 heteroatoms; p is 0 or 1; $R^4$ represents OMe, OH, Me, Et, Pr, OEt, NHMe, $NH_2$, F, CL, Br, O-propargyl, O-butynyl, CN, SMe, $NMe_2$, $CONH_2$, ethynyl, propynyl, butynyl or allyl; and L denotes a linker selected from among optionally substituted phenyl, phenylmethyl, cyclohexyl and branched $C_{1-6}$alkyl, or pharmacologically acceptable salts thereof.

In an additional embodiment of the invention there is provided an additional subset of compounds of formula (III) wherein $R^3$ represents an optionally substituted $C_{1-10}$alkyl, optionally substituted $C_{3-7}$cycloalkyl, optionally substituted $C_{3-6}$heterocycloalkyl or optionally substituted $C_{6-14}$aryl group; p is 0 or 1; $R^4$ represents OMe, OH, Me, Et, Pr, OEt, NHMe, $NH_2$, F, CL, Br, O-propargyl, O-butynyl, CN, SMe, $NMe_2$, $CONH_2$, ethynyl, propynyl, butynyl or allyl; L represents a linker selected from optionally substituted $C_{2-10}$alkyl, optionally substituted $C_{2-10}$alkenyl, optionally substituted $C_{6-14}$aryl, optionally substituted —$C_{2-4}$alkyl-$C_{6-14}$aryl, optionally substituted —$C_{6-14}$aryl-$C_{1-4}$alkyl, optionally substituted $C_{3-12}$cycloalkyl and optionally substituted heteroaryl comprising 1 or 2 nitrogen ring atoms; n denotes 0 or 1; m denotes 1 or 2; $R^5$ denotes hydrogen or a group, which is bound to L via a carbon atom, selected from among —$NR^8R^9$, piperidinyl, piperazinyl, pyrrolidinyl, piperazinylcarbonyl, tropenyl, morpholinyl, granatanyl, oxogranatanyl and azacycloheptyl each optionally substituted by one or more groups as defined for $R^8$; $R^8$, $R^9$ each independently represent hydrogen, $C_{1-6}$alkyl, —$C_{1-4}$alkyl-$C_{3-10}$cycloalkyl, $C_{3-10}$cycloalkyl, $C_{6-14}$aryl, —$C_{1-4}$alkyl-$C_{6-14}$aryl, pyranyl, pyridinyl, pyrimidinyl, $C_{1-4}$alkyloxycarbonyl, $C_{6-14}$arylcarbonyl, $C_{1-4}$alkylcarbonyl, $C_{6-14}$arylmethyloxycarbonyl, $C_{6-14}$arylsulphonyl, $C_{1-4}$alkylsulphonyl or $C_{6-14}$aryl-$C_{1-4}$alkylsulphonyl; $R^1$, $R^2$ are hydrogen; $R^c$, $R^d$ are each independently selected from hydrogen, Me, or Et, or $R^c$ and $R^d$ together represent an ethylene bridge, or pharmacologically acceptable salts thereof.

In an additional embodiment of the invention there is provided an additional subset of compounds of formula (III) wherein $R^3$ represents an optionally substituted $C_{1-10}$alkyl, optionally substituted $C_{3-7}$cycloalkyl, optionally substituted $C_{3-6}$heterocycloalkyl; p is 0, 1 or 2; $R^4$ each independently represents fluoro or OMe; L represents a linker selected from optionally substituted $C_{2-10}$alkyl; n denotes 0 or 1; m denotes 1 or 2; $R^5$ denotes a group selected from among —$NR^8R^9$ and piperidinyl each optionally substituted by one or more groups as defined for $R^8$; $R^8$, $R^9$ each independently represent $C_{1-6}$alkyl; $R^1$, $R^2$ are hydrogen; $R^c$, $R^d$ are each independently selected from hydrogen, Me, or Et, or $R^c$ and $R^d$ together represent an ethylene bridge, or pharmacologically acceptable salts thereof.

In an additional embodiment of the invention there is provided an additional subset of compounds of formula (III) wherein $R^3$ represents an optionally substituted $C_{1-10}$alkyl, optionally substituted $C_{3-7}$cycloalkyl, optionally substituted $C_{3-6}$heterocycloalkyl; p is 0, 1 or 2; $R^4$ each independently represents fluoro or OMe; L represents a linker selected from optionally substituted $C_{2-10}$alkyl; n denotes 0 or 1; m denotes 1 or 2; $R^5$ denotes a group selected from among —$NR^8R^9$ and pyrrolidinyl each optionally substituted by one or more groups as defined for $R^8$; $R^8$, $R^9$ each independently represent $C_{1-6}$alkyl; $R^1$, $R^2$ are hydrogen; $R^c$, $R^d$ are each independently selected from hydrogen, Me, or Et, or $R^c$ and $R^d$ together represent an ethylene bridge, or pharmacologically acceptable salts thereof.

In an additional embodiment of the invention there is provided an additional subset of compounds of formula (III) wherein $R^3$ represents an optionally substituted $C_{1-10}$alkyl, optionally substituted $C_{3-7}$cycloalkyl, optionally substituted $C_{3-6}$heterocycloalkyl; p is 0, 1 or 2; $R^4$ each independently represents fluoro or OMe; L represents a linker selected from optionally substituted $C_{2-10}$alkyl; n denotes 0 or 1; m denotes 1 or 2; $R^5$ denotes a group selected from among —$NR^8R^9$ and granatanyl each optionally substituted by one or more groups as defined for $R^8$; $R^8$, $R^9$ each independently represent $C_{1-6}$alkyl; $R^1$, $R^2$ are hydrogen; $R^c$, $R^d$ are each independently selected from hydrogen, Me, or Et, or $R^c$ and $R^d$ together represent an ethylene bridge, or pharmacologically acceptable salts thereof.

In an additional embodiment of the invention there is provided an additional subset of compounds of formula (IIIa) wherein $R^3$ represents an optionally substituted $C_{1-10}$alkyl, optionally substituted $C_{3-7}$cycloalkyl, optionally substituted $C_{3-6}$heterocycloalkyl; L represents a linker selected from optionally substituted $C_{2-10}$alkyl; n denotes 0 or 1; m denotes 1 or 2; $R^5$ denotes a group selected from among —$NR^8R^9$ and piperidinyl each optionally substituted by one or more groups as defined for $R^8$; $R^8$, $R^9$ each independently represent $C_{1-6}$alkyl; $R^1$, $R^2$ are hydrogen; $R^c$, $R^d$ are each independently selected from hydrogen, Me, or Et, or $R^c$ and $R^d$ together represent an ethylene bridge; p is 0, 1 or 2; and when p is 1, $R^{4b}$ and $R^{4c}$ are hydrogen and $R^{4a}$ represents methoxy, methyl, ethoxy, chlorine or fluorine; and when p is 2, either $R^{4b}$ is hydrogen and $R^{4a}$ and $R^{4b}$ may be the same or different and selected from methoxy, methyl, ethoxy, chlorine or fluorine, or $R^4$, is hydrogen and $R^{4a}$ and $R^{4b}$ together form a OCH$_2$O bridge, or pharmacologically acceptable salts thereof.

In an additional embodiment of the invention there is provided an additional subset of compounds of formula (IIIa) wherein $R^3$ represents an optionally substituted $C_{1-10}$alkyl, optionally substituted $C_{3-7}$cycloalkyl, optionally substituted $C_{3-6}$heterocycloalkyl; L represents a linker selected from optionally substituted $C_{2-10}$alkyl; n denotes 0 or 1; m denotes 1 or 2; $R^5$ denotes a group selected from among —NR$^8$R$^9$ and pyrrolidinyl each optionally substituted by one or more groups as defined for $R^8$; $R^8$, $R^9$ each independently represent $C_{1-6}$alkyl; $R^1$, $R^2$ are hydrogen; $R^c$, $R^d$ are each independently selected from hydrogen, Me, or Et, or $R^c$ and $R^d$ together represent an ethylene bridge; p is 0, 1 or 2; and when p is 1, $R^{4b}$ and $R^{4c}$ are hydrogen and $R^{4a}$ represents methoxy, methyl, ethoxy, chlorine or fluorine; and when p is 2, either $R^{4b}$ is hydrogen and $R^{4a}$ and $R^{4c}$ may be the same or different and selected from methoxy, methyl, ethoxy, chlorine or fluorine, or $R^{4c}$ is hydrogen and $R^{4a}$ and $R^{4b}$ together form a OCH$_2$O bridge, or pharmacologically acceptable salts thereof.

In an additional embodiment of the invention there is provided an additional subset of compounds of formula (IIIa) wherein $R^3$ represents an optionally substituted $C_{1-10}$alkyl, optionally substituted $C_{3-7}$cycloalkyl, optionally substituted $C_{3-6}$heterocycloalkyl; L represents a linker selected from optionally substituted $C_{2-10}$alkyl; n denotes 0 or 1; m denotes 1 or 2; $R^5$ denotes a group selected from among —NR$^8$R$^9$ and granatanyl each optionally substituted by one or more groups as defined for $R^8$; $R^8$, $R^9$ each independently represent $C_{1-6}$alkyl; $R^1$, $R^2$ are hydrogen; $R^c$, $R^d$ are each independently selected from hydrogen, Me, or Et, or $R^c$ and $R^d$ together represent an ethylene bridge; p is 0, 1 or 2; and when p is 1, $R^{4b}$ and $R^{4c}$ are hydrogen and $R^{4a}$ represents methoxy, methyl, ethoxy, chlorine or fluorine; and when p is 2, either $R^{4b}$ is hydrogen and $R^{4a}$ and $R^{4c}$ may be the same or different and selected from methoxy, methyl, ethoxy, chlorine or fluorine, or $R^{4c}$ is hydrogen and $R^{4a}$ and $R^{4b}$ together form a OCH$_2$O bridge, or pharmacologically acceptable salts thereof.

In a further aspect of the invention, there is provided a compound selected from any one of the Examples or pharmacologically acceptable salts thereof.

In a further aspect of the invention, there is provided a compound selected from any one of Examples 4, 7, 26, 27, 47, 51, 53, 56, 77, 97, 99, 101, 104, 106, 108, 110, 113, 114, 135, 176, 182, 184, 191, 197, 202, 219, 234, 238, 239, 242, 269, 278, 279, 281, 282, 285, 289, 290, 293, 294, 295, 301, 302, 309, 310, 311, 330, 331, 390, 405, 411, 413, 416, 419, 429, 451, 1, 2, 3, 6, 8, 10, 11, 12, 13, 14, 15, 16, 17, 18, 19, 20, 21, 22, 25, 28, 29, 30, 31, 32, 33, 34, 35, 36, 37, 38, 39, 41, 43, 44, 45, 46, 48, 49, 50, 52, 54, 55, 57, 58, 59, 60, 61, 62, 63, 64, 66, 67, 68, 69, 70, 71, 72, 73, 74, 75, 76, 78, 79, 80, 81, 82, 83, 84, 85, 86, 88, 90, 91, 92, 93, 94, 95, 96, 98, 109, 181, 185, 188, 189, 193, 194, 199, 200, 201, 203, 205, 206, 207, 208, 209, 210, 212, 213, 217, 235, 236, 237, 240, 241, 243, 244, 245, 246, 280, 283, 288, 291, 292, 298, 299, 300, 303, 304, 305, 306, 307, 308, 312, 313, 314, 315, 316, 317, 318, 319, 320, 321, 322, 323, 325, 326, 327, 328, 329, 333, 334, 335, 336, 337, 338, 340, 341, 342, 343, 344, 345, 346, 347, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 382, 383, 384, 385, 386, 387, 388, 389, 391, 392, 393, 394, 395, 396, 397, 398, 399, 400, 401, 402, 403, 404, 406, 407, 408, 409, 412, 414, 415, 417, 418, 420, 421, 422, 423, 424, 425, 426, 427, 428, 430, 431, 432, 433, 434, 435, 436, 437, 438, 440, 441, 442, 443, 444, 445, 446 and 453 or pharmacologically acceptable salts thereof.

In a further aspect of the invention, there is provided a compound selected from any one of Examples 1, 2, 3, 6, 8, 10, 11, 12, 13, 14, 15, 16, 17, 18, 19, 20, 21, 22, 25, 28, 29, 30, 31, 32, 33, 34, 35, 36, 37, 38, 39, 41, 43, 44, 45, 46, 48, 49, 50, 52, 54, 55, 57, 58, 59, 60, 61, 62, 63, 64, 66, 67, 68, 69, 70, 71, 72, 73, 74, 75, 76, 78, 79, 80, 81, 82, 83, 84, 85, 86, 88, 90, 91, 92, 93, 94, 95, 96, 98, 109, 181, 185, 188, 189, 193, 194, 199, 200, 201, 203, 205, 206, 207, 208, 209, 210, 212, 213, 217, 235, 236, 237, 240, 241, 243, 244, 245, 246, 280, 283, 288, 291, 292, 298, 299, 300, 303, 304, 305, 306, 307, 308, 312, 313, 314, 315, 316, 317, 318, 319, 320, 321, 322, 323, 325, 326, 327, 328, 329, 333, 334, 335, 336, 337, 338, 340, 341, 342, 343, 344, 345, 346, 347, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 382, 383, 384, 385, 386, 387, 388, 389, 391, 392, 393, 394, 395, 396, 397, 398, 399, 400, 401, 402, 403, 404, 406, 407, 408, 409, 412, 414, 415, 417, 418, 420, 421, 422, 423, 424, 425, 426, 427, 428, 430, 431, 432, 433, 434, 435, 436, 437, 438, 440, 441, 442, 443, 444, 445, 446 and 453, or pharmacologically acceptable salts thereof.

The compounds according to the first, second, third, fourth and fifth aspects of the invention may be present in the form of the individual optical isomers, mixtures of the individual enantiomers, diastereomers or racemates, in the form of the tautomers and also as solvates and/or in the form of the free bases or the corresponding acid addition salts with pharmacologically acceptable acids, such as for example acid addition salts with hydrohalic acids, for example hydrochloric or hydrobromic acid, or organic acids, such as for example oxalic, fumaric, diglycolic or methanesulphonic acid or metal salts such as a magnesium, calcium, sodium or potassium salt The compounds of formula (I), (II), (IIa), (III) or (IIIa) above may be converted to a pharmaceutically acceptable salt thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I), (II), (IIa), (III) or (IIIa) are capable of existing in stereoisomeric forms. It will be understood that the invention encompasses the use of all geometric and optical isomers (including atropisomers) of the compounds of formula (I), (II), (IIa), (III) or (IIIa) and mixtures thereof including racemates. The use of tautomers and mixtures thereof also form an aspect of the present invention.

The invention also relates to a process for preparing a compound of general formula (III),

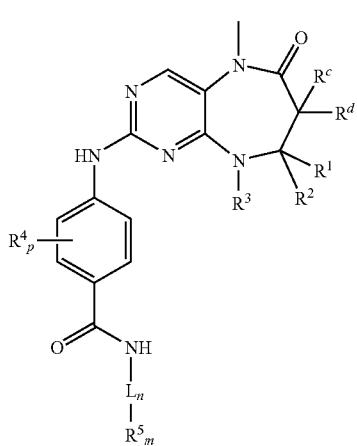

(III)

wherein R$^1$-R$^5$, R$^c$, R$^d$ m, n and L are as hereinbefore defined, comprising either a) reacting a compound of general formula (IV)

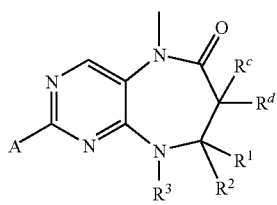

(IV)

wherein R$^1$-R$^3$ are as hereinbefore defined and A is a leaving group, with an optionally substituted compound of general formula (V):

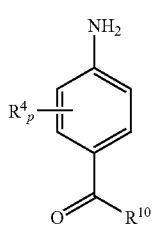

(V)

wherein R$^4$ is as hereinbefore defined; and R$^{10}$ denotes OH, NH-L$_m$-R$^5_n$, OMe, OEt, and when R$^{10}$ denotes OH, OMe or OEt optionally after previous hydrolysis of the ester group —COR$^{10}$, reacting with an amine of general formula (VI):

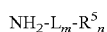

(VI)

wherein R$^5$ is as hereinbefore defined, to give a compound of formula (III); or b) reacting a compound of general formula (VII)

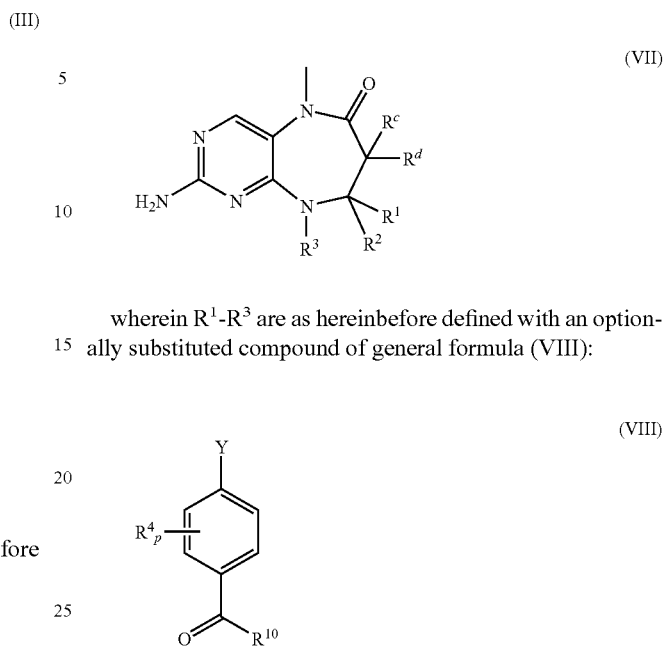

(VII)

wherein R$^1$-R$^3$ are as hereinbefore defined with an optionally substituted compound of general formula (VIII):

(VIII)

wherein Y is a leaving group, p and R$^4$ are as hereinbefore defined; and R$^{10}$ denotes OH, NH-L$_m$-R$^5_n$, OMe, OEt, and when R$^{10}$ denotes OH, OMe or OEt optionally after previous hydrolysis of the ester group —COR$^{10}$, reacting with an amine of general formula (VI):

NH$_2$-L$_m$-R$^5_n$ (VI)

wherein R$^5$ is as hereinbefore defined, to give a compound of formula (III).

In one embodiment R$^{10}$ is a substituent selected from among OH, NH$_2$-LR$^5$, —O-methyl and —O-ethyl.

The term leaving group includes leaving groups such as for example —O-methyl, —SCN, chlorine, bromine, iodine, methanesulphonyl, trifluoromethanesulphonyl or p-toluenesulphonyl. In one embodiment the leaving group A is chlorine.

Methods for the preparation of compounds of Formula (V) are described in WO04/076454 and WO03/020722 and are incorporated herein by reference.

Compounds of Formula (IV) where A is chlorine may also be obtained by the reductive cyclisation of a compound of formula (IX)

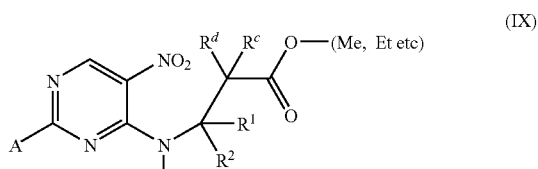

(IX)

for example by palladium coupling.

Compounds of Formula (IV) may also be obtained by the cyclisation of a compound of formula (X)

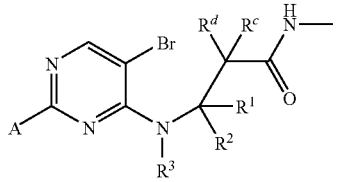
(X)

for example by under catalysis by a suitable palladium coupling compound and in the presence of a suitable ligand and a suitable base.

Furthermore, compounds of formula (IV) may be obtained by reaction of another compound of general formula (IV), wherein R3 is hydrogen, with an alkyl halide, in a polar solvent, such as, for example, N,N-dimethylacetamide, in the presence of a strong base, such as, for example, sodium hydride.

Still furthermore compounds of formula (IV), where $R^c$, $R^d$, $R^1$ & $R^2$ are hydrogen, may be obtained by reaction of a compound of formula (XI)

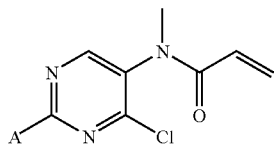
(XI)

with an amine, in the presence of a base, such as triethylamine, and a lewis acid, such as titanium (IV) tetraethoxide.

Compounds of formula (VII) may also be obtained by the reaction of a compound of formula (IV), wherein A is as hereinbefore defined, but typically chloro,

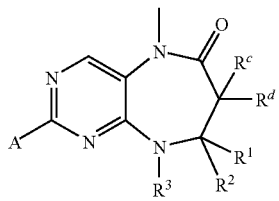
(IV)

with ammonia or a suitably protected equivalent.

Compounds of Formula (IX), wherein A is chlorine, may also be obtained by reaction of 5-nitro-2,4-dichloropyrimidinee

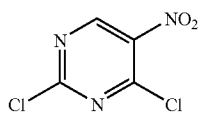

with an amine of Formula (XII)

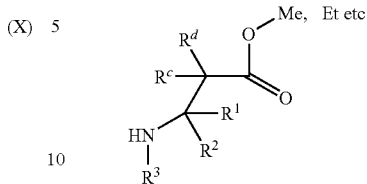
(XII)

for example by heating in the presence of a base, such as potassium carbonate, in a polar organic solvent such as acetone.

Compounds of Formula (IX), wherein A is chlorine, may also be obtained by reaction of 5-bromo-2,4-dichloropyrimide

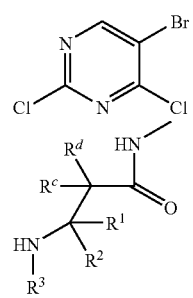
(XIII)

with an amine of Formula (XIII) for example by heating in the presence of a base, such as triethylamine, in a polar organic solvent such as acetonitrile.

Compounds of Formula (XII), may also be obtained by reaction of esters of an appropriately substituted 3-aminopropanoic acid (XIV)

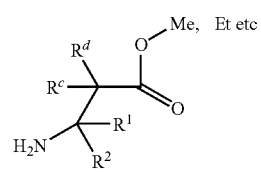
(XIV)

with a ketone or aldehyde, in the presence of a suitable reducing agent, such as, for example, sodium triacetoxyborohydride.

Compounds of Formula (XIII), may also be obtained by reaction of amides of propenoic acid (XV)

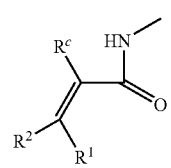
(XV)

with an amine.

Compounds of formula (XI) may also be obtained by the reaction of a compound of formula (XVI),

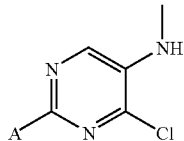
(XVI)

with a compound of formula (XVII),

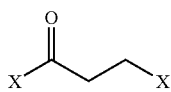
(XVII)

wherein X is a leaving group, typically a halogen, such as chloro, in the presence of a base, such as triethylamine, in an organic solvent, such as dichloromethane.

A compound of formula (XVI) may also be obtained by the sequential reaction of 5-bromouracil,

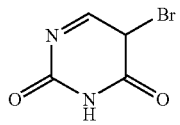

with i) methylamine, in a polar solvent, such as ethanol and;

ii) a chlorinating agent, such as phosphorous oxychloride as for instance exemplified in Journal of Medicinal Chemistry (1966), 9(1), 121-6.

The invention also relates to a process for preparing a compound of general formula (XVIII),

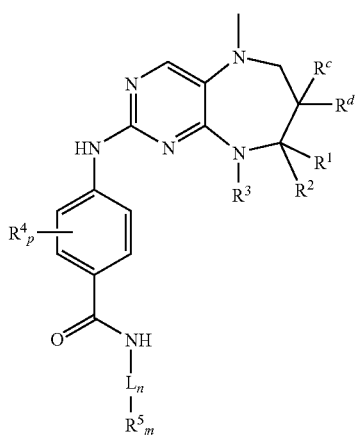
(XVIII)

wherein $R^1$-$R^5$, $R^c$, $R^d$ m, n and L are as hereinbefore defined, comprising reacting a compound of general formula (XIX)

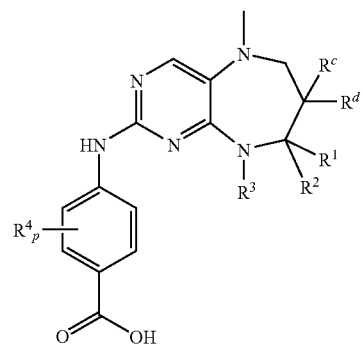
(XIX)

with an amine of general formula (VI):

$$NH_2\text{-}L_m\text{-}R^5_n \quad (VI)$$

wherein L and $R^5$ are as hereinbefore defined.

Compounds of formula (XIX) may be obtained by hydrolysis of the corresponding esters.

Esters of general formula (XX)

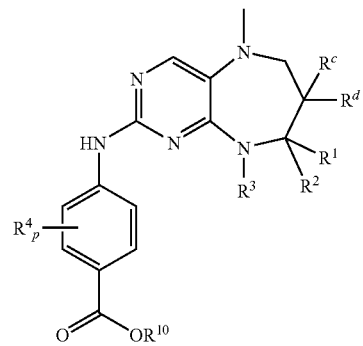
(XX)

may be obtained by the reduction of a compound of formula (XXI)

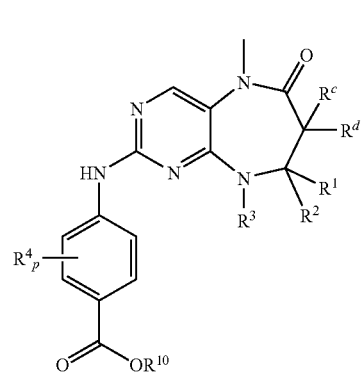
(XXI)

which may be prepared as described above.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I), (II), (IIa), (III) or (IIIa) may involve, at various stages, the addition and removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley Interscience (19911999) and 'Protecting Groups', $3^{rd}$ edition, P. J. Kocienski, Thieme (2005).

The invention further relates to compounds of formula (I), (II), (IIa), (III) or (IIIa) for use as pharmaceutical compositions.

In one embodiment of the invention, compounds of formula (I), (II), (IIa), (III) or (IIIa) are of use as pharmaceutical compositions with an antiproliferative activity.

The invention also relates to the use of a compound of formula (I), (II), (IIa), (III) or (IIIa) for preparing a pharmaceutical composition for the treatment and/or prevention of cancer, infections, inflammatory and autoimmune diseases.

These findings suggest that pharmacological inhibitors of Plk should be of therapeutic value for treatment of proliferative disease including solid tumours such as carcinomas and sarcomas and the leukaemias and lymphoid malignancies. In addition Plk inhibitors should be useful in the treatment of other disorders associated with uncontrolled cellular proliferation.

One aspect of the current invention therefore relates to the use of one or more of the compounds of formula (I), (II), (IIa), (III) or (IIIa) in the treatment of disorders characterised by excessive or anomalous cell proliferation.

Such diseases include for example: viral infections such as HIV and Kaposi's sarcoma; inflammatory and autoimmune diseases such as colitis, rheumatoid arthritis, Alzheimer's disease, glomerulonephritis and wound healing; bacterial, fungal and parasitic infections such as malaria and emphysema; dermatological diseases such as psoriasis; bone diseases; cardiovascular diseases such as restenosis and cardiomyopathy. The compounds in the present invention may be used for the prevention, short- or long-term treatment of the above-mentioned diseases, also in combination with other active substances used for the same indications.

The invention also relates to a method of treating and/or preventing cancer, infections, inflammatory and autoimmune diseases, characterised in that a patient is given an effective amount of a compound of formula (I), (II), (IIa), (III) or (IIIa).

The invention also relates to pharmaceutical preparations, containing as active substance one or more compounds of general formula (I), (II), (IIa), (III) or (IIIa), or the physiologically acceptable salts thereof, optionally combined with conventional excipients and/or carriers.

The compounds of formula (I), (II) and (III) have activity as pharmaceuticals, in particular as modulators or inhibitors of Plk activity, and may be used in the treatment of proliferative and hyperproliferative diseases/conditions, examples of which include the following cancers:

(1) carcinoma, including that of the bladder, brain, breast, colon, kidney, liver, lung, ovary, pancreas, prostate, stomach, cervix, colon, thyroid and skin;

(2) hematopoietic tumours of lymphoid lineage, including acute lymphocytic leukaemia, B cell lymphoma and Burketts lymphoma;

(3) hematopoietic tumours of myeloid lineage, including acute and chronic myelogenous leukaemias and promyelocytic leukaemia;

(4) tumours of mesenchymal origin, including fibrosarcoma and rhabdomyosarcoma; and (5) other tumours, including melanoma, seminoma, tetratocarcinoma, neuroblastoma and glioma.

In one embodiment, the compounds of formula (I), (II) and (III) are useful in the treatment of tumours of the lung, breast and prostate.

Thus, the present invention provides a compound of formula (I), (II), (IIa), (III) or (IIIa), or a pharmaceutically acceptable salt thereof, as hereinbefore defined for use in therapy.

In a further aspect, the present invention provides the use of a compound of formula (I), (II), (IIa), (III) or (IIIa), or a pharmaceutically acceptable salt thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating cancer which comprises administering to a patient in need thereof a therapeutically effective amount of a compound of formula (I), (II), (IIa), (III) or (IIIa), or a pharmaceutically acceptable salt thereof, as hereinbefore defined.

The invention still further provides a method of modulating polo-like kinase (Plk) activity which comprises administering to a patient in need thereof a therapeutically effective amount of a compound of formula (I), (II), (IIa), (III) or (IIIa), or a pharmaceutically acceptable salt thereof, as hereinbefore defined.

The invention still further provides the use of a compound of formula (I), (II), (IIa), (III) or (IIIa), or a pharmaceutically acceptable salt thereof, in the manufacture of a medicament for the treatment of cancer.

The invention still further provides the use of a compound of formula (I), (II), (IIa), (III) or (IIIa), or a pharmaceutically acceptable salt thereof, in the manufacture of a medicament for modulating polo-like kinas (Plk) activity.

The compounds of formula (I), (II) and (III), and pharmaceutically acceptable salts thereof, may be used on their own but will generally be administered in the form of a pharmaceutical composition in which the formula (I), (II), (IIa), (III) or (IIIa) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), (II), (IIa), (III) or (IIIa), or a pharmaceutically acceptable salt thereof, as hereinbefore defined, in association with a pharmaceutically acceptable adjuvant, diluent or carrier.

The invention further provides a process for the preparation of a pharmaceutical composition of the invention which comprises mixing a compound of formula (I), (II), (IIa), (III) or (IIIa), or a pharmaceutically acceptable salt thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate and anti oxidants such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil in water emulsions. The oily phase may be a vegetable oil, such as olive oil or arachis oil, or a mineral oil, such as for example liquid paraffin or a mixture of any of these. Suitable emulsifying agents may be, for example, naturally occurring gums such as gum acacia or gum tragacanth, naturally occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non toxic parenterally acceptable diluent or solvent, for example a solution in 1,3 butanediol.

Suppository formulations may be prepared by mixing the active ingredient with a suitable non irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30µ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo inhaler device, such as is used for insufflation of the known agent sodium cromoglicate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The size of the dose for therapeutic purposes of a compound of the invention will naturally vary according to the nature and severity of the conditions, the age and sex of the animal or patient and the route of administration, according to well known principles of medicine.

In general, a compound of the invention will be administered so that a daily dose in the range, for example, from 0.5 mg to 75 mg active ingredient per kg body weight is received, given if required in divided doses. In general lower doses will be administered when a parenteral route is employed. Thus, for example, for intravenous administration, a dose in the range, for example, from 0.5 mg to 30 mg active ingredient per kg body weight will generally be used. Similarly, for administration by inhalation, a dose in the range, for example, from 0.5 mg to 25 mg active ingredient per kg body weight will generally be used. Also, for example, a formulation intended for oral administration to humans will generally contain, for example, from 0.5 mg to 2 g of active ingredient.

For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The anti cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [Herceptin™], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD 1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy;

(ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies; and (x) other inhibitors of cell cycle such as Eg5, Chk1 or PARP inhibitors.

EXAMPLES

The invention will now be further described with reference to the following illustrative examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel;

(iv) SCX-2 cartridges are Ion Exchange SPE columns where the stationary phase is polymeric propylsulfonic acid. These are used to isolate amines.

(v) in general, the course of reactions was followed by TLC or LCMS and reaction times are given for illustration only;

(vi) final products had satisfactory proton nuclear magnetic resonance (NMR) spectra and/or mass spectral data;

(vii) yields are given for illustration only and are not necessarily those which can be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 400 MHz or 500 MHz, in $CDCl_3$, $DMSO-d_6$ or $DMSO-d6+d_4$-AcOH unless otherwise indicated;

(ix) chemical symbols have their usual meanings; SI units and symbols are used;

(x) solvent ratios are given in volume:volume (v/v) terms; and (xi) Mass spectra (MS) data was generated on an LCMS system where the HPLC component comprised generally either a Agilent 1100 or Waters Alliance HT (2790 & 2795) equipment and was run on a Phemonenex Gemini C18 5 mm, 50×2 mm column (or similar) eluting with either acidic eluent (for example, using a gradient between 0-95% water/acetonitrile with 5% of a 1% formic acid in 50:50 water:acetonitrile (v/v) mixture; or using an equivalent solvent system with methanol instead of acetonitrile), or basic eluent (for example, using a gradient between 0-95% water/acetonitrile with 5% of a 0.1% 880 Ammonia in acetonitrile mixture); and the MS component comprised generally a Waters ZQ mass spectrometer scanning over an appropriate mass range. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is the $(M+H)^+$ for positive ion mode and $(M-H)-$ for negative ion mode;

(xii) Microwave irradiation of reaction mixtures was performed using Emrys Optimiser instrument;

(xiii) the following abbreviations have been used:

| AcOH | acetic acid |
| --- | --- |
| $CDCl_3$ | deuterochloroform |
| DCM | dichloromethane |
| DIPEA | N,N-diisopropylethylamine |
| DMA | N,N-dimethylacetamide |
| DMF | N,N-dimethylformamide |
| DMSO | dimethylsulfoxide |
| $DMSO-d_6$ | hexadeuterodimethylsulfoxide |
| EtOH | ethanol |
| EtOAc | ethyl acetate |
| HATU | 2-(1H-7-Azabenzotriazol-1-yl)--1,1,3,3-tetramethyl uronium hexafluorophosphate Methanaminium |
| HBTU | O-Benzotriazole-N,N,N',N'-tetramethyl-uronium-hexafluoro-phosphate. |
| HPLC | high performance liquid chromatography |
| MeCN | acetonitrile |
| MeOH | methanol |
| MeI | methyl iodide |
| MS | mass spectroscopy |
| m/z | mass to charge ratio |
| NMR | nuclear magnetic resonance |
| SCX-2 | ion exchange SPE column (polymeric propylsulfonic acid stationery phase) |
| THF | terahydrofuran |
| TFA | Trifluoroacetic acid |
| XANTPHOS | 9,9-Dimethyl-4,5-bis(diphenylphosphino)xanthene |

Example 1

4-[(2-Cyclopentyl-6-methyl-5-oxo-2,6,9,11-tetrazabicyclo[5.4.0]undeca-8,10,12-trien-10-yl)amino]-3-methoxy-N-(1-methyl-4-piperidyl)benzamide 10-Chloro-2-cyclopentyl-6-methyl-2,6,9,11-tetrazabicyclo[5.4.0]undeca-8,10,12-trien-5-one (Intermediate 1; 99 mg, 0.34 mmol), 4-amino-3-methoxy-N-(1-methyl-4-piperidyl)benzamide (WO06/018220; 93 mg, 0.35 mmol) and p-toluenesulfonic acid (167 mg, 0.88 mmol) were dissolved in (R/S)-4-methyl-2-pentanol (8 mL) and heated at reflux under a blanket of nitrogen for 24 h. The reaction mixture was cooled and loaded onto an SCX-2 column then washed with MeOH (15 mL). The crude compound was eluted from the SCX-2 column with $NH_3$ (40 mL, 7M in MeOH) and the volatiles were removed under reduced pressure. Purification by column chromatography ($SiO_2$, eluent gradient: 0-10% $NH_3$ [7M in MeOH] in DCM), afforded the title compound (159 mg, 89%) as a solid.

$^1$H NMR (400 MHz, $CDCl_3$): $\delta_H$ 1.26 (t, 5H), 1.56-1.83 (m, 9H), 2.04 (s, 3H), 2.20-2.29 (m, 3H), 2.64-2.71 (m, 2H), 2.85-2.95 (m, 2H), 3.29 (s, 3H), 3.68-3.71 (m, 2H), 4.12 (q, 1H), 4.90 (quintet, 1H), 5.95 (d, 1H), 7.24 (dd, 1H), 7.42 (s, 1H), 7.67 (s, 1H), 7.94 (s, 1H), 8.51 (d, 1H); MS m/z 508 $[M+H]^+$.

Example 2

4-[(2-cyclopentyl-6-methyl-5-oxo-2,6,9,11-tetrazabicyclo[5.4.0]undeca-8,10,12-trien-10-yl)amino]-N-(1-methyl-4-piperidyl)benzamide 10-Chloro-2-cyclopentyl-6-methyl-2,6,9,11-tetrazabicyclo[5.4.0]undeca-8,10,12-trien-5-one (Intermediate 1; 86 mg, 0.31 mmol), 4-amino-N-(1-methyl-4-piperidyl)benzamide (Intermediate 4; 72 mg, 0.31 mmol) and p-toluene sulfonic acid (146 mg, 0.76 mmol) were dissolved in 4-methyl-2-pentanol (5 mL) and refluxed under an atmosphere of nitrogen for 18 hrs. The reaction mixture was loaded onto an SCX-2 column then washed with MeOH (15 mL). The crude compound was eluted from the SCX-2 column with $NH_3$ (40 mL, 7M in MeOH) and the volatiles were removed under reduced pressure. Purification by column chromatography (SiO$_2$, eluent gradient: 0-10% NH$_3$ [7M in MeOH] in DCM) then by preparative HPLC (Sunfire prep RP18, 19×100 mm column, eluting with a gradient of 0.1% solution of TFA in H$_2$O and a 0.1% solution of TFA in MeCN). The product fractions were then loaded onto an SCX-2 column then washed with MeOH (10 mL). The product was eluted from the SCX-2 column with NH$_3$ (30 mL, 7M in MeOH) and the volatiles removed under reduced pressure to give the title compound (38.5 mg, 26%) as a solid.

$^1$H NMR (399.9 MHz, DMSO-d$_6$) $\delta_H$ 1.58-1.78 (10H, m), 1.92-2.04 (4H, m), 2.21 (3H, s), 2.58-2.60 (2H, m), 2.79-2.83 (2H, m), 3.18 (3H, s), 3.60-3.65 (2H, m), 3.71-3.79 (1H, m), 4.81-4.89 (1H, m), 7.76 (2H, d), 7.82 (2H, d), 7.99 (1H, d), 8.09 (1H, s), 9.44 (1H, s); MS m/z 478 [M+H]$^+$.

Example 3

4-[(4R/S)-(2-Cyclopentyl-4,6-dimethyl-5-oxo-2,6,9, 11-tetrazabicyclo[5.4.0]undeca-8,10,12-trien-10-yl) amino]-3-methoxy-N-(1-methyl-4-piperidyl)benzamide (4R/S)-10-Chloro-2-cyclopentyl-4,6-dimethyl-2,6,9,11-tetrazabicyclo[5.4.0]undeca-8,10,12-trien-5-one (Intermediate 5; 106 mg, 0.36 mmol), 4-amino-N-(1-methyl-4-piperidyl)benzamide (WO06018220; 95 mg, 0.36 mmol) and p-toluene sulphonic acid (170 mg, 0.89 mmol) were dissolved in (R/S)-4-methyl-2-pentanol (6 mL) and refluxed under a blanket of nitrogen for 24 hrs. The reaction mixture was cooled to ambient temperature and loaded onto an SCX-2 column and then washed with MeOH (40 mL). The crude compound 5w as eluted from the SCX-2 column with NH$_3$ (40 mL, 7M in MeOH) and the volatiles removed under reduced pressure. The crude material was then purified by column chromatography (SiO$_2$, eluent gradient: 0-10% NH$_3$ [7M in MeOH] in DCM) then by preparative HPLC (Sunfire prep RP18, 19×100 mm column, eluting with a gradient composing of a 0.1% solution of TFA in H$_2$O and a 0.1% solution of TFA in MeCN). The product fractions were loaded onto an SCX-2 column then washed with MeOH (10 mL). The product was eluted from the SCX-2 column with NH$_3$ (30 mL, 7M in MeOH) and the volatiles removed under reduced pressure to give the title compound (43.9 mg, 23%) as a solid.

$^1$H NMR (400 MHz, DMSO-d$_6$) $\delta_H$ 1.04 (d, 3H), 1.51-1.84 (m, 12H), 1.99-2.13 (m, 3H), 2.81-2.91 (m, 6H), 3.20 (s, 3H), 3.45 (q, 2H), 3.78 (m, 1H), 3.96 (s, 3H), 4.08 (s, 1H), 4.75 (quintet, 1H), 7.49 (d, 1H), 7.75 (s, 1H), 8.09 (d, 1H), 8.40 (d, 1H); MS m/z 522 [M+H]$^+$.

Example 4

4-[(2-Cyclopentyl-6-methyl-2,6,9,11-tetrazabicyclo [5.4.0]undeca-8,10,12-trien-10-yl)amino]-3-methoxy-N-(1-methyl-4-piperidyl)benzamide To a solution of 4-[(9-cyclopentyl-5-methyl-6,7,8,9-tetrahydro-5H-pyrimido[4,5-b][1,4]diazepin-2-yl)amino]-3-methoxybenzoic acid (Intermediate 6; 240 mg, 0.60 mmol) and N-[(dimethylamino)(3H-[1,2,3]triazolo[4,5-b]pyridin-3-yloxy)methylene]-N-methylmethanaminium hexafluorophosphate (275 mg, 0.72 mmol) in DMA (10 mL) was added 1-methylpiperidin-4-amine (82 mg, 0.72 mmol) and DIPEA (210 uL, 1.20 mmol), and the reaction stirred at ambient temperature for 2 hr. The reaction mixture was loaded onto an SCX-2 column and washed with MeOH (20 mL). The crude product was then eluted from the SCX-2 column with NH$_3$ (40 mL, 7M in MeOH) and the volatiles removed under reduced pressure. Purification by column chromatography (SiO$_2$, eluent gradient: 5-10% MeOH in DCM) afforded the title compound (160 mg, 54%) as a solid.

$^1$H NMR (400 MHz, DMSO-d6) $\delta_H$ 1.65 (m, 10H), 1.94 (m, 6H), 2.21 (s, 3H), 2.71 (s, 3H), 2.82 (d, 2H), 3.00 (t, 2H), 3.48 (m, 2H), 3.94 (s, 3H), 4.86 (m, 1H), 7.36 (s, 1H), 7.46 (m, 2H), 7.53 (s, 1H), 8.02 (d, 1H), 8.46 (d, 1H); MS m/z 494 [M+H]$^+$.

Example 5

4-[(2,6-Dimethyl-5-oxo-2,6,9,11-tetrazabicyclo [5.4.0]undeca-7,9,11-trien-10-yl)amino]-3-methoxy-N-(1-methyl-4-piperidyl)benzamide 10-Chloro-2,6-dimethyl-2,6,9,11-tetrazabicyclo[5.4.0] undeca-7,9,11-trien-5-one (Intermediate 9; 185 mg, 0.82 mmol), 4-amino-3-methoxy-N-(1-methyl-4-piperidyl)benzamide (215 mg, 0.82 mmol) and p-toluenesulphonic acid (389 mg, 2.05 mmol) in (R/S)-4-methyl-2-pentanol (6 mL) were heated at 115° C. for 5 h. The reaction mixture was cooled to ambient temperature then passed through a SCX-2 cartridge and washed with MeOH (40 mL). The crude product was eluted off the SCX-2 cartridge with NH$_3$ (40 mL, 7M in MeOH). Purification by preparative HPLC (Gemini RP C18 30×100 mm, gradient mobile phase: 10-80% MeCN/water+0.5% NH$_3$) afforded the title compound (180 mg, 48%) as a foam.

$^1$H NMR (400 MHz, DMSO-d$_6$) $\delta_H$ 1.60 (m, 2H), 1.78 (m, 2H), 1.90 (tr, 2H), 2.19 (s, 3H), 2.62 (tr, 2H), 2.79 (d, 2H), 3.09 (s, 3H), 3.20 (s, 3H), 3.73 (m, 3H), 3.95 (s, 3H), 7.51 (m, 2H), 7.75 (m, 1H), 8.05 (d, 1H), 8.11 (s, 1H), 8.48 (d, 1H); MS m/z 454 [M+H]$^+$.

The following examples were prepared by an analogous process to that used in the preparation of Example 5 utilising the appropriate pyrimidine derivative (Intermediates 10-13) as the electrophile and 4-amino-3-methoxy-N-(1-methyl-4-piperidyl)benzamide (WO06/018220) as the aniline:

Example 6

3-Methoxy-4-[(6-methyl-5-oxo-2-propan-2-yl-2,6,9, 11-tetrazabicyclo[5.4.0]undeca-7,9,11-trien-10-yl) amino]-N-(1-methyl-4-piperidyl)benzamide Example 7

3-Methoxy-4-[[6-methyl-2-(3-methylbutyl)-5-oxo-2, 6,9,11-tetrazabicyclo[5.4.0]undeca-7,9,11-trien-10-yl]amino]-N-(1-methyl-4-piperidyl)benzamide Example 8

4-[(2-Cyclohexyl-6-methyl-5-oxo-2,6,9,11-tetrazabicyclo[5.4.0]undeca-7,9,11-trien-10-yl)amino]-3-methoxy-N-(1-methyl-4-piperidyl)benzamide

Example 9

3-Methoxy-4-[[6-methyl-2-(oxan-4-yl)-5-oxo-2,6,9,11-tetrazabicyclo[5.4.0]undeca-7,9,11-trien-10-yl]amino]-N-(1-methyl-4-piperidyl)benzamide

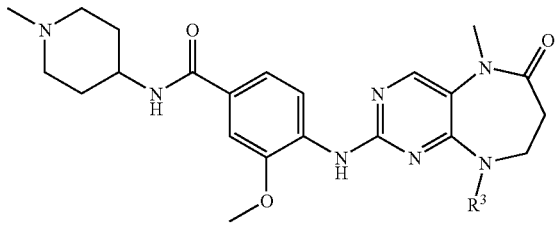

| Example | R³ | ¹H NMR (400 MHz, DMSO-d₆) | MS m/z [M + H]⁺ |
|---|---|---|---|
| 6 | isopropyl | 1.25 (d, 6H), 1.60 (m, 2H), 1.77 (m, 2H), 1.95 (tr, 2H), 2.19 (s, 3H), 2.60 (tr, 2H), 2.70 (d, 2H), 3.19 (s, 3H), 3.62 (m, 2H), 3.75 (m, 1H), 3.96 (s, 3H), 4.80 (m, 1H), 7.51 (m, 2H), 7.69 (s, 1H), 8.08 (d, 2H), 8.41 (d, 1H) | 482 |
| 7 | isobutyl | 0.92 (d, 6H), 1.58 (m, 5H), 1.76 (m, 2H), 1.93 (tr, 2H), 2.19 (s, 3H), 2.61 (tr, 2H), 2.79 (d, 2H), 3.19 (s, 3H), 3.61 (tr, 2H), 3.71 (m, 3H), 3.95 (s, 3H), 7.49 (m, 2H), 7.70 (s, 1H), 8.06 (d, 2H), 8.35 (d, 1H) | 510 |
| 8 | cyclohexyl | 1.17 (m, 1H), 1.41 (m, 2H), 1.55-1.90 (m, 11H), 1.95 (tr, 2H), 2.19 (s, 3H), 2.59 (tr, 2H), 2.80 (d, 2H), 3.18 (s, 3H), 3.65 (m, 2H), 3.77 (m, 1H), 4.49 (tr, 1H), 7.49 (m, 2H), 7.70 (s, 1H), 8.08 (m, 2H), 8.39 (d, 1H) | 522 |
| 9 | tetrahydropyran-4-yl | 1.61 (m, 2H). 1.72-2.00 (m, 7H), 2.20 (s, 3H), 2.61 (tr, 2H), 2.80 (d, 2H), 3.19 (s, 3H), 3.50 (tr, 2H), 3.67 (m, 2H), 3.78 (m, 1H), 3.96 (s, 3H), 4.02 (dd, 2H), 4.62 (tr, 1H), 7.51 (m, 2H), 7.78 (s, 1H), 8.10 (m, 2H), 8.31 (d, 1H) | 524 |

Example 10

4-[(2-Cyclopentyl-6-methyl-5-oxo-2,6,9,11-tetrazabicyclo[5.4.0]undeca-8,10,12-trien-10-yl)amino]-N-(3-dimethylamino-2,2-dimethyl-propyl)-3-methoxy-benzamide hydrochloride 10-Chloro-2-cyclopentyl-6-methyl-2,6,9,11-tetrazabicyclo[5.4.0]undeca-8,10,12-trien-5-one (Intermediate 1; 238 mg, 0.85 mmol), 4-amino-N-(3-dimethylamino-2,2-dimethyl-propyl)-3-methoxy-benzamide (Intermediate 22; 250 mg, 0.85 mmol) and p-toluenesulfonic acid (405 mg, 2.13 mmol) were dissolved in (R/S)-4-methyl-2-pentanol (4 mL) and heated at reflux for 24 h. The reaction mixture was then cooled and loaded onto an SCX-2 column, which was then washed with MeOH (40 mL). The crude product was washed off the SCX-2 column with NH₃ (50 mL, 7M in MeOH). Purification by column chromatography (SiO₂, eluent gradient: 0-10% NH₃ [7M in methanol] in DCM) give a pale yellow oil. HCl (0.43 uL, 2N in Et₂O, 0.85 mmol) was added to a DCM (5 mL) solution of the yellow oil. Concentration under reduced pressure gave the title compound (188 mg, 40%) as a solid.

¹H NMR (400 MHz, CDCl₃): $\delta_H$ 1.00 (s, 6H), 1.60-1.84 (m, 6H), 2.02-2.34 (m, 2H), 2.37 (s, 2H), 2.39 (s, 6H), 2.65-2.69 (m, 2H), 3.29 (s, 3H), 3.38 (d, 2H), 3.68-3.72 (m, 2H), 3.98 (s, 3H), 4.87-4.96 (m, 1H), 7.29 (dd, 1H), 7.51 (d, 1H), 7.67 (s, 1H), 7.95 (s, 1H), 8.51 (d, 1H), 9.14 (t, 1H); MS m/z 524 [M+H]⁺.

Example 11

4-[(6-cyclopentyl-2-methyl-3-oxo-2,6,8,10-tetrazabicyclo[5.4.0]undeca-8,10,12-trien-9-yl)amino]-N-(1-cyclopropyl-4-piperidyl)-3-methoxy-benzamide 4-[(2-cyclopentyl-6-methyl-5-oxo-2,6,9,11-tetrazabicyclo[5.4.0]undeca-7,9,11-trien-10-yl)amino]-3-methoxy-benzoic acid (Example 111; 150 mg, 0.36 mmol), 1-cyclopropylpiperidin-4-amine (Intermediate 24, 77 mg, 0.55 mmol) and HATU (208 mg, 0.55 mmol) were stirred in DMF (92 ml). DIPEA (191 mL, 1.09 mmol) was added and the mixture stirred at room temperature for 3 h. The mixture was absorbed onto an SCX column, washed with methanol and eluted with ammonia in methanol. Product containing fractions were concentrated and purified by preparative HPLC to give the title compound as a pale brown solid (127 mg, 66%).

¹H NMR (399.9 MHz, DMSO-d₆) δ 0.29 (2H, s), 0.43 (2H, d), 1.48-1.81 (11H, m), 1.94 (2H, m), 2.24 (2H, t), 2.60 (2H, t), 2.96 (2H, d), 3.18 (3H, s), 3.63 (2H, t), 3.78 (1H, m), 3.95 (3H, s), 4.78-4.86 (1H, m), 7.46-7.51 (2H, m), 7.73 (1H, s), 8.04 (1H, d), 8.09 (1H, s), 8.39 (1H, d); MS m/z 534 [M+H]⁺.

Example 12

4-[(6-cyclopentyl-2-methyl-3-oxo-2,6,8,10-tetrazabicyclo[5.4.0]undeca-8,10,12-trien-9-yl)amino]-3-methoxy-N-[2-(1-piperidyl)ethyl]benzamide A solution of HATU (147 mg, 0.385 mmol) in DMA (1 mL) was added to a mixture of 4-[(2-cyclopentyl-6-methyl-5-oxo-2,6,9,11-tetrazabicyclo[5.4.0]undeca-7,9,11-trien-10-yl)amino]-3-methoxy-benzoic acid (Example 111; 144 mg, 0.35 mmol), DIPEA (183 uL, 1.05 mmol) and 2-(1-piperidyl)ethanamine (Aldrich, 56 mg 0.44 mmol) in DMA (1 mL). The resulting mixture was stirred at room temperature overnight. The mixture was absorbed onto an SCX column, washed with methanol and eluted with ammonia in methanol. Product containing fractions were concentrated and purified by preparative reverse phase HPLC to give the title compound (86 mg, 47%)

The following examples were prepared by an analogous process to that used in the preparation of Example 12 utilising the acid described in Example 111 and the appropriate amines.

Example 13

4-[(6-cyclopentyl-2-methyl-3-oxo-2,6,8,10-tetrazabicyclo[5.4.0]undeca-8,10,12-trien-9-yl)amino]-3-methoxy-N-(2-morpholin-4-ylethyl)benzamide Example 14

4-[(6-cyclopentyl-2-methyl-3-oxo-2,6,8,10-tetrazabicyclo[5.4.0]undeca-8,10,12-trien-9-yl)amino]-N-(2-dimethylaminoethyl)-3-methoxy-benzamide Example 15

4-[(6-cyclopentyl-2-methyl-3-oxo-2,6,8,10-tetrazabicyclo[5.4.0]undeca-8,10,12-trien-9-yl)amino]-N-[(1-ethylpyrrolidin-2-yl)methyl]-3-methoxy-benzamide Example 16

4-[(6-cyclopentyl-2-methyl-3-oxo-2,6,8,10-tetrazabicyclo[5.4.0]undeca-8,10,12-trien-9-yl)amino]-3-methoxy-N-(2-pyrrolidin-1-ylethyl)benzamide Example 17

4-[(6-cyclopentyl-2-methyl-3-oxo-2,6,8,10-tetrazabicyclo[5.4.0]undeca-8,10,12-trien-9-yl)amino]-N-(5-diethylaminopentan-2-yl)-3-methoxy-benzamide Example 18

4-[(6-cyclopentyl-2-methyl-3-oxo-2,6,8,10-tetrazabicyclo[5.4.0]undeca-8,10,12-trien-9-yl)amino]-N-(2-diethylaminoethyl)-3-methoxy-benzamide Example 19

4-[(6-cyclopentyl-2-methyl-3-oxo-2,6,8,10-tetrazabicyclo[5.4.0]undeca-8,10,12-trien-9-yl)amino]-N-(3-dimethylaminopropyl)-3-methoxy-benzamide Example 20

4-[(6-cyclopentyl-2-methyl-3-oxo-2,6,8,10-tetrazabicyclo[5.4.0]undeca-8,10,12-trien-9-yl)amino]-3-methoxy-N-[3-(4-methylpiperazin-1-yl)propyl]benzamide Example 21

4-[(6-cyclopentyl-2-methyl-3-oxo-2,6,8,10-tetrazabicyclo[5.4.0]undeca-8,10,12-trien-9-yl)amino]-N-(4-dimethylaminobutyl)-3-methoxy-benzamide Example 22

N-(1-azabicyclo[2.2.2]oct-8-yl)-4-[(6-cyclopentyl-2-methyl-3-oxo-2,6,8,10-tetrazabicyclo[5.4.0]undeca-8,10,12-trien-9-yl)amino]-3-methoxy-benzamide Example 23

4-[(6-cyclopentyl-2-methyl-3-oxo-2,6,8,10-tetrazabicyclo[5.4.0]undeca-8,10,12-trien-9-yl)amino]-3-methoxy-N-[2-(2-oxoimidazolidin-1-yl)ethyl]benzamide Example 24

N-(2-acetamidoethyl)-4-[(6-cyclopentyl-2-methyl-3-oxo-2,6,8,10-tetrazabicyclo[5.4.0]undeca-8,10,12-trien-9-yl)amino]-3-methoxy-benzamide Example 25

4-[(6-cyclopentyl-2-methyl-3-oxo-2,6,8,10-tetrazabicyclo[5.4.0]undeca-8,10,12-trien-9-yl)amino]-3-methoxy-N-(3-morpholin-4-ylpropyl)benzamide Example 26

4-[(6-cyclopentyl-2-methyl-3-oxo-2,6,8,10-tetrazabicyclo[5.4.0]undeca-8,10,12-trien-9-yl)amino]-N-(3-imidazol-1-ylpropyl)-3-methoxy-benzamide Example 27

4-[(6-cyclopentyl-2-methyl-3-oxo-2,6,8,10-tetrazabicyclo[5.4.0]undeca-8,10,12-trien-9-yl)amino]-N-(2-imidazol-1-ylethyl)-3-methoxy-benzamide Example 28

4-[(6-cyclopentyl-2-methyl-3-oxo-2,6,8,10-tetrazabicyclo[5.4.0]undeca-8,10,12-trien-9-yl)amino]-N-(1-dimethylaminopropan-2-yl)-3-methoxy-benzamide

Example 29

4-[(6-cyclopentyl-2-methyl-3-oxo-2,6,8,10-tetrazabicyclo[5.4.0]undeca-8,10,12-trien-9-yl)amino]-3-methoxy-N-[1-(2-methoxyethyl)-4-piperidyl]benzamide

Example 30

4-[(6-cyclopentyl-2-methyl-3-oxo-2,6,8,10-tetrazabicyclo[5.4.0]undeca-8,10,12-trien-9-yl)amino]-N-(4-diethylaminobutyl)-3-methoxy-benzamide

Example 31

4-[(6-cyclopentyl-2-methyl-3-oxo-2,6,8,10-tetrazabicyclo[5.4.0]undeca-8,10,12-trien-9-yl)amino]-N-(4-imidazol-1-ylbutyl)-3-methoxy-benzamide

Example 32

4-[(6-cyclopentyl-2-methyl-3-oxo-2,6,8,10-tetrazabicyclo[5.4.0]undeca-8,10,12-trien-9-yl)amino]-3-methoxy-N-[2-(8-oxa-3-azabicyclo[3.2.1]oct-3-yl)ethyl]benzamide

Example 33

4-[(6-cyclopentyl-2-methyl-3-oxo-2,6,8,10-tetrazabicyclo[5.4.0]undeca-8,10,12-trien-9-yl)amino]-3-methoxy-N-(4-pyrrolidin-1-ylbutyl)benzamide

Example 34

4-[(6-cyclopentyl-2-methyl-3-oxo-2,6,8,10-tetrazabicyclo[5.4.0]undeca-8,10,12-trien-9-yl)amino]-3-methoxy-N-[2-(4-methylpiperazin-1-yl)ethyl]benzamide

Example 35

4-[(6-cyclopentyl-2-methyl-3-oxo-2,6,8,10-tetrazabicyclo[5.4.0]undeca-8,10,12-trien-9-yl)amino]-N-[2-(3,3-difluoropyrrolidin-1-yl)ethyl]-3-methoxy-benzamide

Example 36

4-[(6-cyclopentyl-2-methyl-3-oxo-2,6,8,10-tetrazabicyclo[5.4.0]undeca-8,10,12-trien-9-yl)amino]-N-[2-[(3R)-3-fluoropyrrolidin-1-yl]ethyl]-3-methoxy-benzamide

Example 37

4-[(6-cyclopentyl-2-methyl-3-oxo-2,6,8,10-tetrazabicyclo[5.4.0]undeca-8,10,12-trien-9-yl)amino]-N-[2-(4,4-difluoro-1-piperidyl)ethyl]-3-methoxy-benzamide

Example 38

4-[(6-cyclopentyl-2-methyl-3-oxo-2,6,8,10-tetrazabicyclo[5.4.0]undeca-8,10,12-trien-9-yl)amino]-3-methoxy-N-[3-(pyridin-2-ylamino)propyl]benzamide

Example 39

4-[(6-cyclopentyl-2-methyl-3-oxo-2,6,8,10-tetrazabicyclo[5.4.0]undeca-8,10,12-trien-9-yl)amino]-3-methoxy-N-(1-methyl-3-piperidyl)benzamide

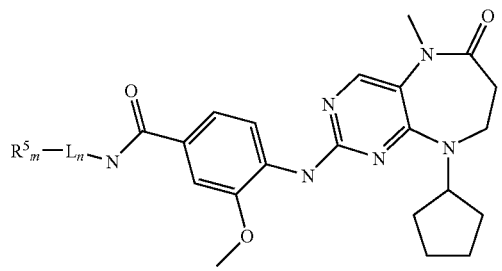

| Example | $R^5_m$—$L_n$— | Supplier Or Source | MS m/z $[M + H]^+$ | Retention time (Minutes) |
|---|---|---|---|---|
| 13 | 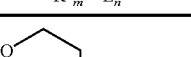 | Aldrich | 524 | 1.88 |
| 14 | 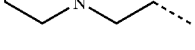 | Aldrich | 482 | 2.00 |

-continued
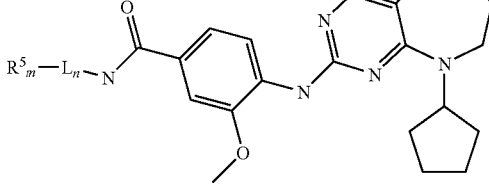
| Example | $R^5{}_m$—$L_n$— | Supplier Or Source | MS m/z [M + H]$^+$ | Retention time (Minutes) |
|---|---|---|---|---|
| 15 | 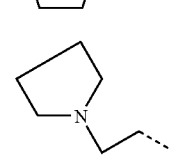 | Aldrich | 522 | 2.45 |
| 16 | 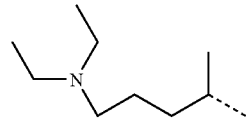 | Aldrich | 509 | 2.35 |
| 17 | 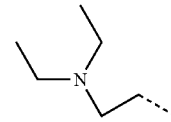 | Aldrich | 553 | 2.4 |
| 18 | 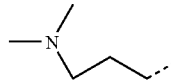 | Aldrich | 511 | 2.2 |
| 19 | 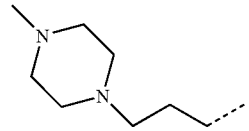 | Aldrich | 497 | 1.99 |
| 20 | 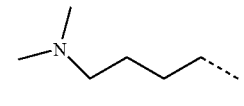 | ABCR | 552 | 1.74 |
| 21 | 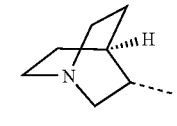 | ABCR | 511 | 2.07 |
| 22 | 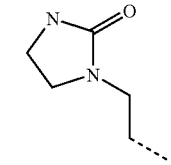 | Aldrich | 521 | 1.97 |
| 23 |  | Maybridge | 524 | 1.73 |

-continued

| Example | $R^5{}_m$—$L_n$— | Supplier Or Source | MS m/z [M + H]⁺ | Retention time (Minutes) |
|---|---|---|---|---|
| 24 | acetamido-ethyl | Aldrich | 497 | 1.7 |
| 25 | morpholino-butyl | ABCR | 539 | 1.87 |
| 26 | imidazol-1-yl-butyl | Aldrich | 520 | 1.87 |
| 27 | imidazol-1-yl-ethyl | ABCR | 506 | 1.79 |
| 28 | dimethylamino-isopropyl | Aldrich | 497 | 2.03 |
| 29 | 4-(2-methoxyethyl)piperidin-1-yl | Chemstep | 553 | 1.96 |
| 30 | diethylamino-pentyl | Frinton | 539 | 2.33 |
| 31 | imidazol-1-yl-pentyl | Asinex | 534 | 1.91 |
| 32 | 8-oxa-3-azabicyclo[3.2.1]octan-3-yl-ethyl | US3856783 | 551 | 2.07 |

-continued
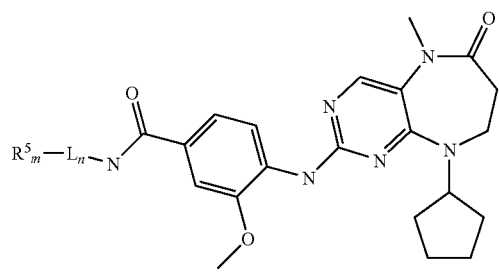
| Example | $R^5_m$—$L_n$— | Supplier Or Source | MS m/z $[M + H]^+$ | Retention time (Minutes) |
|---|---|---|---|---|
| 33 | | Matrix | 537 | 2.27 |
| 34 | | Matrix | 538 | 1.74 |
| 35 | | WO2005097750 | 545 | 2.2 |
| 36 | | US2005209274 | 527 | 2.02 |
| 37 | | Fluorochem | 559 | 2.29 |
| 38 | | US2003069236 | 546 | 2.18 |
| 39 | | Fluorochem | 509 | 2.03 |

The following examples were prepared by an analogous process to that used in the preparation of Example 12 utilising the acid described in Example 111 and the appropriate BOC-protected amines. Prior to SCX purification the reaction mixture was treated with 4N HCl in dioxane (1 mL) and stirred at room temperature for 24 hr. The reaction mixtures were absorbed onto SCX columns, washed with methanol and eluted with ammonia in methanol. Product containing fractions were concentrated and purified by preparative HPLC to give the title compounds

Example 40

N-(4-aminobutyl)-4-[(6-cyclopentyl-2-methyl-3-oxo-2,6,8,10-tetrazabicyclo[5.4.0]undeca-8,10,12-trien-9-yl)amino]-3-methoxy-benzamide

Example 41

4-[(6-cyclopentyl-2-methyl-3-oxo-2,6,8,10-tetrazabicyclo[5.4.0]undeca-8,10,12-trien-9-yl)amino]-3-methoxy-N-(4-piperidyl)benzamide

Example 42

N-(3-aminopropyl)-4-[(6-cyclopentyl-2-methyl-3-oxo-2,6,8,10-tetrazabicyclo[5.4.0]undeca-8,10,12-trien-9-yl)amino]-3-methoxy-benzamide

Example 43

4-[(6-cyclopentyl-2-methyl-3-oxo-2,6,8,10-tetrazabicyclo[5.4.0]undeca-8,10,12-trien-9-yl)amino]-3-methoxy-N-(2-methylaminoethyl)benzamide

Example 44

4-[(6-cyclopentyl-2-methyl-3-oxo-2,6,8,10-tetrazabicyclo[5.4.0]undeca-8,10,12-trien-9-yl)amino]-3-methoxy-N-(3-methylaminopropyl)benzamide

Example 45

4-[(6-cyclopentyl-2-methyl-3-oxo-2,6,8,10-tetrazabicyclo[5.4.0]undeca-8,10,12-trien-9-yl)amino]-3-methoxy-N-pyrrolidin-3-yl-benzamide

Example 46

N-(3-amino-2,2-dimethyl-propyl)-4-[(6-cyclopentyl-2-methyl-3-oxo-2,6,8,10-tetrazabicyclo[5.4.0]undeca-8,10,12-trien-9-yl)amino]-3-methoxy-benzamide

Example 47

4-[(6-cyclopentyl-2-methyl-3-oxo-2,6,8,10-tetrazabicyclo[5.4.0]undeca-8,10,12-trien-9-yl)amino]-3-methoxy-N-[[(3R)-pyrrolidin-3-yl]methyl]benzamide

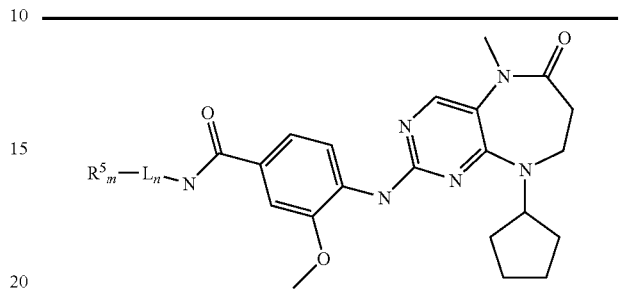

| Example | $R^5_m$—$L_n$— | Supplier or Source of BOC-Protected Amine | MS m/z [M + H]$^+$ | Retention time (Minutes) |
|---|---|---|---|---|
| 40 | | Fluka | 482 | 2.02 |
| 41 | | Aldrich | 494 | 2.02 |
| 42 | | Aldrich | 468 | 1.97 |
| 43 | | ABCR | 468 | 1.9 |
| 44 | | ABCR | 482 | 2.26 |
| 45 | | ABCR | 480 | 2.02 |
| 46 | | ABCR | 496 | 2.16 |
| 47 | | ABCR | 494 | 2.47 |

Example 48

4-[(6-cyclopentyl-2-methyl-3-oxo-2,6,8,10-tetrazabicyclo[5.4.0]undeca-8,10,12-trien-9-yl)amino]-2-fluoro-5-methoxy-N-(1-methyl-4-piperidyl)benzamide 10-chloro-2-cyclopentyl-6-methyl-2,6,9,11-tetrazabicyclo[5.4.0]undeca-8,10,12-trien-5-one (Intermediate 1, 211 mg, 0.75 mmol) and 4-amino-2-fluoro-5-methoxy-N-(1-methyl-4-piperidyl)benzamide (Intermediate 27, 211 mg, 0.75 mmol) were combined with p-TSA (357 mg, 1.88 mmol) in 4-methyl-2-pentanol (1 mL) and heated to 150° C. for 18 hr.

The cooled reaction mixture was diluted with methanol and water (approx 50 mL) and loaded onto a 50 g SCX-2 cartridge washing with methanol (100 mL) and eluting with 7 N methanolic ammonia (100 mL). The concentrated solution was purified by reversed phase HPLC. The title compound was obtained as a beige solid (178 mg, 45%).

$^1$H NMR (399.902 MHz, DMSO-$d_6$) δ 1.50-1.81 (m, 10H), 1.90-2.00 (m, 4H), 2.16 (s, 3H), 2.58-2.61 (m, 2H), 2.72 (br d, 2H), 3.17 (s, 3H), 3.63-3.65 (m, 2H), 3.68-3.75 (m, 1H), 3.92 (s, 3H), 4.83 (quintet, 1H), 7.19 (d, 1H), 7.79-7.82 (m, 2H), 8.11 (s, 1H), 8.33 (d, 1H); MS m/z 526 [M+H]$^+$.

Example 49

4-[(6-cyclopentyl-2-methyl-3-oxo-2,6,8,10-tetrazabicyclo[5.4.0]undeca-8,10,12-trien-9-yl)amino]-3-methoxy-N-(1-propan-2-yl-4-piperidyl)benzamide 4-[(2-cyclopentyl-6-methyl-5-oxo-2,6,9,11-tetrazabicyclo[5.4.0]undeca-7,9,11-trien-10-yl)amino]-3-methoxybenzoic acid (Example 111; 100 mg, 0.24 mmol), N-Isopropyl-4-aminopiperidine (ABCR, 42 mg, 0.29 mmol), HATU (111 mg, 0.29 mmol) and DIPEA (127 uL, 0.73 mmol) and DMF (3 mL) were combined and stirred at room temperature for 3 hours. The solvent was evaporated and the residue partitioned between DCM (10 mL) and water (10 mL). The organic phase was added to a 5 g SCX-2 column pre-wet with MeOH (2 column volumes), flushed with MeOH (2 column volumes) and the crude product eluted with 2M ammonia in MeOH and solvents evaporated. The residue was taken up in DCM and purified on silica, eluting with a gradient of 0-5% MeOH/DCM followed by 5% then 10% and finally 15% MeOH/DCM. Fractions containing product were combined and evaporated to give the tile compound as a white solid (45 mg, 35%).

$^1$H NMR (400.132 MHz, CDCl$_3$) δ 0.99 (d, 6H), 1.55-1.73 (m, 8H), 2.00 (m, 4H), 2.27 (m, 2H), 2.60 (m, 2H), 2.69 (m, 1H), 2.81 (m, 2H), 3.22 (s, 3H), 3.62 (m, 2H), 3.92 (m, 4H), 4.83 (m, 1H), 5.82 (d, 1H), 7.14 (m, 1H), 7.35 (d, 1H), 7.59 (s, 1H), 7.87 (s, 1H), 8.43 (d, 1H); MS m/z 536 [M+H]$^+$.

Example 50 tert-butyl 4-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]piperidine-1-carboxylate 4-[(2-cyclopentyl-6-methyl-5-oxo-2,6,9,11-tetrazabicyclo[5.4.0]undeca-7,9,11-trien-10-yl)amino]-3-methoxybenzoic acid (Example 111; 113 mg, 0.27 mmol), tert-butyl 4-aminopiperidine-1-carboxylate (ABCR, 50 mg, 0.25 mmol), HATU (114 mg, 0.3 mmol) and DIPEA (130 uL, 0.75 mmol) and DMF (3 mL) were combined and stirred at room temperature for 3 hours. Solvent was evaporated and the residue partitioned between DCM (25 mL) and sat. aq. Bicarb. (25 mL) and gravity filtered through a PTFE cup. The organic phase was added to a silica column and eluted with a shallow gradient of 0-10% MeOH/DCM. Fractions containing product were combined and evaporated to a yellow gum to which ether was added and re-evaporated to give the title compound as an orange solid. (89 mg, 55%).

$^1$H NMR (400.132 MHz, CDCl$_3$) δ 1.37 (m, 11H), 1.53-1.71 (m, 6H), 1.97 (m, 4H), 2.60 (m, 2H), 2.86 (m, 2H), 3.22 (s, 3H), 3.62 (m, 2H), 3.91 (s, 3H), 4.05 (m, 3H), 4.83 (m, 1H), 5.83 (d, 1H), 7.15 (m, 1H), 7.35 (m, 1H), 7.60 (s, 1H), 7.87 (s, 1H), 8.44 (d, 1H); MS m/z 594[M+H]$^+$.

Example 51

Benzyl(1S,5R)-6-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]-3-azabicyclo[3.1.0]hexane-3-carboxylate 4-[(2-cyclopentyl-6-methyl-5-oxo-2,6,9,11-tetrazabicyclo[5.4.0]undeca-7,9,11-trien-10-yl)amino]-3-methoxybenzoic acid (Example 111; 113 mg, 0.27 mmol), benzyl(1S,5R)-6-amino-3-azabicyclo[3.1.0]hexane-3-carboxylate (Intermediate 30; 50 mg, 0.25 mmol), HATU (114 mg, 0.3 mmol) and DIPEA (130 uL, 0.75 mmol) and DMF (3 mL) were combined and stirred at room temperature for 3 hours. Solvent was evaporated and the residue partitioned between DCM (2 mL) and sat. aq. Bicarb. (2 mL), gravity filtered through a PTFE cup and solvents evaporated. The residue was taken up in DCM and purified on silica eluting with a gradient of 0-5% MeOH/DCM. Fractions containing product were combined and evaporated. The resultant material was purified by reversed phase HPLC.

$^1$H NMR (400.132 MHz, CDCl$_3$) δ1.64 (m, 8H), 1.97 (m, 2H), 2.58 (m, 3H), 3.22 (s, 3H), 3.46 (m, 2H), 3.62 (m, 2H), 3.78 (m, 2H), 3.90 (s, 3H), 4.82 (m, 1H), 5.05 (s, 2H), 6.08 (s, 1H), 7.12 (m, 1H), 7.26 (m, 5H), 7.34 (d, 1H), 7.61 (s, 1H), 7.87 (s, 1H), 8.43 (d, 1H); MS m/z 626 [M+H]$^+$.

The following examples were prepared by an analogous process to that used in the preparation of Example 51 utilising the acid described in Example 111 and the appropriate amines.

Example 52 tert-butyl (3R)-3-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]pyrrolidine-1-carboxylate Amine available from Chempacific $^1$H NMR (400.132 MHz, CDCl3) δ1.41 (s, 9H), 1.63 (m, 3H), 1.94 (m, 2H), 2.19 (m, 1H), 2.60 (m, 2H), 3.26 (m, 4H), 3.43 (m, 2H), 3.65 (m, 3H), 3.91 (s, 3H), 4.59 (m, 1H), 4.84 (m, 1H), 6.01 (d, 1H), 7.15 (m, 5H), 7.35 (d, 1H), 7.62 (s, 1H), 7.88 (s, 1H), 8.45 (d, 1H); MS m/z 580 [M+H]$^+$.

Example 53 tert-butyl (3S)-3-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]pyrrolidine-1-carboxylate Amine available from Chempacific $^1$H NMR (400.132 MHz, CDCl3) δ1.41 (s, 9H), 1.64 (m, 6H), 1.93 (m, 3H), 2.19 (m, 1H), 2.60 (m, 2H), 3.26 (m, 4H), 3.43 (m, 2H), 3.65 (m, 3H), 3.91 (s, 3H), 4.59 (m, 1H), 4.84 (m, 1H), 6.02 (d, 1H), 7.15 (m, 1H), 7.35 (d, 1H), 7.62 (s, 1H), 7.88 (s, 1H), 8.45 (d, 1H); MS m/z 580 [M+H]$^+$.

Example 54

Benzyl 4-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]piperidine-1-carboxylate 4-[(2-cyclopentyl-6-methyl-5-oxo-2,6,9,11-tetrazabicyclo[5.4.0]undeca-7,9,11-trien-10-yl)amino]-3-methoxybenzoic acid (Example 111, 350 mg, 0.85 mmol), Benzyl 4-aminopiperidine-1-carboxylate (ABCR, 219 mg, 0.94 mmol), HATU (388 mg, 1.02 mmol) and DIPEA (445 uL, 2.55 mmol) and DMF (5 mL) were combined and stirred at room temperature for 3 hours. Solvent was evaporated and the residues partitioned between DCM (2 mL) and sat. aq. Bicarb. (2 mL), gravity filtered through a PTFE cup and solvents evaporated. The residue was taken up in DCM and purified on silica eluting with a gradient of 0-5% MeOH/DCM. Fractions containing product were combined and evaporated. To give the title compound as an orange solid.

$^1$H NMR (400.132 MHz, CDCl$_3$) δ1.38 (m, 2H), 1.62 (m, 6H), 1.97 (m, 4H), 2.60 (m, 2H), 2.94 (m, 2H), 3.22 (s, 3H), 3.62 (m, 2H), 3.91 (s, 3H), 4.11 (m, 3H), 4.83 (m, 1H), 5.07 (s, 2H), 5.82 (d, 1H), 7.14 (m, 1H), 7.27 (m, 5H), 7.34 (d, 1H), 7.61 (s, 1H), 7.87 (s, 1H), 8.44 (d, 1H); MS m/z 628 [M+H]$^+$.

Example 55

4-[(6-cyclopentyl-2-methyl-3-oxo-2,6,8,10-tetrazabicyclo[5.4.0]undeca-8,10,12-trien-9-yl)amino]-3-methoxy-N-[(3R)-pyrrolidin-3-yl]benzamide tert-butyl (3R)-3-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]pyrrolidine-1-carboxylate (630 mg, 1 mmol) was dissolved in DCN (10 mL), TFA (10 mL) added and stirred at room temperature for 2 hr. The reaction mixture was added to a 10 g SCX-2 column pre wet with MeOH (2 column volumes), flushed with MeOH (2 column volumes) then the crude product eluted with 2M ammonia in MeOH and solvents evaporated. The residue was taken up in DCM and purified on silica eluting with a gradient of 0-10% 2M ammonia in MeOH/DCM then 10% 2M ammonia in MeOH/DCM. Fractions containing product were combined and evaporated to a gum, ether was added and re-evaporated to give the title compound as a solid. (300 mg, 74%)

$^1$H NMR (400.132 MHz, CDCl$_3$) δ1.62 (m, 8H), 1.98 (m, 2H), 2.19 (m, 1H), 2.60 (m, 2H), 2.89 (m, 2H), 3.06 (m, 1H), 3.17 (m, 1H), 3.22 (s, 3H), 3.62 (m, 2H), 3.90 (s, 3H), 4.53 (m, 1H), 4.83 (m, 1H), 6.24 (d, 1H), 7.19 (m, 1H), 7.37 (d, 1H), 7.60 (s, 1H), 7.87 (s, 1H), 8.43 (d, 1H); MS m/z 480 [M+H]$^+$.

The following example was prepared by an analogous process to that used in the preparation of Example 56 utilising the BOC-protected material described in Example 54.

Example 56

4-[(6-cyclopentyl-2-methyl-3-oxo-2,6,8,10-tetrazabicyclo[5.4.0]undeca-8,10,12-trien-9-yl)amino]-3-methoxy-N-[(3S)-pyrrolidin-3-yl]benzamide $^1$H NMR (400.132 MHz, CDCl3) δ1.62 (m, 8H), 1.98 (m, 2H), 2.19 (m, 1H), 2.60 (m, 2H), 2.85 (m, 1H), 2.91 (m, 1H), 3.06 (m, 1H), 3.17 (m, 1H), 3.22 (s, 3H), 3.62 (m, 2H), 3.90 (s, 3H), 4.53 (m, 1H), 4.83 (m, 1H), 6.24 (d, 1H), 7.19 (m, 1H), 7.37 (d, 1H), 7.60 (s, 1H), 7.87 (s, 1H), 8.43 (d, 1H); MS m/z 480 [M+H]$^+$.

Example 57

N-[(1S,5R)-3-azabicyclo[3.1.0]hex-6-yl]-4-[(6-cyclopentyl-2-methyl-3-oxo-2,6,8,10-tetrazabicyclo[5.4.0]undeca-8,10,12-trien-9-yl)amino]-3-methoxy-benzamide Benzyl(1S,5R)-6-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]-3-azabicyclo[3.1.0]hexane-3-carboxylate (Example 51, 357 mg, 0.57 mmol) was dissolved in MeOH (30 mL) and passed through the H-cube at 50° C. on full hydrogen mode at 1 mL per minute. The solution added to a 10 g SCX-2 column pre-wet with MeOH (2 column volumes), flushed with MeOH (2 column volumes) and crude product eluted with 2M ammonia in MeOH. The basic fractions were evaporated and the residue dissolved in DCM and purified on silica eluting with a gradient of 0-10% 2M ammonia in MeOH/DCM then 10% 2M ammonia in MeOH/DCM. Fractions containing product were combined and evaporated to a gum to which ether was added and re-evaporated to give the title compound as a cream solid. (172 mg, 42%).

$^1$H NMR (400.132 MHz, CDCl3) δ1.64 (m, 8H), 1.97 (m, 2H), 2.60 (m, 3H), 2.91 (m, 2H), 3.17 (m, 2H), 3.22 (s, 3H), 3.62 (m, 2H), 3.90 (s, 3H), 4.82 (m, 1H), 6.02 (s, 1H), 7.13 (m, 1H), 7.35 (d, 1H), 7.60 (s, 1H), 7.87 (s, 1H), 8.43 (d, 1H); MS m/z 492 [M+H]$^+$.

Example 58

4-[(6-cyclopentyl-2-methyl-3-oxo-2,6,8,10-tetrazabicyclo[5.4.0]undeca-8,10,12-trien-9-yl)amino]-N-(4-diethylaminocyclohexyl)-3-methoxy-benzamide 4-[(2-cyclopentyl-6-methyl-5-oxo-2,6,9,11-tetrazabicyclo[5.4.0]undeca-7,9,11-trien-10-yl)amino]-3-methoxybenzoic acid (Example 111, 100 mg, 0.24 mmol), N,N-diethylcyclohexane-1,4-diamine (ABChem, 46 mg, 0.28 mmol), HATU (111 mg, 0.29 mmol) and DIPEA (127 uL, 0.73 mmol) and DMF (3 mL) were combined and stirred at room temperature for overnight. Solvent was evaporated and the residues partitioned between DCM (2 mL) and sat. aq. Bicarb. (2 mL), gravity filtered through a PTFE cup, solvent evaporated and the residue purified by reverse phase HPLC to give the title compound as a cream solid (114 mg, 83%)

MS m/z 564 [M+H]+. Retention Time 2.20 minutes

The following examples were prepared by an analogous process to that used in the preparation of Example 58 utilising the appropriate amines

Example 59

4-[(6-cyclopentyl-2-methyl-3-oxo-2,6,8,10-tetrazabicyclo[5.4.0]undeca-8,10,12-trien-9-yl)amino]-3-methoxy-N-[(1S,5R)-9-methyl-9-azabicyclo[3.3.1]non-7-yl]benzamide Amine available from Chontech $^1$H NMR (399.902 MHz, CDCl3) δ1.03 (m, 2H), 1.30 (m, 2H), 1.54 (m, 2H), 1.60-1.80 (m, 6H), 1.98 (m, 2H), 2.05 (m, 2H), 2.53 (m, 5H), 2.67 (m, 2H), 3.09 (m, 2H), 3.29 (s, 3H), 3.69 (m, 2H), 3.97 (s, 3H), 4.51 (m, 1H), 4.90 (m, 1H), 5.78

(d, 1H), 7.23 (m, 1H), 7.44 (m, 1H), 7.66 (s, 1H), 7.94 (s, 1H), 8.49 (d, 1H); MS m/z 548 [M+H]+.

Example 60

4-[(6-cyclopentyl-2-methyl-3-oxo-2,6,8,10-tetrazabicyclo[5.4.0]undeca-8,10,12-trien-9-yl)amino]-N-(4-dimethylaminocyclohexyl)-3-methoxy-benzamide Amine available from ABChem
MS m/z 536 [M+H]+. Retention Time 1.92 minutes

Example 61

4-[(6-cyclopentyl-2-methyl-3-oxo-2,6,8,10-tetrazabicyclo[5.4.0]undeca-8,10,12-trien-9-yl)amino]-N-(1-ethyl-4-piperidyl)-3-methoxy-benzamide 4-[(2-cyclopentyl-6-methyl-5-oxo-2,6,9,11-tetrazabicyclo[5.4.0]undeca-7,9,11-trien-10-yl)amino]-3-methoxy-N-(4-piperidyl)benzamide (Example 41; 80 mg, 0.16 mmol), Ethyl Bromide (ABCR, 13 uL, 0.18 mmol), Triethylamine (0.45 uL, 0.32 mmol) and DMF (3 mL) were combined and heated by microwave irradiation at 75° C. for 1 hr and then at 80° C. for 30 minutes. The reaction mixture was purified by reverse phase HPLC to give the title compound as a white solid (56 mg, 66%)

$^1$H NMR (399.902 MHz, CDCl3) δ1.10 (t, 3H), 1.53-1.80 (m, 8H), 2.09 (m, 6H), 2.44 (m, 2H), 2.67 (m, 2H), 2.92 (m, 2H), 3.29 (s, 3H), 3.69 (m, 2H), 4.00 (m, 4H), 4.90 (m, 1H), 5.90 (d, 1H), 7.22 (m, 1H), 7.42 (m, 1H), 7.66 (s, 1H), 7.94 (s, 1H), 8.50 (d, 1H); MS m/z 522 [M+H]+.

Example 62

4-[(6-cyclopentyl-2-methyl-3-oxo-2,6,8,10-tetrazabicyclo[5.4.0]undeca-8,10,12-trien-9-yl)amino]-3-methoxy-N-[(3R)-1-methylpyrrolidin-3-yl]benzamide To 4-[(6-cyclopentyl-2-methyl-3-oxo-2,6,8,10-tetrazabicyclo[5.4.0]undeca-8,10,12-trien-9-yl)amino]-3-methoxy-N-[(3R)-pyrrolidin-3-yl]benzamide (Example 55, 140 mg, 0.29 mmol) dissolved in THF (2 mL) was added acetic acid (17 uL, 0.29 mmol) followed by aqueous formaldehyde (1 mL). The reaction mixture was stirred at room temperature for 30 mins and sodium triacetoxyborohydride (100 mg, 0.47 mmol) added and the reaction mixture stirred for a further 2 hrs. The solvent was evaporated and the residue neutralised with sat. aq. sodium bicarbonate and extracted with DCM (2×5 ml), gravity filtered through a PTFE cup and solvent evaporated. The resultant material was purified by reverse phase HPLC to give the title compound as a white solid (97 mg, 67%)

$^1$H NMR (399.902 MHz, CDCl3) δ1.60-1.80 (m, 7H), 2.05 (m, 2H), 2.22 (m, 1H), 2.38 (s, 3H), 2.44 (m, 1H), 2.55 (m, 1H), 2.67 (m, 2H), 2.77 (m, 1H), 2.96 (m, 1H), 3.29 (s, 3H), 3.69 (m, 2H), 3.97 (s, 3H), 4.69 (m, 1H), 4.91 (m, 1H), 6.45 (d, 1H), 7.27 (m, 1H), 7.43 (m, 1H), 7.67 (s, 1H), 7.94 (s, 1H), 8.50 (d, 1H); MS m/z 494 [M+H]+.

The following example was prepared by an analogous process to that used in the preparation of Example 62 utilising the pyrrolidine analogue from Example 56

Example 63

4-[(6-cyclopentyl-2-methyl-3-oxo-2,6,8,10-tetrazabicyclo[5.4.0]undeca-8,10,12-trien-9-yl)amino]-3-methoxy-N-[(3S)-1-methylpyrrolidin-3-yl]benzamide $^1$H NMR (399.902 MHz, CDCl$_3$) δ1.60-1.80 (m, 7H), 2.05 (m, 2H), 2.22 (m, 1H), 2.38 (s, 3H), 2.44 (m, 1H), 2.55 (m, 1H), 2.67 (m, 2H), 2.77 (m, 1H), 2.96 (m, 1H), 3.29 (s, 3H), 3.69 (m, 2H), 3.97 (s, 3H), 4.68 (m, 1H), 4.91 (m, 1H), 6.45 (d, 1H), 7.27 (m, 1H), 7.43 (m, 1H), 7.67 (s, 1H), 7.94 (s, 1H), 8.50 (d, 1H); MS m/z 494 [M+H]+.

Example 64

4-[(6-cyclopentyl-2-methyl-3-oxo-2,6,8,10-tetrazabicyclo[5.4.0]undeca-8,10,12-trien-9-yl)amino]-3-methoxy-N-[(1S,5R)-3-methyl-3-azabicyclo[3.1.0]hex-6-yl]benzamide To N-[(1S,5R)-3-azabicyclo[3.10]hex-6-yl]-4-[(6-cyclopentyl-2-methyl-3-oxo-2,6,8,10-tetrazabicyclo[5.4.0]undeca-8,10,12-trien-9-yl)amino]-3-methoxy-benzamide (Example 57, 114 mg, 0.23 mmol) dissolved in THF (2 mL) was added acetic acid (13 uL, 0.23 mmol) (material came out of solution), followed by aqueous formaldehyde (0.5 mL, material all dissolved again). The reaction mixture was stirred at room temperature for 30 mins and sodium triacetoxyborohydride (100 mg, 0.47 mmol) added and the reaction mixture stirred for a further 2 hrs. The solvent was evaporated and the residue neutralised with sat. aq. sodium bicarbonate and extracted with DCM (15 mL), filtered through a PTFE cup and evaporated. The resultant material was purified by reverse phase HPLC.

$^1$H NMR (399.902 MHz, CDCl$_3$) δ1.56-1.80 (m, 8H), 2.04 (m, 2H), 2.30 (s, 3H), 2.39 (m, 2H), 2.66 (m, 2H), 3.12 (m, 1H), 3.17 (m, 2H), 3.29 (s, 3H), 3.69 (m, 2H), 3.96 (s, 3H), 4.89 (m, 1H), 6.06 (s, 1H), 7.18 (m, 1H), 7.43 (m, 1H), 7.66 (s, 1H), 7.94 (s, 1H), 8.48 (d, 1H); MS m/z 506 [M+H]+.

Example 65

Methyl(1S,3R)-3-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]cyclopentane-1-carboxylate 4-[(2-cyclopentyl-6-methyl-5-oxo-2,6,9,11-tetrazabicyclo[5.4.0]undeca-7,9,11-trien-10-yl)amino]-3-methoxy-benzoic acid (Example 111_, 1.1 g, 2.7 mmol), methyl(1S,3R)-3-aminocyclopentane-1-carboxylate (Intermediate 31; 528 mg, 2.94 mmol), HATU (1.22 g, 3.22 mmol) and DIPEA (1.86 mL, 10.68 mmol) and DMF (10 mL) were combined and stirred at room temperature overnight. Solvent was evaporated and the residue partitioned between saturated sodium carbonate and DCM then gravity filtered through a PTFE cup. The organic phase was passed through a silica pad eluting with EtOAc. Fractions containing product were combined and evaporated to give a brown gum which was dissolved in MeOH and added to a 50 g SCX-2 column pre-wet with MeOH (2 column volumes). Flushed with MeOH (2 column volumes) and product eluted with 2M ammonia in MeOH. Solvent was evaporated to a yellow gum, ether was added then re-evaporated to give the title compound as a yellow foam (1.21 g, 84%)

¹H NMR (399.902 MHz, CDCl₃) δ1.62 (m, 2H), 1.75 (m, 4H), 1.95 (m, 4H), 2.02-2.22 (m, 4H), 2.67 (m, 2H), 3.02 (m, 1H), 3.29 (s, 3H), 3.69 (m, 2H), 3.72 (s, 3H), 3.99 (s, 3H), 4.60 (m, 1H), 4.91 (m, 1H), 7.25 (m, 1H), 7.38 (m, 1H), 7.49 (m, 1H), 7.67 (s, 1H), 7.94 (s, 1H), 8.53 (d, 1H); MS m/z 537 [M+H]+.

Example 66

4-[(6-cyclopentyl-2-methyl-3-oxo-2,6,8,10-tetrazabicyclo[5.4.0]undeca-8,10,12-trien-9-yl)amino]-N-[2-(dipropan-2-ylamino)ethyl]-3-methoxy-benzamide A solution of 4-[(2-cyclopentyl-6-methyl-5-oxo-2,6,9,11-tetrazabicyclo[5.4.0]undeca-7,9,11-trien-10-yl)amino]-3-methoxy-benzoic acid (Example 111__, 100 mg, 0.24 mmol), DIPEA (0.127 mL, 0.73 mmol) and HATU (120 mg, 0.32 mmol) in DMF (2 mL) was stirred at ambient temperature for 10 mins. The pale brown solution was add to N,N-dipropan-2-ylethane-1,2-diamine (ABCR, 43 mg, 0.3 mmol) and the resulting solution stirred at ambient temperature for 18 hours. The reaction solution was purified by reverse phase HPLC to give the title compound as a white solid (43 mg, 33%); MS m/z 538 [M+H]+. Retention Time 2.49 mins.

The following examples were prepared by an analogous process to that used in the preparation of Example 66, utilising the appropriate amines. NMR data was obtained on a selection of compounds as indicated.

Example 67

4-[(6-cyclopentyl-2-methyl-3-oxo-2,6,8,10-tetrazabicyclo[5.4.0]undeca-8,10,12-trien-9-yl)amino]-3-methoxy-N-pyridin-4-yl-benzamide

Example 68

4-[(6-cyclopentyl-2-methyl-3-oxo-2,6,8,10-tetrazabicyclo[5.4.0]undeca-8,10,12-trien-9-yl)amino]-3-methoxy-N-(3-pyrrolidin-1-ylpropyl)benzamide

Example 69

4-[(6-cyclopentyl-2-methyl-3-oxo-2,6,8,10-tetrazabicyclo[5.4.0]undeca-8,10,12-trien-9-yl)amino]-3-methoxy-N-[3-(1-piperidyl)propyl]benzamide

Example 70

N-[3-(azepan-1-yl)propyl]-4-[(6-cyclopentyl-2-methyl-3-oxo-2,6,8,10-tetrazabicyclo[5.4.0]undeca-8,10,12-trien-9-yl)amino]-3-methoxy-benzamide

Example 71

4-[(6-cyclopentyl-2-methyl-3-oxo-2,6,8,10-tetrazabicyclo[5.4.0]undeca-8,10,12-trien-9-yl)amino]-3-methoxy-N-[(1S,5R)-8-methyl-8-azabicyclo[3.2.1]oct-3-yl]benzamide

Example 72

4-[(6-cyclopentyl-2-methyl-3-oxo-2,6,8,10-tetrazabicyclo[5.4.0]undeca-8,10,12-trien-9-yl)amino]-3-methoxy-N-(1,2,2,6,6-pentamethyl-4-piperidyl)benzamide

Example 73

4-[(6-cyclopentyl-2-methyl-3-oxo-2,6,8,10-tetrazabicyclo[5.4.0]undeca-8,10,12-trien-9-yl)amino]-3-methoxy-N-[1-(1-piperidyl)propan-2-yl]benzamide

Example 74

4-[(6-cyclopentyl-2-methyl-3-oxo-2,6,8,10-tetrazabicyclo[5.4.0]undeca-8,10,12-trien-9-yl)amino]-3-methoxy-N-pyridin-3-yl-benzamide

Example 75

4-[(6-cyclopentyl-2-methyl-3-oxo-2,6,8,10-tetrazabicyclo[5.4.0]undeca-8,10,12-trien-9-yl)amino]-3-methoxy-N-[2-methyl-2-(1-piperidyl)propyl]benzamide

Example 76

4-[(6-cyclopentyl-2-methyl-3-oxo-2,6,8,10-tetrazabicyclo[5.4.0]undeca-8,10,12-trien-9-yl)amino]-3-methoxy-N-(pyridin-3-ylmethyl)benzamide

Example 77

4-[(6-cyclopentyl-2-methyl-3-oxo-2,6,8,10-tetrazabicyclo[5.4.0]undeca-8,10,12-trien-9-yl)amino]-3-methoxy-N-(4-methoxyphenyl)benzamide

Example 78

4-[(6-cyclopentyl-2-methyl-3-oxo-2,6,8,10-tetrazabicyclo[5.4.0]undeca-8,10,12-trien-9-yl)amino]-N-(3-diethylaminopropyl)-3-methoxy-benzamide 1H NMR (400.132 MHz, DMSO-d₆) δ 0.95 (t, 6H), 1.66 (m, 8H), 1.94 (m, 2H), 2.45 (m, 6H), 2.59 (m, 2H), 3.17 (s, 3H), 3.63 (m, 2H), 3.94 (s, 3H), 4.81 (m, 1H), 7.45 (d, 2H), 7.48 (s, 1H), 7.73 (s, 1H), 8.08 (s, 1H), 8.38 (s, 1H), 8.38 (d, 2H)

Example 79

4-[(6-cyclopentyl-2-methyl-3-oxo-2,6,8,10-tetrazabicyclo[5.4.0]undeca-8,10,12-trien-9-yl)amino]-3-methoxy-N-[2-(1-methylpyrrolidin-2-yl)ethyl]benzamide

Example 80

4-[(6-cyclopentyl-2-methyl-3-oxo-2,6,8,10-tetrazabicyclo[5.4.0]undeca-8,10,12-trien-9-yl)amino]-3-methoxy-N-(pyridin-4-ylmethyl)benzamide

Example 81

4-[(6-cyclopentyl-2-methyl-3-oxo-2,6,8,10-tetrazabicyclo[5.4.0]undeca-8,10,12-trien-9-yl)amino]-3-methoxy-N-(2-methyl-1-pyrrolidin-1-yl-propan-2-yl)benzamide ¹H NMR (400.132 MHz, DMSO-d6) δ 1.37 (s, 6H), 1.67 (m, 10H), 1.94 (m, 2H), 2.60 (m, 6H), 2.78 (s, 2H), 3.17 (s, 3H), 3.63 (m, 2H), 3.94 (s, 3H), 4.80 (m, 1H), 7.37 (d, 1H), 7.42 (s, 1H), 7.48 (s, 1H), 7.72 (s, 1H), 8.08 (s, 1H), 8.36 (d, 1H)

Example 82

4-[(6-cyclopentyl-2-methyl-3-oxo-2,6,8,10-tetrazabicyclo[5.4.0]undeca-8,10,12-trien-9-yl)amino]-N-[[(2S)-1-(cyclopropylmethyl)pyrrolidin-2-yl]methyl]-3-methoxy-benzamide $^1$H NMR (400.132 MHz, DMSO-d$_6$) δ 0.01 (m, 2H), 0.34 (m, 2H), 0.80 (m, 1H), 1.59 (m, 10H), 1.84 (m, 2H), 1.96 (m, 1H), 2.12 (m, 1H), 2.50 (m, 3H), 2.64 (m, 1H), 3.01 (m, 2H), 3.08 (s, 3H), 3.32 (m, 1H), 3.53 (m, 2H), 3.84 (s, 3H), 4.71 (m, 1H), 7.36 (d, 1H), 7.39 (s, 1H), 7.63 (s, 1H), 7.98 (s, 1H), 8.12 (t, 1H), 8.28 (d, 1H)

Example 83

4-[(6-cyclopentyl-2-methyl-3-oxo-2,6,8,10-tetrazabicyclo[5.4.0]undeca-8,10,12-trien-9-yl)amino]-3-methoxy-N-[[1-(pyrrolidin-1-ylmethyl)cyclopropyl]methyl]benzamide $^1$H NMR (400.132 MHz, DMSO-d$_6$) δ 0.29 (s, 2H), 0.51 (s, 2H), 1.66 (m, 10H), 1.94 (m, 2H), 2.43 (s, 2H), 2.51 (m, 4H), 2.59 (m, 2H), 3.18 (s, 3H), 3.37 (d, 2H), 3.63 (m, 2H), 3.95 (s, 3H), 4.82 (m, 1H), 7.38 (d, 1H), 7.47 (s, 1H), 7.74 (s, 1H), 8.09 (s, 1H), 8.38 (d, 1H), 8.49 (t, 1H).

Example 84

4-[(6-cyclopentyl-2-methyl-3-oxo-2,6,8,10-tetrazabicyclo[5.4.0]undeca-8,10,12-trien-9-yl)amino]-3-methoxy-N-[(1-methyl-3-piperidyl)methyl]benzamide $^1$H NMR (400.132 MHz, DMSO-d$_6$) δ 0.92 (m, 1H), 1.44 (m, 1H), 1.73 (m, 10H), 1.94 (m, 2H), 2.13 (s, 3H), 2.64 (m, 5H), 3.15 (m, 2H), 3.18 (s, 3H), 3.63 (m, 2H), 3.95 (s, 3H), 4.81 (m, 1H), 7.49 (m, 2H), 7.73 (s, 1H), 8.08 (s, 1H), 8.32 (t, 1H), 8.38 (d, 1H)

Example 85

4-[(6-cyclopentyl-2-methyl-3-oxo-2,6,8,10-tetrazabicyclo[5.4.0]undeca-8,10,12-trien-9-yl)amino]-3-methoxy-N-[2-(1-methyl-2-piperidyl)ethyl]benzamide $^1$H NMR (400.132 MHz, DMSO-d$_6$) δ 1.45 (m, 14H), 1.95 (m, 4H), 2.21 (s, 3H), 2.59 (m, 2H), 2.76 (m, 1H), 3.17 (s, 3H), 3.31 (m, 2H), 3.63 (m, 2H), 3.94 (s, 3H), 4.81 (m, 1H), 7.46 (m, 2H), 7.72 (s, 1H), 8.08 (s, 1H), 8.35 (t, 1H), 8.38 (d, 1H)

| Example | $R^5{}_m$—$L_n$— | Supplier or Source | MS m/z [M + H]$^+$ | Retention time (Minutes) |
|---|---|---|---|---|
| 67 | (4-pyridyl) | Aldrich | 488 | 1.97 |
| 68 | (pyrrolidin-1-yl-propyl) | ABCR | 522 | 2.01 |
| 69 | (piperidin-1-yl-propyl) | ABCR | 536 | 2.17 |
| 70 | (azepan-1-yl-propyl) | ABCR | 550 | 2.33 |

-continued
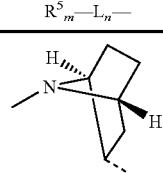
| Example | $R^5{}_m$—$L_n$— | Supplier or Source | MS m/z [M + H]$^+$ | Retention time (Minutes) |
|---|---|---|---|---|
| 71 | 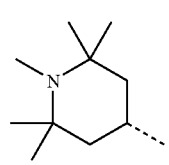 | Flurochem | 534 | 1.85 |
| 72 | 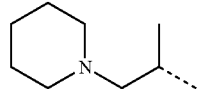 | ABCR | 564 | 2.28 |
| 73 | 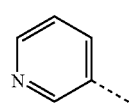 | Journal of the Chemical Society (1947), p 1511-13. | 536 | 2.31 |
| 74 | 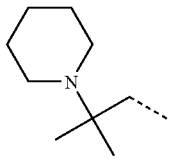 | Aldrich | 488 | 1.96 |
| 75 | 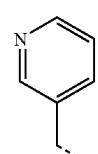 | Matrix | 550 | 2.67 |
| 76 | 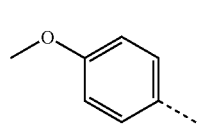 | Aldrich | 502 | 1.81 |
| 77 | 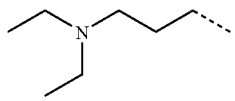 | Aldrich | 517 | 2.35 |
| 78 | 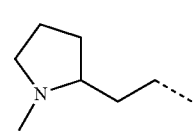 | Aldrich | 524 | 2.11 |
| 79 | | Aldrich | 522 | 1.83 |

| Example | R⁵ₘ—Lₙ— | Supplier or Source | MS m/z [M + H]⁺ | Retention time (Minutes) |
|---------|---------|---------------------|------------------|--------------------------|
| 80 | 4-pyridylmethyl | Aldrich | 502 | 1.73 |
| 81 | (pyrrolidin-1-yl)-neopentyl | Flurochem | 536 | 2.64 |
| 82 | (2S)-1-(cyclopropylmethyl)pyrrolidin-2-yl | Intermediate 32 | 548 | 2.85 |
| 83 | 1-(pyrrolidin-1-ylmethyl)cyclopropyl | Intermediate 33 | 548 | 3.01 |
| 84 | (1-methylpiperidin-3-yl)methyl | Chembridge | 522 | 2.19 |
| 85 | 2-(1-methylpiperidin-2-yl)ethyl | Chembridge | 536 | 2.39 |

Example 86

4-[(6-cyclopentyl-2-methyl-3-oxo-2,6,8,10-tetrazabicyclo[5.4.0]undeca-8,10,12-trien-9-yl)amino]-3-methoxy-N-(1-tert-butyl-4-piperidyl)benzamide A solution of N-[(1S,5R)-3-azabicyclo[3.1.0]hex-6-yl]-4-[(6-cyclopentyl-2-methyl-3-oxo-2,6,8,10-tetrazabicyclo[5.4.0]undeca-8,10,12-trien-9-yl)amino]-3-methoxy-benzamide (Example 57, 250 mg, 0.61 mmol), 1-tert-butylpiperidin-4-amine (Activate, 96 mg, 0.61 mmol), HATU (349 mg, 0.92 mmol) and DIPEA (321 uL, 1.83 mmol) in DMF (5 mL) was stirred at room temperature overnight. The reaction mixture was loaded on to an SCX-3 column pre-wet with methanol. The column was washed with methanol and then with 2% 7N ammonia/methanol to elute the crude product. The product containing fractions were evaporated and the resultant material purified by reverse phase HPLC to give the title compound as a white solid (137 mg, 40.8%).

$^1$H NMR (399.9 MHz, DMSO-d$_6$) δ1.04 (9H, s), 1.55 (2H, s), 1.62-1.63 (3H, m), 1.73 (3H, d), 1.80 (2H, d), 1.95 (2H, t), 2.10 (2H, t), 2.60 (2H, t), 3.01 (2H, d), 3.18 (3H, s), 3.62-3.64 (2H, t), 3.72 (1H, m), 3.95 (3H, s), 4.79-4.84 (1H, m), 7.46 (1H, d), 7.50 (1H, d), 7.73 (1H, s), 8.02 (1H, d), 8.09 (1H, s), 8.39 (1H, d); MS m/z 549 [M+H]+.

Example 87

(1S,3R)-3-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]cyclopentane-1-carboxylic acid To a solution of Methyl(1S,3R)-3-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]cyclopentane-1-carboxylate (Example 65, 1.21 g, 2.25 mmol) in 4:1 THF/water (20 mL) was added lithium hydroxide (472 mg, 11.25 mmol) and the reaction mixture stirred at room temperature overnight. The solvent was evaporated and the residue diluted with water. IM citric acid was added until precipitation ceased (pH 3-4) and the resultant suspension stirred for 20 minutes. The resulting cream precipitate was filtered off, washed with water followed by isohexane and dried under vacuum to yield the title compound (1.08 g, 92%)

$^1$H NMR (399.902 MHz, DMSO-d$_6$) δ1.62-1.95 (m, 12H), 2.07 (m, 1H), 2.59 (m, 3H), 2.72 (m, 2H), 3.18 (s, 3H), 3.63 (m, 2H), 3.95 (s, 3H), 4.28 (m, 1H), 4.81 (m, 1H), 7.51 (m, 2H), 7.74 (s, 1H), 8.09 (s, 1H), 8.38 (d, 1H), 8.85 (s, 1H); MS m/z 523 [M+H]+.

Example 88

4-[(6-cyclopentyl-2-methyl-3-oxo-2,6,8,10-tetrazabicyclo[5.4.0]undeca-8,10,12-trien-9-yl)amino]-N-[(1R,3S)-3-(dimethylcarbamoyl)cyclopentyl]-3-methoxy-benzamide A solution of (1S,3R)-3-[[4-[(6-cyclopentyl-2-methyl-3-oxo-2,6,8,10-tetrazabicyclo[5.4.0]undeca-8,10,12-trien-9-yl)amino]-3-methoxy-benzoyl]amino]cyclopentane-1-carboxylic acid (Example 87, 100 mg, 0.19 mmol), HATU (80 mg, 0.21 mmol) and DIPEA (100 uL, 0.73 mmol) in DMF (3 mL) was stirred at room temperature for 10 minutes. Dimethylamine solution in THF (1 mL) was added and the reaction mixture stirred at room temperature overnight. Solvent was evaporated and the resultant material purified by reverse phase HPLC to yield the title compound as a yellow solid (80 mg, 86%)

$^1$H NMR (400.132 MHz, CDCl$_3$) δ1.62 (m, 2H), 1.75 (m, 4H), 1.84 (m, 2H), 2.06 (m, 6H), 2.67 (m, 2H), 2.99 (s, 3H), 3.11 (s, 3H), 3.31 (m, 4H), 3.69 (m, 2H), 3.99 (s, 3H), 4.58 (m, 1H), 4.91 (m, 1H), 7.53 (m, 2H), 7.67 (s, 1H), 7.93 (s, 1H), 8.44 (d, 1H), 8.51 (d, 1H); MS m/z 550 [M+H]+.

Example 89

N-cyclohexyl-4-[(6-cyclopentyl-2-methyl-3-oxo-2,6,8,10-tetrazabicyclo[5.4.0]undeca-8,10,12-trien-9-yl)amino]benzamide A solution of 4-amino-N-cyclohexyl-benzamide (TimTec, 108 mg, 0.5 mmol), 10-Chloro-2-cyclopentyl-6-methyl-2,6,9,11-tetrazabicyclo[5.4.0]undeca-8,10,12-trien-5-one (Intermediate 1, 140 mg, 0.5 mmol) and p-toluenesulphonic acid monohydrate (238 mg, 1.25 mmol) in 4-methyl-2-pentanol (3 ml) was heated at 140° C. for 3 h. The mixture was allowed to cool causing a solid to form. Methanol and DCM were added to give a solution that was absorbed onto an SCX-3 column and washed with methanol. The product with eluted with ammonia/methanol and the product containing fractions were concentrated. Purification by preparative, reverse phase chromatography (Note 1) gave the title compound as a white solid (35 mg, 15%).

$^1$H NMR (399.9 MHz, DMSO-d$_6$) δ1.11-1.19 (1H, m), 1.26-1.37 (4H, m), 1.60-1.85 (11H, m), 1.97-2.01 (2H, m), 2.59 (2H, m), 3.18 (3H, s), 3.62-3.65 (2H, m), 3.72-1.76 (1H, m), 4.85 (1H, m), 7.75-7.81 (4H, m), 7.93 (1H, d), 8.09 (1H, s), 9.44 (1H, s); MS m/z 463 [M+H]+.

Example 90

N-cyclohexyl-4-[(6-cyclopentyl-2-methyl-3-oxo-2,6,8,10-tetrazabicyclo[5.4.0]undeca-8,10,12-trien-9-yl)amino]-3-methoxy-benzamide A solution of HATU (147 mg, 0.385 mmol) in DMA (1 mL) was added to a mixture of 4-[(2-cyclopentyl-6-methyl-5-oxo-2,6,9,11-tetrazabicyclo[5.4.0]undeca-7,9,11-trien-10-yl)amino]-3-methoxy-benzoic acid (Example 111, 144 mg, 0.35 mmol), DIPEA (183 uL, 0.385 mmol) and Cyclohexylamine (Aldrich, 44 mg, 0.44 mmol) in DMA (1 mL). The resulting mixture was stirred at room temperature overnight. The mixture was absorbed onto an SCX column, washed with methanol and eluted with ammonia in methanol. Product containing fractions were concentrated in vacuo. The resultant material was purified by preparative reverse phase HPLC to yield the title compound as a white solid (7 mg, 4%).

m/z 493 [M+H]+. Retention Time 2.57 minutes

Example 91

4-[(6-cyclopentyl-2-methyl-3-oxo-2,6,8,10-tetrazabicyclo[5.4.0]undeca-8,10,12-trien-9-yl)amino]-3-methoxy-N-methyl-benzamide 4-[(2-cyclopentyl-6-methyl-5-oxo-2,6,9,11-tetrazabicyclo[5.4.0]undeca-7,9,11-trien-10-yl)amino]-3-methoxy-benzoic acid (Example 111_, 100 mg, 0.24 mmol), 2M Methylamine in THF (365 uL, 0.73 mmol), HATU (111 mg, 0.29 mmol) and DIPEA (127 uL, 0.73 mmol) and DMF (3 mL) were combined and stirred at ambient temperature overnight. Solvent was evaporated and the residue partitioned between DCM (2 mL) and sat. aq. Bicarb. (2 mL), and gravity filtered through a PTFE cup. The organic phase was added to a silica column, eluting with a gradient of 0-10% MeOH/DCM and solvent evaporated from product containing fractions. The resultant material was purified by reverse phase HPLC to yield the title compound as a white solid. (45 mg, 44%)

$^1$H NMR (400.132 MHz, CDCl$_3$) δ1.62 (m, 6H), 1.98 (m, 2H), 2.60 (m, 2H), 2.95 (d, 3H), 3.22 (s, 3H), 3.62 (m, 2H), 3.90 (s, 3H), 4.83 (m, 1H), 6.00 (d, 1H), 7.17 (m, 1H), 7.37 (d, 1H), 7.59 (s, 1H), 7.87 (s, 1H), 8.44 (d, 1H); MS m/z 454 [M+H]$^+$.

The following example was prepared by an analogous process to that used in the preparation of Example 91 utilising Ammonium Chloride and 3 additional equivalents of DIPEA and collecting the product as a solid precipitated from the work-up procedure with DCM and saturated aqueous Sodium Bicarbonate solution.

Example 92

4-[(6-cyclopentyl-2-methyl-3-oxo-2,6,8,10-tetrazabicyclo[5.4.0]undeca-8,10,12-trien-9-yl)amino]-3-methoxy-benzamide $^1$H NMR (400.132 MHz, DMSO-d$_6$) δ1.73 (m, 6H), 2.00 (m, 2H), 2.64 (m, 2H), 3.23 (s, 3H), 3.68 (m, 2H), 3.99 (s, 3H), 4.86 (m, 1H), 7.22 (s, 1H), 7.57 (m, 2H), 7.78 (s, 1H), 7.92 (s, 1H), 8.13 (s, 1H), 8.44 (d, 1H); MS m/z 411 [M+H]+.

The following examples were prepared by an analogous process to that used in the preparation of Example 66, utilising the appropriate amines. NMR data was obtained on compounds when indicated.

Example 93

4-[(6-cyclopentyl-2-methyl-3-oxo-2,6,8,10-tetrazabicyclo[5.4.0]undeca-8,10,12-trien-9-yl)amino]-3-methoxy-N-propyl-benzamide

Example 94

4-[(6-cyclopentyl-2-methyl-3-oxo-2,6,8,10-tetrazabicyclo[5.4.0]undeca-8,10,12-trien-9-yl)amino]-N-(cyclopropylmethyl)-3-methoxy-benzamide

Example 95

4-[(6-cyclopentyl-2-methyl-3-oxo-2,6,8,10-tetrazabicyclo[5.4.0]undeca-8,10,12-trien-9-yl)amino]-3-methoxy-N-propan-2-yl-benzamide $^1$H NMR (400.132 MHz, DMSO-$d_6$) δ 1.19 (d, 6H), 1.67 (m, 6H), 1.95 (m, 2H), 2.59 (m, 2H), 3.18 (s, 3H), 3.63 (m, 2H), 3.95 (s, 3H), 4.12 (m, 1H), 4.82 (m, 1H), 7.49 (m, 2H), 7.72 (s, 1H), 8.04 (d, 1H), 8.08 (s, 1H), 8.38 (d, 1H)

Example 96

N-benzyl-4-[(6-cyclopentyl-2-methyl-3-oxo-2,6,8,10-tetrazabicyclo[5.4.0]undeca-8,10,12-trien-9-yl)amino]-3-methoxy-benzamide

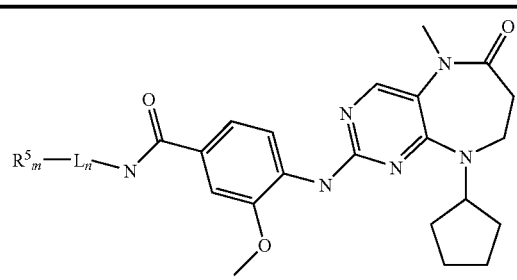

| Example | $R^5_m$—$L_n$— | Supplier Or Source | MS m/z [M + H]+ | Retention time (Minutes) |
|---|---|---|---|---|
| 93 | | Aldrich | 453 | 2.04 |
| 94 | | Aldrich | 465 | 2.09 |
| 5 | | Aldrich | 453 | 2.04 |
| 96 | | ABCR | 501 | 2.31 |

Example 97

4-[(6-cyclopentyl-2-methyl-3-oxo-2,6,8,10-tetrazabicyclo[5.4.0]undeca-8,10,12-trien-9-yl)amino]benzamide 4-amino-N-cyclohexyl-benzamide (TimTec, 108 mg, 0.5 mmol), 10-Chloro-2-cyclopentyl-6-methyl-2,6,9,11-tetrazabicyclo[5.4.0]undeca-8,10,12-trien-5-one (Intermediate 1, 100 mg, 0.36 mmol), the 4-aminobenzamide (Aldrich, 59 mg, 0.43 mmol) and p-toluenesulphonic acid (137 mg, 0.72 mmol) were heated together in 4-methyl-2-pentanol (4 ml) at 120° C. for 22 hours. The reaction was cooled to ambient temperature and passed down a 5 g SCX-2 column pre-wet with methanol. The product was eluted with 2M NH$_3$/MeOH and solvent evaporated. The resultant material was purified by reverse phase HPLC to yield the title compound as a white solid (37 mg, 27%)

$^1$H NMR (400.132 MHz, DMSO-$d_6$) δ 1.67 (m, 6H), 1.97 (m, 2H), 2.59 (m, 2H), 3.18 (s, 3H), 3.63 (m, 2H), 4.84 (m, 1H), 7.08 (s, 1H), 7.77 (s, 1H), 7.79 (s, 4H), 8.08 (s, 1H), 9.46 (s, 1H); MS m/z 381 [M+H]$^+$.

The following example was prepared by an analogous process to that used in the preparation of Example 66 utilising the appropriate amine.

Example 98

N-cyclobutyl-4-[(6-cyclopentyl-2-methyl-3-oxo-2,6,8,10-tetrazabicyclo[5.4.0]undeca-8,10,12-trien-9-yl)amino]-3-methoxy-benzamide $^1$H NMR (400.132 MHz, DMSO-$d_6$) δ 1.67 (m, 8H), 1.95 (m, 2H), 2.09 (m, 2H), 2.23 (m, 2H), 2.59 (m, 2H), 3.18 (s, 3H), 3.63 (m, 2H), 3.95 (s, 3H), 4.43 (m, 1H), 4.82 (m, 1H), 7.48 (m, 2H), 7.72 (s, 1H), 8.09 (s, 1H), 8.41 (m, 2H); MS m/z 465 [M+H]$^+$.

Example 99

4-[(6-cyclopentyl-2-methyl-3-oxo-2,6,8,10-tetrazabicyclo[5.4.0]undeca-8,10,12-trien-9-yl)amino]-3-methoxy-N-phenyl-benzamide 10-Chloro-2-cyclopentyl-6-methyl-2,6,9,11-tetrazabicyclo[5.4.0]undeca-8,10,12-trien-5-one (Intermediate 1, 100 mg, 0.36 mmol), 4-amino-3-methoxy-N-phenyl-benzamide (Apin, 104 mg, 0.43 mmol) and p-toluenesulphonic acid monohydrate (137 mg, 0.72 mmol) were vortexed and heated together in 4-methyl-2-pentanol (4 mL) at 100° C. for 24 hours. The crude reaction mixture was loaded onto an SCX-2 (5 g) column pre-wet with MeOH. The column was washed with MeOH and the product eluted with 2M NH$_3$/MeOH. Solvent was evaporated and the resultant material was purified by reverse phase HPLC to yield the title compound as a white solid (64 mg, 36%). MS m/z 487 [M+H]$^+$. Retention Time 3.81 minutes

Example 100

4-[(6-cyclopentyl-2-methyl-3-oxo-2,6,8,10-tetrazabicyclo[5.4.0]undeca-8,10,12-trien-9-yl)amino]-N-propan-2-yl-benzamide 10-Chloro-2-cyclopentyl-6-methyl-2,6,9,11-tetrazabicyclo[5.4.0]undeca-8,10,12-trien-5-one (Intermediate 1, 134 mg, 0.48 mmol), 4-amino-N-propan-2-yl-benzamide (Butt Park, 86 mg, 0.48 mmol) and p-toluenesulphonic acid monohydrate (227 mg, 1.19 mmol) in 4-methyl-2-pentanol (4 mL) were heated at 140° C. for 2 h. The reaction mixture was loaded onto an SCX-3 column pre-wet with methanol. The column was washed with methanol to remove p-toluenesulphonic acid monohydrate and then eluted with 2% 7N ammonia/methanol. Product containing fractions were evaporated and the resultant material purified by reverse phase HPLC to yield the title compound as a white solid (121 mg, 60%).

$^1$H NMR (399.9 MHz, DMSO-$d_6$) δ1.17 (6H, d), 1.63 (4H, m), 1.74 (2H, m), 1.97-1.99 (2H, d), 2.58-2.61 (2H, t), 3.18 (3H, s), 3.62-3.65 (2H, t), 4.07-4.13 (1H, m), 4.85 (1H, m), 7.71-7.82 (4H, m), 7.95-7.97 (1H, d), 8.09 (1H, s), 9.44 (1H, s); MS m/z 423 [M+H]$^+$.

The following examples were prepared by an analogous process to that used in the preparation of Example 100 utilising the appropriate aniline.

Example 101

4-[(6-cyclopentyl-2-methyl-3-oxo-2,6,8,10-tetrazabicyclo[5.4.0]undeca-8,10,12-trien-9-yl)amino]-N-phenyl-benzamide Amine available from Aldrich
$^1$H NMR (399.9 MHz, DMSO-$d_6$) δ1.64-1.67 (4H, m), 1.72-1.75 (2H, m), 1.99 (2H, m), 2.60 (2H, t), 3.19 (3H, s), 3.63 (2H, t), 4.87 (1H, m), 7.09 (1H, t), 7.35 (2H, m), 7.76-7.79 (2H, d), 7.90 (4H, s), 8.11 (1H, s), 9.55 (1H, s), 10.00 (1H, s); MS m/z 423 [M+H]$^+$.

Example 102

4-[(6-cyclopentyl-2-methyl-3-oxo-2,6,8,10-tetrazabicyclo[5.4.0]undeca-8,10,12-trien-9-yl)amino]-N-methyl-benzamide Amine available from TimTec
$^1$H NMR (399.9 MHz, DMSO-$d_6$) δ1.63 (4H, m), 1.70-1.74 (2H, m), 1.97 (2H, m), 2.58-2.61 (2H, t), 2.78 (3H, d), 3.18 (3H, s), 3.62-3.65 (2H, t), 4.84 (1H, m), 7.75 (2H, d), 7.81 (2H, d), 8.09 (1H, s), 8.20 (1H, d), 9.46 (1H, s); MS m/z 395 [M+H]$^+$.

Example 103

6-cyclopentyl-9-[[2-methoxy-4-(2-pyrrolidin-1-yl-ethylamino)phenyl]amino]-2-methyl-2,6,8,10-tetrazabicyclo[5.4.0]undeca-8,10,12-trien-3-one 10-Chloro-2-cyclopentyl-6-methyl-2,6,9,11-tetrazabicyclo[5.4.0]undeca-8,10,12-trien-5-one (Intermediate 1, 140 mg, 0.5 mmol) 2-methoxy-N'-(2-pyrrolidin-1-ylethyl)benzene-1,4-diamine (Intermediate 35, 141 mg, 0.6 mmol), and p-toluenesulphonic acid monohydrate (227 mg, 1.19 mmol) in 4-methyl-2-pentanol (4 mL) were heated by microwave irradiation at 160° C. for 1 hour. The reaction mixture was absorbed onto an SCX column, washed with methanol and eluted with ammonia in methanol. Product containing fractions were concentrated and the material produced was purified by normal phase chromatography using 0-10% ammonia/methanol to yield the title compound as a solid (100 mg, 42%).

$^1$H NMR (500.13 MHz, DMSO-d6) ä 1.55-1.62 (4H, m), 1.68-1.75 (6H, m), 1.85-1.92 (2H, m), 2.54-2.56 (6H, m), 2.67 (2H, t), 3.15-3.19 (5H, m), 3.58-3.60 (2H, m), 3.80 (3H, s), 4.64-4.71 (1H, m), 4.87 (1H, t), 6.19 (1H, dd), 6.36 (1H, d), 7.12 (1H, s), 7.67 (1H, d), 7.93 (1H, s); MS m/z 480 [M+H]$^+$.

The following examples were prepared by an analogous process to that used in the preparation of Example 103, utilising the appropriate aniline. NMR data is recorded where obtained.

Example 104

6-cyclopentyl-9-[[2-methoxy-4-[methyl-(1-methyl-4-piperidyl)amino]phenyl]amino]-2-methyl-2,6,8,10-tetrazabicyclo[5.4.0]undeca-8,10,12-trien-3-one

Example 105

6-cyclopentyl-9-[[2-methoxy-4-[4-(2-methoxyethyl)piperazin-1-yl]phenyl]amino]-2-methyl-2,6,8,10-tetrazabicyclo[5.4.0]undeca-8,10,12-trien-3-one

Example 106

6-cyclopentyl-9-[[2-methoxy-4-[4-(1-piperidyl)-1-piperidyl]phenyl]amino]-2-methyl-2,6,8,10-tetrazabicyclo[5.4.0]undeca-8,10,12-trien-3-one

Example 107

6-cyclopentyl-9-[[4-(2-dimethylaminoethylamino)-2-methoxy-phenyl]amino]-2-methyl-2,6,8,10-tetrazabicyclo[5.4.0]undeca-8,10,12-trien-3-one $^1$H NMR (400.13 MHz, CDCl$_3$) δ 1.55-1.76 (7H, m), 1.99-2.02 (2H, m), 2.31 (6H, s), 2.60-2.66 (4H, m), 3.19 (2H, t), 3.27 (3H, s), 3.64-3.68 (2H, m), 3.85 (3H, s), 4.80-4.88 (1H, m), 6.23-6.26 (1H, m), 6.29 (1H, d), 7.09 (1H, s), 7.88 (1H, s), 8.03 (1H, d).

Example 108

9-[[4-(4-cyclohexylpiperazin-1-yl)-2-methoxy-phenyl]amino]-6-cyclopentyl-2-methyl-2,6,8,10-tetrazabicyclo[5.4.0]undeca-8,10,12-trien-3-one 1H NMR (400.13 MHz, CDCl$_3$) δ 1.10-1.37 (4H, m), 1.55-1.78 (8H, m), 1.81-1.89 (2H, m), 1.95-2.05 (4H, m), 2.44 (1H, s), 2.65-2.67 (2H, m), 2.85 (4H, s), 3.24 (4H, s), 3.28 (3H, s), 3.66-3.69 (2H, m), 3.89 (3H, s), 4.82-4.91 (1H, m), 6.54-6.57 (2H, m), 7.24 (1H, s), 7.90 (1H, s), 8.19 (1H, d)

Example 109

6-cyclopentyl-9-[[2-methoxy-4-(4-methyl-1,4-diazepan-1-yl)phenyl]amino]-2-methyl-2,6,8,10-tetrazabicyclo[5.4.0]undeca-8,10,12-trien-3-one 1H NMR (400.13 MHz, CDCl$_3$) δ 1.53-1.78 (6H, m), 1.97-2.08 (4H, m), 2.42 (3H, s), 2.62-2.68 (4H, m), 2.75-2.78 (2H, m), 3.27 (3H, s), 3.50 (2H, t), 3.58-3.62 (2H, m), 3.64-3.67 (2H, m), 3.87 (3H, s), 4.81-4.88 (1H, m), 6.27 (1H, d), 6.28 (1H, s), 7.06 (1H, s), 7.88 (1H, m), 8.02 (1H, d)

Example 110
6-cyclopentyl-9-[[2-methoxy-4-(4-pyrrolidin-1-yl-1-piperidyl)phenyl]amino]-2-methyl-2,6,8,10-tetrazabicyclo[5.4.0]undeca-8,10,12-trien-3-one
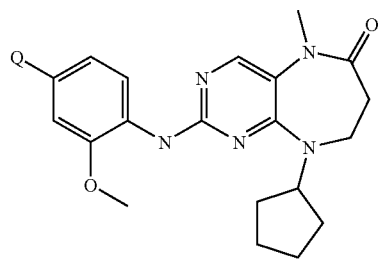
| Example | Q | Source | MS m/z [M + H]+ | Retention time (Minutes) |
|---|---|---|---|---|
| 104 | | Intermediate 36 | 494 | 2.10 |
| 105 | | Intermediate 37 | 510 | 2.14 |
| 106 | | Intermediate 38 | 534 | 2.82 |
| 107 | | Intermediate 39 | 454 | 2.00 |
| 108 | | Intermediate 40 | 534 | 3.49 |

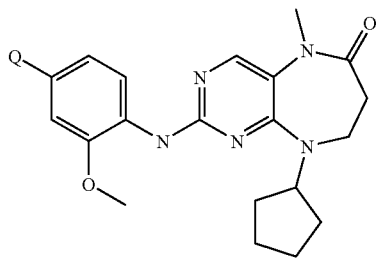

| Example | Q | Source | MS m/z [M + H]+ | Retention time (Minutes) |
|---|---|---|---|---|
| 109 | ![structure] | Intermediate 41 | 480 | 2.33 |
| 110 | ![structure] | Intermediate 42 | 520 | 2.68 |

Example 111

4-[(6-cyclopentyl-2-methyl-3-oxo-2,6,8,10-tetrazabicyclo[5.4.0]undeca-8,10,12-trien-9-yl)amino]-3-methoxy-benzoic acid To a solution of 110-Chloro-2-cyclopentyl-6-methyl-2,6,9,11-tetrazabicyclo[5.4.0]undeca-8,10,12-trien-5-one (Intermediate 1, 10.62 g, 36 mmol) and 4-amino-3-methoxybenzoic acid (Aldrich, 6.795 g, 40.7 mmol) in ethanol (150 mL) was added water (450 mL) and conc hydrochloric acid 96 mL, 72 mmol). The mixture was heated under reflux for 36 hours. The reaction was cooled and a brown solid precipitate formed which was filtered, triturated with cold acetonitrile and dried in vacuo to give the title compound (10.1 g, 68%).

$^1$H NMR (399.9 MHz, DMSO-$d_6$) δ1.55-1.75 (6H, m), 1.87-1.95 (2H, m), 2.71-2.75 (2H, m), 3.18 (3H, s), 3.71-3.76 (2H, m), 3.95 (3H, s), 4.79-4.93 (1H, m), 7.58-7.62 (2H, m), 8.19 (1H, d), 8.19 (1H, s), 9.37 (1H, s); MS m/z 412 [M+H]$^+$.

Example 112

6-cyclopentyl-2-methyl-9-[(2,4,6-trimethoxyphenyl)amino]-2,6,8,10-tetrazabicyclo[5.4.0]undeca-8,10,12-trien-3-one 2,4,6-trimethoxyaniline (Maybridge, 104 mg, 0.56 mmol), 10-Chloro-2-cyclopentyl-6-methyl-2,6,9,11-tetrazabicyclo[5.4.0]undeca-8,10,12-trien-5-one (Intermediate 1, 150 mg, 0.56 mmol) and p-toluenesulphonic acid monohydrate (268 mg, 1.41 mmol) in 4-methyl-2-pentanol (4 mL) were heated at 140° C. for 2 h. The reaction solution was loaded on to an SCX-3 column pre-wet with methanol. The column was washed with methanol to remove p-toluenesulphonic acid monohydrate and then washed with 2% 7N ammonia/methanol to elute the crude product. Product containing fractions were evaporated and the resultant material purified by reverse phase HPLC to yield the title compound as a white solid (140 mg, 58%)

$^1$H NMR (399.9 MHz, DMSO-$d_6$) δ1.32-1.68 (8H, m), 2.46-2.48 (2H, t), 3.13 (3H, s), 3.50 (2H, t), 3.70 (6H, s), 3.79 (3H, s), 4.32 (1H, m), 6.25 (2H, s), 7.37 (1H, s), 7.85 (1H, s); MS m/z 429 [M+H]$^+$.

Example 113

6-cyclopentyl-9-[[2-methoxy-4-[(1-methyl-4-piperidyl)oxy]phenyl]amino]-2-methyl-2,6,8,10-tetrazabicyclo[5.4.0]undeca-8,10,12-trien-3-one 10-Chloro-2-cyclopentyl-6-methyl-2,6,9,11-tetrazabicyclo[5.4.0]undeca-8,10,12-trien-5-one (Intermediate 1, 150 mg, 0.53 mmol), 2-methoxy-4-[(1-methyl-4-piperidyl)oxy] aniline (Intermediate 43 (124 mg, 0.53 mmol) and p-toluenesulphonic acid monohydrate (255 mg, 1.34 mmol) heated in 4-methyl-2-pentanol (4 mL) at 140° C. for 2 h. The reaction solution was loaded on to an SCX-2 column pre-wet with methanol. The column was washed with methanol to remove p-toluenesulphonic acid monohydrate and then washed with 2% 7N ammonia/methanol to elute the crude product. Product containing fractions were evaporated and the resultant material purified by reverse phase HPLC to yield the title compound as a red gum (189 mg, 82%).

$^1$H NMR (399.9 MHz, DMSO-$d_6$) δ1.53-1.56 (4H, m), 1.60 (2H, d), 1.63-1.68 (4H, m), 1.84 (2H, d), 1.92 (2H, d), 2.20 (3H, s), 2.18-2.22 (2H, m), 2.63 (2H, t), 3.15 (3H, s), 3.56-3.59 (2H, t), 3.81 (3H, s), 4.33 (1H, m), 4.64 (1H, m), 6.49-6.52 (1H, m), 6.62 (1H, d), 7.51 (1H, s), 7.82 (1H, d), 7.98 (1H, s); MS m/z 481 [M+H]$^+$.

The following examples were prepared by an analogous process to that used in the preparation of Example 113 utilising the appropriate aniline indicated.

Example 114

6-cyclopentyl-9-[[2-methoxy-4-(1-methylpyrrolidin-3-yl)oxy-phenyl]amino]-2-methyl-2,6,8,10-tetrazabicyclo[5.4.0]undeca-8,10,12-trien-3-one Starting aniline-2-methoxy-4-(1-methylpyrrolidin-3-yl)oxy-aniline Intermediate 45

$^1$H NMR (399.9 MHz, DMSO-$d_6$) δ 1.54 (3H, d), 1.58 (1H, s), 1.66 (2H, s), 1.79-1.83 (2H, m), 1.85 (1H, s), 2.25-2.29 (1H, m), 2.30 (3H, s), 2.43 (1H, m), 2.53-2.56 (2H, t), 2.61-2.65 (1H, m), 2.66-2.68 (1H, m), 2.69-2.70 (1H, m), 2.81-2.85 (1H, m), 3.15 (3H, s), 3.56-3.59 (2H, m), 3.81 (3H, s), 4.65 (1H, m), 4.86-4.89 (1H, m), 6.41-6.44 (1H, m), 6.56 (1H, d), 7.51 (1H, s), 7.82 (1H, d), 7.98 (1H, s); MS m/z 467 [M+H]$^+$.

Example 115

6-cyclopentyl-9-[[2-methoxy-4-(2-morpholin-4-ylethoxy)phenyl]amino]-2-methyl-2,6,8,10-tetrazabicyclo[5.4.0]undeca-8,10,12-trien-3-one Starting aniline-2-methoxy-4-(2-morpholin-4-ylethoxy)aniline Intermediate 47

$^1$H NMR (399.9 MHz, DMSO-$d_6$) δ 1.55 (3H, d), 1.59 (1H, s), 1.67 (2H, s), 1.85 (2H, s), 2.48 (4H, d), 2.53-2.56 (2H, t), 2.69 (2H, t), 3.15 (3H, s), 3.59 (2H, d), 3.59 (4H, d), 3.83 (3H, s), 4.08 (2H, t), 4.67 (1H, s), 6.48-6.51 (1H, m), 6.63 (1H, d), 7.50 (1H, s), 7.86 (1H, d), 7.98 (1H, s); MS m/z 497 [M+H]$^+$.

Example 116

4-[(6-cyclopentyl-2-methyl-3-oxo-2,6,8,10-tetrazabicyclo[5.4.0]undeca-8,10,12-trien-9-yl)amino]-2-(trifluoromethyl)benzonitrile 10-Chloro-2-cyclopentyl-6-methyl-2,6,9,11-tetrazabicyclo[5.4.0]undeca-8,10,12-trien-5-one (Intermediate 1, 157 mg, 0.56 mmol), 4-amino-2-methyl-benzonitrile (Aldrich, 95 mg, 0.51 mmol) and 9,9-Dimethyl-4,5-bis(diphenylphosphino)xanthene (27 mg, 0.05 mmol) were dissolved in 1,4-dioxane (7.5 mL). Caesium carbonate (330 mg, 1.01 mmol) was added and the mixture purged with a stream of nitrogen for 5 minutes. Tris(dibenzylideneacetone) palladium (II) (28 mg, 0.03 mmol) was added and the apparatus was evacuated and backfilled with nitrogen (×3) and then heated at 100° C. for 8 h. The mixture was cooled, filtered and the filtrate absorbed onto an SCX-3 column, washed with methanol and the product eluted with ammonia in methanol. Product containing fractions were concentrated and purified by preparative reverse phase chromatography to give the title compound as a white solid. (21 mg, 10%)

$^1$H NMR (399.9 MHz, DMSO-$d_6$) δ 1.57-1.72 (6H, m), 1.92-2.00 (2H, m), 2.61 (2H, m), 3.19 (3H, s), 3.64-3.66 (2H, m), 4.82-4.90 (1H, m), 7.99-8.07 (2H, m), 8.16 (1H, s), 8.50 (1H, d), 10.15 (1H, s); MS m/z 431 [M+H]$^+$.

Example 117

4-[(6-cyclopentyl-2-methyl-3-oxo-2,6,8,10-tetrazabicyclo[5.4.0]undeca-8,10,12-trien-9-yl)amino]-N-(2-hydroxyethyl)benzenesulfonamide 4-amino-N-(2-hydroxyethyl)benzenesulfonamide (Maybridge; 108 mg, 0.5 mmol), 10-Chloro-2-cyclopentyl-6-methyl-2,6,9,11-tetrazabicyclo[5.4.0]undeca-8,10,12-trien-5-one (Intermediate 1, 140 mg, 0.5 mmol) and p-toluenesulphonic acid monohydrate (238 mg, 1.25 mmol) were heated at 140° C. in 4-methyl-2-pentanol (3 mL) for 3 hours. The mixture was allowed to cool causing a solid to form. Methanol and DCM were added to give a solution that was absorbed onto and SCX-3 column and washed with methanol. The product with eluted with ammonia/methanol and the product containing fractions were concentrated. Purification by preparative, reverse phase chromatography gave the title compound as a white solid (122 mg, 53%).

$^1$H NMR (399.9 MHz, DMSO-$d_6$) δ 1.59-1.74 (6H, d), 1.96-2.01 (2H, m), 2.57-2.61 (2H, m), 2.78 (2H, q), 3.19 (3H, s), 3.35-3.40 (2H, m), 3.62-3.65 (2H, m), 4.63 (1H, t), 4.80-4.88 (1H, m), 7.33 (1H, t), 7.64-7.68 (2H, m), 7.90-7.94 (2H, m), 8.11 (1H, s), 9.65 (1H, s); MS m/z 461 [M+H]$^+$.

The following example was prepared by an analogous process to that used in the preparation of Example 117 utilising the appropriate aniline available from Aldrich.

Example 118

6-cyclopentyl-9-[[4-(2-dimethylaminoethoxy)phenyl]amino]-2-methyl-2,6,8,10-tetrazabicyclo[5.4.0]undeca-8,10,12-trien-3-one $^1$H NMR (399.9 MHz, DMSO-$d_6$) δ 1.55-1.71 (6H, m), 1.89-1.95 (2H, m), 2.22 (6H, s), 2.55-2.57 (2H, m), 2.61 (2H, t), 3.16 (3H, s), 3.58-3.61 (2H, m), 4.00 (2H, t), 4.72-4.81 (1H, m), 6.82-6.86 (2H, m), 7.56-7.60 (2H, m), 8.01 (1H, s), 8.95 (1H, s); MS m/z 425 [M+H]$^+$.

Example 119

N-[4-[(6-cyclopentyl-2-methyl-3-oxo-2,6,8,10-tetrazabicyclo[5.4.0]undeca-8,10,12-trien-9-yl)amino]phenyl]acetamide 10-Chloro-2-cyclopentyl-6-methyl-2,6,9,11-tetrazabicyclo[5.4.0]undeca-8,10,12-trien-5-one (Intermediate 1, 100 mg, 0.36 mmol), N-(4-aminophenyl)acetamide (Aldrich, 64 mg, 0.43 mmol) and p-toluenesulphonic acid (137 mg, 0.72 mmol) were heated together in 4-methyl-2-pentanol (4 mL) at 120° C. for 22 hours. The reactions were cooled to ambient temperature and then passed down a 5 g SCX-2 column pre-wet with methanol. The products were eluted with 2M NH$_3$/MeOH and the solvent evaporated. The resultant material was purified by reverse phase HPLC to yield the title compound as a white solids (22 mg, 16%).

$^1$H NMR (400.132 MHz, DMSO-d6) δ 1.64 (m, 6H), 1.94 (m, 2H), 2.01 (s, 3H), 2.56 (m, 2H), 3.16 (s, 3H), 3.60 (m, 2H), 4.78 (m, 1H), 7.43 (d, 2H), 7.61 (d, 2H), 8.02 (s, 1H), 9.06 (s, 1H), 9.74 (s, 1H); MS m/z 495 [M+H]$^+$.

The following examples were prepared by an analogous process to that used in the preparation of Example 119 utilising the appropriate substituted anilines. NMR analysis was undertaken where indicated.

Example 120

6-cyclopentyl-9-[(4-methoxyphenyl)amino]-2-methyl-2,6,8,10-tetrazabicyclo[5.4.0]undeca-8,10,12-trien-3-one $^1$H NMR (400.132 MHz, DMSO-d6) δ 1.62 (m, 6H), 1.92 (m, 2H), 2.55 (m, 2H), 3.16 (s, 3H), 3.59 (m, 2H), 3.60 (s, 2H), 3.72 (s, 3H), 4.76 (m, 1H), 6.83 (d, 2H), 7.59 (d, 2H), 8.00 (s, 1H), 8.93 (s, 1H)

Example 121

6-cyclopentyl-2-methyl-9-[(4-morpholin-4-ylphenyl) amino]-2,6,8,10-tetrazabicyclo[5.4.0]undeca-8,10,12-trien-3-one $^1$H NMR (400.132 MHz, DMSO-d6) δ 1.63 (m, 6H), 1.92 (m, 2H), 2.55 (m, 2H), 3.02 (m, 4H), 3.15 (s, 3H), 3.59 (m, 2H), 3.74 (m, 4H), 4.76 (m, 1H), 6.85 (d, 2H), 7.56 (d, 2H), 7.99 (s, 1H), 8.89 (s, 1H); MS m/z 423 [M+H]$^+$.

Example 122

6-cyclopentyl-9-[(4-dimethylaminophenyl)amino]-2-methyl-2,6,8,10-tetrazabicyclo[5.4.0]undeca-8,10,12-trien-3-one

Example 123

4-[(6-cyclopentyl-2-methyl-3-oxo-2,6,8,10-tetrazabicyclo[5.4.0]undeca-8,10,12-trien-9-yl)amino]benzenesulfonamide

Example 124

9-[(1-acetyl-2,3-dihydroindol-5-yl)amino]-6-cyclopentyl-2-methyl-2,6,8,10-tetrazabicyclo[5.4.0]undeca-8,10,12-trien-3-one

Example 125

4-[(6-cyclopentyl-2-methyl-3-oxo-2,6,8,10-tetrazabicyclo[5.4.0]undeca-8,10,12-trien-9-yl)amino]-N-(2-methoxyethyl)benzenesulfonamide $^1$H NMR (400.132 MHz, DMSO-d6) δ 1.66 (m, 6H), 1.96 (m, 2H), 2.59 (m, 2H), 2.88 (m, 2H), 3.17 (s, 3H), 3.18 (s, 3H), 3.30 (m, 2H), 3.63 (m, 2H), 4.83 (m, 1H), 7.44 (t, 1H), 7.66 (d, 2H), 7.91 (d, 2H), 8.10 (s, 1H), 9.64 (s, 1H)

Example 126

9-[(3-chloro-4-morpholin-4-yl-phenyl)amino]-6-cyclopentyl-2-methyl-2,6,8,10-tetrazabicyclo[5.4.0] undeca-8,10,12-trien-3-one

Example 127

6-cyclopentyl-2-methyl-9-[(4-methylsulfonylphenyl) amino]-2,6,8,10-tetrazabicyclo[5.4.0]undeca-8,10,12-trien-3-one $^1$H NMR (400.132 MHz, DMSO-d6) δ 1.67 (m, 6H), 1.98 (m, 2H), 2.60 (m, 2H), 3.15 (s, 3H), 3.18 (s, 3H), 3.64 (m, 2H), 4.85 (m, 1H), 7.77 (d, 2H), 7.98 (d, 2H), 8.11 (s, 1H), 9.74 (s, 1H)

Example 128

9-[[4-(4-acetylpiperazin-1-yl)phenyl]amino]-6-cyclopentyl-2-methyl-2,6,8,10-tetrazabicyclo[5.4.0] undeca-8,10,12-trien-3-one

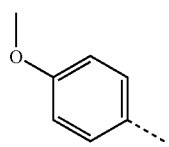

| Example | | Supplier or Source | MS m/z [M + H]$^+$ | Retention Time (Minutes) |
|---|---|---|---|---|
| 120 | (4-methoxyphenyl) | Aldrich | 368 | 2.16 |

-continued
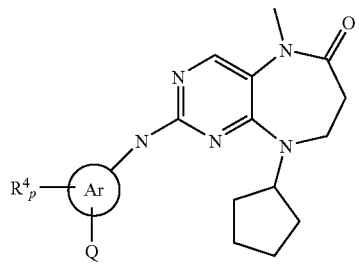
| Example | 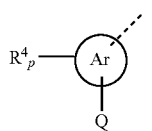 Q | Supplier or Source | MS m/z [M + H]+ | Retention Time (Minutes) |
|---|---|---|---|---|
| 121 | 4-morpholinophenyl | Aldrich | 423 | 1.95 |
| 122 | 4-(dimethylamino)phenyl | Aldrich | 381 | 3.14 |
| 123 | 4-sulfamoylphenyl | ABCR | 417 | 2.6 |
| 124 | 1-acetylindolin-5-yl | Flurochem | 421 | 2.75 |
| 125 | 4-(N-(2-methoxyethyl)sulfamoyl)phenyl | WO2005/116025 | 475 | 2.81 |
| 126 | 3-chloro-4-morpholinophenyl | Flurochem | 457 | 3.26 |
| 127 | 4-(methylsulfonyl)phenyl | Flurochem | 416 | 2.78 |

| Example | $R^4_p$—Ar—Q | Supplier or Source | MS m/z [M + H]⁺ | Retention Time (Minutes) |
|---|---|---|---|---|
| 128 | acetyl-piperazinyl-phenyl | Flurochem | 464 | 2.65 |

Example 129

6-cyclopentyl-2-methyl-9-[(3,4,5-trimethoxyphenyl)amino]-2,6,8,10-tetrazabicyclo[5.4.0]undeca-8,10,12-trien-3-one 3,4,5-trimethoxyaniline (Aldrich, 104 mg, 0.56 mmol), 10-Chloro-2-cyclopentyl-6-methyl-2,6,9,11-tetrazabicyclo[5.4.0]undeca-8,10,12-trien-5-one (Intermediate 1, 150 mg, 0.56 mmol) and p-toluenesulphonic acid monohydrate (268 mg, 1.41 mmol) were heated at 140° C. in 4-methyl-2-pentanol (4 mL) for 2 hours. The reaction solution was loaded onto an SCX-3 column pre-wet methanol. The column was washed with methanol to remove p-toluenesulphonic acid monohydrate and then washed with 2% 7N ammonia/methanol to elute the crude product. The product containing fractions were evaporated and the resultant material purified by reverse phase HPLC to yield the title compound as a purple solid (130 mg, 54%).

¹H NMR (399.9 MHz, DMSO-d₆) δ1.50-1.52 (2H, m), 1.57-1.61 (2H, m), 1.70 (2H, m), 1.95 (2H, m), 2.55-2.58 (2H, t), 3.17 (3H, s), 3.59 (2H, t), 3.63 (3H, s), 3.76 (6H, s), 4.86 (1H, d), 7.09 (2H, s), 8.04 (1H, s), 8.97 (1H, s); MS m/z 429 [M+H]⁺.

The following example was prepared by an analogous process to that used in the preparation of Example 129 utilising the appropriate substituted anilines available as indicated.

Example 130

6-cyclopentyl-2-methyl-9-[(2,3,4-trimethoxyphenyl)amino]-2,6,8,10-tetrazabicyclo[5.4.0]undeca-8,10,12-trien-3-one Substituted aniline available from Apin ¹H NMR (399.9 MHz, DMSO-d₆) δ1.53-1.56 (2H, m), 1.58 (2H, d), 1.67-1.68 (2H, m), 1.88 (2H, t), 2.55-2.57 (2H, m), 3.16 (3H, s), 3.58-3.60 (2H, t), 3.79 (3H, s), 3.78-3.82 (6H, s), 4.69 (1H, m), 6.74 (1H, d), 7.70 (2H, t), 8.00 (1H, s); MS m/z 429 [M+H]⁺.

Example 131

9-[[4-chloro-3-(hydroxymethyl)phenyl]amino]-6-cyclopentyl-2-methyl-2,6,8,10-tetrazabicyclo[5.4.0]undeca-8,10,12-trien-3-one Substituted aniline available from Aldrich ¹H NMR (399.9 MHz, DMSO-d₆) δ1.60 (3H, d), 1.62-1.62 (1H, m), 1.67 (2H, d), 1.96 (2H, s), 2.53-2.59 (2H, t), 3.17 (3H, s), 3.60-3.63 (2H, t), 4.53 (2H, d), 4.88 (1H, m), 5.27 (1H, t), 7.24 (1H, d), 7.62-7.65 (1H, m), 7.96 (1H, d), 8.05 (1H, s), 9.31 (1H, s); MS m/z 402 [M+H]⁺.

Example 132

6-cyclopentyl-2-methyl-9-[(2-pyridin-3-yl-1H-benzoimidazol-5-yl)amino]-2,6,8,10-tetrazabicyclo[5.4.0]undeca-8,10,12-trien-3-one 10-Chloro-2-cyclopentyl-6-methyl-2,6,9,11-tetrazabicyclo[5.4.0]undeca-8,10,12-trien-5-one (Intermediate 1, 134 mg, 0.50 mmol), 2-pyridin-3-yl-1H-benzoimidazol-5-amine (Fluorochem, 117 mg, 0.55 mmol) and cesium carbonate (328 mg, 1.00 mmol) were added to dioxane (4 mL) and the suspension bubbled with nitrogen for 10 minutes. Bis(dibenzylideneacetone)palladium (28 mg, 0.03 mmol) and 9,9-Dimethyl-4,5-bis(diphenylphosphino)xanthene (27 mg, 0.05 mmol) were added and the mixture heated to 110° C. overnight. The mixture was filtered and the filtrate purified by column chromatography with a 5% 7N ammonia in methanol/DCM solvent system. Product containing fractions were combined and evaporated to give the title compound as a solid (73 mg, 32%)

¹H NMR (499.8 MHz, DMSO-d₆ @ 373K) δ1.64 (4H, m), 1.73 (2H, m), 2.00 (2H, m), 2.53-2.56 (2H, t), 3.21 (3H, s), 3.62-3.65 (2H, t), 4.82-4.85 (1H, m), 7.53-7.55 (3H, m), 8.04 (2H, s), 8.45 (1H, d), 8.64-8.65 (1H, m), 8.71 (1H, s), 9.32 (1H, d), 12.51 (1H, s); MS m/z 455 [M+H]$^+$.

Example 133

N-[[4-[(6-cyclopentyl-2-methyl-3-oxo-2,6,8,10-tetrazabicyclo[5.4.0]undeca-8,10,12-trien-9-yl)amino] phenyl]methyl]pyridine-2-carboxamide N-[(4-aminophenyl)methyl]pyridine-2-carboxamide (Intermediate 49: 114 mg, 0.5 mmol), 10-Chloro-2-cyclopentyl-6-methyl-2,6,9,11-tetrazabicyclo[5.4.0]undeca-8,10,12-trien-5-one (Intermediate 1, 141 mg, 0.5 mmol) and p-toluenesulphonic acid monohydrate (239 mg, 1.25 mmol) were heated in 4-methyl-2-pentanol (3 mL) at 140° C. for 2 hours. The mixture was cooled and diluted with methanol/DCM and absorbed on to an SCX-3 column, washed with methanol and eluted with ammonia in methanol. Product containing fractions were concentrated and purred by preparative reverse phase chromatography to give the title compound as a white solid (63 mg, 27%).

$^1$H NMR (399.9 MHz, DMSO-d$_6$) δ1.54-1.71 (6H, m), 1.89-1.96 (2H, m), 2.56-2.58 (2H, m), 3.16 (3H, s), 3.59-3.61 (2H, m), 4.44 (2H, d), 4.79 (1H, m), 7.23 (2H, d), 7.60-7.63 (1H, m), 7.65-7.67 (2H, m), 7.99-8.08 (3H, m), 8.64-8.66 (1H, m), 9.13 (1H, s), 9.18 (1H, t); MS m/z 472 [M+H]$^+$.

The following examples were prepared by an analogous process to that used in the preparation of Example 133 utilising the appropriate substituted anilines available from ABCR Example 134

6-cyclopentyl-2-methyl-9-[[4-(1-piperidylsulfonyl) phenyl]amino]-2,6,8,10-tetrazabicyclo[5.4.0]undeca-8,10,12-trien-3-one $^1$H NMR (399.9 MHz, DMSO-d$_6$) δ1.34-1.39 (2H, m), 1.52-1.75 (10H, m), 1.94-2.00 (2H, m), 2.57-2.61 (2H, m), 2.87 (4H, t), 3.19 (3H, s), 3.62-3.65 (2H, m), 4.84 (1H, m), 7.59 (2H, d), 7.94-7.96 (2H, m), 8.11 (1H, s), 9.71 (1H, s); MS m/z 485 [M+H]$^+$.

Example 135

6-cyclopentyl-2-methyl-9-[[4-(2-morpholin-4-ylethoxy)phenyl]amino]-2,6,8,10-tetrazabicyclo [5.4.0]undeca-8,10,12-trien-3-one $^1$H NMR (399.9 MHz, DMSO-d$_6$) δ1.54-1.72 (6H, m), 1.89-1.95 (2H, m), 2.48 (4H, m), 2.66-2.70 (2H, m), 2.68-2.69 (2H, m), 3.16 (3H, s), 3.59 (6H, m), 4.05 (2H, t), 4.76 (1H, m), 6.84-6.87 (2H, m), 7.57-7.60 (2H, m), 8.01 (1H, s), 8.95 (1H, s); MS m/z 467 [M+H]$^+$.

Example 136 tert-butyl N-[[3-[(6-cyclopentyl-2-methyl-3-oxo-2,6,8,10-tetrazabicyclo[5.4.0]undeca-8,10,12-trien-9-yl) amino]phenyl]methyl]carbamate 10-Chloro-2-cyclopentyl-6-methyl-2,6,9,11-tetrazabicyclo[5.4.0]undeca-8,10,12-trien-5-one (Intermediate 1, 155 mg, 0.55 mmol), tert-butyl N-[(3-aminophenyl)methyl]carbamate (Chembasics, 111 mg, 0.50 mmol) and 9,9-Dimethyl-4,5-bis(diphenylphosphino)xanthene (27 mg, 0.05 mmol) were dissolved in 1,4-dioxane (7.5 mL) Caesium carbonate (326 mg, 1.0 mmol) was added and the mixture purged with a stream of nitrogen for 5 minutes.

Tris(dibenzylideneacetone) palladium (II) (28 mg, 0.03 mmol) was added and the apparatus was evacuated and backfilled with nitrogen (×3) and then heated at 100° C. for 8 h. The mixture was cooled, filtered and the filtrate absorbed onto an SCX-3 column, washed with methanol and the product eluted with ammonia in methanol. Product containing fractions were concentrated and purified by normal phase chromatography (1% methanol/DCM) to give the title compound as a white solid (57 mg, 24%).

$^1$H NMR (399.9 MHz, DMSO-d$_6$) δ1.41 (9H, s), 1.59-1.71 (6H, m), 1.96 (2H, m), 2.58 (2H, m), 3.17 (3H, s), 3.61 (2H, m), 4.09 (2H, d), 4.85 (1H, m), 6.80 (1H, d), 7.18 (1H, t), 7.30 (1H, t), 7.57 (1H, d), 7.62 (1H, s), 8.04 (1H, s), 9.16 (1H, s); MS m/z 467 [M+H]$^+$.

The following example was prepared by an analogous process to that used in the preparation of Example 136 utilising the appropriate substituted aniline available from Fluorochem.

Example 137

4-[(6-cyclopentyl-2-methyl-3-oxo-2,6,8,10-tetrazabicyclo[5.4.0]undeca-8,10,12-trien-9-yl)amino]-2-methyl-isoindole-1,3-dione $^1$H NMR (399.9 MHz, DMSO-d$_6$) δ1.61-1.77 (6H, m), 1.95-1.98 (2H, m), 2.61-2.63 (2H, m), 3.04 (3H, s), 3.20 (3H, s), 3.65-3.68 (2H, m), 4.78 (1H, m), 7.39 (1H, d), 7.74 (1H, t), 8.16 (1H, s), 8.81 (1H, d), 9.14 (1H, s); MS m/z 421 [M+H]$^+$.

Example 138

N-[2-[3-[(6-cyclopentyl-2-methyl-3-oxo-2,6,8,10-tetrazabicyclo[5.4.0]undeca-8,10,12-trien-9-yl) amino]-4-methoxy-phenyl]ethyl]acetamide N-[2-(3-amino-4-methoxy-phenyl)ethyl]acetamide (Compound 4—Organic Process Research & Development 2004, 8, 628-642, 108 mg, 0.5 mmol), 10-Chloro-2-cyclopentyl-6-methyl-2,6,9,11-tetrazabicyclo[5.4.0]undeca-8,10,12-trien-5-one (Intermediate 1, 140 mg, 0.5 mmol) and p-toluenesulphonic acid monohydrate (238 mg, 1.25 mmol) were heated at 140° C. in 4-methyl-2-pentanol (3 mL) for 3 hours. The mixture was allowed to cool causing a solid to form. Methanol and DCM were added to give a solution that was absorbed onto an SCX-3 column and washed with methanol. The product with eluted with ammonia/methanol and the product containing fractions were concentrated. Purification by preparative, reverse phase chromatography gave the title compound as a white solid (45 mg, 20%).

$^1$H NMR (399.9 MHz, DMSO-d$_6$) δ1.55-1.70 (6H, m), 1.79 (3H, s), 1.93-1.96 (2H, m), 2.56-2.59 (2H, m), 2.64 (2H, t), 3.17 (3H, s), 3.20-3.26 (2H, m), 3.61-3.63 (2H, m), 3.86 (3H, s), 4.85 (1H, m), 6.78-6.81 (1H, m), 6.95 (1H, d), 7.55 (1H, s), 7.86 (1H, t), 8.05 (1H, s), 8.12 (1H, d); MS m/z 453 [M+H]$^+$.

Example 139

6-cyclopentyl-9-[(2-methoxyphenyl)amino]-2-methyl-2,6,8,10-tetrazabicyclo[5.4.0]undeca-8,10,12-trien-3-one 2-methoxyaniline (Aldrich, 22 mg, 0.18 mmol), 10-Chloro-2-cyclopentyl-6-methyl-2,6,9,11-tetrazabicyclo[5.4.0]undeca-8,10,12-trien-5-one (Intermediate 1, 50 mg, 0.18 mmol) and p-toluenesulphonic acid monohydrate (84 mg, 0.44 mmol) were heated in 4-methyl-2-pentanol (1 mL) at 135° C. for 24 hours. The mixture was cooled and diluted with methanol/DCM and absorbed on to an SCX-3 column, washed with methanol and eluted with ammonia in methanol. Product containing fractions were concentrated and purred by preparative reverse phase chromatography to give the title compound as a white solid (42 mg, 64%). MS m/z 368 [M+H]$^+$, Retention Time 2.61 mins.

The following examples were prepared by an analogous process to that used in the preparation of Example 139, utilising the appropriate substituted anilines available as indicated.

Example 140

6-cyclopentyl-9-[(2-ethoxyphenyl)amino]-2-methyl-2,6,8,10-tetrazabicyclo[5.4.0]undeca-8,10,12-trien-3-one

Example 141

6-cyclopentyl-2-methyl-9-[(2-methylsulfanylphenyl)amino]-2,6,8,10-tetrazabicyclo[5.4.0]undeca-8,10,12-trien-3-one

Example 142

6-cyclopentyl-9-[(2-hydroxyphenyl)amino]-2-methyl-2,6,8,10-tetrazabicyclo[5.4.0]undeca-8,10,12-trien-3-one

Example 143

6-cyclopentyl-9-[(2-ethylphenyl)amino]-2-methyl-2,6,8,10-tetrazabicyclo[5.4.0]undeca-8,10,12-trien-3-one

Example 144

9-[(2-benzoylphenyl)amino]-6-cyclopentyl-2-methyl-2,6,8,10-tetrazabicyclo[5.4.0]undeca-8,10,12-trien-3-one

Example 145

2-[(6-cyclopentyl-2-methyl-3-oxo-2,6,8,10-tetrazabicyclo[5.4.0]undeca-8,10,12-trien-9-yl)amino]benzenesulfonamide

Example 146

6-cyclopentyl-2-methyl-9-[(2-phenoxyphenyl)amino]-2,6,8,10-tetrazabicyclo[5.4.0]undeca-8,10,12-trien-3-one

Example 147

9-[(2-bromophenyl)amino]-6-cyclopentyl-2-methyl-2,6,8,10-tetrazabicyclo[5.4.0]undeca-8,10,12-trien-3-one

Example 148

6-cyclopentyl-2-methyl-9-[(2-phenylphenyl)amino]-2,6,8,10-tetrazabicyclo[5.4.0]undeca-8,10,12-trien-3-one

Example 149

6-cyclopentyl-2-methyl-9-[(2-methylsulfonylphenyl)amino]-2,6,8,10-tetrazabicyclo[5.4.0]undeca-8,10,12-trien-3-one

Example 150

6-cyclopentyl-2-methyl-9-[(2-propan-2-ylphenyl)amino]-2,6,8,10-tetrazabicyclo[5.4.0]undeca-8,10,12-trien-3-one

Example 151

9-[(2-butylphenyl)amino]-6-cyclopentyl-2-methyl-2,6,8,10-tetrazabicyclo[5.4.0]undeca-8,10,12-trien-3-one

Example 152

6-cyclopentyl-2-methyl-9-[[2-(1-piperidyl)phenyl]amino]-2,6,8,10-tetrazabicyclo[5.4.0]undeca-8,10,12-trien-3-one

Example 153

6-cyclopentyl-2-methyl-9-[[2-(4-tert-butylphenoxy)phenyl]amino]-2,6,8,10-tetrazabicyclo[5.4.0]undeca-8,10,12-trien-3-one

Example 154

2-[(6-cyclopentyl-2-methyl-3-oxo-2,6,8,10-tetrazabicyclo[5.4.0]undeca-8,10,12-trien-9-yl)amino]-N-ethyl-benzenesulfonamide

Example 155

2-[(6-cyclopentyl-2-methyl-3-oxo-2,6,8,10-tetrazabicyclo[5.4.0]undeca-8,10,12-trien-9-yl)amino]-N-methyl-benzenesulfonamide

Example 156

6-cyclopentyl-2-methyl-9-[[2-(2-morpholin-4-yl-ethylamino)phenyl]amino]-2,6,8,10-tetrazabicyclo[5.4.0]undeca-8,10,12-trien-3-one

Example 157

9-[(2-benzylphenyl)amino]-6-cyclopentyl-2-methyl-2,6,8,10-tetrazabicyclo[5.4.0]undeca-8,10,12-trien-3-one

Example 158

6-cyclopentyl-2-methyl-9-[(2-pyrrol-1-ylphenyl)amino]-2,6,8,10-tetrazabicyclo[5.4.0]undeca-8,10,12-trien-3-one

Example 159

6-cyclopentyl-2-methyl-9-[[2-(4-methylphenoxy)phenyl]amino]-2,6,8,10-tetrazabicyclo[5.4.0]undeca-8,10,12-trien-3-one

Example 160

6-cyclopentyl-2-methyl-9-[[2-(morpholin-4-ylmethyl)phenyl]amino]-2,6,8,10-tetrazabicyclo[5.4.0]undeca-8,10,12-trien-3-one

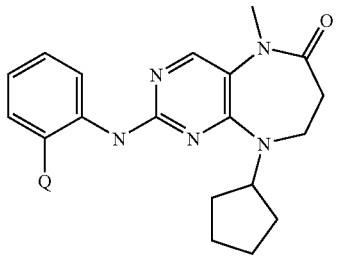

| Example | Q | Substituted Aniline Supplier or Source | MS m/z [M + H]+ | Retention Time (Minutes) |
|---|---|---|---|---|
| 140 | ethoxy | Aldrich | 382 | 2.81 |
| 141 | methylthio | Aldrich | 384 | 2.76 |
| 142 | methoxy (H on CH2) | Aldrich | 354 | 2.01 |
| 143 | ethyl | Aldrich | 366 | 2.7 |
| 144 | benzoyl | Aldrich | 442 | 3.11 |
| 145 | nitro-sulfonyl | Aldrich | 417 | 1.99 |
| 146 | phenoxy | Aldrich | 430 | 3.11 |
| 147 | Br | Aldrich | 418 | 2.82 |
| 148 | phenyl | ABCR | 414 | 3 |
| 149 | methylsulfonyl | Enamine | 416 | 2.38 |

-continued

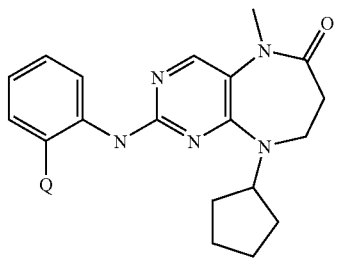

| Example | Q | Substituted Aniline Supplier or Source | MS m/z [M + H]+ | Retention Time (Minutes) |
|---|---|---|---|---|
| 150 | (isopropyl) | Aldrich | 380 | 2.81 |
| 151 | (butyl) | ABCR | 394 | 3.07 |
| 152 | (piperidinyl) | ABCR | 421 | 3.4 |
| 153 | (4-tert-butylphenoxy) | Tim Tec | 486 | 3.73 |
| 154 | (ethyl methanesulfonamido) | Farmaco, Edizione Scientifica (1957), 12 41-8 | 445 | 2.5 |
| 155 | (methyl methanesulfonamido) | Zelinsky | 431 | 2.38 |
| 156 | (morpholinoethylamino) | Journal of the American Chemical Society (1948), 70 416 | 466 | 2.26 |
| 157 | (benzyl) | Aldrich | 428 | 2.99 |
| 158 | (pyrrolyl) | Aldrich | 401 | 2.84 |
| 159 | (4-methylphenoxy) | Tim Tec | 444 | 3.31 |
| 160 | (morpholinomethyl) | Maybridge | 437 | 2.73 |

Example 161

6-cyclopentyl-9-[(3-methoxyphenyl)amino]-2-methyl-2,6,8,10-tetrazabicyclo[5.4.0]undeca-8,10,12-trien-3-one 3-methoxyaniline (Aldrich, 22 mg, 0.18 mmol), 10-Chloro-2-cyclopentyl-6-methyl-2,6,9,11-tetrazabicyclo[5.4.0]undeca-8,10,12-trien-5-one (Intermediate 1, (50 mg, 0.18 mmol), and p-toluene sulphonic acid (84 mg, 0.44 mmol) were combined in 4-methyl-2-pentanol (1 mL). The solution was heated at reflux under a blanket of nitrogen for 12 hours. The reaction mixture was cooled and passed through an SCX-2 column washed with methanol. The crude product were washed off with 7N ammonia in methanol and then concentrated in vacuo. The resultant material was purified by reverse phase HPLC to yield the title compound as a white solid. (39 mg, 59%); MS m/z 368 [M+H]$^+$, Retention Time 2.46 mins.

The following examples were prepared by an analogous process to that used in the preparation of Example 161 utilising the appropriate substituted anilines available as indicated.

Example 162

6-cyclopentyl-9-[(3-ethoxyphenyl)amino]-2-methyl-2,6,8,10-tetrazabicyclo[5.4.0]undeca-8,10,12-trien-3-one

Example 163

6-cyclopentyl-2-methyl-9-[(3-methylsulfanylphenyl)amino]-2,6,8,10-tetrazabicyclo[5.4.0]undeca-8,10,12-trien-3-one

Example 164

3-[(6-cyclopentyl-2-methyl-3-oxo-2,6,8,10-tetrazabicyclo[5.4.0]undeca-8,10,12-trien-9-yl)amino]benzonitrile

Example 165

9-[(3-acetylphenyl)amino]-6-cyclopentyl-2-methyl-2,6,8,10-tetrazabicyclo[5.4.0]undeca-8,10,12-trien-3-one

Example 166

6-cyclopentyl-9-[(3-ethylphenyl)amino]-2-methyl-2,6,8,10-tetrazabicyclo[5.4.0]undeca-8,10,12-trien-3-one

Example 167

3-[(6-cyclopentyl-2-methyl-3-oxo-2,6,8,10-tetrazabicyclo[5.4.0]undeca-8,10,12-trien-9-yl)amino]benzamide

Example 168

6-cyclopentyl-9-[(3-ethynylphenyl)amino]-2-methyl-2,6,8,10-tetrazabicyclo[5.4.0]undeca-8,10,12-trien-3-one

Example 169

9-[(3-benzoylphenyl)amino]-6-cyclopentyl-2-methyl-2,6,8,10-tetrazabicyclo[5.4.0]undeca-8,10,12-trien-3-one

Example 170

3-[(6-cyclopentyl-2-methyl-3-oxo-2,6,8,10-tetrazabicyclo[5.4.0]undeca-8,10,12-trien-9-yl)amino]benzenesulfonamide

Example 171

6-cyclopentyl-2-methyl-9-[(3-phenylphenyl)amino]-2,6,8,10-tetrazabicyclo[5.4.0]undeca-8,10,12-trien-3-one

Example 172

6-cyclopentyl-2-methyl-9-[(3-methylsulfonylphenyl)amino]-2,6,8,10-tetrazabicyclo[5.4.0]undeca-8,10,12-trien-3-one

Example 173

6-cyclopentyl-9-[[3-(hydroxymethyl)phenyl]amino]-2-methyl-2,6,8,10-tetrazabicyclo[5.4.0]undeca-8,10,12-trien-3-one

Example 174

6-cyclopentyl-2-methyl-9-[(3-propan-2-ylphenyl)amino]-2,6,8,10-tetrazabicyclo[5.4.0]undeca-8,10,12-trien-3-one

Example 175

N-[2-[(6-cyclopentyl-2-methyl-3-oxo-2,6,8,10-tetrazabicyclo[5.4.0]undeca-8,10,12-trien-9-yl)amino]phenyl]benzenesulfonamide

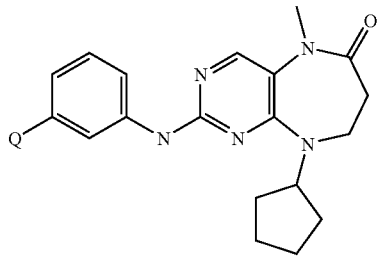

| Example | Q | Substituted Aniline Supplier or Source | MS m/z [M + H]$^+$ | Retention Time (Minutes) |
|---|---|---|---|---|
| 162 | ⋯O⁓ | Aldrich | 382.23 | 2.63 |
| 163 | ⋯S⁄ | Aldrich | 384.19 | 2.65 |

-continued

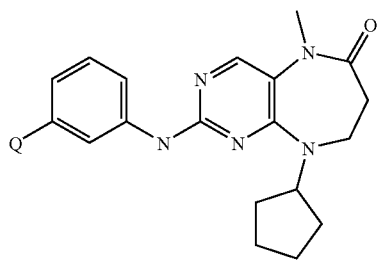

| Example | Q | Substituted Aniline Supplier or Source | MS m/z [M + H]+ | Retention Time (Minutes) |
|---------|---|------|------|------|
| 164 | —C≡N | Aldrich | 363.18 | 2.4 |
| 165 | —C(O)CH3 | Aldrich | 380.23 | 2.3 |
| 166 | —CH2CH3 | Aldrich | 366.21 | 2.78 |
| 167 | —NHC(O)CH3 | Aldrich | 381.2 | 1.78 |
| 168 | —C≡CH | Aldrich | 362.17 | 2.57 |
| 169 | —C(O)Ph | Aldrich | 442.3 | 2.72 |
| 170 | —S(O)2NH2 | ABCR | 417.21 | 1.87 |
| 171 | —Ph | ABCR | 414.26 | 2.94 |
| 172 | —S(O)2CH3 | Enamine | 416.21 | 2.09 |
| 173 | —CH2OCH3 | Aldrich | 368.16 | 1.96 |
| 174 | —CH(CH3)2 | ABCR | 380.26 | 2.92 |
| 175 | —S(O)2Ph | Journal of the Chemical Society (1938), 899-905. | 492.19 | 1.61 |

Example 176

N-[3-[(6-cyclopentyl-2-methyl-3-oxo-2,6,8,10-tetrazabicyclo[5.4.0]undeca-8,10,12-trien-9-yl)amino]-4-methoxy-phenyl]acetamide 10-Chloro-2-cyclopentyl-6-methyl-2,6,9,11-tetrazabicyclo[5.4.0]undeca-8,10,12-trien-5-one (Intermediate 1, 100 mg, 0.36 mmol), N-(3-amino-4-methoxy-phenyl)acetamide (Aldrich, 77 mg, 0.43 mmol) and p-toluenesulphonic acid (137 mg, 0.72 mmol) heated together in 4-methyl-2-pentanol (4 ml) at 120° C. for 22 hours. The reactions were cooled to ambient temperature and then passed down a 5 g SCX-2 column pre-wet with methanol. The column was eluted with 2M NH3/MeOH and the solvent evaporated. The resultant material was purified by reverse phase HPLC to give the title compound as a white solid (46 mg, 30%)

1H NMR (400.132 MHz, DMSO-d6) δ 1.58 (m, 6H), 1.88 (m, 2H), 1.99 (s, 3H), 2.56 (m, 2H), 3.17 (s, 3H), 3.59 (m, 2H), 3.83 (s, 3H), 4.85 (m, 1H), 6.93 (d, 1H), 7.05 (d, 1H), 7.56 (s, 1H), 8.02 (s, 1H), 8.37 (s, 1H), 9.68 (s, 1H); MS m/z 425 [M+H]+.

The following examples were prepared by an analogous process to that used in the preparation of Example 176 utilising the appropriate substituted anilines available from Aldrich Example 177

N-[3-[(6-cyclopentyl-2-methyl-3-oxo-2,6,8,10-tetrazabicyclo[5.4.0]undeca-8,10,12-trien-9-yl)amino] phenyl]acetamide MS m/z 395 [M+H]+. Retention Time 2.65 mins Example 178

6-cyclopentyl-9-[[5-(hydroxymethyl)-2-methyl-phenyl]amino]-2-methyl-2,6,8,10-tetrazabicyclo[5.4.0] undeca-8,10,12-trien-3-one MS m/z 382 [M+H]+. Retention Time 2.76 mins Example 179

6-cyclopentyl-9-[[3-(2-hydroxyethyl)phenyl]amino]-2-methyl-2,6,8,10-tetrazabicyclo[5.4.0]undeca-8,10,12-trien-3-one 10-Chloro-2-cyclopentyl-6-methyl-2,6,9,11-tetrazabicyclo[5.4.0]undeca-8,10,12-trien-5-one (Intermediate 1, 134 mg, 0.48 mmol), 2-(3-aminophenyl)ethanol (ABChem Inc, 92 mg, 0.48 mmol) and p-toluenesulphonic acid monohydrate (227 mg, 1.19 mmol) were heated at 140° C. in 4-methyl-2-pentanol (4 mL) for 2 hours. The reaction solution was loaded onto an SCX-3 column pre-wet with Methanol. The column was washed with methanol to remove p-toluenesulphonic acid monohydrate and then washed with 2% 7N ammonia/methanol to elute the crude product. Fraction containing products were evaporated and the resultant material purified by reverse phase HPLC to give the title compound as a white solid (92 mg, 50%).

1H NMR (399.9 MHz, DMSO-d6) δ1.59-1.60 (4H, m), 1.69-1.71 (2H, m), 1.96-1.98 (2H, m), 2.53-2.59 (2H, t), 2.69 (2H, t), 3.18 (3H, s), 3.60 (2H, t), 3.62 (2H, t), 4.62 (1H, s), 4.87 (1H, ms), 6.77 (1H, d), 7.14 (1H, t), 7.46-7.49 (1H, m), 7.66 (1H, t), 8.04 (1H, s), 9.10 (1H, s); MS m/z 382 [M+H]+.

The following example was prepared by an analogous process to that used in the preparation of Example 183 utilising the appropriate substituted aniline available from sources as indicated

Example 180

6-cyclopentyl-2-methyl-9-[[3-(2-morpholin-4-ylethoxy)phenyl]amino]-2,6,8,10-tetrazabicyclo[5.4.0]undeca-8,10,12-trien-3-one Substituted aniline available from ABCR $^1$H NMR (399.9 MHz, DMSO-$d_6$) δ1.61 (4H, d), 1.71 (2H, s), 1.97 (2H, s), 2.48 (4H, m), 2.59 (2H, t), 2.68 (2H, t), 3.17 (3H, s), 3.59 (4H, m), 3.62 (2H, m), 4.05 (2H, t), 4.80-4.90 (1H, m), 6.49-6.52 (1H, d), 7.13 (1H, t), 7.20 (1H, d), 7.51 (1H, t), 8.05 (1H, s), 9.13 (1H, s); MS m/z 467 [M+H]$^+$.

Example 181

3-[(6-cyclopentyl-2-methyl-3-oxo-2,6,8,10-tetrazabicyclo[5.4.0]undeca-8,10,12-trien-9-yl)amino]-4-methoxy-N-(1-methyl-4-piperidyl)benzamide Synthetic route for substituted aniline available from WO06/018220

$^1$H NMR (399.9 MHz, DMSO-$d_6$) δ1.48-1.62 (8H, m), 1.71-1.77 (2H, d), 1.80-2.00 (4H, m), 2.17 (3H, s), 2.56 (2H, t), 2.77 (2H, d), 3.17 (3H, s), 3.59 (2H, t), 3.71 (1H, m), 3.91 (3H, s), 4.74-4.79 (1H, m), 7.05 (1H, d), 7.48-7.51 (1H, m), 7.69 (1H, s), 7.99 (1H, d), 8.04 (1H, s), 8.57 (1H, d); MS m/z 509 [M+H]$^+$.

Example 182

6-cyclopentyl-9-[[5-(3-dimethylaminopyrrolidin-1-yl)-2-methoxy-phenyl]amino]-2-methyl-2,6,8,10-tetrazabicyclo[5.4.0]undeca-8,10,12-trien-3-one 10-Chloro-2-cyclopentyl-6-methyl-2,6,9,11-tetrazabicyclo[5.4.0]undeca-8,10,12-trien-5-one (Intermediate 1, 150 mg, 0.53 mmol), 1-(3-amino-4-methoxy-phenyl)-N,N-dimethyl-pyrrolidin-3-amine (Intermediate 50; 141 mg, 0.53 mmol) and p-toluenesulphonic acid monohydrate (255 mg, 1.34 mmol) were combined and heated in 4-methyl-2-pentanol (4 mL) at 140° C. for 2 hours. The reaction mixture was loaded onto a 20 g SCX-2 column was pre-wet with methanol. The column was washed with methanol twice to remove p-Toluene Sulphonic acid and then washed twice with 2% 7N ammonia/methanol to elute the crude product. Product containing fractions were evaporated and the resultant material purified by reverse phase HPLC to yield the title compound as a white solid (140 mg, 51.6%).

$^1$H NMR (399.9 MHz, DMSO-$d_6$) δ1.48-1.62 (8H, m), 1.71-1.77 (2H, d), 1.80-2.00 (4H, m), 2.17 (3H, s), 2.56 (2H, t), 2.77 (2H, d), 3.17 (3H, s), 3.59 (2H, t), 3.71 (1H, m), 3.91 (3H, s), 4.74-4.79 (1H, m), 7.05 (1H, d), 7.48-7.51 (1H, m), 7.69 (1H, s), 7.99 (1H, d), 8.04 (1H, s), 8.57 (1H, d); MS m/z 508 [M+H]$^+$.

Example 183

6-cyclopentyl-2-methyl-9-[(3-morpholin-4-ylsulfonylphenyl)amino]-2,6,8,10-tetrazabicyclo[5.4.0]undeca-8,10,12-trien-3-one 10-Chloro-2-cyclopentyl-6-methyl-2,6,9,11-tetrazabicyclo[5.4.0]undeca-8,10,12-trien-5-one (Intermediate 1,150 mg, 0.53 mmol), 3-(morpholinosulphonyl)aniline (Fluorochem; 130 mg, 0.53 mmol) and p-toluenesulphonic acid monohydrate (255 mg, 1.34 mmol) were combined and heated at 140° C. in 4-methyl-2-pentanol (4 mL) for 2 hours. The mixture was cooled and methanol and dichloromethane added to dissolve the solid that formed. The mixture was absorbed on to an SCX-3 column, washed with methanol and eluted with ammonia in methanol. Product containing fractions were concentrated to give a white crystalline solid. This was suspended in methanol and filtered off and dried at 140° C. under vacuum in a desiccator to give the title compound as a white crystalline solid (200 mg, 77%)

$^1$H NMR (399.9 MHz, DMSO-$d_6$) δ1.57-1.70 (6H, m), 1.94-2.00 (2H, m), 2.57-2.60 (2H, m), 2.88 (4H, m), 3.18 (3H, s), 3.61-3.66 (6H, m), 4.91 (1H, m), 7.22-7.25 (1H, m), 7.53 (1H, t), 7.99-8.02 (1H, m), 8.09 (1H, s), 8.23 (1H, t), 9.57 (1H, s)

MS m/z 487 [M+H]$^+$.

Example 184

3-chloro-4-[(6-cyclopentyl-2-methyl-3-oxo-2,6,8,10-tetrazabicyclo[5.4.0]undeca-8,10,12-trien-9-yl)amino]-N-(2-morpholin-4-ylethyl)benzamide 4-amino-3-chloro-N-(2-morpholin-4-ylethyl)benzamide (Intermediate 52, 100 mg, 0.35 mmol), 10-Chloro-2-cyclopentyl-6-methyl-2,6,9,11-tetrazabicyclo[5.4.0]undeca-8,10,12-trien-5-one (Intermediate 1, 124 mg, 0.44 mmol) and p-toluenesulphonic acid monohydrate (168 mg, 0.88 mmol) were heated at 140° C. in 4-methyl-2-pentanol (2.5 mL) for 3 hours. The mixture was allowed to cool causing a solid to form. Methanol and DCM were added to give a solution that was absorbed onto and SCX-3 column and washed with methanol. Elution of the product with ammonia/methanol, concentration and column chromatography (2% 7N ammonia in methanol/DCM) gave material that was further purified by reverse phase HPLC to give the title compound as a white foam (87 mg, 47%).

$^1$H NMR (399.9 MHz, DMSO-$d_6$) δ1.54-1.69 (6H, m), 1.86-1.89 (2H, m), 2.44 (6H, m), 2.59 (2H, m), 3.18 (3H, s), 3.37-3.42 (2H, m), 3.57-3.63 (6H, m), 4.69-4.77 (1H, m), 7.78-7.81 (1H, m), 7.97 (1H, d), 8.09 (1H, s), 8.20 (1H, s), 8.27 (1H, d), 8.40 (1H, t); MS m/z 528 [M+H]$^+$.

The following example was prepared by an analogous process to that used in the preparation of Example 184 utilising 4-amino-3-chloro-N-(1-methyl-4-piperidyl)benzamide Intermediate 55.

Example 185

3-chloro-4-[(6-cyclopentyl-2-methyl-3-oxo-2,6,8,10-tetrazabicyclo[5.4.0]undeca-8,10,12-trien-9-yl)amino]-N-(1-methyl-4-piperidyl)benzamide $^1$H NMR (399.9 MHz, DMSO-$d_6$) δ1.55-1.68 (8H, m), 1.77 (2H, s), 1.86-1.98 (4H, m), 2.18 (3H, s), 2.59 (2H, m), 2.78 (2H, d), 3.18 (3H, s), 3.62 (2H, m), 3.69-3.77 (1H, m), 4.73 (1H, m), 7.79-7.82 (1H, m), 8.00 (1H, d), 8.09 (1H, s), 8.19 (2H, d), 8.26 (1H, d); MS m/z 512 [M+H]$^+$.

Example 186

4-[(6-cyclopentyl-2-methyl-3-oxo-2,6,8,10-tetrazabicyclo[5.4.0]undeca-8,10,12-trien-9-yl)amino]-3-hydroxy-N-(1-methyl-4-piperidyl)benzamide To pyridine (1 mL) was cautiously added conc HCl (1 mL). The mixture was heated at 200° C. until no more water was evolved. The mixture was cooled and 4-[(2-Cyclopentyl-6-methyl-5-oxo-2,6,9,11-tetrazabicyclo[5.4.0]undeca-8,10,12-trien-10-yl)amino]-3-methoxy-N-(1-methyl-4-piperidyl)benzamide (Example 1, 100 mg, 0.2 mmol) was added and the solution reheated and stirred at 200° C. for 30 minutes. The solution was cooled and water added followed by pH adjustment to neutral pH by addition of NaHCO3.

The aqueous solution was adsorbed on an SCX-3 column pre-wet with MeOH. The column was washed with MeOH and water and MeOH. Product was removed from the column by addition of NH3/MeOH (2N). Combined fractions were evaporated and the resultant material purified by reverse phase HPLC to give the title compound as a gum which on trituration with DCM/hexane gave an amorphous solid (17 mg, 17%)

$^1$H NMR (399.9 MHz, DMSO-$d_6$) δ 1.50-1.85 (m, 10H), 1.85-2.10 (m, 4H), 2.20 (s, 3H), 2.55-2.68 (m, 2H), 2.70-2.85 (m, 2H), 3.20 (s, 3H), 3.55-3.70 (m, 2H), 3.60-3.80 (m, 1H), 4.75-4.90 (m, 1H), 7.28-7.35 (d, 1H), 7.38 (s, 1H), 7.83 (s, 1H), 7.95-8.05 (d, 1H), 8.08 (s, 1H), 8.13-8.23 (d, 1H), 10.2-10.5 (bs, 1H); MS m/z 494 [M+H]$^+$.

Example 187

4-[(6-cyclopentyl-2-methyl-3-oxo-2,6,8,10-tetrazabicyclo[5.4.0]undeca-8,10,12-trien-9-yl)amino]-2,6-difluoro-N-(1-methyl-4-piperidyl)benzamide 10-amino-2-cyclopentyl-6-methyl-2,6,9,11-tetrazabicyclo[5.4.0]undeca-7,9,11-trien-5-one (Intermediate 57, 75 mg, 0.29 mmol), 4-bromo-2,6-difluoro-N-(1-methyl-4-piperidyl)benzamide (Intermediate 58, 105 mg, 0.31 mmol) and caesium carbonate (187 mg, 0.57 mmol) were added to dioxane (3 mL) and the suspension bubbled with nitrogen for 10 minutes. Bis(dibenzylideneacetone)palladium (16 mg, 0.028 mmol) and 9,9-Dimethyl-4,5-bis(diphenylphosphino)xanthene (15 mg, 0.026 mmol) were added and the mixture heated to 100° C. overnight. The reaction mixture was cooled to room temperature and filtered. The filter cake was washed with DCM and the filtrate added to a 5 g SCX-2 column pre-wet with MeOH (2 column volumes), flushed with MeOH (2 column volumes) and the crude product eluted with 2M ammonia in MeOH and evaporated to a brown gum. The resultant material was purified by reverse phase HPLC to yield the title compound as a cream solid (107 mg, 73%).

$^1$H NMR (399.902 MHz, CDCl$_3$) δ1.59 (m, 4H), 1.72 (m, 4H), 2.04 (m, 4H), 2.16 (m, 2H), 2.29 (s, 3H), 2.68 (m, 2H), 2.79 (m, 2H), 3.29 (s, 3H), 3.70 (m, 2H), 4.01 (m, 1H), 4.86 (m, 1H), 5.83 (d, 1H), 7.10 (s, 1H), 7.28 (s, 1H), 7.31 (s, 1H), 7.93 (s, 1H); MS m/z 514 [M+H]$^+$.

Example 188

4-[(6-cyclopentyl-2-methyl-3-oxo-2,6,8,10-tetrazabicyclo[5.4.0]undeca-8,10,12-trien-9-yl)amino]-2,5-difluoro-N-(1-methyl-4-piperidyl)benzamide 10-Chloro-2-cyclopentyl-6-methyl-2,6,9,11-tetrazabicyclo[5.4.0]undeca-8,10,12-trien-5-one (Intermediate 1, 100 mg, 0.36 mmol), 4-amino-2,5-difluoro-N-(1-methyl-4-piperidyl)benzamide (Intermediate 59, 87 mg, 0.32 mmol) and caesium carbonate (211 mg, 0.65 mmol) were added to dioxane (3 mL) and the suspension bubbled with nitrogen for 10 minutes. Bis(dibenzylideneacetone)palladium (11 mg, 0.019 mmol) and 9,9-dimethyl-4,5-bis(diphenylphosphino)xanthene (17 mg, 0.029 mmol) were added and the mixture heated to 100° C. overnight. The reaction mixture was cooled to room temperature and filtered. The filter cake was washed with DCM and the filtrate added to a 5 g SCX-2 column pre-wet with MeOH (2 column volumes), washed with MeOH (2 column volumes) and the crude product eluted with 2M ammonia in MeOH and evaporated to a brown gum. The resultant material was purified by reverse phase HPLC to yield the title compound as a white solid (34 mg, 119%).

$^1$H NMR (399.902 MHz, CDCl$_3$) δ1.60 (m, 4H), 1.75 (m, 4H), 2.05 (m, 4H), 2.17 (m, 2H), 2.30 (s, 3H), 2.68 (m, 2H), 2.79 (m, 2H), 3.30 (s, 3H), 3.71 (m, 2H), 4.01 (m, 1H), 4.88 (m, 1H), 6.59 (m, 1H), 7.29 (m, 1H), 7.82 (m, 1H), 7.96 (s, 1H), 8.46 (m, 1H); MS m/z 515 [M+H]$^+$.

The following example was prepared by an analogous process to that used in the preparation of Example 188 utilising 4-amino-2-fluoro-N-(1-methyl-4-piperidyl)benzamide Intermediate 61.

Example 189

4-[(6-cyclopentyl-2-methyl-3-oxo-2,6,8,10-tetrazabicyclo[5.4.0]undeca-8,10,12-trien-9-yl)amino]-2-fluoro-N-(1-methyl-4-piperidyl)benzamide $^1$H NMR (399.902 MHz, CDCl$_3$) δ1.59 (m, 4H), 1.73 (m, 4H), 2.05 (m, 4H), 2.18 (m, 2H), 2.30 (s, 3H), 2.68 (m, 2H), 2.79 (m, 2H), 3.29 (s, 3H), 3.70 (m, 2H), 4.03 (m, 1H), 4.88 (m, 1H), 6.56 (m, 1H), 7.12 (m, 2H), 7.87 (m, 1H), 7.94 (s, 1H), 8.01 (m, 1H); MS m/z 496 [M+H]$^+$.

Example 190 methyl4-[(6-cyclopentyl-2-methyl-3-oxo-2,6,8,10-tetrazabicyclo[5.4.0]undeca-8,10,12-trien-9-yl)amino]-3-hydroxy-benzoate 10-Chloro-2-cyclopentyl-6-methyl-2,6,9,11-tetrazabicyclo[5.4.0]undeca-8,10,12-trien-5-one (Intermediate 1; 180 mg, 0.64 mmol) and methyl3-hydroxy-4-aminobenzoate (ABCR, 123 mg, 0.73 mmol) was taken up in ethanol (4 mL) and water (12 mL). To this was added concentrated hydrochloric acid (36%; 130 µl). The reaction was heated to 80° C. and stirred overnight. The reaction was allowed to stand and cool overnight, before evaporating ethanol. The aqueous residue was diluted to ~30 mL with water and the solution basified to pH 9 by addition of a few drops of aq. Ammonia. The resultant mixture was extracted with DCM (2×50 mL). A solid persisted at the phase boundary. This solid was collected by suction filtration and dried to give the title compound as a purple/grey solid (64 mg).

Combined organic extracts were washed with brine, dried over magnesium sulphate, filtered and evaporated to a pink/brown solid which was taken up in small amount (~5 mL) of DCM and sonicated for 5 minutes. The solid was then collected by suction filtration and dried to give the title compound as a dusky pink solid (79 mg)

$^1$H NMR (400.132 MHz, DMSO-$d_6$) δ 1.56-1.75 (m, 6H), 1.94 (m, 2H), 2.59 (m, 2H), 3.18 (s, 3H), 3.63 (m, 2H), 3.80 (s, 3H), 4.82 (m, 1H), 7.44 (m, 2H), 7.84 (s, 1H), 8.09 (s, 1H), 8.35 (d, 1H), 10.53 (s, 1H); MS m/z 412 [M+H]$^+$.

Example 191

4-[(6-cyclopentyl-2-methyl-3-oxo-2,6,8,10-tetrazabi-cyclo[5.4.0]undeca-8,10,12-trien-9-yl)amino]-N-(2-morpholin-4-ylethyl)benzamide A solution of 4-amino-N-(2-morpholin-4-ylethyl)benzamide (Buttpark; 108 mg, 0.43 mmol) in EtOH (2 mL) was added to 10-Chloro-2-cyclopentyl-6-methyl-2,6,9,11-tetrazabicyclo[5.4.0]undeca-8,10,12-trien-5-one (Intermediate 1, 100 mg, 0.36 mmol). Water (6 mL) was added followed by concentrated hydrochloric acid (36%, 70 ul) and the solution heated at 80° C. for 28 hours and then left to cool over the weekend. The reaction mixture was loaded onto an SCX-2 (5 g) column pre-wet with methanol. Product was eluted with 2M NH3/MeOH. Solvent evaporation gave crude product as a gum which was purified by reverse phase HPLC to yield the title compound as a white solid (71 mg, 40%)

$^1$H NMR (400.132 MHz, DMSO-d$_6$) δ 1.68 (m, 6H), 1.97 (m, 2H), 2.44 (m, 6H), 2.59 (m, 2H), 3.18 (s, 3H), 3.37 (m, 2H), 3.58 (m, 4H), 3.63 (m, 2H), 4.84 (m, 1H), 7.77 (m, 4H), 8.08 (s, 1H), 8.16 (t, 1H), 9.45 (s, 1H); MS m/z 494 [M+H]$^+$.

Example 192

4-[(6-cyclopentyl-2-methyl-3-oxo-2,6,8,10-tetrazabi-cyclo[5.4.0]undeca-8,10,12-trien-9-yl)amino]-N-(2-diethylaminoethyl)benzamide 10-Chloro-2-cyclopentyl-6-methyl-2,6,9,11-tetrazabicyclo[5.4.0]undeca-8,10,12-trien-5-one (Intermediate 1, 100 mg, 0.36 mmol), 4-amino-N-(2-diethylaminoethyl)benzamide (Timtec, 101 mg, 0.43 mmol) and p-toluenesulphonic acid (137 mg, 0.72 mmol) were heated together in 4-methyl-2-pentanol (4 mL) at 100° C. for 24 hours. The crude reaction mixture was loaded onto an SCX-2 (5 g) column pre-wet with MeOH. The column was washed with MeOH and the product eluted with 2M NH3/MeOH. Solvent evaporation gave material that was purified by reverse phase HPLC to yield the title compound as a white solid (123 mg, 71%)

$^1$H NMR (400.132 MHz, DMSO-d$_6$) δ 0.98 (t, 6H), 1.66 (m, 6H), 1.96 (m, 2H), 2.52 (m, 6H), 2.59 (m, 2H), 3.18 (s, 3H), 3.30 (s, 2H), 3.63 (m, 2H), 4.84 (m, 1H), 7.73 (d, 2H), 7.80 (d, 2H), 8.08 (s, 1H), 8.12 (t, 1H), 9.45 (s, 1H); MS m/z 480 [M+H]$^+$.

Example 193

4-[(6-cyclopentyl-2-methyl-3-oxo-2,6,8,10-tetrazabi-cyclo[5.4.0]undeca-8,10,12-trien-9-yl)amino]-3-methyl-N-(1-methyl-4-piperidyl)benzamide A solution of 4-amino-3-methyl-N-(1-methyl-4-piperidyl)benzamide (Intermediate 63, 53 mg, 0.214 mmol), 10-Chloro-2-cyclopentyl-6-methyl-2,6,9,11-tetrazabicyclo [5.4.0]undeca-8,10,12-trien-5-one (Intermediate 1, 60 mg, 0.214 mmol) and p-toluenesulphonic acid monohydrate (102 mg, 0.535 mmol) in 4-methyl-2-pentanol (4 mL) was heated at 100° C. overnight. The reaction was cooled to room temperature (solid formed) dissolved in MeOH and added to a 2 g SCX-2 column pre-wet with MeOH (2 column volumes). The column was washed with MeOH (2 column volumes) and then product eluted with 2M ammonia in MeOH and solvents evaporated. The resultant material was taken up in DCM and purified on silica eluting with a gradient of 0-10% MeOH/DCM then 10% MeOH/DCM. Fractions containing product were combined and evaporated to a clear gum to which ether was added and re-evaporated to a white solid which was further purified by b reverse phase HPLC.

$^1$H NMR (399.902 MHz, CDCl$_3$) δ 1.54-1.70 (m, 6H), 1.75 (m, 2H), 2.02 (m, 4H), 2.17 (m, 2H), 2.31 (s, 3H), 2.37 (s, 3H), 2.67 (m, 2H), 2.82 (m, 2H), 3.29 (s, 3H), 3.68 (m, 2H), 3.99 (m, 1H), 4.85 (m, 1H), 5.86 (d, 1H), 6.79 (s, 1H), 7.59 (m, 2H), 7.92 (s, 1H), 8.32 (d, 1H); MS m/z 492 [M+H]$^+$.

The following example was prepared by an analogous process to that used in the preparation of Example 193 utilising 4-amino-3-fluoro-N-(1-methyl-4-piperidyl)benzamide Intermediate 65

Example 194

4-[(6-cyclopentyl-2-methyl-3-oxo-2,6,8,10-tetrazabi-cyclo[5.4.0]undeca-8,10,12-trien-9-yl)amino]-3-fluoro-N-(1-methyl-4-piperidyl)benzamide $^1$H NMR (399.902 MHz, CDCl$_3$) δ 1.53-1.80 (m, 8H), 2.03 (m, 4H), 2.16 (m, 2H), 2.30 (s, 3H), 2.67 (m, 2H), 2.82 (m, 2H), 3.30 (s, 3H), 3.69 (m, 2H), 3.97 (m, 1H), 4.87 (m, 1H), 5.85 (d, 1H), 7.22 (m, 1H), 7.52 (m, 2H), 7.95 (s, 1H), 8.57 (m, 1H); MS m/z 496 [M+H]$^+$.

Example 195

4-[(6-cyclopentyl-2-methyl-3-oxo-2,6,8,10-tetrazabi-cyclo[5.4.0]undeca-8,10,12-trien-9-yl)amino]-3-(2-methoxyethoxy)-N-(1-methyl-4-piperidyl)benzamide To a suspension of 4-[(2-cyclopentyl-6-methyl-5-oxo-2,6,9,11-tetrazabicyclo[5.4.0]undeca-8,10,12-trien-10-yl) amino]-3-(2-methoxyethoxy)benzoic acid (Intermediate 66, 55 mg, 0.12 mmol) in DMF (2 mL) was added DIPEA (42 ul, 0.16 mmol) and the mixture stirred for 5 minutes. HATU (60 mg, 0.16 mmol) was added to the resultant straw coloured solution. The solution was stirred for a further 10 minutes before addition of 4-amino-1-methylpiperidine (18 mg, 0.16 mmol) in DMF (0.5 mL). The reactions was stirred at ambient temperature for 6 hours and the crude reaction mixture was purified by reverse phase HPLC to afford the title compound as a white solid (50 mg, 76%)

$^1$H NMR (400.132 MHz, DMSO-d$_6$) δ 1.55-1.83 (m, 10H), 1.89-2.10 (m, 4H), 2.23 (s, 3H), 2.59 (m, 2H), 2.84 (m, 2H), 3.18 (s, 3H), 3.38 (s, 3H), 3.64 (m, 2H), 3.73-3.81 (m, 3H), 4.26 (m, 2H), 4.79 (m, 1H), 7.51 (d, 1H), 7.54 (m, 1H), 7.81 (s, 1H), 8.06 (d, 1H), 8.09 (s, 1H), 8.42 (d, 1H); MS m/z 552 [M+H]$^+$.

The following example was prepared by an analogous process to that used in the preparation of Example 195 utilising a 2.0M methylamine solution in THF

Example 196

4-[(6-cyclopentyl-2-methyl-3-oxo-2,6,8,10-tetrazabi-cyclo[5.4.0]undeca-8,10,12-trien-9-yl)amino]-3-(2-methoxyethoxy)-N-methyl-benzamide $^1$H NMR (400.132 MHz, CDCl$_3$) δ 1.55-1.81 (m, 6H), 2.03 (m, 2H), 2.67 (m, 2H), 3.01 (d, 3H), 3.29 (s, 3H), 3.47 (s, 3H), 3.69 (m, 2H), 3.80 (m, 2H), 4.28 (m, 2H), 4.88 (m, 1H), 6.07 (m, 1H), 7.28 (m, 1H), 7.46 (m, 1H), 7.80 (s, 1H), 7.95 (s, 1H), 8.52 (d, 1H); MS m/z 469

Example 197

4-[(6-cyclopentyl-2-methyl-3-oxo-2,6,8,10-tetrazabicyclo[5.4.0]undeca-8,10,12-trien-9-yl)amino]-N-(1-methyl-4-piperidyl)-3-propan-2-yloxy-benzamide To a solution of 4-[(6-cyclopentyl-2-methyl-3-oxo-2,6,8,10-tetrazabicyclo[5.4.0]undeca-8,10,12-trien-9-yl)amino]-3-propan-2-yloxy-benzoic acid (Intermediate 69; 49 mg, 0.11 mmol) in DMF (2 mL) was added DIPEA (42 uL, 0.24 mmol) and HATU (61 mg, 0.16 mmol). The solutions were stirred for 5 minutes before addition of 4-amino-1-methylpiperidine (ABCR, 16 mg, 0.14 mmol). The reaction mixture was stirred, at ambient temperature, overnight.

The crude reaction mixture was purified by reverse phase HPLC to afford the title compound as a white solid (29 mg, 49%)

$^1$H NMR (400.132 MHz, DMSO-$d_6$) δ 1.36 (d, 6H), 1.54-1.80 (m, 10H), 1.94 (m, 4H), 2.17 (s, 3H), 2.59 (m, 2H), 2.78 (m, 2H), 3.18 (s, 3H), 3.64 (m, 2H), 3.74 (m, 1H), 4.78 (m, 2H), 7.48 (m, 1H), 7.52 (m, 1H), 7.67 (s, 1H), 8.04 (d, 1H), 8.08 (s, 1H), 8.41 (d, 1H); MS m/z 536 [M+H]$^+$.

Example 198

N-cyclohexyl-4-[(6-cyclopentyl-2-methyl-3-oxo-2,6,8,10-tetrazabicyclo[5.4.0]undeca-8,10,12-trien-9-yl)amino]-3-(2-dimethylaminoethoxy)benzamide To a stirred solution of Methyl 4-[(2-cyclopentyl-6-methyl-5-oxo-2,6,9,1,1-tetrazabicyclo[5.4.0]undeca-7,9,11-trien-10-yl)amino]-3-(2-dimethylaminoethoxy)benzoate (Intermediate 72; 41 mg, 0.08 mmol) in Ethanol (2 mL) was added a solution of lithium hydroxide (8 mg, 0.33 mmol) in water (1 mL). The reaction was heated at 100° C. by microwave irradiation with stirring, for 30 minutes, cooled, evaporated and the residue diluted with water (5 mL). The resultant solution was treated with a few drops of 2M HCl (aq.) so as to adjust pH to 2-3. The aqueous solution was evaporated to dryness to give the carboxylic acid as a pale yellow gum, which was dissolved in DMF (1 mL) and treated with DIPEA (25 μL, 0.14 mmol) and HATU (40 mg. 0.11 mmol). Cyclohexylamine (11 μL, 0.10 mmol) was added and reaction mixture left to stir, at ambient temperature, overnight.

The crude reaction mixture was purified by reverse phase HPLC to afford the title compound as an off white solid (14 mg, 32%)

$^1$H NMR (400.132 MHz, DMSO-$d_6$) δ 1.10-1.37 (m, 6H), 1.55-1.99 (m, 12H), 2.28 (s, 6H), 2.59 (m, 2H), 2.65 (t, 2H), 3.18 (s, 3H), 3.63 (m, 2H), 3.77 (m, 1H), 4.21 (t, 2H), 4.80 (m, 1H), 7.50 (m, 1H), 7.55 (m, 1H), 7.98 (d, 1H), 8.09 (s, 1H), 8.39 (m, 1H), 8.41 (s, 1H); MS m/z 551 [M+H]$^+$.

Example 199

4-[(6-cyclopentyl-2-methyl-3-oxo-2,6,8,10-tetrazabicyclo[5.4.0]undeca-8,10,12-trien-9-yl)amino]-N-(1-methyl-4-piperidyl)-3-(trifluoromethoxy)benzamide To a solution of 4-amino-N-(1-methyl-4-piperidyl)-3-(trifluoromethoxy)benzamide (Intermediate 74, 104 mg, 0.33 mmol) 10-Chloro-2-cyclopentyl-6-methyl-2,6,9,11-tetrazabicyclo[5.4.0]undeca-8,10,12-trien-5-one (Intermediate 1, 91 mg, 0.32 mmol) in anhydrous 1,4-dioxane (4 mL) was added caesium carbonate (222 mg, 0.68 mmol). Nitrogen was bubbled through the reaction mixture for 10 minutes, prior to addition of Tris(dibenzylideneacetone) palladium (II) (21 mg, 0.07 mmol) and 9,9-Dimethyl-4,5-bis(diphenylphosphino)xanthene (21 mg, 0.11 mmol). The reaction was heated by microwave irradiation at 150° C. for 60 minutes. Further portions of 9,9-Dimethyl-4,5-bis(diphenylphosphino)xanthene (19 mg) & Tris(dibenzylideneacetone) palladium (II (25 mg) added and mixture heated on hot plate at 100° C. overnight. The reaction mixture was cooled and diluted to 10 mL with DCM. Insoluble material was filtered and the filter cake washed with DCM. Evaporation to dryness of filtrate afforded a brown gum, which was taken up in methanol and poured onto an SCX-2 cartridge (5 g, Silicycle). The Cartridge was washed with methanol (~75 mL) before eluting products with 2M ammonia in methanol (~50 mL). The ammoniacal fraction was evaporated to afford a brown gum which was purified by reverse phase HPLC to yield the title compound as a white solid (25 mg, 4%)

$^1$H NMR (400.132 MHz, DMSO-$d_6$) δ 1.51-1.97 (m, 14H), 2.17 (s, 3H), 2.59 (m, 2H), 2.78 (m, 2H), 3.18 (s, 3H), 3.62 (m, 2H), 3.74 (m, 1H), 4.74 (m, 1H), 7.86 (m, 2H), 8.08 (s, 1H), 8.25 (d, 1H), 8.30 (d, 1H), 8.57 (s, 1H) MS m/z 562 [M+H]$^+$.

Example 200

4-[(6-cyclopentyl-2-methyl-3-oxo-2,6,8,10-tetrazabicyclo[5.4.0]undeca-8,10,12-trien-9-yl)amino]-3-ethoxy-N-(1-methyl-4-piperidyl)benzamide A solution of HATU (63 mg, 0.165 mmol) in DMA (1 mL) was added to a mixture 4-[(2-cyclopentyl-6-methyl-5-oxo-2,6,9,11-tetrazabicyclo[5.4.0]undeca-7,9,11-trien-10-yl)amino]-3-ethoxy-benzoic acid (Intermediate 75, 64 mg, 0.15 mmol), DIPEA (79 uL, 0.45 mmol) and the amine in DMA (1 mL). The resulting mixture was stirred at room temperature overnight. The reaction mixture was added to an SCX-3 column pre-wet with Methanol, washed with methanol and product eluted with Ammonia in Methanol. Product containing fractions were evaporated and the resultant material purified by column chromatography, eluting with 0-10% 7N methanolic ammonia in DCM, to give the title compound as clear glass (64 mg, 82%)

$^1$H NMR (399.9 MHz, CDCl$_3$) δ1.51 (3H, t), 1.61-1.82 (8H, m), 2.03-2.09 (2H, m), 2.21-2.29 (4H, m), 2.38 (3H, s), 2.67-2.70 (2H, m), 2.90-2.93 (2H, m), 3.31 (3H, s), 3.70-3.73 (2H, m), 4.00-4.08 (1H, m), 4.22 (2H, q), 4.92 (1H, quin), 6.07 (1H, d), 7.27 (1H, dd), 7.42 (1H, d), 7.72 (1H, s), 7.96 (1H, s), 8.52 (1H, d); MS m/z 522 [M+H]$^+$.

The following example was prepared by an analogous process to that used in the preparation of Example 200 utilising the appropriate amines available from Aldrich

Example 201

N-(1-azabicyclo[2.2.2]oct-8-yl)-4-[(6-cyclopentyl-2-methyl-3-oxo-2,6,8,10-tetrazabicyclo[5.4.0]undeca-8,10,12-trien-9-yl)amino]-3-ethoxy-benzamide $^1$H NMR (399.9 MHz, CDCl$_3$) δ1.51 (3H, t), 1.55-1.89 (10H, m), 2.06-2.03 (6H, m), 2.67-2.70 (2H, m), 2.84-2.97 (4H, m), 3.07-3.13 (1H, m), 3.31 (3H, s), 3.44-3.50 (1H, m), 3.70-3.73 (2H, m), 4.20-4.26 (1H, m), 4.22 (2H, q), 4.91 (1H, quin), 6.55 (1H, d), 7.34 (1H, dd), 7.47 (1H, d), 7.72 (1H, s), 7.96 (1H, s), 8.52 (1H, d); MS m/z 533 [M+H]$^+$.

Example 202

4-[(6-cyclopentyl-2-methyl-3-oxo-2,6,8,10-tetrazabicyclo[5.4.0]undeca-8,10,12-trien-9-yl)amino]-N-(2-dimethylaminoethyl)-3-ethoxy-benzamide $^1$H NMR (399.9 MHz, CDCl$_3$) δ1.52 (3H, t), 1.62-1.82 (6H, m), 2.04-2.09 (2H, m), 2.39 (6H, s), 2.64-2.71 (4H, m), 3.31 (3H, s), 3.58-3.62 (2H, m), 3.70-3.73 (2H, m), 4.24 (2H, q), 4.92 (1H, quin), 7.01 (1H, s), 7.38 (1H, dd), 7.49 (1H, d), 7.71 (1H, s), 7.96 (1H, s), 8.52 (1H, d); MS m/z 494 [M+H]$^+$.

Example 203

3-chloro-4-[(2-methyl-3-oxo-6-propan-2-yl-2,6,8,10-tetrazabicyclo[5.4.0]undeca-7,9,11-trien-9-yl)amino]-N-(1-methyl-4-piperidyl)benzamide 10-chloro-6-methyl-2-propan-2-yl-2,6,9,11-tetrazabicyclo[5.4.0]undeca-7,9,11-trien-5-one (Intermediate 76, 100 mg, 0.39 mmol) and 4-amino-3-chloro-N-(1-methyl-4-piperidyl)benzamide (Intermediate 79; 127 mg, 0.47 mmol) were suspended in 4-methyl-2-pentanol (3 mL) and p-toluenesulphonic acid monohydrate (74 mg, 0.97 mmol) added. The mixture was heated at 140° C. for 4 hours The mixture was cooled causing a white solid to formed. The whole mixture was diluted with MeOH to give a solution which was absorbed on to an SCX-3 column, washed with methanol and eluted with ammonia/methanol. Concentration and column chromatography (1-2-3-5% NH$_3$ in MeOH/DCM) of the product containing fractions gave the title compound as a white solid (58 mg, 31%).

$^1$H NMR (399.9 MHz, DMSO-d$_6$) δ1.23 (6H, d), 1.54-1.64 (2H, m), 1.75-1.78 (2H, m), 1.91-1.97 (2H, m), 2.18 (3H, s), 2.60 (2H, m), 2.78 (2H, d), 3.18 (3H, s), 3.61 (2H, m), 3.69-3.75 (1H, m), 4.72-4.78 (1H, m), 7.81-7.84 (1H, m), 7.99 (1H, d), 8.09 (2H, d), 8.21 (1H, d), 8.32 (1H, d); MS m/z 486 [M+H]$^+$.

Example 204

3-methoxy-4-[(2-methyl-3-oxo-6-propan-2-yl-2,6,8,10-tetrazabicyclo[5.4.0]undeca-7,9,11-trien-9-yl)amino]benzoic acid 10-chloro-6-methyl-2-propan-2-yl-2,6,9,11-tetrazabicyclo[5.4.0]undeca-7,9,11-trien-5-one (Intermediate 76; 739 mg, 2.9 mmol), 4-amino-3-methoxy-benzoic acid (Aldrich, 534 mg, 3.2 mmol), 4:1 Water/Ethanol (6 mL) and concentrated aqueous hydrochloric acid (0.485 mL, 5.8 mmol) were combined and heated at reflux overnight under nitrogen. The reaction mixture was cooled to room temperature and filtered. The filter cake was washed with water followed by diethyl-ether to give the title compound as an off white solid as the Hydrochloride salt (673 mg, 55%)

$^1$H NMR (399.9 MHz, DMSO-d$_6$): δ$_H$, 1.25 (d, 6H), 2.73 (m, 2H), 3.19 (s, 3H), 3.72 (m, 2H), 3.95 (s, 3H), 4.89 (m, 1H), 7.59 (s, 1H), 7.67 (d, 1H), 8.20 (m, 2H), 9.55 (s, 1H); MS m/z 386 [M+H]$^+$.

Example 205

3-methoxy-4-[(2-methyl-3-oxo-6-propan-2-yl-2,6,8,10-tetrazabicyclo[5.4.0]undeca-7,9,11-trien-9-yl)amino]-N-[2-(1-piperidyl)ethyl]benzamide To a solution of the hydrochloride salt of 3-methoxy-4-[(2-methyl-3-oxo-6-propan-2-yl-2,6,8,10-tetrazabicyclo[5.4.0]undeca-7,9,11-trien-9-yl)amino]benzoic acid (Example 204; 127 mg, 0.33 mmol) and 1-(2-aminoethyl)piperidine (Aldrich, 54 uL, 0.38 mmol) and DIPEA (157 uL, 0.9 mmol) in anhydrous DMA (10 mL) at room temperature under nitrogen was added HATU (126 mg, 0.33 mmol) as a solid and the resulting solution stirred at room temperature overnight. The reaction mixture was loaded onto a SCX-3 column pre-wet with Methanol and the column washed with Methanol. The column was eluted with Ammonia in Methanol and product containing fractions evaporated. The resultant material was dissolved in dichloromethane and chromatographed with 2-5-10-20% methanol/dichloromethane followed by 7N ammonia/methanol. Evaporation of product containing fractions gave a yellow foam which was purified by reverse phase HPLC to yield the title compound as an off white gum (75 mg, 46%)

$^1$H NMR (399.9 MHz, DMSO-d$_6$): δ$_H$, 1.25 (d, 6H), 1.39 (m, 2H), 1.50 (m, 6H), 2.40 (m, 6H), 2.60 (m, 2H), 3.19 (s, 3H), 3.37 (m, 2H), 3.61 (m, 2H), 3.95 (s, 3H), 4.81 (m, 1H), 7.49 (m, 2H), 7.69 (s, 1H), 8.07 (s, 1H), 8.22 (tr, 1H), 8.41 (m, 1H); MS m/z 496 [M+H]$^+$.

The following examples were prepared by an analogous process to that used in the preparation of Example 205 utilising the appropriate amines available from Aldrich or Matrix

Example 206

N-(1-azabicyclo[2.2.2]oct-8-yl)-3-methoxy-4-[(2-methyl-3-oxo-6-propan-2-yl-2,6,8,10-tetrazabicyclo[5.4.0]undeca-7,9,11-trien-9-yl)amino]benzamide

Example 207

N-(2-dimethylaminoethyl)-3-methoxy-4-[(2-methyl-3-oxo-6-propan-2-yl-2,6,8,10-tetrazabicyclo[5.4.0]undeca-7,9,11-trien-9-yl)amino]benzamide

Example 208

N-(3-dimethylamino-2,2-dimethyl-propyl)-3-methoxy-4-[(2-methyl-3-oxo-6-propan-2-yl-2,6,8,10-tetrazabicyclo[5.4.0]undeca-7,9,11-trien-9-yl)amino]benzamide

Example 209

3-methoxy-4-[(2-methyl-3-oxo-6-propan-2-yl-2,6,8,10-tetrazabicyclo[5.4.0]undeca-7,9,11-trien-9-yl)amino]-N-(4-pyrrolidin-1-ylbutyl)benzamide

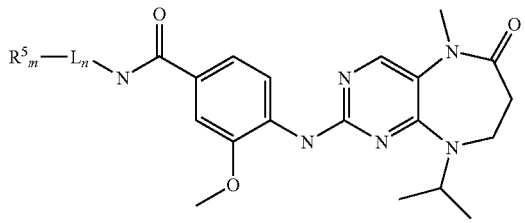

| Example | $R^5{}_m$—$L_n$— | $^1$H NMR (400 MHz, DMSO-d$_6$) | MS m/z [M + H]$^+$ |
|---|---|---|---|
| 206 | (quinuclidinyl structure) | $\delta_H$: 1.23 (d, 6H), 1.30 (m, 1H), 1.60 (m, 2H), 1.85 (m, 2H), 2.60 (m, 2H), 2.70 (m, 4H), 2.90 (m, 1H), 3.11 (m, 1H), 3.20 (s, 3H), 3.62 (m, 2H), 3.95 (m, 4H), 4.81 (m, 1H), 7.49 (s, 1H), 7.56 (d, 1H), 7.30 (s, 1H), 8.06 (m, 2H), 8.42 (d, 1H); | 494 |
| 207 | (dimethylaminopropyl) | $\delta_H$: 1.23 (d, 6H), 2.19 (s, 6H), 2.40 (tr, 2H), 2.60 (m, 2H), 3.18 (s, 3H), 3.36 (m, 2H), 3.61 (d, 2H), 3.96 (s, 3H), 4.81 (m, 1H), 7.50 (m, 2H), 7.69 (s, 1H), 8.07 (s, 1H), 8.24 (tr, 1H), 8.41 (d, 1H); | 456 |
| 208 | (dimethylamino-neopentyl) | $\delta_H$: 0.89 (s, 6H), 1.25 (d, 6H), 2.20 (s, 2H), 2.29 (s, 6H), 2.61 (m 2H), 3.20 (m, 5H), 3.61 (m, 2H), 3.95 (s, 3H), 4.81 (m, 1H), 7.46 (m, 2H), 7.70 (s, 1H), 8.08 (s, 1H), 8.41 (m, 2H) | 498 |
| 209 | (pyrrolidinylbutyl) | $\delta_H$: 1.26 (d, 6H), 1.52 (m, 4H), 1.68 (m, 4H), 2.40 (m, 6H), 2.60 (m, 2H), 3.18 (s, 3H), 3.30 (m, 2H), 3.60 (m, 2H), 3.95 (s, 3H), 4.81 (m, 1H), 7.50 (m, 2H), 7.69 (s, 1H), 8.09 (s, 1H), 8.31 (tr, 1H), 8.41 (d, 1H) | 510 |

Example 210

4-[(6-ethyl-2-methyl-3-oxo-2,6,8,10-tetrazabicyclo[5.4.0]undeca-7,9,11-trien-9-yl)amino]-3-methoxy-N-(1-methyl-4-piperidyl)benzamide 10-chloro-2-ethyl-6-methyl-2,6,9,11-tetrazabicyclo[5.4.0]undeca-8,10,12-trien-5-one Intermediate 81; 180 mg, 0.75 mmol), 4-amino-3-methoxy-N-(1-methyl-4-piperidyl)benzamide (WO06/018220, 198 mg, 0.75 mmol) and p-toluenesulphonic acid (357 mg, 1.88 mmol) were heated in 4-methyl-2-pentanol (3 mL) to 140° C. for 18 hours. The reaction mixture was allowed to cool to room temperature and loaded onto a 10 g SCX-2 cartridge, washing with methanol (10 mL), water (10 mL) and methanol (10 mL) before the product was eluted off with 7 N methanolic ammonia which on evaporation of product containing fractions provided a brown oil which was purified by flash silica chromatography (Companion, 40 g, 0-10% methanolic ammonia/DCM) to give a pale yellow glass which was further purified by reverse phase HPLC to yield the title compound as a white solid (192 mg, 49%)

$^1$H NMR (399.902 MHz, DMSO-d$_6$) δ 1.24 (t, 3H), 1.60 (qd, 2H), 1.73-1.81 (m, 2H), 1.95 (td, 2H), 2.18 (s, 3H), 2.62-2.64 (m, 2H), 2.79 (br d, 2H), 3.18 (s, 3H), 3.62 (q, 2H), 3.70-3.79 (m, 3H), 3.96 (s, 3H), 7.49-7.53 (m, 2H), 7.70 (s, 1H), 8.05-8.08 (m, 2H), 8.41 (d, 1H); MS m/z 468 [M+H]$^+$.

Example 211

3-methoxy-4-[[2-methyl-6-(2-methylpropyl)-3-oxo-2,6,8,10-tetrazabicyclo[5.4.0]undeca-7,9,11-trien-9-yl]amino]-N-(1-methyl-4-piperidyl)benzamide 10-chloro-6-methyl-2-(2-methylpropyl)-2,6,9,11-tetrazabicyclo[5.4.0]undeca-7,9,11-trien-5-one (Intermediate 84; 65 mg, 0.24 mmol), 4-amino-3-methoxy-N-(1-methyl-4-piperidyl)benzamide (WO06/018220, 57 mg, 0.24 mmol) and p-toluene sulphonic acid (110 mg, 0.58 mmol) were taken up in 4-methyl-2-pentanol (1 mL) and heated to 160° C. by microwave irradiation for 1 hour. The reaction mixture was diluted with methanol (5 mL) and water (2 mL) and resultant solution poured onto an SCX-3 cartridge (2 g). The cartridge was washed with methanol (~30 mL) before eluting products with 2M ammonia methanol (20 mL). The Ammoniacal fraction was evaporated to give an amber gum which was purified by reverse phase HPLC to yield the title compound as a colourless glass (scratches down to a white solid) (80 mg, 75%).

$^1$H NMR (400.132 MHz, DMSO-$d_6$) δ 0.90 (d, 6H), 1.60 (m, 2H), 1.77 (m, 2H), 1.94 (m, 2H), 2.11 (m, 1H), 2.17 (s, 3H), 2.64 (m, 2H), 2.78 (m, 2H), 3.19 (s, 3H), 3.50 (d, 2H), 3.68-3.79 (m, 3H), 3.95 (s, 3H), 7.49 (m, 2H), 7.70 (s, 1H), 8.07 (d, 1H), 8.08 (s, 1H), 8.34 (m, 1H); MS m/z 496 [M+H]$^+$.

The following examples were prepared by an analogous process to that used in the preparation of Example 211 utilising the appropriate Chloropyrimidines indicated

Example 212A

4-[(6-butan-2-yl-2-methyl-3-oxo-2,6,8,10-tetrazabicyclo[5.4.0]undeca-7,9,11-trien-9-yl)amino]-3-methoxy-N-(1-methyl-4-piperidyl)benzamide Chloropyrimidine used-2-butan-2-yl-10-chloro-6-methyl-2,6,9,11-tetrazabicyclo[5.4.0]undeca-7,9,11-trien-5-one Intermediate 87

$^1$H NMR (400.132 MHz, DMSO-$d_6$) δ 0.87 (t, 3H), 1.23 (d, 3H), 1.49-1.70 (m, 4H), 1.77 (m, 2H), 1.95 (t, 2H), 2.18 (s, 3H), 2.55-2.68 (m, 2H), 2.79 (m, 2H), 3.18 (s, 3H), 3.50 (m, 1H), 3.62 (m, 1H), 3.74 (m, 1H), 3.95 (s, 3H), 4.63 (m, 1H), 7.48-7.52 (m, 2H), 7.68 (s, 1H), 8.05-8.08 (m, 2H), 8.38 (m, 1H); MS m/z 496 [M+H]$^+$.

Example 212B

4-[(6-cyclobutyl-2-methyl-3-oxo-2,6,8,10-tetrazabicyclo[5.4.0]undeca-8,10,12-trien-9-yl)amino]-3-methoxy-N-(1-methyl-4-piperidyl)benzamide Chloropyrimidine used—10-chloro-2-cyclobutyl-6-methyl-2,6,9,11-tetrazabicyclo[5.4.0]undeca-7,9,11-trien-5-one Intermediate 90

$^1$H NMR (400.132 MHz, DMSO-$d_6$) δ 1.55-1.80 (m, 6H), 1.95 (m, 2H), 2.10 (m, 2H), 2.18 (s, 3H), 2.25 (m, 2H), 2.58 (m, 2H), 2.79 (m, 2H), 3.18 (s, 3H), 3.66 (m, 2H), 3.74 (m, 1H), 3.95 (s, 3H), 4.52 (m, 1H), 7.49 (m, 1H), 7.53 (m, 1H), 7.74 (s, 1H), 8.06 (d, 1H), 8.14 (s, 1H), 8.45 (d, 1H); MS m/z 494 [M+H]$^+$.

Example 213

4-[[6-(cyclopropylmethyl)-2-methyl-3-oxo-2,6,8,10-tetrazabicyclo[5.4.0]undeca-8,10,12-trien-9-yl]amino]-3-methoxy-N-(1-methyl-4-piperidyl)benzamide Chloropyrimidine used 10-chloro-2-(cyclopropylmethyl)-6-methyl-2,6,9,11-tetrazabicyclo[5.4.0]undeca-7,9,11-trien-5-one Intermediate 93

$^1$H NMR (400.132 MHz, DMSO-$d_6$) δ 0.30 (m, 2H), 0.52 (m, 2H), 1.17 (m, 1H), 1.60 (m, 2H), 1.77 (m, 2H), 1.95 (m, 2H), 2.17 (s, 3H), 2.65 (m, 2H), 2.79 (m, 2H), 3.19 (s, 3H), 3.51 (d, 2H), 3.69-3.81 (m, 3H), 3.95 (s, 3H), 7.49 (m, 2H), 7.71 (s, 1H), 8.06 (d, 1H), 8.09 (s, 1H), 8.39 (m, 1H); MS m/z 494 [M+H]$^+$.

Example 214

3-methoxy-4-[(2-methyl-3-oxo-2,6,8,10-tetrazabicyclo[5.4.0]undeca-8,10,12-trien-9-yl)amino]-N-(1-methyl-4-piperidyl)benzamide 10-chloro-2-[(2,4-dimethoxyphenyl)methyl]-6-methyl-2,6,9,11-tetrazabicyclo[5.4.0]undeca-7,9,11-trien-5-one (Intermediate 96; 80 mg, 0.23 mmol), 4-amino-3-methoxy-N-(1-methyl-4-piperidyl)benzamide (WO06/018220; 52 mg, 0.20 mmol) and p-toluene sulphonic acid (110 mg, 0.58 mmol) were taken up in 4-methyl-2-pentanol (1.5 mL) and heated at 160° C. by microwave irradiation for 1 hour. The reaction mixture was dissolved in methanol (5 mL) and water (~5 mL) and poured directly onto an SCX-3 cartridge (2 g). The cartridge was washed through with methanol (~30 mL), before elution of products with 2M ammonia in methanol (~30 mL). Evaporation of ammoniacal fraction gave a brown gum which was purified by reverse phase HPLC to yield the title compound as a white solid (9 mg, 10%)

$^1$H NMR (400.132 MHz, DMSO-$d_6$) δ 1.60 (m, 2H), 1.77 (m, 2H), 1.94 (m, 2H), 2.17 (s, 3H), 2.61 (m, 2H), 2.78 (m, 2H), 3.21 (s, 3H), 3.54 (m, 2H), 3.73 (m, 1H), 3.95 (s, 3H), 7.47 (m, 2H), 7.58 (m, 2H), 8.05 (d, 1H), 8.10 (s, 1H), 8.52 (m, 1H); MS m/z 440 [M+H]$^+$.

Example 215

4-[(6-benzyl-2-methyl-3-oxo-2,6,8,10-tetrazabicyclo[5.4.0]undeca-8,10,12-trien-9-yl)amino]-3-methoxy-N-(1-methyl-4-piperidyl)benzamide 2-benzyl-10-chloro-6-methyl-2,6,9,11-tetrazabicyclo[5.4.0]undeca-7,9,11-trien-5-one (Intermediate 99; 42 mg, 0.14 mmol), 4-amino-3-methoxy-N-(1-methyl-4-piperidyl)benzamide (WO06/018220; 33 mg, 0.13 mmol) and p-toluene sulphonic acid monohydrate (54 mg, 0.28 mmol) were taken up in 4-methyl-2-pentanol (1.5 mL) and heated at 160° C. by microwave irradiation for 1 hour. The reaction mixture was dissolved in methanol (5 mL) and water (~5 mL) and poured directly onto an SCX-3 cartridge (2 g). The cartridge was washed through with methanol (~30 mL), before elution of products with 2M ammonia in methanol (~30 mL). Evaporation of the ammoniacal fraction gave an amber film which was purified by reverse phase HPLC to yield the title compound as an off-white solid (33 mg, 48%)

$^1$H NMR (400.132 MHz, DMSO-$d_6$) δ 1.57 (m, 2H), 1.75 (m, 2H), 1.93 (m, 2H), 2.17 (s, 3H), 2.68 (m, 2H), 2.77 (m, 2H), 3.22 (s, 3H), 3.59-3.77 (m, 3H), 3.91 (s, 3H), 4.87 (s, 2H), 7.24-7.38 (m, 6H), 7.43 (m, 1H), 7.71 (s, 1H), 8.01 (d, 1H), 8.14 (d, 1H), 8.15 (s, 1H); MS m/z 531 [M+H]$^+$.

Example 216

3-methoxy-4-[[2-methyl-6-[(2-methyl1,3-thiazol-4-yl)methyl]-3-oxo-2,6,8,10-tetrazabicyclo[5.4.0]undeca-7,9,11-trien-9-yl]amino]-N-(1-methyl-4-piperidyl)benzamide 10-chloro-6-methyl-2-[(2-methyl-1,3-thiazol-4-yl)methyl]-2,6,9,11-tetrazabicyclo[5.4.0]undeca-7,9,11-trien-5-one (Intermediate 101; 58 mg, 0.18 mmol), 4-amino-3-methoxy-N-(1-methyl-4-piperidyl)benzamide (WO06/018220; 49 mg, 0.19 mmol) and p-toluene sulphonic acid (70 mg, 0.37 mmol) were taken up in 4-methyl-2-pentanol (2 mL) and heated to 160° C. in microwave by microwave irradiation for 1 hour. The reaction mixture was dissolved in methanol (5 mL) and water (~5 mL) and poured directly onto an SCX-3 cartridge (2 g). The cartridge was washed through with methanol (~30 mL), before elution of products with 2M ammonia in methanol (~30 mL). Evaporation of the ammoniacal fraction gave an amber film which was purified by reverse phase HPLC to yield the title compound as an off white solid (43 mg, 26%)

$^1$H NMR (400.132 MHz, DMSO-d$_6$) δ 1.58 (m, 2H), 1.76 (m, 2H), 1.94 (m, 2H), 2.17 (s, 3H), 2.67 (s, 3H), 2.72 (m, 2H), 2.77 (m, 2H), 3.21 (s, 3H), 3.68-3.77 (m, 3H), 3.92 (s, 3H), 4.85 (s, 2H), 7.23 (m, 1H), 7.29 (m, 1H), 7.44 (d, 1H), 7.71 (s, 1H), 8.04 (d, 1H), 8.08 (d, 1H), 8.13 (s, 1H); MS m/z 551 [M+H]$^+$.

The following examples were prepared by an analogous process to that used in the preparation of Example 216 utilising the appropriate Chloropyrimidines indicated

Example 217

4-[[6-(cyclobutylmethyl)-2-methyl-3-oxo-2,6,8,10-tetrazabicyclo[5.4.0]undeca-8,10,12-trien-9-yl]amino]-3-methoxy-N-(1-methyl-4-piperidyl)benzamide Chloropyrimidine used—10-chloro-2-(cyclobutylmethyl)-6-methyl-2,6,9,11-tetrazabicyclo[5.4.0]undeca-7,9,11-trien-5-one (Intermediate 102)

$^1$H NMR (400.132 MHz, DMSO-d$_6$) δ 1.60 (m, 2H), 1.73-2.07 (m, 10H), 2.17 (s, 3H), 2.61 (m, 2H), 2.69-2.81 (m, 3H), 3.17 (s, 3H), 3.66-3.80 (m, 5H), 3.95 (s, 3H), 7.47-7.51 (m, 2H), 7.71 (s, 1H), 8.07 (m, 2H), 8.35 (d, 1H); MS m/z 509 [M+H]$^+$.

Example 218

4-[(2-methyl-3-oxo-6-propan-2-yl-2,6,8,10-tetrazabicyclo[5.4.0]undeca-7,9,11-trien-9-yl)amino]-N-(2-morpholin-4-ylethyl)benzamide 4-amino-N-(2-morpholin-4-ylethyl)benzamide (Buttpark; 188 mg, 0.75 mmol) and 10-chloro-6-methyl-2-propan-2-yl-2,6,9,11-tetrazabicyclo[5.4.0]undeca-7,9,11-trien-5-one (Intermediate 76; 160 mg, 0.63 mmol) were heated together in 1:3 EtOH:water (8 ml) in the presence of concentrated hydrochloric acid (126 ul) for 24 hours. The reaction was cooled to ambient temperature and then loaded onto an SCX-2 (5 g) column pre-wet with methanol. The product was eluted with 2M NH$_3$/MeOH and the solvent evaporated to give product as a brown gum. This was purified by reverse phase HPLC to give the title compound a white solid. (125 mg, 42%)

$^1$H NMR (400.132 MHz, DMSO-d$_6$) δ 1.25 (d, 6H), 2.44 (m, 6H), 2.59 (m, 2H), 3.18 (s, 3H), 3.37 (m, 2H), 3.59 (m, 6H), 4.85 (m, 1H), 7.78 (m, 4H), 8.06 (s, 1H), 8.15 (t, 1H), 9.42 (s, 1H); MS m/z 468 [M+H]$^+$.

The following examples were prepared by an analogous process to that used in the preparation of Example 218 utilising the appropriate substituted anilines and Chloropyrimidines as indicated.

Example 219

3-methoxy-4-[(2-methyl-3-oxo-6-propan-2-yl-2,6,8,10-tetrazabicyclo[5.4.0]undeca-7,9,11-trien-9-yl)amino]-N-(2-morpholin-4-ylethyl)benzamide Prepared from Intermediate 76 and Intermediate 47.

$^1$H NMR (400.132 MHz, DMSO-d$_6$) δ 1.29 (d, 6H), 2.49 (m, 6H), 2.52 (s, 3H), 2.65 (m, 2H), 3.44 (m, 2H), 3.65 (m, 6H), 4.00 (s, 3H), 4.87 (m, 1H), 7.54 (m, 2H), 7.74 (s, 1H), 8.12 (s, 1H), 8.32 (t, 1H), 8.47 (d, 1H).

Example 220

3-methoxy-4-[(2-methyl-3-oxo-6-phenyl-2,6,8,10-tetrazabicyclo[5.4.0]undeca-8,10,12-trien-9-yl)amino]-N-(2-morpholin-4-ylethyl)benzamide Prepared from Intermediate 103 and Intermediate 47.

$^1$H NMR (400.132 MHz, DMSO-d$_6$) δ 2.44 (m, 5H), 2.83 (m, 2H), 3.28 (s, 3H), 3.36 (m, 2H), 3.59 (m, 4H), 3.88 (s, 3H), 4.06 (m, 2H), 6.93 (d, 1H), 7.35 (m, 4H), 7.47 (m, 3H), 7.64 (s, 1H), 8.16 (t, 1H), 8.29 (s, 1H).

Example 221

3-methoxy-4-[(2-methyl-3-oxo-6-phenyl-2,6,8,10-tetrazabicyclo[5.4.0]undeca-8,10,12-trien-9-yl)amino]-N-(1-methyl-4-piperidyl)benzamide Prepared from Intermediate 103 and an intermediate described in WO06/018220.

$^1$H NMR (400.132 MHz, DMSO-d$_6$) δ 1.58 (m, 2H), 1.75 (m, 2H), 1.93 (m, 2H), 2.17 (s, 3H), 2.51 (s, 3H), 2.80 (m, 4H), 3.70 (m, 1H), 3.89 (s, 3H), 4.06 (m, 2H), 6.96 (d, 1H), 7.34 (m, 4H), 7.48 (m, 3H), 7.64 (s, 1H), 7.97 (d, 1H), 8.29 (s, 1H).

Example 222

N-(3-dimethylamino-2,2-dimethyl-propyl)-4-[(2-methyl-3-oxo-6-propan-2-yl-2,6,8,10-tetrazabicyclo[5.4.0]undeca-7,9,11-trien-9-yl)amino]benzamide Prepared from Intermediate 76 and Intermediate 22.

$^1$H NMR (400.132 MHz, DMSO-d$_6$) δ 0.88 (s, 6H), 1.25 (d, 6H), 2.18 (s, 2H), 2.27 (s, 6H), 2.59 (m, 2H), 3.18 (s, 2H), 3.29 (s, 3H), 3.61 (m, 2H), 4.85 (m, 1H), 7.73 (d, 2H), 7.81 (d, 2H), 8.06 (s, 1H), 8.27 (t, 1H), 9.42 (s, 1H);

Example 223

N-(3-dimethylamino-2,2-dimethyl-propyl)-4-[(2-methyl-3-oxo-6-phenyl-2,6,8,10-tetrazabicyclo[5.4.0]undeca-8,10,12-trien-9-yl)amino]benzamide Prepared from Intermediate 103 and Intermediate 22.

$^1$H NMR (400.132 MHz, DMSO-d$_6$) δ 0.87 (s, 6H), 2.18 (s, 2H), 2.28 (s, 6H), 2.81 (m, 2H), 3.14 (d, 2H), 3.28 (s, 3H), 4.06 (m, 2H), 7.33 (m, 7H), 7.47 (m, 2H), 8.21 (t, 1H), 8.31 (s, 1H), 9.52 (s, 1H).

Example 224

4-[(2-methyl-3-oxo-6-phenyl-2,6,8,10-tetrazabicyclo[5.4.0]undeca-8,10,12-trien-9-yl)amino]-N-(1-methyl-4-piperidyl)benzamide Prepared form Intermediate 103 and Intermediate 4.

$^1$H NMR (400.132 MHz, DMSO-d$_6$) δ 1.56 (m, 2H), 1.72 (m, 2H), 1.93 (m, 2H), 2.16 (s, 3H), 2.78 (m, 4H), 3.28 (s, 3H), 3.68 (m, 1H), 4.05 (m, 2H), 7.29 (m, 5H), 7.45 (m, 4H), 7.87 (d, 1H), 8.31 (s, 1H), 9.49 (s, 1H)

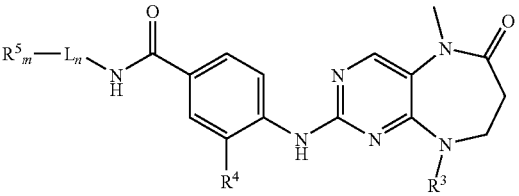

| Example | R³ | R⁴ | R⁵ₘ—Lₙ— | MS m/z [M + H]⁺ |
|---|---|---|---|---|
| 219 | isopropyl | OMe | morpholinoethyl | 498 |
| 220 | phenyl | OMe | morpholinoethyl | 532 |
| 221 | phenyl | OMe | N-methylpiperidinyl | 516 |
| 222 | isopropyl | H | dimethylamino-neopentyl | 468 |
| 223 | phenyl | H | dimethylamino-neopentyl | 502 |
| 224 | phenyl | H | N-methylpiperidinyl | 486 |

Example 225

3-chloro-N-(3-dimethylamino-2,2-dimethyl-propyl)-4-[(2-methyl-3-oxo-6-phenyl-2,6,8,10-tetrazabicyclo[5.4.0]undeca-8,10,12-trien-9-yl)amino]benzamide 4-amino-3-chloro-N-(3-dimethylamino-2,2-dimethyl-propyl)benzamide (Intermediate 107; 99 mg, 0.35 mmol), 10-chloro-6-methyl-2-phenyl-2,6,9,11-tetrazabicyclo[5.4.0]undeca-7,9,11-trien-5-one (Intermediate 103; 99 mg, 0.35 mmol) and p-toluenesulphonic acid monohydrate (165 mg, 0.87 mmol) were heated at 140° C. in 4-methyl-2-pentanol (2.5 mL) for 2 hours. The mixture was allowed to cool forming a dark orange clear solution which was loaded onto an SCX-3 column pre-wet with methanol. The column was washed with methanol to remove p-TsOH. and then eluted with 2% 7N ammonia/methanol to give the crude product which was purified by reverse phase HPLC to yield the title compound as a white solid (15 mg, 8%).

$^1$H NMR (399.9 MHz, DMSO-$d_6$) δ0.88 (6H, s), 2.17 (2H, s), 2.28 (6H, s), 2.82-2.85 (2H, m), 3.16 (2H, d), 4.04-4.08 (2H, m), 7.21-7.24 (1H, m), 7.28-7.30 (1H, m), 7.32-7.35 (2H, m), 7.46 (1H, s), 7.48-7.50 (1H, m), 7.56 (1H, d), 7.82 (1H, d), 8.02 (1H, s), 8.32 (1H, s), 8.37 (1H, t); MS m/z 537 [M+H]⁺.

The following example was prepared by an analogous process to that used in the preparation of Example 225 utilising the appropriate substituted aniline (Intermediate 52)

Example 226

3-chloro-4-[(2-methyl-3-oxo-6-phenyl-2,6,8,10-tetrazabicyclo[5.4.0]undeca-8,10,12-trien-9-yl)amino]-N-(2-morpholin-4-ylethyl)benzamide $^1$H NMR (399.9 MHz, DMSO-$d_6$) δ2.41-2.47 (6H, m), 2.84 (2H, t), 3.33-3.41 (2H, m), 3.59 (4H, t), 4.05-4.08 (2H, m), 7.24-7.27 (1H, m), 7.31-7.35 (3H, m), 7.49 (2H, t), 7.55 (1H, q), 7.85 (1H, d), 8.00 (1H, s), 8.31 (2H, s); MS m/z 537 [M+H]⁺.

Example 227

4-[(2-methyl-3-oxo-6-phenyl-2,6,8,10-tetrazabicyclo[5.4.0]undeca-8,10,12-trien-9-yl)amino]-N-(2-morpholin-4-ylethyl)benzamide 10-chloro-6-methyl-2-phenyl-2,6,9,11-tetrazabicyclo[5.4.0]undeca-7,9,11-trien-5-one (Intermediate 103; 150 mg, 0.52 mmol), 4-amino-N-(2-morpholin-4-ylethyl)benzamide (Buttpark; 130 mg, 0.52 mmol) and p-toluenesulphonic acid monohydrate (248 mg, 1.30 mmol) were heated in 4-methyl-2-pentanol (3 mL) at 140° C. for 2 hours. The reaction mixture was cooled and loaded onto an SCX-3 column pre-wet methanol. The column was washed with methanol to remove p-toluenesulphonic acid monohydrate and then washed with 2% 7N ammonia/methanol to elute the crude product. The product containing fractions were evaporated and the resultant material purified by reverse phase HPLC to give the title compound as a white solid (81 mg, 32.2%).

$^1$H NMR (399.9 MHz, DMSO-$d_6$) δ 2.41-2.44 (6H, m), 2.82 (2H, t), 3.35 (3H, s), 3.38-3.39 (2H, t), 3.59 (4H, t), 4.06-4.08 (2H, t), 7.26 (1H, s), 7.29 (1H, s), 7.31-7.35 (2H, m), 7.34-7.34 (1H, m), 7.40-7.42 (2H, m), 7.49 (2H, t), 8.05 (1H, t), 8.31 (1H, s), 9.53 (1H, s); MS m/z 503 [M+H]$^+$.

Example 228

3-chloro-4-[(2-methyl-3-oxo-6-propan-2-yl-2,6,8,10-tetrazabicyclo[5.4.0]undeca-7,9,11-trien-9-yl) amino]-N-(2-morpholin-4-ylethyl)benzamide 10-chloro-6-methyl-2-propan-2-yl-2,6,9,11-tetrazabicyclo[5.4.0]undeca-7,9,11-trien-5-one (Intermediate 76; 150 mg, 0.59 mmol), 4-amino-3-chloro-N-(2-morpholin-4-ylethyl)benzamide (Intermediate 52; 168 mg, 0.59 mmol), and p-toluenesulphonic acid monohydrate (281 mg, 1.47 mmol) were heated in 4-methyl-2-pentanol (4 mL) at 140° C. for 2 hours. The reaction mixture was cooled and loaded onto an SCX-3 column pre-wet with Methanol. The column was washed with methanol to remove p-toluenesulphonic acid monohydrate and then washed with 2% 7N ammonia/methanol to elute the crude product. Product containing fractions were evaporated and the resultant material purified by reverse phase HPLC to yield the title compound as an orange gum (46 mg, 15.6%).

$^1$H NMR (399.9 MHz, DMSO-$d_6$) δ 1.20 (6H, d), 2.42-2.43 (3H, m), 2.44-2.49 (2H, m), 2.60 (2H, t), 3.18 (4H, t), 3.39 (2H, q), 3.60-3.62 (6H, m), 4.75 (1H, m), 7.80-7.82 (1H, m), 7.96 (1H, d), 8.07 (1H, s), 8.12 (1H, s), 8.32 (1H, d), 8.40 (1H, t); MS m/z 503 [M+H]$^+$.

Example 229

3-methoxy-4-[[6-(2-methoxyethyl)-2-methyl-3-oxo-2,6,8,10-tetrazabicyclo[5.4.0]undeca-8,10,12-trien-9-yl]amino]-N-(1-methyl-4-piperidyl)benzamide 10-chloro-2-(2-methoxyethyl)-6-methyl-2,6,9,11-tetrazabicyclo[5.4.0]undeca-7,9,11-trien-5-one (Intermediate 109; 70 mg, 0.26 mmol), 4-amino-3-methoxy-N-(1-methyl-4-piperidyl)benzamide (WO06/018220; 63 mg, 0.26 mmol), and p-toluenesulphonic acid monohydrate (123 mg, 0.65 mmol) were combined in 4-Methyl-2-pentanol (2 mL) and heated at 100° C. overnight. The reaction was cooled to room temperature and taken up in MeOH and added to a 2 g SCX-2 column pre-wet with MeOH (2 column volumes). The column was washed with MeOH (2 column volumes) and the product eluted with 2M ammonia in MeOH and solvents evaporated. The resultant material was dissolved in DCM and purified on silica eluting with a gradient of 0-10% MeOH/DCM then 10% MeOH/DCM. Fractions containing product combined and evaporated to a clear gum to which ether was added and re-evaporated and the resultant material purified by reverse phase HPLC to give the title compound as a white solid. (40 mg, 31%).

$^1$H NMR (399.902 MHz, CDCl$_3$) δ 1.58 (m, 2H), 2.06 (m, 2H), 2.17 (m, 2H), 2.31 (s, 3H), 2.72 (m, 2H), 2.83 (m, 2H), 3.29 (s, 3H), 3.36 (s, 3H), 3.72 (m, 2H), 3.87 (m, 4H), 4.00 (m, 4H), 5.90 (d, 1H), 7.23 (m, 1H), 7.44 (d, 1H), 7.65 (s, 1H), 7.95 (s, 1H), 8.42 (d, 1H); MS m/z 503 [M+H]$^+$.

Example 230

3-methoxy-4-[[6-(1-methoxypropan-2-yl)-2-methyl-3-oxo-2,6,8,10-tetrazabicyclo[5.4.0]undeca-7,9,11-trien-9-yl]amino]-N-(1-methyl-4-piperidyl)benzamide 10-chloro-2-(1-methoxypropan-2-yl)-6-methyl-2,6,9,11-tetrazabicyclo[5.4.0]undeca-7,9,11-trien-5-one (Intermediate 112 60 mg, 0.21 mmol), 4-amino-3-methoxy-N-(1-methyl-4-piperidyl)benzamide (WO06/018220; 56 mg, 0.21 mmol), and p-toluenesulphonic acid monohydrate (100 mg, 0.53 mmol) were combined in 4-Methyl-2-pentanol (2 mL) and heated at 100° C. for 16 hrs. The reaction mixture was cooled to room temperature and dissolved in Methanol. The resultant solution was added to a 5 g SCX-3 column pre wet with MeOH (2 column volumes). Flushed with MeOH (2 column volumes) and crude product eluted with 2M ammonia in MeOH and solvents evaporated. The resultant residue was dissolved in DCM and purified on silica eluting with a gradient of 5-15% MeOH/DCM. Product containing fractions were combined and evaporated to a yellow gum which was purified by base modified reverse phase HPLC to give the title compound as a beige solid. (35 mg, 32%)

$^1$H NMR (399.902 MHz, CDCl$_3$) δ 1.32 (d, 3H), 1.58 (m, 2H), 2.05 (m, 2H), 2.17 (m, 2H), 2.31 (s, 3H), 2.68 (m, 2H), 2.83 (m, 2H), 3.29 (s, 3H), 3.36 (s, 3H), 3.51 (m, 1H), 3.62 (m, 1H), 3.73 (m, 2H), 4.00 (m, 4H), 5.00 (m, 1H), 5.90 (d, 1H), 7.23 (m, 1H), 7.43 (m, 1H), 7.65 (s, 1H), 7.94 (s, 1H), 8.47 (d, 1H); MS m/z 503 [M+H]$^+$.

Example 231

4-[[6-(3-furylmethyl)-2-methyl-3-oxo-2,6,8,10-tetrazabicyclo[5.4.0]undeca-8,10,12-trien-9-yl]amino]-3-methoxy-N-(1-methyl-4-piperidyl)benzamide 10-chloro-2-(3-furylmethyl)-6-methyl-2,6,9,11-tetrazabicyclo[5.4.0]undeca-7,9,11-trien-5-one one (Intermediate 116; 67 mg, 0.23 mmol), 4-amino-3-methoxy-N-(1-methyl-4-piperidyl)benzamide (WO06/018220; 60 mg, 0.23 mmol), and p-toluenesulphonic acid monohydrate (109 mg, 0.57 mmol) were combined in 4-Methyl-2-pentanol (2 mL) and heated at 100° C. for 16 hrs. The reaction mixture was cooled to room temperature and dissolved in Methanol. The resultant solution was added to a 5 g SCX-3 column pre wet with MeOH (2 column volumes). Flushed with MeOH (2 column volumes) and crude product eluted with 2M ammonia in MeOH and solvents evaporated. The resultant residue was dissolved in DCM and purified on silica eluting with a gradient of 0-15% MeOH/DCM. Product containing fractions were combined and evaporated to a yellow gum which was purified by base modified reverse phase HPLC to give the title compound as a yellow solid. (50 mg, 42%)

$^1$H NMR (400.132 MHz, CDCl$_3$) δ 1.57 (m, 2H), 2.04 (m, 2H), 2.17 (m, 2H), 2.31 (s, 3H), 2.64 (m, 2H), 2.82 (m, 2H), 3.31 (s, 3H), 3.71 (m, 2H), 3.98 (m, 4H), 4.67 (s, 2H), 5.88 (d, 1H), 6.43 (s, 1H), 7.14 (m, 1H), 7.40 (m, 1H), 7.43 (m, 2H), 7.71 (s, 1H), 7.99 (s, 1H), 8.45 (d, 1H); MS m/z 520 [M+H]$^+$.

Example 232

4-[(6-cyclopropyl-2-methyl-3-oxo-2,6,8,10-tetrazabicyclo[5.4.0]undeca-8,10,12-trien-9-yl)amino]-3-methoxy-N-(1-methyl-4-piperidyl)benzamide 10-chloro-2-cyclopropyl-6-methyl-2,6,9,11-tetrazabicyclo[5.4.0]undeca-7,9,11-trien-5-one (Intermediate 117 42 mg, 0.16 mmol), 4-amino-3-methoxy-N-(1-methyl-4-piperidyl)benzamide (WO06/018220; 44 mg, 0.216 mmol), and p-toluenesulphonic acid monohydrate (79 mg, 0.41 mmol) were combined in 4-Methyl-2-pentanol (2 mL) and heated at 100° C. for 16 hrs. The reaction mixture was cooled to room temperature and dissolved in methanol. The resultant solution was added to a 5 g SCX-3 column pre wet with MeOH (2 column volumes). Flushed with MeOH (2 column volumes) and crude product eluted with 2M ammonia in MeOH and solvents evaporated. The resultant residue was dissolved in DCM and purified on silica eluting with a gradient of 0-15% MeOH/DCM. Product containing fractions were combined and evaporated to a yellow gum which was purified by base modified reverse phase HPLC to give the title compound as a white solid. (34 mg, 43%)

$^1$H NMR (400.132 MHz, CDCl$_3$) δ 0.64 (m, 2H), 0.92 (m, 2H), 1.59 (m, 2H), 2.05 (m, 2H), 2.17 (m, 2H), 2.31 (s, 3H), 2.67 (m, 2H), 2.86 (m, 3H), 3.26 (s, 3H), 3.82 (m, 2H), 4.00 (m, 4H), 5.90 (d, 1H), 7.22 (m, 1H), 7.44 (d, 1H), 7.82 (s, 1H), 7.99 (s, 1H), 8.76 (d, 1H); MS m/z 503 [M+H]$^+$.

Example 233

N-cyclohexyl-3-methoxy-4-[[2-methyl-6-(1-methyl-4-piperidyl)-3-oxo-2,6,8,10-tetrazabicyclo[5.4.0]undeca-7,9,11-trien-9-yl]amino]benzamide 10-chloro-6-methyl-2-(1-methyl-4-piperidyl)-2,6,9,11-tetrazabicyclo[5.4.0]undeca-7,9,11-trien-5-one (Intermediate 118; 39 mg, 0.13 mmol), 4-amino-N-cyclohexyl-3-methoxy-benzamide (Intermediate 119; 31 mg, 0.13 mmol) and p-toluenesulphonic acid monohydrate (60 mg, 0.31 mmol) were combined in 4-Methyl-2-pentanol (2 mL) and heated at 100° C. for 16 hrs. The reaction mixture was cooled to room temperature and dissolved in Methanol and added to a 5 g SCX-3 column pre wet with MeOH (2 column volumes). Flushed with MeOH (2 column volumes) then crude product eluted with 2M ammonia in MeOH and solvents evaporated. The resultant material was dissolved in DCM and purified on silica eluting with a shallow (25 column volumes) gradient of 0-10% MeOH/DCM. Product containing fractions were combined and evaporated to a yellow gum which was purified by base modified reverse phase HPLC to give the title compound as a white solid. (15 mg, 23%).

$^1$H NMR (400.132 MHz, CDCl$_3$) δ 1.26 (m, 4H), 1.45 (m, 2H), 1.77 (m, 2H), 1.91 (m, 4H), 2.05 (m, 2H), 2.17 (m, 2H), 2.35 (s, 3H), 2.67 (m, 2H), 3.02 (m, 2H), 3.28 (s, 3H), 3.71 (m, 2H), 3.98 (m, 4H), 4.51 (m, 1H), 5.88 (d, 1H), 7.26 (m, 1H), 7.38 (d, 1H), 7.66 (s, 1H), 7.94 (s, 1H), 8.45 (d, 1H); MS m/z 522 [M+H]$^+$.

Example 234

4-[(6-cyclopentyl-2,5-dimethyl-3-oxo-2,6,8,10-tetrazabicyclo[5.4.0]undeca-8,10,12-trien-9-yl)amino]-3-methoxy-N-(1-methyl-4-piperidyl)benzamide 10-chloro-2-cyclopentyl-3,6-dimethyl-2,6,9,11-tetrazabicyclo[5.4.0]undeca-8,10,12-trien-5-one (Intermediate 120; 25 mg, 0.42 mmol) and), 4-amino-3-methoxy-N-(1-methyl-4-piperidyl)benzamide (WO06/018220; 112 mg, 0.42 mmol) were combined with p-toluenesulphonic acid monohydrate (202 mg, 1.06 mmol) in 4-methyl-2-pentanol (1 mL) and heated to 150° C. for 2 hr. The cooled reaction mixture was diluted with methanol (approx 50 mL) and loaded onto a 50 g SCX-2 cartridge washing with methanol (100 mL) and eluting with 7 N methanolic ammonia (100 mL). The concentrated solution was purified by base modified reverse phase HPLC to give the title compound as a white solid (65 mg, 30%)

$^1$H NMR (399.902 MHz, CDCl3) δ 1.29 (d, 3H), 1.54-1.89 (m, 9H), 1.95-2.23 (m, 6H), 2.32 (s, 3H), 2.56 (dd, 1H), 2.72 (dd, 1H), 2.84 (br d, 2H), 3.31 (s, 3H), 3.98 (s, 3H), 4.00-4.07 (m, 1H), 4.63-4.71 (m, 1H), 5.91 (d, 1H), 7.23 (dd, 1H), 7.42 (d, 1H), 7.67 (s, 1H), 7.97 (s, 1H), 8.47 (d, 1H); MS m/z 522 [M+H]$^+$.

Example 235

4-[(2-cyclopentyl-4,4,6-trimethyl-5-oxo-2,6,9,11-tetrazabicyclo[5.4.0]undeca-7,9,11-trien-10-yl)amino]-3-methoxy-N-(1-methyl-4-piperidyl)benzamide A solution of HATU (221 mg, 0.55 mmol) in DMA (10 mL) was added to a mixture of the 4-[(2-cyclopentyl-4,4,6-trimethyl-5-oxo-2,6,9,11-tetrazabicyclo[5.4.0]undeca-7,9,11-trien-10-yl)amino]-3-methoxy-benzoic acid (Example 242; 220 mg, 0.5 mmol), DIPEA (261 uL, 1.5 mmol) and 4-amino-3-methoxy-N-(1-methyl-4-piperidyl)benzamide (WO06/018220; 72 mg, 0.62 mmol) in DMA (10 mL). The resulting mixture was stirred at room temperature for 2 hours, then partially purified by SCX. The compound was retrieved from the SCX column using 7N ammonia in methanol, then concentrated in vacuo, and further purified by column chromatography, eluting with 0-10% ammonia (7N in methanol) in DCM. The pure material was recovered as an orange oil, which foamed and solidified under high vacuum. Trituration under ether gave the title compound as a pale yellow amorphous solid. (154 mg, 58%)

$^1$H NMR (399.9 MHz, CDCl$_3$) δ1.22 (6H, s), 1.56-1.63 (2H, m), 1.72-1.93 (6H, m), 1.99-2.03 (2H, m), 2.14 (2H, d), 2.41-2.45 (2H, m), 2.48 (3H, s), 3.06-3.09 (2H, m), 3.32 (3H, s), 3.40 (2H, s), 4.00 (3H, s), 4.10-4.14 (1H, m), 5.29-5.38 (1H, m), 6.12 (1H, d), 7.28 (1H, dd), 7.44 (1H, d), 7.65 (1H, s), 7.88 (1H, s), 8.52 (1H, d); MS m/z 536 [M+H]$^+$.

Example 236

Example 237

4-[[(4S)-2-cyclopentyl-4-ethyl-6-methyl-5-oxo-2,6,9,11-tetrazabicyclo[5.4.0]undeca-8,10,12-trien-10-yl]amino]-3-methoxy-N-(1-methyl-4-piperidyl)benzamide and 4-[[(4R)-2-cyclopentyl-4-ethyl-6-methyl-5-oxo-2,6,9,11-tetrazabicyclo[5.4.0]undeca-8,10,12-trien-10-yl]amino]-3-methoxy-N-(1-methyl-4-piperidyl)benzamide 10-chloro-2-cyclopentyl-4-ethyl-6-methyl-2,6,9,11-tetrazabicyclo[5.4.0]undeca-8,10,12-trien-5-one (Intermediate 123; 186 mg, 0.6 mmol), 4-amino-3-methoxy-N-(1-methyl-4-piperidyl)benzamide (WO06/018220; 159 mg, 0.6 mmol) were combined with p-toluenesulphonic acid monohydrate (286 mg, 1.5 mmol) in 4-methyl-2-pentanol (01 mL) and at 115° C. overnight. The cooled reaction mixture was dissolved in methanol, passed through an SCX-2 column and washed with methanol. The product was eluted off with 7N ammonia/ methanol. Product containing fractions were evaporated and the resultant material was purified using base modified reverse phase HPLC to give a mixture of the title compounds as a brown foam (110 mg)

The individual enantiomers were separated by chiral column chromatography to as white foams Enantiomer 1 (26 mg)

$^1$H NMR (399.9 MHz, DMSO-d6): $\delta_H$, 0.89 (tr, 3H), 1.31 (m, 2H), 1.50-1.90 (m, 12H), 2.11 (m, 2H), 2.36 (m, 5H), 2.61 (m, 1H), 3.00 (m, 2H), 3.21 (s, 3H), 3.42 (m, 2H), 3.84 (m, 1H), 3.97 (s, 3H), 4.79 (tr, 1H), 7.50 (m, 2H), 7.77 (m, 1H), 8.12 (m, 2H), 8.39 (d, 1H); MS m/z 536 [M+H]$^+$.

Enantiomer 2 (26 mg)

$^1$H NMR (399.9 MHz, DMSO-d6): $\delta_H$, 0.89 (tr, 3H), 1.31 (m, 2H), 1.50-1.90 (m, 12H), 2.11 (m, 2H), 2.36 (m, 5H), 2.61 (m, 1H), 3.00 (m, 2H), 3.21 (s, 3H), 3.42 (m, 2H), 3.84 (m, 1H), 3.97 (s, 3H), 4.79 (tr, 1H), 7.50 (m, 2H), 7.77 (m, 1H), 8.12 (m, 2H), 8.39 (d, 1H). MS m/z 536 [M+H]$^+$.

Example 238

Example 239

4-[[(4S)-2-cyclopentyl-6-methyl-5-oxo-4-propyl-2,6,9,11-tetrazabicyclo[5.4.0]undeca-8,10,12-trien-10-yl]amino]-3-methoxy-N-(1-methyl-4-piperidyl)benzamide and 4-[[(4R)-2-cyclopentyl-6-methyl-5-oxo-4-propyl-2,6,9,11-tetrazabicyclo[5.4.0]undeca-8,10,12-trien-10-yl]amino]-3-methoxy-N-(1-methyl-4-piperidyl)benzamide 10-chloro-2-cyclopentyl-6-methyl-4-propyl-2,6,9,11-tetrazabicyclo[5.4.0]undeca-8,10,12-trien-5-one (Intermediate 124; 194 mg, 0.6 mmol), 4-amino-3-methoxy-N-(1-methyl-4-piperidyl)benzamide (WO06/018220; 159 mg, 0.6 mmol) were combined with p-toluenesulphonic acid monohydrate (286 mg, 1.5 mmol) in 4-methyl-2-pentanol (01 mL) and at 115° C. overnight. The cooled reaction mixture was dissolved in methanol, passed through an SCX-2 column and washed with methanol. The product was eluted with 7N ammonia/ methanol. Product containing fractions were evaporated and the resultant material purified using basic prep HPLC to give a mixture of the title compounds as a light brown foam (65 mg)

The individual enantiomers were separated by chiral column chromatography to as white foams Enantiomer 1 (15 mg)

$^1$H NMR (399.9 MHz, DMSO-d6): δ 0.84 (tr, 3H), 1.29 (m, 3H), 1.50-1.90 (m, 13H), 2.11 (m, 2H), 2.41 (m, 5H), 2.69 (m, 1H), 3.02 (m, 2H), 3.20 (s, 3H), 3.40 (m, 2H), 3.85 (m, 1H), 3.95 (s, 3H), 4.79 (tr, 1H), 7.50 (m, 2H), 7.76 (m, 1H), 8.12 (s, 1H), 8.14 (d, 1H), 8.40 (d, 1H); MS m/z 550 [M+H]$^+$.

Enantiomer 2 (22 mg)

$^1$H NMR (399.9 MHz, DMSO-d6): δ 0.84 (tr, 3H), 1.29 (m, 3H), 1.50-1.90 (m, 13H), 2.11 (m, 2H), 2.41 (m, 5H), 2.69 (m, 1H), 3.02 (m, 2H), 3.20 (s, 3H), 3.40 (m, 2H), 3.85 (m, 1H), 3.95 (s, 3H), 4.79 (tr, 1H), 7.50 (m, 2H), 7.76 (m, 1H), 8.12 (s, 1H), 8.14 (d, 1H), 8.40 (d, 1H); MS m/z 550 [M+H]$^+$.

Example 240

Example 241

4-[[(4S)-2-cyclopentyl-4,6-dimethyl-5-oxo-2,6,9,11-tetrazabicyclo[5.4.0]undeca-8,10,12-trien-10-yl]amino]-3-methoxy-N-(1-methyl-4-piperidyl)benzamide and 4-[[(4R)-2-cyclopentyl-4,6-dimethyl-5-oxo-2,6,9,11-tetrazabicyclo[5.4.0]undeca-8,10,12-trien-10-yl]amino]-3-methoxy-N-(1-methyl-4-piperidyl)benzamide 10-chloro-2-cyclopentyl-4,6-dimethyl-2,6,9,11-tetrazabicyclo[5.4.0]undeca-8,10,12-trien-5-one (Intermediate 125; 674 mg, 2.29 mmol), 4-amino-3-methoxy-N-(1-methyl-4-piperidyl)benzamide (WO06/018220; 602 mg, 2.29 mmol) and p-toluene sulphonic acid (1.09 g, 0.89 mmol) were dissolved in 4-methyl-2-pentanol (15 mL) and refluxed under a blanket of nitrogen for 24 hours. The reaction mixture was cooled and passed through an SCX-2 column washed with methanol. The crude product was eluted with 7N ammonia in methanol. Product containing fractions were evaporated and the resultant material purified by column chromatography, eluting with 0-10% ammonia methanol (7N) in DCM. The resultant material was purified by base modified reverse phase HPLC to give a mixture of the title compounds as a white solid (480 mg, 40%).

The individual enantiomers were separated by chiral column chromatography to as white gums which were dissolved separately in DCM then passed through SCX-2 columns and washed with methanol. The products were eluted off the columns using 7N ammonia in methanol and concentrated under reduced pressure to yield the enantiomers as white solids.

Enantiomer 1 (118 mg)

$^1$H NMR (399.902 MHz, DMSO-d6) δ 1.04 (d, 3H), 1.51-1.84 (m, 12H), 1.99-2.13 (m, 3H), 2.81-2.91 (m, 6H), 3.20 (s, 3H), 3.45 (q, 2H), 3.78 (m, 1H), 3.96 (s, 3H), 4.08 (s, 1H), 4.75 (quintet, 1H), 7.49 (d, 1H), 7.75 (s, 1H), 8.09 (d, 1H), 8.40 (d, 1H); MS m/z 523 [M+H]$^+$.

Enantiomer 2 (59 mg)

$^1$H NMR (399.902 MHz, DMSO-d$_6$) δ 1.04 (d, 3H), 1.51-1.84 (m, 12H), 1.99-2.13 (m, 3H), 2.81-2.91 (m, 6H), 3.20 (s, 3H), 3.45 (q, 2H), 3.78 (m, 1H), 3.96 (s, 3H), 4.08 (s, 1H), 4.75 (quintet, 1H), 7.49 (d, 1H), 7.75 (s, 1H), 8.09 (d, 1H), 8.40 (d, 1H); MS m/z 523 [M+H]$^+$.

Example 242

4-[(2-cyclopentyl-4,4,6-trimethyl-5-oxo-2,6,9,11-tetrazabicyclo[5.4.0]undeca-7,9,11-trien-10-yl)amino]-3-methoxy-benzoic acid To a solution of 10-chloro-2-cyclopentyl-4,4,6-trimethyl-2,6,9,11-tetrazabicyclo[5.4.0]undeca-7,9,11-trien-5-one (Intermediate 126; 616 mg, 2.0 mmol) and 4-amino-3-methoxy-benzoic acid (378 mg, 2.2 mmol) in ethanol (5 mL) was added water (15 mL) and conc hydrochloric acid (0.335 mL). The mixture was heated under reflux for 36 hours. The reaction was cooled and a brown solid precipitated. This was filtered, dried and triturated under cold acetonitrile and then dried in vacuo to give the product as a pale brown solid (420 mg), 48%)

¹H NMR (400.13 MHz, DMSO-d₆) δ1.15 (6H, s), 1.55-1.90 (8H, m), 3.19 (3H, s), 3.53 (2H, s), 3.95 (3H, s), 5.07-5.16 (1H, m), 7.59-7.61 (2H, m), 8.11 (1H, s), 8.13 (1H, d), 9.53 (1H, s); MS m/z 440 [M+H]⁺.

Example 243

4-[(2-cyclopentyl-4,4,6-trimethyl-5-oxo-2,6,9,11-tetrazabicyclo[5.4.0]undeca-7,9,11-trien-10-yl)amino]-3-methoxy-N-(1-methyl-3-piperidyl)benzamide A solution of HATU (126 mg, 0.33 mmol) in DMA (5 mL) was added to a mixture of the 4-[(2-cyclopentyl-4,4,6-trimethyl-5-oxo-2,6,9,11-tetrazabicyclo[5.4.0]undeca-7,9,11-trien-10-yl)amino]-3-methoxy-benzoic acid (Example 242 132 mg, 0.3 mmol), DIPEA (261 uL, 1.5 mmol) and 3-amino N-methylpiperidine dihydrochloride (71 mg, 0.375 mmol) in DMA (5 mL). The resulting mixture was stirred at room temperature for 2 hours, then partially purified by SCX. The compound was eluted from the SCX column using 7N ammonia in methanol, then concentrated in vacuo, and further purified by column chromatography, eluting with 0-10% ammonia (7N in methanol) in DCM. The pure material was recovered as an orange oil, which foamed and solidified under high vacuum. Trituration under ether gave the title compound as a pale yellow amorphous solid (65 mg, 41%)

¹H NMR (400.13 MHz, CDCl₃) δ1.03 (6H, s), 1.34-1.87 (12H, m), 2.17 (5H, s), 2.41 (2H, s), 3.13 (3H, s), 3.20 (2H, s), 3.82 (3H, s), 4.19 (1H, s), 5.10-5.20 (1H, m), 7.09 (1H, s), 7.20 (1H, s), 7.34 (1H, s), 7.43 (1H, s), 7.68 (1H, s), 8.31 (1H, d); MS m/z 536 [M+H]⁺.

Example 244

4-[(2-cyclopentyl-4,4,6-trimethyl-5-oxo-2,6,9,11-tetrazabicyclo[5.4.0]undeca-7,9,11-trien-10-yl)amino]-3-methoxy-N-[1-(2-methoxyethyl)-4-piperidyl]benzamide A solution of HATU (126 mg, 0.33 mmol) in DMA (5 mL) was added to a mixture of 4-[(2-cyclopentyl-4,4,6-trimethyl-5-oxo-2,6,9,11-tetrazabicyclo[5.4.0]undeca-7,9,11-trien-10-yl)amino]-3-methoxy-benzoic acid (Example 242 132 mg, 0.3 mmol), DIPEA (261 uL, 1.5 mmol) and 4-amino N-(2-methoxyethyl)piperidine (60 mg, 0.375) in DMA (5 mL). The resulting mixture was stirred at room temperature for 2 hours, then partially purified by SCX. The compound was retrieved from the SCX column using 7N ammonia in methanol, then concentrated in vacuo, and further purified by column chromatography, eluting with 0-10% ammonia (7N in methanol) in DCM. The pure material was recovered as an orange oil, which foamed and solidified under high vacuum. Trituration under ether gave a pale yellow amorphous solid. (55 mg, 32%)

¹H NMR (400.13 MHz, CDCl₃) δ1.13 (6H, s), 1.43-1.56 (2H, m), 1.58-1.74 (4H, m), 1.87-1.97 (4H, m), 2.04 (2H, d), 2.44 (2H, t), 2.76 (2H, t), 3.10-3.12 (2H, m), 3.23 (3H, s), 3.29-3.30 (2H, m), 3.30 (3H, s), 3.59-3.62 (2H, m), 3.90 (2H, s), 4.03-4.07 (1H, m), 5.20-5.28 (1H, m), 6.04 (1H, d), 7.17-7.20 (2H, m), 7.34 (1H, d), 7.55 (1H, s), 7.79 (1H, s), 8.42 (1H, d). MS m/z 580 [M+H]⁺.

Example 245

4-[(2-cyclopentyl-4,4,6-trimethyl-5-oxo-2,6,9,11-tetrazabicyclo[5.4.0]undeca-7,9,11-trien-10-yl)amino]-N-(1-methyl-4-piperidyl)benzamide A solution of HATU (126 mg, 0.33 mmol) in DMA (5 mL) was added to a mixture of 4-[(2-cyclopentyl-4,4,6-trimethyl-5-oxo-2,6,9,11-tetrazabicyclo[5.4.0]undeca-7,9,11-trien-10-yl)amino]benzoic acid, (Intermediate 129; 123 mg, 0.3 mmol) DIPEA (261 uL, 1.5 mmol) and 4-amino N-methylpiperidine (43 mg, 0.375) in DMA (5 mL). The resulting mixture was stirred at room temperature for 2 hours, then partially purified by SCX. The compound was eluted from the SCX column using 7N ammonia in methanol, then concentrated in vacuo, and further purified by column chromatography, eluting with 0-10% ammonia (7N in methanol) in DCM. The pure material was recovered as an orange oil, which foamed and solidified under high vacuum. Trituration under ether gave a pale yellow amorphous solid. (100 mg, 66%)

¹H NMR (400.13 MHz, CDCl₃) δ1.13 (6H, s), 1.43-1.53 (2H, m), 1.60-1.73 (4H, m), 1.83-1.95 (4H, m), 2.01-2.09 (2H, m), 2.37-2.42 (2H, m), 2.44 (3H, s), 3.06 (2H, d), 3.22 (3H, s), 3.30 (2H, s), 4.01-4.07 (1H, m), 5.16-5.25 (1H, m), 6.07 (1H, d), 6.99 (1H, s), 7.58 (2H, d), 7.65 (2H, d), 7.77 (1H, s); MS m/z 506 [M+H]⁺.

Example 246

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(1-methylpiperidin-4-yl)-3-methoxybenzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 153 mg, 0.5 mmol) 4-amino-3-methoxy-N-(1-methyl-4-piperidyl)benzamide (WO06/018220; 158 mg, 0.6 mmol) were combined with p-toluenesulphonic acid monohydrate (190 mg, 1.0 mmol) in 4-methyl-2-pentanol (4 mL) mixed and heated by microwave irradiation at 160° C. for 1 hour, cleaned up partially by SCX, then purified by column chromatography, eluting with 0-6% methanolic ammonia in DCM, to give the product as a clear oil, which solidified on trituration with ether to give the title compound as a white solid (160 mg, 60%)

¹H NMR (400.13 MHz, CDCl₃) δ 0.61-0.64 (2H, m), 1.09-1.12 (2H, m), 1.42-1.52 (2H, m), 1.61-1.76 (6H, m), 1.98-2.11 (4H, m), 2.23 (2H, t), 2.35 (3H, s), 2.89 (2H, d), 3.30 (3H, s), 3.47 (2H, s), 3.99 (3H, s), 3.99-4.10 (1H, m), 4.93-4.99 (1H, m), 5.99 (1H, d), 7.26 (1H, dd), 7.43 (1H, d), 7.65 (1H, s), 7.87 (1H, s), 8.53 (1H, d) MS m/z 534 [M+H]⁺.

Example 247

3-chloro-N-(2-morpholin-4-ylethyl)-4-[(3-oxo-6-phenyl-2,6,8,10-tetrazabicyclo[5.4.0]undeca-7,9,11-trien-9-yl)amino]benzamide 4-amino-3-chloro-N-(2-morpholin-4-ylethyl)benzamide (Intermediate 104; 104 mg, 0.36 mmol), 10-chloro-2-phenyl-2,6,9,11-tetrazabicyclo[5.4.0]undeca-7,9,11-trien-5-one (Intermediate 52; 100 mg, 0.36 mmol) and p-toluenesulphonic acid monohydrate (174 mg, 0.91 mmol) were heated at 140° C. in 4-methyl-2-pentanol (2.5 ml) for 4.5 hrs. The reaction mixture was cooled and absorbed onto an SCX column, washed with methanol and eluted with ammonia in methanol.

After concentration of the product containing fractions methanol was added to the residue and the suspension filtered to give the title compound as an off-white coloured solid (42 mg, 22%)

$^1$H NMR (399.9 MHz, DMSO-d$_6$) δ 2.41-2.47 (6H, m), 2.89 (2H, m), 3.36 (2H, t), 3.59 (4H, m), 4.01-4.03 (2H, m), 7.19-7.22 (1H, m), 7.36-7.43 (3H, m), 7.51-7.55 (3H, m), 7.69 (1H, s), 7.83 (1H, d), 7.97 (1H, s), 8.27 (1H, t), 9.66 (1H, s); MS m/z 522 [M+H]$^+$.

The following example was prepared by an analogous process to that used in the preparation of Example 255 utilising 4-amino-3-chloro-N-(1-methyl-4-piperidyl)benzamide Intermediate 55 to give the title compound as a white solid (31 mg, 17%)

Example 248

3-chloro-N-(1-methyl-4-piperidyl)-4-[(3-oxo-6-phenyl-2,6,8,10-tetrazabicyclo[5.4.0]undeca-8,10,12-trien-9-yl)amino]benzamide $^1$H NMR (399.9 MHz, DMSO-d$_6$) δ1.54-1.58 (2H, m), 1.74 (2H, d), 1.91-1.97 (2H, m), 2.17 (3H, s), 2.74-2.79 (2H, m), 2.89 (2H, m), 3.64-3.74 (1H, m), 4.00-4.03 (2H, m), 7.20-7.23 (1H, m), 7.35-7.41 (3H, m), 7.53 (3H, d), 7.68 (1H, s), 7.87 (1H, d), 7.96 (1H, s), 8.10 (1H, d), 9.65 (1H, s); MS m/z 506 [M+H]$^+$.

Example 249

N-(2-morpholin-4-ylethyl)-4-[(3-oxo-6-phenyl-2,6,8,10-tetrazabicyclo[5.4.0]undeca-7,9,11-trien-9-yl)amino]benzamide 4-amino-N-(2-morpholin-4-ylethyl)benzamide (Buttpark; 188 mg, 0.75 mmol) and 10-chloro-2-phenyl-2,6,9,11-tetrazabicyclo[5.4.0]undeca-7,9,11-trien-5-one (Intermediate 104; 160 mg, 0.63 mmol) were heated together in EtOH:water (8 ml, 1:3) in the presence of concentrated hydrochloric acid (126 ul) for 24 hours. The mixture was cooled to ambient temperature and then loaded onto an SCX-2 (5 g) column pre-wet with methanol. The product was eluted with 2M NH3/MeOH and the solvent evaporated to give product as a brown gum, which was purified by base, modified reverse phase HPLC to yield the title compound as a white solid. (35 mg, 13%)

$^1$H NMR (400.132 MHz, DMSO-d6) δ 2.43 (m, 4H), 2.88 (m, 3H), 3.34 (m, 2H), 3.59 (m, 4H), 3.99 (m, 3H), 7.18 (d, 2H), 7.38 (m, 5H), 7.53 (t, 2H), 7.93 (s, 1H), 8.00 (m, 1H), 9.28 (s, 1H), 9.57 (s, 1H); MS m/z 488 [M+H]$^+$.

Example 250

4-[(6-cyclopentyl-3-oxo-2,6,8,10-tetrazabicyclo[5.4.0]undeca-8,10,12-trien-9-yl)amino]-3-methoxy-N-(2-morpholin-4-ylethyl)benzamide 4-amino-3-methoxy-N-(2-morpholin-4-ylethyl)benzamide (Intermediate 135 176 mg, 0.75 mmol) and 10-chloro-2-phenyl-2,6,9,11-tetrazabicyclo[5.4.0]undeca-7,9,11-trien-5-one (Intermediate 2 168 mg, 0.63 mmol) were heated together in EtOH:water (8 ml, 1:3) in the presence of concentrated hydrochloric acid (126 ul) for 24 hours. The mixture was cooled to ambient temperature and then loaded onto an SCX-2 (5 g) column pre-wet with methanol. The product was eluted with 2M NH3/MeOH and the solvent evaporated to give product as a brown gum, which was purified by base, modified reverse phase HPLC to yield the title compound as a white solid. (154 mg, 54%)

$^1$H NMR (400.132 MHz, DMSO-d$_6$) δ 1.73 (m, 8H), 2.45 (m, 6H), 2.62 (m, 2H), 3.39 (m, 4H), 3.58 (m, 6H), 3.94 (s, 3H), 5.09 (m, 1H), 7.46 (m, 2H), 7.60 (s, 1H), 7.80 (s, 1H), 8.25 (t, 1H), 8.38 (d, 1H), 9.41 (s, 1H); MS m/z 510 [M+H]$^+$.

Example 251

3-methoxy-N-(1-methyl-4-piperidyl)-4-[(3-oxo-6-phenyl-2,6,8,10-tetrazabicyclo[5.4.0]undeca-8,10,12-trien-9-yl)amino]benzamide 4-amino-3-methoxy-N-(1-methyl-4-piperidyl)benzamide (WO06/018220; 173 mg, 0.66 mmol) and 10-chloro-2-phenyl-2,6,9,11-tetrazabicyclo[5.4.0]undeca-7,9,11-trien-5-one (Intermediate 104; 150 mg, 0.55 mmol) were heated together in EtOH:water (8 mL, 1:3) in the presence of concentrated hydrochloric acid (110 ul) for 24 hours. p-toluenesulphonic acid monohydrate (105 mg, 0.55 mmol) was added and the mixture heated at 150 deg for 3 h by microwave irradiation. The mixture was cooled to ambient temperature and loaded onto an SCX-2 (5 g) column pre-wet with methanol. The product was eluted with 2M NH3/MeOH and solvent evaporated to give a brown gum which was purified by base modified reverse phase HPLC to yield the title compound as a white solid (73 mg, 27%)

$^1$H NMR (400.132 MHz, DMSO-d$_6$) δ 1.57 (m, 2H), 1.75 (m, 2H), 1.93 (m, 2H), 2.17 (s, 3H), 2.84 (m, 4H), 3.70 (m, 1H), 3.87 (s, 3H), 4.01 (m, 2H), 6.91 (d, 1H), 7.39 (m, 6H), 7.53 (m, 2H), 7.93 (s, 1H), 7.95 (s, 1H), 9.60 (s, 1H); MS m/z 502 [M+H]$^+$.

Example 252

N-(3-dimethylamino-2,2-dimethyl-propyl)-3-methoxy-4-[(3-oxo-6-phenyl-2,6,8,10-tetrazabicyclo[5.4.0]undeca-8,10,12-trien-9-yl)amino]benzamide 4-amino-N-(3-dimethylamino-2,2-dimethyl-propyl)-3-methoxy-benzamide (Intermediate 22; 183 mg, 0.66 mmol) and 10-chloro-2-phenyl-2,6,9,11-tetrazabicyclo[5.4.0]undeca-7,9,11-trien-5-one (Intermediate 104; 150 mg, 0.55 mmol) were heated together in EtOH:water (8 mL, 1:3) in the presence of concentrated hydrochloric acid (110 ul) for 24 hours. IPA/DMA was added to aid solution followed by p-toluenesulphonic acid monohydrate (52 mg, 0.27 mmol) and the mixture heated by microwave irradiation for 1 hour at 150° C. The mixture was cooled to ambient temperature and loaded onto an SCX-2 (5 g) column pre-wet with methanol. The product was eluted with 2M NH3/MeOH and the solvent evaporated to give product as a brown gum which was purified by base modified reverse phase HPLC to yield the title compound as a gum (13 mg, 5%)

ES+518 (M+H), ES– 516 (M–H) Retention Time 2.18 minutes

Example 253

4-[(6-cyclopentyl-3-oxo-2,6,8,10-tetrazabicyclo[5.4.0]undeca-8,10,12-trien-9-yl)amino]-N-(3-dimethylamino-2,2-dimethyl-propyl)benzamide 4-amino-N-(3-dimethylamino-2,2-dimethyl-propyl)benzamide (Intermediate 136; 113 mg, 0.45 mmol) and 10-chloro-2-cyclopentyl-2,6,9,11-tetrazabicyclo[5.4.0]undeca-7,9,11-trien-5-one (Intermediate 2; 120 mg, 0.45 mmol) were heated together in EtOH:water (8 ml, 1:3) in the presence of 4-toluenesulphonic acid (214 mg, 1.13 mmol) for 23 hours. The reaction mixture was heated by microwave irradiation at 150° C. for 20 minutes cooled to ambient temperature and loaded onto an SCX-2 (5 g) column pre-wet with methanol. The product was eluted with 2M NH3/MeOH and the solvent evaporated to give product as a gum, which was purified by base modified reverse phase HPLC to yield the title compound as a white solid. (77 mg, 36%)

$^1$H NMR (400.132 MHz, DMSO-d6) δ 0.88 (s, 6H), 1.61 (m, 4H), 1.74 (m, 2H), 1.90 (m, 2H), 2.19 (s, 2H), 2.27 (s, 6H), 2.61 (m, 2H), 3.18 (d, 2H), 3.57 (m, 2H), 5.14 (m, 1H), 7.69 (d, 2H), 7.78 (d, 2H), 7.79 (s, 1H), 8.30 (t, 1H), 9.31 (s, 1H), 9.38 (s, 1H); MS m/z 480 [M+H]$^+$.

Example 254

4-[(6-cyclopentyl-3-oxo-2,6,8,10-tetrazabicyclo [5.4.0]undeca-8,10,12-trien-9-yl)amino]-N-(1-methyl-4-piperidyl)benzamide 4-amino-N-(1-methyl-4-piperidyl)benzamide (Intermediate 4; 131 mg, 0.56 mmol) and 10-chloro-2-cyclopentyl-2,6,9,11-tetrazabicyclo[5.4.0]undeca-7,9,11-trien-5-one (Intermediate 2; 150 mg, 0.56 mmol) were heated together in 4-methyl-2-pentanol (4 ml) in the presence of p-toluenesulphonic acid (266 mg, 1.40 mmol) for 24 hours. The mixture was cooled to ambient temperature and then loaded onto an SCX-2 (5 g) column pre-wet with methanol. The product was eluted with 2M NH3/MeOH and the solvent evaporated to give crude product, which was purified by base modified reverse phase HPLC to yield the title compound as a white solid. (56 mg, 22%)

$^1$H NMR (400.132 MHz, DMSO-d$_6$) δ 1.58 (m, 6H), 1.75 (m, 4H), 1.92 (m, 4H), 2.17 (s, 3H), 2.61 (m, 2H), 2.77 (m, 2H), 3.57 (m, 2H), 3.72 (m, 1H), 5.14 (m, 1H), 7.75 (m, 4H), 7.79 (s, 1H), 7.95 (d, 1H), 9.29 (s, 1H), 9.38 (s, 1H); MS m/z 464 [M+H]$^+$.

Example 255

3-chloro-4-[(6-cyclopentyl-3-oxo-2,6,8,10-tetrazabicyclo[5.4.0]undeca-8,10,12-trien-9-yl)amino]-N-(3-dimethylamino-2,2-dimethyl-propyl)benzamide 4-amino-3-chloro-N-(3-dimethylamino-2,2-dimethyl-propyl)benzamide (Intermediate 107; 118 mg, 0.37 mmol), 10-chloro-2-cyclopentyl-2,6,9,11-tetrazabicyclo[5.4.0]undeca-7,9,11-trien-5-one (Intermediate 2; 100 mg, 0.37 mmol) and p-toluenesulphonic acid monohydrate (179 mg, 0.94 mmol) were heated at 140° C. in 4-methyl-2-pentanol for 2 h. LC-MS indicated the reaction had not gone to completion with 50% of product in the mixture. An SCX-3 column was washed with methanol then the solution was loaded onto it. The column was washed with methanol and eluted with 7N ammonia/methanol to give the crude product. The mixture was concentrated the resultant material purified by base modified reverse phase HPLC to yield the title compound as an odd-white solid (24 mg, 12.6%).

$^1$H NMR (399.9 MHz, DMSO-d$_6$) δ0.89 (6H, s), 1.56 (4H, m), 1.71 (2H, s), 1.83-1.85 (2H, m), 2.18 (2H, s), 2.27 (6H, s), 2.62 (2H, t), 3.18-3.20 (2H, s), 3.57 (2H, t), 5.03 (1H, m), 7.73-7.76 (1H, m), 7.80 (1H, s), 7.94 (1H, d), 8.03 (1H, s), 8.28 (1H, d), 8.46 (1H, s), 9.44 (1H, s); MS m/z 514 [M+H]$^+$.

Example 256

4-[(6-cyclopentyl-3-oxo-2,6,8,10-tetrazabicyclo [5.4.0]undeca-8,10,12-trien-9-yl)amino]-N-(2-morpholin-4-ylethyl)benzamide 10-chloro-2-cyclopentyl-2,6,9,11-tetrazabicyclo[5.4.0] undeca-7,9,11-trien-5-one (Intermediate 2; 150 mg, 0.56 mmol), 4-amino-N-(2-morpholin-4-ylethyl)benzamide (Buttpark; 141 mg, 0.56 mmol) and p-toluenesulphonic acid monohydrate (268 mg, 1.41 mmol) were heated in 4-methyl-2-pentanol (4 mL) for 2 hours at 140° C. The reaction mixture was loaded onto an SCX-3 column pre-wet with methanol. The column was washed with methanol and 7N ammonia/methanol to elute the crude product. Product containing fractions were evaporated, dissolved in DMF and purified by base modified reverse phase HPLC to yield the title compound as a white solid (77 mg, 28.5%)

$^1$H NMR (399.9 MHz, DMSO-d$_6$) δ1.62 (2H, m), 1.67 (2H, m), 1.76 (2H, m), 1.91 (2H, m), 2.43-2.46 (6H, m), 2.62 (2H, t), 3.38 (2H, q), 3.58 (6H, t), 5.12-5.16 (1H, m), 7.74-7.77 (3H, m), 7.77 (2H, d), 8.15 (1H, t), 9.33 (1H, s), 9.40 (1H, s); MS m/z 481 [M+H]$^+$.

The following example was prepared by an analogous process to that used in the preparation of Example 256 utilising 4-amino-3-chloro-N-(2-morpholin-4-ylethyl)benzamide Intermediate 50 to give the title compound as a yellow solid (44 mg, 15%)

Example 257

3-chloro-4-[(6-cyclopentyl-3-oxo-2,6,8,10-tetrazabicyclo[5.4.0]undeca-8,10,12-trien-9-yl)amino]-N-(2-morpholin-4-ylethyl)benzamide $^1$H NMR (399.9 MHz, DMSO-d$_6$) δ1.57 (4H, d), 1.68-1.72 (2H, m), 1.85 (2H, s), 2.43 (6H, m), 2.62 (2H, t), 3.39 (2H, q), 3.58 (6H, t), 5.03 (1H, m), 7.78 (2H, t), 7.95 (1H, d), 8.00 (1H, s), 8.30 (1H, d), 8.39 (1H, t), 9.44 (1H, s); MS m/z 515 [M+H]$^+$.

Example 258

3-methoxy-4-[[6-(1-methoxypropan-2-yl)-3-oxo-2,6,8,10-tetrazabicyclo[5.4.0]undeca-7,9,11-trien-9-yl] amino]-N-(1-methyl-4-piperidyl)benzamide 10-chloro-2-(1-methoxypropan-2-yl)-2,6,9,11-tetrazabicyclo[5.4.0]undeca-7,9,11-trien-5-one (Intermediate 137; 35 mg, 0.13 mmol)), 4-amino-3-methoxy-N-(1-methyl-4-piperidyl)benzamide (WO06/018220; 34 mg, 0.13 mmol) and p-toluenesulphonic acid monohydrate (61 mg, 0.32 mmol) were dissolved in 4-methyl-2-pentanol (2 mL) and heated at 100° C. for 18 hrs. The reaction mixture was cooled to room temperature dissolved in MeOH and added to a 2 g SCX-2 column pre wet with MeOH (2 column volumes). Flushed with MeOH (2 column volumes) and the product eluted with 2M ammonia in MeOH. Product containing fractions were evaporated and the resultant material purified by base modified reverse phase HPLC to yield the title compound as a cream coloured solid (13 mg, 20%)

$^1$H NMR (399.902 MHz, CDCl$_3$) δ1.29 (d, 3H), 1.61 (m, 2H), 2.06 (m, 2H), 2.18 (m, 2H), 2.31 (s, 3H), 2.77 (m, 2H), 2.84 (m, 2H), 3.36 (s, 3H), 3.54 (m, 2H), 3.68 (m, 2H), 3.97

(s, 3H), 4.00 (m, 1H), 5.27 (m, 1H), 5.90 (d, 1H), 6.94 (s, 1H), 7.23 (m, 1H), 7.42 (d, 1H), 7.60 (s, 1H), 7.70 (s, 1H), 8.43 (d, 1H); MS m/z 498 [M+H]$^+$.

Example 259

4-[(6-cyclopentyl-2-ethyl-3-oxo-2,6,8,10-tetrazabicyclo[5.4.0]undeca-8,10,12-trien-9-yl)amino]-3-methoxy-N-(1-methyl-4-piperidyl)benzamide 10-chloro-2-cyclopentyl-6-ethyl-2,6,9,11-tetrazabicyclo[5.4.0]undeca-8,10,12-trien-5-one (Intermediate 139; 221 mg, 0.75 mmol), 4-amino-3-methoxy-N-(1-methyl-4-piperidyl)benzamide (WO06/018220; 198 mg, 0.75 mmol) and p-toluenesulphonic acid (357 mg, 1.88 mmol) were heated in 4-methyl-2-pentanol (3 mL) at 140° C. for 18 hours. The reaction mixture was allowed to cool to room temperature and loaded onto a 10 g SCX-2 cartridge, washing with methanol (10 mL), water (10 mL) and methanol (10 mL) before the product was eluted off with 7 N methanolic ammonia to provide a brown oil upon evaporation of product containing fractions. The resultant material was purified by flash silica chromatography, 0-10% methanolic ammonia/DCM to give a pale yellow glass which was purified by base modified reverse phase HPLC to yield the title compound as a white solid (192 mg, 0.36 mmol, 49%).

$^1$H NMR (399.902 MHz, DMSO-d$_6$) δ 1.00 (t, 3H), 1.55-1.82 (m, 12H), 1.91-1.98 (m, 4H), 2.18 (s, 3H), 2.79 (d, 2H), 3.60-3.63 (m, 2H), 3.69-3.79 (m, 3H), 3.96 (s, 3H), 4.74 (quintet, 1H), 7.48-7.51 (m, 2H), 7.77 (s, 1H), 8.08 (d, 1H), 8.13 (s, 1H), 8.39 (d, 1H); MS m/z 523 [M+H]$^+$.

The following example was prepared by an analogous process to that used in the preparation of Example 259 utilising 10-chloro-2-cyclopentyl-6-propan-2-yl-2,6,9,11-tetrazabicyclo[5.4.0]undeca-8,10,12-trien-5-one (Intermediate 142 to give the title compound as a white solid (77 mg, 14%)

Example 260

4-[(6-cyclopentyl-3-oxo-2-propan-2-yl-2,6,8,10-tetrazabicyclo[5.4.0]undeca-8,10,12-trien-9-yl)amino]-3-methoxy-N-(1-methyl-4-piperidyl)benzamide $^1$H NMR (399.902 MHz, DMSO-d$_6$) δ 1.14 (d, 6H), 1.54-1.81 (m, 12H), 1.92-1.98 (m, 4H), 2.18 (s, 3H), 2.79 (br d, 2H), 3.56-3.59 (m, 2H), 3.70-3.80 (m, 1H), 3.96 (s, 3H), 4.40 (septet, 1H), 4.63 (quintet, 1H), 7.48-7.51 (m, 2H), 7.80 (s, 1H), 8.03 (s, 1H), 8.08 (d, 1H), 8.40 (d, 1H); MS m/z 536 [M+H]$^+$.

Example 261

2-[(6-cyclopentyl-2-methyl-3-oxo-2,6,8,10-tetrazabicyclo[5.4.0]undeca-8,10,12-trien-9-yl)amino]-N-(1-methyl-4-piperidyl)1,3-thiazole-4-carboxamide 10-Chloro-2-cyclopentyl-6-methyl-2,6,9,11-tetrazabicyclo[5.4.0]undeca-8,10,12-trien-5-one (Intermediate 1; 150 mg, 0.53 mmol), 2-amino-N-(1-methyl-4-piperidyl)-1,3-thiazole-4-carboxamide (Intermediate 145; 123 mg, 0.48 mmol) and 9,9-Dimethyl-4,5-bis(diphenylphosphino)xanthene (26 mg, 0.04 mmol) were dissolved in 1,4-dioxane (4.5 mL)

Caesium carbonate (315 mg, 0.97 mmol) was added and the mixture purged with a stream of nitrogen for 5 minutes. Tris(dibenzylideneacetone) palladium (II) (27 mg, 0.03 mmol) was added and the apparatus was evacuated and back-filled three times with nitrogen and then heated at 100° C. overnight. The mixture was cooled, filtered and the filtrate absorbed onto an SCX column, washed with methanol and the product eluted with ammonia in methanol. Product containing fractions were concentrated and purified by reverse phase preparative chromatography to give the title compound as a pale brown solid (80 mg, 34%)

$^1$H NMR (399.9 MHz, DMSO-d$_6$) δ1.49-1.83 (10H, m), 1.99-2.05 (4H, m), 2.18 (3H, s), 2.61 (2H, t), 2.67-2.75 (2H, m), 3.19 (3H, s), 3.64-3.72 (3H, m), 5.00 (1H, m), 7.48 (1H, d), 7.66 (1H, s), 8.14 (1H, s), 11.28 (1H, s); MS m/z 485 [M+H]$^+$.

The following example was prepared by an analogous process to that used in the preparation of Example 261 utilising 2-amino-4-methyl-N-(1-methyl-4-piperidyl)-1,3-thiazole-5-carboxamide Intermediate 146. A solid that precipitated from the basic fractions of the SCX column was filtered off. The filtrate was concentrated and methanol added to the residue giving further precipitated material, which was filtered and combined with the original precipitate to give the title compound as a white solid (95 mg, 40%)

Example 262

2-[(6-cyclopentyl-2-methyl-3-oxo-2,6,8,10-tetrazabicyclo[5.4.0]undeca-8,10,12-trien-9-yl)amino]-4-methyl-N-(1-methyl-4-piperidyl)1,3-thiazole-5-carboxamide $^1$H NMR (399.9 MHz, DMSO-d$_6$) δ1.50-1.76 (10H, m), 1.90-2.03 (4H, m), 2.16 (3H, s), 2.43 (3H, s), 2.61 (2H, m), 2.74 (2H, d), 3.19 (3H, s), 3.60-3.67 (3H, m), 5.07 (1H, m), 7.60 (1H, d), 8.13 (1H, s), 11.33 (1H, s);

1H NMR (399.9 MHz, DMSO-d6) +d4 AcOH 61.63-1.90 (10H, m), 1.86-1.92 (2H, m), 2.01 (2H, s), 2.44 (3H, s), 2.46 (3H, s), 2.61 (2H, t), 3.08 (2H, m), 3.18 (3H, s), 3.65 (2H, m), 3.78-3.85 (1H, m), 5.05 (1H, d), 8.12 (1H, s); MS m/z 499 [M+H]$^+$.

Example 263

2-[(6-cyclopentyl-2-methyl-3-oxo-2,6,8,10-tetrazabicyclo[5.4.0]undeca-8,10,12-trien-9-yl)amino]-N-(1-methyl-4-piperidyl)1,3-thiazole-5-carboxamide 10-Chloro-2-cyclopentyl-6-methyl-2,6,9,11-tetrazabicyclo[5.4.0]undeca-8,10,12-trien-5-one (Intermediate 1; 148 mg, 0.53 mmol), 2-amino-N-(1-methyl-4-piperidyl)-1,3-thiazole-5-carboxamide (Intermediate 147; 115 mg, 0.48 mmol) and 9,9-Dimethyl-4,5-bis(diphenylphosphino)xanthene (25 mg, 0.04 mmol) were dissolved in 1,4-dioxane (5 mL) Caesium carbonate (312 mg, 0.96 mmol) was added and the mixture purged with a stream of nitrogen for 5 minutes. Tris(dibenzylideneacetone) palladium (II) (27 mg, 0.03 mmol) was added and the apparatus was evacuated and back-filled three times with nitrogen and then heated at 100° C. overnight. The mixture was cooled, filtered and the filtrate absorbed onto an SCX column, washed with methanol and the product eluted with ammonia in methanol. Product containing fractions were concentrated and purified by normal phase chromatography (5% ammonia in methanol/DCM) to give a yellow solid which was suspended in DCM, filtered and dried on the filter to give the title compound as a white solid (48 mg, 21%).

$^1$H NMR (399.9 MHz, DMSO-d$_6$) δ1.50-1.79 (10H, m), 1.90-2.04 (4H, m), 2.17 (3H, s), 2.62 (2H, t), 2.77 (2H, d), 3.19 (3H, s), 3.65-3.71 (3H, m), 5.09 (1H, m), 8.03 (1H, s), 8.07 (1H, d), 8.15 (1H, s), 11.45 (1H, s); MS m/z 485 [M+H]$^+$.

The following example was prepared by an analogous process to that used in the preparation of Example 263 utilising 2-amino-N-(1-methyl-4-piperidyl)-1,3-oxazole-5-carboxamide Intermediate 148 the final product being purified by base modified reverse phase HPLC to give the title compound as a pale brown solid (25 mg, 41%)

Example 264

2-[(6-cyclopentyl-2-methyl-3-oxo-2,6,8,10-tetrazabicyclo[5.4.0]undeca-8,10,12-trien-9-yl)amino]-N-(1-methyl-4-piperidyl)1,3-oxazole-5-carboxamide $^1$H NMR (399.9 MHz, DMSO-d$_6$) δ1.48-1.76 (10H, m), 1.85-1.97 (4H, m), 2.17 (3H, s), 2.56-2.61 (2H, m), 2.76 (2H, d), 3.18 (3H, s), 3.59-3.68 (3H, m), 4.79 (1H, m), 7.63 (1H, s), 8.03 (1H, d), 8.07 (1H, s), 10.64 (1H, s); MS m/z 469 [M+H]$^+$.

Example 265

2-[(6-cyclopentyl-2-methyl-3-oxo-2,6,8,10-tetrazabicyclo[5.4.0]undeca-8,10,12-trien-9-yl)amino]-N-(1-methyl-4-piperidyl)1,3-oxazole-4-carboxamide 2-[(2-cyclopentyl-6-methyl-5-oxo-2,6,9,11-tetrazabicyclo[5.4.0]undeca-7,9,11-trien-10-yl)amino]-1,3-oxazole-4-carboxylic acid (Intermediate 150; 85 mg, 0.23 mmol), HATU (131 mg, 0.34 mmol) and 4-amino-1-methylpiperidine (40 mg, 0.34 mmol) were stirred in DMF (5 mL) and DIPEA (120 μL, 0.68 mmol) added. The mixture was stirred overnight, absorbed on to an SCX column, washed with methanol and eluted with ammonia in methanol. Product containing fractions were concentrated and purified by normal phase chromatography (5% ammonia in methanol/DCM) to give the title compound as a white solid (66 mg, 61%)

$^1$H NMR (399.9 MHz, DMSO-d$_6$) δ1.50-1.74 (10H, m), 1.88-1.98 (4H, m), 2.16 (3H, s), 2.58 (2H, t), 2.82 (2H, d), 3.18 (3H, s), 3.60-3.63 (2H, m), 3.66-3.75 (1H, m), 4.71-4.80 (1H, m), 7.54 (1H, d), 8.06 (1H, s), 8.26 (1H, s), 10.46 (1H, s); MS m/z 469 [M+H]$^+$.

Example 266

9-[(6-chloropyridin-3-yl)amino]-6-cyclopentyl-2-methyl-2,6,8,10-tetrazabicyclo[5.4.0]undeca-8,10,12-trien-3-one 10-Chloro-2-cyclopentyl-6-methyl-2,6,9,11-tetrazabicyclo[5.4.0]undeca-8,10,12-trien-5-one (Intermediate 1; 157 mg, 0.56 mmol), 5-amino-2-chloropyridine (65 mg, 0.51 mmol) and 9,9-Dimethyl-4,5-bis(diphenylphosphino)xanthene (27 mg, 0.05 mmol) were dissolved in 1,4-dioxane (7.5 mL). Caesium carbonate (330 mg, 1.01 mmol) was added and the mixture purged with a stream of nitrogen for 5 minutes. Tris(dibenzylideneacetone) palladium (II) (28 mg, 0.03 mmol) was added and the apparatus was evacuated and backfilled three times with nitrogen and then heated at 100° C. for 8 h. The mixture was cooled, filtered and the filtrate absorbed onto an SCX column, washed with methanol and the product eluted with ammonia in methanol. Product containing fractions were concentrated and purified by preparative reverse phase chromatography to give the title compound as a white solid (14 mg, 7%)

$^1$H NMR (399.9 MHz, DMSO-d$_6$) δ1.56-1.74 (6H, m), 1.93-1.98 (2H, m), 2.57-2.60 (2H, m), 3.18 (3H, s), 3.61-3.64 (2H, m), 4.79 (1H, m), 7.40 (1H, d), 8.09 (1H, s), 8.18-8.20 (1H, m), 8.75 (1H, d), 9.51 (1H, s); MS m/z 373 [M+H]$^+$.

Utilising the appropriate commercially available anilines, the following examples were prepared by an analogous process to that used in the preparation of Example 266.

Example 267

6-cyclopentyl-9-[(6-methoxypyridin-3-yl)amino]-2-methyl-2,6,8,10-tetrazabicyclo[5.4.0]undeca-8,10,12-trien-3-one $^1$H NMR (399.9 MHz, DMSO-d$_6$) δ1.52-1.73 (6H, m), 1.89-2.08 (2H, m), 2.53-2.58 (2H, m), 3.16 (3H, s), 3.58-3.61 (2H, m), 3.81 (3H, s), 4.69-4.77 (1H, m), 6.75 (1H, d), 7.98-8.04 (2H, m), 8.39-8.40 (1H, m), 9.04 (1H, s); MS m/z 369 [M+H]$^+$.

Example 268

6-cyclopentyl-2-methyl-9-(pyridin-4-ylamino)-2,6,8,10-tetrazabicyclo[5.4.0]undeca-8,10,12-trien-3-one $^1$H NMR (399.9 MHz, DMSO-d$_6$) δ1.61-1.78 (6H, m), 1.97-2.08 (2H, m), 2.59-2.62 (2H, m), 3.19 (3H, s), 3.63-3.66 (2H, m), 4.81-4.89 (1H, m), 7.76-7.78 (2H, m), 8.13 (1H, s), 8.34 (2H, d), 9.81 (1H, s) MS m/z 339 [M+H]$^+$.

Example 269

6-[(6-cyclopentyl-2-methyl-3-oxo-2,6,8,10-tetrazabicyclo[5.4.0]undeca-8,10,12-trien-9-yl)amino]-N-(1-methyl-4-piperidyl)pyridine-3-carboxamide 10-Chloro-2-cyclopentyl-6-methyl-2,6,9,11-tetrazabicyclo[5.4.0]undeca-8,10,12-trien-5-one (Intermediate 1; 100 mg, 0.36 mmol), 6-amino-N-(1-methyl-4-piperidyl)pyridine-3-carboxamide (Intermediate 152; 76 mg, 0.32 mmol) and caesium carbonate (211 mg, 0.65 mmol) were added to dioxane (3 mL) and the suspension bubbled with nitrogen for 10 minutes. Tris(dibenzylideneacetone)dipalladium(0) (18 mg, 0.02 mmol) and 9,9-dimethyl-4,5-bis(diphenylphosphino)xanthene (17 mg, 0.03 mmol) were added and the mixture heated at 100° C. overnight. The reaction mixture was cooled to room temperature filtered and the filter cake washed with DCM. The filtrate added to a 5 g SCX-2 column pre wet with MeOH (2 column volumes). Flushed with MeOH (2 column volumes) and the crude product eluted with 2M ammonia in MeOH. Product containing fractions were evaporated to give a brown gum which was purified by base modified reverse phase HPLC to give the title compound as a white solid (117 mg, 75%)

$^1$H NMR (399.902 MHz, CDCl$_3$) δ1.54-1.80 (m, 8H), 2.03 (m, 4H), 2.17 (m, 2H), 2.31 (s, 3H), 2.68 (m, 2H), 2.82 (m, 2H), 3.30 (s, 3H), 3.70 (m, 2H), 4.00 (m, 1H), 4.84 (m, 1H), 5.85 (d, 1H), 7.94 (s, 1H), 7.99 (s, 1H), 8.05 (m, 1H), 8.40 (d, 1H), 8.63 (m, 1H); MS m/z 479 [M+H]$^+$.

The following example was prepared by an analogous process to that used in the preparation of Example 269 utilising 5-amino-N-(1-methyl-4-piperidyl)pyridine-2-carboxamide (Intermediate 153), to give the title compound as a yellow solid (104 mg, 61%)

Example 270

5-[(6-cyclopentyl-2-methyl-3-oxo-2,6,8,10-tetrazabicyclo[5.4.0]undeca-8,10,12-trien-9-yl)amino]-N-(1-methyl-4-piperidyl)pyridine-2-carboxamide $^1$H NMR (399.902 MHz, CDC$_{l3}$) δ 1.68 (m, 8H), 2.02 (m, 4H), 2.18 (m, 2H), 2.31 (s, 3H), 2.67 (m, 2H), 2.82 (m, 2H), 3.30 (s, 3H), 3.69 (m, 2H), 3.98 (m, 1H), 4.85 (m, 1H), 7.11 (s, 1H), 7.78 (d, 1H), 7.94 (s, 1H), 8.13 (d, 1H), 8.31 (m, 1H), 8.59 (d, 1H); MS m/z 479 [M+H]$^+$.

Example 271

3-methoxy-4-[(6-methyl-5-oxo-2-prop-2-ynyl-2,6,9,11-tetrazabicyclo[5.4.0]undeca-7,9,11-trien-10-yl)amino]-N-(1-methyl-4-piperidyl)benzamide 9-chloro-2-methyl-6-prop-2-ynyl-2,6,8,10-tetrazabicyclo[5.4.0]undeca-7,9,11-trien-3-one (Intermediate 154; 53 mg, 0.21 mmol), 4-amino-3-methoxy-N-(1-methyl-4-piperidyl)benzamide (WO06/018220; 66 mg, 0.25 mmol) p-toluenesulphonic acid monohydrate acid (80 mg, 0.42 mmol) and isopropanol (4 mL) were combined in a 10 mL microwave reactor tube and heated in by microwave irradiation at 150° C. for 80 minutes. The sample was transferred to an SCX (10 g) cartridge pre-wet with methanol, washed with methanol and eluted with methanolic ammonia. Product containing fractions were combined and evaporated and the resultant material purified by base modified reverse phase preparative HPLC to yield the title compound as an off white gum (4 mg, 3%).

MS m/z 478 [M+H]$^+$. Retention Time 1.03 minutes Monitor Acid

Example 272

3-methoxy-4-[[6-methyl-2-[(4-methylpentan-2-yloxycarbonimidoyl)methyl]-5-oxo-2,6,9,11-tetrazabicyclo[5.4.0]undeca-7,9,11-trien-10-yl]amino]-N-(1-methyl-4-piperidyl)benzamide 2-(10-chloro-6-methyl-5-oxo-2,6,9,11-tetrazabicyclo[5.4.0]undeca-7,9,11-trien-2-yl)acetonitrile (Intermediate 155; 97 mg, 0.39 mmol), 4-amino-3-methoxy-N-(1-methyl-4-piperidyl)benzamide (WO06/018220; 124 mg, 0.47 mmol) and p-toluenesulphonic acid monohydrate (148 mg, 0.78 mmol) were heated together in 4-methyl-2-pentanol (4 mL) at 100° C. for 24 hours. The reaction mixture was diluted with water and methanol and the solution loaded onto an SCX-2 (5 g) column pre-wet with methanol. The column was washed with methanol (×2) and eluted with 2M NH3/MeOH. Fractions containing product identified as the addition product of the solvent and nitrile group were combined and evaporated. To the residue was added 4-amino-3-methoxy-N-(1-methyl-4-piperidyl)benzamide (WO06/018220 62 mg, 0.24 mmol) and p-toluenesulphonic acid monohydrate (74 mg, 0.39 mmol) and the mixture heated by microwave irradiation in isopropanol (4 mL) for 20 minutes at 150° C. The cooled mixture was loaded onto an SCX-2 (5 g) column pre-wet with MeOH. The column was washed with MeOH and eluted with 2M NH3/MeOH. Product containing fractions were combined and evaporated and the resultant material purified by base modified reverse phase preparative HPLC to yield the title compound as a light brown solid (21 mg, 9%).

$^1$H NMR (400.132 MHz, DMSO-d$_6$) δ 0.75 (m, 2H), 0.81 (d, 3H), 1.13 (d, 3H), 1.24 (m, 1H), 1.52 (m, 5H), 1.76 (m, 2H), 1.94 (m, 2H), 2.17 (s, 3H), 2.46 (m, 2H), 2.75 (m, 4H), 3.22 (s, 3H), 3.75 (m, 3H), 3.95 (s, 3H), 4.22 (s, 1H), 4.91 (m, 1H), 7.48 (m, 2H), 7.59 (s, 1H), 7.80 (s, 1H), 8.04 (d, 1H), 8.43 (d, 1H); MS m/z 582 [M+H]$^+$.

Example 273

4-[[2-[(3,5-dimethyl-1,2-oxazol-4-yl)methyl]-6-methyl-5-oxo-2,6,9,11-tetrazabicyclo[5.4.0]undeca-7,9,11-trien-10-yl]amino]-3-methoxy-N-(1-methyl-4-piperidyl)benzamide 9-chloro-6-[(3,5-dimethyl-1,2-oxazol-4-yl)methyl]-2-methyl-2,6,8,10-tetrazabicyclo[5.4.0]undeca-7,9,11-trien-3-one (Intermediate 156; 81 mg, 0.25 mmol), 4-amino-3-methoxy-N-(1-methyl-4-piperidyl)benzamide (WO06/018220; 80 mg, 0.30 mmol) p-toluenesulphonic acid monohydrate acid (96 mg, 0.5 mmol) and isopropanol (4 mL) were combined in a 10 mL microwave reactor tube and heated in by microwave irradiation at 150° C. for 80 minutes. The sample was transferred to an SCX (20 g) cartridge pre-wet with methanol, washed with methanol and eluted with methanolic ammonia. Product containing fractions were combined and evaporated and the resultant material purified by base modified reverse phase preparative HPLC to yield the title compound as an off white gum (61 mg, 45%).

$^1$H NMR (400.132 MHz, DMSO-d$_6$) δ 1.58 (2H, m), 1.76 (2H, m), 1.94 (2H, m), 2.08 (3H, s), 2.17 (3H, s), 2.36 (3H, s), 2.61 (2H, m), 2.78 (2H, m), 3.17 (3H, s), 3.53 (2H, m), 3.73 (1H, m), 3.95 (3H, s), 4.61 (2H, s), 7.49 (2H, m), 7.83 (1H, s), 8.05 (1H, d), 8.19 (1H, s), 8.35 (1H, d).

Example 274

4-[[2-(2-fluoroethyl)-6-methyl-5-oxo-2,6,9,11-tetrazabicyclo[5.4.0]undeca-7,9,11-trien-10-yl]amino]-3-methoxy-N-(1-methyl-4-piperidyl)benzamide 10-chloro-2-(2-fluoroethyl)-6-methyl-2,6,9,11-tetrazabicyclo[5.4.0]undeca-7,9,11-trien-5-one (Intermediate 157; 86 mg, 0.33 mmol), 4-amino-3-methoxy-N-(1-methyl-4-piperidyl)benzamide (WO06/018220; 104 mg, 0.40 mmol) and p-toluenesulphonic acid monohydrate (126 mg, 0.66 mmol) were heated together in 4-methyl-2-pentanol (4 mL) at 100° C. for 24 hours. The reaction mixture was diluted with water and methanol and the solution loaded onto an SCX-2 (5 g) column pre-wet with methanol. The column was washed with methanol (×2) and the product eluted with 2M NH3/MeOH. Product containing fractions were combined and evaporated. The resultant material was purified by base modified reverse phase preparative HPLC to yield the title compound as a yellow solid (60 mg, 37%).

$^1$H NMR (400.132 MHz, DMSO-d6) δ 1.59 (m, 2H), 1.75 (m, 2H), 1.94 (m, 2H), 2.17 (s, 3H), 2.73 (m, 4H), 3.13 (s, 3H), 3.57 (m, 2H), 3.72 (s, 3H), 3.72 (m, 1H), 3.83 (t, 2H), 4.05 (t, 2H), 6.91 (d, 1H), 7.32 (m, 2H), 7.89 (s, 1H), 7.91 (d, 1H); MS m/z 466 [M+H]$^+$—HF.

Example 275

N-cyclohexyl-4-[[2-(2-dimethylaminoethyl)-6-methyl-5-oxo-2,6,9,11-tetrazabicyclo[5.4.0]undeca-7,9,11-trien-10-yl]amino]-3-methoxy-benzamide 10-chloro-2-(2-dimethylaminoethyl)-6-methyl-2,6,9,11-tetrazabicyclo[5.4.0]undeca-7,9,11-trien-5-one (Intermediate 158; 84 mg, 0.30 mmol), 4-amino-3-methoxy-N-(1-methyl-4-piperidyl)benzamide (WO06/018220; 90 mg, 0.36 mmol) and p-toluenesulphonic acid monohydrate (113 mg, 0.60 mmol) were heated together in IPA (4 mL) by microwave irradiation at 150° C. for 20 minutes. The reaction mixture was loaded onto an SCX-2 (5 g) column pre-wet with methanol; the column was washed with methanol and the product eluted with 2M NH3/MeOH. Product containing fractions were combined and evaporated. The resultant material was purified by base modified reverse phase preparative HPLC to yield the title compound as a white solid (59 mg, 40%).

$^1$H NMR (400.132 MHz, DMSO-d6) δ 1.24 (m, 5H), 1.72 (m, 6H), 2.19 (s, 6H), 2.54 (t, 2H), 2.62 (m, 2H), 3.17 (s, 3H), 3.70 (t, 3H), 3.75 (m, 2H), 3.95 (s, 3H), 7.48 (m, 2H), 7.70 (s, 1H), 8.01 (d, 1H), 8.07 (s, 1H), 8.35 (d, 1H); MS m/z 496 [M+H]$^+$.

Example 276

N-cyclohexyl-3-methoxy-4-[[6-methyl-5-oxo-2-[2-(1-piperidyl)ethyl]-2,6,9,11-tetrazabicyclo[5.4.0] undeca-7,9,11-trien-10-yl]amino]benzamide 10-chloro-6-methyl-2-[2-(1-piperidyl)ethyl]-2,6,9,11-tetrazabicyclo[5.4.0]undeca-7,9,11-trien-5-one (Intermediate 159; 90 mg, 0.28 mmol), 4-amino-3-methoxy-N-(1-methyl-4-piperidyl)benzamide (WO06/018220; 83 mg, 0.34 mmol) and p-toluenesulphonic acid monohydrate (107 mg, 0.56 mmol) were heated together in IPA (4 mL) by microwave irradiation at 150° C. for 20 minutes. The reaction mixture was loaded onto an SCX-2 (5 g) column pre-wet with methanol; the column was washed with methanol and the product eluted with 2M NH3/MeOH. Product containing fractions were combined and evaporated. The resultant material was purified by base modified reverse phase preparative HPLC to yield the title compound as a white solid (40 mg, 27%).

$^1$H NMR (400.132 MHz, DMSO-d6) δ 1.15 (m, 1H), 1.34 (m, 6H), 1.47 (m, 4H), 1.72 (m, 6H), 2.35 (m, 4H), 2.54 (t, 2H), 2.62 (m, 2H), 3.17 (s, 3H), 3.69 (t, 2H), 3.74 (m, 2H), 3.94 (s, 3H), 7.49 (m, 2H), 7.69 (s, 1H), 8.01 (d, 1H), 8.06 (s, 1H), 8.33 (d, 1H); MS m/z 536 [M+H]$^+$.

Example 277

N-cyclohexyl-3-methoxy-4-[[6-methyl-2-(2-morpholin-4-ylethyl)-5-oxo-2,6,9,11-tetrazabicyclo[5.4.0] undeca-7,9,11-trien-10-yl]amino]benzamide 10-chloro-6-methyl-2-(2-morpholin-4-ylethyl)-2,6,9,11-tetrazabicyclo[5.4.0]undeca-7,9,11-trien-5-one (Intermediate 160; 95 mg, 0.29 mmol), -amino-3-methoxy-N-(1-methyl-4-piperidyl)benzamide (WO06/018220; 86 mg, 0.35 mmol) and p-toluenesulphonic acid monohydrate (110 mg, 0.58 mmol) were heated together in IPA (4 mL) by microwave irradiation at 150° C. for 20 minutes. The reaction mixture was loaded onto an SCX-2 (5 g) column pre-wet with methanol; the column was washed with methanol and the product eluted with 2M NH3/MeOH. Product containing fractions were combined and evaporated. The resultant material was purified by base modified reverse phase preparative HPLC to yield the title compound as a white solid (56 mg, 36%).

$^1$H NMR (400.132 MHz, DMSO-d6) δ 1.15 (m, 1H), 1.32 (m, 4H), 1.72 (m, 6H), 2.39 (m, 4H), 2.60 (m, 4H), 3.17 (s, 3H), 3.55 (t, 4H), 3.73 (m, 4H), 3.94 (s, 3H), 7.48 (m, 2H), 7.72 (s, 1H), 8.01 (d, 1H), 8.06 (s, 1H), 8.30 (d, H); MS m/z 538 [M+H]$^+$.

Example 278

4-[(2-cyclopentyl-4,4-dimethyl-5-oxo-2,6,9,11-tetrazabicyclo[5.4.0]undeca-7,9,11-trien-10-yl)amino]-3-methoxy-N-[(1S,5R)-9-methyl-9-azabicyclo[3.3.1] non-7-yl]benzamide 10-chloro-2-cyclopentyl-4,4-dimethyl-2,6,9,11-tetrazabicyclo[5.4.0]undeca-7,9,11-trien-5-one (Intermediate 127; 62 mg, 0.21 mmol) and 4-amino-3-methoxy-N-[(1S,5R)-9-methyl-9-azabicyclo[3.3.1]non-7-yl]benzamide (Intermediate 161; 63 mg, 0.21 mmol) were taken up in 4-methyl-2-pentanol (2 mL) and p-toluenesulphonic acid monohydrate (81 mg, 0.42 mmol) added. The reaction mixture was heated at 160° C. by microwave irradiation for 60 minutes. The cooled reaction mixture was treated with a mixture of methanol & water (5:2 v/v, 7 mL). The resultant solution was loaded onto an SCX-3 cartridge (5 g) pre-wet with methanol. The cartridge was washed through with Methanol (~40 mL). Products were then eluted with 2M ammonia in methanol (~30 mL). The ammoniacal solution was evaporated and the resultant material was purified by base modified reverse phase preparative HPLC to yield the title compound as a white solid (64 mg, 54%).

1H NMR (400.132 MHz, DMSO-d6) δ 0.90-0.95 (2H, m), 1.14 (6H, s), 1.41-1.50 (3H, m), 1.54-1.68 (4H, m), 1.71-1.78 (2H, m), 1.83-1.96 (4H, m), 2.01-2.10 (1H, m), 2.15-2.23 (2H, m), 2.42 (3H, s), 2.95-3.01 (2H, m), 3.27-3.28 (2H, m), 3.95 (3H, s), 4.28-4.39 (1H, m), 5.23 (1H, quintet), 7.45-7.49 (2H, m), 7.59 (1H, s), 7.88-7.90 (2H, m), 8.35 (1H, d), 9.45 (1H, s); MS m/z 562 [M+H]$^+$.

Example 279

4-(9'-cyclopentyl-6'-oxo-5',6',8',9'-tetrahydrospiro [cyclopropane-1,7'-pyrimido[5,4-b][1,4]diazepine]-2'-ylamino)-3-fluoro-N-((1R,3r,5S)-9-methyl-9-azabicyclo[3.3.1]nonan-3-yl)benzamide 2'-chloro-9'-cyclopentyl-8',9'-dihydrospiro[cyclopropane-1,7'-pyrimido[4,5-b][1,4]diazepin]-6'(5'H)-one (Intermediate 131; 256 mg, 0.875 mmol) and 4-amino-3-fluoro-N-[(1S,5R)-9-methyl-9-azabicyclo[3.3.1]non-7-yl]benzamide (Intermediate 162; 255 mg, 0.875 mmol) and the p-toluenesulphonic acid monohydrate (416 mg, 2.19 mmol) and 4-Methyl-2-pentanol (5 mL) were heated by microwave irradiation for 30 minutes at 160° C. The cooled reaction mixture was dissolved up in methanol (50 mL) and loaded onto a SCX-2 cartridge (20 g) pre-wet with methanol. The cartridge was washed through with methanol (3×35 mL) and the product eluted with 7 N methanolic ammonia (~100 mL). The ammoniacal solution was evaporated and the resultant material purified on a silica column loaded as a solution in DCM (20 mL) and eluted with a linear gradient of 0 to 10% 7N NH$_3$/MeOH in DCM. Product containing fractions were combined and evaporated and the resultant material purified by base modified reverse phase preparative HPLC to yield the title compound as a white solid after trituration under diethyl ether (104 mg, 22%)

$^1$H NMR (400.13 MHz, CDCl$_3$) δ 0.77-0.80 (2H, m), 0.93-1.00 (2H, m), 1.17-1.30 (4H, m), 1.34-1.37 (2H, m), 1.47 (1H, s), 1.62-1.68 (4H, m), 1.88-1.93 (5H, m), 2.43 (3H, s), 2.40-2.49 (2H, m), 3.02 (2H, d), 3.27 (2H, s), 4.37-4.49 (1H, m), 4.98-5.07 (1H, m), 5.67 (1H, d), 7.11 (1H, d), 7.20 (1H, s), 7.41-7.44 (1H, m), 7.45-7.48 (1H, m), 7.63 (1H, s), 8.46 (1H, t); MS m/z 548 [M+H]⁺.

Example 280

4-(9'-cyclopentyl-6'-oxo-5',6',8',9'-tetrahydrospiro [cyclopropane-1,7'-pyrimido[5,4-b][1,4]diazepine]-2'-ylamino)-3-methoxy-N-((1R,3r,5S)-9-methyl-9-azabicyclo[3.3.1]nonan-3-yl)benzamide 2'-chloro-9'-cyclopentyl-8',9'-dihydrospiro[cyclopropane-1,7'-pyrimido[4,5-b][1,4]diazepin]-6'(5'H)-one (Intermediate 131; 293 mg, 1.0 mmol) and 4-amino-3-methoxy-N-[(1S,5R)-9-methyl-9-azabicyclo[3.3.1]non-7-yl]benzamide (Intermediate 161; 303 mg, 1.0 mmol) and the p-toluenesulphonic acid monohydrate (476 mg, 2.5 mmol) and 4-Methyl-2-pentanol (10 mL) were combined and heated with stirring at 120° C. overnight. The cooled reaction mixture was dissolved up in methanol (60 mL) and loaded onto a SCX-2 cartridge (20 g) pre-wet with methanol. The cartridge was washed through with methanol (3×35 mL) and the product eluted with 7 N methanolic ammonia (~100 mL). The ammoniacal solution was evaporated and the resultant material purified on a silica column loaded as a solution in DCM (17 mL) and eluted with a linear gradient of 0 to 10% 2N NH₃/MeOH in DCM. Product containing fractions were combined and evaporated and the resultant material triturated under diethyl ether. The resultant filtered solid was treated with warm DMF (3 mL) and acetonitrile (8 mL) upon cooling in an ice/water bath a solid precipitate formed which was filtered and dried to yield the title compound as a white solid (251 mg, 45%)

¹H NMR (400.13 MHz, CDCl₃) δ 0.77-0.79 (2H, m), 0.96 (2H, d), 1.19-1.33 (4H, m), 1.35-1.37 (2H, m), 1.44-1.48 (1H, m), 1.60-1.68 (4H, m), 1.85-1.98 (5H, m), 2.41-2.50 (2H, m), 2.43 (3H, s), 3.02 (2H, d), 3.25 (2H, s), 3.90 (3H, s), 4.41-4.46 (1H, m), 5.00-5.09 (1H, m), 5.75 (1H, d), 7.16 (1H, dd), 7.36 (1H, d), 7.55 (1H, s), 7.67 (1H, s), 7.75 (1H, s), 8.39 (1H, d); MS m/z 560 [M+H]⁺.

Example 281

3-ethoxy-4-[(6-methyl-5-oxo-2-propan-2-yl-2,6,9, 11-tetrazabicyclo[5.4.0]undeca-7,9,11-trien-10-yl) amino]-N-(1-methyl-4-piperidyl)benzamide To a stirred solution of 3-ethoxy-4-[(6-methyl-5-oxo-2-propan-2-yl-2,6,9,11-tetrazabicyclo[5.4.0]undeca-7,9,11-trien-10-yl)amino]benzoic acid (Intermediate 163; 80 mg, 0.20 mmol), HATU (115 mg, 0.30 mmol) and 4-amino-1-methylpiperidine (Fluorochem; 35 mg, 0.30 mmol) in DMF (5 mL) was added diisopropylethylamine (105 μl, 0.60 mmol). The mixture was stirred for 2 hours at room temperature and then absorbed on to an SCX column, washed with methanol and eluted with ammonia in methanol. Product containing fractions were concentrated and purified by column chromatography (5% ammonia in methanol/DCM) to yield the title compound as a white foam (87 mg, 88%).

¹H NMR (399.9 MHz, DMSO-d6) δ1.26 (6H, d), 1.44 (3H, t), 1.55-1.65 (2H, m), 1.77 (2H, d), 1.92-1.98 (2H, m), 2.18 (3H, s), 2.60 (2H, m), 2.79 (2H, d), 3.18 (3H, s), 3.62 (2H, m), 3.70-3.78 (1H, m), 4.21 (2H, q), 4.78-4.85 (1H, m), 7.49-7.53 (2H, m), 7.67 (1H, s), 8.05 (2H, m), 8.41 (1H, d); MS m/z 496 [M+H]⁺.

Example 282

3-ethoxy-N-(1-ethyl-4-piperidyl)-4-[(6-methyl-5-oxo-2-propan-2-yl-2,6,9,11-tetrazabicyclo[5.4.0] undeca-7,9,11-trien-10-yl)amino]benzamide The title compound was prepared by an analogous method to the preparation of Example 281, on a 0.2 mmol scale, utilising 4-amino-1-ethylpiperidine (Fluorochem; 39 mg, 0.3 mmol), as a white foam (67 mg, 66%).

¹H NMR (399.9 MHz, DMSO-d6) δ1.01 (3H, t), 1.26 (6H, d), 1.44 (3H, t), 1.52-1.62 (2H, m), 1.77-1.80 (2H, m), 1.94 (2H, m), 2.34 (2H, q), 2.60 (2H, m), 2.89 (2H, d), 3.18 (3H, s), 3.62 (2H, m), 3.72-3.80 (1H, m), 4.21 (2H, q), 4.78-4.85 (1H, m), 7.48-7.52 (2H, m), 7.67 (1H, s), 8.05 (2H, m), 8.41 (1H, d); MS m/z 510 [M+H]⁺.

Example 283

3-ethoxy-N-[(1S,5R)-9-methyl-9-azabicyclo[3.3.1] non-7-yl]-4-[(6-methyl-5-oxo-2-propan-2-yl-2,6,9, 11-tetrazabicyclo[5.4.0]undeca-8,10,12-trien-10-yl) amino]benzamide The title compound was prepared by an analogous method to the preparation of Example 281, on a 0.2 mmol scale, utilising Endo-9-methyl-9-azabicyclo[3,3,1]nonane-3-one (Chempacific; 47 mg, 0.3 mmol), as a white foam (71 mg, 66%).

¹H NMR (399.9 MHz, DMSO-d6) δ0.94 (2H, d), 1.27 (6H, d), 1.41-1.49 (6H, m), 1.89-1.96 (2H, m), 2.06 (1H, m), 2.15-2.23 (2H, m), 2.42 (3H, s), 2.61 (2H, m), 2.99 (2H, d), 3.18 (3H, s), 3.63 (2H, m), 4.22 (2H, q), 4.30-4.38 (1H, m), 4.78-4.85 (1H, m), 7.49-7.53 (2H, m), 7.67 (1H, s), 7.90 (1H, d), 8.07 (1H, s), 8.42 (1H, d); MS m/z 536 [M+H]⁺.

Example 284

3-ethoxy-4-[(6-methyl-5-oxo-2-propan-2-yl-2,6,9, 11-tetrazabicyclo[5.4.0]undeca-7,9,11-trien-10-yl) amino]-N-[(3R)-1-methylpyrrolidin-3-yl]benzamide 10-Chloro-6-methyl-2-propan-2-yl-2,6,9,11-tetrazabicyclo[5.4.0]undeca-7,9,11-trien-5-one (Intermediate 10; 100 mg, 0.39 mmol), 4-amino-3-ethoxy-N-[(3R)-1-methylpyrrolidin-3-yl]benzamide (Intermediate 166; 104 mg, 0.39 mmol) and 4-toluenesulphonic acid monohydrate (187 mg, 0.98 mmol) were heated in 4-methyl-2-pentanol (3 mL) at 140° C. for 3 hours. The cooled reaction mixture was absorbed on to an SCX column, washed with methanol and eluted with ammonia in methanol. Product containing fractions were concentrated and purified by base modified preparative reverse phase HPLC to yield the title compound as a white solid (114 mg, 61%).

¹H NMR (399.9 MHz, DMSO-d6) δ 1.26 (6H, d), 1.44 (3H, t), 1.73-1.81 (1H, m), 2.12-2.20 (1H, m), 2.27 (3H, s), 2.37-2.46 (2H, m), 2.57-2.70 (4H, m), 3.18 (3H, s), 3.62 (2H, m), 4.21 (2H, q), 4.38-4.44 (1H, m), 4.78-4.85 (1H, m), 7.51-7.55 (2H, m), 7.67 (1H, s), 8.07 (1H, s), 8.28 (1H, d), 8.41 (1H, d); MS m/z 482 [M+H]⁺.

Example 285

N-(4-dimethylaminocyclohexyl)-3-ethoxy-4-[(6-methyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 284, on a 0.26 mmol scale, utilising 4-amino-N-((1s,4s)-4-(dimethylamino)cyclohexyl)-3-ethoxybenzamide (Intermediate 167; 66 mg, 0.36 mmol), as a white solid (39 mg, 29%).

$^1$H NMR (399.9 MHz, DMSO-d6) δ 1.26 (6H, d), 1.42-1.54 (7H, m), 1.72-1.80 (2H, m), 1.86-1.90 (2H, m), 2.99-2.03 (1H, m), 2.19 (6H, s), 2.60 (2H, m), 3.18 (3H, s), 3.62 (2H, m), 3.89-3.93 (1H, m), 4.21 (2H, q), 4.78-4.85 (1H, m), 7.51-7.56 (2H, m), 7.66 (1H, s), 8.00 (1H, d), 8.07 (1H, s), 8.41 (1H, d); MS m/z 525 [M+H]$^+$.

Example 286

N-(4-dimethylaminocyclohexyl)-3-ethoxy-4-[(6-methyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 284, on a 0.26 mmol scale, utilising 4-amino-N-((1r,4r)-4-(dimethylamino)cyclohexyl)-3-ethoxybenzamide (Intermediate 168; 66 mg, 0.26 mmol), as a white solid (80 mg, 59%).

$^1$H NMR (399.9 MHz, DMSO-d6) δ 1.23-1.39 (10H, m), 1.44 (3H, t), 1.83-1.91 (4H, m), 2.11-2.19 (7H, m), 2.60 (2H, m), 3.18 (3H, s), 3.62 (2H, m), 3.71-3.75 (1H, m), 4.21 (2H, q), 4.78-4.85 (1H, m), 7.48-7.52 (2H, m), 7.67 (1H, s), 8.01 (1H, d), 8.07 (1H, s), 8.41 (1H, d); MS m/z 525 [M+H]$^+$.

Example 287

5-ethoxy-2-fluoro-4-[(6-methyl-5-oxo-2-propan-2-yl-2,6,9,11-tetrazabicyclo[5.4.0]undeca-7,9,11-trien-10-yl)amino]-N-(1-methyl-4-piperidyl)benzamide The title compound was prepared by an analogous method to the preparation of Example 284, on a 0.39 mmol scale, utilising 4-amino-5-ethoxy-2-fluoro-N-(1-methyl-4-piperidyl)benzamide (Intermediate 169; 116 mg, 0.39 mmol), heating at 140° C. for 2 hours, as a white solid (73 mg, 37%).

$^1$H NMR (399.9 MHz, DMSO-d6) δ 1.27 (6H, d), 1.42 (3H, t), 1.52-1.62 (2H, m), 1.78 (2H, d), 1.99 (2H, t), 2.17 (3H, s), 2.62 (2H, m), 2.74 (2H, d), 3.19 (3H, s), 3.64 (2H, m), 3.69-3.79 (1H, m), 4.18 (2H, q), 4.77-4.84 (1H, m), 7.20 (1H, d), 7.74 (1H, d), 7.79-7.82 (1H, m), 8.10 (1H, s), 8.35 (1H, d); MS m/z 515 [M+H]$^+$.

Example 288

5-ethoxy-2-fluoro-N-[(1S,5R)-9-methyl-9-azabicyclo[3.3.1]non-7-yl]-4-[(6-methyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 284, on a 0.39 mmol scale, utilising 4-amino-5-ethoxy-2-fluoro-N-[(1S,5R)-9-methyl-9-azabicyclo[3.3.1]non-7-yl]benzamide (Intermediate 170; 132 mg, 0.39 mmol), heating at 140° C. for 2 hours, as a white solid (92 mg, 43%).

$^1$H NMR (399.9 MHz, DMSO-d6) δ 0.92 (2H, d), 1.28 (6H, d), 1.39-1.46 (6H, m), 1.87-1.94 (2H, m), 1.99-2.10 (1H, m), 2.17-2.25 (2H, m), 2.42 (3H, s), 2.62 (2H, m), 2.98 (2H, d), 3.19 (3H, s), 3.64 (2H, m), 4.18 (2H, q), 4.26-4.34 (1H, m), 4.78-4.85 (1H, m), 7.22 (1H, d), 7.65-7.68 (1H, m), 7.75 (1H, d), 8.11 (1H, s), 8.36 (1H, d); MS m/z 555 [M+H]$^+$.

Example 289

5-chloro-2-fluoro-N-(1-methyl-4-piperidyl)-4-[(4,4,6-trimethyl-5-oxo-2-propan-2-yl-2,6,9,11-tetrazabicyclo[5.4.0]undeca-7,9,11-trien-10-yl)amino]benzamide 4-amino-5-chloro-2-fluoro-N-(1-methyl-4-piperidyl)benzamide (Intermediate 173; 91 mg, 0.32 mmol), 10-chloro-4,4,6-trimethyl-2-propan-2-yl-2,6,9,11-tetrazabicyclo[5.4.0]undeca-8,10,12-trien-5-one (Intermediate 178; 100 mg, 0.35 mmol) and XANTPHOS (17 mg, 0.03 mmol) were dissolved in 1,4-dioxane (7.5 mL). Caesium carbonate (225 mg, 0.64 mmol) was added and the system purged with a stream of nitrogen for 15 minutes before tris(dibenzylideneacetone)palladium (II) (18 mg, 0.02 mmol) was added. The apparatus was evacuated and backfilled with nitrogen (×3) and then heated at 100° C. for 3 hours. The mixture was cooled, filtered and the filtrate absorbed on to an SCX column, which was washed with methanol and eluted with ammonia in methanol. Product containing fractions were concentrated and purified by column chromatography (2.5% 3.5N ammonia in methanol/DCM) to yield the title compound as a white solid (96 mg, 56%).

$^1$H NMR (399.9 MHz, DMSO-d6) δ 1.12 (6H, s), 1.21 (6H, d), 1.50-1.60 (2H, m), 1.77-1.80 (2H, m), 1.93-2.00 (2H, m), 2.17 (3H, s), 2.74 (2H, d), 3.21 (3H, s), 3.38 (2H, s), 3.67-3.72 (1H, m), 5.07-5.14 (1H, m), 7.67 (1H, d), 8.03-8.08 (3H, m), 8.31-8.36 (1H, m); MS m/z 532 [M+H]$^+$.

Example 290

5-chloro-N-(1-ethyl-4-piperidyl)-2-fluoro-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 289, on a 0.39 mmol scale, utilising 4-amino-5-chloro-N-(1-ethyl-4-piperidyl)-2-fluoro-benzamide (Intermediate 174; 96 mg, 0.32 mmol), as a white solid (67 mg, 38%).

$^1$H NMR (399.9 MHz, DMSO-d6) δ 1.00 (3H, t), 1.12 (6H, s), 1.21 (6H, d), 1.48-1.58 (2H, m), 1.80 (2H, d), 1.96 (2H, t), 2.32 (2H, q), 2.84 (2H, d), 3.21 (3H, s), 3.38 (2H, s), 3.68-3.76 (1H, m), 5.07-5.14 (1H, m), 7.67 (1H, d), 8.03-8.07 (3H, m), 8.32-8.36 (1H, m); MS m/z 546 [M+H]$^+$.

Example 291

5-chloro-N-(4-dimethylaminocyclohexyl)-2-fluoro-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 289, on a 0.39 mmol scale, utilising 4-amino-5-chloro-N-(4-dimethylaminocyclohexyl)-2-fluoro-benzamide (Intermediate 175; 100 mg, 0.32 mmol), as a white solid (109 mg, 61%).

¹H NMR (399.9 MHz, DMSO-d6) δ 1.12 (6H, s), 1.17-1.37 (8H, m), 1.46-1.58 (2H, m), 1.68-1.94 (4H, m), 2.13-2.18 (7H, m), 3.20 (3H, s), 3.38 (2H, s), 3.64-3.71 and 3.91-4.95 (each 0.5H, m), 5.08-5.15 (1H, m), 7.62-7.67 (1H, m), 7.98-8.04 (3H, m), 8.29-8.34 (1H, m); MS m/z 560 [M+H]⁺.

Example 292

2-fluoro-5-methoxy-N-[(3R)-1-methylpyrrolidin-3-yl]-4-[(4,4,6-trimethyl-5-oxo-2-propan-2-yl-2,6,9,11-tetrazabicyclo[5.4.0]undeca-7,9,11-trien-10-yl)amino]benzamide 10-chloro-4,4,6-trimethyl-2-propan-2-yl-2,6,9,11-tetrazabicyclo[5.4.0]undeca-8,10,12-trien-5-one (Intermediate 178; 100 mg, 0.35 mmol), 4-amino-2-fluoro-5-methoxy-N-[(3R)-1-methylpyrrolidin-3-yl]benzamide (Intermediate 182; 95 mg, 0.35 mmol) and p-toluenesulphonic acid monohydrate (169 mg, 0.88 mmol) were heated in 4-methyl-2-pentanol (3 mL) at 140° C. for 3 hours. The mixture was cooled and absorbed on to an SCX column, which was washed with methanol and eluted with ammonia in methanol. Product containing fractions were concentrated and purified by base modified preparative reverse phase HPLC to yield the title compound as a white solid (60 mg, 33%).

¹H NMR (399.9 MHz, DMSO-d6) δ 1.12 (6H, s), 1.23 (6H, d), 1.68-1.76 (1H, m), 2.13-2.22 (1H, m), 2.27 (3H, s), 2.36-2.45 (2H, m), 2.59-2.64 (1H, m), 2.67-2.71 (1H, m), 3.20 (3H, s), 3.39 (2H, s), 3.93 (3H, s), 4.35-4.43 (1H, m), 5.09-5.16 (1H, m), 7.22 (1H, d), 7.75 (1H, d), 7.96-7.99 (1H, m), 8.03 (1H, s), 8.34 (1H, d); MS m/z 516 [M+H]⁺.

Example 293

3-ethoxy-N-[(3R)-1-methylpyrrolidin-3-yl]-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 292, on a 0.35 mmol scale, utilising 4-amino-3-ethoxy-N-[(3R)-1-methylpyrrolidin-3-yl]benzamide (Intermediate 166; 94 mg, 0.35 mmol), as a white solid (106 mg, 59%).

¹H NMR (399.9 MHz, DMSO-d6) δ 1.11 (6H, s), 1.23 (6H, d), 1.44 (3H, t), 1.74-1.80 (1H, m), 2.15-2.19 (1H, m), 2.27 (3H, s), 2.38-2.47 (2H, m), 2.61-2.71 (2H, m), 3.20 (3H, s), 3.38 (2H, s), 4.21 (2H, q), 4.39-4.43 (1H, m), 5.09-5.16 (1H, m), 7.51-7.54 (2H, m), 7.63 (1H, s), 7.98 (1H, s), 8.28 (1H, d), 8.38 (1H, d); MS m/z 511 [M+H]⁺.

Example 294

N-(4-dimethylaminocyclohexyl)-3-ethoxy-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 292, on a 0.26 mmol scale, utilising 4-amino-N-((1s,4s)-4-(dimethylamino)cyclohexyl)-3-ethoxybenzamide (Intermediate 167; 80 mg, 0.26 mmol), as a white solid (91 mg, 59%).

¹H NMR (399.9 MHz, DMSO-d6) δ 1.11 (6H, s), 1.23 (6H, d), 1.40-1.55 (7H, m), 1.72-1.81 (2H, m), 1.86-1.90 (2H, m), 2.01-2.05 (1H, m), 2.19 (6H, s), 3.20 (3H, s), 3.38 (2H, s), 3.88-3.95 (1H, m), 4.21 (2H, q), 5.09-5.16 (1H, m), 7.51-7.55 (2H, m), 7.62 (1H, s), 7.97-8.01 (2H, m), 8.37 (1H, d); MS m/z 553 [M+H]⁺.

Example 295

N-(4-dimethylaminocyclohexyl)-3-ethoxy-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 292, on a 0.26 mmol scale, utilising 4-amino-N-((1r,4r)-4-(dimethylamino)cyclohexyl)-3-ethoxybenzamide (Intermediate 168; 80 mg, 0.26 mmol), as a white solid (77 mg, 54%).

¹H NMR (399.9 MHz, DMSO-d6) δ 1.11 (6H, s), 1.23 (6H, d), 1.27-1.39 (4H, m), 1.44 (3H, t), 1.83-1.92 (4H, m), 2.15-2.21 (7H, m), 3.20 (3H, s), 3.38 (2H, s), 3.71-3.75 (1H, m), 4.21 (2H, q), 5.09-5.15 (1H, m), 7.48-7.51 (2H, m), 7.63 (1H, s), 7.98-8.02 (2H, m), 8.37 (1H, d); MS m/z 553 [M+H]⁺.

Example 296

5-ethoxy-2-fluoro-N-(1-methyl-4-piperidyl)-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 292, on a 0.39 mmol scale, utilising 4-amino-5-ethoxy-2-fluoro-N-(1-methyl-4-piperidyl)benzamide (Intermediate 169; 116 mg, 0.39 mmol), as a white solid (92 mg, 48%).

¹H NMR (399.9 MHz, DMSO-d6) δ 1.12 (6H, s), 1.21-1.24 (6H, d), 1.42 (3H, t), 1.52-1.62 (2H, m), 1.77-1.80 (2H, m), 1.94-2.00 (2H, m), 2.17 (3H, s), 2.69-2.75 (2H, m), 3.20 (3H, s), 3.39 (2H, s), 3.69-3.76 (1H, m), 4.18 (2H, q), 5.07-5.14 (1H, m), 7.20 (1H, d), 7.71 (1H, d), 7.77-7.80 (1H, m), 8.02 (1H, s), 8.31 (1H, d); MS m/z 543 [M+H]⁺.

Example 297

//5-ethoxy-2-fluoro-N-[(3R)-1-methylpyrrolidin-3-yl]-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 292, on a 0.32 mmol scale, utilising 4-amino-5-ethoxy-2-fluoro-N-[(3R)-1-methylpyrrolidin-3-yl]benzamide (Intermediate 186; 90 mg, 0.32 mmol), as a white foam (61 mg, 36%).

¹H NMR (399.9 MHz, DMSO-d6) δ 1.12 (6H, s), 1.24 (6H, d), 1.42 (3H, t), 1.67-1.75 (1H, m), 2.13-2.22 (1H, m), 2.26 (3H, s), 2.34-2.47 (2H, m), 2.58-2.63 (1H, m), 2.66-2.70 (1H, m), 3.20 (3H, s), 3.39 (2H, s), 4.18 (2H, q), 4.34-4.43 (1H, m), 5.07-5.14 (1H, m), 7.21 (1H, d), 7.71 (1H, s), 7.95-7.98 (1H, m), 8.02 (1H, s), 8.31 (1H, d); MS m/z 529 [M+H]⁺.

Example 298

3-fluoro-N-[(1S,5R)-9-methyl-9-azabicyclo[3.3.1]non-3-yl]-4-[(4,4,6-trimethyl-5-oxo-2-propan-2-yl-2,6,9,11-tetrazabicyclo[5.4.0]undeca-8,10,12-trien-10-yl)amino]benzamide 10-chloro-4,4,6-trimethyl-2-propan-2-yl-2,6,9,11-tetrazabicyclo[5.4.0]undeca-8,10,12-trien-5-one (Intermediate 178; 43 mg, 0.15 mmol) and 4-amino-3-fluoro-N-(9-methyl-9-azabicyclo[3.3.1]non-7-yl)benzamide (Intermediate 162; 44 mg, 0.15 mmol) were combined with p-toluenesulphonic acid monohydrate (72 mg, 0.38 mmol) in 4-methyl-2-pentanol (1 mL) and heated by microwave irradiation for 50 minutes at 160° C. The cooled reaction mixture was diluted with methanol (5 mL) and loaded onto an SCX-3 cartridge (2 g) pre-wet with Methanol. The cartridge was washed with methanol (2×3 mL) and product eluted with 7 N methanolic ammonia (10 mL). The basic fraction was evaporated to give a yellow gum which was purified by base modified reverse phase HPLC to give the title compound as a white solid (46 mg, 57%).

$^1$H NMR (400 MHz, DMSO-d6) δ 0.9 (2H, d), 1.1 (6H, s), 1.15 (6H, d), 1.45 (4H, t), 1.9 (2H, m), 2.05 (1H, m), 2.2 (3H, m), 2.4 (3H, s), 2.95 (2H, d), 3.20 (3H, s), 3.3 (2H, s), 4.3 (1H, m), 5.1 (1H, m), 7.65 (2H, m), 7.95 (2H, m), 8.15 (2H, m), 8.15 (1H, t), 8.55 (1H, s); MS m/z 539 [M+H]$^+$.

Example 299

3-methoxy-N-[(3R)-1-methylpyrrolidin-3-yl]-4-[(4,4,6-trimethyl-5-oxo-2-propan-2-yl-2,6,9,11-tetrazabicyclo[5.4.0]undeca-7,9,11-trien-10-yl)amino]benzamide 10-chloro-4,4,6-trimethyl-2-propan-2-yl-2,6,9,11-tetrazabicyclo[5.4.0]undeca-7,9,11-trien-5-one (Intermediate 178; 75 mg, 0.27 mmol), 4-amino-3-methoxy-N-(1-methylpyrrolidin-3-yl)benzamide (Intermediate 187; 67 mg, 0.27 mmol) and p-toluenesulphonic acid monohydrate (127 mg, 0.66 mmol) were heated at 140° C. in 4-methyl-2-pentanol (4 mL) for 2 hours. The reaction mixture was loaded onto an SCX-3 column pre-wet with methanol. The column was washed with methanol and eluted with 2% 7N ammonia/methanol to. Product containing fractions were evaporated and the residue dissolved in DMF and purified by base modified reverse phase HPLC to give the title compound as a white solid (23 mg, 17.5%).

$^1$H NMR (399.9 MHz, DMSO-d$_6$) δ 1.08 (6H, s), 1.22 (6H, d), 1.78 (1H, m), 2.18 (1H, m), 2.23 (3H, s), 2.38 (1H, m), 2.41 (1H, m), 2.61 (1H, m), 2.64 (1H, m), 3.18 (3H, s), 3.37 (2H, s), 3.95 (3H, s), 4.41 (1H, m), 5.16 (1H, m), 7.52 (1H, s), 7.53 (1H, dd), 7.65 (1H, s), 7.99 (1H, s), 8.29 (1H, d), 8.40 (1H, d); MS m/z 496 [M+H]$^+$.

Example 300

N-(1-ethyl-4-piperidyl)-3-methoxy-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 299, on a 0.27 mmol scale, utilising 4-amino-N-(1-ethyl-4-piperidyl)-3-methoxy-benzamide (Intermediate 190; 74 mg, 0.27 mmol), as a white solid (31 mg, 22%).

$^1$H NMR (399.9 MHz, DMSO-d$_6$) δ 1.00 (3H, t), 1.10 (6H, s), 1.22 (6H, d), 1.55 (2H, q), 1.78 (2H, d), 1.95 (2H, t), 2.31 (2H, q), 2.89 (2H, d), 3.17 (3H, s), 3.37 (2H, s), 3.75 (1H, m), 3.95 (3H, s), 5.16 (1H, m), 7.52 (1H, s), 7.53 (1H, dd), 7.65 (1H, s), 7.99 (1H, s), 8.29 (1H, d), 8.40 (1H, d); MS m/z 524 [M+H]$^+$.

Example 301

3-methoxy-N-(2-pyrrolidin-1-ylethyl)-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 299, on a 0.27 mmol scale, utilising 4-amino-N-(1-ethyl-4-piperidyl)-3-methoxy-benzamide (Intermediate 192; 70 mg, 0.27 mmol), as a white solid (52 mg, 38%).

$^1$H NMR (399.9 MHz, DMSO-d$_6$) δ 1.10 (6H, s), 1.22 (6H, d), 1.68 (4H, m), 2.49 (4H, m), 2.60 (2H, t), 3.18 (3H, s), 3.38 (2H, s), 3.40 (2H, m), 3.95 (3H, s), 5.16 (1H, m), 7.52 (1H, s), 7.53 (1H, dd), 7.65 (1H, s), 7.99 (1H, s), 8.29 (1H, d), 8.40 (1H, d); MS m/z 510 [M+H]$^+$.

Example 302

N-(2-dimethylaminoethyl)-3-methoxy-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 299, on a 0.27 mmol scale, utilising 4-amino-N-(2-dimethylaminoethyl)-3-methoxy-benzamide (Intermediate 194; 63 mg, 0.27 mmol), as a white solid (38 mg, 30%).

$^1$H NMR (399.9 MHz, DMSO-d$_6$) δ 1.10 (6H, s), 1.22 (6H, d), 2.18 (6H, s), 2.39 (2H, t), 3.18 (3H, s), 3.35 (2H, t), 3.37 (2H, s), 3.95 (3H, s), 5.16 (1H, m), 7.52 (1H, s), 7.53 (1H, dd), 7.65 (1H, s), 7.99 (1H, s), 8.29 (1H, d), 8.40 (1H, d); MS m/z 510 [M+H]$^+$.

Example 303

N-(3-dimethylaminopropyl)-3-methoxy-4-[(4,4,6-trimethyl-5-oxo-2-propan-2-yl-2,6,9,11-tetrazabicyclo[5.4.0]undeca-7,9,11-trien-10-yl)amino]benzamide The title compound was prepared by an analogous method to the preparation of Example 299, on a 0.27 mmol scale, utilising 4-amino-N-(2-dimethylaminoethyl)-3-methoxy-benzamide (Intermediate 196; 67 mg, 0.27 mmol), as a white solid (8 mg, 6%).

$^1$H NMR (399.9 MHz, DMSO-d$_6$) δ 1.10 (6H, s), 1.22 (6H, d), 1.68 (2H, m), 2.18 (3H, s), 2.28 (2H, t), 3.17 (3H, s), 3.29 (2H, t), 3.37 (2H, s), 3.95 (3H, s), 5.16 (1H, m), 7.52 (1H, s), 7.53 (1H, dd), 7.65 (1H, s), 7.99 (1H, s), 8.29 (1H, d), 8.40 (1H, d); MS m/z 498 [M+H]$^+$.

Example 304

4-[(4,4-diethyl-6-methyl-5-oxo-2-propan-2-yl-2,6,9,11-tetrazabicyclo[5.4.0]undeca-7,9,11-trien-10-yl)amino]-3-methoxy-N-(1-methyl-4-piperidyl)benzamide 10-chloro-4,4-diethyl-6-methyl-2-propan-2-yl-2,6,9,11-tetrazabicyclo[5.4.0]undeca-7,9,11-trien-5-one (Intermediate 198; 100 mg, 0.322 mmol), p-toluene sulphonic acid monohydrate (153 mg, 0.81 mmol) and 4-amino-3-methoxy-N-(1-methyl-4-piperidyl)benzamide (WO06/018220; 84 mg, 0.322 mmol) were added to 4-methyl-2-pentanol (7 mL). The reaction was heated at 120° C. over the weekend. The reaction mixture was loaded on to an SCX column (10 g), pre-wet with methanol, washed with methanol and eluted with ammonia in methanol. Product containing fractions were combined and evaporated and the resultant material purified by base modified reverse phase preparative HPLC to yield the title compound, after drying under vacuum at 70° C., as a white solid (97 mg, 56%)

$^1$H NMR (400.132 MHz, CDCl$_3$) δ 0.84 (t, 6H), 1.25 (d, 6H), 1.63-1.49 (m, 4H), 1.70 (sextet, 2H), 2.07-2.04 (m, 2H), 2.19-2.13 (m, 2H), 2.30 (s, 3H), 2.84-2.81 (m, 2H), 3.28 (s, 3H), 3.40 (s, 2H), 4.04-3.92 (m, 4H), 5.32 (sextet, 1H), 5.93 (d, 1H), 7.24 (dd, 1H), 7.43 (d, 1H), 7.59 (s, 1H), 7.83 (s, 1H), 8.48 (d, 1H); MS m/z 538 [M+H]$^+$.

Example 305

4-[(4,4-diethyl-6-methyl-5-oxo-2-propan-2-yl-2,6,9,11-tetrazabicyclo[5.4.0]undeca-7,9,11-trien-10-yl)amino]-N-(1-ethyl-4-piperidyl)-3-methoxy-benzamide The title compound was prepared by an analogous method to the preparation of Example 304, on a 0.322 mmol scale, utilising 4-amino-N-(1-ethyl-4-piperidyl)-3-methoxy-benzamide (Intermediate 190; 89 mg, 0.322 mmol), as a white solid (89 mg, 30%).

$^1$H NMR (400.132 MHz, CDCl$_3$) δ 0.84 (t, 6H), 1.10 (t, 3H), 1.25 (d, 6H), 1.63-1.49 (m, 4H), 1.75-1.66 (m, 2H), 2.17-2.06 (m, 4H), 2.44 (q, 2H), 2.93-2.90 (m, 2H), 3.28 (s, 3H), 3.40 (s, 2H), 4.05-3.97 (m, 4H), 5.32 (septet, 1H), 5.91 (d, 1H), 7.23 (dd, 1H), 7.43 (d, 1H), 7.59 (s, 1H), 7.83 (s, 1H), 8.47 (d, 1H); MS m/z 552 [M+H]$^+$.

Example 306

4-[(4,4-diethyl-6-methyl-5-oxo-2-propan-2-yl-2,6,9,11-tetrazabicyclo[5.4.0]undeca-8,10,12-trien-10-yl)amino]-3-methoxy-N-[(1S,5R)-9-methyl-9-azabicyclo[3.3.1]non-7-yl]benzamide The title compound was prepared by an analogous method to the preparation of Example 304, on a 0.322 mmol scale, utilising 4-amino-3-methoxy-N-[(1S,5R)-9-methyl-9-azabicyclo[3.3.1]non-3-yl]benzamide (Intermediate 202; 97 mg, 0.322 mmol), as a white solid (83 mg, 45%).

$^1$H NMR (400.132 MHz, DMSO-d6) δ 0.78 (t, 6H), 1.22 (d, 6H), 1.60-1.40 (m, 6H), 1.89-1.77 (m, 2H), 2.16-2.03 (m, 2H), 2.42-2.33 (m, 2H), 3.18 (s, 3H), 3.29 (s, 4H), 3.41 (s, 2H), 3.69-3.57 (m, 2H), 3.97 (s, 3H), 4.70-4.52 (m, 1H), 5.24-5.18 (m, 1H), 7.53-7.51 (m, 2H), 7.67 (s, 1H), 7.98 (s, 1H), 8.31-8.22 (m, 1H), 8.41 (d, 1H), 9.27-9.18 (m, 1H); MS m/z 578 [M+H]$^+$.

Example 307

4-[(4,4-diethyl-6-methyl-5-oxo-2-propan-2-yl-2,6,9,11-tetrazabicyclo[5.4.0]undeca-8,10,12-trien-10-yl)amino]-2-fluoro-5-methoxy-N-[(1S,5R)-9-methyl-9-azabicyclo[3.3.1]non-7-yl]benzamide The title compound was prepared by an analogous method to the preparation of Example 304, on a 0.322 mmol scale, utilising 4-amino-3-methoxy-N-[(1S,5R)-9-methyl-9-azabicyclo[3.3.1]non-3-yl]benzamide (Intermediate 204; 103 mg, 0.322 mmol), as a white solid (100 mg, 52%).

$^1$H NMR (400.132 MHz, CDCl$_3$) δ 0.85 (t, 6H), 1.05-1.03 (m, 2H), 1.34-1.26 (m, 8H), 1.59-1.49 (m, 3H), 1.70 (sextet, 2H), 2.02-1.91 (m, 3H), 2.57-2.50 (m, 5H), 3.10-3.07 (m, 2H), 3.29 (s, 3H), 3.42 (s, 2H), 3.95 (s, 3H), 4.57-4.46 (m, 1H), 5.30 (septet, 1H), 6.55 (dd, 1H), 7.57 (d, 1H), 7.64 (s, 1H), 7.85 (s, 1H), 8.38 (d, 1H); MS m/z 596 [M+H]$^+$.

Example 308

4-[(4,4-diethyl-6-methyl-5-oxo-2-propan-2-yl-2,6,9,11-tetrazabicyclo[5.4.0]undeca-7,9,11-trien-10-yl)amino]-N-(1-ethyl-4-piperidyl)-2-fluoro-5-methoxy-benzamide The title compound was prepared by an analogous method to the preparation of Example 304, on a 0.322 mmol scale, utilising 4-amino-N-(1-ethyl-4-piperidyl)-2-fluoro-5-methoxy-benzamide (Intermediate 205; 95 mg, 0.322 mmol), as a white solid (87 mg, 48%).

$^1$H NMR (400.132 MHz, CDCl$_3$) δ 0.85 (t, 6H), 1.10 (t, 3H), 1.27 (d, 6H), 1.75-1.49 (m, 6H), 2.08-2.06 (m, 2H), 2.20-2.14 (m, 2H), 2.44 (q, 2H), 2.88-2.85 (m, 2H), 3.29 (s, 3H), 3.42 (s, 2H), 3.95 (s, 3H), 4.10-4.00 (m, 1H), 5.33-5.26 (m, 1H), 6.68 (dd, 1H), 7.55 (d, 1H), 7.65 (s, 1H), 7.85 (s, 1H), 8.38 (d, 1H); MS m/z 570 [M+H]$^+$.

Example 309

4-[(4,4-diethyl-6-methyl-5-oxo-2-propan-2-yl-2,6,9,11-tetrazabicyclo[5.4.0]undeca-7,9,11-trien-10-yl)amino]-N-(2,2-dimethyl-3-pyrrolidin-1-yl-propyl)-3-methoxy-benzamide The title compound was prepared by an analogous method to the preparation of Example 304, on a 0.33 mmol scale, utilising 4-amino-N-(2,2-dimethyl-3-pyrrolidin-1-yl-propyl)-3-methoxy-benzamide (Intermediate 206; 100 mg, 0.33 mmol), as a white solid (76 mg, 40%).

$^1$H NMR (400.132 MHz, CDCl$_3$) δ 0.84 (t, 6H), 1.01 (s, 6H), 1.24 (d, 6H), 1.53 (sextet, 2H), 1.71 (sextet, 2H), 1.86-1.81 (m, 4H), 2.57 (s, 2H), 2.72-2.68 (m, 4H), 3.28 (s, 3H), 3.40-3.39 (m, 4H), 3.97 (s, 3H), 5.34 (septet, 1H), 7.20 (dd, 1H), 7.58 (d, 1H), 7.62 (s, 1H), 7.84 (s, 1H), 8.44 (d, 1H), 9.28 (s, 1H); MS m/z 5780 [M+H]$^+$.

Example 310

(R)-5-chloro-2-fluoro-4-(9'-isopropyl-5'-methyl-6'-oxo-5',6',8',9'-tetrahydrospiro[cyclopropane-1,7'-pyrimido[5,4-b][1,4]diazepine]-2'-ylamino)-N-(1-methylpyrrolidin-3-yl)benzamide 2'-chloro-9'-isopropyl-5'-methyl-8',9'-dihydrospiro[cyclopropane-1,7'-pyrimido[5,4-b][1,4]diazepin]-6'(5'H)-one (Intermediate 208; 88 mg, 0.32 mmol), 4-amino-5-chloro-2- fluoro-N-[(3R)-1-methylpyrrolidin-3-yl]benzamide (Intermediate 207; 101 mg, 0.36 mmol) and XANTPHOS (17 mg, 0.03 mmol) were dissolved in 1,4-dioxane (7.5 mL). Caesium carbonate (229 mg, 0.65 mmol) was added and the system purged with a stream of nitrogen for 15 minutes before tris(dibenzylideneacetone) palladium (II) (18 mg, 0.02 mmol) was added. The apparatus was evacuated and backfilled with nitrogen (×3) and then heated at 100° C. for 3 hours. The mixture was cooled, filtered and the filtrate absorbed on to an SCX column, which was washed with methanol and eluted with ammonia in methanol. Product containing fractions were concentrated and purified by column chromatography (2.5% 7N ammonia in MeOH/DCM) to yield the title compound as a pale yellow foam (148 mg, 90%).

$^1$H NMR (399.9 MHz, DMSO-$d_6$) δ0.70-0.73 (2H, m), 0.94-0.96 (2H, m), 1.15 (6H, d), 1.67-1.75 (1H, m), 2.12-2.21 (1H, m), 2.26 (3H, s), 2.33-2.43 (2H, m), 2.56-2.62 (1H, m), 2.67-2.71 (1H, m), 3.19 (3H, s), 3.49 (2H, s), 4.31-4.40 (1H, m), 4.79-4.86 (1H, m), 7.69 (1H, d), 8.04 (2H, m), 8.23-8.25 (1H, m), 8.36-8.41 (1H, m); MS m/z 516 [M+H]$^+$.

Example 311

5-chloro-N-(1-ethylpiperidin-4-yl)-2-fluoro-4-(9'-isopropyl-5'-methyl-6'-oxo-5',6',8',9'-tetrahydrospiro [cyclopropane-1,7'-pyrimido[5,4-b][1,4]diazepine]-2'-ylamino)benzamide The title compound was prepared by an analogous method to the preparation of Example 310, on a 0.29 mmol scale, utilising 4-amino-5-chloro-N-(1-ethyl-4-piperidyl)-2-fluoro-benzamide (Intermediate 174; 87 mg, 0.29 mmol), after purification by base modified reverse phase preparative HPLC, as a white solid (98 mg, 62%).

$^1$H NMR (399.9 MHz, DMSO-$d_6$) δ 0.72 (2H, m), 0.94 (2H, m), 1.00 (3H, t), 1.17 (6H, d), 1.51-1.57 (2H, m), 1.80 (2H, d), 1.96 (2H, t), 2.32 (2H, q), 2.84 (2H, d), 3.18 (3H, s), 3.49 (2H, s), 3.67-3.78 (1H, m), 4.79-4.86 (1H, m), 7.67 (1H, d), 8.02-8.07 (3H, m), 8.38 (1H, d); MS m/z 544 [M+H]$^+$.

Example 312

4-(9'-isopropyl-5'-methyl-6'-oxo-5',6',8',9'-tetrahydrospiro[cyclopropane-1,7'-pyrimido[5,4-b][1,4] diazepine]-2'-ylamino)-3-methoxy-N-(2-(pyrrolidin-1-yl)ethyl)benzamide The title compound was prepared by an analogous method to the preparation of Example 284, on a 0.36 mmol scale, utilising 4-amino-3-methoxy-N-(2-pyrrolidin-1-ylethyl) benzamide (Intermediate 192; 94 mg, 0.36 mmol), heating at 140° C. for 2 hours, as a white solid (65 mg, 36%).

$^1$H NMR (399.9 MHz, DMSO-d6) δ0.69 (2H, t). 0.93 (2H, t), 1.19 (6H, d), 1.69-1.72 (4H, s), 2.71 (4H, s), 2.80 (2H, s), 3.17 (3H, s), 3.39-3.41 (2H, t), 3.48 (2H, s), 3.95 (3H, s), 4.82-4.86 (1H, m), 7.49 (1H, d), 7.50 (1H, s), 7.63 (1H, s), 7.99 (1H, s), 8.32 (1H, t), 8.43 (1H, d); MS m/z 509 [M+H]$^+$.

Example 313

N-(3-(dimethylamino)-2,2-dimethylpropyl)-4-(9'-isopropyl-5'-methyl-6'-oxo-5',6',8',9'-tetrahydrospiro [cyclopropane-1,7'-pyrimido[5,4-b][1,4]diazepine]-2'-ylamino)-3-methoxybenzamide The title compound was prepared by an analogous method to the preparation of Example 284, on a 0.36 mmol scale, utilising 4-amino-N-(2,2-dimethyl-3-pyrrolidin-1-yl-propyl)-3-methoxy-benzamide (Intermediate 206; 100 mg, 0.36 mmol), heating at 140° C. for 2 hours, as a white solid (78 mg, 42%).

$^1$H NMR (399.9 MHz, DMSO-d6) δ0.69 (2H, t), 0.89 (6H, s), 0.93 (2H, t), 1.18 (6H, d), 2.21 (2H, s), 2.25 (6H, s), 3.17 (3H, s), 3.21 (2H, d), 3.48 (2H, s), 3.95 (3H, s), 4.82-4.86 (1H, m), 7.49 (1H, d), 7.50 (1H, s), 7.63 (1H, s), 7.99 (1H, s), 8.32 (1H, t), 8.43 (1H, d); MS m/z 525 [M+H]$^+$.

Example 314

4-[(2-cyclopentyl-6-methyl-5-oxo-2,6,9,11-tetrazabicyclo[5.4.0]undeca-7,9,11-trien-10-yl)amino]-3-methoxy-N-(1-propyl-4-piperidyl)benzamide 4-[(2-cyclopentyl-6-methyl-5-oxo-2,6,9,11-tetrazabicyclo[5.4.0]undeca-7,9,11-trien-10-yl)amino]-3-methoxy-benzoic acid (Example 111; 231 mg, 0.56 mmol), DIPEA (0.3 mL, 1.68 mmol) and HATU (283 mg, 0.75 mmol) were stirred together in DMA (4 mL) at ambient temperature for 10 minutes. 4-amino-1-propylpiperidine (Fluorochem; 100 mg, 0.70 mmol) was added and the mixture stirred at room temperature for 4 hours. The reaction mixture was loaded onto an SCX-2 (10 g) column pre-wet with MeOH. The column was washed with MeOH (×2) and the product eluted with 2M NH3/MeOH. Product containing fractions were combined and evaporated and the residue purified by base modified reverse phase preparative HPLC. Product containing fractions were combined and evaporated to yield the title compound as a gum (194 mg, 65%).

$^1$H NMR (400.132 MHz, DMSO-d6) δ 0.86 (t, 3H), 1.44 (m, 2H), 1.66 (m, 10H), 1.94 (m, 4H), 2.24 (t, 2H), 2.59 (m, 2H), 2.87 (m, 2H), 3.18 (s, 3H), 3.63 (m, 2H), 3.76 (m, 1H), 3.95 (s, 3H), 4.82 (m, 1H), 7.48 (m, 2H), 7.72 (s, 1H), 8.05 (d, 1H), 8.08 (s, 1H), 8.38 (d, 1H); MS m/z 536 [M+H]$^+$.

Example 315

3-chloro-4-[(2-cyclopentyl-6-methyl-5-oxo-2,6,9,11-tetrazabicyclo[5.4.0]undeca-7,9,11-trien-10-yl) amino]-N-(2-dimethylaminoethyl)benzamide 10-Chloro-2-cyclopentyl-6-methyl-2,6,9,11-tetrazabicyclo[5.4.0]undeca-8,10,12-trien-5-one (Intermediate 1; 80 mg, 0.285 mmol) and 4-amino-3-chloro-N-(2-dimethylaminoethyl)benzamide (Intermediate 213; 69 mg, 0.285 mmol), p-toluenesulphonic acid monohydrate (136 mg, 0.713 mmol) were combined in 4-Methyl-2-pentanol (2 mL) and heated at 100° C. overnight. Methanol was added to the cooled reaction mixture and the solution loaded onto an SCX-3 column (5 g) pre-wet with MeOH (2 column volumes). The column was flushed with MeOH (2 column volumes) and eluted with 2M ammonia in MeOH. Product containing fractions were evaporated and the residue dissolved in DCM with a little MeOH. The resultant solution was purified on a silica column, eluting with a gradient of 0-5% 2M ammonia in MeOH/DCM then 10% 2M ammonia in MeOH/DCM. Product containing fractions were combined and evaporated and the residue purified by base modified reverse phase preparative HPLC to yield the title compound as a white solid (21 mg, 15%).

$^1$H NMR (399.902 MHz, CDCl$_3$) δ1.56-1.79 (m, 6H), 2.02 (m, 2H), 2.29 (s, 6H), 2.53 (m, 2H), 2.68 (m, 2H), 3.30 (s, 3H), 3.51 (m, 2H), 3.70 (m, 2H), 4.87 (m, 1H), 6.71 (s, 1H), 7.53 (s, 1H), 7.68 (m, 1H), 7.83 (m, 1H), 7.95 (s, 1H), 8.63 (d, 1H); MS m/z 486 [M+H]$^+$.

Example 316

3-chloro-4-[(2-cyclopentyl-6-methyl-5-oxo-2,6,9,11-tetrazabicyclo[5.4.0]undeca-7,9,11-trien-10-yl)amino]-N-(1-ethyl-4-piperidyl)benzamide 10-Chloro-2-cyclopentyl-6-methyl-2,6,9,11-tetrazabicyclo[5.4.0]undeca-8,10,12-trien-5-one (Intermediate 1; 80 mg, 0.285 mmol) and 4-amino-3-chloro-N-(1-ethyl-4-piperidyl)benzamide (Intermediate 212; 76 mg, 0.285 mmol), p-toluenesulphonic acid monohydrate (136 mg, 0.713 mmol) were combined in 4-Methyl-2-pentanol (2 mL) and heated at 100° C. overnight. Methanol was added to the cooled reaction mixture and the solution loaded onto an SCX-3 column (5 g) pre-wet with MeOH (2 column volumes). The column was flushed with MeOH (2 column volumes) and eluted with 2M ammonia in MeOH. Product containing fractions were evaporated and the residue dissolved in DCM with a little MeOH. The resultant solution was purified on a silica column, eluting with a gradient of 0-5% 2M ammonia in MeOH/DCM then 10% 2M ammonia in MeOH/DCM. Product containing fractions were combined and evaporated and the residue purified by base modified reverse phase preparative HPLC to yield the title compound as a white solid (22 mg, 15%).

$^1$H NMR (399.902 MHz, CDCl$_3$) δ1.11 (t, 3H), 1.54-1.79 (m, 8H), 2.08 (m, 6H), 2.44 (q, 2H), 2.68 (m, 2H), 2.92 (m, 2H), 3.30 (s, 3H), 3.70 (m, 2H), 3.99 (m, 1H), 4.87 (m, 1H), 5.84 (d, 1H), 7.54 (s, 1H), 7.62 (m, 1H), 7.80 (m, 1H), 7.96 (s, 1H), 8.64 (d, 1H); MS m/z 526 [M+H]$^+$.

Example 317

3-chloro-4-[(2-cyclopentyl-6-methyl-5-oxo-2,6,9,11-tetrazabicyclo[5.4.0]undeca-7,9,11-trien-10-yl)amino]-N-(3-dimethylaminopropyl)benzamide The title compound was prepared by an analogous method to the preparation of Example 316, on a 0.356 mmol scale, utilising 4-amino-3-chloro-N-(3-dimethylaminopropyl)benzamide (Intermediate 214; 91 mg, 0.356 mmol), as a white solid (31 mg, 17%).

$^1$H NMR (399.902 MHz, CDCl$_3$) δ1.55-1.80 (m, 8H), 2.03 (m, 2H), 2.33 (s, 6H), 2.53 (m, 2H), 2.68 (m, 2H), 3.30 (s, 3H), 3.56 (m, 2H), 3.70 (m, 2H), 4.88 (m, 1H), 7.54 (s, 1H), 7.65 (d, 1H), 7.84 (s, 1H), 7.96 (s, 1H), 8.57 (s, 1H), 8.63 (d, 1H); MS m/z 500 [M+H]$^+$.

Example 318

3-chloro-4-[(2-cyclopentyl-6-methyl-5-oxo-2,6,9,11-tetrazabicyclo[5.4.0]undeca-7,9,11-trien-10-yl)amino]-N-(2-pyrrolidin-1-ylethyl)benzamide The title compound was prepared by an analogous method to the preparation of Example 316, on a 0.356 mmol scale, utilising 4-amino-3-chloro-N-(2-pyrrolidin-1-ylethyl)benzamide (Intermediate 215; 95 mg, 0.356 mmol), as a white solid (39 mg, 21%).

$^1$H NMR (399.902 MHz, CDCl$_3$) δ1.56-1.82 (m, 10H), 2.02 (m, 2H), 2.58 (m, 4H), 2.70 (m, 4H), 3.30 (s, 3H), 3.55 (m, 2H), 3.70 (m, 2H), 4.87 (m, 1H), 6.74 (s, 1H), 7.53 (s, 1H), 7.67 (m, 1H), 7.84 (m, 1H), 7.95 (s, 1H), 8.63 (d, 1H); MS m/z 512 [M+H]$^+$.

Example 319

4-[(2-cyclopentyl-6-methyl-5-oxo-2,6,9,11-tetrazabicyclo[5.4.0]undeca-7,9,11-trien-10-yl)amino]-N-[1-(cyclopropylmethyl)-4-piperidyl]-3-methoxy-benzamide The title compound was prepared by an analogous method to the preparation of Example 314, on a 0.24 mmol scale, utilising 1-(cyclopropylmethyl)-4-piperidinamine dihydrochloride (Aldrich; 95 mg, 0.356 mmol) and DIPEA (210 µL, 1.3 mmol) and stirring at ambient temperature for 24 hours, as a white solid (85 mg, 64%).

$^1$H NMR (400.132 MHz, DMSO-d6) δ 0.00 (m, 2H), 0.38 (m, 2H), 0.75 (m, 1H), 1.60 (m, 10H), 1.90 (m, 4H), 2.11 (d, 2H), 2.51 (m, 2H), 2.91 (m, 2H), 3.10 (s, 3H), 3.55 (m, 2H), 3.68 (m, 1H), 3.87 (s, 3H), 4.74 (m, 1H), 7.40 (m, 2H), 7.64 (s, 1H), 7.98 (d, 1H), 8.00 (s, 1H), 8.30 (d, 1H); MS m/z 548 [M+H]$^+$.

Example 320

2-chloro-4-[(2-cyclopentyl-6-methyl-5-oxo-2,6,9,11-tetrazabicyclo[5.4.0]undeca-7,9,11-trien-10-yl)amino]-5-methoxy-N-(1-methyl-4-piperidyl)benzamide The title compound was prepared by an analogous method to the preparation of Example 316, on a 0.285 mmol scale, utilising 4-amino-2-chloro-5-methoxy-N-(1-methyl-4-piperidyl)benzamide (Intermediate 216; 85 mg, 0.285 mmol), as a white solid (108 mg, 70%).

$^1$H NMR (399.902 MHz, CDCl$_3$) δ1.61 (m, 4H), 1.76 (m, 4H), 2.09 (m, 4H), 2.20 (m, 2H), 2.31 (s, 3H), 2.68 (m, 2H), 2.78 (m, 2H), 3.29 (s, 3H), 3.71 (m, 2H), 3.94 (s, 3H), 4.03 (m, 1H), 4.97 (m, 1H), 6.56 (d, 1H), 7.40 (s, 1H), 7.63 (s, 1H), 7.94 (s, 1H), 8.62 (s, 1H); MS m/z 542 [M+H]$^+$.

Example 321

5-chloro-4-[(2-cyclopentyl-6-methyl-5-oxo-2,6,9,11-tetrazabicyclo[5.4.0]undeca-7,9,11-trien-10-yl)amino]-2-fluoro-N-[(3R)-pyrrolidin-3-yl]benzamide tert-butyl (3R)-3-[[5-chloro-4-[(2-cyclopentyl-6-methyl-5-oxo-2,6,9,11-tetrazabicyclo[5.4.0]undeca-7,9,11-trien-10-yl)amino]-2-fluoro-benzoyl]amino]pyrrolidine-1-carboxylate (Example 324; 175 mg, 0.29 mmol) was dissolved in 1,4-dioxane (5 mL) and 4M HCl$_{(aq)}$ in 1,4-dioxane (10 mL) added. The mixture was stirred at room temperature for 2 hours. TFA (2 mL) was added an the reaction stirred for a further 1 hour. The reaction was concentrated, dissolved in DCM (10 mL) and TFA (3 mL) added. The reaction was stirred at room temperature for 1 hour, concentrated and the residue dissolved in methanol, absorbed on to an SCX column, washed with methanol and eluted with ammonia in methanol. Product containing fractions were combined and evaporated and the residue purified by column chromatography (7.5% ammonia in methanol/DCM) to yield the title compound as a white foam (112 mg, 77%).

$^1$H NMR (399.9 MHz, DMSO-d6) δ1.58-1.77 (8H, m), 1.92-2.02 (3H, m), 2.60-2.77 (5H, m), 2.87-3.01 (2H, m), 3.19 (3H, s), 3.65 (2H, m), 4.23-4.31 (1H, m), 4.76-4.84 (1H, m), 7.70 (1H, d), 8.07-8.17 (3H, m), 8.33 (1H, d); MS m/z 502 [M+H]$^+$.

Example 322

5-chloro-4-[(2-cyclopentyl-6-methyl-5-oxo-2,6,9,11-tetrazabicyclo[5.4.0]undeca-7,9,11-trien-10-yl)amino]-2-fluoro-N-(1-methyl-4-piperidyl)benzamide 5-chloro-4-[(2-cyclopentyl-6-methyl-5-oxo-2,6,9,11-tetrazabicyclo[5.4.0]undeca-7,9,11-trien-10-yl)amino]-2-fluoro-benzoic acid (Intermediate 219; 100 mg, 0.23 mmol), 4-amino-1-methylpiperidine (Fluorochem; 40 mg, 0.35 mmol) and HATU (132 mg, 0.35 mmol) were stirred in DMF (3 mL). N,N-diisopropylethylamine (121 µl, 0.69 mmol) was added and the mixture heated at 50° C. for 2 hours. The mixture was cooled and absorbed on to an SCX column, which was subsequently washed with methanol and eluted with ammonia in methanol. Product containing fractions were concentrated and the residue purified by base modified reverse phase preparative chromatography to yield the title compound as a white solid (58 mg, 48%)

$^1$H NMR (399.9 MHz, DMSO-d6) δ1.50-1.80 (10H, m), 1.92-1.99 (4H, m), 2.17 (3H, s), 2.61 (2H, m), 2.74 (2H, d), 3.19 (3H, s), 3.63-3.74 (3H, m), 4.76-4.84 (1H, m), 7.67 (1H, d), 8.07 (1H, d) 8.14 (1H, m), 8.31-8.36 (1H, m); MS m/z 530 M+H]$^+$.

Example 323

5-chloro-4-[(2-cyclopentyl-6-methyl-5-oxo-2,6,9,11-tetrazabicyclo[5.4.0]undeca-7,9,11-trien-10-yl)amino]-N-(1-ethyl-4-piperidyl)-2-fluoro-benzamide The title compound was prepared by an analogous method to the preparation of Example 322, on a 0.23 mmol scale, utilising 4-amino-1-ethylpiperidine (Fluorochem; 45 mg, 0.35 mmol), as a white solid (60 mg, 48%).

$^1$H NMR (399.9 MHz, DMSO-d6) δ1.00 (3H, t), 1.59 (8H, d), 1.80 (2H, d), 1.93-1.98 (4H, m), 2.32 (2H, q), 2.61 (2H, m), 2.84 (2H, d), 3.19 (3H, s), 3.63-3.76 (3H, m), 4.76-4.84 (1H, m), 7.67 (1H, d), 8.08 (1H, d), 8.14 (2H, d), 8.31-8.36 (1H, m); MS m/z 544 [M+H]$^+$.

Example 324 tert-butyl (3R)-3-[[5-chloro-4-[(2-cyclopentyl-6-methyl-5-oxo-2,6,9,11-tetrazabicyclo[5.4.0]undeca-7,9,11-trien-10-yl)amino]-2-fluoro-benzoyl]amino]pyrrolidine-1-carboxylate The title compound was prepared by an analogous method to the preparation of Example 322, on a 0.46 mmol scale, utilising boc-R-(3R)-aminopyrrolidine (Aldrich; 130 mg, 0.75 mmol) and purification by normal phase chromatography (5% MeOH/DCM), as a white foam (179 mg, 65%).

$^1$H NMR (399.9 MHz, DMSO-d6) δ1.42 (9H, s), 1.56-1.74 (7H, m), 1.87-1.97 (3H, m), 2.09-2.13 (1H, m), 2.60-2.64 (2H, m), 3.19 (4H, m), 3.37-3.44 (1H, m), 3.49-3.57 (1H, m), 3.63-3.67 (2H, m), 4.38 (1H, m), 4.80 (1H, m), 7.70 (1H, d), 8.09-8.25 (2H, m), 8.32-8.37 (1H, m), 8.44 (1H, d); MS m/z 602 [M+H]$^+$.

Example 325

5-chloro-4-[(2-cyclopentyl-6-methyl-5-oxo-2,6,9,11-tetrazabicyclo[5.4.0]undeca-7,9,11-trien-10-yl)amino]-2-fluoro-N-[(3R)-1-methylpyrrolidin-3-yl]benzamide 5-chloro-4-[(2-cyclopentyl-6-methyl-5-oxo-2,6,9,11-tetrazabicyclo[5.4.0]undeca-7,9,11-trien-10-yl)amino]-2-fluoro-N-[(3R)-pyrrolidin-3-yl]benzamide (Example 321; 95 mg, 0.19 mmol) was dissolved in 37% aqueous formaldehyde solution (1.1 mL) and acetic acid (120 µl, 1.89 mmol). Sodium acetate (156 mg, 1.89 mmol) was added and the mixture cooled in an ice/water bath. Sodium cyanoborohydride (12 mg, 0.19 mmol) was added and the mixture allowed to warm to room temperature. After stirring for 1 hour, the mixture was absorbed on to an SCX column, and subsequently washed with methanol and eluted with ammonia in methanol. The product containing fractions were concentrated and purified by column chromatography (2% 7N ammonia in methanol/DCM) to yield the title compound as a white foam (69 mg, 70%).

$^1$H NMR (399.9 MHz, DMSO-d6) δ1.58-1.73 (7H, m), 1.90-1.96 (2H, m), 2.12-2.21 (1H, m), 2.26 (3H, s), 2.38-2.43 (3H, m), 2.56-2.64 (3H, m), 2.67-2.71 (1H, m), 3.19 (3H, s), 3.63-3.67 (2H, m), 4.34-4.36 (1H, m), 4.80 (1H, m), 7.69 (1H, d), 8.14 (2H, m), 8.27 (1H, d), 8.33 (1H, d); MS m/z 516 [M+H]$^+$.

Example 326

4-[(2-cyclopentyl-6-methyl-5-oxo-2,6,9,11-tetrazabicyclo[5.4.0]undeca-7,9,11-trien-10-yl)amino]-N-[(3R)-1-ethylpyrrolidin-3-yl]-3-methoxy-benzamide 4-[(6-cyclopentyl-2-methyl-3-oxo-2,6,8,10-tetrazabicyclo[5.4.0]undeca-8,10,12-trien-9-yl)amino]-3-methoxy-N-[(3R)-pyrrolidin-3-yl]benzamide (Example 55; 100 mg, 0.21 mmol) in DMF (3 mL) was added triethylamine (59 ul, 0.42 mmol) and ethyl bromide (Acros; 24 ul, 0.31 mmol). The reaction mixture was heated to 90° C. by microwave irradiation for 1 hour. The cooled reaction mixture was poured onto an SCX-3 cartridge (5 g) and the cartridge washed through with methanol (40 mL) and then eluted with 2M ammonia in methanol. Ammoniacal fractions were combined and evaporated. The residue was purified by base modified reverse phase preparative HPLC and product containing fractions combined and evaporated to yield the title compound as a white solid (27 mg, 25%)

$^1$H NMR (400.132 MHz, DMSO-d6) δ 0.97 (t, 3H), 1.51-1.75 (m, 7H), 1.87 (m, 2H), 2.08 (m, 1H), 2.32-2.68 (m, 8H), 3.10 (s, 3H), 3.56 (m, 2H), 3.88 (s, 3H), 4.32 (m, 1H), 4.75 (m, 1H), 7.44 (m, 2H), 7.65 (s, 1H), 8.01 (s, 1H), 8.22 (d, 1H), 8.31 (d, 1H); MS m/z 508 [M+H]$^+$.

Example 327

4-[(2-cyclopentyl-6-methyl-5-oxo-2,6,9,11-tetrazabicyclo[5.4.0]undeca-7,9,11-trien-10-yl)amino]-3-methoxy-N-[(3R)-1-propylpyrrolidin-3-yl]benzamide The title compound was prepared by an analogous method to the preparation of Example 326, on a 0.21 mmol scale, utilising n-propyl bromide (Aldrich; 29 µL, 0.31 mmol) and heating for 45 minutes at 90° C., as an off-white gum (63 mg, 58%).

¹H NMR (400.132 MHz, DMSO-d6) δ 0.88 (t, 3H), 1.45 (m, 2H), 1.56-1.82 (m, 7H), 1.95 (m, 2H), 2.14 (m, 1H), 2.35 (m, 2H), 2.44 (m, 2H), 2.61 (m, 3H), 2.74 (m, 1H), 3.17 (s, 3H), 3.63 (m, 2H), 3.95 (s, 3H), 4.39 (m, 1H), 4.82 (m, 1H), 7.50 (m, 2H), 7.72 (s, 1H), 8.08 (s, 1H), 8.27 (d, 1H), 8.38 (d, 1H); MS m/z 522 [M+H]⁺.

Example 328

4-[(2-cyclopentyl-6-methyl-5-oxo-2,6,9,11-tetrazabicyclo[5.4.0]undeca-7,9,11-trien-10-yl)amino]-3-methoxy-N-[(3R)-1-(2-methoxyethyl)pyrrolidin-3-yl]benzamide The title compound was prepared by an analogous method to the preparation of Example 326, on a 0.21 mmol scale, utilising 2-bromoethyl methylether (Aldrich; 30 μL, 0.31 mmol) and heating for 45 minutes at 90° C., as an off-white gum (57 mg, 50%).

¹H NMR (400.132 MHz, DMSO-d6) δ 1.57-1.82 (m, 7H), 1.95 (m, 2H), 2.13 (m, 1H), 2.52 (d, 2H)[obscured by DMSO], 2.59 (m, 4H), 2.69 (m, 1H), 2.79 (m, 1H), 3.17 (s, 3H), 3.24 (s, 3H), 3.43 (t, 2H), 3.63 (m, 2H), 3.95 (s, 3H), 4.39 (m, 1H), 4.82 (m, 1H), 7.51 (m, 2H), 7.72 (s, 1H), 8.08 (s, 1H), 8.29 (d, 1H), 8.38 (d, 1H); MS m/z 538 [M+H]⁺.

Example 329

4-[(2-cyclopentyl-6-methyl-5-oxo-2,6,9,11-tetrazabicyclo[5.4.0]undeca-8,10,12-trien-10-yl)amino]-3-fluoro-N-[(1S,5R)-9-methyl-9-azabicyclo[3.3.1]non-3-yl]benzamide 4-amino-3-fluoro-N-[(1S,5R)-9-methyl-9-azabicyclo[3.3.1]non-7-yl]benzamide (Intermediate 162; 1.0 g, 3.43 mmol), 110-Chloro-2-cyclopentyl-6-methyl-2,6,9,11-tetrazabicyclo[5.4.0]undeca-8,10,12-trien-5-one (Intermediate 1; 0.96 g, 3.43 mmol) and p-toluenesulphonic acid monohydrate (1.63 g, 8.56 mmol) were stirred and heated together at 110° C. in 4-methyl-2-pentanol (30 mL) for 18 hours. The cooled reaction mixture was diluted with water and methanol and the solution loaded onto an SCX-2 (20 g) column pre-wet with MeOH. The column was washed with MeOH (2 column volumes) and the product eluted with 2M NH₃-MeOH (2 column volumes). Product containing fractions were combined and evaporated and the residue purified by chromatography on a silica column eluting with a 0-100% gradient of 10% 2M NH₃-MeOH in DCM. Product containing fractions were combined and evaporated to give a foam which on trituration with ethyl acetate yielded, on filtration, the title compound as a white solid (473 mg, 26%) 536 (M+H), ES– 534 (M–H)

¹H NMR (400.132 MHz, DMSO-d6) δ 0.94 (m, 2H), 1.55 (m, 9H), 1.90 (m, 4H), 2.03 (m, 1H), 2.19 (m, 3H), 2.42 (s, 3H), 2.58 (m, 2H), 2.98 (m, 2H), 3.17 (s, 3H), 3.60 (m, 2H), 4.32 (m, 1H), 4.74 (m, 1H), 7.69 (m, 2H), 8.00 (d, 1H), 8.06 (s, 1H), 8.12 (m, 1H), 8.72 (s, 1H);
MS m/z 536 [M+H]+.

Example 330

3,5-dichloro-4-[(2-cyclopentyl-6-methyl-5-oxo-2,6,9,11-tetrazabicyclo[5.4.0]undeca-7,9,11-trien-10-yl)amino]-2-fluoro-N-(1-methyl-4-piperidyl)benzamide 3,5-dichloro-4-[(2-cyclopentyl-6-methyl-5-oxo-2,6,9,11-tetrazabicyclo[5.4.0]undeca-7,9,11-trien-10-yl)amino]-2-fluoro-benzoic acid (Intermediate 221; 85 mg, 0.18 mmol), HATU (104 mg, 0.27 mmol) and 4-amino-1-methylpiperidine (32 mg, 0.27 mmol) were stirred in DMF (3 mL) and diisopropylethylamine (95 μl, 0.54 mmol) added. The mixture was stirred for 2 hours and absorbed on to an SCX column, which was subsequently washed with methanol and eluted with ammonia in methanol. Product containing fractions were combined and evaporated and the residue purified by column chromatography (4% ammonia in methanol/DCM) to yield the title compound as a white solid (67 mg, 66%).

¹H NMR (399.9 MHz, DMSO-d₆) δ1.26-1.65 (10H, m), 1.79 (2H, d), 1.98 (2H, t), 2.17 (3H, s), 2.55 (2H+DMSO, m), 2.73 (2H, d), 3.15 (3H, s), 3.53-3.55 (2H, m), 3.67-3.74 (1H, m), 4.37 (1H, t), 7.65 (1H, d), 7.96 (1H, s), 8.43 (1H, d), 9.01 (1H, s); MS m/z 564 [M+H]+.

Example 331

3,5-dichloro-4-[(2-cyclopentyl-6-methyl-5-oxo-2,6,9,11-tetrazabicyclo[5.4.0]undeca-7,9,11-trien-10-yl)amino]-N-(4-dimethylaminocyclohexyl)-2-fluorobenzamide The title compound was prepared by an analogous method to the preparation of Example 330, on a 0.21 mmol scale, utilising 1-amino-4-dimethylaminocyclohexane (ABChem. Inc.; 30 μL, 0.31 mmol) and separation of the cis-isomer by column chromatography, as a white solid (21 mg, 19%).

¹H NMR (500.13 MHz, DMSO-d₆) δ1.38-1.92 (16H, m), 2.04-2.08 (1H, m), 2.18 (6H, s), 2.55 (2H+DMSO, m), 3.15 (3H, s), 3.53-3.55 (2H, m), 3.91-3.95 (1H, m), 4.39 (1H, m), 7.63 (1H, d), 7.95 (1H, s), 8.39 (1H, d), 9.00 (1H, s); MS m/z 592 [M+H]+.

Example 332

3,5-dichloro-4-[(2-cyclopentyl-6-methyl-5-oxo-2,6,9,11-tetrazabicyclo[5.4.0]undeca-7,9,11-trien-10-yl)amino]-N-(4-dimethylaminocyclohexyl)-2-fluorobenzamide The title compound was prepared by an analogous method to the preparation of Example 330, on a 0.21 mmol scale, utilising 1-amino-4-dimethylaminocyclohexane (ABChem. Inc.; 30 μL, 0.31 mmol) and separation of the trans-isomer by column chromatography, as a white solid (42 mg, 39%).

¹H NMR (399.9 MHz, DMSO-d₆) δ1.22-1.68 (12H, m), 1.80-1.85 (2H, m), 1.90-1.95 (2H, m), 2.10-2.14 (1H, m), 2.18 (6H, s), 2.55 (2H+DMSO, m), 3.15 (3H, s), 3.53-3.56 (2H, m), 3.63-3.71 (1H, m), 4.33-4.42 (1H, m), 7.64 (1H, d), 7.95 (1H, s), 8.39 (1H, d), 9.01 (1H, s); MS m/z 592 [M+H]+.

Example 333

4-[(2-cyclopentyl-6-methyl-5-oxo-2,6,9,11-tetrazabicyclo[5.4.0]undeca-7,9,11-trien-10-yl)amino]-2-fluoro-5-methoxy-N-(2-pyrrolidin-1-ylethyl)benzamide 10-Chloro-2-cyclopentyl-6-methyl-2,6,9,11-tetrazabicyclo[5.4.0]undeca-8,10,12-trien-5-one (Intermediate 1; 80 mg, 0.285 mmol), 4-amino-2-fluoro-5-methoxy-N-(2-pyrrolidin-1-ylethyl)benzamide (Intermediate 228; 80 mg, 0.285 mmol), p-toluenesulphonic acid monohydrate (136 mg, 0.732 mmol) and 4-Methyl-2-pentanol (3 mL) were combined and heated at 100° C. overnight. The cooled reaction mixture was added to an SCX-2 column (5 g), pre-wet with MeOH (2 column volumes). The column was flushed with MeOH (2 column volumes) and eluted with 2M ammonia in MeOH. Product containing fractions were combined and evaporated and the resultant material purified by base modified reverse phase preparative HPLC and product containing fractions combined and evaporated to yield the title compound as a cream solid (94 mg, 36%)

$^1$H NMR (399.902 MHz, CDCl$_3$) δ1.63 (m, 2H), 1.77 (m, 8H), 2.06 (m, 2H), 2.58 (m, 4H), 2.68 (m, 2H), 2.72 (m, 2H), 3.30 (s, 3H), 3.60 (m, 2H), 3.71 (m, 2H), 3.95 (s, 3H), 4.91 (m, 1H), 7.31 (m, 1H), 7.57 (d, 1H), 7.72 (s, 1H), 7.95 (s, 1H), 8.40 (d, 1H); MS m/z 526 [M+H]+.

Example 334

4-[(2-cyclopentyl-6-methyl-5-oxo-2,6,9,11-tetrazabicyclo[5.4.0]undeca-7,9,11-trien-10-yl)amino]-2,5-difluoro-N-[(3R)-1-methylpyrrolidin-3-yl]benzamide 10-Chloro-2-cyclopentyl-6-methyl-2,6,9,11-tetrazabicyclo[5.4.0]undeca-8,10,12-trien-5-one (Intermediate 1; 100 mg, 0.356 mmol), 4-amino-2,5-difluoro-N-[(3R)-1-methylpyrrolidin-3-yl]benzamide (Intermediate 229; 83 mg, 0.324 mmol) and caesium carbonate (211 mg, 0.648 mmol) was added to dioxane (3 mL) and the suspension bubbled with nitrogen for 10 minutes. Tris(dibenzylideneacetone) palladium (II) (11 mg, 0.019 mmol) and XANTPHOS (17 mg, 0.029 mmol) were added and the mixture heated to 100° C. overnight. The cooled reaction mixture was filtered and the filter cake washed with DCM and the filtrate evaporated. The residue was dissolved in DCM and purified on a silica column eluting with a gradient of 0-5% 2M ammonia in MeOH/DCM over 30 column volumes. Product containing fractions were combined and evaporated and the resultant material purified by base modified reverse phase preparative HPLC to yield the title compound as a yellow solid (91 mg, 56%)

$^1$H NMR (399.902 MHz, CDCl$_3$) δ1.64 (m, 2H), 1.75 (m, 5H), 2.05 (m, 2H), 2.30 (m, 1H), 2.41 (m, 4H), 2.67 (m, 4H), 2.89 (m, 1H), 3.30 (s, 3H), 3.71 (m, 2H), 4.65 (m, 1H), 4.88 (m, 1H), 6.95 (m, 1H), 7.30 (m, 1H), 7.81 (m, 1H), 7.96 (s, 1H), 8.45 (m, 1H); MS m/z 500 [M+H]+.

Example 335

4-[(2-cyclopentyl-6-methyl-5-oxo-2,6,9,11-tetrazabicyclo[5.4.0]undeca-7,9,11-trien-10-yl)amino]-2,5-difluoro-N-(2-pyrrolidin-1-ylethyl)benzamide The title compound was prepared by an analogous method to the preparation of Example 334, on a 0.324 mmol scale, utilising 4-amino-2,5-difluoro-N-(2-pyrrolidin-1-ylethyl)benzamide (Intermediate 230; 87 mg, 0.324 mmol), as a white solid (117 mg, 70%).

$^1$H NMR (399.902 MHz, CDCl$_3$) δ1.63 (m, 2H), 1.77 (m, 8H), 2.05 (m, 2H), 2.57 (m, 4H), 2.70 (m, 4H), 3.30 (s, 3H), 3.58 (m, 2H), 3.71 (m, 2H), 4.88 (m, 1H), 7.28 (m, 2H), 7.82 (m, 1H), 7.96 (s, 1H), 8.46 (m, 1H); MS m/z 514 [M+H]+.

Example 336

2-chloro-4-[(2-cyclopentyl-6-methyl-5-oxo-2,6,9,11-tetrazabicyclo[5.4.0]undeca-7,9,11-trien-10-yl)amino]-5-methoxy-N-[(3R)-1-methylpyrrolidin-3-yl]benzamide 2-chloro-4-[(2-cyclopentyl-6-methyl-5-oxo-2,6,9,11-tetrazabicyclo[5.4.0]undeca-7,9,11-trien-10-yl)amino]-5-methoxy-benzoic acid (Intermediate 231; 100 mg, 0.224 mmol), (3R)-1-methylpyrrolidin-3-amine di Hydrochloride (Intermediate 184; 40 mg, 0.235 mmol), HATU (94 mg, 0.246 mmol) and DIPEA (195 μL, 1.12 mmol) were combined in DMF (3 mL) and stirred at room temperature overnight. The reaction mixture was added to an SCX-2 column (5 g) pre-wet with MeOH (2 column volumes), flushed with MeOH (2 column volumes) and eluted with 2M ammonia in MeOH. Product containing fractions were combined and evaporated and the resultant material purified by base modified reverse phase preparative HPLC to yield the title compound as a white solid (76 mg, 64%).

$^1$H NMR (399.902 MHz, CDCl$_3$) δ1.62 (m, 2H), 1.78 (m, 5H), 2.11 (m, 2H), 2.31 (m, 1H), 2.42 (m, 4H), 2.69 (m, 4H), 2.90 (m, 1H), 3.29 (s, 3H), 3.71 (m, 2H), 3.94 (s, 3H), 4.68 (m, 1H), 4.97 (m, 1H), 6.97 (m, 1H), 7.38 (s, 1H), 7.63 (s, 1H), 7.93 (s, 1H), 8.61 (s, 1H); MS m/z 528 [M+H]+.

Example 337

2-chloro-4-[(2-cyclopentyl-6-methyl-5-oxo-2,6,9,11-tetrazabicyclo[5.4.0]undeca-7,9,11-trien-10-yl)amino]-N-(1-ethyl-4-piperidyl)-5-methoxy-benzamide The title compound was prepared by an analogous method to the preparation of Example 336, on a 0.224 mmol scale, utilising 4-amino-1-ethyl piperidine (Fluorochem; 32 mg, 0.246 mmol), as a white solid (97 mg, 79%).

$^1$H NMR (399.902 MHz, CDCl$_3$) δ1.11 (t, 3H), 1.60 (m, 4H), 1.75 (m, 4H), 2.09 (m, 4H), 2.19 (m, 2H), 2.44 (m, 2H), 2.68 (m, 2H), 2.88 (m, 2H), 3.29 (s, 3H), 3.71 (m, 2H), 3.94 (s, 3H), 4.06 (m, 1H), 4.97 (m, 1H), 6.58 (d, 1H), 7.40 (s, 1H), 7.63 (s, 1H), 7.94 (s, 1H), 8.61 (s, 1H); MS m/z 556 [M+H]+.

Example 338

2-chloro-4-[(2-cyclopentyl-6-methyl-5-oxo-2,6,9,11-tetrazabicyclo[5.4.0]undeca-7,9,11-trien-10-yl)amino]-N-(4-dimethylaminocyclohexyl)-5-methoxy-benzamide The title compound was prepared by an analogous method to the preparation of Example 336, on a 0.224 mmol scale, utilising 1-amino-4-dimethylaminocyclohexane (ABChem. Inc.; 35 mg, 0.246 mmol), as a white solid (84 mg, 66%).

$^1$H NMR (399.902 MHz, CDCl$_3$) δ1.26-1.76 (m, 11H), 1.94 (m, 2H), 2.10 (m, 2H), 2.21 (m, 2H), 2.30 (m, 6H), 2.68 (m, 2H), 3.29 (m, 3H), 3.71 (m, 2H), 3.94 (m, 3.5H), 4.25 (m, 0.5H), 4.97 (m, 1H), 6.46 (d, 0.5H), 6.85 (d, 0.5H), 7.39 (s, 0.5H), 7.45 (s, 0.5H), 7.63 (m, 1H), 7.94 (m, 1H), 8.62 (m, 1H); MS m/z 570 [M+H]+.

Example 339

2-chloro-4-[(2-cyclopentyl-6-methyl-5-oxo-2,6,9,11-tetrazabicyclo[5.4.0]undeca-8,10,12-trien-10-yl)amino]-5-methoxy-N-[(1S,5R)-9-methyl-9-azabicyclo[3.3.1]non-7-yl]benzamide The title compound was prepared by an analogous method to the preparation of Example 336, on a 0.224 mmol scale, utilising Endo-9-methyl-9-azabicyclo[3,3,1]-nonan-3-amine (Chempacific; 38 mg, 0.246 mmol), as a white solid (84 mg, 64%).

$^1$H NMR (399.902 MHz, CDCl$_3$) δ1.05 (m, 2H), 1.30 (m, 2H), 1.52-1.66 (m, 4H), 1.76 (m, 4H), 1.97 (m, 2H), 2.11 (m, 2H), 2.55 (m, 5H), 2.68 (m, 2H), 3.10 (m, 2H), 3.29 (s, 3H), 3.71 (m, 2H), 3.94 (s, 3H), 4.52 (m, 1H), 4.98 (m, 1H), 6.42 (d, 1H), 7.41 (s, 1H), 7.63 (s, 1H), 7.94 (s, 1H), 8.61 (s, 1H); MS m/z 582 [M+H]+.

Example 340

4-[(2-cyclopentyl-6-methyl-5-oxo-2,6,9,11-tetrazabicyclo[5.4.0]undeca-7,9,11-trien-10-yl)amino]-3-methoxy-N-[1-(2-methylpropyl)-4-piperidyl]benzamide The title compound was prepared by an analogous method to the preparation of Example 316, on a 0.49 mmol scale, utilising 1-isobutylpiperidin-4-amine hydrochloride (Ambinter; 96 mg, 0.61 mmol) and DIPEA (340 μL, 1.6 mmol) and stirring at ambient temperature for 24 hours, as a white solid (159 mg, 59%).

$^1$H NMR (400.132 MHz, DMSO-d6) δ 0.87 (d, 6H), 1.68 (m, 11H), 1.94 (m, 4H), 2.04 (d, 2H), 2.59 (m, 2H), 2.84 (m, 2H), 3.17 (s, 3H), 3.63 (m, 2H), 3.77 (m, 1H), 3.95 (s, 3H), 4.81 (m, 1H), 7.47 (s, 1H), 7.50 (s, 1H), 7.72 (s, 1H), 8.04 (d, 2H), 8.08 (s, 1H), 8.38 (d, 1H); MS m/z 550 [M+H]+.

Example 341

7-[(2-cyclopentyl-6-methyl-5-oxo-2,6,9,11-tetrazabicyclo[5.4.0]undeca-7,9,11-trien-10-yl)amino]-N-(1-methyl-4-piperidyl)benzo[1,3]dioxole-4-carboxamide 7-amino-N-(1-methyl-4-piperidyl)benzo[1,3]dioxole-4-carboxamide (Intermediate 223; 60 mg, 0.2 μmol), 10-Chloro-2-cyclopentyl-6-methyl-2,6,9,11-tetrazabicyclo[5.4.0]undeca-8,10,12-trien-5-one (Intermediate 1; 60 mg, 0.21 mmol) and p-toluenesulphonic acid monohydrate (102 mg, 0.53 mmol) were heated in 4-methyl-2-pentanol (3 mL) at 140° C. for 2 hours. The cooled reaction mixture was absorbed on to an SCX column, washed with methanol and eluted with ammonia in methanol. Product containing fractions were evaporated and the residue purified by normal phase chromatography (2.5% 7N NH3 in methanol/DCM) and then base modified reverse phase preparative HPLC to yield the title compound as a white solid (35 mg, 32%).

$^1$H NMR (399.9 MHz, DMSO-d$_6$) δ 1.48-1.60 (6H, m), 1.63-1.69 (2H, m), 1.79-1.83 (4H, m), 2.00-2.05 (2H, m), 2.17 (3H, s), 2.55-2.58 (2H, m), 2.67-2.70 (2H, m), 3.17 (3H, s), 3.59 (2H, m), 3.74-3.78 (1H, m), 4.69-1.77 (1H, m), 6.14 (2H, s), 7.23 (1H, d), 7.27 (1H, d), 7.48-7.51 (1H, m), 8.04 (1H, s), 8.60 (1H, s); MS m/z 522 [M+H]$^+$.

Example 342

4-[(2-cyclopentyl-6-methyl-5-oxo-2,6,9,11-tetrazabicyclo[5.4.0]undeca-7,9,11-trien-10-yl)amino]-3-methoxy-N-(1-methyl-3,4,4a,5,6,7,8,8a-octahydro-2H-quinolin-4-yl)benzamide The title compound was prepared by an analogous method to the preparation of Example 314, on a 0.49 mmol scale, utilising 1-methyl-3,4,4a,5,6,7,8,8a-octahydro-2H-quinolin-4-amine (CBI Building Blocks; 103 mg, 0.61 mmol) and DIPEA (260 μL, 1.47 mmol) and stirring at ambient temperature for 2 hours, as a single isomer of unspecified stereochemistry, as a white solid (52 mg, 19%).

$^1$H NMR (400.132 MHz, DMSO-d$_6$) δ 1.09 (6H, m), 1.66 (11H, m), 1.94 (2H, m), 2.07 (2H, m), 2.16 (3H, s), 2.59 (2H, m), 2.81 (1H, m), 3.18 (3H, s), 3.63 (3H, m), 3.95 (3H, s), 4.81 (1H, m), 7.49 (2H, m), 7.73 (1H, s), 7.97 (1H, d), 8.08 (1H, s), 8.37 (1H, d); MS m/z 562 [M+H]$^+$.

Example 343

4-[(2-cyclopentyl-6-methyl-5-oxo-2,6,9,11-tetrazabicyclo[5.4.0]undeca-7,9,11-trien-10-yl)amino]-3-methoxy-N-(1-methyl-3,4,4a,5,6,7,8,8a-octahydro-2H-quinolin-4-yl)benzamide The title compound was prepared by an analogous method to the preparation of Example 314, on a 0.49 mmol scale, utilising 1-methyl-3,4,4a,5,6,7,8,8a-octahydro-2H-quinolin-4-amine (CBI Building Blocks; 103 mg, 0.61 mmol) and DIPEA (260 μL, 1.47 mmol) and stirring at ambient temperature for 2 hours, as a single isomer of unspecified stereochemistry, as a white solid (102 mg, 37%).

$^1$H NMR (400.132 MHz, DMSO-d$_6$) δ 0.94 (1H, m), 1.21 (3H, m), 1.44 (2H, m), 1.66 (10H, m), 1.88 (3H, m), 2.10 (2H, m), 2.19 (3H, s), 2.59 (2H, m), 3.18 (3H, s), 3.63 (2H, m), 3.96 (3H, s), 4.17 (1H, m), 4.81 (1H, m), 7.40 (1H, s), 7.45 (2H, d), 7.56 (1H, d), 7.75 (1H, s), 8.08 (1H, s), 8.37 (1H, d); MS m/z 562 [M+H]$^+$.

Example 344

4-[(2-cyclopentyl-6-methyl-5-oxo-2,6,9,11-tetrazabicyclo[5.4.0]undeca-8,10,12-trien-10-yl)amino]-2-fluoro-5-methoxy-N-[(1S,5R)-9-methyl-9-azabicyclo[3.3.1]non-7-yl]benzamide 4-amino-2-fluoro-5-methoxy-N-(9-methyl-9-azabicyclo[3.3.1]non-7-yl)benzamide (Intermediate 204; 50 mg, 0.16 mmol), 10-chloro-2-cyclopentyl-6-methyl-2,6,9,11-tetrazabicyclo[5.4.0]undeca-7,9,11-trien-5-one (Intermediate 1; 45 mg, 0.16 mmol) and p-toluenesulphonic acid monohydrate (76 mg, 0.40 mmol) were stirred and heated together in 4-methyl-2-pentanol (3 mL) at 110° C. for 18 hours.

A further portion of 10-chloro-2-cyclopentyl-6-methyl-2,6,9,11-tetrazabicyclo[5.4.0]undeca-7,9,11-trien-5-one (Intermediate 1; 20 mg, 0.07 mmol) was added and the mixture heated by microwave irradiation at 150° C. for 1 hour and 30 minutes.

The cooled reaction mixture was loaded onto an SCX-3 (5 g) column pre-wet with MeOH. The column was washed with MeOH (2 column volumes) and eluted with 2M NH3/MeOH. Product containing fractions were evaporated and the residue purified by base modified reverse phase preparative HPLC to yield the title compound as a white solid (48 mg, 53%).

$^1$H NMR (400.132 MHz, DMSO-d$_6$) δ 0.90 (m, 2H), 1.42 (m, 3H), 1.69 (m, 6H), 1.96 (m, 5H), 2.21 (m, 2H), 2.41 (s, 3H), 2.61 (m, 2H), 2.97 (m, 2H), 3.18 (s, 3H), 3.65 (m, 2H), 3.93 (s, 3H), 4.30 (m, 1H), 4.84 (m, 1H), 7.22 (d, 1H), 7.67 (m, 1H), 7.81 (s, 1H), 8.12 (s, 1H), 8.34 (d, 1H); MS m/z 566 [M+H]+.

Example 345

4-[(2-cyclopentyl-6-methyl-5-oxo-2,6,9,11-tetrazabicyclo[5.4.0]undeca-8,10,12-trien-10-yl)amino]-N-(1-ethyl-4-piperidyl)-3-fluoro-benzamide 10-chloro-2-cyclopentyl-6-methyl-2,6,9,11-tetrazabicyclo[5.4.0]undeca-7,9,11-trien-5-one (Intermediate 1; 212 mg, 0.75 mmol), 4-amino-N-(1-ethylpiperidin-4-yl)-3-fluorobenzamide (Intermediate 225; 200 mg, 0.75 mmol) and p-toluenesulphonic acid monohydrate (0.335 mL, 1.88 mmol) were suspended in 4-Methyl-2-pentanol (5 mL) and sealed in a microwave tube. The reaction was heated to 160° C. for 30 minutes in the microwave reactor and allowed to cool to room temperature.

The crude product was purified by ion exchange chromatography, using an SCX column. The desired product was eluted from the column using 7M NH3/MeOH and pure fractions were evaporated to dryness to afford the crude product as an orange oil which was purified by base modified reverse phase preparative HPLC. Fractions containing the desired compound were evaporated to dryness to afford the title compound as a white solid (35 mg, 9%).

$^1$H NMR DMSO-d6 δ 0.65 (t, 2H), 0.9 (t, 2H), 1.0 (t. 3H), 1.5 (m, 7H), 1.6 (m, 2H), 1.9 (t, 2H), 2.3 (q, 2H), 2.9 (d, 2H), 3.2 (s, 3H), 3.4 (s, 2H), 3.6 (m, 1H), 4.75 (m, 1H), 7.65 (m, 1H), 7.7 (m, 1H), 7.95 (s, 1H), 8.15 (m, 1H), 8.6 (s, 1H); MS m/z 510 [M+H]+.

Example 346

N-[4-(azetidin-1-yl)cyclohexyl]-4-[(2-cyclopentyl-6-methyl-5-oxo-2,6,9,11-tetrazabicyclo[5.4.0]undeca-7,9,11-trien-10-yl)amino]-3-methoxy-benzamide To a solution of 10-chloro-2-cyclopentyl-6-methyl-2,6,9,11-tetrazabicyclo[5.4.0]undeca-7,9,11-trien-5-one (Intermediate 1; 70 mg, 0.17 mmol) in DMF (3 mL) was added a solution of 4-(azetidin-1-yl)cyclohexan-1-amine (Intermediate 226; 39 mg, 0.25 mmol) in DMF (1 mL). DIPEA (90 uL, 0.51 mmol) was added, followed by HATU (98 mg, 0.26 mmol). The resultant mixture was stirred at ambient temperature for 4 hours.

The reaction mixture was evaporated and the residue partitioned between DCM (5 mL) and saturated aqueous sodium bicarbonate solution (5 mL). The organic phase was separated by gravity elution through a PTFE filter cup and evaporated to an amber gum which was purified by base modified reverse phase preparative HPLC to yield the title compound as an white solid (29 mg, 31%) assigned as the trans isomer.

The cis isomer (Example 347) was isolated as a tan coloured solid (32 mg, 34%)

$^1$H NMR (400.132 MHz, DMSO-d$_6$) δ 0.92-1.00 (2H, m), 1.29-1.38 (2H, m), 1.57-1.99 (15H, m), 2.58-2.60 (2H, m), 3.07 (4H, t), 3.17 (3H, s), 3.61-3.65 (2H, m), 3.66-3.76 (1H, m), 3.95 (3H, s), 4.82 (1H, quintet), 7.45-7.48 (2H, m), 7.72 (1H, s), 8.01 (1H, d), 8.08 (1H, s), 8.37 (1H, d); MS m/z 548 [M+H]$^+$.

Example 347

N-[4-(azetidin-1-yl)cyclohexyl]-4-[(2-cyclopentyl-6-methyl-5-oxo-2,6,9,11-tetrazabicyclo[5.4.0]undeca-7,9,11-trien-10-yl)amino]-3-methoxy-benzamide The title compound was isolated from the reaction above to produce Example 346 as a tan coloured solid (32 mg, 34%).

$^1$H NMR (400.132 MHz, DMSO-d6) δ 1.30-1.40 (2H, m), 1.43-1.50 (2H, m), 1.56-1.77 (10H, m), 1.86-1.98 (4H, m), 2.18-2.23 (1H, m), 2.58-2.60 (2H, m), 3.07 (4H, t), 3.18 (3H, s), 3.62-3.65 (2H, m), 3.77-3.87 (1H, m), 3.95 (3H, s), 4.82 (1H, quintet), 7.50-7.54 (2H, m), 7.71 (1H, s), 8.04 (1H, d), 8.08 (1H, s), 8.37 (1H, d); MS m/z 548 [M+H]$^+$.

Example 348 tert-butyl 3-[[4-[(2-cyclopentyl-6-methyl-5-oxo-2,6,9,11-tetrazabicyclo[5.4.0]undeca-7,9,11-trien-10-yl)amino]-3-methoxy-benzoyl]amino]azepane-1-carboxylate The title compound was prepared by an analogous method to the preparation of Example 314, on a 0.30 mmol scale, utilising tert-butyl 3-aminoazepane-1-carboxylate (Anichem; 78 mg, 0.36 mmol) and DIPEA (151 µL, 0.91 mmol) and stirring at ambient temperature for 19 hours, as an amber gum (153 mg, 83%).

$^1$H NMR (400.132 MHz, DMSO-d6) δ 1.24-1.46 (11H, m), 1.50-2.00 (14H, m), 2.57-2.61 (2H, m), 3.06-3.19 & 3.30-3.37 (1H, m), 3.18 (3H, s), 3.54-3.70 (3H, m), 3.95 (3H, s), 4.08-4.22 (1H, m), 4.75-4.87 (1H, m), 7.36-7.49 (2H, m), 7.74 (1H, s), 8.01 & 8.16 (2×d, 1H), 8.09 (1H, s), 8.39 (1H, d); MS m/z 608 (M+H)$^+$

Example 349

4-[(2-cyclopentyl-4,4,6-trimethyl-5-oxo-2,6,9,11-tetrazabicyclo[5.4.0]undeca-7,9,11-trien-10-yl)amino]-3-methoxy-N-(4-piperidyl)benzamide 10-chloro-2-cyclopentyl-4,4-dimethyl-2,6,9,11-tetrazabicyclo[5.4.0]undeca-8,10,12-trien-5-one (Intermediate 127; 50 mg, 0.16 mmol) and tert-butyl 4-[(4-amino-3-methoxy-benzoyl)amino]piperidine-1-carboxylate (Intermediate 234; 85 mg, 0.24 mmol) were dissolved in 4-methyl-2-pentanol (1 mL) and p-toluenesulphonic acid monohydrate (44 mg, 0.32 mmol) added. The reaction mixture was heated at 90° C. by microwave irradiation for 20 minutes and then at 150° C. for a further 45 minutes.

The reaction mixture was diluted with water (3 mL) and methanol (3 mL) and the solution poured directly onto an SCX-3 (2 g) cartridge. The cartridge was washed with methanol (30 mL) and then eluted with 2M ammonia in methanol. Evaporation to dryness of the ammoniacal fractions afforded an amber gum, which was purified by base modified reverse phase, preparative HPLC to yield the title compound as a white solid (32 mg, 38%).

$^1$H NMR (400.132 MHz, DMSO-d6) δ 1.10 (s, 6H), 1.43 (m, 2H), 1.55-1.79 (m, 10H), 1.89 (m, 2H), 2.96 (m, 2H), 3.19 (s, 3H), 3.38 (s, 2H), 3.83 (m, 1H), 3.95 (s, 3H), 5.19 (m, 1H), 7.48 (m, 2H), 7.67 (s, 1H), 7.99 (s, 1H), 8.05 (d, 1H), 8.36 (d, 1H); MS m/z 522 [M+H]$^+$.

Example 350

4-[(2-cyclopentyl-4,4,6-trimethyl-5-oxo-2,6,9,11-tetrazabicyclo[5.4.0]undeca-7,9,11-trien-10-yl)amino]-N-(1-ethyl-4-piperidyl)-3-methoxy-benzamide 10-chloro-2-cyclopentyl-4,4-dimethyl-2,6,9,11-tetrazabicyclo[5.4.0]undeca-8,10,12-trien-5-one (Intermediate 127; 115 mg, 0.37 mmol) and 4-amino-N-(1-ethyl-4-piperidyl)-3-methoxy-benzamide (Intermediate 190; 104 mg, 0.37 mmol) were dissolved 4-methyl-2-pentanol (3 mL). p-Toluenesulphonic acid monohydrate (142 mg, 0.74 mmol) was added and mixture heated by microwave irradiation at 160° C. for 1 hour.

After cooling, the reaction mixture was diluted with MeOH (5 mL) and poured directly onto an SCX-3 (5 g) cartridge. The cartridge was washed with methanol (40 mL) and eluted with 2M ammonia in methanol (40 mL). Evaporation to dryness of the ammoniacal fractions afforded a yellow gum which was purified by base modified reverse phase, preparative HPLC to yield the title compound as a white solid (125 mg, 61%).

$^1$H NMR (400.132 MHz, DMSO-d6) δ 1.01 (t, 3H), 1.11 (s, 6H), 1.53-1.97 (m, 14H), 2.34 (q, 2H), 2.90 (m, 2H), 3.20 (s, 3H), 3.39 (s, 2H), 3.78 (m, 1H), 3.96 (s, 3H), 5.20 (m, 1H), 7.48 (m, 2H), 7.68 (s, 1H), 8.00 (s, 1H), 8.07 (d, 1H), 8.37 (d, 1H); MS m/z 550 [M+H]$^+$.

Example 351

4-[(2-cyclopentyl-4,4,6-trimethyl-5-oxo-2,6,9,11-tetrazabicyclo[5.4.0]undeca-7,9,11-trien-10-yl)amino]-N-(3-dimethylamino-2,2-dimethyl-propyl)-3-methoxy-benzamide The title compound was prepared by an analogous method to the preparation of Example 350, on a 0.24 mmol scale, utilising 4-amino-N-(3-dimethylamino-2,2-dimethyl-propyl)-3-methoxy-benzamide (Intermediate 22; 68 mg, 0.24 mmol), as a white foam (47 mg, 53%).

$^1$H NMR (400.132 MHz, DMSO-d6) δ 0.90 (s, 6H), 1.11 (s, 6H), 1.62 (m, 4H), 1.75 (m, 2H), 1.90 (m, 2H), 2.21 (s, 2H), 2.29 (s, 6H), 3.21 (m, 5H), 3.40 (s, 2H), 3.96 (s, 3H), 5.20 (m, 1H), 7.42 (m, 1H), 7.47 (d, 1H), 7.70 (s, 1H), 8.00 (s, 1H), 8.39 (d, 1H), 8.44 (t, 1H); MS m/z 552 [M+H]$^+$.

Example 352

4-[(2-cyclopentyl-4,4,6-trimethyl-5-oxo-2,6,9,11-tetrazabicyclo[5.4.0]undeca-8,10,12-trien-10-yl)amino]-2-fluoro-5-methoxy-N-[(1S,5R)-9-methyl-9-azabicyclo[3.3.1]non-7-yl]benzamide The title compound was prepared by an analogous method to the preparation of Example 350, on a 0.31 mmol scale, utilising 4-amino-2-fluoro-5-methoxy-N-[(1S,5R)-9-methyl-9-azabicyclo[3.3.1]non-7-yl]benzamide (Intermediate 204; 96 mg, 0.31 mmol) heating by microwave irradiation at 150° C. for 1 hour, as a white foam (47 mg, 53%).

$^1$H NMR (400.132 MHz, CDCl$_3$) δ 1.16-1.23 (8H, m), 1.52-1.65 (4H, m), 1.73-1.83 (5H, m), 1.97-2.11 (5H, m), 2.54-2.65 (5H, m), 3.17-3.26 (2H, m), 3.31 (3H, s), 3.40 (2H, s), 3.96 (3H, s), 4.51-4.62 (1H, m), 5.29 (1H, quintet), 6.60-6.74 (1H, m), 7.57 (1H, d), 7.70 (1H, s), 7.88 (1H, s), 8.39 (1H, d); MS m/z 594 [M+H]$^+$.

Example 353

4-[(2-cyclopentyl-4,4,6-trimethyl-5-oxo-2,6,9,11-tetrazabicyclo[5.4.0]undeca-8,10,12-trien-10-yl)amino]-3-fluoro-N-[(1S,5R)-9-methyl-9-azabicyclo[3.3.1]non-7-yl]benzamide The title compound was prepared by an analogous method to the preparation of Example 350, on a 0.34 mmol scale, utilising 4-amino-3-fluoro-N-[(1S,5R)-9-methyl-9-azabicyclo[3.3.1]non-7-yl]benzamide (Intermediate 162; 100 mg, 0.34 mmol) heating by microwave irradiation at 150° C. for 40 minutes, as a white foam (52 mg, 27%).

$^1$H NMR (399.902 MHz, DMSO-d6) δ 0.9 (2H, d), 1.1 (6H, s), 1.45 (3H, m), 1.55 (4H, m), 1.7 (2H, m), 1.8 (2H, m), 1.9 (2H, m), 2.05 (1H, m) 2.2 (2H, m), 2.40 (2H, s), 3.0 (2H, d), 3.2 (3H, s), 3.35 (2H, s) 4.3 (1H, m), 5.2 (1H, m), 7.65 (1H, d), 7.70 (1H, d), 8.0 (2H, m), 8.15 (1H, t), 8.65 (1H, s); MS m/z 564 [M+H]$^+$.

Example 354

4-[(2-cyclopentyl-4,4,6-trimethyl-5-oxo-2,6,9,11-tetrazabicyclo[5.4.0]undeca-8,10,12-trien-10-yl)amino]-3-methoxy-N-[(1S,5R)-9-methyl-9-azabicyclo[3.3.1]non-7-yl]benzamide The title compound was prepared by an analogous method to the preparation of Example 350, on a 0.32 mmol scale, utilising 4-amino-3-methoxy-N-[(1S,5R)-9-methyl-9-azabicyclo[3.3.1]non-3-yl]benzamide (Intermediate 202; 99 mg, 0.32 mmol) heating thermally at 140° C. for 2 hours, as a white solid (104 mg, 56%).

$^1$H NMR (399.9 MHz, DMSO-d$_6$) δ0.94 (2H, d), 1.10 (6H, s), 1.42-1.49 (3H, m), 1.63 (4H, s), 1.75 (2H, s), 1.89-1.96 (3H, m), 1.92-1.95 (2H, m), 2.16-2.21 (2H, m), 2.42 (3H, s), 2.99 (2H, d), 3.20 (3H, s), 3.39 (2H, s), 3.96 (3H, s), 4.32-4.38 (1H, m), 5.21 (1H, m), 7.47 (1H, d), 7.50 (1H, s), 7.68 (1H, s), 7.92 (1H, d), 8.00 (1H, s), 8.38 (1H, d); MS m/z 576 [M+H]$^+$.

Example 355

4-[(2-cyclopentyl-4,4,6-trimethyl-5-oxo-2,6,9,11-tetrazabicyclo[5.4.0]undeca-7,9,11-trien-10-yl)amino]-N-(1-ethyl-4-piperidyl)-2,5-difluoro-benzamide 10-chloro-2-cyclopentyl-4,4-dimethyl-2,6,9,11-tetrazabicyclo[5.4.0]undeca-8,10,12-trien-5-one (Intermediate 127; 100 mg, 0.32 mmol), 4-amino-N-(1-ethyl-4-piperidyl)-2,5-difluoro-benzamide (Intermediate 235; 101 mg, 0.36 mmol) and caesium carbonate (22 mg, 0.65 mmol) added to dioxane (5 mL) and the suspension bubbled with nitrogen for 10 minutes. tris(dibenzylideneacetone) palladium (II) (18 mg, 0.02 mmol) and XANTPHOS (17 mg, 0.03 mmol) were added and the mixture heated at 110° C. overnight. The mixture was filtered and the filtrate loaded onto an SCX (10 g) cartridge pre-wet with methanol, washed with methanol and eluted with methanolic ammonia. Product containing fractions were combined and evaporated and the resultant material purified by base modified reverse phase preparative HPLC to yield the title compound as a white crystalline solid (97 mg, 54%).

$^1$H NMR (399.9 MHz, DMSO-d6) δ1.00 (3H, t), 1.11 (6H, s), 1.48-1.55 (2H, m), 1.60 (4H, d), 1.73 (2H, s), 1.77-1.82 (2H, m), 1.88 (2H, d), 1.93-1.99 (2H, m), 2.32 (2H, q), 2.83 (2H, d), 3.20 (3H, s), 3.39 (2H, s), 3.70-3.74 (1H, m), 5.21 (1H, m), 7.40-7.45 (1H, m), 7.95-7.98 (1H, m), 8.02 (1H, s), 8.20-8.25 (1H, m), 8.88 (1H, s); MS m/z 556 [M+H]$^+$.

Example 356

4-[(2-cyclopentyl-4,4,6-trimethyl-5-oxo-2,6,9,11-tetrazabicyclo[5.4.0]undeca-7,9,11-trien-10-yl)amino]-2,5-difluoro-N-(1-methyl-4-piperidyl)benzamide The title compound was prepared by an analogous method to the preparation of Example 355, on a 0.32 mmol scale, utilising 4-amino-2,5-difluoro-N-(1-methyl-4-piperidyl)benzamide (Intermediate 59; 96 mg, 0.32 mmol), as a white solid (38 mg, 22%).

$^1$H NMR (399.9 MHz, DMSO-d6) δ1.11 (6H, s), 1.54-1.58 (2H, m), 1.59 (3H, s), 1.74 (3H, d), 1.79 (2H, s), 1.87 (2H, s), 1.95 (1H, d), 1.99 (1H, s), 2.17 (3H, s), 2.75 (2H, d), 3.20 (3H, s), 3.37 (2H, s), 3.70 (1H, m), 5.22 (1H, m), 7.40-7.45 (1H, m), 7.95-7.98 (1H, m), 8.02 (1H, s), 8.20-8.25 (1H, m), 8.88 (1H, s); MS m/z 540 [M+H]+.

Example 357

4-[(2-cyclopentyl-4,4,6-trimethyl-5-oxo-2,6,9,11-tetrazabicyclo[5.4.0]undeca-7,9,11-trien-10-yl)amino]-N-(3-dimethylaminopropyl)-3-methoxy-benzamide The title compound was prepared by an analogous method to the preparation of Example 350, on a 0.32 mmol scale, utilising 4-amino-N-(3-dimethylaminopropyl)-3-methoxy-benzamide (Intermediate 196; 82 mg, 0.32 mmol) heating thermally at 140° C. for 2 hours, as a white solid (84 mg, 50%).

$^1$H NMR (399.9 MHz, DMSO-d6) δ 1.11 (6H, s), 1.63 (2H, m), 1.65-1.71 (4H, m), 1.75 (2H, s), 1.86-1.89 (2H, t), 2.16 (6H, s), 2.28-2.34 (2H, t), 3.15-3.20 (3H, s), 3.28-3.31 (2H, m), 3.36-3.39 (2H, s), 3.95 (3H, s), 5.18-5.22 (1H, m), 7.47-7.50 (1H, m), 7.51 (1H, s), 7.68 (1H, s), 8.02 (1H, s). 8.37 (1H, s), 8.39 (1H, t); MS m/z 524 [M+H]+.

Example 358

4-[(2-cyclopentyl-4,4,6-trimethyl-5-oxo-2,6,9,11-tetrazabicyclo[5.4.0]undeca-7,9,11-trien-10-yl)amino]-3-methoxy-N-(2-pyrrolidin-1-ylethyl)benzamide The title compound was prepared by an analogous method to the preparation of Example 350, on a 0.32 mmol scale, utilising 4-amino-3-methoxy-N-(2-pyrrolidin-1-ylethyl)benzamide (Intermediate 192; 86 mg, 0.32 mmol) heating thermally at 140° C. for 2 hours, as a white solid (56 mg, 32%).

$^1$H NMR (399.9 MHz, DMSO-d6) δ 1.11 (6H, s), 1.63 (3H, m), 1.68-1.71 (3H, m), 1.74 (3H, d), 1.86-1.89 (3H, m), 2.48 (4H, m), 2.58 (2H, t), 3.18 (3H, s), 3.39 (4H, t), 3.92-3.98 (3H, s), 5.18 (1H, m), 7.47-7.50 (1H, m), 7.51 (1H, s), 7.68 (1H, s), 8.02 (1H, s). 8.29 (1H, 4), 8.39 (1H, d); MS m/z 536 [M+H]+.

Example 359

4-[(2-cyclopentyl-4,4,6-trimethyl-5-oxo-2,6,9,11-tetrazabicyclo[5.4.0]undeca-7,9,11-trien-10-yl)amino]-N-(2-dimethylaminoethyl)-3-methoxy-benzamide The title compound was prepared by an analogous method to the preparation of Example 350, on a 0.32 mmol scale, utilising 4-amino-N-(2-dimethylaminoethyl)-3-methoxy-benzamide (Intermediate 194; 77 mg, 0.32 mmol) heating thermally at 140° C. for 2 hours, as a white solid (37 mg, 22%).

$^1$H NMR (399.9 MHz, DMSO-d6) δ 1.11 (6H, s), 1.63-1.68 (4H, m), 1.75 (2H, m), 1.92 (2H, m), 2.15 (6H, s), 2.40 (2H, t), 3.19 (3H, s), 3.33-3.37 (4H, m), 3.95 (3H, s), 5.18 (1H, m), 7.47-7.50 (1H, m), 7.51 (1H, s), 7.68 (1H, s), 8.02 (1H, s). 8.29 (1H, 4), 8.39 (1H, d); MS m/z 510 [M+H]+.

Example 360

4-[(2-cyclopentyl-4,4,6-trimethyl-5-oxo-2,6,9,11-tetrazabicyclo[5.4.0]undeca-7,9,11-trien-10-yl)amino]-3-methoxy-N-(4-pyrrolidin-1-ylcyclohexyl)benzamide To a solution of 4-[(2-cyclopentyl-4,4,6-trimethyl-5-oxo-2,6,9,11-tetrazabicyclo[5.4.0]undeca-7,9,11-trien-10-yl)amino]-3-methoxy-benzoic acid (Intermediate 236; 83 mg, 0.19 mmol) in DMF (3 mL) was added a solution of 4-pyrrolidin-1-ylcyclohexan-1-amine (Intermediate 237; 78 mg, 0.46 mmol). DIPEA (100 uL, 0.57 mmol) was added, followed by HATU (107 mg, 0.28 mmol). The resultant mixture was stirred at ambient temperature for 2 hours. The reaction mixture was evaporated to a gum, which was partitioned between DCM (20 mL) and saturated aqueous sodium bicarbonate solution (20 mL). The organic phase was separated by gravity elution through a PTFE filter cup and evaporated to an amber gum which was purified by base modified reverse phase preparative HPLC to yield the title compound as an off white solid (34 mg, 30%).

$^1$H NMR (400.132 MHz, CDCl$_3$) δ 1.20 (s, 6H), 1.29 (m, 2H), 1.41-1.83 (m, 12H), 1.95-2.20 (m, 7H), 2.60 (m, 4H), 3.30 (s, 3H), 3.37 (s, 2H), 3.94 (m, 1H), 3.97 (s, 3H), 5.31 (m, 1H), 5.83 (d, 1H), 7.20 (m, 1H), 7.42 (d, 1H), 7.60 (s, 1H), 7.85 (s, 1H), 8.47 (d, 1H); MS m/z 590 [M+H]+.

Example 361

4-[(2-cyclopentyl-4,4,6-trimethyl-5-oxo-2,6,9,11-tetrazabicyclo[5.4.0]undeca-7,9,11-trien-10-yl)amino]-2-fluoro-5-methoxy-N-(1-methyl-4-piperidyl)benzamide The title compound was prepared by an analogous method to the preparation of Example 350, on a 0.49 mmol scale, utilising 4-amino-2-fluoro-5-methoxy-N-(1-methyl-4-piperidyl)benzamide (Intermediate 27; 144 mg, 0.51 mmol), as a white foam (66 mg, 24%).

$^1$H NMR (400.132 MHz, DMSO-d6) δ 1.11 (s, 6H), 1.52-1.68 (m, 6H), 1.76 (m, 4H), 1.95 (m, 4H), 2.16 (s, 3H), 2.73 (m, 2H), 3.20 (s, 3H), 3.40 (s, 2H), 3.73 (m, 1H), 3.92 (s, 3H), 5.19 (m, 1H), 7.19 (d, 1H), 7.79 (m, 2H), 8.02 (s, 1H), 8.31 (d, 1H); MS m/z 554 [M+H]+.

Example 362

3-chloro-4-[(2-cyclopentyl-4,4,6-trimethyl-5-oxo-2,6,9,11-tetrazabicyclo[5.4.0]undeca-7,9,11-trien-10-yl)amino]-N-(3-dimethylaminopropyl)benzamide The title compound was prepared by an analogous method to the preparation of Example 355, on a 0.34 mmol scale, utilising 4-amino-3-chloro-N-(3-dimethylaminopropyl)benzamide (Intermediate 214; 98 mg, 0.38 mmol), as an off-white solid (27 mg, 15%).

$^1$H NMR (400.132 MHz, DMSO-d6) δ 1.10 (s, 6H), 1.50-1.74 (m, 8H), 1.83 (m, 2H), 2.15 (s, 6H), 2.27 (t, 2H), 3.19 (s, 3H), 3.28 (m, 2H), 3.37 (s, 2H), 5.11 (m, 1H), 7.77 (m, 1H), 7.96 (d, 1H), 7.99 (s, 1H), 8.11 (s, 1H), 8.27 (d, 1H), 8.48 (t, 1H); MS m/z 528 [M+H]+.

Example 363

4-[(2-cyclopentyl-4,4,6-trimethyl-5-oxo-2,6,9,11-tetrazabicyclo[5.4.0]undeca-7,9,11-trien-10-yl)amino]-N-(4-dimethylaminocyclohexyl)-3-methoxy-benzamide The title compound was prepared by an analogous method to the preparation of Example 350, on a 0.49 mmol scale, utilising 4-amino-N-(4-dimethylaminocyclohexyl)-3-methoxy-benzamide (Intermediate 239; 144 mg, 0.51 mmol), as a white foam (39 mg, 14%).

$^1$H NMR (400.132 MHz, DMSO-d6) δ 1.10 (s, 6H), 1.21-2.04 (m, 16H), 2.10-2.21 (m, 7H), 3.19 (s, 3H), 3.38 (s, 2H), 3.72 & 3.92 (m, 1H), 3.95 (s, 3H), 5.19 (m, 1H), 7.49 (m, 2H), 7.66 (d, 1H), 7.99 (s, 1H), 8.01 (d, 1H), 8.36 (d, 1H); MS m/z 564 [M+H]+.

Example 364

4-[(2-cyclopentyl-4,4,6-trimethyl-5-oxo-2,6,9,11-tetrazabicyclo[5.4.0]undeca-7,9,11-trien-10-yl)amino]-2-fluoro-5-methoxy-N-[(3R)-1-methylpyrrolidin-3-yl]benzamide The title compound was prepared by an analogous method to the preparation of Example 350, on a 0.32 mmol scale, utilising 4-amino-2-fluoro-5-methoxy-N-[(3R)-1-methylpyrrolidin-3-yl]benzamide (Intermediate 182; 77 mg, 0.32 mmol) heating thermally at 140° C. for 3 hours, as a white solid (84 mg, 49%).

$^1$H NMR (399.9 MHz, DMSO-d$_6$) δ 1.11 (6H, s), 1.64-1.76 (7H, m), 1.87-1.94 (2H, m), 2.13-2.22 (1H, m), 2.26 (3H, s), 2.34-2.45 (2H, m), 2.58-2.64 (1H, m), 2.66-2.71 (1H, m), 3.20 (3H, s), 3.41 (2H, s), 3.93 (3H, s), 4.36-4.41 (1H, m), 5.15-5.24 (1H, m), 7.22 (1H, d), 7.78 (1H, d), 7.97-8.00 (1H, m), 8.03 (1H, s), 8.32 (1H, d); MS m/z 540 [M+H]+.

Example 365

4-[(2-cyclopentyl-4,4,6-trimethyl-5-oxo-2,6,9,11-tetrazabicyclo[5.4.0]undeca-8,10,12-trien-10-yl)amino]-2-fluoro-N-[(1S,5R)-9-methyl-9-azabicyclo[3.3.1]non-7-yl]benzamide The title compound was prepared by an analogous method to the preparation of Example 355, on a 0.32 mmol scale, utilising 4-amino-2-fluoro-N-[(1S,5R)-9-methyl-9-azabicyclo[3.3.1]non-7-yl]benzamide (Intermediate 241; 93 mg, 0.34 mmol), as an off-white solid (113 mg, 62%).

$^1$H NMR (399.9 MHz, DMSO-d6) δ0.91 (2H, d), 1.11 (6H, s), 1.38 (1H, m), 1.42 (2H, m), 1.61 (2H, s), 1.64 (2H, t), 1.75 (1H, s), 1.84 (2H, m), 1.89 (2H, m), 2.03 (1H, m), 2.20 (2H, m), 2.39 (3H, s), 2.98 (2H, d), 3.17 (3H, s), 3.40 (2H, s), 4.28 (1H, m), 5.23 (1H, m), 7.38 (1H, d), 7.52 (1H, t), 7.64 (1H, m), 7.89 (1H, d), 8.01 (1H, s), 9.62 (1 h, s); MS m/z 565 [M+H]+.

Example 366

5-chloro-4-[(2-cyclopentyl-4,4,6-trimethyl-5-oxo-2,6,9,11-tetrazabicyclo[5.4.0]undeca-7,9,11-trien-10-yl)amino]-N-(4-dimethylaminocyclohexyl)-2-fluoro-benzamide The title compound was prepared by an analogous method to the preparation of Example 355, on a 0.29 mmol scale, utilising 4-amino-5-chloro-N-(4-dimethylaminocyclohexyl)-2-fluoro-benzamide (Intermediate 175; 92 mg, 0.29 mmol) heating at 110° C. for 3 hours, as an off-white solid (55 mg, 32%).

$^1$H NMR (399.9 MHz, DMSO-d$_6$) δ 1.11 (6H, s), 1.25-1.37 (3H, m), 1.47-2.01 (13.5H, m), 2.13 (6.5H, d), 3.20 (3H, s), 3.40 (2H, s), 3.62-3.71 and 3.88-3.95 (each 0.5H, m), 5.12-5.20 (1H, m), 7.65-7.68 (1H, m), 7.99-8.04 (2H, m), 8.10 (1H, d), 8.30-8.35 (1H, m); MS m/z 587 [M+H]+.

Example 367

3-chloro-4-[(2-cyclopentyl-4,4,6-trimethyl-5-oxo-2,6,9,11-tetrazabicyclo[5.4.0]undeca-7,9,11-trien-10-yl)amino]-N-(2,2-dimethyl-3-pyrrolidin-1-yl-propyl)benzamide The title compound was prepared by an analogous method to the preparation of Example 355, on a 0.34 mmol scale, utilising 4-amino-3-chloro-N-(2,2-dimethyl-3-pyrrolidin-1-yl-propyl)benzamide (Intermediate 244; 123 mg, 0.39 mmol) heating at 110° C. for 3 hours, as an off-white solid (35 mg, 18%).

$^1$H NMR (400.132 MHz, DMSO-d$_6$) δ 0.90 (s, 6H), 1.10 (s, 6H), 1.49-1.85 (m, 12H), 2.42 (s, 2H), 2.60 (m, 4H), 3.19 (s, 3H), 3.21 (d, 2H), 3.36 (s, 2H), 5.09 (m, 1H), 7.73 (m, 1H), 7.88 (d, 1H), 7.98 (s, 1H), 8.15 (s, 1H), 8.25 (d, 1H), 8.69 (t, 1H); MS m/z 582 [M+H]+.

Example 368

4-[(2-cyclopentyl-4,4,6-trimethyl-5-oxo-2,6,9,11-tetrazabicyclo[5.4.0]undeca-7,9,11-trien-10-yl)amino]-N-(2,2-dimethyl-3-pyrrolidin-1-yl-propyl)-3-methoxy-benzamide The title compound was prepared by an analogous method to the preparation of Example 350, on a 0.33 mmol scale, utilising 4-amino-N-(2,2-dimethyl-3-pyrrolidin-1-yl-propyl)-3-methoxy-benzamide (Intermediate 206; 100 mg, 0.33 mmol) heating thermally at 120° C. for 3 days, as a white solid (55 mg, 29%).

$^1$H NMR (400.132 MHz, CDCl$_3$) δ 1.01 (s, 3H), 1.20 (s, 3H), 1.54-160 (m, 8H), 1.80-1.63 (m, 8H), 2.03-1.95 (m, 2H), 2.56 (s, 2H), 2.72-2.65 (m, 4H), 3.29 (s, 3H), 3.37 (s, 2H), 3.39 (d, 2H), 3.98 (s, 3H), 5.34 (quintet, 1H), 7.20 (d, 1H), 7.55 (s, 1H), 7.61 (s, 1H), 7.86 (s, 1H), 8.43 (d, 1H), 9.16-9.10 (m, 1H); MS m/z 578 [M+H]+.

Example 369

4-[(2-cyclopentyl-4,4,6-trimethyl-5-oxo-2,6,9,11-tetrazabicyclo[5.4.0]undeca-7,9,11-trien-10-yl)amino]-N-[(3R)-1-ethylpyrrolidin-3-yl]-3-methoxy-benzamide The title compound was prepared by an analogous method to the preparation of Example 350, on a 0.22 mmol scale, utilising 4-amino-N-[(3R)-1-ethylpyrrolidin-3-yl]-3-methoxy-benzamide (Intermediate 245; 70 mg, 0.26 mmol) heating by microwave irradiation at 160° C. for 1 hour, as a white solid (50 mg, 42%).

$^1$H NMR (400.132 MHz, DMSO-d$_6$) δ 1.04 (t, 3H), 1.10 (s, 6H), 1.55-1.93 (m, 9H), 2.15 (m, 1H), 2.43 (m, 4H), 2.65 (m, 1H), 2.73 (m, 1H), 3.19 (s, 3H), 3.38 (s, 2H), 3.95 (s, 3H), 4.40 (m, 1H), 5.19 (m, 1H), 7.51 (m, 2H), 7.67 (s, 1H), 7.99 (s, 1H), 8.28 (d, 1H), 8.37 (d, 1H); MS m/z 536 [M+H]+.

Example 370

4-[(2-cyclopentyl-4,4,6-trimethyl-5-oxo-2,6,9,11-tetrazabicyclo[5.4.0]undeca-8,10,12-trien-10-yl)amino]-N-(1-ethyl-4-piperidyl)-2-fluoro-5-methoxy-benzamide 10-chloro-2-cyclopentyl-4,4,6-trimethyl-2,6,9,11-tetrazabicyclo[5.4.0]undeca-7,9,11-trien-5-one (Intermediate 127; 52 mg, 0.17 mmol), 4-amino-N-(1-ethyl-4-piperidyl)-2-fluoro-5-methoxy-benzamide (Intermediate 205; 50 mg, 0.17 mmol) and p-toluenesulphonic acid monohydrate (81 mg, 0.43 mmol) were stirred and heated together in 4-methyl-2-pentanol (2 mL) by microwave irradiation at 150° C. for 1 hour. A further portion of 10-chloro-2-cyclopentyl-4,4,6-trimethyl-2,6,9,11-tetrazabicyclo[5.4.0]undeca-7,9,11-trien-5-one (10 mg) was added and reaction continued for a further 1 hour. The cooled solution was loaded onto an SCX-3 (5 g) column pre-wet with MeOH. The column was washed with MeOH (2 column volumes) and eluted with 2M NH3/MeOH. Product containing fractions were combined and evaporated and the residue purified by base modified reverse phase preparative HPL to yield the title compound as a white solid (49 mg, 51%)

$^1$H NMR (400.132 MHz, DMSO-$d_6$) δ 1.00 (t, 3H), 1.11 (s, 6H), 1.74 (m, 12H), 2.32 (q, 2H), 2.83 (m, 2H), 3.17 (s, 3H), 3.40 (s, 2H), 3.73 (m, 1H), 3.92 (s, 3H), 5.19 (m, 1H), 7.19 (d, 1H), 7.77 (s, 1H), 7.80 (m, 1H), 8.02 (s, 1H), 8.31 (d, 1H); MS m/z 568 [M+H]+.

Example 371

4-[(2-cyclopentyl-4,4,6-trimethyl-5-oxo-2,6,9,11-tetrazabicyclo[5.4.0]undeca-8,10,12-trien-10-yl)amino]-3-fluoro-N-(1-methyl-4-piperidyl)benzamide The title compound was prepared by an analogous method to the preparation of Example 350, on a 0.45 mmol scale, utilising 4-amino-3-fluoro-N-(1-methyl-4-piperidyl)benzamide (Intermediate 65; 114 mg, 0.45 mmol) heating by microwave irradiation at 160° C. for 30 minutes, as a white solid (96 mg, 41%).

$^1$H NMR (400.132 MHz, DMSO-$d_6$) δ 1.1 (s, 6H), 1.55 (m, 6H), 1.7-1.85 (m, 6H), 1.95 (t, 2H), 2.8 (d, 2H), 3.2 (s, 3H), 3.35 (s, 2H), 3.75 (m, 1H), 5.15 (m, 1H), 7.65 (m, 1H), 7.7 (m, 1H), 7.95 (s, 1H), 8.15 (m, 1H), 8.85 (s, 1H); MS m/z 525 [M+H]+.

Example 372

4-[(2-cyclopentyl-4,4,6-trimethyl-5-oxo-2,6,9,11-tetrazabicyclo[5.4.0]undeca-7,9,11-trien-10-yl)amino]-N-(4-dimethylaminocyclohexyl)-2-fluoro-5-methoxy-benzamide The title compound was prepared by an analogous method to the preparation of Example 350, on a 0.16 mmol scale, utilising 4-amino-N-(4-dimethylaminocyclohexyl)-2-fluoro-5-methoxy-benzamide (single undefined isomer) (Intermediate 248; 50 mg, 0.16 mmol) heating by microwave irradiation at 150° C. for 1 hour, as a white solid (30 mg, 32%).

$^1$H NMR (400.132 MHz, DMSO-$d_6$) δ 1.11 (6H, s), 1.63 (14H, m), 1.90 (2H, m), 2.07 (1H, m), 2.17 (6H, s), 3.20 (3H, s), 3.40 (2H, s), 3.92 (3H, s), 3.94 (1H, m), 5.19 (1H, m), 7.19 (1H, d), 7.71 (1H, m), 7.77 (1H, s), 8.02 (1H, s), 8.31 (1H, d); MS m/z 582 [M+H]+.

Example 373

4-[(2-cyclopentyl-4,4,6-trimethyl-5-oxo-2,6,9,11-tetrazabicyclo[5.4.0]undeca-7,9,11-trien-10-yl)amino]-N-(4-dimethylaminocyclohexyl)-2-fluoro-5-methoxy-benzamide The title compound was prepared by an analogous method to the preparation of Example 350, on a 0.16 mmol scale, utilising 4-amino-N-(4-dimethylaminocyclohexyl)-2-fluoro-5-methoxy-benzamide (single undefined isomer) (Intermediate 249; 50 mg, 0.16 mmol) heating by microwave irradiation at 150° C. for 1 hour, as a white solid (50 mg, 54%).

$^1$H NMR (400.132 MHz, DMSO-$d_6$) δ 1.11 (6H, s), 1.30 (4H, m), 1.75 (12H, m), 2.12 (1H, m), 2.18 (6H, s), 3.20 (3H, s), 3.40 (2H, s), 3.69 (1H, m), 3.92 (3H, s), 5.18 (1H, m), 7.19 (1H, d), 7.73 (1H, m), 7.76 (1H, s), 8.02 (1H, s), 8.30 (1H, d); MS m/z 582 [M+H]+.

Example 374

N-[4-(azetidin-1-yl)cyclohexyl]-4-[(2-cyclopentyl-4,4,6-trimethyl-5-oxo-2,6,9,11-tetrazabicyclo[5.4.0]undeca-7,9,11-trien-10-yl)amino]-3-methoxy-benzamide The title compound was prepared by an analogous method to the preparation of Example 346, utilising 10-chloro-2-cyclopentyl-4,4-dimethyl-2,6,9,11-tetrazabicyclo[5.4.0]undeca-8,10,12-trien-5-one (Intermediate 127; 75 mg, 0.17 mmol) and 4-(azetidin-1-yl)cyclohexan-1-amine (Intermediate 226; 39 mg, 0.25 mmol) as an off white solid (35 mg, 36%) assigned as the trans isomer.

$^1$H NMR (400.132 MHz, DMSO-$d_6$) δ 0.92-1.00 (2H, m), 1.10 (6H, s), 1.29-1.39 (2H, m), 1.58-1.94 (15H, m), 3.07 (4H, t), 3.19 (3H, s), 3.38 (2H, s), 3.67-3.76 (1H, m), 3.94 (3H, s), 5.19 (1H, quintet), 7.45-7.48 (2H, m), 7.67 (1H, s), 7.99 (1H, s), 8.00 (1H, d), 8.36 (1H, d); MS m/z 576 [M+H]+.

Example 375

N-[4-(azetidin-1-yl)cyclohexyl]-4-[(2-cyclopentyl-4,4,6-trimethyl-5-oxo-2,6,9,11-tetrazabicyclo[5.4.0]undeca-7,9,11-trien-10-yl)amino]-3-methoxy-benzamide The title compound was isolated from the reaction above to produce Example 374, as an off white solid (35 mg, 36%) assigned as the cis isomer.

$^1$H NMR (400.132 MHz, DMSO-$d_6$) δ 1.03 (6H, s), 1.24-1.31 (2H, m), 1.37-1.42 (2H, m), 1.50-1.70 (10H, m), 1.78-1.86 (4H, m), 2.12-2.16 (1H, m), 2.96-3.04 (4H, m), 3.12 (3H, s), 3.31 (2H, s), 3.69-3.79 (1H, m), 3.87 (3H, s), 5.12 (1H, quintet), 7.42-7.46 (2H, m), 7.58 (1H, s), 7.91 (1H, s), 7.96 (1H, d), 8.28 (1H, d); MS m/z 576 [M+H]+.

Example 376

4-[(2-cyclopentyl-4,4-diethyl-6-methyl-5-oxo-2,6,9,11-tetrazabicyclo[5.4.0]undeca-7,9,11-trien-10-yl)amino]-N-(2,2-dimethyl-3-pyrrolidin-1-yl-propyl)-3-methoxy-benzamide 10-chloro-2-cyclopentyl-4,4-diethyl-6-methyl-2,6,9,11-tetrazabicyclo[5.4.0]undeca-7,9,11-trien-5-one (Intermediate 250; 111 mg, 0.33 mmol), p-toluenesulphonic acid monohydrate (155 mg, 0.81 mmol) and 4-amino-N-(2,2-dimethyl- 3-pyrrolidin-1-yl-propyl)-3-methoxy-benzamide (Intermediate 206; 100 mg, 0.33 mmol) were added to 4-methyl-2-pentanol (7 mL). The reaction was heated at 120° C. over the weekend. The sample was transferred to an SCX cartridge (10 g) pre-wet with methanol, then washed with methanol and eluted with methanolic ammonia. Product containing fractions were combined and evaporated and the resultant material purified by base modified reverse phase preparative HPLC to yield the title compound as a white solid (55 mg, 27%).

¹H NMR (400.132 MHz, CDCl₃) δ 0.84 (t, 6H), 1.01 (s, 6H), 1.80-1.48 (m, 14H), 2.02-1.94 (m, 2H), 2.56 (s, 2H), 2.69 (s, 4H), 3.28 (s, 3H), 3.39 (d, 2H), 3.42 (s, 2H), 3.98 (s, 3H), 5.42 (quintet, 1H), 7.20 (d, 1H), 7.55 (s, 1H), 7.61 (s, 1H), 7.84 (s, 1H), 8.43 (d, 1H), 9.14 (s, 1H); MS m/z 606 [M+H]⁺.

Example 377

4-[(2-cyclopentyl-4,4-diethyl-6-methyl-5-oxo-2,6,9, 11-tetrazabicyclo[5.4.0]undeca-8,10,12-trien-10-yl) amino]-3-methoxy-N-[(1S,5R)-9-methyl-9-azabicyclo[3.3.1]non-7-yl]benzamide 10-chloro-2-cyclopentyl-4,4-diethyl-6-methyl-2,6,9,11-tetrazabicyclo[5.4.0]undeca-7,9,11-trien-5-one (Intermediate 250; 100 mg, 0.30 mmol), p-toluenesulphonic acid monohydrate (142 mg, 0.75 mmol) and 4-amino-3-methoxy-N-[(1S,5R)-9-methyl-9-azabicyclo[3.3.1]non-3-yl]benzamide (Intermediate 202; 91 mg, 0.30 mmol) were added to 4-methyl-2-pentanol (7 mL). The reaction was heated at 120° C. over the weekend. The sample was transferred to an SCX cartridge (10 g) pre-wet with methanol, then washed with methanol and eluted with methanolic ammonia. Product containing fractions were combined and evaporated and the resultant material purified by base modified reverse phase preparative HPLC to yield the title compound as a white solid (80 mg, 44%)

¹H NMR (400.132 MHz, CDCl₃) δ 0.84 (t, 6H), 1.09-1.07 (m, 2H), 1.44-1.38 (m, 2H), 1.63-1.48 (m, 6H), 1.80-1.66 (m, 6H), 2.03-1.94 (m, 3H), 2.56-2.49 (m, 4H), 3.14-3.11 (m, 2H), 3.28 (s, 3H), 3.42 (s, 2H), 3.97 (s, 3H), 4.58-4.47 (m, 1H), 5.42-5.32 (m, 1H), 5.94 (d, 1H), 7.25 (dd, 1H), 7.25 (d, 1H), 7.25 (d, 1H), 7.44 (d, 1H), 7.60 (s, 1H), 7.83 (s, 1H), 8.47 (d, 1H); MS m/z 604 [M+H]⁺.

Example 378

4-[(2-cyclopentyl-4,4-diethyl-6-methyl-5-oxo-2,6,9, 11-tetrazabicyclo[5.4.0]undeca-8,10,12-trien-10-yl) amino]-2-fluoro-5-methoxy-N-[(1S,5R)-9-methyl-9-azabicyclo[3.3.1]non-7-yl]benzamide The title compound was prepared by an analogous method to the preparation of Example 377, utilising 4-amino-2-fluoro-5-methoxy-N-[(1S,5R)-9-methyl-9-azabicyclo[3.3.1]non-7-yl]benzamide (Intermediate 204; 96 mg, 0.30 mmol), as a white solid (25 mg, 13%).

¹H NMR (400.132 MHz, CDCl3) δ 0.84 (t, 6H), 1.07-1.04 (m, 2H), 1.36-1.30 (m, 2H), 1.63-1.49 (m, 6H), 1.82-1.66 (m, 7H), 2.04-1.91 (m, 4H), 2.57-2.51 (m, 4H), 3.11-3.08 (m, 2H), 3.29 (s, 3H), 3.44 (s, 2H), 3.95 (s, 3H), 4.58-4.46 (m, 1H), 5.36 (quintet, 1H), 6.55 (dd, 1H), 7.57 (d, 1H), 7.67 (s, 1H), 7.85 (s, 1H), 8.37 (d, 1H); MS m/z 622 [M+H]⁺.

Example 379

4-[(2-cyclopentyl-4,4-diethyl-6-methyl-5-oxo-2,6,9, 11-tetrazabicyclo[5.4.0]undeca-7,9,11-trien-10-yl) amino]-N-(1-ethyl-4-piperidyl)-2-fluoro-5-methoxy-benzamide The title compound was prepared by an analogous method to the preparation of Example 377, utilising 4-amino-N-(1-ethyl-4-piperidyl)-2-fluoro-5-methoxy-benzamide (Intermediate 205; 89 mg, 0.30 mmol), as a white solid (35 mg, 20%).

¹H NMR (400.132 MHz, CDCl₃) δ 0.84 (t, 6H), 1.10 (t, 3H), 1.62-1.49 (m, 6H), 1.81-1.65 (m, 6H), 2.08-1.98 (m, 4H), 2.19-2.13 (m, 2H), 2.43 (q, 2H), 2.89-2.86 (m, 2H), 3.29 (s, 3H), 3.44 (s, 2H), 3.95 (s, 3H), 4.09-3.99 (m, 1H), 5.34 (quintet, 1H), 6.68 (dd, 1H), 7.55 (d, 1H), 7.67 (s, 1H), 7.84 (s, 1H), 8.37 (d, 1H); MS m/z 596 [M+H]⁺.

Example 380

4-[(2-cyclopentyl-4,4-diethyl-6-methyl-5-oxo-2,6,9, 11-tetrazabicyclo[5.4.0]undeca-7,9,11-trien-10-yl) amino]-3-methoxy-N-(1-methyl-4-piperidyl)benzamide The title compound was prepared by an analogous method to the preparation of Example 377, utilising 4-amino-3-methoxy-N-(1-methyl-4-piperidyl)benzamide (WO06/018220; 79 mg, 0.30 mmol), as a white solid (30 mg, 18%).

¹H NMR (400.132 MHz, CDCl₃) δ 0.84 (t, 6H), 1.64-1.48 (m, 6H), 1.80-1.66 (m, 6H), 2.00-1.92 (m, 2H), 2.07-2.05 (m, 2H), 2.20-2.14 (m, 2H), 2.31 (s, 3H), 2.84-2.81 (m, 2H), 3.28 (s, 3H), 3.42 (s, 2H), 4.03-3.92 (m, 4H), 5.38 (quintet, 1H), 5.89 (d, 1H), 7.22 (dd, 1H), 7.41 (d, 1H), 7.59 (s, 1H), 7.84 (s, 1H), 8.48 (d, 1H); MS m/z 564 [M+H]⁺.

Example 381

4-[(2-cyclopentyl-4,4-diethyl-6-methyl-5-oxo-2,6,9, 11-tetrazabicyclo[5.4.0]undeca-7,9,11-trien-10-yl) amino]-N-(1-ethyl-4-piperidyl)-3-methoxy-benzamide The title compound was prepared by an analogous method to the preparation of Example 377, utilising 4-amino-N-(1-ethyl-4-piperidyl)-3-methoxy-benzamide (Intermediate 190; 83 mg, 0.30 mmol), as a white solid (90 mg, 52%).

¹H NMR (400.132 MHz, CDCl₃) δ 0.77 (t, 6H), 1.03 (t, 3H), 1.56-1.41 (m, 6H), 1.73-1.59 (m, 6H), 1.95-1.87 (m, 2H), 2.10-1.98 (m, 4H), 2.37 (q, 2H), 2.86-2.83 (m, 2H), 3.22 (s, 3H), 3.35 (s, 2H), 3.98-3.91 (m, 4H), 5.31 (quintet, 1H), 5.82 (d, 1H), 7.15 (dd, 1H), 7.34 (d, 1H), 7.52 (s, 1H), 7.77 (s, 1H), 8.41 (d, 1H); MS m/z 578 [M+H]⁺.

Example 382

3-chloro-4-(9'-cyclopentyl-5'-methyl-6'-oxo-5',6',8', 9'-tetrahydrospiro[cyclopropane-1,7'-pyrimido[5,4-b] [1,4]diazepine]-2'-ylamino)-N-(1-ethylpiperidin-4-yl)benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 108 mg, 0.35 mmol) 4-amino-3-chloro- N-(1-ethyl-4-piperidyl)benzamide (Intermediate 212; 118 mg, 0.42 mmol), and p-toluenesulphonic acid monohydrate (133 mg, 0.7 mmol) were combined in 4-methyl-2-pentanol (4 mL) and heated by microwave irradiation at 160° C. for 1 hour. The reaction mixture was loaded onto to an SCX cartridge (10 g) pre-wet with methanol, then washed with methanol and eluted with methanolic ammonia. Product containing fractions were combined and evaporated and the resultant material purified by base modified reverse phase preparative HPLC to yield the title compound as a white solid (38 mg, 20%).

$^1$H NMR (400.13 MHz, DMSO-d$_6$) δ 0.66-0.69 (2H, m), 0.90-0.93 (2H, m), 1.00 (3H, t), 1.41-1.70 (8H, m), 1.77-1.85 (4H, m), 1.90-1.96 (2H, m), 2.32 (2H, q), 2.88 (2H, d), 3.18 (3H, s), 3.47 (2H, s), 3.72-3.76 (1H, m), 4.74-4.82 (1H, m), 7.79 (1H, dd), 7.98-8.00 (2H, m), 8.08 (1H, s), 8.20 (1H, d), 8.30-8.34 (1H, m)
MS m/z 552 [M+H]$^+$.

Example 383

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(1-ethyl-4-piperidyl)-3-methoxy-benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 100 mg, 0.33 mmol), 4-amino-N-(1-ethyl-4-piperidyl)-3-methoxy-benzamide (Intermediate 190; 91 mg, 0.33 mmol) and p-toluenesulphonic acid monohydrate (156 mg, 0.81 mmol) were heated at 140° C. in 4-methyl-2-pentanol (4 mL) for 2 hours. The reaction mixture was loaded onto to an SCX-3 cartridge (10 g) pre-wet with methanol, then washed with methanol and eluted with 2% 7N ammonia/methanol. Product containing fractions were combined and evaporated and the resultant material purified by base modified reverse phase preparative HPLC to yield the title compound as a white solid (89 mg, 50%).

$^1$H NMR (399.9 MHz, DMSO-d$_6$) δ 0.67-0.69 (2H, t), 0.90-0.93 (2H, t), 1.01 (3H, t), 1.51-1.51 (1H, m), 1.52 (1H, d), 1.56-1.62 (4H, m), 1.68 (1H, s), 1.70 (1H, d), 1.78 (1H, d), 1.81 (1H, s), 1.93 (4H, d), 2.33 (2H, q), 2.90 (2H, d), 3.19 (3H, s), 3.49 (2H, s), 3.61-3.65 (1H, m), 3.96 (3H, s), 4.86 (1H, m), 7.47 (1H, t), 7.50 (1H, d), 7.68 (1H, s), 8.00 (1H, s), 8.07 (1H, d), 8.40 (1H, d); MS m/z 549 [M+H]$^+$.

Example 384

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-3-methoxy-N-(2-pyrrolidin-1-ylethyl)benzamide The title compound was prepared by an analogous method to the preparation of Example 383, utilising 4-amino-3-methoxy-N-(2-pyrrolidin-1-ylethyl)benzamide (Intermediate 192; 86 mg, 0.30 mmol), as a white solid (20 mg, 111%).

$^1$H NMR (399.9 MHz, DMSO-d6) δ 0.67-0.69 (2H, t), 0.90-0.93 (2H, t), 1.52 (2H, d), 1.61 (2H, t), 1.65-1.71 (7H, m), 1.89-1.92 (3H, m), 2.58 (2H, t), 3.18 (3H, s), 3.20 (2H, t)—found under water, 3.39 (2H, q), 3.49 (2H, s), 3.95 (3H, s), 4.86 (1H, s), 7.46 (1H, d), 7.48-7.51 (1H, m), 7.69 (1H, s), 7.99 (1H, s), 8.31 (1H, t), 8.40-8.42 (1H, m); MS m/z 535 [M+H]$^+$.

Example 385

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-3-methoxy-N-[(1S,5R)-9-methyl-9-azabicyclo[3.3.1]non-7-yl]benzamide The title compound was prepared by an analogous method to the preparation of Example 383, utilising 4-amino-3-methoxy-N-[(1S,5R)-9-methyl-9-azabicyclo[3.3.1]non-3-yl]benzamide (Intermediate 202; 99 mg, 0.30 mmol), as a white solid (114 mg, 61%).

$^1$H NMR (399.9 MHz, DMSO-d$_6$) δ 0.67-0.70 (2H, t), 0.90-0.93 (2H, t), 0.95 (2H, s), 1.42-1.48 (2H, m), 1.43-1.49 (2H, m), 1.54 (2H, t), 1.60-1.63 (1H, m), 1.68 (1H, s), 1.70 (1H, d), 1.89-1.97 (4H, m), 2.08 (1H, d), 2.16-2.24 (2H, m), 2.42 (3H, s), 2.98-3.01 (2H, d), 3.18 (3H, s), 3.49 (2H, s), 3.97 (3H, s), 4.34 (1H, m), 4.87 (1H, m), 7.47 (1H, d), 7.50 (1H, t), 7.68 (1H, s), 7.92 (1H, d), 8.00 (1H, s), 8.40 (1H, d); MS m/z 575 [M+H]$^+$.

Example 386

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(3-dimethylamino-2,2-dimethyl-propyl)-3-methoxy-benzamide The title compound was prepared by an analogous method to the preparation of Example 383, utilising 4-amino-N-(3-dimethylamino-2,2-dimethyl-propyl)-3-methoxy-benzamide (Intermediate 22; 92 mg, 0.30 mmol), as a white solid (89 mg, 50%).

$^1$H NMR (399.9 MHz, DMSO-d6) δ 0.67-0.69 (2H, m), 0.89 (6H, s), 0.90-0.93 (2H, t), 1.51 (1H, d), 1.54 (1H, s), 1.58 (1H, d), 1.61-1.62 (1H, m), 1.69 (2H, d), 1.90 (2H, d), 2.21 (2H, s), 2.29 (6H, s), 3.19 (3H, s), 3.21 (2H, d), 3.48 (2H, s), 3.96 (3H, s), 4.86 (1H, m), 7.41-7.43 (1H, m), 7.47 (1H, d), 7.70 (1H, s), 7.99 (1H, s), 8.41 (1H, d), 8.44 (1H, t); MS m/z 551 [M+H]$^+$.

Example 387

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(2-dimethylaminoethyl)-3-methoxy-benzamide The title compound was prepared by an analogous method to the preparation of Example 383, utilising 4-amino-N-(2-dimethylaminoethyl)-3-methoxy-benzamide (Intermediate 194; 78 mg, 0.30 mmol), as a white solid (82 mg, 50%).

$^1$H NMR (399.9 MHz, DMSO-d$_6$) δ 0.67-0.70 (2H, t), 0.92 (2H, t), 1.51 (1H, d), 1.55 (1H, d), 1.60-1.63 (2H, m), 1.70 (2H, t), 1.90 (2H, s), 2.19 (6H, s), 2.41 (2H, t), 3.18 (3H, s), 3.37 (2H, q), 3.49 (2H, s), 3.95 (3H, s), 4.86 (1H, m), 7.46 (1H, d), 7.48-7.51 (1H, d), 7.69 (1H, s), 7.99 (1H, d), 8.27 (1H, t), 8.39-8.42 (1H, m); MS m/z 509 [M+H]$^+$.

Example 388

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-3-fluoro-N-[(1S,5R)-9-methyl-9-azabicyclo[3.3.1]non-7-yl]benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 108 mg, 0.35 mmol) and 4-amino-3-fluoro-N-(9-methyl-9-azabicyclo[3.3.1]non-7-yl)benzamide (Intermediate 162; 102 mg, 0.35 mmol) were combined with p-toluenesulphonic acid monohydrate (167 mg, 0.88 mmol) in 4-methyl-2-pentanol (2 mL) and heated by microwave irradiation for 25 minutes at 160° C. The cooled reaction mixture was diluted with methanol (10 mL) and loaded onto an SCX-3 cartridge (5 g) pre-wet with methanol. The cartridge was washed with methanol (2×5 mL) and eluted with 7 N methanolic ammonia (10 mL). Product containing fractions were evaporated and the resultant material purified by base modified reverse phase preparative HPLC to give the title compound as a white solid (54 mg, 28%).

$^1$H NMR (400 MHz, DMSO-$d_6$) δ 0.65 (t, 2H), 0.9 (m, 4H), 1.5 (m. 7H), 1.65 (m, 2H), 1.85 (m, 4H), 2.05 (m, 1H), 2.2 (m, 2H), 2.4 (s, 3H), 3.0 (d, 2H), 3.2 (s, 3H), 3.45 (s, 2H), 4.3 (m, 1H), 4.8 (m, 1H) 7.65 (m, 1H), 7.75 (m, 1H), 7.95 (m, 2H), 8.15 (t, 1H), 8.65 (s, 1H); MS m/z 562 [M+H]$^+$.

Example 389

5-chloro-4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-2-fluoro-N-(1-methyl-4-piperidyl)benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 85 mg, 0.30 mmol), 4-amino-5-chloro-2-fluoro-N-(1-methyl-4-piperidyl)benzamide (Intermediate 173; 101 mg, 0.33 mmol) and XANTPHOS (16 mg, 0.03 mmol) were dissolved in 1,4-dioxane (7.5 mL). Caesium carbonate (210 mg, 0.59 mmol) was added and the system purged with a stream of nitrogen for 15 minutes before tris(dibenzylideneacetone) palladium (II) (17 mg, 0.02 mmol) was added. The apparatus was evacuated and backfilled with nitrogen (×3) and then heated at 100° C. for 3 hours. The mixture was cooled, filtered and the filtrate absorbed on to an SCX column, which was subsequently washed with methanol and eluted with ammonia in methanol. Product containing fractions were concentrated and purified by base modified reverse phase preparative HPLC to yield the title compound as a white solid (100 mg, 60%).

$^1$H NMR (399.9 MHz, DMSO-$d_6$) δ0.69-0.71 (2H, m), 0.92-0.95 (2H, m), 1.51-1.64 (6H, m), 1.66-1.71 (2H, m), 1.77-1.80 (2H, m), 1.85-1.99 (4H, m), 2.17 (3H, s), 2.74 (2H, d), 3.19 (3H, s), 3.50 (2H, s), 3.66-3.73 (1H, m), 4.80-4.88 (1H, m), 7.68 (1H, d), 8.04-8.09 (3H, m), 8.35-8.39 (1H, m); MS m/z 556 [M+H]$^+$.

Example 390

3-chloro-4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(2-dimethylaminoethyl)benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 100 mg, 0.33 mmol) and 4-amino-3-chloro-N-(2-dimethylaminoethyl)benzamide (Intermediate 213; 89 mg, 0.37 mmol) were dissolved in 1,4 dioxane (4 mL) and caesium carbonate (234 mg, 0.72 mmol) was added. The reaction mixture was sparged with nitrogen for 15 minutes prior to addition of tris-dibenzylideneacetone dipalladium (II) (19 mg, 0.02 mmol) followed by XANTPHOS (19 mg, 0.03 mmol). The reaction mixture was heated at 100° C. overnight, cooled to room temperature and diluted with DCM (20 mL). The resultant mixture was filtered and the filtrate loaded onto an SCX-3 (5 g) cartridge. The cartridge was washed through with methanol (50 mL) and then eluted with 2M ammonia in methanol (50 mL). Evaporation of the ammoniacal fraction afforded an amber gum which was purified by acid modified reverse phase preparative HPLC. The resultant material was dissolved in MeOH/Water and poured onto an SCX-3 cartridge (2 g) and cartridge which was then washed with methanol and eluted with 2M ammonia in methanol, and the ammoniacal solution evaporated to yield the title compound as a solid (7 mg, 3%).

$^1$H NMR (400.132 MHz, DMSO-d6) δ 0.67 (m, 2H), 0.91 (m, 2H), 1.41-1.69 (m, 6H), 1.83 (m, 2H), 2.19 (s, 6H), 2.41 (t, 2H), 3.18 (s, 3H), 3.35 (m, 2H), 3.47 (s, 2H), 4.78 (m, 1H), 7.78 (m, 1H), 7.97 (d, 1H), 7.99 (s, 1H), 8.10 (s, 1H), 8.32 (d, 1H), 8.37 (t, 1H); MS m/z 512 [M+H]$^+$.

Example 391

3-chloro-4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(2-pyrrolidin-1-ylethyl)benzamide The title compound was prepared by an analogous method to the preparation of Example 390, utilising 4-amino-3-chloro-N-(2-pyrrolidin-1-ylethyl)benzamide (Intermediate 215; 97 mg, 0.36 mmol), as a white solid (7 mg, 3%).

$^1$H NMR (400.132 MHz, DMSO-$d_6$) δ 0.67 (m, 2H), 0.91 (m, 2H), 1.50 (m, 4H), 1.67 (m, 6H), 1.83 (m, 2H), 2.58 (t, 2H), 3.18 (s, 3H), 3.38 (m, 2H), 3.47 (s, 2H), 4.78 (m, 1H), 7.79 (m, 1H), 7.97 (d, 1H), 7.99 (s, 1H), 8.10 (s, 1H), 8.32 (d, 1H), 8.42 (t, 1H); MS m/z 538 [M+H]$^+$.

Example 392

3-chloro-4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(3-dimethylamino-2,2-dimethyl-propyl)benzamide The title compound was prepared by an analogous method to the preparation of Example 390, utilising 4-amino-3-chloro-N-(3-dimethylamino-2,2-dimethyl-propyl)benzamide (Intermediate 107; 103 mg, 0.36 mmol), as a white solid (4 mg, 2%).

$^1$H NMR (400.132 MHz, DMSO-$d_6$) δ 0.67 (m, 2H), 0.88 (s, 6H), 0.91 (m, 2H), 1.41-1.70 (m, 6H), 1.83 (m, 2H), 2.18 (s, 2H), 2.27 (s, 6H), 3.19 (m, 5H), 3.46 (s, 2H), 4.77 (m, 1H), 7.75 (m, 1H), 7.94 (d, 1H), 7.99 (s, 1H), 8.13 (s, 1H), 8.29 (d, 1H), 8.46 (t, 1H); MS m/z 554 [M+H]$^+$.

Example 393

5-chloro-4-(9'-cyclopentyl-5'-methyl-6'-oxo-5',6',8', 9'-tetrahydrospiro[cyclopropane-1,7'-pyrimido[5,4-b] [1,4]diazepine]-2'-ylamino)-N-(1-ethyl-4-piperidyl)-2-fluoro-benzamide The title compound was prepared by an analogous method to the preparation of Example 389, utilising 4-amino-5-chloro-N-(1-ethyl-4-piperidyl)-2-fluoro-benzamide (Intermediate 174; 90 mg, 0.30 mmol), as a white solid (102 mg, 60%).

$^1$H NMR (399.9 MHz, DMSO-d$_6$) δ 0.69-0.71 (2H, m), 0.92-0.95 (2H, m), 1.00 (3H, t), 1.49-2.01 (14H, m), 2.32 (2H, q), 2.84 (2H, d), 3.19 (3H, s), 3.50 (2H, s), 3.68-3.74 (1H, m), 4.82-4.88 (1H, m), 7.68 (1H, d), 8.04-8.08 (3H, m), 8.35-8.39 (1H, m); MS m/z 570 [M+H]$^+$.

Example 394

5-chloro-4-(9'-cyclopentyl-5'-methyl-6'-oxo-5',6',8', 9'-tetrahydrospiro[cyclopropane-1,7'-pyrimido[5,4-b] [1,4]diazepine]-2'-ylamino)-N-(4-dimethylaminocyclohexyl)-2-fluoro-benzamide The title compound was prepared by an analogous method to the preparation of Example 389, utilising 4-amino-5-chloro-N-(4-dimethylaminocyclohexyl)-2-fluoro-benzamide (Intermediate 175; 94 mg, 0.30 mmol), as a white solid (65 mg, 37%).

$^1$H NMR (399.9 MHz, DMSO-d6) δ 0.69-0.71 (2H, m), 0.92-0.95 (2H, m), 1.340-1.35 (2H, m), 1.49-1.94 (14H, m), 2.25-2.30 (7H, m), 3.19 (3H, s), 3.50 (2H, s), 3.67-3.71 and 3.91-3.97 (each 0.5H. m), 4.80-4.88 (1H, m), 7.65-7.68 (1H, m), 8.01-8.04 (2H, m), 8.08 (1H, d), 8.34-8.38 (1H, m); MS m/z 584 [M+H]$^+$.

Example 395

4-(9'-cyclopentyl-5'-methyl-6'-oxo-5',6',8',9'-tetrahydrospiro[cyclopropane-1,7'-pyrimido[5,4-b][1,4] diazepine]-2'-ylamino)-N-(1-ethyl-4-piperidyl)-2,5-difluoro-benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 100 mg, 0.33 mmol), 4-amino-N-(1-ethyl-4-piperidyl)-2,5-difluoro-benzamide (Intermediate 235; 102 mg, 0.36 mmol) and caesium carbonate (213 mg, 0.65 mmol) added to dioxane (5 mL) and the suspension bubbled with nitrogen for 10 minutes. tris-dibenzylideneacetonedipalladium (II) (18 mg, 0.02 mmol) and XANTPHOS (17 mg, 0.03 mmol) were added and the mixture heated at 110° C. overnight. The mixture was filtered, and the filtrate loaded onto to an SCX-3 cartridge (10 g) pre-wet with methanol, then washed with methanol and eluted with ammonia in methanol. Product containing fractions were combined and evaporated and the resultant material purified by base modified reverse phase preparative HPLC to yield the title compound as a light orange gum (99 mg, 55%).

$^1$H NMR (399.9 MHz, DMSO-d$_6$) δ0.69 (2H, t), 0.93 (2H, t), 1.05 (3H, t), 1.52-1.58 (4H, m), 1.61 (2H, m), 1.65-1.67 (2 h, m), 1.80 (2H, d), 1.85 (2H, d), 2.10-2.12 (2H, t), 2.41 (2 h, q), 2.91 (2H, d), 3.17 (3H, s), 3.45 (2H, s), 3.75 (1H, m), 4.80-4.85 (1H, m), 7.40 (1 h, dd), 7.95 (1 h, d), 8.19 (1H, s), 8.25 (1H, dd), 8.84 (1 h, s); MS m/z 554 [M+H]$^+$.

Example 396

4-(9'-cyclopentyl-5'-methyl-6'-oxo-5',6',8',9'-tetrahydrospiro[cyclopropane-1,7'-pyrimido[5,4-b][1,4] diazepine]-2'-ylamino)-2,5-difluoro-N-(1-methyl-4-piperidyl)benzamide The title compound was prepared by an analogous method to the preparation of Example 395, utilising 4-amino-2,5-difluoro-N-(1-methyl-4-piperidyl)benzamide (Intermediate 59; 97 mg, 0.36 mmol), as an off-white solid (122 mg, 69%)

$^1$H NMR (399.9 MHz, DMSO-d$_6$) δ0.69 (2H, t), 0.93 (2H, t), 1.05 (3H, t), 1.52-1.58 (4H, m), 1.61 (2H, m), 1.65-1.67 (2 h, m), 1.80 (2H, d), 1.85 (2H, d), 2.10-2.12 (2H, t), 2.22 (3H, s), 2.91 (2H, d), 3.17 (3H, s), 3.45 (2H, s), 3.75 (1H, m), 4.80-4.85 (1H, m), 7.40 (1 h, dd), 7.95 (1 h, d), 8.19 (1H, s), 8.25 (1H, dd), 8.84 (1 h, s); MS m/z 540 [M+H]$^+$.

Example 397

4-(9'-cyclopentyl-5'-methyl-6'-oxo-5',6',8',9'-tetrahydrospiro[cyclopropane-1,7'-pyrimido[5,4-b][1,4] diazepine]-2'-ylamino)-2,5-difluoro-N-(2-pyrrolidin-1-ylethyl)benzamide The title compound was prepared by an analogous method to the preparation of Example 395, utilising 4-amino-2,5-difluoro-N-(2-pyrrolidin-1-ylethyl)benzamide (Intermediate 230; 97 mg, 0.36 mmol), as a pale yellow gum (121 mg, 69%).

$^1$H NMR (399.9 MHz, DMSO-d6) δ0.69 (2H, t), 0.93 (2H, t), 1.48-1.55 (4H, m), 1.58-1.64 (6H, m), 1.85-1.92 (2H, m), 2.57 (4H, m), 2.68 (2H, t), 3.17 (3H, s), 3.40 (2H, m), 3.45 (2H, s), 4.80-4.85 (1H, m), 7.40 (1 h, dd), 7.95 (1 h, d), 8.19 (1H, s), 8.25 (1H, dd), 8.84 (1 h, s); MS m/z 540 [M+H]$^+$.

Example 398

4-(9'-cyclopentyl-5'-methyl-6'-oxo-5',6',8',9'-tetrahydrospiro[cyclopropane-1,7'-pyrimido[5,4-b][1,4] diazepine]-2'-ylamino)-2-fluoro-5-methoxy-N-(2-pyrrolidin-1-ylethyl)benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 80 mg, 0.26 mmol), 4-amino-3-methoxy-N-(2-pyrrolidin-1-ylethyl)benzamide (Intermediate 192; 73 mg, 0.26 mmol) and p-toluenesulphonic acid monohydrate (124 mg, 0.65 mmol) were combined in 4-methyl-2-pentanol (3 mL) and heated at 100° C. for 18 hours. The cooled reaction mixture was loaded on to an SCX-2 column (5 g) pre-wet with MeOH (2 column volumes), flushed with MeOH (2 column volumes) then eluted with 2M ammonia in MeOH. Product containing fractions were combined and evaporated and the resultant material purified by base modified reverse phase preparative HPLC to yield the title compound as a white solid (85 mg, 59%)

$^1$H NMR (399.902 MHz, CDCl$_3$) δ0.62 (m, 2H), 1.11 (m, 2H), 1.46 (m, 2H), 1.72 (m, 4H), 1.79 (m, 4H), 2.03 (m, 2H), 2.58 (m, 4H), 2.72 (m, 2H), 3.29 (s, 3H), 3.47 (s, 2H), 3.60 (m, 2H), 3.95 (s, 3H), 4.96 (m, 1H), 7.31 (m, 1H), 7.56 (d, 1H), 7.70 (s, 1H), 7.87 (s, 1H), 8.41 (d, 1H); MS m/z 552 [M+H]$^+$.

Example 399

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-2-fluoro-5-methoxy-N-[(3R)-1-methylpyrrolidin-3-yl]benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 100 mg, 0.32 mmol), 4-amino-2-fluoro-5-methoxy-N-[(3R)-1-methylpyrrolidin-3-yl]benzamide (Intermediate 182; 87 mg, 0.32 mmol) and 4-toluenesulphonic acid monohydrate (154 mg, 0.81 mmol) were heated in 4-methyl-2-pentanol (3 mL) at 140° C. for 3 hours. The mixture was cooled and absorbed on to an SCX column, washed with methanol and eluted with ammonia in methanol. Product containing fractions were concentrated and purified by base modified reverse phase preparative HPLC to yield the title compound as a white solid (80 mg, 46%).

$^1$H NMR (399.9 MHz, DMSO-d6) δ 0.67-0.72 (2H, m), 0.91-0.96 (2H, m), 1.53-1.75 (7H, m), 1.87-1.96 (2H, m), 2.13-2.22 (1H, m), 2.26 (3H, s), 2.34-2.45 (2H, m), 2.57-2.64 (1H, m), 2.66-2.70 (1H, m), 3.18 (3H, s), 3.50 (2H, s), 3.93 (3H, s), 4.35-4.43 (1H, m), 4.83-4.92 (1H, m), 7.22 (1H, d), 7.77 (1H, s), 7.98-8.00 (1H, m), 8.03 (1H, s), 8.35 (1H, d); MS m/z 539 [M+H]$^+$.

Example 400

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-2,5-difluoro-N-[(3R)-1-methylpyrrolidin-3-yl]benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 109 mg, 0.36 mmol), aniline (Intermediate 229; 83 mg, 0.324 mmol), and caesium carbonate (211 mg, 0.648 mmol) added to dioxane (3 mL) and the suspension bubbled with nitrogen for 10 minutes. Tris-dibenzylideneacetone dipalladium (II) (11 mg, 0.02 mmol) and XANTPHOS (17 mg, 0.03 mmol) were added and the mixture heated to 100° C. for 16 hours. The reaction mixture was cooled to room temperature filtered, and the filter cake washed with DCM and the filtrate evaporated. The residue was dissolved in DCM and purified on a silica column eluting with a gradient of 0-5% 2M ammonia in MeOH/DCM over 30 column volumes. Product containing fractions were combined and evaporated and the residue purified by base modified reverse phase preparative HPLC to yield the title compound as a white solid (95 mg, 56%).

$^1$H NMR (399.902 MHz, CDCl$_3$) δ0.64 (m, 2H), 1.12 (m, 2H), 1.46 (m, 2H), 1.74 (m, 5H), 2.02 (m, 2H), 2.29 (m, 1H), 2.42 (m, 4H), 2.67 (m, 2H), 2.90 (m, 1H), 3.29 (s, 3H), 3.48 (s, 2H), 4.65 (m, 1H), 4.93 (m, 1H), 6.96 (m, 1H), 7.28 (m, 1H), 7.80 (m, 1H), 7.88 (s, 1H), 8.46 (m, 1H); MS m/z 526 [M+H]$^+$.

Example 401

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(2,2-dimethyl-3-pyrrolidin-1-yl-propyl)-3-methoxy-benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 101 mg, 0.33 mmol), p-toluenesulphonic acid monohydrate (155 mg, 0.81 mmol) and 4-amino-N-(2,2-dimethyl-3-pyrrolidin-1-yl-propyl)-3-methoxy-benzamide (Intermediate 206; 100 mg, 0.33 mmol) were added to 4-methyl-2-pentanol (7 mL). The reaction was heated at 120° C. over the weekend. The sample was transferred to an SCX cartridge (10 g) pre-wet with methanol, then washed with methanol and eluted with methanolic ammonia. Product containing fractions were combined and evaporated and the resultant material purified by base modified reverse phase preparative HPLC to yield the title compound as a white solid (34 mg, 18%).

$^1$H NMR (400.132 MHz, CDCl$_3$) δ 0.63-0.60 (m, 2H), 1.01 (s, 6H), 1.10-1.07 (m, 2H), 1.51-1.43 (m, 2H), 1.74-1.61 (m, 4H), 1.83-1.76 (m, 4H), 2.05-1.98 (m, 2H), 2.56 (s, 2H), 2.72-2.65 (m, 4H), 3.28 (s, 3H), 3.39 (d, 2H), 3.46 (s, 2H), 3.98 (s, 3H), 4.98 (quintet, 1H), 7.20 (dd, 1H), 7.55 (d, 1H), 7.65 (s, 1H), 7.87 (s, 1H), 8.46 (d, 1H), 9.15 (s, 1H); MS m/z 576 [M+H]$^+$.

Example 402

3-chloro-4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-[(1S,5R)-9-methyl-9-azabicyclo[3.3.1]non-7-yl]benzamide 4-[(2-cyclopentyl-4,4,6-trimethyl-5-oxo-2,6,9,11-tetrazabicyclo[5.4.0]undeca-7,9,11-trien-10-yl)amino]-3-chloro-benzoic acid (Intermediate 253; 52 mg, 0.12 mmol) was suspended in DMF (4 mL). DIPEA (62 ul, 0.35 mmol) was added to give a straw coloured solution. Endo-9-methyl-9-azabicyclo[3,3,1]-nonan-3-amine (Chempacific; 26 mg, 0.16 mmol) was added, followed by HATU (67 mg, 0.17 mmol) and the resultant mixture was stirred at ambient temperature overnight.

The reaction mixture was evaporated to an amber gum, which was partitioned between DCM (5 mL) and saturated aqueous sodium bicarbonate solution (5 mL). The organic phase was separated by gravity elution through a PTFE filter cup and the filtrate evaporated to dryness to afford an amber oil which was purified by base modified reverse phase preparative HPLC to yield the title compound as a white solid (46 mg, 56%)

$^1$H NMR (400.132 MHz, DMSO-d6) δ 0.68 (m, 2H), 0.92 (m, 4H), 1.39-1.70 (m, 9H), 1.80-2.08 (m, 5H), 2.19 (m, 2H), 2.41 (s, 3H), 2.98 (m, 2H), 3.18 (s, 3H), 3.47 (s, 2H), 4.31 (m, 1H), 4.78 (m, 1H), 7.80 (m, 1H), 7.99 (s, 1H), 8.00 (d, 1H), 8.05 (d, 1H), 8.08 (s, 1H), 8.32 (d, 1H); MS m/z 578 [M+H]$^+$.

Example 403

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-[(3R)-1-ethylpyrrolidin-3-yl]-3-methoxy-benzamide The title compound was prepared by an analogous method to the preparation of Example 350, utilising, 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 75 mg, 0.24 mmol), and 4-amino-N-[(3R)-1-ethylpyrrolidin-3-yl]-3-methoxy-benzamide (Intermediate 245; 70 mg, 0.26 mmol) heating by microwave irradiation at 160° C. for 1 hour, as an off-white foam (50 mg, 39%).

$^1$H NMR (400.132 MHz, DMSO-d6) δ 1.04 (t, 3H), 1.10 (s, 6H), 1.55-1.93 (m, 9H), 2.15 (m, 1H), 2.43 (m, 4H), 2.65 (m,

1H), 2.73 (m, 1H), 3.19 (s, 3H), 3.38 (s, 2H), 3.95 (s, 3H), 4.40 (m, 1H), 5.19 (m, 1H), 7.51 (m, 2H), 7.67 (s, 1H), 7.99 (s, 1H), 8.28 (d, 1H), 8.37 (d, 1H); MS m/z 536 [M+H]$^+$.

Example 404

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-2-fluoro-5-methoxy-N-[(1S,5R)-9-methyl-9-azabicyclo[3.3.1]non-3-yl]benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 55 mg, 0.17 mmol), 4-amino-2-fluoro-5-methoxy-N-[(1S,5R)-9-methyl-9-azabicyclo[3.3.1]non-7-yl]benzamide (Intermediate 204; 53 mg, 0.17 mmol) and p-toluenesulphonic acid monohydrate (82 mg, 0.43 mmol) were heated in 4-methyl-2-pentanol (3 mL) at 140° C. for 2 hours. The reaction mixture was cooled and absorbed on to an SCX column, which was then washed with methanol and eluted with ammonia in methanol. Product containing fractions were evaporated and the residue purified by base modified reverse phase preparative HPLC to yield the title compound as a white solid (35 mg, 35%).

$^1$H NMR (399.9 MHz, DMSO-d6) δ 0.68-0.71 (2H, m), 0.91-0.94 (4H, m), 1.40-1.46 (3H, m), 1.51-1.73 (6H, m), 1.86-1.94 (4H, m), 1.99-2.09 (1H, m), 2.18-2.25 (2H, m), 2.42 (3H, s), 2.98 (2H, d), 3.19 (3H, s), 3.51 (2H, s), 3.94 (3H, s), 4.27-4.35 (1H, m), 4.84-4.92 (1H, m), 7.22 (1H, d), 7.66-7.69 (1H, m), 7.77 (1H, s), 8.03 (1H, s), 8.35 (1H, d); MS m/z 592 [M+H]$^+$.

Example 405

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-2-fluoro-5-methoxy-N-[[1-(pyrrolidin-1-ylmethyl)cyclopropyl]methyl]benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 70 mg, 0.23 mmol), 4-amino-2-fluoro-5-methoxy-N-[[1-(pyrrolidin-1-ylmethyl)cyclopropyl]methyl]benzamide (Intermediate 254; 70 mg, 0.22 mmol), and p-toluenesulphonic acid monohydrate (136 mg, 0.71 mmol) were stirred and heated together in 4-methyl-2-pentanol (3 mL) at 110° C. for 18 hours.

The cooled reaction solution was loaded onto an SCX-3 (5 g) column pre-wet with MeOH. The column was washed with MeOH (2 column volumes) and the product eluted with 2M NH3/MeOH. Product containing fractions were combined and evaporated and the residue purified by base modified reverse phase preparative HPLC to yield the title compound as a white solid (38 mg, 29%).

$^1$H NMR (400.132 MHz, DMSO-d$_6$) δ 0.34 (2H, m), 0.50 (2H, m), 0.69 (2H, m), 0.92 (2H, m), 1.61 (12H, m), 1.92 (2H, m), 2.44 (2H, s), 2.50 (2H, s), 3.18 (3H, s), 3.36 (2H, d), 3.51 (2H, s), 3.93 (3H, s), 4.89 (1H, m), 7.37 (1H, d), 7.80 (1H, s), 8.03 (1H, s), 8.37 (2H, d), 8.41 (1H, m); MS m/z 592 [M+H]$^+$.

Example 406

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(1-ethyl-4-piperidyl)-3-fluoro-benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 231 mg, 0.75 mmol), 4-amino-N-(1-ethylpiperidin-4-yl)-3-fluorobenzamide (200 mg, 0.75 mmol) and p-toluenesulfonic acid monohydrate (335 mg, 1.88 mmol) were suspended in 4-Methyl-2-pentanol (5 mL) and sealed into a microwave tube. The reaction was heated to 160° C. for 30 minutes in the microwave reactor and allowed to cool to room temperature.

The crude product was purified by ion exchange chromatography, using an SCX column. The desired product was eluted from the column using 7M NH3/MeOH and pure fractions were evaporated to dryness to afford an orange/brown oil which was purified by preparative HPLC using decreasingly polar mixtures of water (containing 1% NH3) and MeCN as eluents. Fractions containing the desired compound were evaporated to dryness to yield the title compound as a white solid (48 mg, 12%).

$^1$H NMR (400 MHz, DMSO-d6) δ 0.65 (t, 2H), 0.9 (t, 2H), 1.0 (t. 3H), 1.5 (m, 7H), 1.6 (m, 2H), 1.9 (t, 2H), 2.3 (q, 2H), 2.9 (d, 2H), 3.2 (s, 3H), 3.4 (s, 2H), 3.6 (m, 1H), 4.75 9m, 1H), 7.65 (m, 1H), 7.7 (m, 1H), 7.95 (s, 1H), 8.15 (m, 1H), 8.6 (s, 1H); MS m/z 537 [M+H]$^+$.

Example 407

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(1-ethyl-4-piperidyl)-2-fluoro-5-methoxy-benzamide 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 121 mg, 0.39 mmol) and 4-amino-N-(1-ethyl-4-piperidyl)-2-fluoro-5-methoxy-benzamide (Intermediate 205; 116 mg, 0.39 mmol) were taken up in 4-methyl-2-pentanol (4 mL) and p-toluenesulphonic acid monohydrate (150 mg, 0.79 mmol) added. The reaction mixture was heated at 160° C. by microwave irradiation for 1 hour. The cooled reaction mixture was poured into a mixture of methanol & water (5:2 v/v, 7 mL) and the resultant solution loaded onto an SCX-3 cartridge (5 g), which had been pre-wet with methanol. The cartridge was washed through with methanol (40 mL) and eluted with 2M ammonia in methanol (30 mL). The ammoniacal solution was evaporated to give an amber gum afforded which was purified by base modified reverse phase preparative HPLC which was re-purified by flash chromatography on a silica column eluting with 2.5-10% ammonia/methanol in DCM. Product containing fractions were combined and evaporated and the residue triturated with diethyl ether and resultant solid dried under vacuum, at 60° C., for 3 hours to yield the title compound as a flocculent white solid (86 mg, 39%)

$^1$H NMR (400.132 MHz, DMSO-d6) δ 0.67-0.70 (2H, m), 0.91-0.94 (2H, m), 1.00 (3H, t), 1.48-1.99 (14H, m), 2.32 (2H, q), 2.82-2.85 (2H, m), 3.18 (3H, s), 3.50 (2H, s), 3.69-3.79 (1H, m), 3.93 (3H, s), 4.82-4.91 (1H, m), 7.20 (1H, d), 7.76 (1H, s), 7.79-7.82 (1H, m), 8.02 (1H, s), 8.34 (1H, d); MS m/z 566 [M+H]$^+$.

Example 408

7-(9'-cyclopentyl-5'-methyl-6'-oxo-5',6',8',9'-tetrahydrospiro[cyclopropane-1,7'-pyrimido[5,4-b][1,4]diazepine]-2'-ylamino)-N-(1-methyl-4-piperidyl)benzo[1,3]dioxole-4-carboxamide To 2'-chloro-9'-cyclopentyl-5'-methyl-8',9'-dihydrospiro[cyclopropane-1,7'-pyrimido[4,5-b][1,4]diazepin]-6'(5'H)-one (Intermediate 130; 108 mg, 0.35 mmol) and 7-amino-N-(1-methylpiperidin-4-yl)benzo[d][1,3]dioxole-4-carboxamide (Intermediate 223; 98 mg, 0.35 mmol) in 4-methyl-2-pentanol (3 mL) was added p-toluenesulphonic acid monohydrate (139 mg, 0.73 mmol) and the reaction mixture heated at 160° C. by microwave irradiation for 1 hour.

After cooling the reaction mixture was diluted with MeOH (5 mL) and water (2 mL). The mixture was then submitted to ion exchange chromatography, using an SCX-2 column (10 g). After eluting through with methanol (100 mL) the crude product was eluted from the column using 2M ammonia in methanol (50 mL) and evaporated to afford a brown residue, which was purified by preparative HPLC using decreasingly polar mixtures of water (containing 1% NH3) and MeCN as eluents. Fractions containing the desired compound were evaporated to dryness to yield the title compound as a grey solid (43 mg, 22%).

$^1$H NMR (400.132 MHz, DMSO-d6) δ 0.57-0.59 (2H, m), 0.81-0.83 (2H, m), 1.31-1.60 (8H, m), 1.69-1.78 (4H, m), 1.92-1.97 (2H, m), 2.09 (3H, s), 2.58-2.65 (2H, m), 3.09 (3H, s), 3.36 (2H, s), 3.63-3.73 (1H, m), 4.71 (1H, quintet), 6.07 (2H, s), 7.14 (1H, d), 7.22 (1H, d), 7.45 (1H, d), 7.87 (1H, s), 8.51 (1H, s); MS m/z 548 [M+H]$^+$.

Example 409

4-(9'-cyclopentyl-5'-methyl-6'-oxo-5',6',8',9'-tetrahydrospiro[cyclopentane-1,7'-pyrimido[5,4-b][1,4]diazepine]-2'-ylamino)-3-methoxy-N-(1-methylpiperidin-4-yl)benzamide 2'-chloro-9'-cyclopentyl-5'-methyl-8',9'-dihydrospiro[cyclohexane-1,7'-pyrimido[5,4-b][1,4]diazepin]-6'(5'H)-one (Intermediate 255; 80 mg, 0.24 mmol), 4-amino-3-methoxy-N-(1-methyl-4-piperidyl)benzamide (WO06/018220; 63 mg, 0.24 mmol) and p-toluenesulphonic acid monohydrate (114 mg, 0.60 mmol) were heated in 4-methyl-2-pentanol (3 mL) at 140° C. for 3 hours. The mixture was cooled and absorbed on to an SCX column, which was then washed with methanol and eluted with ammonia in methanol. Product containing fractions were evaporated and the residue purified on a silica column (2% 7N ammonia in methanol/DCM) to give the title compound as a white solid. (70 mg, 52%)

$^1$H NMR (399.9 MHz, DMSO-d6) δ 1.31-1.37 (2H, m), 1.50-1.80 (14H, m), 1.89-2.06 (6H, m), 2.18 (3H, s), 2.79 (2H, d), 3.21 (3H, s), 3.43 (2H, s), 3.71-3.79 (1H, m), 3.96 (3H, s), 4.98-5.06 (1H, m), 7.47-7.51 (2H, m), 7.70 (1H, s), 8.02 (1H, s), 8.07 (1H, d), 8.38 (1H, d); MS m/z 562 [M+H]$^+$.

Example 410

3-methoxy-4-[[6-methyl-5-oxo-2-(2-oxocyclopentyl)-2,6,9,11-tetrazabicyclo[5.4.0]undeca-7,9,11-trien-10-yl]amino]-N-(1-methyl-4-piperidyl)benzamide 10-chloro-6-methyl-2-(2-oxocyclopentyl)-2,6,9,11-tetrazabicyclo[5.4.0]undeca-7,9,11-trien-5-one (Intermediate 261; 58 mg, 0.19 mmol), 4-amino-3-methoxy-N-(1-methyl-4-piperidyl)benzamide (WO06/018220; 53 mg, 0.20 mmol) and p-toluene sulphonic acid monohydrate (80 mg, 0.42 mmol) were dissolved in 4-methyl-2-pentanol (2 mL) and heated by microwave irradiation at 150° C. for 30 minutes. After cooling, the reaction mixture was dissolved in methanol (5 mL) and water (5 mL) and poured directly onto an SCX-3 cartridge (5 g). The cartridge was washed with methanol (50 mL), before elution of products with 2M ammonia in methanol (50 mL). The ammoniacal fraction was evaporated and the residue was purified by base modified reverse phase preparative HPLC to yield the title compound as a yellow solid (11 mg, 7%).

$^1$H NMR (400.132 MHz, DMSO-d6) δ 1.60 (m, 2H), 1.73-2.09 (m, 8H), 2.17 (s, 3H), 2.25 (m, 2H), 2.62 (m, 2H), 2.78 (m, 2H), 3.19 (s, 3H), 3.60 (m, 2H), 3.74 (m, 1H), 3.93 (s, 3H), 4.67 (m, 1H), 7.48 (m, 2H), 7.74 (s, 1H), 8.06 (d, 1H), 8.13 (s, 1H), 8.18 (d, 1H); MS m/z 522 [M+H]$^+$.

Example 411

2-chloro-4-[(2-cyclohexyl-6-methyl-5-oxo-2,6,9,11-tetrazabicyclo[5.4.0]undeca-7,9,11-trien-10-yl)amino]-5-fluoro-N-(1-methyl-4-piperidyl)benzamide 2-amino-9-cyclohexyl-5-methyl-8,9-dihydro-5H-pyrimido[5,4-b][1,4]diazepin-6(7H)-one (Intermediate 263; 100 mg, 0.36 mmol), 4-bromo-2-chloro-5-fluoro-N-(1-methylpiperidin-4-yl)benzamide (Intermediate 262; 133 mg, 0.38 mmol), xantphos (12.61 mg, 0.02 mmol), palladium(II) acetate (163 mg, 0.73 mmol) and caesium carbonate (14.20 mg, 0.04 mmol) were added to dioxane (10 mL) and heated at 103° C. overnight. The resulting solution was filtered and passed through a 5 g SCX-3 column. The obtained yellow foam was triturated with hot ethyl acetate to afford a yellow solid.

$^1$H NMR (400.132 MHz, DMSO-d6) δ 1.16-1.08 (m, 1H), 1.43-1.35 (m, 2H), 1.63-1.48 (m, 5H), 1.80-1.71 (m, 6H), 2.08-1.99 (m, 2H), 2.19 (s, 3H), 2.59-2.56 (m, 2H), 2.78-2.75 (m, 2H), 3.17 (s, 3H), 3.71-3.60 (m, 3H), 4.41-4.36 (m, 1H), 7.30 (d, 1H), 8.06 (s, 1H), 8.16 (d, 1H), 8.26 (d, 1H), 8.78 (s, 1H); MS m/z 544 [M+H]$^+$.

Example 412

4-[(2-cyclohexyl-6-methyl-5-oxo-2,6,9,11-tetrazabicyclo[5.4.0]undeca-7,9,11-trien-10-yl)amino]-2,5-difluoro-N-(1-methyl-4-piperidyl)benzamide 10-chloro-2-cyclohexyl-6-methyl-2,6,9,11-tetrazabicyclo[5.4.0]undeca-7,9,11-trien-5-one (Intermediate 266; 33 mg, 0.113 mmol), 4-amino-2,5-difluoro-N-(1-methyl-4-piperidyl)benzamide (Intermediate 59; 29 mg, 0.108 mmol) and caesium carbonate were added to dioxane (3 mL) and the suspension bubbled with nitrogen for 10 minutes. tris(dibenzylideneacetone) palladium (II) (4 mg, 0.006 mmol) and XANTPHOS (6 mg, 0.1 mmol) were added and the mixture heated at 100° C. for 16 hours. The reaction mixture was cooled to room temperature and filtered. The filter-cake was washed with DCM and the filtrate evaporated. The residue was dissolved in DCM and purified on a silica column eluting with a gradient of 0-5% 2M ammonia in MeOH/DCM over 30 column volumes. Fractions containing product were combined and evaporated to a solid, which was triturated with isohexane then filtered and dried to yield the title compound as a pale yellow solid (46 mg, 81%).

¹H NMR (399.902 MHz, CDCl₃) δ1118 (m, 1H), 1.57 (m, 6H), 1.78 (m, 1H), 1.91 (m, 4H), 2.06 (m, 2H), 2.17 (m, 2H), 2.30 (s, 3H), 2.68 (m, 2H), 2.80 (m, 2H), 3.29 (s, 3H), 3.71 (m, 2H), 4.01 (m, 1H), 4.48 (m, 1H), 6.58 (m, 1H), 7.29 (m, 1H), 7.82 (m, 1H), 7.94 (s, 1H), 8.38 (m, 1H); MS m/z 528 [M+H]⁺.

Example 413

4-[(2-cyclohexyl-6-methyl-5-oxo-2,6,9,11-tetrazabi-cyclo[5.4.0]undeca-7,9,11-trien-10-yl)amino]-2,5-difluoro-N-[[1-(pyrrolidin-1-ylmethyl)cyclopropyl]methyl]benzamide The title compound was prepared by an analogous method to the preparation of Example 411, utilising 4-amino-2,5-difluoro-N-[[1-(pyrrolidin-1-ylmethyl)cyclopropyl]methyl]benzamide (Intermediate 269; 50 mg, 0.161 mmol) triturating the final product with diethyl ether prior to filtration and drying, as a white solid (42 mg, 46%).

¹H NMR (399.902 MHz, CDCl₃) δ0.39 (m, 2H), 0.57 (m, 2H), 1.17 (m, 1H), 1.54 (m, 4H), 1.75 (m, 5H), 1.92 (m, 4H), 2.49 (s, 2H), 2.54 (m, 4H), 2.68 (m, 2H), 3.29 (s, 3H), 3.46 (m, 2H), 3.72 (m, 2H), 4.50 (m, 1H), 7.29 (m, 1H), 7.83 (m, 1H), 7.94 (s, 1H), 8.32 (m, 1H), 8.64 (m, 1H); MS m/z 569 [M+H]⁺.

Example 414

4-[(2-cyclohexyl-6-methyl-5-oxo-2,6,9,11-tetrazabi-cyclo[5.4.0]undeca-7,9,11-trien-10-yl)amino]-2,5-difluoro-N-[(3R)-1-methylpyrrolidin-3-yl]benzamide The title compound was prepared by an analogous method to the preparation of Example 411, utilising 4-amino-2,5-difluoro-N-[(3R)-1-methylpyrrolidin-3-yl]benzamide (Intermediate 229; 41 mg, 0.161 mmol) triturating the final product with diethyl ether prior to filtration and drying, as a white solid (49 mg, 59%).

¹H NMR (399.902 MHz, CDCl₃) δ1118 (m, 1H), 1.54 (m, 4H), 1.76 (m, 2H), 1.91 (m, 4H), 2.29 (m, 1H), 2.42 (m, 4H), 2.68 (m, 4H), 2.90 (m, 1H), 3.29 (s, 3H), 3.72 (m, 2H), 4.48 (m, 1H), 4.66 (m, 1H), 6.94 (m, 1H), 7.29 (m, 1H), 7.81 (m, 1H), 7.94 (s, 1H), 8.37 (m, 1H); MS m/z 514 [M+H]⁺.

Example 415

4-[(2-cyclohexyl-6-methyl-5-oxo-2,6,9,11-tetrazabi-cyclo[5.4.0]undeca-7,9,11-trien-10-yl)amino]-N-(1-ethyl-4-piperidyl)-2,5-difluoro-benzamide The title compound was prepared by an analogous method to the preparation of Example 411, utilising 4-amino-N-(1-ethyl-4-piperidyl)-2,5-difluoro-benzamide (Intermediate 235; 46 mg, 0.161 mmol) triturating the final product with diethyl ether prior to filtration and drying, as a white solid (60 mg, 69%).

¹H NMR (399.902 MHz, CDCl₃) δ1110 (t, 3H), 1.18 (m, 1H), 1.55 (m, 6H), 1.78 (m, 1H), 1.91 (m, 4H), 2.11 (m, 4H), 2.43 (q, 2H), 2.68 (m, 2H), 2.89 (m, 2H), 3.29 (s, 3H), 3.71 (m, 2H), 4.04 (m, 1H), 4.48 (m, 1H), 6.59 (m, 1H), 7.28 (m, 1H), 7.82 (m, 1H), 7.94 (s, 1H), 8.38 (m, 1H); MS m/z 542 [M+H]⁺.

Example 416

4-[(2-cyclohexyl-6-methyl-5-oxo-2,6,9,11-tetrazabi-cyclo[5.4.0]undeca-7,9,11-trien-10-yl)amino]-2,5-difluoro-N-(2-pyrrolidin-1-ylethyl)benzamide The title compound was prepared by an analogous method to the preparation of Example 411, utilising 4-amino-2,5-difluoro-N-(2-pyrrolidin-1-ylethyl)benzamide (Intermediate 230; 43 mg, 0.161 mmol) triturating the final product with diethyl ether prior to filtration and drying, as a white solid (64 mg, 76%).

¹H NMR (399.902 MHz, CDCl₃) δ1118 (m, 1H), 1.54 (m, 4H), 1.77 (m, 5H), 1.90 (m, 4H), 2.57 (m, 4H), 2.70 (m, 4H), 3.29 (s, 3H), 3.58 (m, 2H), 3.71 (m, 2H), 4.49 (m, 1H), 7.29 (m, 2H), 7.82 (m, 1H), 7.94 (s, 1H), 8.39 (m, 1H); MS m/z 526 [M+H]⁺.

Example 417

4-[(2-cyclohexyl-6-methyl-5-oxo-2,6,9,11-tetrazabi-cyclo[5.4.0]undeca-7,9,11-trien-10-yl)amino]-3-fluoro-N-[(1S,5R)-9-methyl-9-azabicyclo[3.3.1]non-7-yl]benzamide The title compound was prepared by an analogous method to the preparation of Example 411, utilising 4-amino-3-fluoro-N-[(1S,5R)-9-methyl-9-azabicyclo[3.3.1]non-7-yl]benzamide (Intermediate 162; 150 mg, 0.515 mmol), the final product being taken up in methanol (1 mL) diluted with water and freeze dried, as a cream coloured solid (201 mg, 71%).

¹H NMR (399.902 MHz, CDCl₃) d1.06 (m, 2H), 1.18 (m, 1H), 1.33 (m, 2H), 1.52 (m, 4H), 1.77 (m, 1H), 1.95 (m, 8H), 2.52 (m, 5H), 2.67 (m, 2H), 3.11 (m, 2H), 3.29 (s, 3H), 3.70 (m, 2H), 4.49 (m, 2H), 5.75 (d, 1H), 7.24 (m, 1H), 7.52 (m, 2H), 7.92 (s, 1H), 8.56 (m, 1H); MS m/z 550 [M+H]⁺.

Example 418

4-[(2-cyclohexyl-6-methyl-5-oxo-2,6,9,11-tetrazabi-cyclo[5.4.0]undeca-7,9,11-trien-10-yl)amino]-3-methoxy-N-[(1R,5S)-9-methyl-9-azabicyclo[3.3.1]non-7-yl]benzamide The title compound was prepared by an analogous method to the preparation of Example 411, utilising 4-amino-3-methoxy-N-[(1S,5R)-9-methyl-9-azabicyclo[3.3.1]non-3-yl]benzamide (Intermediate 202; 154 mg, 0.509 mmol), the final product being purified by base modified reverse phase preparative HPLC, as a white solid (137 mg, 48%).

¹H NMR (399.902 MHz, CDCl₃) d1.04 (m, 2H), 1.19 (m, 1H), 1.31 (m, 2H), 1.53 (m, 6H), 1.79 (m, 1H), 1.96 (m, 6H), 2.54 (m, 5H), 2.67 (m, 2H), 3.10 (m, 2H), 3.28 (s, 3H), 3.70 (m, 2H), 3.97 (s, 3H), 4.50 (m, 2H), 5.77 (d, 1H), 7.25 (m, 1H), 7.40 (d, 1H), 7.69 (s, 1H), 7.91 (s, 1H), 8.49 (d, 1H); MS m/z 562 [M+H]⁺.

Example 419

4-[(2-cyclohexyl-6-methyl-5-oxo-2,6,9,11-tetrazabi-cyclo[5.4.0]undeca-7,9,11-trien-10-yl)amino]-2-fluoro-5-methoxy-N-[[1-(pyrrolidin-1-ylmethyl)cyclopropyl]methyl]benzamide The title compound was prepared by an analogous method to the preparation of Example 411, utilising 4-amino-2-fluoro-5-methoxy-N-[[1-(pyrrolidin-1-ylmethyl)cyclopropyl]methyl]benzamide (Intermediate 254; 65 mg, 0.204 mmol), the final product being purified by base modified reverse phase preparative HPLC, as a white solid (4 mg, 3%).

MS m/z 580 [M+H]$^+$. Retention time 3.69 minutes

Example 420

4-[(2-cyclohexyl-6-methyl-5-oxo-2,6,9,11-tetrazabicyclo[5.4.0]undeca-7,9,11-trien-10-yl)amino]-2-fluoro-5-methoxy-N-[(3R)-1-methylpyrrolidin-3-yl]benzamide The title compound was prepared by an analogous method to the preparation of Example 411, utilising 4-amino-2-fluoro-5-methoxy-N-[(3R)-1-methylpyrrolidin-3-yl]benzamide (Intermediate 182; 55 mg, 0.204 mmol), the final product being purified by base modified reverse phase preparative HPLC, as a white solid (20 mg, 19%).

$^1$H NMR (399.902 MHz, CDCl$_3$) δ1.20 (m, 1H), 1.56 (m, 4H), 1.78 (m, 2H), 1.92 (m, 4H), 2.32 (m, 1H), 2.43 (m, 4H), 2.68 (m, 4H), 2.89 (m, 1H), 3.28 (s, 3H), 3.72 (m, 2H), 3.95 (s, 3H), 4.52 (m, 1H), 4.67 (m, 1H), 7.00 (m, 1H), 7.56 (m, 1H), 7.76 (s, 1H), 7.92 (s, 1H), 8.31 (d, 1H); MS m/z 526 [M+H]$^+$.

Example 421

4-[(2-cyclohexyl-6-methyl-5-oxo-2,6,9,11-tetrazabicyclo[5.4.0]undeca-7,9,11-trien-10-yl)amino]-3-methoxy-N-[(3R)-1-methylpyrrolidin-3-yl]benzamide The title compound was prepared by an analogous method to the preparation of Example 411, utilising 4-amino-3-methoxy-N-(1-methylpyrrolidin-3-yl)benzamide (Intermediate 187; 51 mg, 0.204 mmol), the final product being purified by base modified reverse phase preparative HPLC, as a white solid (37 mg, 36%).

$^1$H NMR (399.902 MHz, CDCl$_3$) δ1.22 (m, 1H), 1.52 (m, 4H), 1.77 (m, 2H), 1.94 (m, 4H), 2.23 (m, 1H), 2.44 (m, 4H), 2.56 (m, 1H), 2.67 (m, 2H), 2.81 (m, 1H), 2.98 (m, 1H), 3.28 (s, 3H), 3.70 (m, 2H), 3.97 (s, 3H), 4.51 (m, 1H), 4.70 (m, 1H), 6.48 (d, 1H), 7.31 (m, 1H), 7.41 (m, 1H), 7.70 (s, 1H), 7.91 (s, 1H), 8.49 (d, 1H); MS m/z 508 [M+H]$^+$.

Example 422

4-[(2-cyclohexyl-6-methyl-5-oxo-2,6,9,11-tetrazabicyclo[5.4.0]undeca-7,9,11-trien-10-yl)amino]-N-(1-ethyl-4-piperidyl)-2-fluoro-5-methoxy-benzamide The title compound was prepared by an analogous method to the preparation of Example 411, utilising 4-amino-N-(1-ethyl-4-piperidyl)-2-fluoro-5-methoxy-benzamide (Intermediate 205; 60 mg, 0.204 mmol), the final product being purified by base modified reverse phase preparative HPLC, as a white solid (27 mg, 24%).

$^1$H NMR (399.902 MHz, CDCl$_3$) δ1.10 (t, 3H), 1.21 (m, 1H), 1.55 (m, 6H), 1.78 (m, 1H), 1.92 (m, 4H), 2.12 (m, 4H), 2.43 (q, 2H), 2.68 (m, 2H), 2.89 (m, 2H), 3.28 (s, 3H), 3.71 (m, 2H), 3.95 (s, 3H), 4.05 (m, 1H), 4.52 (m, 1H), 6.67 (m, 1H), 7.56 (d, 1H), 7.74 (s, 1H), 7.92 (s, 1H), 8.32 (d, 1H); MS m/z 554 [M+H]$^+$.

Example 423

4-[(2-cyclohexyl-6-methyl-5-oxo-2,6,9,11-tetrazabicyclo[5.4.0]undeca-7,9,11-trien-10-yl)amino]-N-(1-ethyl-4-piperidyl)-3-methoxy-benzamide The title compound was prepared by an analogous method to the preparation of Example 411, utilising 4-amino-N-(1-ethyl-4-piperidyl)-3-methoxy-benzamide (Intermediate 190; 57 mg, 0.204 mmol), the final product being purified by base modified reverse phase preparative HPLC, as a white solid (61 mg, 56%).

$^1$H NMR (399.902 MHz, CDCl$_3$) δ1.11 (t, 3H), 1.21 (m, 1H), 1.54 (m, 6H), 1.78 (m, 1H), 1.94 (m, 4H), 2.12 (m, 4H), 2.44 (q, 2H), 2.67 (m, 2H), 2.92 (m, 2H), 3.28 (s, 3H), 3.70 (m, 2H), 3.97 (s, 3H), 4.03 (m, 1H), 4.50 (m, 1H), 5.88 (d, 1H), 7.23 (m, 1H), 7.39 (m, 1H), 7.68 (s, 1H), 7.91 (s, 1H), 8.50 (d, 1H); MS m/z 536 [M+H]$^+$.

Example 424

4-[(2-cyclohexyl-6-methyl-5-oxo-2,6,9,11-tetrazabicyclo[5.4.0]undeca-7,9,11-trien-10-yl)amino]-N-(3-dimethylaminopropyl)-3-methoxy-benzamide The title compound was prepared by an analogous method to the preparation of Example 411, utilising 4-amino-N-(3-dimethylaminopropyl)-3-methoxy-benzamide (Intermediate 196; 51 mg, 0.204 mmol), the final product being purified by base modified reverse phase preparative HPLC, as a white solid (50 mg, 48%).

$^1$H NMR (399.902 MHz, CDCl$_3$) δ1.22 (m, 1H), 1.54 (m, 4H), 1.76 (m, 3H), 1.95 (m, 4H), 2.30 (s, 6H), 2.51 (m, 2H), 2.67 (m, 2H), 3.28 (s, 3H), 3.58 (m, 2H), 3.70 (m, 2H), 3.97 (s, 3H), 4.53 (m, 1H), 7.27 (m, 1H), 7.48 (m, 1H), 7.72 (s, 1H), 7.91 (s, 1H), 8.38 (m, 1H), 8.50 (d, 1H); MS m/z 510 [M+H]$^+$.

Example 425

4-[(2-cyclohexyl-6-methyl-5-oxo-2,6,9,11-tetrazabicyclo[5.4.0]undeca-7,9,11-trien-10-yl)amino]-2-fluoro-5-methoxy-N-(2-pyrrolidin-1-ylethyl)benzamide The title compound was prepared by an analogous method to the preparation of Example 411, utilising 4-amino-2-fluoro-5-methoxy-N-(2-pyrrolidin-1-ylethyl)benzamide (Intermediate 228; 57 mg, 0.204 mmol), the final product being purified by base modified reverse phase preparative HPLC, as a white solid (19 mg, 17%).

$^1$H NMR (399.902 MHz, CDCl3) δ1.20 (m, 1H), 1.56 (m, 4H), 1.77 (m, 5H), 1.91 (m, 4H), 2.58 (m, 4H), 2.70 (m, 4H), 3.28 (s, 3H), 3.60 (m, 2H), 3.71 (m, 2H), 3.95 (s, 3H), 4.53 (m, 1H), 7.32 (m, 1H), 7.57 (d, 1H), 7.73 (s, 1H), 7.92 (s, 1H), 8.33 (d, 1H); MS m/z 540 [M+H]$^+$.

Example 426

4-[(2-cyclohexyl-6-methyl-5-oxo-2,6,9,11-tetrazabicyclo[5.4.0]undeca-7,9,11-trien-10-yl)amino]-N-(2-dimethylaminoethyl)-3-methoxy-benzamide The title compound was prepared by an analogous method to the preparation of Example 411, utilising 4-amino-N-(2-dimethylaminoethyl)-3-methoxy-benzamide (Intermediate 194; 48 mg, 0.204 mmol), the final product being purified by base modified reverse phase preparative HPLC, as a white solid (31 mg, 31%).

¹H NMR (399.902 MHz, CDCl₃) δ1.22 (m, 1H), 1.54 (m, 4H), 1.76 (m, 1H), 1.94 (m, 4H), 2.29 (s, 6H), 2.54 (m, 2H), 2.67 (m, 2H), 3.28 (s, 3H), 3.53 (m, 2H), 3.70 (m, 2H), 3.97 (s, 3H), 4.51 (m, 1H), 6.74 (m, 1H), 7.32 (m, 1H), 7.43 (m, 1H), 7.67 (s, 1H), 7.91 (s, 1H), 8.50 (d, 1H); MS m/z 496 [M+H]⁺.

Example 427

4-[(2-cyclohexyl-6-methyl-5-oxo-2,6,9,11-tetrazabicyclo[5.4.0]undeca-7,9,11-trien-10-yl)amino]-2-fluoro-5-methoxy-N-[(1R,5S)-9-methyl-9-azabicyclo[3.3.1]non-7-yl]benzamide The title compound was prepared by an analogous method to the preparation of Example 411, utilising 4-amino-2-fluoro-5-methoxy-N-[(1S,5R)-9-methyl-9-azabicyclo[3.3.1]non-7-yl]benzamide (Intermediate 204; 65 mg, 0.204 mmol), the final product being purified by base modified reverse phase preparative HPLC, as a white solid (52 mg, 44%).

¹H NMR (399.902 MHz, CDCl₃) δ1.04 (m, 2H), 1.21 (m, 1H), 1.32 (m, 2H), 1.56 (m, 6H), 1.79 (m, 1H), 1.95 (m, 6H), 2.54 (m, 5H), 2.68 (m, 2H), 3.09 (m, 2H), 3.28 (s, 3H), 3.72 (m, 2H), 3.95 (s, 3H), 4.53 (m, 2H), 6.53 (m, 1H), 7.59 (d, 1H), 7.75 (s, 1H), 7.93 (s, 1H), 8.31 (d, 1H); MS m/z 580 [M+H]⁺.

Example 428

4-[(2-cyclohexyl-6-methyl-5-oxo-2,6,9,11-tetrazabicyclo[5.4.0]undeca-8,10,12-trien-10-yl)amino]-2-fluoro-N-(1-methyl-4-piperidyl)benzamide 10-chloro-2-cyclohexyl-6-methyl-2,6,9,11-tetrazabicyclo[5.4.0]undeca-8,10,12-trien-5-one (Intermediate 267; 89 mg, 0.3 mmol) and 4-amino-3-fluoro-N-(1-methyl-4-piperidyl)benzamide (Intermediate 61; 76 mg, 0.3 mmol) were combined with p-toluenesulphonic acid monohydrate (143 mg, 0.75 mmol) in 4-methyl-2-pentanol (2 mL) and heated by microwave irradiation for 30 minutes at 160° C. The cooled reaction mixture was diluted with methanol (10 mL) and filtered and the filtrate loaded onto an SCX-3 cartridge (5 g) pre-wet with methanol. The cartridge was washed with methanol (2×10 mL) and eluted with 7 N methanolic ammonia (20 mL). The basic fraction was evaporated to give a yellow solid, which was purified by base modified reverse phase preparative HPLC to yield the title compound as a white solid (55 mg, 37%).

¹H NMR (400 MHz, DMSO-d6) δ1.15 (m, 2H), 1.45 (m, 3H), 1.6 (m, 4H), 1.7 (m, 1H), 1.8 (m, 6H), 1.95 (t, 2H), 2.15 (s, 3H), 2.6 (m, 2H), 2.7 (m, 2H), 3.15 (s, 3H), 3.65 (m, 2H), 3.7 (m, 1H), 4.4 (t, 1H), 7.5 (m, 2H), 7.7 (m, 2H), 8.1 (s, 1H), 9.6 (s, 1H); MS m/z 511 [M+H]⁺.

Example 429

4-[(2-cyclohexyl-6-methyl-5-oxo-2,6,9,11-tetrazabicyclo[5.4.0]undeca-8,10,12-trien-10-yl)amino]-3-fluoro-N-(1-methyl-4-piperidyl)benzamide 10-chloro-2-cyclohexyl-6-methyl-2,6,9,11-tetrazabicyclo[5.4.0]undeca-8,10,12-trien-5-one (Intermediate 267; 89 mg, 0.3 mmol) and 4-amino-3-fluoro-N-(1-methyl-4-piperidyl)benzamide (Intermediate 65; 76 mg, 0.3 mmol) were combined with p-toluenesulphonic acid monohydrate (143 mg, 0.75 mmol) in 4-methyl-2-pentanol (2 mL) and heated by microwave irradiation for 30 minutes at 160° C. The cooled reaction mixture was diluted with methanol (10 mL) and filtered and the filtrate loaded onto an SCX-3 cartridge (5 g) pre-wet with methanol. The cartridge was washed with methanol (2×10 mL) and eluted with 7 N methanolic ammonia (20 mL). The basic fraction was evaporated to give a yellow gum, which was purified by base modified reverse phase preparative HPLC to give the title compound as a white solid (56 mg, 37%).

¹H NMR (400 MHz, DMSO-d6) δ1.1 (m, 1H), 1.3 (q, 2H), 1.55 (m, 5H), 1.75 (m, 6H), 1.95 (t, 2H), 2.2 (s, 3H), 2.6 (m, 2H), 2.75 (d, 2H), 3.2 (s, 3H), 2.6 (m, 2H), 2.75 (d, 2H), 3.2 (s, 3H), 3.6 (m, 2H), 3.7 (m, 1H), 4.3 (m, 1H), 7.65 (m, 1H), 7.7 (m, 1H), 8.0 (s, 1H), 8.1 (m, 2H), 8.7 (s, 1H); MS m/z 511 [M+H]⁺.

Example 430

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-3-methoxy-N-(1-methyl-4-piperidyl)benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 100 mg, 0.31 mmol), 4-amino-3-methoxy-N-(1-methyl-4-piperidyl)benzamide (WO06/018220; 83 mg, 0.31 mmol) and p-toluenesulphonic acid monohydrate (149 mg, 0.78 mmol) were heated at 140° C. in 4-methyl-2-pentanol (4 mL) for 2 hours. The reaction mixture was loaded onto an SCX-3 column was pre-wet with methanol and the column washed with methanol and eluted with 2% 7N ammonia/methanol. The ammoniacal fraction was evaporated and the residue purified by base modified reverse phase preparative HPLC to yield the title compound as a white solid (97 mg, 57%)

¹H NMR (399.9 MHz, DMSO-d6) δ0.68-0.71 (2H, t), 0.92-0.95 (2H, t), 1.40-1.50 (4H, m), 1.59-1.63 (2H, m), 1.65-1.68 (1H, m), 1.77 (2H, s), 1.79 (4H, t), 1.86 (1H, s), 1.93-1.98 (2H, m), 2.18 (3H, s), 2.80 (2H, d), 3.17 (3H, s), 3.51 (2H, s), 3.70-3.76 (1H, m), 3.96 (3H, s), 4.45 (1H, m), 7.46 (1H, m), 7.48-7.51 (1H, d), 7.67 (1H, s), 7.96 (1H, s), 8.09 (1H, d), 8.39 (1H, d); MS m/z 547 [M+H]⁺.

Example 431

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-N-(3-dimethylaminopropyl)-3-methoxy-benzamide The title compound was prepared by an analogous method to the preparation of Example 430, utilising 4-amino-N-(3-dimethylaminopropyl)-3-methoxy-benzamide (Intermediate 196; 79 mg, 0.31 mmol), as a white solid (96 mg, 58%).

¹H NMR (399.9 MHz, DMSO-d6) δ0.68-0.71 (2H, t), 0.92-0.95 (2H, t), 1.47-1.51 (2H, m), 1.68 (4H, q), 1.76-1.78 (4H, m), 1.85 (2H, d), 2.15 (6H, s), 2.28 (2H, t), 3.17 (3H, s), 3.25 (2H, t), 3.51 (2H, s), 3.96 (3H, s), 4.45 (1H, m), 7.45-7.47 (1H, m), 7.51 (1H, d), 7.67 (1H, s), 7.96 (1H, s), 8.40 (1H, d), 8.41 (1H, d); MS m/z 537 [M+H]⁺.

Example 432

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-3-methoxy-N-[(1S,5R)-9-methyl-9-azabicyclo[3.3.1]non-7-yl]benzamide The title compound was prepared by an analogous method to the preparation of Example 430, utilising 4-amino-3-methoxy-N-[(1S,5R)-9-methyl-9-azabicyclo[3.3.1]non-3-yl]benzamide (Intermediate 202; 95 mg, 0.31 mmol), as a white solid (111 mg, 61%).

$^1$H NMR (399.9 MHz, DMSO-d6) δ0.68-0.71 (2H, m), 0.93 (2H, d), 0.93 (2H, d), 1.42 (2H, d), 1.45-1.47 (3H, m), 1.49 (2H, d), 1.77 (4H, d), 1.85 (4H, d), 1.93 (2H, t), 2.21 (1H, d), 2.42 (3H, s), 2.99 (2H, d), 3.17 (3H, s), 3.51 (2H, s), 3.98 (3H, s), 4.29-4.34 (1H, m), 4.45 (1H, m), 7.47 (1H, d), 7.48-7.52 (1H, s), 7.67 (1H, s), 7.92 (1H, d), 7.97 (1H, s), 8.39-8.41 (1H, d); MS m/z 589 [M+H]$^+$.

Example 433

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-N-(1-ethyl-4-piperidyl)-3-methoxy-benzamide The title compound was prepared by an analogous method to the preparation of Example 430, utilising 4-amino-N-(1-ethyl-4-piperidyl)-3-methoxy-benzamide (Intermediate 190; 87 mg, 0.31 mmol), as a white solid (122 mg, 70%).

$^1$H NMR (399.9 MHz, DMSO-d6) δ0.68-0.71 (2H, t), 0.92-0.95 (2H, t), 1.01 (3H, t), 1.45 (3H, t), 1.57-1.61 (2H, m), 1.77 (4H, d), 1.82-1.86 (3H, m), 1.88 (2H, t), 1.93 (2H, d), 2.33 (2H, q), 2.90 (2H, d), 3.17 (3H, s), 3.51 (2H, s), 3.74-3.78 (1H, m), 3.96 (3H, s), 4.41-4.45 (1H, m), 7.46 (1H, d), 7.48-7.51 (1H, m), 7.67 (1H, s), 7.96 (1H, s), 8.09 (1H, d), 8.39-8.41 (1H, m); MS m/z 563 [M+H]$^+$.

Example 434

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-N-(1-ethyl-4-piperidyl)-2,5-difluoro-benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 100 mg, 0.31 mmol), 4-amino-N-(1-ethyl-4-piperidyl)-2,5-difluoro-benzamide (Intermediate 235; 98 mg, 0.34 mmol) and caesium carbonate (204 mg, 0.62 mmol) added to dioxane (5 mL) and the suspension bubbled with nitrogen for 10 minutes. Tris(dibenzylideneacetone) palladium (II) (18 mg, 0.02 mmol) and XANTPHOS (17 mg, 0.03 mmol) added and the mixture heated at 110° C. overnight. The mixture was filtered and the filtrate loaded onto an SCX-3 column was pre-wet with methanol and the column washed with methanol and eluted with 2% 7N ammonia/methanol. The ammoniacal fraction was evaporated and the residue purified by base modified reverse phase preparative HPLC to yield the title compound as a white crystalline solid (19 mg, 11%).

$^1$H NMR (399.9 MHz, DMSO-d6) δ0.69-0.72 (2H, t), 0.93-0.96 (2H, t), 1.00 (3H, t), 1.42 (2H, t), 1.48 (2H, d), 1.49-1.54 (2H, m), 1.63 (2H, d), 1.70 (2H, d), 1.78 (4H, s), 1.95 (2H, d), 2.30-2.35 (2H, m), 2.84 (2H, d), 3.17 (3H, s), 3.50 (2H, s), 3.75 (1H, m), 4.46 (1H, m), 7.41-7.45 (1H, m), 7.98 (1H, d), 7.99 (1H, s), 8.13-8.18 (1H, m), 8.79 (1H, s); MS m/z 589 [M+H]$^+$.

Example 435

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-3-fluoro-N-[(1S,5R)-9-methyl-9-azabicyclo[3.3.1]non-7-yl]benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 97 mg, 0.3 mmol) and 4-amino-3-fluoro-N-(9-methyl-9-azabicyclo[3.3.1]non-7-yl)benzamide (Intermediate 162; 88 mg, 0.3 mmol) were combined with p-toluenesulphonic acid monohydrate (143 mg, 0.75 mmol) in 4-methyl-2-pentanol (2 mL) and heated by microwave irradiation for 30 minutes at 160° C. The cooled reaction mixture was diluted with methanol (5 mL) and loaded onto an SCX-3 (5 g) cartridge pre-wet with methanol. The cartridge was washed with methanol (2×10 mL) and product eluted with 7 N methanolic ammonia (20 mL). Product containing fractions were evaporated and the resultant material purified by base modified reverse phase preparative HPLC to yield the title compound as a white solid (82 mg, 48%).

$^1$H NMR (400 MHz, DMSO-d6) δ0.7 (m, 2H), 0.95 (m, 4H), 1.15 (m, 1H), 1.35 (m, 2H), 1.45 (m, 4H), 1.7 (m, 4H), 1.8 (d, 2H), 1.95 (m, 2H), 2.05 (m, 1H), 2.15 (m, 2H), 2.9 (s, 3H), 2.95 (d, 2H), 3.15 (s, 3H), 3.45 (s, 2H), 4.35 (m, 2H), 7.65 (m, 1H), 7.7 (m, 1H), 7.9 (s, 1H), 7.95 (m, 1H), 8.2 (t, 1H), 8.55 (s, 1H); MS m/z 576 [M+H]$^+$.

Example 436

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-2,5-difluoro-N-(1-methyl-4-piperidyl)benzamide The title compound was prepared by an analogous method to the preparation of Example 434, utilising 4-amino-2,5-difluoro-N-(1-methyl-4-piperidyl)benzamide (Intermediate 59; 93 mg, 0.34 mmol), as a white solid (76 mg, 44%).

$^1$H NMR (399.9 MHz, DMSO-d6) δ0.69-0.72 (2H, t), 0.93-0.96 (2H, t), 1.44 (4H, m), 1.54-1.61 (2H, m), 1.71 (2H, d), 1.78 (4H, d), 1.94-1.99 (2H, m), 2.17 (3H, s), 2.73 (2H, d), 3.17 (3H, s), 3.29 (2H, d), 3.50 (2H, s), 3.65-3.72 (1H, m), 4.46 (1H, m), 7.41-7.45 (1H, m), 7.96 (1H, d), 7.98 (1H, s), 8.13-8.18 (1H, m), 8.78 (1H, s); MS m/z 554 [M+H]$^+$.

Example 437

5-chloro-4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-N-(4-dimethylaminocyclohexyl)-2-fluoro-benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 103 mg, 0.32 mmol), 4-amino-5-chloro-N-(4-dimethylaminocyclohexyl)-2-fluoro-benzamide (Intermediate 175; 92 mg, 0.29 mmol), and XANTPHOS (16 mg, 0.03 mmol) were dissolved in 1,4-dioxane (7.5 mL). Caesium carbonate (210 mg, 0.59 mmol) was added and the system purged with a stream of nitrogen for 15 minutes before tris(dibenzylideneacetone) palladium (II) (17 mg, 0.02 mmol)

was added. The apparatus was evacuated and backfilled with nitrogen (×3) and then heated at 100° C. for 3 hours. The mixture was cooled, filtered and the filtrate absorbed on to an SCX column, and the column then washed with methanol and eluted with ammonia in methanol. Product containing fractions were combined and evaporated and the residue purified by base modified reverse phase preparative HPLC to yield the title compound as a white solid (49 mg, 28%).

$^1$H NMR (399.9 MHz, DMSO-d6) δ 0.71 (2H, m), 0.94 (2H, m), 1.10 (2H, m), 1.25-1.84 (16H, m), 2.09-2.19 (7H, m), 3.18 (3H, s), 3.52 (2H, s), 3.63-3.70 and 3.88-3.94 (each 0.5H, m), 4.43 (1H, m), 7.67 (1H, d), 8.00-8.04 (3H, m), 8.27 (1H, d); MS m/z 598 [M+H]$^+$.

Example 438

4-(9'-cyclohexyl-5'-methyl-6'-oxo-5',6',8',9'-tetrahydrospiro[cyclopropane-1,7'-pyrimido[5,4-b][1,4] diazepine]-2'-ylamino)-2-fluoro-5-methoxy-N-[(3R)-1-methylpyrrolidin-3-yl]benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 103 mg, 0.32 mmol), 4-amino-2-fluoro-5-methoxy-N-[(3R)-1-methylpyrrolidin-3-yl]benzamide (Intermediate 182; 87 mg, 0.32 mmol) and p-toluenesulphonic acid monohydrate (154 mg, 0.81 mmol) were heated in 4-methyl-2-pentanol (3 mL) at 140° C. for 3 hours. The mixture was cooled and absorbed on to an SCX column, which was then washed with methanol and eluted with ammonia in methanol. Product containing fractions were combined and evaporated and purified by base modified reverse phase preparative HPLC to yield the title compound as a white solid (70 mg, 40%).

$^1$H NMR (399.9 MHz, DMSO-d6) δ 0.70-0.73 (2H, m), 0.93-0.96 (2H, m), 1.10 1.20 (1H, m), 1.40-1.54 (4H, m), 1.64-1.84 (6H, m), 2.13-2.22 (1H, m), 2.26 (3H, s), 2.33-2.47 (2H, m), 2.56-2.64 (1H, m), 2.66-2.71 (1H, m), 3.17 (3H, s), 3.53 (2H, s), 3.94 (3H, s), 4.34-4.41 (1H, m), 4.45-4.50 (1H, m), 7.22 (1H, d), 7.74 (1H, s), 7.99 (1H, s), 8.01-8.03 (1H, m), 8.26 (1H, d); MS m/z 554 [M+H]$^+$.

Example 439

4-(9'-cyclohexyl-5'-methyl-6'-oxo-5',6',8',9'-tetrahydrospiro[cyclopropane-1,7'-pyrimido[5,4-b][1,4] diazepine]-2'-ylamino)-N-(3-dimethylamino-2,2-dimethyl-propyl)-3-methoxy-benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 86 mg, 0.27 mmol) and 4-amino-N-(3-dimethylamino-2,2-dimethyl-propyl)-3-methoxy-benzamide (Intermediate 22; 75 mg, 0.27 mmol) were taken up in 4-methyl-2-pentanol (3 mL) and p-toluenesulphonic acid monohydrate (102 mg, 0.54 mmol) added. The reaction mixture was heated at 160° C. for 1 hour by microwave irradiation. After cooling, the reaction mixture was diluted with methanol (5 mL) and water (5 mL) and the resultant solution loaded onto an SCX-3 (5 g) cartridge. The cartridge was washed with methanol (40 mL) and then eluted with 2M ammonia in methanol (25 mL). Evaporation of the ammoniacal solution gave an opaque cream coloured film which was purified by base modified reverse phase preparative HPLC to yield the title compound as a white foam (83 mg, 55%)

$^1$H NMR (400.132 MHz, DMSO-d6) δ 0.69 (m, 2H), 0.90 (s, 6H), 0.93 (m, 2H), 1.16 (m, 1H), 1.44 (m, 4H), 1.62-1.88 (m, 5H), 2.22 (s, 2H), 2.28 (s, 6H), 3.17 (s, 3H), 3.21 (d, 2H), 3.50 (s, 2H), 3.96 (s, 3H), 4.45 (m, 1H), 7.40 (m, 1H), 7.47 (d, 1H), 7.68 (s, 1H), 7.96 (s, 1H), 8.40 (d, 1H), 8.50 (t, 1H); MS m/z 564 [M+H]$^+$.

Example 440

4-(9'-cyclohexyl-5'-methyl-6'-oxo-5',6',8',9'-tetrahydrospiro[cyclopropane-1,7'-pyrimido[5,4-b][1,4] diazepine]-2'-ylamino)-N-(2,2-dimethyl-3-pyrrolidin-1-yl-propyl)-3-methoxy-benzamide The title compound was prepared by an analogous method to the preparation of Example 439, on a 0.33 mmol scale, utilising 4-amino-N-(2,2-dimethyl-3-pyrrolidin-1-yl-propyl)-3-methoxy-benzamide (Intermediate 206; 100 mg, 0.33 mmol) heating thermally at 120° C. over the weekend, as a white solid (46 mg, 24%).

$^1$H NMR (400.132 MHz, CDCl$_3$) δ 0.57-0.54 (m, 2H), 0.93 (s, 6H), 1.12-1.02 (m, 4H), 1.46-1.25 (m, 4H), 1.74-1.64 (m, 4H), 1.82 (d, 4H), 2.48 (s, 2H), 2.64-2.58 (m, 4H), 3.20 (s, 3H), 3.33 (d, 2H), 3.39 (s, 2H), 3.90 (s, 3H), 4.53-4.47 (m, 1H), 7.19-7.17 (m, 1H), 7.43 (s, 1H), 7.58 (s, 1H), 7.77 (s, 1H), 8.38 (d, 1H), 8.92-8.88 (m, 1H); MS m/z 590 [M+H]$^+$.

Example 441

4-(9'-cyclohexyl-5'-methyl-6'-oxo-5',6',8',9'-tetrahydrospiro[cyclopropane-1,7'-pyrimido[5,4-b][1,4] diazepine]-2'-ylamino)-N-[(3R)-1-ethylpyrrolidin-3-yl]-3-methoxy-benzamide The title compound was prepared by an analogous method to the preparation of Example 439, on a 0.24 mmol scale, utilising 4-amino-N-[(3R)-1-ethylpyrrolidin-3-yl]-3-methoxy-benzamide (Intermediate 245; 70 mg, 0.26 mmol), as a white solid (57 mg, 38%).

$^1$H NMR (400.132 MHz, DMSO-d6) δ 0.69 (m, 2H), 0.93 (m, 2H), 1.04 (t, 3H), 1.15 (m, 1H), 1.45 (m, 4H), 1.76 (m, 6H), 2.15 (m, 1H), 2.43 (m, 4H), 2.66 (m, 1H), 2.72 (m, 1H), 3.16 (s, 3H), 3.50 (s, 2H), 3.96 (s, 3H), 4.42 (m, 2H), 7.50 (m, 1H), 7.54 (d, 1H), 7.66 (s, 1H), 7.96 (s, 1H), 8.31 (d, 1H), 8.40 (d, 1H); MS m/z 548 [M+H]$^+$.

Example 442

4-(9'-cyclohexyl-5'-methyl-6'-oxo-5',6',8',9'-tetrahydrospiro[cyclopropane-1,7'-pyrimido[5,4-b][1,4] diazepine]-2'-ylamino)-2-fluoro-5-methoxy-N-[(1S, 5R)-9-methyl-9-azabicyclo[3.3.1]non-3-yl] benzamide The title compound was prepared by an analogous method to the preparation of Example 439, on a 0.17 mmol scale, utilising 4-amino-3-methoxy-N-[(1S,5R)-9-methyl-9-azabicyclo[3.3.1]non-3-yl]benzamide (Intermediate 204; 55 mg, 0.17 mmol), heating thermally at 140° C. for 2 hours, as a white solid (24 mg, 23%).

$^1$H NMR (399.9 MHz, DMSO-d6) δ 0.70-0.73 (2H, m), 0.90-0.96 (4H, m), 1.13-1.20 (1H, m), 1.40-1.55 (7H, m), 1.67 (1H, d), 1.75-1.95 (6H, m), 2.01-2.11 (1H, m), 2.18-2.26 (2H, m), 2.42 (3H, s), 2.98 (2H, d), 3.17 (3H, s), 3.53 (2H, s), 3.94 (3H, s), 4.27-4.34 (1H, m), 4.45-1.52 (1H, m), 7.22 (1H, d), 7.68-7.72 (1H, m), 7.74 (1H, s), 8.00 (1H, s), 8.26 (1H, d); MS m/z 606 [M+H]+.

Example 443

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-N-(1-ethyl-4-piperidyl)-2-fluoro-5-methoxy-benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 54 mg, 0.17 mmol), 4-amino-N-(1-ethyl-4-piperidyl)-2-fluoro-5-methoxy-benzamide (Intermediate 205; 50 mg, 0.17 mmol), and p-toluenesulphonic acid monohydrate (81 mg, 0.43 mmol) were stirred together in 4-methyl-2-pentanol (3 mL) and heated at 110° C. for 18 hours. The cooled reaction mixture was loaded onto an SCX-3 (5 g) column pre-wet with MeOH. The column was washed with MeOH (2 column volumes) and eluted with 2M NH3/MeOH. Solvent evaporation of the combined ammoniacal fractions gave a brown gum which was purified by base modified reverse phase preparative HPLC to yield the title compound as a white solid (48 mg, 49%)
$^1$H NMR (400.132 MHz, DMSO-d6) δ 0.70 (m, 2H), 0.94 (m, 2H), 1.00 (t, 3H), 1.14 (m, 2H), 1.61 (m, 12H), 1.96 (m, 2H), 2.32 (q, 3H), 2.83 (d, 2H), 3.17 (s, 3H), 3.52 (s, 2H), 3.72 (m, 1H), 3.93 (s, 3H), 4.47 (m, 1H), 7.19 (d, 1H), 7.73 (s, 1H), 7.82 (m, 1H), 7.99 (s, 1H), 8.26 (d, 1H); MS m/z 580 [M+H]+.

Example 444

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-2-fluoro-5-methoxy-N-(2-pyrrolidin-1-ylethyl)benzamide The title compound was prepared by an analogous method to the preparation of Example 443, on a 0.18 mmol scale, utilising 4-amino-2-fluoro-5-methoxy-N-(2-pyrrolidin-1-ylethyl)benzamide (Intermediate 228; 50 mg, 0.18 mmol), as a white solid (58 mg, 57%).
$^1$H NMR (400.132 MHz, DMSO-d6) δ 0.71 (m, 2H), 0.94 (m, 2H), 1.15 (m, 2H), 1.61 (m, 12H), 2.50 (m, 4H), 2.58 (t, 3H), 3.16 (s, 3H), 3.39 (m, 2H), 3.52 (s, 2H), 3.93 (s, 3H), 4.48 (m, 1H), 7.30 (d, 1H), 7.76 (bs, 1H), 7.91 (m, 1H), 7.99 (s, 1H), 8.27 (d, 1H); MS m/z 566 [M+H]+.

Example 445

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-2-fluoro-5-methoxy-N-[[1-(pyrrolidin-1-ylmethyl)cyclopropyl]methyl]benzamide The title compound was prepared by an analogous method to the preparation of Example 443, on a 0.16 mmol scale, utilising 4-amino-2-fluoro-5-methoxy-N-[[1-(pyrrolidin-1-ylmethyl)cyclopropyl]methyl]benzamide (Intermediate 254; 52 mg, 0.16 mmol), as a white solid (53 mg, 55%).
$^1$H NMR (400.132 MHz, DMSO-d$_6$) δ 0.34 (2H, m), 0.51 (2H, m), 0.71 (2H, m), 0.94 (2H, m), 1.16 (1H, m), 1.47 (5H, m), 1.72 (10H, m), 2.44 (2H, s), 2.49 (2H, s), 3.17 (3H, s), 3.37 (2H, d), 3.53 (2H, s), 3.93 (3H, s), 4.48 (1H, m), 7.39 (1H, d), 7.78 (1H, s), 7.99 (1H, s), 8.26 (1H, d), 8.37 (1H, m); MS m/z 606 [M+H]+.

Example 446

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-3-fluoro-N-(1-methyl-4-piperidyl)benzamide 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 200 mg, 0.62 mmol), 4-amino-3-fluoro-N-(1-methylpiperidin-4-yl)benzamide (Intermediate 65; 157 mg, 0.62 mmol) and p-toluenesulfonic acid monohydrate (296 mg, 1.56 mmol) were suspended in 4-Methyl-2-pentanol (5 mL) and sealed into a microwave tube. The reaction was heated at 160° C. for 30 minutes in the microwave reactor and then allowed to cool to room temperature.

The reaction mixture was purified by ion exchange chromatography, using an SCX column. The desired product was eluted from the column using 7M NH3/MeOH and pure fractions were evaporated to dryness to afford a cream coloured solid which was purified by preparative HPLC using decreasingly polar mixtures of water (containing 1% NH3) and MeCN as eluents. Fractions containing the desired compound were evaporated to dryness to yield the title compound as a white solid (125 mg, 37%).
$^1$H NMR (400.132 MHz, DMSO-d$_6$) δ0.65 (t, 2H), 0.95 (t, 2H), 1.1 (m, 1H), 1.35 (q, 2H), 1.45 (q, 2H), 1.5-1.7 (m, 5H), 1.8 (m, 4H), 1.95 (t, 2H), 2.15 (t, 2H), 2.2 (s, 3H), 2.8 (d, 2H), 3.2 (s, 3H), 3.45 (s, 2H), 3.7 (m, 1H), 4.4 (m, 1H), 7.65 (m, 1H), 7.7 (m, 1H), 7.95 (s 1H), 8.15 (m, 2H), 8.6 (s, 1H); MS m/z 536 [M+H]+.

Example 447

4-[(2-cyclopentyl-6-methyl-5-oxo-2,6,9,11-tetrazabicyclo[5.4.0]undeca-7,9,11-trien-10-yl)amino]-2,5-difluoro-N-[(1S,5R)-9-methyl-9-azabicyclo[3.3.1]non-7-yl]benzamide p-Toluenesulphonic acid monohydrate (338 mg, 1.78 mmol) was added to 4-amino-2,5-difluoro-N-[(1S,5R)-9-methyl-9-azabicyclo[3.3.1]non-7-yl]benzamide (Intermediate 274; 220 mg, 0.71 mmol), and 2-chloro-9-cyclopentyl-5-methyl-8,9-dihydro-5H-pyrimido[5,4-b][1,4]diazepin-6(7H)-one (Intermediate 1; 200 mg, 0.71 mmol) in 4-methyl-2-pentanol (4 mL) at 25° C. The resulting mixture was heated by microwave irradiation at 150° C. for 1 hour. The crude product was purified by ion exchange chromatography, using an SCX-3 (5 g) column. The desired product was eluted from the column using 2M NH$_3$/MeOH and product-containing fractions were evaporated to dryness. The residue was further purified by base modified reverse phase preparative HPLC to yield the title compound as a white solid (91 mg, 23.%).
$^1$H NMR (400.132 MHz, DMSO-d$_6$) δ 0.90-0.93 (2H, m), 1.37-1.44 (4H, m), 1.57-1.71 (6H, m), 1.86-2.04 (4H, m), 2.17-2.24 (2H, m), 2.41 (3H, s), 2.58-2.61 (2H, m), 2.96-2.99 (2H, m), 3.18 (3H, s), 3.62-3.64 (2H, m), 4.21-4.33 (1H, m), 4.78-4.86 (1H, m), 7.42-7.46 (1H, m), 7.81 (1H, d), 8.11 (1H, s), 8.20-8.25 (1H, m), 8.91 (1H, s); MS m/z 555 [M+H]+.

Example 448

4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-2,5-difluoro-N-((1R,3r,5S)-9-methyl-9-azabicyclo[3.3.1]nonan-3-yl)benzamide The title compound was prepared by an analogous method to the preparation of Example 446, on a 0.65 mmol scale, utilising 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 200 mg, 0.65 mmol), as a white solid (50 mg, 13%).

$^1$H NMR (400.132 MHz, DMSO-$d_6$) δ 0.67-0.70 (2H, m), 0.90-0.93 (4H, m), 1.36-1.60 (7H, m), 1.64-1.71 (2H, m), 1.85-1.93 (4H, m), 1.97-2.04 (1H, m), 2.17-2.24 (2H, m), 2.40 (3H, s), 2.96-2.98 (2H, m), 3.18 (3H, s), 3.48 (2H, s), 4.21-4.32 (1H, m), 4.82-4.91 (1H, m), 7.42-7.46 (1H, m), 7.79-7.82 (1H, m), 8.02 (1H, s), 8.23-8.28 (1H, m), 8.85 (1H, s); MS m/z 581 [M+H]$^+$.

Example 449

4-(9'-cyclohexyl-5'-methyl-6'-oxo-5',6',8',9'-tetrahydrospiro[cyclopropane-1,7'-pyrimido[5,4-b][1,4]diazepine]-2'-ylamino)-2,5-difluoro-N-((1R,3r,5S)-9-methyl-9-azabicyclo[3.3.1]nonan-3-yl)benzamide The title compound was prepared by an analogous method to the preparation of Example 446, on a 0.62 mmol scale, utilising 2'-chloro-9'-cyclohexyl-5'-methyl-8',9'-dihydrospiro[cyclopropane-1,7'-pyrimido[5,4-b][1,4]diazepin]-6'(5'H)-one (Intermediate 270; 200 mg, 0.62 mmol), as a white solid (37 mg, 10%).

$^1$H NMR (400.132 MHz, DMSO-$d_6$) δ 0.69-0.72 (2H, m), 0.90-0.95 (4H, m), 1.09-1.16 (1H, m), 1.33-1.50 (8H, m), 1.61-1.80 (4H, m), 1.86-1.92 (2H, m), 1.97-2.04 (1H, m), 2.16-2.24 (2H, m), 2.41 (3H, s), 2.96-2.98 (2H, m), 3.17 (3H, s), 3.50 (2H, s), 4.21-4.32 (1H, m), 4.43-4.49 (1H, m), 7.42-7.47 (1H, m), 7.81-7.84 (1H, m), 7.99 (1H, s), 8.13-8.18 (1H, m), 8.76 (1H, s); MS m/z 595 [M+H]$^+$.

Example 450

4-(9'-cyclohexyl-6'-oxo-5',6',8',9'-tetrahydrospiro[cyclopropane-1,7'-pyrimido[5,4-b][1,4]diazepine]-2'-ylamino)-3-fluoro-N-((1R,3r,5S)-9-methyl-9-azabicyclo[3.3.1]nonan-3-yl)benzamide 2'-chloro-9'-cyclohexyl-8',9'-dihydrospiro[cyclopropane-1,7'-pyrimido[5,4-b][1,4]diazepin]6'(5'H)-one (100 mg, 0.33 mmol), 4-amino-3-fluoro-N-((1R,3r,5S)-9-methyl-9-azabicyclo[3.3.1]nonan-3-yl)benzamide (95 mg, 0.33 mmol) and p-Toluenesulfonic acid. H2O (155 mg, 0.81 mmol) were suspended in 4-Methyl-2-pentanol (2 mL) and sealed into a microwave tube. The reaction was heated to 160° C. for 25 minutes by microwave irradiation and then cooled to room temperature. The reaction mixture was filtered through a PTFE Filter cup to give an off white solid which was purified by preparative HPLC using decreasingly polar mixtures of water (containing 1% NH3) and MeCN as eluents. Fractions containing the desired compound were evaporated to dryness to yield the title compound as a white solid (27 mg, 15%).

$^1$H NMR (400.132 MHz, DMSO-$d_6$) δ 0.8 (t, 2H), 0.9 (d, 2H), 1.1 (t, 2H), 1.2-1.5 (m, 8H), 1.6 (b, 3H), 1.75 (d, 2H), 1.9 (m, 2H), 2.0 (m, 1H), 2.2 (m, 2H), 2.4 (s, 3H), 2.95 (d, 2H), 3.4 (s, 2H), 4.3 (m, 1H), 4.5 (m, 1H), 7.55 (d, 1H), 7.6 (d, 1H), 7.85 (s, 1H), 7.95 (d, 1H), 8.15 (t, 1H), 8.5 (s, 1H), 9.5 (s, 1H); MS m/z 563 [M+H]$^+$.

Example 451

4-[(2-cyclopentyl-6-methyl-5-oxo-2,6,9,11-tetrazabicyclo[5.4.0]undeca-8,10,12-trien-10-yl)amino]-3-methoxy-N-[(1R,5S)-9-methyl-3-oxa-9-azabicyclo[3.3.1]non-7-yl]benzamide p-Toluenesulphonic acid monohydrate (143 mg, 0.83 mmol) was added to 10-Chloro-2-cyclopentyl-6-methyl-2,6,9,11-tetrazabicyclo[5.4.0]undeca-8,10,12-trien-5-one (Intermediate 1; 93 mg, 0.33 mmol) and 4-amino-3-methoxy-N-[(1R,5S)-9-methyl-3-oxa-9-azabicyclo[3.3.1]non-7-yl]benzamide (Intermediate 275; 100 mg, 0.33 mmol) in 4-methyl-2-pentanol (3 mL) at 25° C. The resulting suspension was stirred at 110° C. for 18 hours. The reaction mixture was cooled to ambient temperature and purified by ion exchange chromatography, using an SCX-2 (5 g) column. The desired product was eluted from the column using 2M NH3/MeOH and fractions were evaporated to dryness to afford the crude product as a gum which was purified by preparative HPLC using decreasingly polar mixtures of water (containing 1% NH3) and MeCN as eluent. Fractions containing the desired compound were combined and evaporated to dryness to afford the title compound as a white solid (15 mg, 8%).

$^1$H NMR (400.132 MHz, DMSO-$d_6$) δ 1.36-1.40 (2H, m), 1.57-1.72 (6H, m), 1.89-1.95 (2H, m), 2.33-2.41 (2H, m), 2.45 (3H, s), 2.57-2.63 (4H, m), 3.17 (3H, s), 3.61-3.64 (2H, m), 3.71-3.74 (2H, m), 3.89-3.91 (2H, m), 3.93 (3H, s), 4.39-4.45 (1H, m), 4.74-4.82 (1H, m), 7.29 (1H, d), 7.38 (1H, s), 7.75 (1H, s), 8.07 (1H, s), 8.37 (1H, d), 8.83 (1H, d); MS m/z 551 [M+H]$^+$.

Example 452

N-(azepan-3-yl)-4-[(2-cyclopentyl-6-methyl-5-oxo-2,6,9,11-tetrazabicyclo[5.4.0]undeca-7,9,11-trien-10-yl)amino]-3-methoxy-benzamide A solution of tert-butyl 3-[[4-[(2-cyclopentyl-6-methyl-5-oxo-2,6,9,11-tetrazabicyclo[5.4.0]undeca-7,9,11-trien-10-yl)amino]-3-methoxy-benzoyl]amino]azepane-1-carboxylate (Example 348; 149 mg, 0.25 mmol) in DCM (2 mL) was treated with TFA (1 mL) The resulting solution was stirred at ambient temperature for 5 hours.

The reaction mixture was diluted with DCM (10 mL) and submitted to ion exchange chromatography, using an SCX-3 column. The column was eluted with DCM (50 mL) and methanol (50 mL) before the desired product was eluted from the column using 2M NH3/MeOH. The ammoniacal solution was evaporated to dryness to afford the title compound as an amber gum (95 mg, 76%).

$^1$H NMR (400.132 MHz, DMSO-$d_6$) δ 1.41-1.92 (16H, m), 2.51-2.53 (2H, m), 2.60-2.67 (1H, m), 2.73 (1H, t), 2.92 (1H, dd), 3.10 (3H, s), 3.54-3.58 (2H, m), 3.88 (3H, s), 3.90-3.99 (1H, m), 4.70-4.79 (1H, m), 7.38-7.43 (2H, m), 7.66 (1H, s), 7.93 (1H, d), 8.01 (1H, s), 8.31 (1H, d); MS m/z 508 (M+H)$^+$

Example 453

4-[(2-cyclopentyl-6-methyl-5-oxo-2,6,9,11-tetrazabicyclo[5.4.0]undeca-7,9,11-trien-10-yl)amino]-3-methoxy-N-(1-methylazepan-3-yl)benzamide To a solution of N-(azepan-3-yl)-4-[(2-cyclopentyl-6-methyl-5-oxo-2,6,9,1,1-tetrazabicyclo[5.4.0]undeca-7,9,11-trien-10-yl)amino]-3-methoxy-benzamide (Example 453; 88 mg, 0.17 mmol) in formaldehyde (1 mL, 13.35 mmol) and acetic acid (100 µL, 1.75 mmol), was added sodium acetate (142 mg, 1.73 mmol). The reaction mixture was cooled to 0° C. with stirring. Sodium cyanoborohydride (12 mg, 0.19 mmol) was added and the reaction mixture stirred at 0° C. for 5 minutes before removing the cooling bath. The reaction mixture was allowed to warm to ambient temperature and stirred for 2 hours and then submitted to ion exchange chromatography, using an SCX-3 column. The column was washed with methanol, before the crude products were eluted from the column using 2M NH3/MeOH. Evaporation of the ammoniacal solution afforded the crude product as an amber gum which was purified by flash silica chromatography, elution gradient 5 to 10% 2M ammonia/MeOH in DCM. Pure fractions were combined and evaporated to dryness to give 4-(9-cyclopentyl-5-methyl-6-oxo-6,7,8,9-tetrahydro-5H-pyrimido[5,4-b][1,4]diazepin-2-ylamino)-3-methoxy-N-(1-methylazepan-3-yl)benzamide as an amber glass (44 mg, 49%)

$^1$H NMR (400.132 MHz, CDCl$_3$) δ 1.53-1.86 (12H, m), 1.91-1.96 (1H, m), 2.03-2.10 (2H, m), 2.45 (3H, s), 2.65-2.70 (3H, m), 2.79-2.86 (2H, m), 3.30 (3H, s), 3.68-3.72 (2H, m), 3.99 (3H, s), 4.25-4.33 (1H, m), 4.91 (1H, quintet), 7.18-7.25 (1H, m), 7.31 (1H, d), 7.48 (1H, d), 7.65 (1H, s), 7.95 (1H, s), 8.51 (1H, d); MS m/z 522 (M+H)$^+$

PREPARATION OF INTERMEDIATES

Intermediate 1

10-Chloro-2-cyclopentyl-6-methyl-2,6,9,11-tetrazabicyclo[5.4.0]undeca-8,10,12-trien-5-one To a cold (0° C.) solution of 9-chloro-6-cyclopentyl-2,6,8,10-tetrazabicyclo[5.4.0]undeca-8,10,12-trien-3-one (Intermediate 2; 241 mg, 0.90 mmol) in DMA (20 mL) was added MeI (62 uL, 0.99 mmol) followed by NaH (39 mg, 0.96 mmol) and the reaction mixture stirred at 0° C. for 30 mins then at ambient temperature for 1 hr. The solution was diluted with Ethyl Acetate (20 mL), washed with water (2×30 mL), brine (30 mL), dried (MgSO$_4$) and the volatiles were removed under reduced pressure. Purification by column chromatography (SiO$_2$, eluent gradient: 2% MeOH in DCM) afforded the title compound (187 mg, 74%) as a solid.

$^1$H NMR (400 MHz, DMSO-D6) δ$_H$ 1.52-1.66 (m, 4H), 1.66-1.75 (m, 2H), 1.85-1.96 (m, 2H), 2.63-2.67 (m, 2H), 3.18 (s, 3H), 3.64-3.68 (m, 2H), 4.71-4.79 (m, 1H), 8.15 (s, 1H);
MS 281, 283 [M+H]$^+$.

Intermediate 2

9-Chloro-6-cyclopentyl-2,6,8,10-tetrazabicyclo[5.4.0]undeca-8,10,12-trien-3-one

To a solution of methyl3-[(2-chloro-5-oxidoazonoyl-pyrimidin-4-yl)-cyclopentyl-amino]propanoate (Intermediate 3; 1.00 g, 3.04 mmol) in AcOH (50 mL) was added powdered Fe (1.00 g, 3.04 mmol) and the reaction stirred at 70° C. for 30 mins. The reaction mixture was filtered hot through a pad of celite, washed with AcOH (25 mL) and the volatiles removed under reduced pressure. Purification by column chromatography (SiO$_2$, eluent gradient: 0-100% Ethyl Acetate in hexane) gave the title compound (480 mg, 43%) as a solid.

$^1$H NMR (400 MHz, CDCl$_3$) δ$_H$ 1.46-1.56 (m, 2H), 1.62-1.80 (m, 3H), 1.94-2.04 (m, 3H), 2.77-2.79 (m, 2H), 3.60-3.63 (m, 2H), 5.17-5.26 (m, 1H), 7.79 (s, 1H), 7.99 (s, 1H); MS m/z 267, 269 [M+H]$^+$.

Intermediate 3

Methyl3-[(2-chloro-5-oxidoazonoyl-pyrimidin-4-yl)-cyclopentyl-amino]propanoate

To a solution of methyl3-(cyclopentylamino)propanoate (2.46 g, 14.37 mmol) in acetone (40 mL) was added K$_2$CO$_3$ (2.03 g, 14.65 mmol) and 2,4-dichloro-5-nitropyrimidine (3.07 g, 15.80 mmol) and the reaction mixture stirred at ambient temperature under an atmosphere of nitrogen for 18 hrs. The volatiles were removed under reduced pressure and the crude material was dissolved in Ethyl Acetate (50 mL), washed with water (2×50 mL), brine (50 mL), dried (MgSO$_4$) and the volatiles removed under reduced pressure. Purification by column chromatography (SiO$_2$, eluent gradient: 0-10% Ethyl Acetate in hexane) afforded the title compound (2.23 g, 53%) as a solid.

$^1$H NMR (400 MHz, DMSO-d$_6$): δ$_H$ 1.44-1.54 (m, 2H), 1.62-1.78 (m, 4H), 1.86-1.96 (m, 2H), 2.69 (t, 2H), 3.61 (s, 3H), 3.66 (t, 2H), 3.71-3.80 (m, 1H), 8.84 (s, 1H); MS m/z 329, 331 [M+H]$^+$.

Intermediate 4

4-Amino-N-(1-methyl-4-piperidyl)benzamide p-Aminobenozoic acid (137 mg, 1 mmol), 4-amino-N-methylpiperidine (114 mg, 1 mmol) and DIPEA (522 uL, 3 mmol) were dissolved in DMA (5 mL). HATU (570 mg, 1.5 mmol) in DMA (5 mL) was added and the reaction stirred at ambient temperature for 2 h. The volatiles were removed under reduced pressure and NaHCO$_3$ (50 mL, sat. aq.) was added. The resulting precipitate was removed by filtration and the aqueous phase neutralised with HCL (2N). The reaction mixture was then loaded onto an SCX-2 cartridge washing with copious quantities of water. The crude product was the eluted from the SCX-2 cartridge with NH$_3$ (60 mL, 7M in MeOH). Purification by column chromatography (SiO$_2$, eluent: 10% NH$_3$ [7M in MeOH] in DCM) afforded the title compound (167 mg, 72%) as a solid.

$^1$H NMR (400 MHz, DMSO-d$_6$) δ$_H$ 1.50-1.60 (2H, m), 1.69-1.73 (1H, m), 1.72 (1H, t), 1.89-1.96 (2H, m), 2.16 (3H, s), 2.75 (2H, d), 3.65-3.71 (1H, m), 5.52-5.54 (1H, m), 6.52-6.55 (2H, m), 7.56-7.59 (2H, m), 7.69 (1H, d); MS m/z 234 [M+H]$^+$.

Intermediate 5

10-chloro-2-cyclopentyl-4,6-dimethyl-2,6,9,11-tetrazabicyclo[5.4.0]undeca-8,10,12-trien-5-one To a cold (−78° C.) solution of 10-chloro-2-cyclopentyl-6-methyl-2,6,9,11-tetrazabicyclo[5.4.0]undeca-8,10,12-trien-5-one (90 mg, 0.32 mmol) in dry THF (4 mL) was added LiHMDS (640 µL, 1M in THF, 0.64 mmol) dropwise over 10 mins. MeI (40 µL, 0.64 mmol) in THF (1 mL) was added and the reaction mixture was stirred at −78° C. for 20 mins and then at 0° C. for 1 hr. The reaction mixture was diluted with DCM (20 mL) and washed with water (2×20 mL), brine (40 mL), dried (MgSO₄), filtered and the volatiles removed under reduced pressure to yield the title compound (106 mg, 100%) as a solid.

MS m/z 295, 297 [M+H]⁺.

Intermediate 6

4-[(9-Cyclopentyl-5-methyl-6,7,8,9-tetrahydro-5H-pyrimido[4,5-b][1,4]diazepin-2-yl)amino]-3-methoxybenzoic acid Methyl4-[(9-cyclopentyl-5-methyl-6,7,8,9-tetrahydro-5H-pyrimido[4,5-b][1,4]diazepin-2-yl)amino]-3-methoxybenzoate (Intermediate 7; 250 mg, 0.61 mmol) and HCl (2 mL, concentrated aqueous) were suspended in water (4 mL) and heated at reflux for 24 h. The reaction mixture was then cooled to ambient temperature and the volatiles were removed under reduced pressure. The solid obtained was dissolved in MeOH:DCM (1:10, 40 mL) and washed with NaHCO₃ (saturated aqueous, 40 mL). The organic layer was then dried (MgSO₄), filtered and the volatiles removed under reduced pressure to afford the title compound (240 mg, 99%) as a solid.

$^1$H NMR (400 MHz, DMSO-d$_6$) $\delta_H$ 1.57 (m, 4H), 1.73 (m, 2H), 1.88 (m, 4H), 2.70 (s, 3H), 2.95 (t, 2H), 3.47 (m, 2H), 3.87 (s, 3H), 4.86 (quintet, 1H), 7.20 (s, 1H), 7.42 (d, 1H), 7.50 (s, 1H), 7.52 (s, 1H), 7.96 (s, 1H), 8.28 (d, 1H); MS m/z 398 [M+H]⁺.

Intermediate 7

Methyl4-[(9-cyclopentyl-5-methyl-6,7,8,9-tetrahydro-5H-pyrimido[4,5-b][1,4]diazepin-2-yl)amino]-3-methoxybenzoate BH₃.SMe₂ (1.36 mL, 5.0 M in Et₂O, 6.8 mmol) was added to solution of methyl4-[(9-cyclopentyl-5-methyl-6-oxo-6,7,8,9-tetrahydro-5H-pyrimido[4,5-b][1,4]diazepin-2-yl)amino]-3-methoxybenzoate (Intermediate 8; 290 mg, 0.68 mmol) in THF (4 mL) and stirred for 5 h at ambient temperature under an atmosphere of nitrogen. HCl (10 mL, concentrated aqueous) was added and the resulting solution was stirred at ambient temperature for 16 h. The HCl solution was then diluted with water (50 mL), and loaded onto an SCX-2 column. The SCX-2 column was then washed with water (50 mL) and MeOH (50 mL). The product was then eluted from the SCX-2 column with NH₃ (50 mL, 7M in MeOH). The volatiles were then removed under reduced pressure to afford the title compound (250 mg, 89%) as a solid.

$^1$H NMR (400 MHz, DMSO-d$_6$) $\delta_H$ 1.67 (m, 6H), 1.96 (m, 4H), 2.77 (s, 3H), 3.06 (t, 2H), 3.58 (m, 2H), 3.88 (s, 3H), 4.00 (s, 3H), 4.91 (quintet, 1H), 7.57 (m, 3H), 7.71 (s, 1H), 8.59 (d, 1H); MS m/z 412 [M+H]⁺.

Intermediate 8

Methyl4-[(9-cyclopentyl-5-methyl-6-oxo-6,7,8,9-tetrahydro-5H-pyrimido[4,5-b][1,4]diazepin-2-yl)amino]-3-methoxybenzoate 2-Chloro-9-cyclopentyl-5-methyl-5,7,8,9-tetrahydro-6H-pyrimido[4,5-b][1,4]diazepin-6-one (Intermediate 1; 500 mg, 1.78 mmol), methyl4-amino-3-methoxybenzoate (324 mg, 1.78 mmol) and p-toluenesulfonic acid (847 mg, 4.45 mmol) were suspended in (2R/S)-4-methyl-2-pentanol (10 mL) and heated at reflux for 5 h. The reaction mixture was cooled and loaded onto an SCX-2 column and washed with MeOH (20 mL). The crude product was then eluted from the SCX-2 column with NH₃ (40 mL, 7M in MeOH) and the volatiles removed under reduced pressure. Purification by column chromatography (SiO₂, eluent gradient 0-10% MeOH in DCM) afforded the title compound (290 mg, 38%) as a solid.

$^1$H NMR (400.132 MHz, DMSO-d$_6$) $\delta_H$ 1.71 (m, 6H), 2.00 (m, 2H), 2.65 (m, 2H), 3.23 (s, 3H), 3.69 (m, 2H), 3.89 (s, 3H), 4.01 (s, 3H), 4.87 (m, 1H), 7.56 (d, 1H), 7.64 (d, 1H), 7.90 (s, 1H), 8.16 (s, 1H), 8.55 (d, 1H); MS m/z 426 [M+H]⁺.

Intermediate 9

10-Chloro-2,6-dimethyl-2,6,9,11-tetrazabicyclo[5.4.0]undeca-7,9,11-trien-5-one

3-[(5-Bromo-2-chloro-pyrimidin-4-yl)-methyl-amino]-N-methyl-propanamide (Intermediate 15; 2.09 g, 6.20 mmol), tris(dibenzylideneacetone)dipalladium(0) (171 mg, 0.19 mmol), (5-diphenylphosphanyl-9,9-dimethyl-xanthen-4-yl)-diphenyl-phosphane (288 mg, 0.50 mmol) and Cs₂CO₃ (2930 mg, 8.99 mmol) in 1,4-dioxane (50 mL) were heated at reflux for 16 h under an atmosphere of nitrogen. The reaction mixture was evaporated then suspended in DCM (20 mL) and filtered through a layer of celite washing with DCM (40 mL). Purification by column chromatography (SiO₂, eluent gradient: 2-10% MeOH in DCM) afforded the title compound (190 mg, 19%) as a foam.

$^1$H NMR (400 MHz, DMSO-d$_6$) $\delta_H$ 2.67 (tr, 2H), 3.08 (s, 3H), 3.20 (s, 3H), 3.72 (tr, 2H), 8.19 (s, 1H); MS m/z 227 [M+H]⁺.

Intermediate 10

10-Chloro-6-methyl-2-propan-2-yl-2,6,9,11-tetrazabicyclo[5.4.0]undeca-7,9,11-trien-5-one Intermediate 11

10-Chloro-6-methyl-2-(3-methylbutyl)-2,6,9,11-tetrazabicyclo[5.4.0]undeca-7,9,11-trien-5-one Intermediate 12

10-Chloro-2-cyclohexyl-6-methyl-2,6,9,11-tetrazabicyclo[5.4.0]undeca-7,9,11-trien-5-one Intermediate 13

10-Chloro-6-methyl-2-(oxan-4-yl)-2,6,9,11-tetrazabicyclo[5.4.0]undeca-7,9,11-trien-5-one

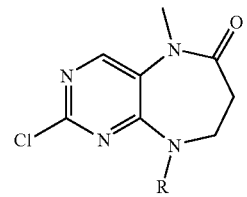

Intermediates 10-13 were prepared, using the appropriate secondary amide (Intermediates 14, 16-18), by an analogous process to that used in the preparation of Intermediate 9.

| Example | R | $^1$H NMR (400 MHz, DMSO-d$_6$) | MS m/z [M + H]$^+$ |
|---|---|---|---|
| 10 |  | 1.18 (d, 6H), 2.65 (tr, 2H), 3.19 (s, 3H), 3.61 (tr, 2H), 8.12 (s, 1H). | 225 |
| 11 |  | 0.99 (d, 6H), 1.57 (m, 3H), 2.71 (tr, 2H), 3.22 (s, 3H), 3.63 (tr, 2H), 3.78 (tr, 2H), 8.19 (s, 1H). | 283 |
| 12 |  | 1.14 (m, 1H), 1.32 (m, 2H), 1.60 (m, 3H), 1.78 (m, 4H). 2.61 (tr, 2H), 3.18 (s, 3H), 3.65 (tr, 2H), 4.30 (m, 1H), 8.12 (s, 1H). | 295 |
| 13 |  | 1.68 (m, 2H), 1.83 (m, 2H), 2.63 (tr, 2H), 3.41 (tr, 2H), 3.69 (m, 2H), 3.93 (m, 2H) 4.51 (m, 1H), 8.18 (s, 1H). | 297 |

Intermediate 14

3-[(5-Bromo-2-chloro-pyrimidin-4-yl)-propan-2-yl-amino]-N-methyl-propanamide

5-Bromo-2,4-dichloropyrimidine (1.83 g, 8.00 mmol), N-methyl-3-(propan-2-ylamino)propanamide (Intermediate 14, 1.16 g, 8.00 mmol) and Et$_3$N (1.2 mL, 8.16 mmol) were combined in MeCN (50 mL) and shaken at ambient temperature for 3 days before the solvent was removed under reduced pressure. Purification by column chromatography (SiO$_2$, eluent gradient 2-10% MeOH to DCM) to afford the title compound (2.08 g, 78%) as a gum.

$^1$H NMR (400 MHz, DMSO-d$_6$) δ$_H$ 1.16-1.20 (6H, m), 2.31 (2H, t), 2.55-2.58 (3H, d), 3.65 (2H, t), 4.55-4.62 (1H, septet), 7.71-7.72 (1H, br s), 8.39 (1H, s); MS m/z 337 [M+H]$^+$.

Intermediate 15

3-[(5-Bromo-2-chloro-pyrimidin-4-yl)-methyl-amino]-N-methyl-propanamide

Intermediate 16

3-[(5-Bromo-2-chloro-pyrimidin-4-yl)-(3-methylbutyl)amino]-N-methyl-propanamide

Intermediate 17

3-[(5-Bromo-2-chloro-pyrimidin-4-yl)-cyclohexyl-amino]-N-methyl-propanamide

Intermediate 18

3-[(5-Bromo-2-chloro-pyrimidin-4-yl)-(oxan-4-yl)amino]-N-methyl-propanamide

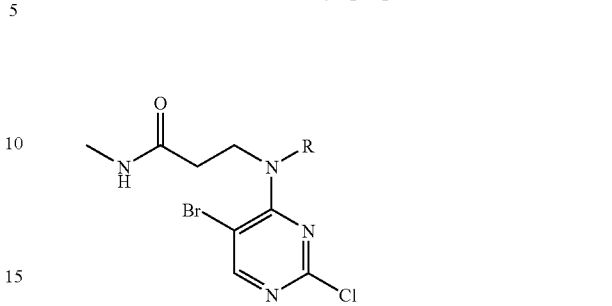

Intermediates 15-18 were prepared in an analogous manner to Intermediate 14 using 5-bromo-2,4-dichloropyrimidine as the electrophile and the appropriate known or described (Intermediates 19-21) β-aminoamides:

| Example | R | $^1$H-NMR (400 MHz, DMSO-d$_6$) | MS m/z [M + H]$^+$ |
|---|---|---|---|
| 15 | Me | 2.46 (2H, t), 2.56-2.57 (3H, d), 3.19 (3H, s), 3.86 (2H, t), 7.86 (1H, br s), 8.33 (1H, s) | 309 |
| 16 | 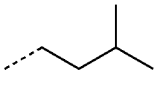 | 0.92 (6H, d), 1.48-1.52 (2H, m), 1.59 (1H, m), 2.45 (2H, t), 2.57 (3H, d), 3.63 (2H, m), 3.83 (2H, t), 7.84 (1H, br s), 8.32 (1H, s) | 365 |
| 17 | 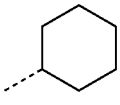 | 1.10-1.15 (1H, m), 1.27 (2H, q), 1.54-1.57 (1H, m), 1.59 (1H, d), 1.62-1.63 (1H, m), 1.69-1.72 (2H, m), 1.78 (2H, d), 2.31 (2H, t), 2.55 (3H, d), 3.67 (2H, t), 4.14-4.20 (1H, m), 7.70 (1H, br s), 8.38 (1H, s) | 377 |
| 18 | 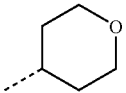 | 1.62-1.66 (2H, m), 1.82-1.89 (2H, m), 2.32 (2H, t), 2.56 (3H, d), 3.33 (2H, d), 3.69 (2H, t), 3.91-3.95 (2H, m), 4.34-4.40 (1H, m), 7.72 (1H, br s), 8.43 (1H, s) | 379 |

Intermediate 19

N-Methyl-3-(propan-2-ylamino)propanamide

N-Methylacrylamide (851 mg, 10.00 mmol) and isopropylamine (1.71 mL, 1.18 g, 20.00 mmol) in MeOH (10 mL) were irradiated to 140° C. for 30 mins in a microwave reaction vessel. The reaction mixture was cooled and loaded onto a SCX-2 column and washed with MeOH (100 mL). The crude product was then eluted from the SCX-2 column with NH$_3$ (100 mL, 7M in MeOH) and the volatiles removed under reduced pressure to afford the title compound (1.56 g, Quant.) as an oil, which was used without further purification.

$^1$H NMR (400 MHz, DMSO-d$_6$) δ$_H$ 0.96 (d, 6H), 2.18 (t, 2H), 2.57 (d, 3H), 2.65-2.71 (m, 3H), 7.81 (br s, 1H).

Intermediate 20

N-Methyl-3-(3-methylbutylamino)propanamide

Intermediate 21

N-Methyl-3-(oxan-4-ylamino)propanamide

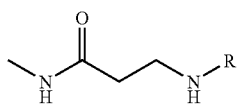

Intermediates 20 and 21 were prepared in an analogous manner to Intermediate 19 using the N-methylacrylamide as the α,β-unsaturated amide and the appropriate commercially available primary amine:

| Example | R | $^1$H NMR (400 MHz, DMSO-d$_6$) |
|---|---|---|
| 20 | isopentyl | 0.87 (d, 6H), 1.28 (dt, 2H), 1.60 (septet, 1H), 2.19 (t, 2H), 2.46-2.52 (m, 3H), 2.56 (d, 3H), 2.67 (t, 2H), 7.81 (br s, 1H) |
| 21 | tetrahydropyran-4-yl | 1.14-1.27 (m, 2H), 1.64 (d, 1H), 1.73 (d, 2H), 2.19 (t, 2H), 2.57 (d, 3H), 2.72 (t, 2H), 3.23-3.31 (m, 3H), 3.78-3.84 (m, 2H), 7.80 (br s, 1H) |

Intermediate 22

4-amino-N-(3-dimethylamino-2,2-dimethyl-propyl)-3-methoxy-benzamide

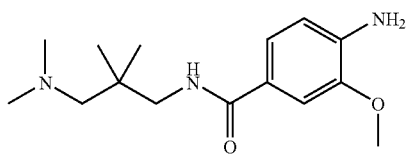

A suspension of N-(3-dimethylamino-2,2-dimethyl-propyl)-3-methoxy-4-nitro-benzamide (Intermediate 23; 5.7 g, 18.40 mmol), 5% Pd on charcoal (569 mg) in EtOH (300 mL) was stirred at 40° C. under a hydrogen atmosphere for 16 h. The reaction mixture was then filtered through celite, washed with copious MeOH and the volatiles removed under reduced pressure to afford the title compound (5.36 g, Quant.) as a foam.

$^1$H NMR (400 MHz, DMSO-d$_6$): δ$_H$ 0.88 (m, 6H), 2.18 (s, 2H), 2.28 (s, 6H), 3.18 (m, 2H), 3.82 (s, 3H), 5.21 (m, 2H), 6.63 (d, 1H), 7.25 m, 2H), 8.11 (m, 1H); MS m/z 280 [M+H]$^+$.

Intermediate 23

N-(3-Dimethylamino-2,2-dimethyl-propyl)-3-methoxy-4-nitro-benzamide

To a suspension of 4-nitro-3-methoxybenzoic acid (Aldrich; 5.0 g, 25.3 mmol), N,N-2-tetramethyl-1,3-propanediamine (Aldrich; 4.64 mL, 27.83 mmol) and DIPEA (8.8 mL, 50.60 mmol) in anhydrous DMA (100 mL) under nitrogen at ambient temperature was added HATU (10.6 g, 27.83 mmol) and the resulting reaction mixture was stirred at 50° C. for 3 h and ambient temperature for a further 12 h. Evaporation removed any volatiles and the residue was dissolved in DCM (100 mL) and washed with NaHCO$_3$ (100 mL), brine (100 mL), dried (MgSO$_4$) and the volatiles removed under reduced pressure. Purification by column chromatography (SiO$_2$, eluent gradient: 2-10% MeOH in DCM) afforded the title compound (5.7 g, 73%) as a solid.

$^1$H NMR (400 MHz, DMSO-d$_6$): δ$_H$ 1.06 (s, 6H), 2.42 (s, 2H), 2.82 (s, 6H), 3.30 (s, 2H), 3.98 (s, 3H), 7.57 (dd, 1H), 7.71 (s, 1H), 8.93 (d, 1H); MS m/z 310 [M+H]$^+$.

Intermediate 24

1-cyclopropylpiperidin-4-amine

N-benzyl-1-cyclopropyl-piperidin-4-amine (Intermediate 25; 2.3 g 10 mmol), 10% Palladium on Carbon (230 mg) and Methanol (230 mL) were combined and heated with stirring at 30° C. under Hydrogen at 5 bar pressure for 16 hours.

The mixture was filtered and concentrated, taken up in DCM, dried (MgSO$_4$) and concentrated to give the title compound (1.29 g, 64%) as a yellow liquid $^1$H NMR (399.9 MHz, CDCl$_3$) δ 0.36-0.46 (4H, m), 1.26-1.36 (4H, m), 1.52-1.58 (1H, m), 1.76-1.82 (2H, m), 2.18-2.25 (2H, m), 2.63-2.70 (1H, m), 2.94-2.99 (2H, m); MS m/z 161.90 [M+H]$^+$.

Intermediate 25

N-benzyl-1-cyclopropyl-piperidin-4-amine 1-cyclopropylpiperidin-4-one Intermediate 26 (3 g, 21.55 mmol), benzylamine (4.7 ml, 43.10 mmol) and acetic acid (1.25 ml) were stirred together and sodium triacetoxyborohydride (6.86 g, 32.33 mmol) added portion-wise. DCM (20 ml) was added and the mixture stirred at room temperature overnight. The mixture was concentrated and partitioned between ethyl acetate and 2M potassium carbonate solution. The aqueous layer was re-extracted with ethyl acetate and the combined organics washed with brine, dried (MgSO$_4$) and concentrated. Column chromatography (2% 7N ammonia in methanol/DCM) gave a brown liquid which contained Benzylamine and thus was taken up in DCM and stirred with PS-benzaldehyde (NovaBiochem, ≈3.2 mmol/g; 11.5 equivalents compared to benzylamine) for 3 h. The mixture was filtered and the combined filtrates concentrated to give the title compound (2.33 g, 47%) as a brown oil.

$^1$H NMR (399.9 MHz, CDCl$_3$) δ 0.38-0.43 (4H, m), 1.33-1.40 (2H, m), 1.46 (1H, s), 1.52-1.57 (1H, m), 1.86-1.90 (2H, m), 2.18-2.24 (2H, m), 2.51-2.56 (1H, m), 2.96-3.01 (2H, m), 3.82 (2H, s), 7.22-7.25 (1H, m), 7.29-7.33 (4H, m)

Intermediate 26

1-cyclopropylpiperidin-4-one

1-Ethyl-1-methyl-4-oxopiperidinium iodide (Journal of the Chemical Society (1949), 708-15; 15 g, 55.74 mmol) was added to cyclopropylamine (Aldrich; 19.3 mL, 278.69 mmol) in toluene (150 mL). Sodium hydrogen carbonate (469 mg, 5.57 mmol) in water (21 mL) was added and the mixture heated at 78° C. over night. The mixture was cooled and the layers separated. The aqueous layer was extracted (×2) with ethyl acetate and the combined organics washed with brine, dried (MgSO$_4$) and concentrated. Column chromatography of the residue (2% MeOH/DCM) gave the title compound (4.1 g, 53%) as a pale brown liquid.

$^1$H NMR (399.9 MHz, CDCl$_3$) δ0.47-0.53 (4H, m), 1.74 (1H, d), 2.40-2.44 (4H, m), 2.92 (4H, t)

Intermediate 27

4-amino-2-fluoro-5-methoxy-N-(1-methyl-4-piperidyl)benzamide 2-fluoro-5-methoxy-N-(1-methyl-4-piperidyl)-4-nitro-benzamide Intermediate 28; 1.3 g, 4.2 mmol) 10% Palladium on Carbon (100 mg) and Methanol (50 mL) were combined and stirred at 25° C. under Hydrogen at 1 bar pressure for 18 hours.

The reaction mixture was filtered through a plug of celite, washing with ethanol and concentrated under reduced pressure to give the title compound (1.16 g, 100%) as a yellow solid.

$^1$H NMR (399.902 MHz, DMSO-D6) δ 1.54 (qd, 2H), 1.72-1.80 (m, 2H), 1.97 (td, 2H), 2.16 (s, 3H), 2.70 (br d, 2H), 3.67-3.74 (m, 1H), 3.78 (s, 3H), 5.55 (s, 2H), 6.39 (d, 1H), 7.05 (d, 1H), 7.34 (t, 1H); MS m/z 282.27 [M+H]$^+$.

Intermediate 28

2-fluoro-5-methoxy-N-(1-methyl-4-piperidyl)-4-nitro-benzamide

To a stirred solution of 2-fluoro-5-methoxy-4-nitro-benzoic acid (Intermediate 29; 861 mg, 4.00 mmol) in DMA (20 mL) was added 4-amino-1-methylpiperidine (Fluorochem; 503 mg, 4.40 mmol) followed by DIPEA (1.4 mL, 8.00 mmol) and HATU (1.68 g, 4.40 mmol) and the resulting yellow solution stirred at room temperature for 1 hr. The solvent was removed under reduced pressure and the residue taken up in methanol (approx 10 mL) and loaded onto a 20 g SCX-2 cartridge washing with methanol (50 mL) and eluting with 7 N methanolic ammonia (50 mL) to give a yellow solid, 1.47 g. This was purified by flash silica chromatography (Companion, 40 g, 0-5% ammonia in methanol/DCM) to give the desired product as a pale yellow solid (1.25 g, 4.00 mmol, 100%.)

$^1$H NMR (399.902 MHz, DMSO-D6) δ 1.54 (qd, 2H), 1.77-1.85 (m, 2H), 1.98 (td, 2H), 2.17 (s, 3H), 2.74 (br d, 2H), 3.72 (m, 1H), 3.96 (s, 3H), 7.43 (d, 1H), 7.98 (d, 1H), 8.46 (d, 1H); MS m/z 161.90 [M+H]$^+$.

Intermediate 29

2-fluoro-5-methoxy-4-nitro-benzoic acid 2,5-Difluoro-4-nitrobenzoic acid (Fluorochem; 100 mg, 0.43 mmol) and caesium carbonate (708 mg, 2.17 mmol) were taken up in dry DMF (2 mL) and dry methanol (120 uL, 2.88 mmol) was added and the reaction stirred at room temperature for 2 hrs. The reaction mixture was diluted with Ethyl Acetate (50 mL) and water (50 mL) and acidified to pH1 with 2N HCl solution. The organics were removed and the aqueous further extracted with Ethyl Acetate (2×50 mL). The combined organics were washed with water (50 mL), brine (50 mL), dried over MgSO$_4$ and concentrated under reduced pressure to give the title compound as a yellow solid (91 mg, 0.42 mmol, 98%).

$^1$H NMR (399.902 MHz, CDCl3) δ 4.00 (s, 3H), 7.63 (d, 1H), 7.70 (d, 1H), 10.78 (br s, 1H);
MS m/z 215.27 [M+H]$^+$.

Intermediate 30

Benzyl(1R,5S)-6-amino-3-azabicyclo[3.1.0]hexane-3-carboxylate

Benzyl(1R,5S)-6-[(2-methylpropan-2-yl)oxycarbonylamino]-3-azabicyclo[3.1.0]hexane-3-carboxylate (Bioorganic & Medicinal Chemistry Letters (2004), 14(11), 2773-2776, Compound 9; 6.74 g, 20.3 mmol) was stirred and dissolved in DCM (90 mL) at ambient temperature and TFA (10 ml) was added. The solution was stirred at room temperature for 2 hours. Sat. bicarbonate (100 ml) was added followed by potassium carbonate solid until neutral. The DCM layer was separated and washed once more with water. The DCM solution was dried (MgSO4), filtered and evaporated to a gum.

Yield=4.05 g (86%)
$^1$H NMR (400.132 MHz, CDCl3) δ 1.48 (s, 2H), 2.00 (s, 1H), 3.43 (m, 4H), 5.02 (s, 2H), 7.25 (m, 7H).

Intermediate 31

Methyl(1S,3R)-3-aminocyclopentane-1-carboxylate Hydrochloride Salt (1S,3R)-3-aminocyclopentane-1-carboxylic acid (Acros; 952 mg, 7.37 mmol) was suspended in MeOH (15 ml) and cooled in an acetone/ice bath. Thionyl chloride (1.11 mL, 14.74 mmol) was added dropwise and the resulting pale yellow solution stirred in the acetone/ice bath for 30 minutes and then allowed to warm to room temperature, stirred at room temperature for 1 hr then heated at reflux for 1 hr. Solvents were evaporated to give the title compound as a cream solid after drying under high vacuum. (1.32 g 100%)

$^1$H NMR (399.902 MHz, DMSO-D6) δ1.65 (m, 1H), 1.76 (m, 1H), 1.93 (m, 3H), 2.27 (m, 1H), 2.87 (m, 1H), 3.49 (m, 1H), 3.64 (s, 3H), 8.09 (s, 3H)

Intermediate 32

[(2R)-1-(cyclopropylmethyl)pyrrolidin-2-yl]methanamine

Preparation contained in WO98/39295

Intermediate 33

[1-(pyrrolidin-1-ylmethyl)cyclopropyl]methanamine

To a solution of 1-(pyrrolidine-1-carbonyl)cyclopropane-1-carboxamide (Intermediate 34; 5.0 g, 27.5 mmol) in anhydrous THF (150 mL) was slowly added a 1 M anhydrous THF solution of Lithium Aluminium Hydride (138 mL, 138 mmol) controlling the reaction temperature at 40° C. with an ice/water bath.

The resultant clear solution was stirred overnight at room temperature under an inert gas flow to give a cloudy suspension.

Water (5.24 mL) was carefully added to the reaction mixture maintaining the reaction temperature at <30° C. with an ice/water bath to give thick white slurry. 15% w/v aqueous Sodium Hydroxide solution (5.24 mL) was carefully added followed by water (15.71 mL). The reaction was filtered and the filtrate evaporated to dryness to give the title compound (3.26 g, 77%)

Intermediate 34

1-(pyrrolidine-1-carbonyl)cyclopropane-1-carboxamide

To 1-(aminocarbonyl)-1-cyclopropane carboxylic acid (Aldrich; 25 g, 193.6 mmol) in DCM (625 mL) was added HATU (73.61 g, 193.6 mmol) and the suspension stirred for 30 minutes. Pyrrolidine (Aldrich; 24.25 mL) and Hunig's base (67 mL) was added and the reaction stirred at room temperature over the weekend.

The reaction was evaporated to dryness, DCM added and extracted with water (3×150 mL). The aqueous extracts were evaporated to dryness and the resultant material triturated with Ethyl acetate to give the title compound as a white solid 11.14 g, 32%)

Intermediate 35

2-methoxy-N'-(2-pyrrolidin-1-ylethyl)benzene-1,4-diamine

To a stirred solution of 4-fluoro-2-methoxy-1-nitro-benzene (Fluorochem; 2.57 g; 15 mmol) in DMA was 2-pyrrolidin-1-ylethanamine (Aldrich; 1.88 g, 16.5 mmol) followed by DIPEA (2.97 mL, 18 mmol). The mixture was heated at 80° C. for 20 hours, then cooled to room temp. The mixture was concentrated in vacuo, dissolved in DCM and purified by SCX (50 g SCX 2 column). The product was eluted from the column with 7N ammonia in methanol, concentrated in vacuo to give the title compound (53 mg) which was dissolved in Methanol as a 0.05 mmol solution and reduced using an H-cube hydrogenator. 10% Pd/C catalyst, 1 bar hydrogen (full hydrogen setting), 3 mL/min flow-rate at 50° C. The resultant solution was concentrated in vacuo, and the resultant material purified by column chromatography, eluting with 0-10% ammonia/methanol in DCM, to give the title compound as a solid.

MS m/z 236 [M+H]$^+$, Retention Time 1.50 minutes.

In a similar manner intermediates 36-42 were prepared from the specified amines

Intermediate 36

2-methoxy-N'-methyl-N'-(1-methyl-4-piperidyl)benzene-1,4-diamine

Intermediate 37

2-methoxy-4-[4-(2-methoxyethyl)piperazin-1-yl]aniline

Intermediate 38

2-methoxy-4-[4-(1-piperidyl)-1-piperidyl]aniline

Intermediate 39

N'-(2-dimethylaminoethyl)-2-methoxy-benzene-1,4-diamine

Intermediate 40

4-(4-cyclohexylpiperazin-1-yl)-2-methoxy-aniline

Intermediate 41

2-methoxy-4-(4-methyl-1,4-diazepan-1-yl)aniline

Intermediate 42

2-methoxy-4-(4-pyrrolidin-1-yl-1-piperidyl)aniline

| Intermediate | R | Source | MS m/z [M + H]+ | Retention time |
|---|---|---|---|---|
| 36 | 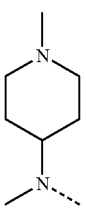 | Aldrich | 250 | 1.39 |
| 37 | 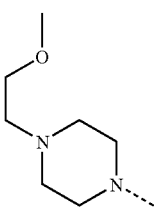 | Fluorochem | 266 | 1.45 |

-continued

| Intermediate | R | Source | MS m/z [M + H]+ | Retention time |
|---|---|---|---|---|
| 38 | 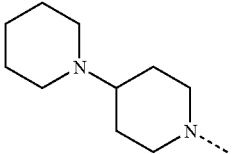 | Aldrich | 290 | 1.84 |
| 39 | 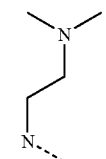 | Aldrich | 210 | 1.26 |
| 40 | 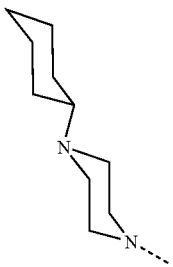 | Bulletin of the Chemical Society of Japan (1961), 34 655-9 | 290 | 2.02 |
| 41 | 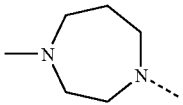 | Aldrich | 236 | 1.48 |
| 42 | 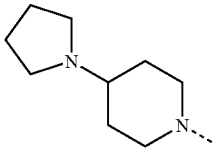 | Fluorochem | 279 | 1.79 |

Intermediate 43

2-methoxy-4-[(1-methyl-4-piperidyl)oxy]aniline

To a stirred solution of 4-(3-methoxy-4-nitro-phenoxy)-1-methyl-piperidine (Intermediate 44; 12.86 g, 48.34 mmol) in ethanol (250 mL) under nitrogen was added in one portion the Pd/C catalyst (10%, 1.29 g). The resulting mixture was evacuated and backfilled with nitrogen 4× before hydrogen gas was introduced via a balloon. The reaction mixture was stirred at room temperature for 18 hrs. The catalyst was removed by filtration through celite and the filtrate concentrated under reduced pressure to give a light red oil (11.1 g, 47.0 mmol, 97%).

$^1$H NMR (399.902 MHz, DMSO-D6) δ 1.52-1.63 (m, 2H), 1.82-1.90 (m, 2H), 2.06-2.15 (m, 2H), 2.17 (s, 3H), 2.56-2.65 (m, 2H), 3.73 (s, 3H), 4.10 (septet, 1H), 4.28 (s, 2H), 6.32 (dd, 1H), 6.45 (d, 1H), 6.53 (d, 1H); MS m/z 237.21 [M+H]$^+$.

Intermediate 44

4-(3-methoxy-4-nitro-phenoxy)-1-methyl-piperidine

To a solution of 4-Fluoro-2-methoxy-1-nitrobenzene (Apollo Scientific; 10.3 g, 60 mmol) in toluene (50 mL) and 25% KOH aq. (50 mL), were added at room temperature, 4-hydroxy-1-methylpiperidine (13.8 g, 120 mmol) and tetra-n-butylammonium bromide (3.87 g, 12 mmol). The mixture was heated at 60° C. for 18 hrs. The reaction mixture was cooled to room temperature, poured onto ice-water (300 mL) and extracted with Ethyl Acetate (3×150 mL). The organic layer was extracted with dil HCl (2 M HCl, 300 mL)

The acidic aqueous layer was taken to pH 4/5 with 2 M NaOH solution and split between 2×50 g SCX-2 cartridges, washing with water and eluting with 7 N methanolic ammonia to give the title compound as a yellow oil, which slowly solidified over time (12.86 g, 80%)

$^1$H NMR (399.902 MHz, DMSO-D6) δ 1.64-1.72 (m, 2H), 1.93-2.00 (m, 2H), 2.17-2.24 (m, 5H), 2.59-2.64 (m, 2H), 3.92 (s, 3H), 4.60 (septet, 1H), 6.71 (dd, 1H), 6.78 (d, 1H), 7.94 (d, 1H); MS m/z 267.24 [M+H]$^+$.

Intermediate 45

2-methoxy-4-(1-methylpyrrolidin-3-yl)oxy-aniline

To a stirred solution of 3-(3-methoxy-4-nitro-phenoxy)-1-methyl-pyrrolidine (Intermediate 46; 5.50 g, 20.68 mmol) in ethanol (125 mL) under nitrogen was added in one portion the Pd/C catalyst (10%, 500 mg). The resulting mixture was evacuated and backfilled with nitrogen (×4) before hydrogen gas was introduced via a balloon. The reaction mixture was stirred at room temperature for 18 hrs. The catalyst was removed by filtration through celite and the filtrate concentrated under reduced pressure to give a the title compound as a light red oil (4.74 g, 100%)

$^1$H NMR (399.902 MHz, CDCl3) δ 1.94-2.02 (m, 1H), 2.22-2.30 (m, 1H), 2.36-2.45 (m, 1H), 2.38 (s, 3H), 2.73-2.83 (m, 3H), 3.50 (s, 2H), 3.81 (s, 3H), 4.74 (octet, 1H), 6.26 (dd, 1H), 6.45 (d, 1H), 6.61 (d, 1H); MS m/z 223.22 [M+H]$^+$.

Intermediate 46

3-(3-methoxy-4-nitro-phenoxy)-1-methyl-pyrrolidine

To a solution of 4-Fluoro-2-methoxy-1-nitrobenzene (Apollo Scientific; 4.28 g, 25 mmol) in toluene (20 mL) and 25% KOH aq. (20 mL), were added at room temperature, 1-methyl-3-pyrrolidinol (5.0 g, 50 mmol) and tetra-n-butylammonium bromide (1.66 g, 5 mmol). The mixture was heated at 60° C. for 18 hrs. The reaction mixture was cooled to room temperature, poured onto ice-water (200 mL) and extracted with Ethyl Acetate (3×100 mL). The organic layer was washed with 2 M HCl (250 ml) and then loaded onto a 50 g SCX-2 cartridge, washing with water and eluting with 7 N methanolic ammonia to give the title compound as a yellow oil, which solidified on standing (5.50 g, 87%).

$^1$H NMR (399.902 MHz, DMSO-D6) δ 1.73-1.84 (m, 1H), 2.27 (s, 3H), 2.31-2.37 (m, 2H), 2.65 (dd, 1H), 2.68-2.73 (m, 1H), 2.77 (dd, 1H), 3.92 (s, 3H), 5.02-5.07 (m, 1H), 6.62 (dd, 1H), 6.73 (d, 1H), 7.95 (d, 1H); MS m/z 253.23 [M+H]$^+$.

Intermediate 47

2-methoxy-4-(2-morpholin-4-ylethoxy)aniline

To 4-[2-(3-methoxy-4-nitro-phenoxy)ethyl]morpholine (Intermediate 48; 16.97 g, 60 mmol, 1 eq) in ethanol (120 mL) was added 10% palladium on charcoal (850 mg, 5% wt). The reaction was stirred at room temperature for 19 hours. After filtering off the palladium residues the solvent was evaporated under reduced pressure. The product was dissolved in ethyl acetate (100 ml) and extracted twice with 2M HCl. The aqueous layers were combined, washed with ethyl acetate then basified by the addition of 2N NaOH. The basic layer was re-acidified and captured onto mp-TsOH resin. After washing several times with methanol the product was released using 10% ammonia in methanol. After evaporation in vacuo the title compound was obtained as a dark brown oil. (14.5 g, 89%)

$^1$H NMR (300.132 MHz, DMSO-D6) δ2.49-2.51 (4H, m), 2.69 (2H, t), 3.60 (4H, t), 3.74 (3H, s), 3.98 (2H, t), 4.62 (2H, s), 6.30 (1H, dd), 6.46 (1H, d), 6.54 (1H, d); MS m/z 253 [M+H]$^+$.

Intermediate 48

4-[2-(3-methoxy-4-nitro-phenoxy)ethyl]morpholine

To a solution of 4-fluoro-2-methoxy-1-nitro-benzene (Apollo Scientific; 10.27 g, 60 mmol) in toluene (50 mL) and 25% KOH (aq) (50 mL), was added 4-(2-hydroxyethyl)morpholine
(Aldrich; 15.75 g, 120 mmol) and tetra-n-butylammonium bromide (3.87 g, 12 mmol) at room temperature. The mixture was heated at 60° C. for 22 hours. The reaction mixture was cooled to room temperature, poured into water and extracted three times with ethyl acetate. The organic layers were combined and washed twice with 2M sodium hydroxide then brine. Dried with magnesium sulphate, filtered and evaporated under reduced pressure to yield the title compound as a yellow oil (16.97 g, 100%)

$^1$H NMR (300.132 MHz, DMSO-D6) δ2.48 (4H, t), 2.72 (2H, t), 3.58 (4H, t), 3.93 (3H, s), 4.23 (2H, t), 6.68 (1H, dd), 6.81 (1H, d), 7.94 (1H, d); MS m/z 283 [M+H]$^+$.

Intermediate 49

N-[(4-aminophenyl)methyl]pyridine-2-carboxamide

Pyridine-2-carboxylate (Aldrich; 0.35 g, 2.84 mmol), 4-aminobenzylamine (Aldrich; 0.51 g, 4.26 mmol) and HATU (1.65 g, 4.26 mmol) were dissolved in DMF (7.5 ml). N,N-Diisopropylethylamine (1.5 ml, 8.53 mmol) was added and the mixture stirred at room temperature for 2 h. The mixture was absorbed on to an SCX column, washed with methanol and eluted with ammonia in methanol. Product containing fractions were concentrated and the residue purified by normal phase chromatography (2% MeOH/DCM) to give a yellow solid (440 mg). which was suspended in DCM/Et$_2$O and filtered to give the title compound as a pale yellow solid (235 mg, 36%).

$^1$H NMR (399.9 MHz, DMSO-d$_6$) δ4.33 (2H, d), 4.94 (2H, s), 6.50-6.53 (2H, m), 7.00-7.03 (2H, m), 7.58-7.62 (1H, m), 7.98-8.07 (2H, m), 8.62-8.64 (1H, m), 8.98 (1H, t); MS m/z 228.03 [M+H]$^+$.

Intermediate 50

1-(3-amino-4-methoxy-phenyl)-N,N-dimethyl-pyrrolidin-3-amine 4-methoxy-N-(1-methyl-4-piperidyl)-3-nitro-benzamide (Intermediate 51; 400 mg, 1.4 mmol) 10% Palladium on Carbon (40 mg) and Methanol (50 mL) were combined and stirred at 25° C. under Hydrogen at 5 bar pressure for 2 hours.

The reaction mixture was filtered and evaporated to dryness. The residue was purified by column chromatography using 5% 7N ammonia in MeOH/DCM as the solvent system. Product containing fractions were combined and evaporated to give the title compound as a white solid (305 mg, 85%).

$^1$H NMR (399.9 MHz, DMSO-d$_6$) δ1.55-1.61 (2H, m), 1.70-1.74 (2H, d), 1.89-1.96 (2H, t), 2.16 (3H, s), 2.74-2.77 (2H, d), 3.68 (1H, m), 3.81 (3H, s), 4.79 (2H, s), 6.81 (1H, d), 7.06-7.09 (1H, m), 7.14 (1H, d), 7.86 (1H, d); MS m/z 264.28 [M+H]$^+$.

Intermediate 51

4-methoxy-N-(1-methyl-4-piperidyl)-3-nitro-benzamide

3-Nitro-4-methoxybenzoic acid (Aldrich; 300 mg, 1.52 mmol), 1-methyl-4-aminopiperidine (Fluorochem; 174 mg, 1.52 mmol), HATU (868 mg, 2.28 mmol) and DIPEA (796 uL, 4.56 mmol) were stirred in DMF (6 mL) at room temperature for 2 hours. The reaction mixture was loaded onto an SCX-3 column pre-washed with methanol. The column was washed with methanol and then eluted with 2% 7N ammonia/methanol. Product containing fractions were combined and evaporated to give the title compound as an orange solid (341 mg, 76.4%).
$^1$H NMR (399.9 MHz, DMSO-$d_6$) δ1.55-1.59 (2H, m), 1.75 (2H, d), 1.91-1.95 (2H, m), 2.17 (3H, s), 2.70-2.79 (2H, d), 3.68-3.78 (1H, m), 3.99 (3H, s), 7.46 (1H, d), 8.16-8.19 (1H, m), 8.41 (2H, d); MS m/z 294.31 [M+H]$^+$.

Intermediate 52

4-amino-3-chloro-N-(2-morpholin-4-ylethyl)benzamide 3-chloro-N-(2-morpholin-4-ylethyl)-4-nitro-benzamide (Intermediate 53; 1.2 g, 3.82 mmol), iron powder (1.29 g, 22.95 mmol) and ammonium chloride (144 mg, 2.68 mmol) were heated in ethanol (27 mL) and water (9 mL at reflux for 1 h. A few drops of acetic acid were added and heating continued for a further 1 h. The reaction mixture was cooled, filtered and the filtrate concentrated. The residue was partitioned between DCM and sat NaHCO$_3$. The organic layer was washed with brine, dried (MgSO$_4$) and concentrated. Column chromatography of the residue gave the title compound as a white crystalline solid. (650 mg, 60%)
$^1$H NMR (399.9 MHz, DMSO-$d_6$+D$_2$O) δ2.38-2.46 (6H, m), 3.30-3.36 (2H, m), 3.55-3.59 (4H, m), 5.83 (1H, partially exchanged NH$_2$), 6.79 (1H, d), 7.53-7.55 (1H, m), 7.73 (1H, d), 8.10 (1H, s); MS m/z 284.08 [M+H]$^+$.

Intermediate 53

3-chloro-N-(2-morpholin-4-ylethyl)-4-nitro-benzamide 3-chloro-4-nitro-benzoyl chloride (Intermediate 54; 1.1 g, 5.00 mmol) was dissolved in DCM (10 mL) and N,N-diisopropylethylamine (1.05 mL, 6.00 mmol) added. The mixture was cooled in an ice/water bath and 4-(2-aminoethyl)morpholine (Aldrich; 0.66 mL, 5.00 mmol) in DCM (5 mL) added dropwise. The mixture was allowed to warm to room temperature and stirred for 0.5 hr. The reaction mixture was washed with brine, 2N NaOH, dried (MgSO$_4$) and concentrated. Column chromatography of the residue (2% MeOH/DCM) gave the title compound as a yellow solid. (1.2 g, 76%)
$^1$H NMR (399.9 MHz, DMSO-$d_6$) δ2.43 (4H, t), 2.48 (2H, t), 3.39-3.44 (2H, m), 3.58 (4H, m), 7.98-8.01 (1H, m), 8.16 (1H, m), 8.19 (1H, d), 8.78 (1H, t); MS m/z 314.16 [M+H]$^+$.

Intermediate 54

3-chloro-4-nitro-benzoyl chloride

3-Chloro-4-nitrobenzoic acid (Apin; 1 g, 4.96 mmol) was suspended in toluene (10 mL) and thionyl chloride (1.11 mL, 14.88 mmol) added. The mixture was heated to 85° C. for 45 min Further thionyl chloride (1.1 mL) was added and the mixture heated at reflux. 0.5 hr. The reaction mixture was allowed to cool and stand overnight. The mixture was concentrated to give the title compound as a yellow liquid (1.15 g, 100%).
$^1$H NMR (399.9 MHz, CDCl$_3$) δ7.87 (1H, s), 8.07-8.10 (1H, m), 8.23 (1H, d); MS m/z 198.92 [M+H]$^+$.

Intermediate 55

4-amino-3-chloro-N-(1-methyl-4-piperidyl)benzamide 3-chloro-N-(1-methyl-4-piperidyl)-4-nitro-benzamide (Intermediate 56; 1.8 g, 6 mmol) hydrogenated over 2 hours with agitation at 298K and pressure of 5 bar using a 5% Pt/C catalyst and EtOH (50 mL) solvent. The catalyst was filtered and the filtrate concentrated to give a yellow crystalline solid which was dissolved in DCM and purified by column chromatography (5% MeOH/DCM) to give the title compound as a pale yellow crystalline solid (1.62 g, 100%)
$^1$H NMR (399.9 MHz, DMSO-$d_6$) δ1.53-1.60 (2H, m), 1.71-1.74 (2H, m), 1.90-1.95 (2H, m), 2.16 (3H, s), 2.33-2.35 (1H, m), 2.67-2.69 (1H, m), 2.76 (2H, d), 3.66-3.70 (1H, m), 5.82 (2H, d), 6.78 (1H, d), 7.56-7.58 (1H, m), 7.76 (1H, d), 7.89 (1H, d); MS m/z 268.14 [M+H]$^+$.

Intermediate 56

3-chloro-N-(1-methyl-4-piperidyl)-4-nitro-benzamide 3-chloro-4-nitro-benzoyl chloride (Intermediate 54; 2.2 g, 10.00 mmol) was dissolved in DCM (20 mL) and N,N-diisopropylethylamine (2.095 mL, 12.00 mmol) added. The mixture was cooled in an ice/water bath and 4-amino-1-methylpiperidine (Fluorochem; 1.14 g, 10.00 mmol) in DCM (10 mL) added dropwise. The mixture was allowed to warm to room temperature and stirred for 0.5 hr. A white precipitate resulted. The reaction mixture was washed with 2N NaOH, filtered and the filter cake washed with water and dried on a sinter over the weekend to give the title compound as a white solid (1.80 g, 60%) as a white solid.
$^1$H NMR (399.9 MHz, DMSO-$d_6$) δ1.53-1.63 (2H, m), 1.79 (2H, t), 1.92-1.99 (2H, m), 2.17 (3H, s), 2.78 (2H, d), 3.70-3.77 (1H, m), 7.99-8.02 (1H, m), 8.18 (2H, t), 8.60 (1H, d); MS m/z 298.2 [M+H]$^+$.

Intermediate 57

10-amino-2-cyclopentyl-6-methyl-2,6,9,11-tetrazabicyclo[5.4.0]undeca-7,9,11-trien-5-one 10-Chloro-2-cyclopentyl-6-methyl-2,6,9,11-tetrazabicyclo[5.4.0]undeca-8,10,12-trien-5-one (Intermediate 1; 250 mg; 0.89 mmol), Diphenylmethanimine (Fluka; 178 mg, 0.979 mmol) and caesium carbonate (580 mg, 1.78 mmol) were added to dioxane (3 mL and the suspension bubbled with nitrogen for 10 minutes. Tris(Dibenzylideneacetone) Dipalladium(0) (49 mg; 0.053 mmol) and XANTPHOS (46 mg, 0.080 mmol) were added and the mixture heated to 100° C. for 16 hrs. The reaction mixture was cooled to room temperature filtered and the filter cake washed with DCM. The filtrate was evaporated and the resultant material taken up in DCM and purified on silica (the column was made neutral prior to purification. by wetting with iso-hexane, running a solution of 5% triethylamine in iso-hexane through followed by iso-hexane, material was then added) eluting with a gradient of 40-60% Ethyl Acetate/iso-hexane then 60% Ethyl Acetate/iso-hexane. Fractions containing the imine intermediate were combined and evaporated to a yellow solid (162 mg, 43%), which was dissolved in THF (10 ml). 2M aq HCl (3 mL) was added and the solution stirred at room temperature for 20 minutes. The reaction mixture was added to a 5 g SCX-2 column pre-wet with MeOH (2 column volumes), flushed with MeOH (2 column volumes) and the a product eluted with 2M ammonia in MeOH. Solvents were evaporated to give the title compound as a white solid (80 mg, 80% from imine)

$^1$H NMR (399.902 MHz, DMSO-D6) ?1.46 (m, 4H), 1.59 (m, 2H), 1.83 (m, 2H), 3.03 (s, 3H), 3.46 (m, 2H), 4.60 (m, 1H), 5.99 (s, 2H), 7.75 (s, 1H); MS m/z 262 [M+H]$^+$.

Intermediate 58

4-bromo-2,6-difluoro-N-(1-methyl-4-piperidyl)benzamide 4-bromo-difluorobenzoic acid (Fluorochem; 3.0 g, 12.66 mol) and HBTU (5.3 g, 13.92 mol) were added to DMF (80 mL), to this was added the required 4-amino-1-methylpiperidine (Fluorochem; 1.59 g, 13.93 mol) and DIPEA (5.0 mL, 27.85 mol), the reaction was stirred for 48 hours, after which the solvent was removed in vacuo to yield a brown gum. The gum was treated with 2.0 M NaOH (50 mL) and extracted with DCM (3×200 ml). Combined extracts were dried and solvent removed in vacuo to yield a dark orange gum which was recrystallised from hot acetonitrile to give the title compound as a white solid (1.9 g, 45%)

$^1$H NMR (400.132 MHz, DMSO-D6) δ 8.64 (d, 1H), 7.55 (d, 2H), 3.74-3.64 (m, 1H), 2.74-2.65 (m, 2H), 2.15 (s, 3H), 1.98 (t, 2H), 1.82-1.74 (m, 2H), 1.52-1.42 (m, 2H); MS m/z 334 [M+H]$^+$.

Intermediate 59

4-amino-2,5-difluoro-N-(1-methyl-4-piperidyl)benzamide 2,5-difluoro-N-(1-methyl-4-piperidyl)-4-nitro-benzamide (Intermediate 60; 633 mg 2.1 mmol), 10% Palladium on Carbon (70 mg) and Methanol (50 mL) were combined and stirred at 25 $^\circ$C under Hydrogen at 3 bar pressure for 16 hours.

The catalyst was filtered off and the filtrate evaporated to give the title compound as a yellow solid. (554 mg, 97%)

$^1$H NMR (400.132 MHz, CDCl3) δ1.58 (m, 2H), 2.03 (m, 2H), 2.18 (m, 2H), 2.30 (s, 3H), 2.78 (m, 2H), 3.99 (m, 1H), 4.14 (s, 2H), 6.47 (m, 2H), 7.71 (m, 1H); MS m/z 334 [M+H]$^+$.

Intermediate 60

2,5-difluoro-N-(1-methyl-4-piperidyl)-4-nitro-benzamide 1,5-Difluoro-4-nitrobenzoic acid (Fluorochem; 1 g, 4.92 mmol), 4-Amino-1-methylpiperidine (Fluorochem; 620 mg, 5.41 mmol), HAT (2.05 g, 5.41 mmol), DIPEA (2.57 mL, 14.76 mmol) and DMF (10 mL) were combined and stirred at room temperature for 18 hrs. Solvents were evaporated and the resultant material partitioned between DCM and water. Both phases were acidified with 2M aq HCl and added to a 50 g SCX-2 column pre-wet with MeOH (2 column volumes). The column was flushed with MeOH (2 column volumes) and the crude product eluted with 2M ammonia in MeOH. Product containing fractions were evaporated in vacuo and the resultant material taken up in DCM and purified on silica eluting with a gradient of 0-5% 2M ammonia in MeOH/DCM then 5% 2M ammonia in MeOH/DCM. Fractions containing product were combined and evaporated to give the title compound as a yellow solid. (635 mg, 43%)

$^1$H NMR (400.132 MHz, DMSO-D6) δ 1.53 (m, 2H), 1.80 (m, 2H), 1.98 (m, 2H), 2.16 (s, 3H), 2.73 (m, 2H), 3.70 (m, 1H), 7.79 (m, 1H), 8.21 (m, 1H), 8.59 (d, 1H); MS m/z 300 [M+H]$^+$.

Intermediate 61

4-amino-2-fluoro-N-(1-methyl-4-piperidyl)benzamide 2-fluoro-N-(1-methyl-4-piperidyl)-4-nitro-benzamide (Intermediate 62; 1.62 g, 5.8 mmol), 10% Palladium on Carbon (160 mg) and Methanol (50 mL) were combined and stirred at 25 $^\circ$C under Hydrogen at 5 bar pressure for 16 hours.

The catalyst was filtered off and the filtrate evaporated to give a brown solid which was triturated with 5% MeOH/DCM. The precipitate was collected by filtration and dried under vacuum to yield the title compound as a beige solid (560 mg, 39%).

$^1$H NMR (400.132 MHz, DMSO-D6) δ1.74 (m, 2H), 1.99 (m, 2H), 2.76 (s, 3H), 3.09 (m, 2H), 3.42 (m, 2H), 3.97 (m, 1H), 5.89 (s, 2H), 6.30 (m, 1H), 6.39 (m, 1H), 7.37 (m, 1H), 7.67 (s, 1H), 9.11 (s, 1H); MS m/z 252 [M+H]$^+$.

Intermediate 62

2-fluoro-N-(1-methyl-4-piperidyl)-4-nitro-benzamide

2-Fluoro-4-nitrobenzoic acid (Aldrich; 3 g, 16.21 mmol), 4-Amino-1-methylpiperidine (Fluorochem; 2.03 g, 17.83 mmol), HATU (6.77 g, 17.83 mmol), DIPEA (8.5 mL, 48.63 mmol) and DMF (30 mL) were combined and stirred at ambient temperature for 18 hrs. Solvents evaporated and partitioned between DCM (200 ml) and water (100 ml). The aqueous phase was re-extracted with DCM (100 ml). The combined organic phases were dried (MgSO4) and evaporated. The resultant material was taken up in DCM and purified on silica eluting with a gradient of 0-5% 2M ammonia in MeOH/DCM then 5% 2M ammonia in MeOH/DCM. Fractions containing product were combined and evaporated to give the title compound as a yellow solid (2.67 g, 59%)

$^1$H NMR (400.132 MHz, DMSO-D6) δ1.53 (m, 2H), 1.80 (m, 2H), 2.26 (m, 5H), 2.85 (m, 2H), 3.74 (m, 1H), 7.72 (m, 1H), 8.06 (m, 1H), 8.12 (m, 1H), 8.54 (d, 1H); MS m/z 282 [M+H]$^+$.

Intermediate 63

4-amino-3-methyl-N-(1-methyl-4-piperidyl)benzamide 3-methyl-N-(1-methyl-4-piperidyl)-4-nitro-benzamide (Intermediate 64: 3.34 g) 10% Palladium on Carbon (350 mg) and Methanol (50 mL) were combined and stirred at 25 $^\circ$C under Hydrogen at 5 bar pressure for 16 hours.

The catalyst was filtered off and washed with EtOH. The filtrate was evaporated to yield a cream solid, which was triturated with DCM filtered and dried under vacuum to give the title compound as a white solid (1.2 g)

$^1$H NMR (400.132 MHz, DMSO-D6) δ1.75 (m, 2H), 1.96 (m, 2H), 2.08 (s, 3H), 2.74 (s, 3H), 3.04 (m, 2H), 3.38 (m, 2H), 3.96 (m, 1H), 5.36 (s, 2H), 6.58 (d, 1H), 7.47 (m, 2H), 7.86 (d, 1H), 9.13 (s, 1H); MS m/z 248 [M+H]$^+$.

The following intermediate was prepared in a manner analogous to Intermediate 62 utilising 3-Methyl-4-nitrobenzoic acid, available form Aldrich, as the starting Nitro acid.

Intermediate 64

3-methyl-N-(1-methyl-4-piperidyl)-4-nitro-benzamide 3-methyl-N-(1-methyl-4-piperidyl)-4-nitro-benzamide was prepared in a manner analogous to Intermediate 62 utilising 3-Methyl-4-nitrobenzoic acid, available form Aldrich, as the starting Nitro acid.

$^1$H NMR (400.132 MHz, DMSO-D6) δ1.71 (m, 2H), 1.92 (m, 2H), 3.16 (m, 2H), 3.91 (m, 1H), 7.86 (m, 1H), 7.92 (s, 1H), 8.06 (d, 1H), 8.56 (d, 1H); MS m/z 278 [M+H]$^+$.

Intermediate 65

4-amino-3-fluoro-N-(1-methyl-4-piperidyl)benzamide

4-Amino-3-Fluorobenzoic acid (Fluorochem; 1 g, 6.44 mmol), 4-Amino-1-methylpiperidine (Fluorochem; 811 mg, 7.09 mmol), HATU (2.70 g, 7.09 mmol), DIPEA (3.4 mL, 19.32 mmol) and DMF (15 mL) were combined and stirred for 18 hrs at room temperature. The solvent was evaporated and the resultant material dissolved in DCM (with a little MeOH to aid solubility) and chromatographed on silica eluting with a gradient of 0-10% 2M ammonia in MeOH/DCM. Fractions containing product were combined and evaporated to give an orange solid which was dissolved in MeOH and added to a 50 g SCX-2 column pre-wet with MeOH (2 column volumes). The column was flushed with MeOH (2 column volumes) and the product eluted with 2M ammonia in MeOH. Product containing fractions were evaporated to yield the title compound as a beige solid. (1.72 g, 100%)

$^1$H NMR (399.902 MHz, CDCl3) ?1.55 (m, 2H), 2.03 (m, 2H), 2.14 (m, 2H), 2.29 (s, 3H), 2.81 (m, 2H), 3.95 (m, 1H), 4.01 (s, 2H), 5.77 (d, 1H), 6.75 (m, 1H), 7.34 (m, 1H), 7.45 (m, 1H); MS m/z 252 [M+H]$^+$.

Intermediate 66

4-[(2-cyclopentyl-6-methyl-5-oxo-2,6,9,11-tetrazabicyclo[5.4.0]undeca-8,10,12-trien-10-yl)amino]-3-(2-methoxyethoxy)benzoic acid To a stirred solution of Methyl4-[(6-cyclopentyl-2-methyl-3-oxo-2,6,8,10-tetrazabicyclo[5.4.0]undeca-8,10,12-trien-9-yl)amino]-3-(2-methoxyethoxy)benzoate (Intermediate 67; 164 mg, 0.35 mmol) in ethanol (3 mL) was added a solution of lithium hydroxide (22 mg, 0.92 mmol) in water (1 ml). The reaction was stirred at ambient temperature overnight. A further addition of lithium hydroxide (20 mg) as a solution in water (1 ml) was added and stirring continued for 2.5 hrs and then heated to 50° C. for 4 hrs. The reaction mixture was evaporated and the residue diluted with water (5 mL). The resultant opaque solution was treated with a few drops of 2M HCl (aq.) to adjust the pH to 2-3. A precipitate formed which was collected by suction filtration, washing through with more water and dried under vacuum, at 55° C., for 3 hours to afford the title compound as an off white solid (113 mg, 71%)

$^1$H NMR (400.132 MHz, DMSO-D6) δ 1.65 (m, 6H), 1.91 (m, 2H), 2.67 (m, 2H), 3.18 (s, 3H), 3.70 (m, 2H), 3.75 (m, 2H), 4.27 (m, 2H), 4.84 (m, 1H), 7.57-7.63 (m, 2H), 8.13 (s, 1H), 8.27 (d, 1H), 8.72 (m, 1H); MS m/z 456.4 [M+H]$^+$.

Intermediate 67

Methyl4-[(6-cyclopentyl-2-methyl-3-oxo-2,6,8,10-tetrazabicyclo[5.4.0]undeca-8,10,12-trien-9-yl)amino]-3-(2-methoxyethoxy)benzoate To 10-Chloro-2-cyclopentyl-6-methyl-2,6,9,11-tetrazabicyclo[5.4.0]undeca-8,10,12-trien-5-one (Intermediate 1, 222 mg, 0.79 mmol) was added a solution of Methyl4-amino-3-(2-methoxyethoxy)benzoate (Intermediate 68; 203 mg, 0.90 mmol) in ethanol (4 mL). Water (12 mL) was added followed by concentrated hydrochloric acid (36%; 160 μl). The reaction was heated to 80° C. and stirred overnight. The reaction was allowed to stand and cool overnight, before evaporating ethanol. The aqueous residue was diluted to ~50 mL with water and the solution basified to pH 9 by addition of a few drops of aq. Ammonia. The resultant emulsion was treated with a little brine and extracted with DCM (2×50 mL). Combined organic extracts were washed with brine, dried over magnesium sulphate, filtered and evaporated to give an amber gum which was purified by flash chromatography on silica (40 g Si cartridge; ISCO companion), eluting first with a rising gradient of 25-75% ethyl acetate in iso-hexane and then a rising gradient of 0-10% methanol in DCM. Product containing fractions were combined and evaporated to give a yellow oil which crystallised on standing overnight. This solid was triturated with diethyl ether, solid collected by suction filtration and dried to afford the title compound as a cream solid (173 mg, 47%)

$^1$H NMR (400.132 MHz, CDCl$_3$)? 1.59-1.81 (m, 6H), 2.04 (m, 2H), 2.67 (m, 2H), 3.29 (s, 3H), 3.48 (s, 3H), 3.70 (m, 2H), 3.81 (m, 2H), 3.90 (s, 3H), 4.27 (m, 2H), 4.89 (m, 1H), 7.58 (m, 1H), 7.69 (m, 1H), 7.87 (s, 1H), 7.95 (s, 1H), 8.56 (d, 1H); MS m/z 470 [M+H]$^+$.

Intermediate 68

Methyl4-amino-3-(2-methoxyethoxy)benzoate

To a solution of Methyl3-hydroxy-4-aminobenzoate (ABCR: 97 mg, 0.58 mmol) in acetone (3 mL), in a microwave tube, was added Methoxyethyl bromide (Aldrich; 85 μl, 0.90 mmol) and powdered potassium carbonate (120 mg, 0.87 mmol). The reaction was heated in a microwave (150 W, CEM explorer) to 100° C. and held for 30 minutes.

A further addition of Methoxyethyl bromide (40 μl, 0.43 mmol) was made and the reaction heated to 120° C. for a further 30 minutes.

The reaction was repeated in two batches as follows. To a solution of Methyl3-hydroxy-4-aminobenzoate (135 mg, 0.81 mmol) in acetone (4 ml), in a microwave tube. Was added Potassium Carbonate (185 mg, 1.34 mmol) and Methoxyethyl bromide (115 μl, 1.22 mmol) The reaction was heated to 120° C. in a microwave and held for 1 hour. The reactions was cooled, treated with a further aliquot of methoxyethyl bromide (58 μl, 0.62 mmol) and re-heated to 120° C. holding for a further hour.

All three batches were combined and evaporated to dryness. The residue was partitioned between DCM (25 mL) and water (25 mL). The organic phase was separated and the aqueous phase re-extracted with DCM (20 mL). Combined organic phases were washed with brine, dried over magnesium sulphate and evaporated to give a brown oil which was purified by flash chromatography on silica (40 g Cartridge)

eluting with a rising gradient of 25-50% ethyl acetate in iso-hexane. Product containing fractions were combined and evaporated to give the title compound as a dark orange oil (256 mg, 56%).

$^1$H NMR (400.132 MHz, DMSO-D6) δ 3.38 (s, 3H), 3.74 (m, 2H), 3.80 (s, 3H), 4.16 (m, 2H), 5.61 (s, 2H), 6.72 (d, 1H), 7.37 (m, 1H), 7.45 (m, 1H); MS m/z 226 [M+H]$^+$.

Intermediate 69

4-[(6-cyclopentyl-2-methyl-3-oxo-2,6,8,10-tetrazabicyclo[5.4.0]undeca-8,10,12-trien-9-yl)amino]-3-propan-2-yloxy-benzoic acid To a stirred solution of Methyl4-[(6-cyclopentyl-2-methyl-3-oxo-2,6,8,10-tetrazabicyclo[5.4.0]undeca-8,10,12-trien-9-yl)amino]-3-propan-2-yloxy-benzoate (Intermediate 70; 128 mg, 0.28 mmol) in Ethanol (3 mL) was added a solution of lithium hydroxide (26 mg, 0.92 mmol) in water (1.5 mL). The reaction was allowed to stir at 70° C. for 4 hours, cooled, evaporated and the residue diluted with water (10 mL). The resultant solution was treated with a few drops of 2M HCl (aq.) until a precipitate persisted, pH ~3-4. The precipitate was collected by suction filtration, washing through with more water. Solid was dried under suction overnight to afford the title compound as a white solid (108 mg, 88

$^1$H NMR (400.132 MHz, DMSO-D6) δ 1.36 (d, 6H), 1.57-1.77 (m, 6H), 1.95 (m, 2H), 2.61 (m, 2H), 3.18 (s, 3H), 3.65 (m, 2H), 4.69-4.85 (m, 2H), 7.52-7.56 (m, 2H), 7.83 (s, 1H), 8.10 (s, 1H), 8.46 (d, 1H), 12.62 (s, 1H); MS m/z 440 [M+H]$^+$.

Intermediate 70

Methyl4-[(6-cyclopentyl-2-methyl-3-oxo-2,6,8,10-tetrazabicyclo[5.4.0]undeca-8,10,12-trien-9-yl) amino]-3-propan-2-yloxy-benzoate To 10-Chloro-2-cyclopentyl-6-methyl-2,6,9,11-tetrazabicyclo[5.4.0]undeca-8,10,12-trien-5-one (Intermediate 1, 190 mg, 0.68 mmol) was added a solution of Methyl4-amino-3-propan-2-yloxy-benzoate (Intermediate 71, 145 mg, 0.69 mmol) in ethanol (4 mL), followed by water (12 mL). Concentrated hydrochloric acid (36%; 140 µl) was added and the reaction heated to 80° C., with stirring, overnight. The reaction was allowed to stand and cool overnight, before evaporating ethanol. The aqueous residue was diluted to ~40 mL with water and the solution basified to pH 9 by addition of a few drops of aq. ammonia, The resultant emulsion was treated with a little brine and extracted with DCM (2×30 mL). The biphasic mixture was poured into a PTFE cup and the organic phase allowed to drip through under gravity. Evaporation of the organic phase afforded an amber gum, which was purified by flash chromatography on silica (40 g Si cartridge; ISCO companion), eluting with a rising gradient of 25-100% ethyl acetate in iso-hexane. Product containing fractions were combined and evaporated to give a colourless gum which was triturated with a small amount of diethyl ether and the resultant solid collected by suction filtration and dried to afford the title compound as a white solid (132 mg, 43%)

$^1$H NMR (400.132 MHz, DMSO-D6) δ 1.36 (d, 6H), 1.58-1.77 (m, 6H), 1.95 (m, 2H), 2.60 (m, 2H), 3.18 (s, 3H), 3.64 (m, 2H), 3.83 (s, 3H), 4.77 (m, 2H), 7.53 (m, 1H), 7.57 (m, 1H), 7.78 (s, 1H), 8.10 (s, 1H), 8.51 (d, 1H); MS m/z 452 [M+H]$^+$.

Intermediate 71

Methyl4-amino-3-propan-2-yloxy-benzoate

Methyl3-hydroxy-4-aminobenzoate (ABCR: 100 mg, 0.60 mmol) & caesium carbonate (396 mg, 1.22 mmol) were taken up in acetone (4 mL) and 2-iodopropane (90 µl, 0.90 mmol) added and reaction heated in microwave (CEM discover; 150 W) to 120° C. and held for 30 mins A further aliquot of 2-iodopropane (90 µl, 0.90 mmol) was added and reaction heated again to 120° C. in microwave, holding for a further 30 mins The reaction was repeated twice on a 0.89 mmol scale Reaction mixtures were combined and evaporated to dryness and the residue partitioned between, ethyl acetate (40 ml) and water (50 ml). The organic phase was separated and the aqueous re-extracted with ethyl acetate (40 ml). Combined organic extracts were washed with brine, dried over magnesium sulphate and evaporated to give a brown oil which was purified by column chromatography, on silica (40 g cartridge; ISCO companion) eluting with a rising gradient of 5-50% ethyl acetate in iso-hexane. Product containing fractions were combined and evaporated to dryness to afford the product as a yellow oil (301 mg, 60%)

$^1$H NMR (400.132 MHz, DMSO-D6) δ 1.28 (d, 6H), 3.75 (s, 3H), 4.53 (m, 1H), 5.51 (s, 2H), 6.66 (d, 1H), 7.31 (m, 1H), 7.37 (m, 1H); MS m/z 209.4 [M+H]$^+$.

Intermediate 72

4-[(2-cyclopentyl-6-methyl-5-oxo-2,6,9,11-tetrazabicyclo[5.4.0]undeca-8,10,12-trien-10-yl)amino]-3-(2-dimethylaminoethoxy)benzoic acid Methyl4-[(2-cyclopentyl-6-methyl-5-oxo-2,6,9,11-tetrazabicyclo[5.4.0]undeca-8,10,12-trien-10-yl)amino]-3-hydroxy-benzoate (Intermediate 73; 63 mg, 0.15 mmol) was dissolved in DMA (2 mL) and treated sequentially with potassium carbonate powder (fine mesh; 106 mg, 0.79 mmol) and dimethylaminoethyl bromide hydrobromide (ASDI; 61 mg, 0.26 mmol). The reaction mixture was heated to 100° C., with stirring for 1 hour and allowed to cool overnight, before pouring into water (40 ml). The mixture was extracted with DCM (2×30 ml) and the organic extracts washed with brine, dried over magnesium sulphate, filtered and evaporated to give a brown liquid which was taken up in methanol and poured onto an SCX-3 cartridge (2 g). The cartridge was washed with methanol (~30 ml) before eluting products with 2M ammonia/methanol (~20 ml). The ammoniacal wash was evaporated to give the title compound as a brown gum (41 mg, 57%)

MS m/z 483.4 [M+H]$^+$, Retention Time 2.41 minutes.

Intermediate 73

Methyl4-[(2-cyclopentyl-6-methyl-5-oxo-2,6,9,11-tetrazabicyclo[5.4.0]undeca-8,10,12-trien-10-yl) amino]-3-hydroxy-benzoate 10-Chloro-2-cyclopentyl-6-methyl-2,6,9,11-tetrazabicyclo[5.4.0]undeca-8,10,12-trien-5-one (Intermediate 1; 180 mg, 0.64 mmol) and Methyl3-hydroxy-4-aminobenzoate (ABCR; 123 mg, 0.73 mmol) were taken up in ethanol (4 mL)

and water (12 mL). Concentrated hydrochloric acid (36%; 130 µl) was added and the reaction heated to 80° C. and stirred overnight. The reaction was allowed to stand and cool overnight, before evaporating ethanol. The aqueous residue was diluted to ~30 ml with water and the solution basified to pH 9 by addition of a few drops of aqueous Ammonia. The resultant mixture was extracted with DCM (2×50 ml). A solid persisted at the phase boundary. This solid was collected by suction filtration and dried to give the title compound as a purple/grey solid (64 mg, 24%)

The combined organic extracts were washed with brine, dried over magnesium sulphate, filtered and evaporated to a pink/brown solid (153 mg) which was triturated with DCM (5 mL). The solid was then collected by suction filtration and dried to give the title compound as a dusky pink solid (79 mg, 30%)

$^1$H NMR (400.132 MHz, DMSO-D6) δ 1.57-1.75 (m, 6H), 1.95 (m, 2H), 2.59 (m, 2H), 3.18 (s, 3H), 3.63 (m, 2H), 3.80 (s, 3H), 4.82 (m, 1H), 7.44 (m, 2H), 7.84 (s, 1H), 8.09 (s, 1H), 8.36 (d, 1H); MS m/z 412.3 [M+H]$^+$.

Intermediate 74

4-amino-N-(1-methyl-4-piperidyl)-3-(trifluoromethoxy)benzamide

To a solution of 4-amino-3-(trifluoromethoxy)benzoic acid (Maybridge; 1.05 g, 4.75 mmol) in DMF (20 ml) was added 4-amino-1-methylpiperidine (Fluorochem; 604 mg, 5.29 mmol) followed by DIPEA (1.6 ml, 9.19 mmol) and HATU (2.06 g, 5.42 mmol). The reaction mixture was stirred at ambient temperature O/N. The reaction mixture was evaporated to dryness and the residue partitioned between DCM (75 mL) and saturated aqueous sodium bicarbonate solution (75 mL). The aqueous phase was re-extraced with DCM (50 ml) and the combined organic phases washed with brine, dried over magnesium sulphate, filtered and evaporated to give the title compound as an amber gum (1.17 g, 78%)

$^1$H NMR (400.132 MHz, DMSO-D6) δ 1.75 (m, 2H), 1.93 (m, 2H), 2.64 (s, 3H), 2.87 (m, 2H), 3.93 (m, 1H), 5.93 (s, 2H), 6.80 (d, 1H), 7.64 (m, 2H), 8.08 (d, 1H); MS m/z 316.4 [M+H]$^+$.

Intermediate 75

4-[(2-cyclopentyl-6-methyl-5-oxo-2,6,9,11-tetrazabicyclo[5.4.0]undeca-7,9,11-trien-10-yl)amino]-3-ethoxy-benzoic acid To a solution of 10-Chloro-2-cyclopentyl-6-methyl-2,6,9,11-tetrazabicyclo[5.4.0]undeca-8,10,12-trien-5-one (Intermediate 1; 280 mg, 1 mmol) and 4-amino-3-ethoxybenzoic acid (WO 2001077101; 205 mg, 1.13 mmol) in ethanol (5 mL) was added water (15 mL) and conc hydrochloric acid (0.17 mL, 2 mmol). The mixture was heated under reflux for 36 hours. The reaction was cooled and a brown solid precipitated. This was filtered and dried, triturated under cold acetonitrile and then dried in vacuo. To yield the title compound as a brown solid (190 mg; 45%)

MS m/z 426 [M+H]$^+$. Retention Time 1.58 minutes

Intermediate 76

10-chloro-6-methyl-2-propan-2-yl-2,6,9,11-tetrazabicyclo[5.4.0]undeca-7,9,11-trien-5-one 3-[(5-bromo-2-chloro-pyrimidin-4-yl)-propan-2-yl-amino]-N-methyl-propanamide (Intermediate 77; 2.67 g, 7.9 6 mmol) was dissolved in dioxane (80 mL) and tris(dibenzylideneacetone) palladium (II) (146 mg, 0.16 mmol), XANTPHOS (277 mg, 0.48 mmol) and Caesium carbonate (3.76 g, 11.54 mmol) added. The apparatus was evacuated and backfilled with nitrogen (×3) and then heated at 100° C. for 24 hours. The mixture was filtered and concentrated and the residue purified by column chromatography (1% MeOH/DCM) to give the title compound as a viscous yellow oil (1.25 g, 62%).

$^1$H NMR (399.9 MHz, CDCl$_3$) δ1.18 (6H, d), 2.59-2.61 (2H, m), 3.22 (3H, s), 3.59-3.62 (2H, m), 4.82-4.88 (1H, m), 7.87 (1H, s); MS m/z 255.16 [M+H]$^+$.

Intermediate 77

3-[(5-bromo-2-chloro-pyrimidin-4-yl)-propan-2-ylamino]-N-methyl-propanamide

N-methyl-3-(propan-2-ylamino)propanamide (Intermediate 78; 2 g, 13.87 mmol), 5-bromo-2,4-dichloropyrimidine (Aldrich; 3.8 g, 16.64 mmol) and triethylamine (2.3 mL, 16.64 mmol) were heated in acetonitrile (85 mL) at 100° C. for 3 h. The mixture was cooled and concentrated. The residue was dissolved in DCM, washed with water, dried (MgSO$_4$) and concentrated. Column chromatography (0.5-1-2% 7N ammonia in methanol/DCM) gave:

The title compound as a pale yellow oil that crystallised on standing (2.67 g, 20%)

$^1$H NMR (399.9 MHz, DMSO-d$_6$) δ1.20 (6H, d), 2.31 (2H, t), 2.55 (3H, d), 3.65 (2H, t), 4.55-4.62 (1H, m), 7.72 (1H, s), 8.39 (1H, s); MS m/z 337.05 [M+H]$^+$.

Intermediate 78

N-methyl-3-(propan-2-ylamino)propanamide

Isopropylamine (Aldrich; 1.5 ml, 17.62 mmol) and methyl acrylamide (ABCR; 1.0 g, 11.75 mmol) were combined in methanol (10 ml). The mixture was heated in a microwave at 140° C. for 30 min. The reaction was repeated and the combined reaction mixtures were concentrated to remove excess amine. The residue was re-dissolved in methanol and absorbed onto an SCX column (50 g), washed with methanol and eluted with ammonia/methanol. Concentration of the product containing fractions gave the title compound as a colourless oil (3.2 g, 94%).

$^1$H NMR (399.9 MHz, CDCl$_3$) δ1.00 (6H, d), 2.27 (2H, t), 2.70-2.74 (4H, m), 2.76-2.80 (2H, m), 7.50 (1H, s)

Intermediate 79

4-amino-3-chloro-N-(1-methyl-4-piperidyl)benzamide 3-chloro-N-(1-methyl-4-piperidyl)-4-nitro-benzamide (Intermediate 80; 270 mg, 1 mmol), 10% Palladium on Carbon (30 mg) and Methanol (50 mL) were combined and stirred at 25 )C under Hydrogen at 5 bar pressure for 16 hours.

The catalyst was filtered off and solvents evaporated to give the title compound as a cream solid. (280 mg, 98%)

$^1$H NMR (400.132 MHz, CDCl3) δ1.49 (m, 2H), 1.95 (m, 2H), 2.09 (m, 2H), 2.24 (s, 3H), 2.75 (m, 2H), 3.89 (m, 1H), 4.27 (s, 2H), 5.69 (d, 1H), 6.68 (m, 1H), 7.41 (m, 1H), 7.62 (m, 1H); MS m/z 268 [M+H]$^+$.

Intermediate 80

3-chloro-N-(1-methyl-4-piperidyl)-4-nitro-benzamide

Reagents combined and stirred at room temperature overnight. LCMS after 18 hrs shows complete reaction. Solvents evaporated and residues partitioned between DCM (25 ml) and water (25 ml) then gravity filtered through a PTFE cup. Taken up in DCM and purified on silica eluting with a gradient of 0-5% 2M ammonia in MeOH/DCM then 5% 2M ammonia in MeOH/DCM. The peak corresponding to the product (which was only 1 spot by tlc) was clearly split into 2 on the chromatography trace. The first peak (fractions 6-10) was labelled PH17082/048/1 and evaporated to a brown gum. The second peak (fractions 11-14) was labelled as PH17082/048/2 and evaporated to a white solid. Both products had identical LCMS traces and showed the mass ion for the desired product. NMR showed a difference in the aliphatic region and an additional small broad peak in the aromatic region of PH17082/048/1. It was concluded that PH17082/048/1 was a salt (possibly PF6 from HATU).

PH17082/048/1 was dissolved in MeOH and added to a 2 g SCX-2 column pre-wet with MeOH (2 column volumes). The column was then flushed with MeOH (2 column volumes) and the product eluted with 2M ammonia in MeOH. This was then combined with the solid of PH17082/048/2 and evaporated to an off-white solid, 315 mg.

$^1$H NMR (500.133 MHz, DMSO-D6) δ1.66 (m, 2H), 1.85 (m, 2H), 2.14 (m, 2H), 2.25 (s, 3H), 2.83 (m, 2H), 3.78 (m, 1H), 7.97 (m, 1H), 8.09 (m, 1H), 8.12 (m, 1H), 8.26 (d, 1H); MS m/z 298 [M+H]$^+$.

Intermediate 81

10-chloro-2-ethyl-6-methyl-2,6,9,11-tetrazabicyclo[5.4.0]undeca-8,10,12-trien-5-one Tris(dibenzylideneacetone)dipalladium(0) (52 mg, 0.06 mmol), XANTPHOS (98 mg, 0.17 mmol) and caesium carbonate (1.32 g, 4.06 mmol) were added to a stirred solution of 3-[(5-bromo-2-chloro-pyrimidin-4-yl)-ethyl-amino]-N-methyl-propanamide (Intermediate 82; 900 mg, 2.80 mmol) in 1,4-dioxane (28 mL). The apparatus was evacuated and backfilled with nitrogen twice and then heated to 100° C. for 18 hrs. The reaction mixture was filtered through a celite pad and dry loaded onto silica for purification by flash silica chromatography (companion, 40 g, 0-10% MeOH/DCM) to give the title compound as a yellow solid (638 mg, 2.65 mmol, 95%).

$^1$H NMR (399.902 MHz, DMSO-D6) δ 1.17 (t, 3H), 2.66-2.69 (m, 2H), 3.19 (s, 3H), 3.57 (q, 2H), 3.72-3.74 (m, 2H), 8.13 (s, 1H); MS m/z 241.14 [M+H]$^+$.

Intermediate 82

3-[(5-bromo-2-chloro-pyrimidin-4-yl)-ethyl-amino]-N-methyl-propanamide

5-Bromo-2,4-dichloropyrimidine (Aldrich; 1.14 g, 5.00 mmol), 3-ethylamino-N-methyl-propanamide (Intermediate 83; 0.642 g, 5.00 mmol) and triethylamine (0.71 mL, 5.10 mmol) were combined in acetonitrile (25 mL) and heated to 100° C. for 4 hrs. The solvent was removed under reduced pressure and the residue taken up in Ethyl Acetate, washed with water and purified by flash silica chromatography (companion, 40 g, 0-10% Methanol/DCM) to give the title compound as a white solid (1.06 g, 3.3 mmol, 66%).

$^1$H NMR (399.902 MHz, DMSO-D6) δ 1.18 (t, 3H), 2.46 (t, 2H), 2.58 (d, 3H), 3.67 (q, 2H), 3.81 (t, 2H), 7.85 (m, 1H), 8.31 (s, 1H); MS m/z 320.95 [M+H]$^+$.

Intermediate 83

3-ethylamino-N-methyl-propanamide

N-methylacrylamide (ABCR: 851 mg, 10.00 mmol) and ethylamine (2 M in methanol, 10 mL, 20.00 mmol) were combined in a microwave reaction vessel, which was sealed and irradiated at 140° C. for 30 mins. The reaction mixture was allowed to cool and then loaded directly onto a 50 g SCX-2 cartridge, washing with methanol (100 mL) and eluting the desired product with 7 N methanolic ammonia (100 mL). Concentration under reduced pressure of product containing fractions gave the title compound as a clear oil (1.285 g; 99%)

$^1$H NMR (399.9 MHz, DMSO-d$_6$) δ0.93-0.99 (3H, m), 2.19 (2H, t), 2.52-2.52 (2H, m), 2.54-2.59 (3H, d), 2.68 (2H, t), 7.80 (1H, br s)

Intermediate 84

10-chloro-6-methyl-2-(2-methylpropyl)-2,6,9,11-tetrazabicyclo[5.4.0]undeca-7,9,11-trien-5-one 3-[(5-bromo-2-chloro-pyrimidin-4-yl)-(2-methylpropyl)amino]-N-methyl-propanamide (Intermediate 85; 3.26 g, 9.32 mmol)) was suspended in dioxane (70 mL), Caesium Carbonate (6 g, 18.64 mmol) was added and the mixture bubbled with nitrogen for 10 minutes. Tris(dibenzylideneacetone)dipalladium(0) (512 mg, 0.56 mmol) and XANTPHOS (485 mg, 0.839 mmol) were added and the mixture heated at 100° C. for 24 hrs. The reaction mixture was cooled to room temperature, solvent evaporated and the residues partitioned between DCM (250 mL) and water (250 mL). The aqueous phase was re-extracted with DCM (200 mL) and the combined organic phases dried over MgSO4 and evaporated to a dark brown gum which was taken up in DCM and purified on silica, eluting with a gradient of 30-50% Ethyl Acetate/iso-hexane then 50% Ethyl Acetate/iso-hexane. Fractions containing product were combined and evaporated to a yellow solid, which was heated at reflux in iso-hexane (50 mL) for 15 minutes and allowed to cool to room temperature overnight. The resulting solid was filtered and dried to give the title compound as a pale yellow solid (1.02 g, 41%)

$^1$H NMR (400.132 MHz, CDCl3) δ0.85 (d, 6H), 2.03 (m, 1H), 2.65 (m, 2H), 3.23 (s, 3H), 3.45 (d, 2H), 3.69 (m, 2H), 7.89 (s, 1H); MS m/z 269 [M+H]$^+$.

Intermediate 85

3-[(5-bromo-2-chloro-pyrimidin-4-yl)-(2-methylpropyl)amino]-N-methyl-propanamide 5-Bromo-2,4-dichloropyrimidine (Aldrich; 2.82 g, 12.37 mmol), N-methyl-3-(2-methylpropylamino)propanamide (Intermediate 86; 1.78 g; 11.25 mmol), Triethylamine (1.65 mL, 11.81 mmol) and DCM (40 mL) were combined and stirred over the weekend at room temperature. The reaction mixture was washed saturated aqueous sodium bicarbonate solution and gravity filtered through a PTFE cup and solvent evaporated. The residue was dissolved in DCM and passed through a silica column eluting with a gradient of 30-50% Ethyl Acetate/iso-hexane over 10 column volumes then 50%

Ethyl Acetate/iso-hexane. Fractions containing product combined and evaporated to give the title compound as a white solid. (3.26 g, 83%)

$^1$H NMR (400.132 MHz, CDCl$_3$) δ0.84 (d, 6H), 1.98 (m, 1H), 2.44 (m, 2H), 2.75 (d, 3H), 3.58 (m, 2H), 3.91 (m, 2H), 5.57 (s, 1H), 8.11 (s, 1H); MS m/z 351 [M+H]$^+$.

Intermediate 86

N-methyl-3-(2-methylpropylamino)propanamide

N-methylacrylamide (ABCR; 1 g, 11.75 mmol) was dissolved in EtOH (5 mL). Isobutylamine (Aldrich; 2.33 mL, 23.5 mmol) was added and stirred at ambient temperature in a stoppered flask over the weekend. The reaction was then transferred to a microwave reactor vessel and heated in a microwave for 10 minutes at 140° C. Solvents were evaporated in vacuo to give the title compound as a colourless liquid. (1.78 g, 96%)

$^1$H NMR (400.132 MHz, CDCl3) δ0.93 (d, 6H), 1.74 (m, 1H), 2.35 (m, 2H), 2.43 (d, 2H), 2.78 (d, 3H), 2.85 (m, 2H), 7.88 (s, 1H)

Intermediate 87

2-butan-2-yl-10-chloro-6-methyl-2,6,9,11-tetrazabicyclo[5.4.0]undeca-7,9,11-trien-5-one To a solution of 3-[(5-bromo-2-chloro-pyrimidin-4-yl)-butan-2-yl-amino]-N-methyl-propanamide (Intermediate 88; 559 mg, 1.60 mmol) in anhydrous 1,4-dioxane (15 mL) was added Caesium Carbonate (1.04 g, 3.19 mmol). Nitrogen was bubbled through the reaction mixture for 10 minutes, prior to addition of Tris(dibenzylideneacetone)dipalladium(0) (87 mg, 0.095 mmol) and XANTPHOS (88 mg, 0.152 mmol). The reaction was heated to 100° C. and stirred under nitrogen m for 18 hrs. The reaction mixture was cooled and diluted to ~40 ml with DCM. The reaction mixture was filtered to remove insoluble material, washing filter cake through with DCM. The filtrate was evaporated to give a brown gum which was purified by flash chromatography on silica (40 g cartridge; ISCO companion) eluting with a 25-75% gradient of ethyl acetate in iso-hexane. Product containing fractions were combined and evaporated to give a waxy off white solid which was trituration with hot iso-hexane afforded, on cooling, and collection by suction filtration the title compound as a pale yellow solid (121 mg, 28%)

H NMR (400.132 MHz, DMSO-D6) δ 0.83 (t, 3H), 1.16 (d, 3H), 1.57 (m, 2H), 2.65 (m, 2H), 3.18 (s, 3H), 3.49-3.66 (m, 2H), 4.57 (m, 1H), 8.12 (s, 1H); MS m/z 269 [M+H]$^+$.

Intermediate 88

3-[(5-bromo-2-chloro-pyrimidin-4-yl)-butan-2-yl-amino]-N-methyl-propanamide

To a solution of 3-(butan-2-ylamino)-N-methyl-propanamide (Intermediate 89; 563 mg, 3.56 mmol) in DCM (7 mL) was added triethylamine (550 µl, 3.94 mmol) and, as a solid, 5-bromo-2,4-dichloropyrimidine (Aldrich; 890 mg, 3.90 mmol). The reaction was stirred at ambient temperature overnight.

Saturated aqueous Sodium Bicarbonate solution (10 mL) was added and the mixture shaken. The organic phase was collected by gravity elution through a PTFE filter cup. The DCM solution was injected directly onto 40 g Si cartridge and eluted with a 25-75% gradient of ethyl acetate in hexane. Product containing fractions were combined and evaporated to afford the title compound as a colourless crystalline solid (565 mg; 45%)

$^1$H NMR (400.132 MHz, CDCl3) δ 0.83 (t, 3H), 1.28 (d, 3H), 1.58 (m, 1H), 1.72 (m, 1H), 2.44 (m, 2H), 2.83 (d, 3H), 3.64 (m, 1H), 3.85 (m, 1H), 4.58 (m, 1H), 5.78 (m, 1H), 8.23 (s, 1H); MS m/z 351 [M+H]$^+$.

Intermediate 89

3-(butan-2-ylamino)-N-methyl-propanamide

A mixture of N-methylacrylamide (ABCR; 500 mg, 5.87 mmol), sec-butylamine (Aldrich; 530 mL, 5.22 mmol) and ethanol (4 mL) was heated in a microwave to 140° C. for 45 minutes and then at 150° C. for 30 minutes. The reaction mixture was cooled and poured onto an SCX-2 cartridge (5 g) and cartridge washed through with methanol (~50 mL). Products were then eluted with 2M ammonia in methanol (~50 mL) and evaporated to afford the title compound as a straw coloured oil (563 mg; 61%)

$^1$H NMR (400.132 MHz, CDCl3) δ 0.92 (t, 3H), 1.06 (d, 3H), 1.31-1.53 (m, 2H), 2.34 (m, 2H), 2.57 (m, 1H), 2.78-2.94 (m, 5H), 7.77 (s, 1H)

Intermediate 90

10-chloro-2-cyclobutyl-6-methyl-2,6,9,11-tetrazabicyclo[5.4.0]undeca-7,9,11-trien-5-one To a solution of 3-[(5-bromo-2-chloro-pyrimidin-4-yl)-cyclobutyl-amino]-N-methyl-propanamide (Intermediate 91; 600 mg, 1.73 mmol) in anhydrous 1,4-dioxane (15 mL) was added Caesium Carbonate (1.1 g, 3.38 mmol). Nitrogen was bubbled through the reaction mixture for 10 minutes, prior to addition of Tris(dibenzylideneacetone)dipalladium(0) (99 mg, 0.11 mmol) and XANTPHOS (95 mg, 0.16 mmol). The reaction was heated to 100° C. and stirred under nitrogen overnight The reaction mixture was cooled and diluted to ~40 ml with DCM, filtered to remove insoluble material, washing filter cake through with DCM and evaporated to give a brown/green solid which was purified by flash chromatography on silica (120 g cartridge; ISCO companion) eluting with a 25-100% gradient of ethyl acetate in iso-hexane. Product containing fractions were combined and evaporated to give a waxy off white solid which was trituration with warm iso-hexane which afforded, on cooling and collection by suction filtration the title compound as a pale yellow solid (216 mg, 47%)

$^1$H NMR (400.132 MHz, DMSO-D6) δ 1.68 (m, 2H), 2.09 (m, 2H), 2.21 (m, 2H), 2.63 (m, 2H), 3.19 (s, 3H), 3.69 (m, 2H), 4.43 (m, 1H), 8.19 (s, 1H); MS m/z 267.4 [M+H]$^+$.

Intermediate 91

3-[(5-bromo-2-chloro-pyrimidin-4-yl)-cyclobutylamino]-N-methyl-propanamide

Using 3-(cyclobutylamino)-N-methyl-propanamide—Intermediate 92 and analogous conditions to Intermediate 88 the title compound was obtained as a white solid (609 mg)

¹H NMR (400.132 MHz, CDCl3) δ 1.62-1.79 (m, 2H), 2.16-2.34 (m, 4H), 2.45 (m, 2H), 2.81 (d, 3H), 3.95 (m, 2H), 4.72 (m, 1H), 5.72 (m, 1H), 8.24 (s, 1H)

Intermediate 92

3-(cyclobutylamino)-N-methyl-propanamide

Using cyclobutanamine—Aldrich and analogous conditions to Intermediate 89 the title compound was obtained as a pale yellow oil (541 mg)

¹H NMR (400.132 MHz, CDCl3) δ 1.64-1.75 (m, 4H), 2.23 (m, 2H), 2.33 (m, 2H), 2.77-2.81 (m, 5H), 3.26 (m, 1H), 7.32 (m, 1H)

Intermediate 93

10-chloro-2-(cyclopropylmethyl)-6-methyl-2,6,9,11-tetrazabicyclo[5.4.0]undeca-7,9,11-trien-5-one To a partial solution of 3-[(5-bromo-2-chloro-pyrimidin-4-yl)-(cyclopropylmethyl)amino]-N-methyl-propanamide (Intermediate 94; 426 mg, 1.18 mmol) in anhydrous 1,4-dioxane (15 mL) was added Caesium Carbonate (790 mg, 2.42 mmol). Nitrogen was bubbled through the reaction mixture for 10 minutes, prior to addition of Tris(dibenzylideneacetone)dipalladium(0) (69 mg, 0.075 mmol) and XANTPHOS (62 mg, 0.107 mmol). The reaction was heated to 100° C. and stirred under nitrogen for 18 hrs.

The reaction mixture was cooled and diluted to ~40 ml with DCM, filtered to remove insoluble material, washing the filter cake through with DCM, and evaporated to give a brown gum which was purified by flash chromatography on silica (40 g cartridge; ISCO companion) eluting with a 25-75% gradient of ethyl acetate in iso-hexane. Product containing fractions were combined and evaporated to give a crystalline yellow translucent solid. Trituration with hot iso-hexane afforded, on cooling, and collection by suction filtration the title compound as a pale yellow solid (165 mg, 50%)

¹H NMR (400.132 MHz, DMSO-D6) δ 0.00 (m, 2H), 0.33 (m, 2H), 0.59 (m, 1H), 1.44 (q, 2H), 2.60 (m, 2H), 3.11 (s, 3H), 3.55 (m, 2H), 3.68 (m, 2H), 8.05 (s, 1H)

MS m/z 281.4 [M+H]⁺.

Intermediate 94

3-[(5-bromo-2-chloro-pyrimidin-4-yl)-(cyclopropylmethyl)amino]-N-methyl-propanamide Using 3-(cyclopropylmethylamino)-N-methyl-propanamide—Intermediate 95 and analogous conditions to Intermediate 88 the title compound was obtained as a white solid (431 mg)

¹H NMR (400.132 MHz, CDCl3) δ 0.35 (m, 2H), 0.60 (m, 2H), 1.14 (m, 1H), 2.57 (m, 2H), 2.84 (d, 3H), 3.66 (d, 2H), 4.03 (m, 2H), 5.79 (m, 1H), 8.21 (s, 1H); MS m/z 349.0 [M+H]⁺.

Intermediate 95

3-(cyclopropylmethylamino)-N-methyl-propanamide

Using 2-Cyclopropylethanamine—Aldrich and analogous conditions to Intermediate 89 the title compound was obtained as a pale yellow oil (590 mg)

¹H NMR (400.132 MHz, CDCl3) δ 0.13 (m, 3H), 0.51 (m, 2H), 0.94 (m, 1H), 2.36 (m, 2H), 2.49 (d, 2H), 2.81 (d, 3H), 2.90 (m, 2H), 7.59 (s, 1H).

Intermediate 96

10-chloro-2-[(2,4-dimethoxyphenyl)methyl]-6-methyl-2,6,9,11-tetrazabicyclo[5.4.0]undeca-7,9,11-trien-5-one To a solution of 3-[(5-bromo-2-chloro-pyrimidin-4-yl)-[(3,5-dimethoxyphenyl)methyl]amino]-N-methyl-propanamide (Intermediate 97; 2.1 g, 4.73 mmol) in 1,4-dioxane (50 mL) was added Caesium Carbonate (3.4 g, 10.44 mmol) and the reaction mixture sparged with argon for 20 minutes.

Tris(dibenzylideneacetone)dipalladium(0) (260 mg, 0.28 mmol) and XANTPHOS (248 mg, 0.43 mmol) were added and reaction mixture heated to 100° C. and left to stir under nitrogen overnight.

The reaction mixture was cooled and diluted to ~100 ml with DCM, filtered to remove insoluble material, washing filter cake through with DCM and evaporated to give a dark yellow oil with some solid which was taken up in DCM (~20 ml) and insoluble material removed by filtration. The filtrate was purified by flash chromatography on silica (120 g cartridge) eluting with a rising gradient of 25-100% ethyl acetate in hexane. Product containing fractions were combined and evaporated to give the title compound as a pale yellow solid (690 mg)

¹H NMR (400.132 MHz, DMSO-D6) δ 2.71 (m, 2H), 3.20 (s, 3H), 3.63 (m, 2H), 3.75 (s, 3H), 3.78 (s, 3H), 4.68 (s, 2H), 6.48 (m, 1H), 6.59 (d, 1H), 7.06 (d, 1H), 8.17 (s, 1H); MS m/z 363.3 [M+H]⁺.

Intermediate 97

3-[(5-bromo-2-chloro-pyrimidin-4-yl)-[(3,5-dimethoxyphenyl)methyl]amino]-N-methyl-propanamide 3-[(3,5-dimethoxyphenyl)methylamino]-N-methyl-propanamide (Intermediate 98; 1 g, 3.96 mmol) was dissolved in DCM (10 mL) and triethylamine (0.68 mL, 4.36 mmol). 5-bromo-2,4-dichloropyrimidine (Aldrich; 993 mg, 4.36 mmol) was added and the mixture stirred at room temperature for 18 hours. The mixture was diluted with DCM and washed with water, brine, dried (MgSO₄), filtered and evaporated to give a yellow gum which was purified on a 40 g ISCO companion eluting with 50-70% ethyl acetate in iso-hexane to give the title compound as a white solid (461 mg, 26%).

1H NMR (400.13 MHz; DMSO-d₆) δ 2.5 (m, 2H) under DMSO, 2.55 (d, 3H), 3.72 (s, 6H), 3.8 (t, 2H), 4.85 (s, 2H), 6.41 (s, 3H), 7.84 (bm, 1H), 8.38 (s, 1H); MS m/z 443/445 [M+H]⁺.

Intermediate 98

3-[(3,5-dimethoxyphenyl)methylamino]-N-methyl-propanamide

N-methylacrylamide (ABCR; 500 mg, 5.87 mmol) and 3,5-dimethoxybenzylamine (Aldrich; 0.98 mL, 6.46 mmol) were dissolved in ethanol (4 mL) and heated in a microwave at 140° C. for 45 minutes. The mixture was poured onto a 20 g SCX-2 column, washed with methanol and eluted with 3.5N NH₃ in methanol. The product fractions were evaporated to the title compound as a yellow oil (1.3 g, 88%).

1H NMR (CDCl3) 2.36 (t, 2H), 2.78 (d, 3H), 2.88 (t, 2H), 3.72 (s, 2H), 3.79 (s, 6H), 6.36 (m, 1H), 6.45 (m, 2H), 7.31 (bs, 1H); MS m/z 253 [M+H]$^+$.

Intermediate 99

2-benzyl-10-chloro-6-methyl-2,6,9,11-tetrazabicyclo [5.4.0]undeca-7,9,11-trien-5-one To a cooled (ice/water bath) suspension of sodium hydride (60% dispersion in mineral oil; 6.5 mg, 0.16 mmol) in DMA (0.5 mL) was added a solution of 10-chloro-6-methyl-2,6,9, 11-tetrazabicyclo[5.4.0]undeca-7,9,11-trien-5-one (Intermediate 100; 32 mg, 0.15 mmol) in DMA (1.0 mL). The reaction mixture was allowed to stir, under nitrogen, in an ice bath for 15 minutes prior to addition of Benzyl bromide (Aldrich; 20 μl, 0.17 mmol). The reaction mixture was stirred on an ice bath for 15 minutes and then at ambient temperature for 3 hrs A further addition of Sodium hydride (2 mg) was made and stirring continued for 6 hrs. Saturated ammonium chloride (0.5 ml) was added and the reaction mixture poured directly onto an SCX-3 cartridge (2 g). The cartridge was washed with methanol (~30 mL) before eluting products with 2M ammonia in methanol (~30 mL). Product containing fractions were evaporated to dryness to give a colourless gum, which was combined with the cartridge methanol pre-wash and this solution evaporated to dryness. The resultant material was partitioned between DCM (10 mL) and water (10 mL). The organic phase was collected by gravity elution through a PTFE filter cup and evaporated to give the title compound as a pale yellow opaque gum (46 mg, 89%)

$^1$H NMR (400.132 MHz, DMSO-D6) δ 2.71 (m, 2H), 3.22 (s, 3H), 3.66 (m, 2H), 4.82 (s, 2H), 7.27-7.38 (m, 5H), 8.21 (s, 1H); MS m/z 303.3 [M+H]$^+$.

Intermediate 100

10-chloro-6-methyl-2,6,9,11-tetrazabicyclo[5.4.0] undeca-7,9,11-trien-5-one

3-[(5-bromo-2-chloro-pyrimidin-4-yl)-[(3,5-dimethoxyphenyl)methyl]amino]-N-methyl-propanamide (Intermediate 97; 83 mg, 0.23 mmol) was taken up in DCM (1 mL) and TFA (1 mL) and stirred for 30 minutes. A further addition of TFA (1 mL) was made and stirring continued overnight. The reaction mixture was diluted with DCM (25 mL) and poured directly onto a SCX-3 cartridge (2 g). The cartridge was washed through with methanol (50 mL). Products were eluted with 2M ammonia in methanol and ammoniacal eluant evaporated to dryness to afford the title compound as an off white solid (34 mg, 70%)

$^1$H NMR (400.132 MHz, DMSO-D6) δ 2.66 (m, 2H), 3.21 (s, 3H), 3.52 (m, 2H), 8.14 (m, 1H), 8.28 (m, 1H); MS m/z 213.4 [M+H]$^+$.

Intermediate 101

10-chloro-6-methyl-2-[(2-methyl-1,3-thiazol-4-yl) methyl]-2,6,9,11-tetrazabicyclo[5.4.0]undeca-7,9,11-trien-5-one To a cooled (ice/water bath) suspension of sodium hydride (60% dispersion in mineral oil; 13 mg, 0.38 mmol) in DMA (0.5 mL) was added a solution of 10-chloro-6-methyl-2,6,9, 11-tetrazabicyclo[5.4.0]undeca-7,9,11-trien-5-one (Intermediate 100; 63 mg, 0.30 mmol) in DMA (1 mL). The reaction mixture was allowed to stir, under nitrogen, in ice bath for 10 minutes prior to addition of 4-chloromethyl-2-methylthiazole (ASDI; 75 mg, 0.51 mmol). The reaction mixture was stirred in an ice bath for 20 minutes and then warmed to ambient temperature over 1 hour.

The reaction mixture was quenched by careful addition of saturated aqueous ammonium chloride (0.5 ml) and the reaction mixture was partitioned between DCM (10 mL) and water (10 mL). The organic phase was separated by gravity filtration through a PTFE filter cup and evaporation to dryness to give the title compound as a straw coloured gum (61 mg; 63%)

$^1$H NMR (400.132 MHz, DMSO-D6) δ 2.64 (s, 3H), 2.74 (m, 2H), 3.21 (s, 3H), 3.78 (m, 2H), 4.82 (m, 2H), 7.31 (m, 1H), 8.20 (s, 1H); MS m/z 324.3 [M+H]$^+$.

Intermediate 102

10-chloro-2-(cyclobutylmethyl)-6-methyl-2,6,9,11-tetrazabicyclo[5.4.0]undeca-7,9,11-trien-5-one To a cooled (ice/water bath) suspension of sodium hydride (60% dispersion in mineral oil; 13 mg, 0.38 mmol) in DMA (0.5 ml) was added a solution of (Intermediate 100; 63 mg, 0.30 mmol) in DMA (1 mL). The reaction mixture was allowed to stir, under nitrogen, on an ice bath for 10 minutes prior to addition of Bromomethyl cyclobutane (Aldrich; 40 μl, 0.36 mmol). The reaction mixture was stirred on an ice bath for 20 minutes and then warmed to ambient temperature over 1 hour.

A further addition of Sodium hydride (2 mg) and Bromomethyl cyclobutane (20 μl, 0.18 mmol was made and the reaction stirred for a further hour The reaction mixture was quenched by careful addition of saturated aqueous ammonium chloride (0.5 ml) and the reaction mixture partitioned between DCM (10 mL) and water (10 mL). The organic phase was separated by gravity filtration through a PTFE filter cup and evaporation to dryness gave the title compound as a pale yellow gum (71 mg, 84%)

$^1$H NMR (400.132 MHz, DMSO-D6) δ 1.71-1.86 (m, 4H), 2.01 (m, 2H), 2.66 (m, 3H), 3.17 (s, 3H), 3.63 (d, 2H), 3.70 (m, 2H), 8.12 (s, 1H); MS m/z 281.3 [M+H]$^+$.

Intermediate 103

10-chloro-6-methyl-2-phenyl-2,6,9,11-tetrazabicyclo [5.4.0]undeca-7,9,11-trien-5-one To a solution of 10-chloro-2-phenyl-2,6,9,11-tetrazabicyclo[5.4.0]undeca-7,9,11-trien-5-one (Intermediate 104; 1.185 g, 4.31 mmol) in DMA (100 mL) at 0° C., was added methyl iodide (282 μL, 4.53 mmol) followed by sodium hydride (60% oil dispersion, 182 mg, 4.53 mmol) in one portion. The mixture was stirred at 0° C. for 4 hrs and ice was then added, resulting in a brown sticky precipitate, which was filtered and washed with water. A white solid precipitated from the filtrate, which was filtered off and triturated with diethylether to give the title compound (494 mg).

The sticky brown precipitate was dissolved in DCM and suction columned in 2-5% methanol/dichloromethane to give a yellow oil.

The aqueous filtrate was extracted with DCM and methanol, washed with saturated aqueous brine and evaporated to give a yellow oil which was purified by suction columned as above to give a yellow oil.

Both yellow oils were combined and triturated with diethylether to give the title compound as a white solid (401 mg)

¹H NMR (399.9 MHz, DMSO-D6): δ_H, 2.89 (m, 2H), 3.29 (s, 3H), 4.06 (m, 2H), 7.30 (m, 3H), 7.42 (m, 2H), 8.38 (s, 1H); MS m/z 289 [M+H]⁺.

Intermediate 104

10-chloro-2-phenyl-2,6,9,11-tetrazabicyclo[5.4.0] undeca-7,9,11-trien-5-one

Methyl3-[(2-chloro-5-nitro-pyrimidin-4-yl)-phenyl-amino]propanoate (Intermediate 105; 21.855 g, 64.9 mmol), iron powder (5.44 g, 97.35 mmol) and acetic acid (200 mL) were heated at 80° C. for 2 hrs and then stirred at room temperature overnight.

The reaction mixture was filtered through celite and the filter cake washed with dichloromethane. The solvent was evaporated and the resultant material was pre-absorbed onto silica with methanol/dichloromethane and then purified by vacuum filtration chromatography eluting with dichloromethane, diethylether, ethylacetate and finally. 20% methanol/dichloromethane. Product containing fractions were combined and evaporated To give a brown solid which was triturated with diethylether and then methanol and small % of dichloromethane to give the title compound as an off white solid (2.29 g)

The silica from the filtration column was suspended in 20% methanol/dichloromethane and filtered and washed with a further portion of 20% methanol/dichloromethane. Evaporation afforded a yellow solid which was triturated with methanol and small % of dichloromethane to give the title compound as an off white solid (1.35 g)
¹H NMR (399.9 MHz, DMSO-D6): δ_H, 2.89 (m, 2H), 3.98 (m, 2H), 7.32 (m, 3H), 7.42 (m, 2H), 8.01 (s, 1H), 9.90 (s, 1H); MS m/z 275 [M+H]⁺.

Intermediate 105

Methyl3-[(2-chloro-5-nitro-pyrimidin-4-yl)-phenyl-amino]propanoate

To a solution of; 3,4-dichloro-5-nitropyrimidine (Aldrich; 12.59 g, 64.9 mmol) in anhydrous THF (300 mL) at room temperature under a nitrogen atmosphere was added dropwise over 6 hrs a solution of Methyl3-anilinopropanoate (Intermediate 106; 12.795 g, 71.39 mmol) and Hunigs base (13.54 mL, 77.88 mmol) in anhydrous THF (300 mL) The reaction mixture was stirred over night at room temperature.

The solvent was evaporated at 40° C. and the residue dissolved in DCM and washed with water and saturated brine. The resulting organic phase was dried over anhydrous sodium sulphate then pre-absorbed onto silica and purified by vacuum filtration chromatography eluting with dichloromethane. Evaporation of product containing fractions afforded the title compound as a dark red oil (24.25 g, >100%)
MS m/z 275 [M+H]⁺. Retention time 2.32 mins Intermediate 106

Methyl3-anilinopropanoate

Aniline (Acros; 59.89 mL, 657 mmol), Methylacrylate (Acros; 62.54 mL, 690 mmol) and Glacial acetic acid (15 mL) and were combined and heated at 79° C. overnight The reaction mixture was cooled to room temperature and added to ice water, a solid precipitated and was filtered off and dissolved in dichloromethane aliquot taken and pre-absorbed onto silica and purified by vacuum filtration chromatography eluting with DCM. Product containing fractions were combined and evaporated to give the title compound as a pale yellow sticky solid (14.33 g, 12%)
¹H NMR (399.9 MHz, DMSO-D6): δ_H, 2.57 (tr, 2H), 3.29 (tr, 2H), 3.61 (s, 3H), 5.57 (tr, 1H), 6.55 (m, 3H), 7.08 (m, 1H); MS m/z 180 [M+H]⁺.

Intermediate 107

4-amino-3-chloro-N-(3-dimethylamino-2,2-dimethyl-propyl)benzamide 3-chloro-N-(3-dimethylamino-2,2-dimethyl-propyl)-4-nitro-benzamide (2.29 g, 7.67 mmol), iron powder (2.45 g, 43.79 mmol) and ammonium chloride (781 mg, 14.60 mmol) were heated in ethanol (50 mL) and water (18 mL) at reflux for one hour. A few drops of acetic acid were added and heating continued for a further hour. The reaction mixture was cooled, filtered and the filtrate concentrated. This residue was partitioned between saturated NaHCO₃ (aq.) and DCM. The organic phase was washed with brine, dried with MgSO₄ and concentrated. Column chromatography gave the title compound as an orange crystalline solid. (850 mg, 39%)
¹H NMR (399.9 MHz, DMSO-d₆) δ0.86 (6H, s), 2.16 (2H, s), 2.26 (6H, s), 3.14 (2H, d), 5.83 (2H, s), 6.80 (1H, d), 7.52-7.54 (1H, m), 7.72 (1H, d), 8.15 (1H, t); MS m/z 286.16 [M+H]⁺.

Intermediate 108

3-chloro-N-(3-dimethylamino-2,2-dimethyl-propyl)-4-nitro-benzamide 3-chloro-4-nitro-benzoyl chloride (Intermediate 54; 2.2 g, 10.00 mmol) was dissolved in DCM (20 mL) and N,N-diisopropylethylamine (2.095 mL, 12.00 mmol) added. The mixture was cooled in an ice/water bath and N,N,2,2-tetramethyl-1,3-propanediamine (3.652 mL, 10.00 mmol) in DCM (10 mL) added dropwise. The mixture was allowed to warm to room temperature and stirred for 0.5 h. The mixture was washed with brine, 2N NaOH (aq.), dried (MgSO₄) and concentrated. Column chromatography of the residue (2% MeOH/DCM) gave the title compound as a yellow oil 17171/2/1 (2.29 g, 77%).
¹H NMR (399.9 MHz, DMSO-d₆) δ0.89 (6H, s), 2.17 (2H, s), 2.26 (6H, s), 3.21 (2H, d), 7.96-7.98 (1H, m), 8.13 (1H, d), 8.18 (1H, d), 8.73 (1H, t); MS m/z 314.21 [M+H]⁺.

Intermediate 109

10-chloro-2-(2-methoxyethyl)-6-methyl-2,6,9,11-tetrazabicyclo[5.4.0]undeca-7,9,11-trien-5-one 3-[(5-bromo-2-chloro-pyrimidin-4-yl)-(2-methoxyethyl) amino]-N-methyl-propanamide (Intermediate 110; 1.12 g, 3.185 mmol) was suspended in dioxane (70 mL), Caesium Carbonate (2.08 g, 6.37 mmol) added and the mixture bubbled with nitrogen for 10 minutes. Tris(dibenzylideneacetone)dipalladium(0) (175 mg, 0.151 mmol) and XANTPHOS (166 mg, 0.287 mmol) were added and the mixture heated to 100° C. for 20 hrs. A further 0.06 equivalent of Tris(dibenzylideneacetone)dipalladium(0) and 0.09 equivalent of XANTPHOS were added and heating continued for a further 2 hrs. The reaction mixture was cooled to room temperature filtered and the filter cake washed with DCM. The filtrate was evaporated and dissolved in DCM and purified on silica eluting with a gradient of 40-55% Ethyl Acetate/isohexane then 55% Ethyl Acetate/iso-hexane and finally 70% Ethyl Acetate/iso-hexane. Fractions containing product were combined and evaporated to a yellow solid. Which was purified by base modified reverse phase HPLC to yield the title compound as a white solid (157 mg, 18%)

$^1$H NMR (399.902 MHz, CDCl3) δ2.73 (m, 2H), 3.29 (s, 3H), 3.35 (s, 3H), 3.68 (m, 2H), 3.84 (m, 2H), 3.90 (m, 2H), 7.95 (s, 1H); MS m/z 271 [M+H]$^+$.

Intermediate 110

3-[(5-bromo-2-chloro-pyrimidin-4-yl)-(2-methoxyethyl)amino]-N-methyl-propanamide 3-(2-methoxyethylamino)-N-methyl-propanamide (Intermediate 111; 608 mg, 3.79 mmol) 5-Bromo-2,4-dichloropyrimidine (Aldrich; 950 mg, 4.17 mmol), Triethylamine (555 μL, 3.98 mmol), and DCM (5 mL) were combined and stirred over the weekend at room temperature.

The reaction mixture was washed with saturated aqueous sodium bicarbonate solution then gravity filtered through a PTFE cup and organic solvents evaporated. The residue was dissolved in DCM and passed through a silica column, eluting with 50% Ethyl Acetate/iso-hexane then 60% Ethyl Acetate/iso-hexane and finally 70% Ethyl Acetate/iso-hexane. Fractions containing product combined and evaporated to a colourless liquid which crystallised under high vacuum to give the title compound as a white solid (1.12 g, 84%)

$^1$H NMR (399.902 MHz, CDCl$_3$) δ2.57 (m, 2H), 2.82 (d, 3H), 3.35 (s, 3H), 3.63 (m, 2H), 3.95 (m, 2H), 4.01 (m, 2H), 5.80 (s, 1H), 8.20 (s, 1H); MS m/z 353 [M+H]$^+$.

Intermediate 111

3-(2-methoxyethylamino)-N-methyl-propanamide

N-Methylacrylamide (ABCR; 500 mg, 5.87 mmol), 2-Methoxyethylamine (Aldrich; 441 mg, 5.87 mmol), and EtOH (2 mL) were combined and heated in a microwave at 140° C. for 40 minutes. The reaction mixture was cooled and added to a 5 g SCX-2 column pre-wet with MeOH (2 column volumes), flushed with MeOH (2 column volumes) then the product eluted with 2M ammonia in MeOH. Product containing fractions were evaporated in vacuo to give the title compound as a clear oil (608 mg, 65%)

$^1$H NMR (399.902 MHz, CDCl3) δ2.35 (m, 2H), 2.79 (m, 5H), 2.88 (m, 2H), 3.37 (s, 3H), 3.49 (m, 2H), 7.55 (s, 1H)

Intermediate 112

10-chloro-2-(1-methoxypropan-2-yl)-6-methyl-2,6,9,11-tetrazabicyclo[5.4.0]undeca-7,9,11-trien-5-one N-(2,4-dichloropyrimidin-5-yl)-N-methyl-prop-2-enamide (Intermediate 113; 318 mg, 1.37 mmol), 2-Amino-1-methoxypropane (152 μl, 1.44 mmol), Triethylamine (382 μl, 2.74 mmol), Titanium Tetra-ethoxide (29 μl, 0.137 mmol) and DCM (5 mL) were combined and stirred at room temperature for 1 hr, heated to 40° C. for 3 hrs, cooled to room temperature, washed with water and gravity filtered through a PTFE. The organic solution was purified by chromatographic separation on silica eluting with a shallow gradient (25 column volumes) of 10-50% Ethyl Acetate/iso-hexane. Product containing fractions were combined and evaporated to give the title compound as a clear gum (54 mg, 18%).

$^1$H NMR (399.902 MHz, CDCl3) δ1.25 (m, 3H), 2.69 (m, 2H), 3.29 (s, 3H), 3.34 (s, 3H), 3.53 (m, 2H), 3.75 (m, 2H), 4.99 (m, 1H), 7.94 (s, 1H); MS m/z 285 [M+H]$^+$.

Intermediate 113

N-(2,4-dichloropyrimidin-5-yl)-N-methyl-prop-2-enamide

5-Methylamino-2,4-Dichloropyrimidine (800 mg, 4.5 mmol) was dissolved in THF (18 mL) and triethylamine (1.88 mL, 13.5 mmol) was added. A solution of 3-chloropropionyl chloride (644 μl, 6.55 mmol) in DCM (2 mL) was added dropwise giving an instantaneous precipitate The reaction was stirred at room temperature for 30 minutes. The precipitate was filtered off and the filtrate evaporated and the resultant material dissolved in DCM, washed with water, saturated aqueous sodium bicarbonate solution and then gravity filtered through a PTFE cup. The organic solvent was evaporated to give the crude product as a yellow gum which was dissolved in THF (18 mL). Triethylamine (1.8 mL) was added and a further portion of 3-chloropropionyl chloride (215 μl, 2.25 mmol). The reaction was stirred at room temp for 1 hr then worked up as previously to give the title compound as a brown gum (624 mg, 60%)

MS m/z 232 [M+H]$^+$. Retention Time 1.39 mins

Intermediate 114

5-Methylamino-2,4-Dichloropyrimidine

To the methylamino-5-uracil (Intermediate 115; 6.81 g, 48.25 mmol) was added triethylamine (13.45 mL, 96.51 mmol) followed by phosphorus oxychloride (67.5 mL, 723 mmol) very slowly. The reaction was heated to reflux for 3 hrs cooled to room temperature and POCl3 evaporated and the residues azeotroped with toluene. The residue was diluted with toluene (100 mL). Ice (200 mL) was added and the mixture stirred for 5 minutes. The mixture was then neutralised to pH8 with saturated aqueous sodium bicarbonate solution and extracted with toluene (300 mL). The aqueous phase was re-extracted with DCM (5×300 mL). The toluene solution was washed with water (100 mL), dried (MgSO4) and evaporated. The combined DCM solutions were also washed with water (300 mL), dried (MgSO4), combined with the toluene solution and evaporated to a brown gum which was dissolved in DCM with a little MeOH and chromatographed on silica eluting with a gradient of 0-10% Ethyl Acetate/iso-hexane followed by 10% Ethyl Acetate/iso-hexane then 15% Ethyl Acetate/iso-hexane. Fractions containing impure product were re-chromatographed eluting with 10% Ethyl Acetate/iso-hexane until the impurity had come off then 15% Ethyl Acetate/iso-hexane. Product containing fractions were evaporated to give the title compound as a cream solid (2.58 g, 30%)

$^1$H NMR (399.902 MHz, CDCl3) δ2.98 (d, 3H), 4.35 (s, 1H), 7.90 (s, 1H); MS m/z 175 [M−H]$^+$.

Intermediate 115

Methylamino-5-uracil

5 Bromo Uracil (Aldrich; 49.66 g, 260 mmol) and 25% Methylamine in Ethanol (Aldrich; 200 mL) were combined and heated in an autoclave at 160° C. for 6 hours.

The solution was cooled and evaporated and the residue washed with water, acetone and diethylether to give the title compound as a white solid (28 g, 70%)

Intermediate 116

10-chloro-2-(3-furylmethyl)-6-methyl-2,6,9,11-tetrazabicyclo[5.4.0]undeca-7,9,11-trien-5-one one 3-Furylmethylamine (Maybridge; 175 mg, 1.8 mmol), N-(2,4-dichloropyrimidin-5-yl)-N-methyl-prop-2-enamide (Intermediate 113; 347 mg, 1.5 mmol), Triethylamine (420 µL, 3 mmol), Titanium Tetra-ethoxide (157 µL, 0.75 mmol) and DCM (5 mL) were combined and stirred at room temp for 1 hr, heated at 40° C. overnight then cooled to room temperature. The reaction mixture was washed with water then gravity filtered through a PTFE cup, the aqueous layer containing the titanium emulsion was washed with further DCM (3×10 mL) and the combined organic solutions gravity filtered through a PTFE cup and solvents evaporated. The residue was dissolved in DCM and purified by chromatographic separation on silica eluting with a shallow gradient (25 column volumes) of 10-50% Ethyl Acetate/iso-hexane. Product containing fractions were combined and evaporated to give the title compound as a yellow gum (67 mg, 15%)

$^1$H NMR (399.902 MHz, CDCl3) δ2.63 (m, 2H), 3.31 (s, 3H), 3.75 (m, 2H), 4.60 (s, 2H), 6.49 (m, 1H), 7.41 (m, 1H), 7.50 (m, 1H), 8.00 (s, 1H); MS m/z 293 [M+H]$^+$.

Intermediate 117

10-chloro-2-cyclopropyl-6-methyl-2,6,9,11-tetrazabicyclo[5.4.0]undeca-7,9,11-trien-5-one Cyclopropylamine (Aldrich; 150 µL, 2.18 mmol), N-(2,4-dichloropyrimidin-5-yl)-N-methyl-prop-2-enamide (Intermediate 113; 337 mg, 1.45 mmol) Triethylamine (404 µL, 2.9 mmol), Titanium Tetra-ethoxide (152 µL, 0.725 mmol) and DCM (5 mL) were combined and stirred at room temp for 1 hr, heated at 40° C. for 4 hrs then cooled to room temperature. The reaction mixture was washed with water then gravity filtered through a PTFE cup, the aqueous layer containing the titanium emulsion was washed with further DCM (3×10 mL) and the combined organic solutions gravity filtered through a PTFE cup and solvents evaporated. The residue was dissolved in DCM and purified by chromatographic separation on silica eluting with a shallow gradient (25 column volumes) of 10-50% Ethyl Acetate/iso-hexane. Product containing fractions were combined and evaporated to give the title compound as a cream solid (42 mg, 11%)

$^1$H NMR (399.902 MHz, CDCl3) δ0.58 (m, 2H), 0.91 (m, 2H), 2.68 (m, 2H), 2.85 (m, 1H), 3.28 (s, 3H), 3.84 (m, 2H), 8.02 (s, 1H); MS m/z 253 [M+H]$^+$.

Intermediate 118

10-chloro-6-methyl-2-(1-methyl-4-piperidyl)-2,6,9,11-tetrazabicyclo[5.4.0]undeca-7,9,11-trien-5-one 4-Amino-1-methylpiperidine (Fluorochem; 200 mg, 1.74 mmol), N-(2,4-dichloropyrimidin-5-yl)-N-methyl-prop-2-enamide (Intermediate 113; 337 mg, 1.45 mmol) Triethylamine (404 µL, 2.9 mmol), Titanium Tetra-ethoxide (152 µL, 0.725 mmol) and DCM (5 mL) were combined and stirred at room temp for 1 hr, heated at 40° C. for 3 hrs then cooled to room temperature. The reaction mixture was washed with water then gravity filtered through a PTFE cup, the aqueous layer containing the titanium emulsion was washed with further DCM (3×10 mL) and the combined organic solutions gravity filtered through a PTFE cup and solvents evaporated. The residue was dissolved in DCM and purified by chromatographic separation on silica eluting with a shallow gradient (25 column volumes) of 0-5% 2M ammonia in MeOH/DCM. Product containing fractions were combined and evaporated to give the title compound as a yellow solid (39 mg)

Intermediate 119

4-amino-N-cyclohexyl-3-methoxy-benzamide

EDAC (7.46 g, 3.90 mmol) was added to a stirred solution of 4-amino-3-methoxy acid (Aldrich; 5 g, 2.9 mmol), cyclohexylamine (Aldrich; 5.13 mL, 4.49 mmol) and DMAP (11 g, 9 mmol) in DCM (200 mL) and the reaction mixture was stirred for a 18 hrs. under an atmosphere of nitrogen. The mixture was washed with 1M citric acid solution (×3), saturated sodium bicarbonate solution and dried. The solvent was evaporated off and the residue triturated with diethylether to give the title compound as a pink solid (5.3 g, 71%)

MS m/z 293 [M+H]$^+$.

Intermediate 120

10-chloro-2-cyclopentyl-3,6-dimethyl-2,6,9,11-tetrazabicyclo[5.4.0]undeca-8,10,12-trien-5-one 3-[(5-bromo-2-chloro-pyrimidin-4-yl)-cyclopentyl-amino]-N-methyl-butanamide (Intermediate 121; 196 mg, 0.52 mmol) was dissolved in 1,4-dioxane (5 mL) and Tris (dibenzylideneacetone)dipalladium(0) 10 mg, 0.02 mmol), XANTPHOS (20 mg, 0.02 mmol) and Caesium Carbonate (247 m, 0.76 mmol) were added to a microwave reaction vessel which was sealed and irradiated at 150° C. for 30 min. A further addition of Tris(dibenzylideneacetone)dipalladium (0) (10 mg, 0.02 mmol) and XANTPHOS (20 mg, 0.02 mmol) was made and the reaction mixture irradiated at 150° C. for 2 hrs. The cooled reaction mixture was filtered through a pad of celite and the filtrate concentrated down onto silica and purified by flash silica chromatography (companion, 12 g, 0-5% methanol/DCM). Product containing fractions were combined and evaporated to give the title compound as a yellow solid (126 mg, 82%).

$^1$H NMR (399.902 MHz, CDCl$_3$) δ 1.34 (d, 3H), 1.44-1.95 (m, 8H), 2.63 (dd, 1H), 2.77 (dd, 1H), 3.32 (s, 3H), 3.98 (ddq, 1H), 4.56 (quintet, 1H), 7.94 (s, 1H); MS m/z 295.2 [M+H]$^+$.

Intermediate 121

3-[(5-bromo-2-chloro-pyrimidin-4-yl)-cyclopentyl-amino]-N-methyl-butanamide

A stirred solution of 3-(cyclopentylamino)-N-methyl-butanamide (Intermediate 122; 887 mg, 4.80 mmol), 5-bromo-2,4-dichloropyrimidine (1.15 g, 5.04 mmol) and potassium carbonate (1.34 g, 9.60 mmol) in acetone (20 mL) were heated under reflux conditions to 65° C. for 3 days and then at 75° C. for a further 16 hrs. The solvent was evaporated and the residue taken up in Ethyl Acetate (200 mL) and water (200 mL). The aqueous phase was separated and the organic phase further washed with water (200 mL) and brine (200 mL). The organic phase was evaporated and the residue purified by flash silica chromatography (companion, 40 g, 0-10% MeOH/DCM) followed by base modified preparative HPLC (30-50% gradient) to give the title compound as a yellow solid (117 mg, 6%).

$^1$H NMR (399.902 MHz, DMSO-d$_6$) δ 1.29 (d, 3H), 1.36-1.51 (m, 2H), 1.65-1.93 (m, 6H), 4.03 (quintet, 1H), 4.48 (sextet, 1H), 7.69 (q, 1H), 8.26 (s, 1H), 5 protons obscured in DMSO signal. MS m/z 375.17 [M+H]$^+$.

Intermediate 122

3-(cyclopentylamino)-N-methyl-butanamide

But-2-Enoic Acid Methylamide (Journal of Organic Chemistry (1981), 46(1), 27-34; 1 g, 10.0 mmol) and cyclopentylamine (Aldrich; 1.49 mL, 15.0 mmol) were combined in methanol (6 mL) in a 10 mL microwave reaction vessel and the resultant solution heated to 140° C. for 60 minutes. The reaction mixture was concentrated under reduced pressure re-dissolved in methanol (6 mL) and reintroduced to a microwave reaction vessel with cyclopentylamine (1.49 mL, 15.0 mmol) and the sealed reaction vessel heated to 140° C. for a further 60 mins.

The process was repeated with cyclopentylamine (3.0 mL, 30 mmol) added and the sealed reaction vessel irradiated to 140° C. for 2 hrs. The solvent was removed under reduced pressure and the residue dissolved in methanol (approx 10 mL) and loaded directly onto a 50 g SCX-2 cartridge, washing with methanol (100 mL) and eluting the desired product with 7 N methanolic ammonia (100 mL). Product containing fractions were combined and evaporated to give the title compound as a brown oil (1.65 g, 90%)

$^1$H NMR (399.902 MHz, DMSO-d$_6$) δ 0.96 (d, 3H), 1.17-1.81 (m, 8H), 1.99 (dd, 1H), 2.16 (dd, 1H), 2.56 (d, 3H), 2.93 (m, 1H), 3.09 (quintet, 1H), 3.31 (br s, 1H), 7.87 (br s, 1H)

Intermediate 123

10-chloro-2-cyclopentyl-4-ethyl-6-methyl-2,6,9,11-tetrazabicyclo[5.4.0]undeca-8,10,12-trien-5-one To a solution of 10-Chloro-2-cyclopentyl-6-methyl-2,6,9,11-tetrazabicyclo[5.4.0]undeca-8,10,12-trien-5-one (Intermediate 1; 1 g, 3.56 mmol) in anhydrous THF (50 mL) at 0° C. was added dropwise a 2N solution of sodium bis(trimethylsilyl)amide in THF (1.96 mL, 3.92 mmol). The resulting solution was stirred at 0° C. for 10 minutes. Ethyl iodide (314 µL, 3.92 mmol) was added dropwise via a syringe and the reaction stirred at 0° C. for 2 hrs and then at room temperature overnight.

The reaction mixture was evaporated, taken up in water and extracted with DCM. The organic phase was washed with saturated brine and dried over magnesium sulphate. Evaporation afforded a gum, which was dissolved in DCM and purified by vacuum filtration chromatography, eluting with DCM and then 2. 2-5% Methanol/DCM.

Product containing fractions were evaporated to give the title compound as a white foam (483 mg, 44%)

$^1$H NMR (399.9 MHz, DMSO-D6): δ$_H$, 0.81 (tr, 3H), 1.21-2.01 (m, 10H), 2.60 (m, 1H), 3.15 (s, 3H), 3.39 (m, 2H), 4.68 (m, 1H), 8.11 (s, 1H); MS m/z 309 [M+H]$^+$.

Intermediate 124

10-chloro-2-cyclopentyl-6-methyl-4-propyl-2,6,9,11-tetrazabicyclo[5.4.0]undeca-8,10,12-trien-5-one To a solution of 10-Chloro-2-cyclopentyl-6-methyl-2,6,9,11-tetrazabicyclo[5.4.0]undeca-8,10,12-trien-5-one (Intermediate 1; 1 g, 3.56 mmol) in anhydrous THF (50 mL) at 0° C. was added dropwise a 2N solution of sodium bis(trimethylsilyl)amide in THF (1.96 mL, 3.92 mmol). The resulting solution was stirred at 0° C. for 10 minutes. 1-Iodopropane (Aldrich; 382 µL, 3.92 mmol) was added dropwise via a syringe and the reaction stirred at 0° C. for 2 hrs and then at room temperature overnight.

The reaction mixture was evaporated, taken up in water and extracted with DCM. The organic phase was washed with saturated brine and dried over magnesium sulphate Evaporation afforded a gum, which was dissolved in DCM and purified by vacuum filtration chromatography, eluting with DCM and then 2. 2-5% Methanol/DCM.

Product containing fractions were evaporated to give the title compound as a yellow foam (467 mg, 41%)

$^1$H NMR (399.9 MHz, DMSO-d$_6$): δ$_H$, 0.81 (tr, 3H), 1.21-2.1 (m, 12H), 2.70 (m, 1H), 3.20 (s, 3H), 3.40 (m, 2H), 4.71 (m, 1H), 8.13 (s, 1H). MS m/z 323 [M+H]$^+$.

Intermediate 125

10-chloro-2-cyclopentyl-4,6-dimethyl-2,6,9,11-tetrazabicyclo[5.4.0]undeca-8,10,12-trien-5-one To a cold (−78° C.) magnetically stirred solution of 10-Chloro-2-cyclopentyl-6-methyl-2,6,9,11-tetrazabicyclo[5.4.0]undeca-8,10,12-trien-5-one (Intermediate 1; 801 mg, 2.85 mmol) in dry THF (15 mL) was added dropwise LHMDS (1 M in THF, 5.71 mL, 5.70 mmol). After 10 minutes at this temperature a solution of methyl iodide (356 uL, 5.70 mmol) in THF (3 mL) was added. The reaction mixture was stirred at −78° C. for 20 minutes and then at 0° C. one hour. The reaction mixture was diluted with DCM and washed with water, followed by brine. The separated organic phase was dried over MgSO$_4$, filtered and concentrated in vacuo. The crude material was dry-loaded onto silica and purified via column chromatography (0-50% Ethyl Acetate in hexane) to provide the title compound as a white solid. (613 mg, 73%)

MS m/z 323 [M+H]$^+$.

Intermediate 126

10-chloro-2-cyclopentyl-4,4,6-trimethyl-2,6,9,11-tetrazabicyclo[5.4.0]undeca-7,9,11-trien-5-one

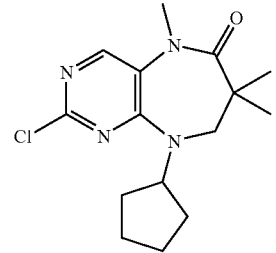

To a stirred solution of 10-chloro-2-cyclopentyl-4,4-dimethyl-2,6,9,11-tetrazabicyclo[5.4.0]undeca-8,10,12-trien-5-one (Intermediate 127; 9.67 g, 32.8 mmol) in DMA (710 mL) under nitrogen was added methyl iodide (2.25 mL, 36.08 mmol). The mixture was cooled in ice/water to 2.5° C. Sodium hydride (60% dispersion in mineral oil, 1.45 g, 36.08 mmol) was added in one portion. A small exotherm to 4° C. was observed. The reaction mixture was stirred on an ice/water bath for 1 hour, and then stirred at room temperature overnight. Solvent was removed in vacuo and the light-brown liquid residue was treated with water. This afforded a solid, which was filtered off and washed with water. The solid material was dissolved in DCM (200 mL) and the solution dried using MgSO₄, filtered and evaporated to give an off white solid which was purified on a 330 g Si column (Companion). loading as a solution in DCM (60 mL) The column having been equilibrated with 30% Ethyl Acetate in isohexane, and eluted with 30% Ethyl Acetate in isohexane for the first 5 minutes and then with a linear gradient slowly rising to 100% Ethyl Acetate. Product containing fractions were combined and evaporated to dryness to give the title compound as a white solid (9.29 g, 92%)

1H NMR (400.13 MHz, CDCl$_3$) δ 1.20 (6H, s), 1.47-1.56 (2H, m), 1.64-1.80 (4H, m), 1.94-2.02 (2H, m), 3.29 (3H, s), 3.40 (2H, s), 5.25-5.34 (1H, m), 7.86 (1H, s); MS m/z 309 [M+H]$^+$.

Intermediate 127

10-chloro-2-cyclopentyl-4,4-dimethyl-2,6,9,11-tetrazabicyclo[5.4.0]undeca-8,10,12-trien-5-one Ethyl3-[(2-chloro-5-nitro-pyrimidin-4-yl)-cyclopentylamino]-2,2-dimethyl-propanoate (Intermediate 127; 23.73 g, 64 mmol) was dissolved in acetic acid (512 mL) by heating to 70-75° C. under nitrogen in an oil bath. Iron powder (9.6 g) was added in portions over 10 minutes and the reaction stirred at 70° C. for 3 hours. The reaction mixture was filtered whilst still hot through a bed of celite and the bed washed with DCM. The combined filtrate and washings was evaporated to dryness and the resulting residue azeotroped three times with toluene. The residue was taken up in DCM and celite added before filtering through a small bed of celite The volume of DCM was reduced and the solution purified in two batches by loading directly onto Biotage Flash 75 and a 400 g Si cartridge pre-conditioned with 50% Ethyl Acetate in isohexane. The cartridge was eluted with ~500 ml of 50% Ethyl Acetate in isohexane followed by Ethyl Acetate. Product containing fractions were combined and evaporated and the resulting yellow solid triturated under isohexane. The solid material was collected by filtration, washed with isohexane and dried by desiccation under high vacuum at room temperature to constant weight to give the title compound as an off white solid (9.67 g, 51%)

1H NMR (400.13 MHz, DMSO-d$_6$) δ 1.14 (6H, s), 1.51-1.62 (4H, m), 1.69-1.74 (2H, m), 1.75-1.85 (2H, m), 3.32 (2H, s), 5.02-5.11 (1H, m), 7.93 (1H, s), 9.72 (1H, s); MS m/z 295.3 [M+H]$^+$.

Intermediate 128

Ethyl3-[(2-chloro-5-nitro-pyrimidin-4-yl)-cyclopentyl-amino]-2,2-dimethyl-propanoate To a stirred clear colourless solution of Ethyl3-(cyclopentylamino)-2,2-dimethyl-propanoate (US 2004/0176380 A1; 29.8 g, 139.7 mmol) in the acetone (700 mL) at room temperature was added potassium carbonate (21.3 g, 153.7 mmol) followed by 2,4-dichloro-5-nitropyrimidine (Aldrich; 29.81 g, 153.7 mmol). The reaction mixture was stirred vigorously at room temperature overnight. Potassium carbonate (7.75 g, 56 mmol) was added stirring continued for a further 4 hours. The reaction mixture was concentrated in vacuo to low volume and partitioned between Ethyl Acetate (600 mL) and water (400 mL). Phases were separated and the aqueous phase re-extracted with Ethyl Acetate (1×200 ml, 1×100 ml). The combined organic extracts were dried using MgSO4 and evaporated to dryness The residue was dissolved in DCM (150 mL) and purified in two batches using a Biotage Flash 75 system with 400 g Si column, conditioned with 10% Ethyl Acetate in isohexane and eluted with 10% Ethyl Acetate in isohexane. Product containing fractions were combined and evaporated giving the title compound as a yellow oil which solidified on standing in a freezer (27.90 g 54%)

1H NMR (399.9 MHz, CDCl$_3$) δ 1.22 (6H, s), 1.24 (3H, t), 1.50-1.62 (4H, m), 1.70-1.75 (2H, m), 1.89-1.95 (2H, m), 3.50-3.55 (1H, m), 3.82 (2H, s), 4.13 (2H, q), 8.74 (1H, s); MS m/z 371 [M+H]$^+$.

Intermediate 129

4-[(2-cyclopentyl-4,4,6-trimethyl-5-oxo-2,6,9,11-tetrazabicyclo[5.4.0]undeca-7,9,11-trien-10-yl)amino]benzoic acid To a solution of 10-chloro-2-cyclopentyl-4,4,6-trimethyl-2,6,9,11-tetrazabicyclo[5.4.0]undeca-7,9,11-trien-5-one (Intermediate 126; 308 mg, 1 mmol) and 4-amino-3-methoxy-benzoic acid (Aldrich; 155 mg, 1.13 mmol) in ethanol (5 mL) was added water (15 mL) and concentrated hydrochloric acid (0.17 mL, 2 mmol). The mixture was heated under reflux for 36 hours. The reaction was cooled and a precipitate formed. This was filtered, dried and triturated under cold acetonitrile refiltered and dried in vacuo. To give the title compound as a brown solid (394 mg, 96%)

MS m/z 410 [M+H]$^+$.

Intermediate 130

2'-chloro-9'-cyclopentyl-5'-methyl-8',9'-dihydrospiro[cyclopropane-1,7'-pyrimido[5,4-b][1,4]diazepin]-6'(5'H)-one To a stirred solution of 2'-chloro-9'-cyclopentyl-8',9'-dihydrospiro[cyclopropane-1,7'-pyrimido[4,5-b][1,4]diazepin]-6'(5'H)-one (Intermediate 131; 15 g, 51.24 mmol) in DMA (1 L) under nitrogen was added methyl iodide 3.51 mL, 56.36 mL). The mixture was cooled in ice/water to 4° C. Sodium hydride (60% mineral oil dispersion; 2.26 g, 56.36 mmol) was added in one portion. A small exotherm to 6° C. was observed. The reaction mixture was stirred on an ice/water bath for 1 hour, the cooling bath was removed and the reaction stirred at room temperature overnight. Solvent was evaporated in vacuo and the residue treated with water. This afforded a solid, which was filtered off and washed with water to give an off white solid, which was crystallised from IPA (100 mL) with hot filtration through fluted paper to remove a small amount insoluble matter. The crystallised material was filtered, washed with chilled IPA, and dried by dessication under high vacuum at room temperature over the weekend to give the title compound as a white crystalline solid (12.78_g, 81%)

$^1$H NMR (400.13 MHz, CDCl$_3$) δ 0.56-0.59 (2H, m), 1.04-1.07 (2H, m), 1.28-1.37 (2H, m), 1.57-1.63 (4H, m), 1.88-1.96 (2H, m), 3.20 (3H, s), 3.40 (2H, s), 4.82-4.91 (1H, m), 7.79 (1H, s); MS m/z 307.09 [M+H]$^+$.

Intermediate 131

2'-chloro-9'-cyclopentyl-8',9'-dihydrospiro[cyclopropane-1,7'-pyrimido[4,5-b][1,4]diazepin]-6'(5'H)-one Ethyl1-[[(2-chloro-5-nitro-pyrimidin-4-yl)-cyclopentyl-amino]methyl]cyclopropane-1-carboxylate (Intermediate 132; 35.92 g, 97.4 mmol) was dissolved in the acetic acid (750 mL) and the solution stirred and heated to 70° C. under nitrogen. Iron powder (14.61 g) was added in portions over 10 minutes. Over the next 10-15 minutes the resulting exotherm took the reaction mixture temperature up to a maximum of 92° C. The temperature then slowly dropped back to 75° C. The dark reaction mixture was then stirred at 75° C. for 3 hours. The reaction mixture was filtered whilst still hot through a bed of celite and the bed washed through with DCM. The acetic acid/DCM filtrate was evaporated to dryness and the resulting residue azeotroped three times with toluene. The residue was left under high vacuum at room temperature overnight, taken up in DCM and filtered through a small bed of celite. The celite was washed with DCM and the filtrate concentrated down to 250 mL and loaded onto a dry silica column pre-conditioned with DCM. The column was eluted with a 5-10% gradient of 7N $NH_3$/MeOH in DCM and product containing fractions were combined and evaporated. The resultant material was recrystallised from isopropanol. The solid precipitate was collected by filtration, washed with chilled isopropanol and dried by desiccation under high vacuum at room temperature to constant weight to yield the title compound as a grey solid (17.1 g.

$^1$H NMR (399.9 MHz, $CDCl_3$) δ 0.79-0.84 (2H, m), 1.19-1.29 (2H, m), 1.36-1.41 (2H, m), 1.56-1.67 (4H, m), 1.85-1.95 (2H, m), 3.25 (2H, s), 4.95-5.04 (1H, m), 7.75 (1H, s), 8.56 (1H, s); MS m/z 292.97 [M+H]$^+$.

Intermediate 132

Ethyl1-[[(2-chloro-5-nitro-pyrimidin-4-yl)-cyclopentyl-amino]methyl]cyclopropane-1-carboxylate To a stirred solution of Ethyl1-[(cyclopentylamino)methyl]cyclopropane-1-carboxylate in acetone (700 mL) at room temperature was added potassium carbonate (29.0 g, 209.6 mmol) followed by the 2,4-dichloro-5-nitropyrimidine (Frontier Scientific; 29.81 g, 153.7 mmol).

The reaction mixture was stirred vigorously at room temperature overnight, concentrated in vacuo to low volume and the brown residue partitioned between Ethyl Acetate (600 mL) and water (400 mL). Phases were separated and the aqueous re-extracted with Ethyl Acetate (1×200 mL, 1×100 mL). The combined organic extracts were dried using $MgSO_4$ and evaporated to dryness giving a clear brown oil which solidified on standing. The resultant material was recrystallised from IPA. The solid was collected by filtration, washed with chilled IPA, sucked as dry as possible then dried to constant weight by desiccation under high vacuum at room temperature to yield the title compound as a light-brown solid (35.92 g, 70%)

$^1$H NMR (400.13 MHz, $CDCl_3$) δ 0.88-0.91 (2H, m), 1.07 (3H, t), 1.26-1.29 (2H, m), 1.44-1.53 (2H, m), 1.71-1.88 (6H, m), 3.65 (2H, s), 3.65-3.71 (1H, m), 4.01 (2H, q), 8.65 (1H, s); MS m/z 369.03 [M+H]$^+$.

Intermediate 133

Ethyl1-[(cyclopentylamino)methyl]cyclopropane-1-carboxylate

To a stirred clear solution of Ethyl1-(aminomethyl)cyclopropane-1-carboxylate (Intermediate 134; 74.15 g, 191.6 mmol) in DCM (900 mL) under nitrogen at room temperature was added cyclopentanone (Aldrich; 17.5 mL, 195.4 mmol). The reaction was stirred at room temperature for 1.25 hours. Sodium acetate (Aldrich; 16.03 g, 195.4 mmol) was added, followed by sodium triacetoxyborohydride (Aldrich; 60.93 g, 287.4 mmol). The resulting suspension was stirred at room temperature overnight.

The reaction mixture was treated with saturated aqueous sodium bicarbonate solution (1 L) followed by slow addition of 2M NaOH (aq.) to pH 8-9. The aqueous phase was separated re-extracted with DCM (3×250 mL). The combined organic solutions were combined, dried with $MgSO_4$ and evaporated. to give the title compound as a clear pale-yellow thin oil (39.39 g, 97%).

$^1$H NMR (400.13 MHz, $CDCl_3$) δ 0.79-0.81 (2H, m), 1.23 (3H, t), 1.24-1.28 (2H, m), 1.30-1.33 (2H, m), 1.46-1.57 (2H, m), 1.63-1.73 (2H, m), 1.77-1.86 (2H, m), 1.91 (1H, s), 2.69 (2H, s), 3.03-3.10 (1H, m), 4.11 (2H, q)

Intermediate 134

Ethyl1-(aminomethyl)cyclopropane-1-carboxylate

Ethyl1-cyanocyclopropane-1-carboxylate (Aldrich; 76.45 g, 550 mmol), Platinum Oxide (7.5 g) and Acetic acid (1 L) were combined then stirred at room temperature under hydrogen at 4 bar pressure for 8 hours. The reaction mixture was filtered and the filtrate concentrated in vacuo to give the title compound as a colourless oil containing 4.5 equivalents of acetic acid. (115 g, 51%)

$^1$H NMR (400.13 MHz, $CDCl_3$) δ 0.81-0.84 (2H, m), 1.01 (3H, t), 1.12-1.15 (2H, m), 1.77 (13.5H, s–AcOH), 2.89 (2H, s), 3.92 (2H, q), 10.12 (6.5H, br s–AcOH+$NH_2$).

Intermediate 135

4-amino-3-methoxy-N-(2-morpholin-4-ylethyl)benzamide 4-amino-3-methoxybenzoic acid (Aldrich; 5 g, 29.9 mmol) was stirred and dissolved in DMF (100 mL) at ambient temperature. 4-(2-aminoethyl)morpholine (Aldrich; 4.7 mL, 35.8 mmol) was added followed by DIPEA (15.6 mL, 89.7 mmol) and HATU (13.7 g, 36.0 mmol) causing a slight exotherm. The brown solution was stirred for 24 h and the solvent evaporated to a brown gum.

A sample (1.2 g) was dissolved in methanol and purified by loading on an SCX-2 (20 g) column pre-wet with methanol and eluted with 2M NH3/MeOH. Product containing fractions were combined and evaporated to give the title compound as a gum (726 mg)

The remaining product was purified in the same manner on SCX-2 columns (5 g per 50 g column). To give the title compound as an orange solid (9.55 g)

$^1$H NMR (400.132 MHz, DMSO-$D_6$) δ 2.43 (4H, m), 3.18 (2H, m), 3.34 (2H, m), 3.57 (4H, m), 3.80 (3H, s), 5.20 (2H, s), 6.61 (1H, d), 7.27 (2H, m), 7.96 (1H, t); MS m/z 280 [M+H]$^+$.

Intermediate 136

4-amino-N-(3-dimethylamino-2,2-dimethyl-propyl)benzamide

To a solution of 4-aminobenzoic acid (Aldrich; 4.0 g, 29.17 mmol) in DMF (100 mL) was added N,N,2,2-tetramethyl-1,3-diaminopropane (Aldrich; 5 mL, 31.38 mmol). An immediate solid precipitate formed. DIPEA (15 ml, 86.11 mmol) was added and the resultant suspension stirred HATU (13 g, 34.18 mmol) was added portionwise at such a rate and time interval as to maintain internal reaction temp <30° C.}. The resultant yellow solution was stirred at ambient temperature, overnight.

The solvent was removed in vacuo, and the residue partitioned between saturated aqueous sodium bicarbonate solution (250 mL) and DCM (250 mL). The organic phase was separated and the aqueous phase re-extracted with DCM (250 mL). Combined organic extracts were washed with brine, dried over magnesium sulphate, filtered and evaporated to a viscous orange syrup which was purified by flash chromatography on silica eluting with 0-10% 0.2M methanolic ammonia in DCM. Product containing fractions were combined and evaporated to give the title compound as a pale straw coloured gum (1.134 g, 15%)

$^1$H NMR (400.132 MHz, DMSO-$d_6$) δ 0.90 (m, 6H), 2.07-2.40 (m, 6H), 2.67-2.95 (m, 2H), 3.15-3.20 (m, 2H), 5.57 (s, 2H), 6.56 (m, 2H), 7.55 (m, 2H), 7.97-8.17 (m, 1H); MS m/z 250.5 [M+H]$^+$.

Intermediate 137

10-chloro-2-(1-methoxypropan-2-yl)-2,6,9,11-tetrazabicyclo[5.4.0]undeca-7,9,11-trien-5-one To a solution of N-(2,4-dichloropyrimidin-5-yl)prop-2-enamide (Intermediate 138; 104 mg, 0.477 mmol) n THF (2 mL) was added triethylamine (73 μL, 0.525 mmol) followed by 2-amino-1-methoxypropane (Aldrich; 50 μL, 0.477 mmol) and the reaction stirred at room temperature for 90 minutes.

The reaction mixture was heated in a microwave at 150° C. for 30 minutes. And then at 160° C. for a further 90 minutes. The solvents were evaporated and the residue chromatographed on silica eluting with a gradient of 30-100% Ethyl Acetate/iso-hexane. Product containing fractions were combined and evaporated to give the title compound as an off white solid (35 mg, 29%)

MS m/z 250.5 [M+H]$^+$.

Intermediate 138

N-(2,4-dichloropyrimidin-5-yl)prop-2-enamide

To a solution of 5-Amino-2,4-dichloropyrimidine (Chempacific; 100 mg, 0.610 mmol) in THF (2 mL) was added triethylamine (170 μL, 1.22 mmol) followed by 3-Chloropropionyl Chloride (Aldrich; 64 mL, 0.671 mmol) The reaction was stirred at room temperature for 18 hrs.

The reaction was filtered and the solvent evaporated. The residue was dissolved in DCM and washed with water then gravity filtered through a PTFE cup and the organic filtrate evaporated to give the title compound as a yellow gum (104 mg).

MS m/z 218 [M+H]$^+$.

Intermediate 139

10-chloro-2-cyclopentyl-6-ethyl-2,6,9,11-tetrazabicyclo[5.4.0]undeca-8,10,12-trien-5-one Tris(dibenzylideneacetone)dipalladium(0) (81 mg, 0.09 mmol), XANTPHOS (153 mg, 0.26 mmol) and Caesium Carbonate (2.08 g, 6.37 mmol) were added to a stirred solution of 3-[(5-bromo-2-chloro-pyrimidin-4-yl)-cyclopentyl-amino]-N-ethyl-propanamide (Intermediate 140; 1.65 g, 4.39 mmol) in 1,4-dioxane (44 mL). The apparatus was evacuated and backfilled with nitrogen twice and then heated to 100° C.

for 18 hrs. The reaction mixture was filtered through a celite pad and dry loaded onto silica for purification by flash silica chromatography (companion, 40 g, 0-10% MeOH/DCM) to give the title compound as a yellow gum (1.26 g, 4.27 mmol, 97%).

$^1$H NMR (399.902 MHz, DMSO-$d_6$) δ 1.02 (t, 3H), 1.50-1.76 (m, 6H), 1.85-1.95 (m, 2H), 2.58-2.61 (m, 2H), 3.64-3.66 (m, 2H), 3.74 (q, 2H), 4.69 (quintet, 1H), 8.21 (s, 1H); MS m/z 295.15 [M+H]$^+$.

Intermediate 140

3-[(5-bromo-2-chloro-pyrimidin-4-yl)-cyclopentyl-amino]-N-ethyl-propanamide

5-Bromo-2,4-dichloropyrimidine (Aldrich; 1.825 g, 8.00 mmol), 3-(cyclopentylamino)-N-ethyl-propanamide (Intermediate 141; 1.48 g, 8.00 mmol) and triethylamine (1.2 mL, 8.16 mmol) were combined in acetonitrile (50 mL) and heated at 100° C. for 4 hours. The solvent was removed under reduced pressure and the residue taken up in Ethyl Acetate, washed with water and purified by flash silica chromatography (companion, 40 g, 0-10% Methanol/DCM) to give the title compound as a brown oil, (2.14 g, 71%).

$^1$H NMR (399.902 MHz, DMSO-$d_6$) δ 0.99 (t, 3H), 1.45-1.58 (m, 2H), 1.60-1.77 (m, 4H), 1.78-1.90 (m, 2H), 2.33 (t, 2H), 3.03 (qd, 2H), 3.66 (t, 2H), 4.57 (quintet, 1H), 7.79 (t, 1H), 8.39 (s, 1H); MS m/z 376.78 [M+H]$^+$.

Intermediate 141

3-(cyclopentylamino)-N-ethyl-propanamide

N-ethylacrylamide (ABCR: 1.045 g, 10.50 mmol) and cyclopentylamine (Aldrich; 987 uL, 10.00 mmol) in methanol (10 mL) were combined in a microwave reaction vessel, which was sealed and irradiated to 140° C. for 30 minutes. The reaction mixture was allowed to cool and loaded directly onto a 50 g SCX-2 cartridge, washing with methanol (100 mL) and eluting the desired product with 7 N methanolic ammonia (100 mL). Concentration under reduced pressure of combined product containing fractions afforded the title compound as a brown oil (1.48 g, 80%)

$^1$H NMR (399.9 MHz, DMSO-$d_6$) δ1.01 (3H, t), 1.27-1.32 (2H, m), 1.41-1.53 (2H, m), 1.55-1.64 (2H, m), 1.65-1.69 (2H, m), 2.18 (2H, t), 2.67 (2H, t), 2.94-3.01 (1H, m), 3.03-3.09 (2H, m), 7.89 (1H, br s)

Intermediate 142

10-chloro-2-cyclopentyl-6-propan-2-yl-2,6,9,11-tetrazabicyclo[5.4.0]undeca-8,10,12-trien-5-one Tris(dibenzylideneacetone)dipalladium(0) (47 mg, 0.05 mmol), XANTPHOS (90 mg, 0.15 mmol) and Caesium carbonate (2.425 g, 7.44 mmol) were added to a stirred solution of PH17075-018 (purified reaction mixture, 2.00 g, 5.13 mmol) in 1,4-dioxane (50 mL). The apparatus was evacuated and backfilled with nitrogen twice and then heated to 100° C. for 1.5 hrs Tris(dibenzylideneacetone)dipalladium(0) (47 mg, 0.05 mmol) and XANTPHOS (90 mg, 0.15 mmol) were added and heating continued for a further 18 h.

Tris(dibenzylideneacetone)dipalladium(0) (47 mg, 0.05 mmol) was added and the temperature increased to 120° C. for 18 hr. The reaction mixture was transferred to a microwave vessel and irradiated at 150° C. for 30 minutes.

The reaction mixture was filtered through a pad of celite, concentrated down onto silica and purified by flash silica chromatography (Companion, 40 g, 0-5% MeOH/DCM). Product containing fractions were combined and evaporated to give the title compound as a yellow oil (532 mg, 33%)

$^1$H NMR (399.902 MHz, CDCl$_3$) δ 1.24 (d, 6H), 1.50-1.80 (m, 6H), 1.97-2.07 (m, 2H), 2.57-2.60 (m, 2H), 3.66-3.69 (m, 2H), 4.52 (septet, 1H), 4.73 (quintet, 1H), 8.03 (s, 1H); MS m/z 309 [M+H]+.

Intermediate 143

3-[(5-bromo-2-chloro-pyrimidin-4-yl)-cyclopentyl-amino]-N-propan-2-yl-propanamide To a stirred solution of 3-(cyclopentylamino)-N-propan-2-yl-propanamide (Intermediate 144; 1.90 g, 9.58 mmol) and triethylamine (1.36 mL, 9.77 mmol) in acetonitrile (100 mL) was added 5-bromo-2,4-dichloropryimidine (Aldrich; 2.30 g, 10.06 mmol) and the resulting solution heated at 100° C. for 18 hrs. The solvent was removed under reduced pressure and the residue was taken up in Ethyl Acetate (200 mL) and water (200 mL). The aqueous phase was removed and the organic phase washed with water (200 mL). The organic solution was loaded onto a 50 g SCX-2 cartridge, washing with methanol (50 mL), and Ethyl Acetate (50 mL), before eluting with 7 N methanolic ammonia. Product containing fractions were combined and evaporated and the residue purified by flash silica chromatography (companion, 120 g, 0-10% MeOH/DCM) to give clean the title compound as a white solid (1.17 g, 31%)

$^1$H NMR (399.902 MHz, DMSO-d$_6$) δ 1.06 (d, 6H), 1.53-1.62 (m, 2H), 1.66-1.80 (m, 4H), 1.84-1.94 (m, 2H), 2.35 (t, 2H), 3.69 (t, 2H), 3.84 (sextet, 1H), 4.60 (quintet, 1H), 7.71 (d, 1H), 8.44 (s, 1H); MS m/z 391 [M+H]+.

Intermediate 144

3-(cyclopentylamino)-N-propan-2-yl-propanamide

N-Isopropylacrylamide (Aldrich; 1.19 g, 10.50 mmol) and cyclopentlyamine (Aldrich; 0.98 mL, 10.0 mmol) were combined in methanol (6 mL) in a 10 mL microwave reaction vessel and the resultant solution heated to 140° C. for 30 mins. The reaction mixture was loaded directly onto a 50 g SCX-2 cartridge, washing with methanol (100 mL) and eluting the desired product with 7 N methanolic ammonia (100 mL). The eluted product was concentrated under reduced pressure to give the title compound as a light brown oil (1.90 g, 96%)

$^1$H NMR (399.902 MHz, DMSO-d$_6$) δ 1.04 (d, 6H), 1.22-1.32 (m, 2H), 1.41-1.53 (m, 2H), 1.54-1.74 (m, 4H), 2.16 (t, 2H), 2.65 (t, 2H), 2.97 (quintet, 1H), 3.76-3.88 (m, 1H), 7.83 (br d, 1H); MS m/z 199 [M+H]+.

Intermediate 145

2-amino-N-(1-methyl-4-piperidyl)-1,3-thiazole-4-carboxamide

2-Aminothiazole-4-carboxylate hydrobromide salt (Chempacific; 1.13 g, 5.02 mmol), HATU (2.87 g, 7.53 mmol) and 4-amino-1-methylpiperidine (0.86 g, 7.53 mmol) were stirred in DMF (5 mL) and DIPEA (5.2 mL, 30.12 mmol) added. The mixture was stirred at room temperature overnight. The reaction mixture was concentrated and the residue taken up in methanol, absorbed onto an SCX column, washed with methanol and eluted with ammonia in methanol.

Product containing fractions were combined, evaporated and the residue and further purified by column chromatography (5% 7N NH$_3$ in MeOH/DCM) Product containing fractions were combined and evaporated to give the title compound as a yellow solid (635 mg, 53%).

$^1$H NMR (399.9 MHz, DMSO-d$_6$) δ1.49-1.59 (2H, m), 1.72-1.76 (2H, m), 1.98 (2H, t), 2.16 (3H, s), 2.67-2.70 (2H, m), 3.60-3.69 (1H, m), 7.09 (2H, s), 7.17 (1H, s), 7.38-7.40 (1H, m); MS m/z 241.44 [M+H]$^+$.

Intermediate 146

2-amino-4-methyl-N-(1-methyl-4-piperidyl)-1,3-thiazole-5-carboxamide

Utilising 2-amino-4-methyl-1,3-thiazole-5-carboxylic acid—Buttpark and an analogous method to Intermediate 145 the title compound was obtained $^1$H NMR (399.9 MHz, DMSO-d$_6$) δ1.49-1.59 (2H, m), 1.67-1.70 (2H, m), 1.88-1.94 (2H, m), 2.15 (3H, s), 2.31 (3H, s), 2.72 (2H, m), 3.56-3.62 (1H, m), 7.22-7.26 (3H, m); MS m/z 255.45 [M+H]$^+$.

Intermediate 147

2-amino-N-(1-methyl-4-piperidyl)-1,3-thiazole-5-carboxamide

Utilising 2-amino-1,3-thiazole-5-carboxylic acid Journal of Medicinal Chemistry (1972), 15(12), 1310-12. Compound I and an analogous method to Intermediate 145 the title compound was obtained $^1$H NMR (399.9 MHz, DMSO-d$_6$) δ1.47-1.57 (2H, m), 1.71 (2H, d), 1.94 (2H, t), 2.17 (3H, s), 2.75 (2H, d), 3.59-3.65 (1H, m), 7.08 (2H, s), 7.36 (1H, s), 7.68 (1H, d). MS m/z 241.06 [M+H]$^+$.

Intermediate 148

2-amino-N-(1-methyl-4-piperidyl)-1,3-oxazole-5-carboxamide

Utilising 2-amino-1,3-oxazole-5-carboxylic acid—Intermediate 149 and an analogous method to Intermediate 145 the title compound was obtained $^1$H NMR (399.9 MHz, DMSO-d$_6$) δ1.46-1.56 (2H, m), 1.70-1.74 (2H, m), 1.89-1.96 (2H, m), 2.16 (3H, s), 2.76 (2H, d), 3.59-3.63 (1H, m), 7.38 (2H, s), 7.63 (1H, s), 7.82 (1H, d)); MS m/z 225.14 [M+H]$^+$.

Intermediate 149

2-amino-1,3-oxazole-5-carboxylic acid

Ethyl 2-aminooxazole-4-carboxylate (Apollo Scientific; 1.175 g, 7.50 mmol) was dissolved in THF (15 mL) and water (8 mL). Lithium hydroxide monohydrate (1.58 g, 37.52 mmol) was added and the mixture stirred overnight at room temperature. The mixture was neutralised with 2N HCl$_{(aqu)}$ and concentrated. The residue was suspended in water and filtered and the solid collected dissolved in 2N NaOH$_{(aqu)}$, filtered and then acidified with acetic acid to approximately pH4. The mixture was allowed to stand in an ice bath for 10 minutes and then filtered. The solid was dried on the filter and then in a dessicator overnight to give the title compound as a yellow solid (194 mg, 20%)

¹H NMR (399.9 MHz, DMSO-d₆) δ7.37 (2H, s), 7.45 (1H, s), 12.60 (1H, brS).

Intermediate 150

2-[(2-cyclopentyl-6-methyl-5-oxo-2,6,9,11-tetrazabicyclo[5.4.0]undeca-7,9,11-trien-10-yl)amino]-1,3-oxazole-4-carboxylic acid Ethyl2-[(2-cyclopentyl-6-methyl-5-oxo-2,6,9,11-tetrazabicyclo[5.4.0]undeca-7,9,11-trien-10-yl)amino]-1,3-oxazole-4-carboxylate (Intermediate 151; 160 mg, 0.40 mmol) was dissolved in THF (1 mL) and water (0.5 mL). Lithium hydroxide monohydrate (84 mg, 2.0 mmol) was added and a few drops of methanol and the mixture stirred at room temperature overnight. The mixture was neutralised with 2N HCl$_{(aqu)}$ and concentrated. The residue was taken up in MeOH/Water and absorbed onto an SCX column, washed with methanol/water and eluted with ammonia in methanol. Product containing fractions were concentrated, the residue taken-up in DCM, dried (MgSO₄) and concentrated to give the title compound as a white solid (90 mg, 60%).

¹H NMR (399.9 MHz, DMSO-d₆) δ1.54-1.66 (6H, m), 1.92 (2H, s), 2.57-2.60 (2H, m), 3.17 (3H, s), 3.61 (2H, t), 4.77 (1H, t), 7.96 (1H, s), 8.06 (1H, s); MS m/z 373.20 [M+H]⁺.

Intermediate 151

Ethyl2-[(2-cyclopentyl-6-methyl-5-oxo-2,6,9,11-tetrazabicyclo[5.4.0]undeca-7,9,11-trien-10-yl)amino]-1,3-oxazole-4-carboxylate 10-Chloro-2-cyclopentyl-6-methyl-2,6,9,11-tetrazabicyclo[5.4.0]undeca-8,10,12-trien-5-one (Intermediate 1; 248 mg, 0.88 mmol), ethyl2-aminooxazole-4-carboxylate (Fluorochem; 125 mg, 0.80 mmol) and XANTPHOS (42 mg, 0.07 mmol) were dissolved in 1,4-dioxane (7.5 mL). Caesium carbonate (522 mg, 1.60 mmol) was added and the mixture purged with a stream of nitrogen for 5 minutes. Tris(dibenzylideneacetone) palladium (II) (44 mg, 0.05 mmol) was added and the apparatus was evacuated and backfilled with nitrogen (×3) and the reaction heated at 100° C. overnight. The mixture was cooled, filtered and the filtrate absorbed onto an SCX column, washed with methanol and the product eluted with ammonia in methanol. Product containing fractions were concentrated and purified by normal phase chromatography (5% methanol/DCM) to give the title compound as a white solid (165 mg, 51%)

¹H NMR (399.9 MHz, DMSO-d₆) δ1.29 (3H, t), 1.59 (6H, m), 1.95 (2H, m), 2.54-2.60 (2H, m), 3.18 (3H, s), 3.60-3.63 (2H, m), 4.27 (2H, q), 4.83 (1H, t), 8.08 (1H, s), 8.50 (1H, s), 10.65 (1H, s); MS m/z 401.24 [M+H]⁺.

Intermediate 152

6-amino-N-(1-methyl-4-piperidyl)pyridine-3-carboxamide

6-Aminonicotinic acid (Aldrich; 2 g, 14.48 mmol) and 4-amino-1-methylpiperidine (Fluorochem; 1.82 g, 15.92 g) were suspended in DMF (20 mL), DIPEA (7.5 mL, 43.44 mmol) and HATU (6.05 g, 15.92 mmol) were added and the reaction stirred at ambient temperature for 18 hrs. The solvent was evaporated and the residues stirred with water (50 mL for 1 hr filtered, acidified with 2M aq HCl and added to a 50 g SCX-2 column pre-wet with MeOH (2 column volumes). Flushed with MeOH (2 column volumes) then the crude product eluted with 2M ammonia in MeOH and evaporated. The residue was dissolved in DCM with a little MeOH to help solubility and purified on silica eluting with a gradient of 10-20% 2M ammonia in MeOH/DCM. Fractions containing product combined and evaporated to give the title compound as a cream solid (1.75 g, 52%)

¹H NMR (400.132 MHz, DMSO-d₆) δ1.47 (m, 2H), 1.65 (m, 2H), 1.85 (m, 2H), 2.09 (s, 3H), 2.68 (m, 2H), 3.61 (m, 1H), 6.33 (m, 3H), 7.73 (m, 1H), 7.78 (d, 1H), 8.36 (m, 1H); MS m/z 235 [M+H]⁺.

Intermediate 153

5-amino-N-(1-methyl-4-piperidyl)pyridine-2-carboxamide

Utilising 5-aminopyridine-2-carboxylic acid—Chempacific and an analogous method to intermediate 152 the title compound was obtained as cream solid (1.29 g, 31%)

¹H NMR (400.132 MHz, DMSO-d₆) δ1.60 (m, 2H), 1.72 (m, 2H), 1.97 (m, 2H), 2.16 (s, 3H), 2.71 (m, 2H), 3.69 (m, 1H), 5.89 (s, 2H), 6.97 (m, 1H), 7.69 (d, 1H), 7.91 (m, 1H), 7.97 (d, 1H); MS m/z 235 [M+H]⁺.

Intermediate 154

9-chloro-2-methyl-6-prop-2-ynyl-2,6,8,10-tetrazabicyclo[5.4.0]undeca-7,9,11-trien-3-one To a cooled (ice/water bath) suspension of sodium hydride (60% dispersion in mineral oil; 15 mg, 0.38 mmol) in DMA (1 mL) was carefully added a solution of 10-chloro-6-methyl-2,6,9,11-tetrazabicyclo[5.4.0]undeca-7,9,11-trien-5-one (Intermediate 100; 65 mg, 0.31 mmol) in DMA (1.5 mL). The reaction mixture was allowed to stir, under nitrogen, on an ice bath for 1 hour prior to addition of propargyl chloride (34 mg, 0.47 mmol). The reaction mixture was left to stir at ambient temperature overnight and then quenched by addition of saturated aqueous ammonium chloride solution (0.5 mL) and stirred for 15 minutes. The resultant mixture was partitioned between DCM (10 mL) and water (10 mL). The organic phase was separated by filtration through PTFE filter cup. The aqueous phase was re-extracted with DCM (5 mL) and the combined organic solutions evaporated to dryness to yield the title compound as a beige coloured solid (52 mg, 67%)

¹H NMR (400.132 MHz, DMSO) δ 2.70 (m, 2H), 3.20 (s, 3H), 3.26 (t, 1H), 3.80 (m, 2H), 4.33 (d, 2H), 8.25 (s, 1H); MS m/z 251 [M+H]⁺.

Intermediate 155

2-(10-chloro-6-methyl-5-oxo-2,6,9,11-tetrazabicyclo[5.4.0]undeca-7,9,11-trien-2-yl)acetonitrile The title compound was prepared by an analogous method to the preparation of Intermediate 154, on a 0.31 mmol scale, utilising bromoacetonitrile (Aldrich; 33 μL, 0.47 mmol), as an amber gum containing 0.6 equivalents of DMF (97 mg, 100%).

¹H NMR (400.132 MHz, DMSO) δ 2.74 (m, 2H), 3.21 (s, 3H), 3.81 (m, 2H), 4.53 (s, 2H), 8.36 (s, 1H); MS m/z 252 [M+H]⁺.

Intermediate 156

9-chloro-6-[(3,5-dimethyl-1,2-oxazol-4-yl)methyl]-2-methyl-2,6,8,10-tetrazabicyclo[5.4.0]undeca-7,9,11-trien-3-one To a stirred solution of 10-chloro-6-methyl-2,6,9,11-tetrazabicyclo[5.4.0]undeca-7,9,11-trien-5-one (Intermediate 100; 64 mg, 0.3 mmol) in DMF (2 mL) was added sodium hydride (60% mineral oil dispersion; 18 mg, 0.36 mmol) and the solution stirred at room temperature until effervescence had ceased. 3 chloromethyl-2,4-dimethylisoxazole (Aldrich; 52 mg, 0.36 mmol) was added and the reaction heated at 50° C. with stirring overnight. The solvent was evaporated and residue dissolved in methanol, transferred to an SCX cartridge pre-wet with methanol, washed with methanol and eluted with methanolic ammonia. Product containing fractions were combined and evaporated to yield the title compound as an off white solid (82 mg, 85%)

Intermediate 157

10-chloro-2-(2-fluoroethyl)-6-methyl-2,6,9,11-tetrazabicyclo[5.4.0]undeca-7,9,11-trien-5-one The title compound was prepared by an analogous method to the preparation of Intermediate 154, on a 0.31 mmol scale, utilising 1-bromo-2-fluoroethane (Apollo Scientific; 235 mg, 1.44 mmol), as a white crystalline solid containing 0.6 equivalents of DMF (86 mg, 100%).

1H NMR (400.132 MHz, DMSO) d 2.71 (m, 2H), 3.19 (s, 3H), 3.81 (m, 2H), 3.88-3.97 (m, 2H), 4.62-4.77 (m, 2H), 8.18 (s, 1H); MS m/z 259 [M+H]$^+$.

Intermediate 158

10-chloro-2-(2-dimethylaminoethyl)-6-methyl-2,6,9,11-tetrazabicyclo[5.4.0]undeca-7,9,11-trien-5-one The title compound was prepared by an analogous method to the preparation of Intermediate 156, on a 0.3 mmol scale, utilising 2 chloroethyldimethylamine hydrochloride (Aldrich; 52 mg, 0.36 mmol) and Sodium Hydride (60% mineral oil dispersion; 36 mg, 0.75 mmol), as a solid (84 mg, 98%).

Intermediate 159

10-chloro-6-methyl-2-[2-(1-piperidyl)ethyl]-2,6,9,11-tetrazabicyclo[5.4.0]undeca-7,9,11-trien-5-one The title compound was prepared by an analogous method to the preparation of Intermediate 156, on a 0.3 mmol scale, utilising 2-chloroethylpiperidine hydrochloride (Aldrich; 55 mg, 0.36 mmol) and Sodium Hydride (60% mineral oil dispersion; 36 mg, 0.75 mmol), as a solid (90 mg, 93%).

Intermediate 160

10-chloro-6-methyl-2-(2-morpholin-4-ylethyl)-2,6,9,11-tetrazabicyclo[5.4.0]undeca-7,9,11-trien-5-one The title compound was prepared by an analogous method to the preparation of Intermediate 156, on a 0.3 mmol scale, utilising N-(2-chloroethyl)morpholine hydrochloride (Aldrich; 67 mg, 0.36 mmol) and Sodium Hydride (60% mineral oil dispersion; 36 mg, 0.75 mmol), as a solid (95 mg, 97%).

Intermediate 161

4-amino-3-methoxy-N-[(1S,5R)-9-methyl-9-azabicyclo[3.3.1]non-7-yl]benzamide

A mixture of 4-Amino-3-Methoxybenzoic Acid (Aldrich; 5.015 g, 30 mmol) and Endo-9-methyl-9-azabicyclo[3,3,1]nonane-3-one (Chempacific; 5.095 g, 33 mol) were dissolved in DMF (150 mL), and to the solution was added DIPEA (10.4 mL, 60 mmol). The reaction was cooled on an ice-bath, and to the reaction was added, portionwise, HATU (12.55 g, 33 mmol).

The reaction mixture was stirred at ambient temperature for 18 hours. The solvent was removed by evaporation, and the residue was partitioned between Ethyl Acetate (200 mL), and saturated aqueous sodium carbonate solution (3×50 mL), washed with brine (3×50 mL), dried over anhydrous magnesium sulphate, filtered, and the solvent removed by evaporation to give the crude product as an oil (14 g), which was purified on SCX-2 columns (4×50 g), developing and eluting with: 1) water; 2) MeOH; and 3) 3.5M NH$_3$-MeOH. The solvent was removed by evaporation to give the product as a semi-solid, which was triturated with diethylether and filtered to yield the title compound as a tan coloured solid (4.84 g, 53%).

$^1$H NMR (400.1 MHz; DMSO-d$_6$) δ 0.88-0.96 (1H, d), 1.38-1.50 (3H, m), 1.86-1.96 (2H, m), 2.00-2.10 (1H, m), 2.10-2.20 (2H, m), 2.42 (3H, s), 2.92-3.00 (2H, d), 3.82 (3H, s), 4.22-4.38 (1H, m), 5.17 (2H, s), 6.58-6.62 (1H, d), 7.28 (1H, s), 7.30 (1H, s), 7.60-7.64 (1H, d). MS m/z 292 [M+H]$^+$.

Intermediate 162

4-amino-3-fluoro-N-[(1S,5R)-9-methyl-9-azabicyclo[3.3.1]non-7-yl]benzamide 4-amino-3-fluorobenzoic acid (Fluorochem; 5.0 g, 32.2 mmol), HATU (13.5 g, 35.4 mmol) and DIPEA (18.5 mL, 106 mmol) were stirred together in anhydrous DMA (100 mL) for 25 minutes. Endo-9-methyl-9-azabicyclo[3,3,1]nonane-3-one (Chempacific; 5.5 g, 35.4 mmol) was added and the solution stirred at ambient temperature overnight.

The solvent was evaporated and the residue dissolved in MeOH and loaded onto an SCX-2 column (50 g×4) pre-wet with MeOH. The column was washed with MeOH (2 column volumes) and the product eluted with 2M NH3/MeOH (2 column volumes). The ammoniacal solution was evaporated and the resultant material purified on a silica column eluted with 0-10% 2NH3/MeOH/DCM. Product containing fractions were evaporated to yield the title compound as a white solid after trituration with ethyl acetate (5.7 g, 61%)

$^1$H NMR (400.132 MHz, DMSO-d6) δ 0.91 (m, 2H), 1.42 (m, 3H), 1.90 (m, 4H), 2.03 (m, 1H), 2.14 (m, 3H), 2.40 (s, 3H), 2.96 (m, 2H), 4.27 (m, 1H), 5.60 (bs, 2H), 6.74 (m, 1H), 7.46 (m, 1H), 7.53 (m, 1H), 7.70 (d, 1H); MS m/z 292 [M+H]$^+$.

Intermediate 163

3-ethoxy-4-[(6-methyl-5-oxo-2-propan-2-yl-2,6,9,11-tetrazabicyclo[5.4.0]undeca-7,9,11-trien-10-yl)amino]benzoic acid 10-Chloro-6-methyl-2-propan-2-yl-2,6,9,11-tetrazabicyclo[5.4.0]undeca-7,9,11-trien-5-one (Intermediate 10; 625 mg, 2.45 mmol), 4-amino-3-ethoxybenzoic acid (Intermediate 164; 509 mg, 2.82 mmol) and 4-toluenesulphonic acid mono hydrate (1.17 g, 6.13 mmol) were heated at 140° C. in 4-methyl-2-pentanol (15 mL) for 1.5 hours. The mixture was cooled and filtered to yield the title compound as a white solid (135 mg, 14%). The filtrate was absorbed on to an SCX column, washed with methanol and eluted with ammonia in methanol. Product containing fractions were concentrated and purified by column chromatography (1%-3% MeOH/DCM) to yield the title compound as a white solid (115 mg, 12%)

$^1$H NMR (399.9 MHz, DMSO-d6) δ1.26 (6H, d), 1.44 (3H, t), 2.74 (2H, m), 3.18 (3H, s), 3.73 (2H, m), 4.22 (2H, q), 4.85-4.92 (1H, m), 7.57 (1H, d), 7.63-7.66 (1H, m), 8.20 (2H, m), 9.41 (1H, brs), 12.90 (1H, brs); MS m/z 400 [M+H]+.

Intermediate 164

4-amino-3-ethoxybenzoic acid

A solution of 3-ethoxy-4-nitrobenzoic acid (Intermediate 165; 1.0 g, 4.74 mmol) ethanol:DMF (50 mL:5 mL) over 5% Pd/C catalyst (100 mg) was hydrogenated with stirring at ambient temperature for 4 hours. The mixture was filtered and the catalyst washed with ethanol and the solvent evaporated and the residue that on trituration with diethyl ether yielded the title compound as an off white solid (688 mg, 81%)

$^1$H NMR (400.132 MHz, DMSO-d6) δ 1.36 (t, 3H), 4.04 (q, 2H), 5.45 (bs, 2H), 6.63 (d, 1H), 7.28 (s, 1H), 7.35 (d, 1H), 12.03 (bs, 1H).

Intermediate 165

3-ethoxy-4-nitrobenzoic acid 3-fluoro-4-nitrobenzoic acid (Apollo Scientific; 15 g, 81 mmol) and potassium hydroxide (10.5 g, 186.3 mmol) were stirred together in ethanol (150 mL) at ambient temperature. The reaction mixture was slowly heating to reflux over 10 minutes. The reaction refluxed vigorously and a solid precipitate formed. The reaction was cooled, diluted with water (100 mL) and acidified with 2N HCl to give a precipitate which was filtered, washed with water and air dried to yield the title compound as a pale brown solid (16.88 g, 99%)

$^1$H NMR (400.132 MHz, DMSO-d6) δ 1.35 (t, 3H), 4.29 (q, 2H), 7.63 (d, 1H), 7.75 (s, 1H), 7.95 (d, 1H), 13.58 (s, 1H); MS m/z 210 [M+H]+.

Intermediate 166

4-amino-3-ethoxy-N-[(3R)-1-methylpyrrolidin-3-yl]benzamide 4-amino-3-ethoxybenzoic acid (Intermediate 164; 400 mg, 2.21 mmol), HATU (1.26 g, 3.31 mmol) and (3R)-1-methylpyrrolidin-3-amine di Hydrochloride (Intermediate 184; 453 mg, 3.31 mmol) were stirred in DMF (5 mL) and diisopropylethylamine (1.7 ml, 9.95 mmol) added. The mixture was stirred for 2 hours and then absorbed on to an SCX column, washed with methanol and eluted with ammonia in methanol. Product containing fractions were concentrated and purified by column chromatography (2.5% ammonia in methanol/DCM) to yield the title compound as a yellow foam (396 mg, 68%).

$^1$H NMR (399.9 MHz, DMSO-d6) δ1.37 (3H, t), 1.70-1.78 (1H, m), 2.09-2.17 (1H, m), 2.25 (3H, s), 2.35-2.42 (2H, m), 2.56-2.62 (1H, m), 2.65-2.69 (1H, m), 4.05 (2H, q), 4.33-4.41 (1H, m), 5.16 (2H, s), 6.61 (1H, d), 7.30-7.54 (2H, m), 7.98 (1H, d); MS m/z 264 [M+H]+.

Intermediate 167

4-amino-N-((1s,4s)-4-(dimethylamino)cyclohexyl)-3-ethoxybenzamide

The title compound was prepared by an analogous method to the preparation of Intermediate 166, on a 2.21 mmol scale, utilising 1-amino-4-dimethylaminocyclohexane (ABChem. Inc.; 472 mg, 3.31 mmol) and diisopropylethylamine 1.15 mL, 6.62 mmol), after separation of the cis isomer by column chromatography, as a yellow foam (162 mg, 24%).

$^1$H NMR (399.9 MHz, DMSO-d6) δ1.35-1.50 (7H, m), 1.68-1.78 (2H, m), 1.83-1.86 (2H, m), 2.00 (1H, m), 2.18 (6H, s), 3.87 (1H, m), 4.05 (2H, q), 5.13 (2H, s), 6.60 (1H, d), 7.31 (2H, m), 7.70 (1H, d); MS m/z 306 [M+H]+.

Intermediate 168

4-amino-N-((1r,4r)-4-(dimethylamino)cyclohexyl)-3-ethoxybenzamide

The title compound was prepared by an analogous method to the preparation of Intermediate 166, on a 2.21 mmol scale, utilising 1-amino-4-dimethylaminocyclohexane (ABChem. Inc.; 472 mg, 3.31 mmol) and diisopropylethylamine 1.15 mL, 6.62 mmol), after separation of the trans isomer by column chromatography, as a white solid (164 mg, 24%).

$^1$H NMR (399.9 MHz, DMSO-d6) δ1.20-1.39 (7H, m), 1.81-1.88 (4H, m), 2.12 (1H, t), 2.18 (6H, m), 3.64-3.70 (1H, m), 4.04 (2H, q), 5.14 (2H, s), 6.60-6.62 (1H, d), 7.28 (2H, m), 7.71 (1H, d); MS m/z 306 [M+H]+.

Intermediate 169

4-amino-5-ethoxy-2-fluoro-N-(1-methyl-4-piperidyl)benzamide

17328/52/1

4-amino-5-ethoxy-2-fluorobenzoic acid (Intermediate 171; 190 mg, 0.95 mmol), HATU (545 mg, 1.43 mmol) and 4-amino-1-methylpiperidine (Fluorochem; 164 mg, 1.43 mmol) were stirred in DMF (3 mL) and diisopropylethylamine (0.58 ml, 2.86 mmol) added. The mixture was stirred over night and then absorbed on to an SCX column, washed with methanol and eluted with ammonia in methanol. Product containing fractions were concentrated and purified by column chromatography (3% ammonia in methanol/DCM) to yield the title compound as a white crystalline solid (245 mg, 86%).

$^1$H NMR (399.9 MHz, DMSO-d$_6$) δ 1.35 (3H, t), 1.50-1.55 (2H, m), 1.71-1.79 (2H, m), 1.94-1.99 (2H, m), 2.16 (3H, s), 2.68-2.71 (2H, m), 3.65-3.73 (1H, m), 4.00 (2H, q), 5.50 (2H, s), 6.40 (1H, d), 7.04 (1H, d), 7.33 (1H, t); MS m/z 296 [M+H]+.

Intermediate 170

4-amino-5-ethoxy-2-fluoro-N-[(1S,5R)-9-methyl-9-azabicyclo[3.3.1]non-7-yl]benzamide The title compound was prepared by an analogous method to the preparation of Intermediate 169, on a 0.5 mmol scale, utilising Endo-9-methyl-9-azabicyclo[3,3,1]nonane-3-one (Chempacific; 111 mg, 0.75 mmol), as a white solid (171 mg, 100%).

¹H NMR (399.9 MHz, DMSO-d₆) δ 0.91 (2H, d), 1.32-1.44 (6H, m), 1.86-1.92 (2H, m), 1.99-2.10 (1H, m), 2.14-2.22 (2H, m), 2.40 (3H, s), 2.96 (2H, d), 4.01 (2H, q), 4.21-4.30 (1H, m), 5.48 (2H, s), 6.40 (1H, d), 7.05 (1H, d), 7.24 (1H, t); MS m/z 336 [M+H]+.

Intermediate 171

4-amino-5-ethoxy-2-fluorobenzoic acid 5-ethoxy-2-fluoro-4-nitrobenzoic acid (Intermediate 172; 1.24 g, 5.40 mmol) was stirred and dissolved in ethanol:DMF (50 mL:5 mL) over 5% Pd/C (125 mg) and hydrogenated at ambient temperature for 4 hours. The catalyst was filtered and washed with ethanol and the solvent evaporated. The resultant material was purified on a silica column, eluting with 0-5% MeOH/DCM. Product containing fractions were combined and evaporated to yield the title compound as a pale brown solid (433 mg, 40%)
¹H NMR (400.132 MHz, DMSO-d₆) δ 1.33 (3H, t), 4.25 (2H, q), 7.66 (1H, d), 7.99 (1H, m), 13.99 (1H, s).

Intermediate 172

5-ethoxy-2-fluoro-4-nitrobenzoic acid 2,5-difluoro-4-nitrobenzoic acid (Fluorochem; 1 g, 4.92 mmol) was stirred and dissolved in DMF (10 mL) and caesium carbonate (4.8 g, 14.7 mmol) was added followed by ethanol (2.3 g, 49.9 mmol). The resulting white mixture was stirred at ambient temperature for 3 hours, diluted with water, acidified to pH1 with 2N HCl (aq), extracted with EtOAc (×3). Combined extracts were washed with water, dried (MgSO4), filtered and evaporated to yield the title compound as a yellow solid (1.24 g, 100%).
¹H NMR (400.132 MHz, DMSO-d₆) δ 1.34 (3H, t), 4.00 (2H, q), 5.79 (2H, s), 6.38 (1H, d), 7.14 (1H, d), 12.32 (1H, s).

Intermediate 173

4-amino-5-chloro-2-fluoro-N-(1-methyl-4-piperidyl) benzamide 4-amino-5-chloro-2-fluorobenzoic acid (Intermediate 176; 500 mg, 2.64 mmol), 4-amino-1-methylpiperidine (452 mg, 3.96 mmol) and diisopropylethylamine (1.38 ml, 7.91 mmol) were stirred in DMF (5 mL) and HATU (1.50 g, 3.96 mmol) added. The reaction mixture was stirred for 3 hours at room temperature. The mixture was absorbed on to an SCX column, which was washed with methanol and eluted with ammonia in methanol. Product containing fractions were concentrated to give a crystalline solid that was suspended in diethyl ether and filtered to yield the title compound as a pale brown solid (572 mg, 76%).
¹H NMR (399.9 MHz, DMSO-d6) δ1.47-1.58 (2H, m), 1.71-1.76 (2H, m), 1.95 (2H, t), 2.15 (3H, s), 2.69-2.72 (2H, m), 3.67 (1H, m), 6.09 (2H, s), 6.55 (1H, d), 7.49 (1H, d), 7.61 (1H, d); MS m/z 286 [M+H]+.

Intermediate 174

4-amino-5-chloro-N-(1-ethyl-4-piperidyl)-2-fluoro-benzamide

The title compound was prepared by an analogous method to the preparation of Intermediate 173, on a 2.64 mol scale, utilising 4-amino-1-methylpiperidine (Fluorochem; 508 mg, 3.96 mmol) after purification on a silica column (gradient (3-4% ammonia in methanol/DCM), as a pale brown foam (647 mg, 82%).
¹H NMR (399.9 MHz, DMSO-d6) δ0.99 (3H, t), 1.46-1.55 (2H, m), 1.75-1.78 (2H, m), 1.92-1.97 (2H, m), 2.31 (2H, q), 2.81 (2H, d), 3.67-3.71 (1H, m), 6.09 (2H, s), 6.53-6.57 (1H, m), 7.48 (1H, d), 7.59-7.62 (1H, m); MS m/z 300 [M+H]+.

Intermediate 175

4-amino-5-chloro-N-(4-dimethylaminocyclohexyl)-2-fluoro-benzamide

The title compound was prepared by an analogous method to the preparation of Intermediate 173, on a 2.64 mol scale, utilising 1-amino-4-dimethylaminocyclohexane (ABChem. Inc.; 472 mg, 3.31 mmol) after purification on a silica column (gradient (3-4% ammonia in methanol/DCM), as a pale brown foam (716 mg, 86%).
¹H NMR (399.9 MHz, DMSO-d₆) δ1.19-1.35 (2H, m), 1.47-1.54 (2H, m), 1.62-1.91 (4H, m), 2.03-2.13 (1H, m), 2.17 (6H, s), 3.59-3.68 and 3.85-3.90 (both 0.5H, m), 6.08 (2H, s), 6.53-6.57 (1H, m), 7.47-7.49 (1H, m), 7.52-7.56 (1H, m); MS m/z 314 [M+H]+.

Intermediate 176

4-amino-5-chloro-2-fluorobenzoic acid

4-Amino-5-chloro-2-fluorobenzoic acid tert-butyl ester (Intermediate 177; 3.0 g, 12.21 mmol) was dissolved in DCM (75 mL) and trifluoroacetic acid (25 mL) added. The mixture was stirred for 1 hour at room temperature and then concentrated to yield the title compound as a pale yellow solid (2.45 g, 100%).
¹H NMR (399.9 MHz, DMSO-d₆) δ6.40 (2H, s), 6.53-6.56 (1H, m), 7.67 (1H, d), 12.56 (1H, s).

Intermediate 177

4-Amino-5-chloro-2-fluorobenzoic acid tert-butyl ester

4-Amino-2-fluorobenzoic acid tert-butyl ester (ABChem. Inc.; 1 g, 4.73 mmol) in DMF (15 mL) was added dropwise to N-chlorosuccinimide (633 mg, 4.73 mmol) in DMF (20 mL). The mixture was stirred at room temperature for 72 hours. The reaction mixture was poured into water (130 mL) and extracted with ethyl acetate (2×50 mL). The combined extracts were washed with water, brine, dried (MgSO₄) and concentrated. Column chromatography (5% ethyl acetate/isohexane) yielded the title compound as a pale yellow, crystalline solid (321 mg, 27.5%).
¹H NMR (399.9 MHz, DMSO-d₆) δ1.50 (9H, s), 6.41 (2H, s), 6.54 (1H, d), 7.61 (1H, d)

Intermediate 178

10-chloro-4,4,6-trimethyl-2-propan-2-yl-2,6,9,11-tetrazabicyclo[5.4.0]undeca-8,10,12-trien-5-one To a stirred solution of 10-Chloro-4,4-dimethyl-2-propan-2-yl-2,6,9,11-tetrazabicyclo[5.4.0]undeca-8,10,12-trien-5-one (Intermediate 179; 2.96 g, 11.01 mmol) in DMA (240 mL), under nitrogen, was added methyl iodide (0.754 mL, 12.12 mmol). The mixture was cooled in an ice/water bath to 3° C. Sodium hydride (60% mineral oil dispersion; 485 mg, 12.12 mmol) was added in one portion. The reaction mixture was stirred on an ice/water bath for 1 hour and then at room temperature overnight. The solvent was removed in vacuo and water was added to the resultant residue to afford a white solid, which was filtered off and washed well with water and dissolved in DCM (125 mL). The solution was dried using MgSO$_4$, filtered and evaporated and the resultant solid, dissolved in DCM (25 mL), purified on a Silica column, equilibrated with 30% EtOAc in isohexane, and eluted with 30%-100% EtOAc in isohexane gradient. Product containing fractions were combined and evaporated to yield the title compound as a white solid (2.7 g, 87%)

$^1$H NMR (400.13 MHz, CDCl$_3$) δ 1.12 (6H, s), 1.13 (6H, d), 3.21 (3H, s), 3.29 (2H, s), 5.15-5.22 (1H, m), 7.78 (1H, s); MS m/z 283 [M+H]+.

Intermediate 179

10-Chloro-4,4-dimethyl-2-propan-2-yl-2,6,9,11-tetrazabicyclo[5.4.0]undeca-8,10,12-trien-5-one 4-amino-5-chloro-N-(4-dimethylaminocyclohexyl)-2-fluoro-benzamide (Intermediate 180; 6.7 g, 19.43 mmol) was stirred and dissolved in the acetic acid (155 mL) by heating to 70° C. under nitrogen. Iron powder (2.92 g) was added in one portion and the reaction mixture stirred at 70° C. for 2.5 hours. The reaction mixture was filtered whilst hot through a bed of celite and the bed washed with DCM. The filtrate was evaporated to dryness and the resulting residue azeotroped three times with toluene. The resultant residue was purified on a Silica column pre-conditioned the column with 50% EtOAc in isohexane, loading as a solution in DCM to which had been added celite and the resultant mixture filtered through a small bed of celite. The column was eluted with a 50%-100% EtOAc in isohexane, gradient. Product containing fractions were combined and evaporated to yield the title compound as a white solid (2.96 g, 57%)

$^1$H NMR (400.13 MHz, CDCl$_3$) δ 1.13 (6H, d), 1.19 (6H, s), 3.21 (2H, s), 5.23-5.30 (1H, m), 7.75 (1H, s), 8.39 (1H, s); MS m/z 269 [M+H]+.

Intermediate 180

4-amino-5-chloro-N-(4-dimethylaminocyclohexyl)-2-fluoro-benzamide

To a stirred solution of the Name (Intermediate 181; 10 g; 53.4 mmol)) in acetone (250 mL) at room temperature was added potassium carbonate (11.07 g, 80.1 mmol) followed by the 2,4-dichloro-5-nitropyrimidine (Apollo Scientific; 10.35 g, 53.4 mmol). The resulting yellow suspension was stirred vigorously at room temperature over the weekend.

The reaction mixture was evaporated to dryness and the residue partitioned between EtOAc (250 mL) and water (150 mL). The phases were separated after filtration through a pad of celite, and the aqueous phase was re-extracted with EtOAc (2×100 mL, 1×75 mL). The combined organic extracts were dried using MgSO$_4$ and evaporated to dryness. The resultant brown oil was purified on a silica column pre-conditioned with 10% EtOAc in isohexane and eluted with 10% EtOAc in isohexane. Product containing fractions were combined and evaporated to yield the title compound as a yellow crystalline solid (6.71 g, 36%)

MS m/z 350 [M+H]+. Retention time 2.72 minutes

Intermediate 181 ethyl2,2-dimethyl-3-(propan-2-ylamino)propanoate

To a stirred solution of ethyl, 3-amino-2,2-dimethylpropanoate (Macromolecules (1976), 9(2), 227-30; 30.85 g, 150.3 mmol) in DCM (500 mL) under nitrogen at room temperature was added acetone (13.25 mL, 180.36 mmol). After stirring at room temperature for 1 hour sodium acetate (12.57 g, 153.31 mmol) was added, followed by sodium triacetoxyborohydride (47.8 g, 225.45 mmol). The resulting suspension was stirred at room temperature overnight.

Acetone (7 mL, 90 mmol), sodium acetate (7 g, 75 mmol) and sodium triacetoxyborohydride (24 g, 112 mmol) were added and the reaction stirred again at room temperature overnight. This procedure of adding additional reagents was repeated.

A saturated aqueous sodium hydrogen carbonate (1.1 L) was cautiously added to the stirred reaction mixture followed by 2N sodium hydroxide to pH=8. The phases were separated and the aqueous phased re-extracted with DCM (2×500, 1×400 ml). The combined organic extracts were dried using MgSO$_4$ and then evaporated at no less than 350 mbar! This afforded the title compound as a clear almost-colourless liquid (27.50 g, 98%)

$^1$H NMR (400.13 MHz, CDCl$_3$) δ 1.02 (6H, d), 1.18 (6H, s), 1.24 (3H, t), 2.65 (2H, s), 4.08-4.16 (2H, m).

Intermediate 182

4-amino-2-fluoro-5-methoxy-N-[(3R)-1-methylpyrrolidin-3-yl]benzamide 4-amino-2-fluoro-5-methoxybenzoic acid (Intermediate 183; 500 mg, 2.70 mmol), HATU (1.55 g, 4.05 mmol) and (3R)-1-methylpyrrolidin-3-amine di Hydrochloride (Intermediate 184; 631 mg, 3.31 mmol) were stirred in DMF (7.5 mL) and diisopropylethylamine (2.36 ml, 13.50 mmol) added. The reaction mixture was stirred for 2 hours and then absorbed on to an SCX column, which was then washed with methanol and eluted with ammonia in methanol. Product containing fractions were concentrated and purified by column chromatography (2.5% ammonia in methanol/DCM) to yield the title compound as a viscous brown oil. (662 mg, 92%).

$^1$H NMR (399.9 MHz, DMSO-d$_6$) δ1.62-1.70 (1H, m), 2.11-2.20 (1H, m), 2.25 (3H, s), 2.32-2.46 (2H, m), 2.54-2.67 (2H, m), 3.78 (3H, s), 4.34-4.39 (1H, m), 5.57 (2H, s), 6.39 (1H, d), 7.07 (1H, d), 7.51 (1H, t); MS m/z 268 [M+H]+.

Intermediate 183

4-amino-2-fluoro-5-methoxy-benzoic acid 2-fluoro-5-methoxy-4-nitrobenzoic acid (Intermediate 12; 7.76 g, 36.1 mmol) was stirred and dissolved in ethanol (200 mL) over 5% Pd/C (770 mg) and hydrogenated at ambient temperature for 4 hours. During this time product precipitated in the reaction. DMF (20 mL) was added to give a solution. The catalyst was filtered off and washed with EtOH and the solvent evaporated. The residue was triturated with diethyl ether to yield the title compound as a dark brown solid (3.06 g, 46%)

¹H NMR (400.132 MHz, DMSO-d6) δ 3.78 (s, 3H), 5.84 (bs, 2H), 6.37 (d, 1H), 7.14 (d, 1H), 12.25 (bs, 1H).

Intermediate 184

(3R)-1-methylpyrrolidin-3-amine di Hydrochloride tert-butyl N-[(3R)-1-methylpyrrolidin-3-yl]carbamate (Intermediate 185; 1.18 g, 5.67 mmol) was dissolved in 1,4-dioxane (10 mL) and 4M HCl in dioxane (10 mL) added. The mixture was stirred at room temperature for 1 hour and then concentrated to yield the title compound as a white hygroscopic solid (810 mg, 100%).
¹H NMR (399.9 MHz, D$_2$O) 2.19-2.29 (1H, m), 2.60-2.71 (1H, m), 3.10 (3H, M), 3.48-3.67 (3H, m), 3.85-3.93 (1H, m), 4.18-4.26 (1H, m).

Intermediate 185 tert-butyl N-[(3R)-1-methylpyrrolidin-3-yl]carbamate (3R)-3-(Bocamino)pyrrolidine (Fluorochem; 2.5 g, 13.42 mmol) was dissolved in 37% aqueous formaldehyde (78 mL) and acetic acid (8.5 mL, 134.23 mmol). Sodium acetate (11.0 g, 134.23 mmol) was added and the mixture cooled in an ice/water bath. Sodium cyanoborohydride (844 mg, 13.42 mmol) was added and the mixture allowed to stir for 3 hours. Saturated aqueous sodium hydrogen carbonate was added until the mixture was basic. The mixture was extracted with DCM (×2) and the combined extracts dried (MgSO$_4$) and concentrated. Column chromatography (2.5-5% 7N ammonia in methanol) yielded the title compound as a colourless liquid that crystallised on standing (1.20 g, 45%).
¹H NMR (399.9 MHz, DMSO-d$_6$) δ1.38 (9H, s), 1.51-1.59 (1H, m), 1.97-2.06 (1H, m), 2.20 (4H, m), 2.34-2.47 (2H, m), 2.61-2.65 (1H, m), 3.89 (1H, m), 6.90 (1H, d).

Intermediate 186

4-amino-5-ethoxy-2-fluoro-N-[(3R)-1-methylpyrrolidin-3-yl]benzamide

The title compound was prepared by an analogous method to the preparation of Intermediate 169, on a 0.5 mmol scale, utilising (3R)-1-methylpyrrolidin-3-amine dihydrochloride (Intermediate 184; 129 mg, 0.75 mmol), as a white solid (95 mg, 68%).
¹H NMR (399.9 MHz, DMSO-d$_6$) δ 1.35 (3H, t), 1.62-1.70 (1H, m), 2.13-2.18 (1H, m), 2.25 (3H, s), 2.32-2.46 (2H, m), 2.59-2.68 (2H, m), 4.00 (2H, q), 4.30-4.38 (1H, m), 5.53 (2H, s), 6.40 (1H, d), 7.06 (1H, d), 7.50 (1H, t); MS m/z 282 [M+H]+.

Intermediate 187

4-amino-3-methoxy-N-(1-methylpyrrolidin-3-yl) benzamide

A solution of 3-methoxy-N-[(3R)-1-methylpyrrolidin-3-yl]-4-nitro-benzamide (Intermediate 188; 227 mg, 0.81 mmol) in methanol (25 mL) was hydrogenated using 10% Pd/C catalyst. Catalyst was filtered off and solvent evaporated to yield the title compound as a yellow gum (200 mg, 100%).
¹H NMR (399.9 MHz, DMSO-d$_6$) δ1.76 (1H, m), 2.12 (1H, m), 2.28 (3H, s), 2.41 (2H, m), 2.61 (1H, m), 2.69 (1H, m), 3.80 (3H, s), 4.36 (1H, m), 5.18 (2H, s), 6.60 (1H, d), 7.29 (1H, s), 7.31 (1H, s), 7.99 (1H, d); MS m/z 250 [M+H]+.

Intermediate 188

3-methoxy-N-[(3R)-1-methylpyrrolidin-3-yl]-4-nitro-benzamide 3-methoxy-4-nitro-benzoyl chloride (Intermediate 189; 374 mg, 1.73 mmol) was dissolved in DCM (20 mL) and N,N-diisopropylethylamine (0.96 mL, 5.54 mmol) added. The mixture was cooled in an ice/water bath and (3R)-1-methylpyrrolidin-3-amine dihydrochloride (Intermediate 184; 300 mg, 1.73 mmol) in DCM (10 mL) added dropwise. The mixture was allowed to warm to room temperature and stirred for 0.5 hour. The mixture was washed with brine, 2N NaOH$_{(aq)}$, dried with MgSO$_4$ and evaporated to yield the title compound as a brown solid (227 mg, 46.9%).
¹H NMR (399.9 MHz, DMSO-d$_6$) δ1.78 (1H, m), 2.19 (2H, s), 2.26 (3H, s), 2.38 (1H, m), 2.65 (1H, m), 4.05 (3H, s), 4.41 (1H, m), 7.57 (1H, d), 7.72 (1H, s), 7.93 (1H, d), 8.70 (1H, d); MS m/z 280 [M+H]+.

Intermediate 189

3-methoxy-4-nitro-benzoyl chloride 3-methoxy-4-nitrobenzoic acid (Aldrich; 9 g, 45.65 mmol) was suspended in toluene (90 mL) and thionyl chloride (9.99 mL, 136.95 mmol) added and the mixture heated to reflux for 1 hour. The reaction was evaporated to yield the title compound as a brown solid (9.84 g, 100%).
¹H NMR (399.9 MHz, DMSO-d6) δ4.00 (3H, s), 7.64-7.67 (1H, m), 7.78 (1H, d), 7.97 (1H, m).

Intermediate 190

4-amino-N-(1-ethyl-4-piperidyl)-3-methoxy-benzamide

The title compound was prepared in quantitative yield by an analogous method to the preparation of Intermediate 187, on a 2 g scale utilising N-(1-ethyl-4-piperidyl)-3-methoxy-4-nitro-benzamide (Intermediate 191).
¹H NMR (399.9 MHz, DMSO-d$_6$) δ0.99-1.02 (3H, t), 1.49-1.59 (2H, m), 1.75 (2H, d), 1.92 (2H, t), 2.32 (2H, q), 2.87 (2H, d), 3.68-3.76 (1H, m), 3.81 (3H, s), 5.19 (2H, s), 6.59-6.62 (1H, m), 7.28-7.30 (2H, m), 7.77 (1H, d); MS m/z 280 [M+H]+.

Intermediate 191

N-(1-ethyl-4-piperidyl)-3-methoxy-4-nitro-benzamide

The title compound was prepared by an analogous method to the preparation of Intermediate 188, on a 9.28 mmol scale utilising 1-ethylpiperidin-4-amine (Fluorochem; 1.19 g, 9.28 mmol), as a brown solid (3.3 g, 100%)
¹H NMR (399.9 MHz, DMSO-d$_6$) δ1.01 (3H, t), 1.56-1.63 (2H, m), 1.82 (2H, m), 1.92-1.98 (2H, m), 2.34 (2H, q), 2.89 (2H, d), 3.75-3.79 (1H, m), 4.00 (3H, s), 7.54-7.57 (1H, m), 7.70 (1H, d), 7.96 (1H, d), 8.49 (1H, d); MS m/z 308 [M+H]+.

Intermediate 192

4-amino-3-methoxy-N-(2-pyrrolidin-1-ylethyl)benzamide

The title compound was prepared in quantitative yield by an analogous method to the preparation of Intermediate 187, on a 2 g scale utilising 3-methoxy-4-nitro-N-(2-pyrrolidin-1-ylethyl)benzamide (Intermediate 193).

$^1$H NMR (399.9 MHz, DMSO-d$_6$) δ1.68 (4H, t), 2.49 (4H, s), 2.55 (2H, t), 3.36 (2H, d), 3.81 (3H, s), 5.20 (2H, s), 6.59-6.62 (1H, m), 7.26-7.29 (1H, m), 7.31 (1H, s), 8.00 (1H, s); MS m/z 280 [M+H]+.

Intermediate 193

3-methoxy-4-nitro-N-(2-pyrrolidin-1-ylethyl)benzamide

The title compound was prepared by an analogous method to the preparation of Intermediate 188, on a 9.28 mmol scale utilising 2-pyrrolidin-1-ylethanamine (Aldrich; 1.06 g, 9.28 mmol), as a brown solid (2.3 g, 85%)

$^1$H NMR (399.9 MHz, DMSO-d$_6$) δ1.67-1.72 (4H, m), 2.47-2.54 (4H, m), 2.60 (2H, t), 3.39-3.44 (2H, m), 3.99 (3H, s), 7.54-7.56 (1H, m), 7.72 (1H, d), 7.96 (1H, d), 8.71 (1H, t); MS m/z 294 [M+H]+.

Intermediate 194

4-amino-N-(2-dimethylaminoethyl)-3-methoxy-benzamide

The title compound was prepared in quantitative yield by an analogous method to the preparation of Intermediate 187, on a 2 g scale utilising N-(2-dimethylaminoethyl)-3-methoxy-4-nitro-benzamide (Intermediate 195).

$^1$H NMR (399.9 MHz, DMSO-d$_6$) δ2.19 (6H, s), 2.38 (2H, t), 3.38 (2H, m), 3.81 (3H, s), 5.20 (2H, s), 6.61 (1H, d), 7.25-7.28 (1H, m), 7.30 (1H, s), 7.96 (1H, t); MS m/z 238 [M+H]+.

Intermediate 195

N-(2-dimethylaminoethyl)-3-methoxy-4-nitro-benzamide

The title compound was prepared by an analogous method to the preparation of Intermediate 188, on a 9.28 mmol scale utilising N,N-dimethylethane-1,2-diamine (Aldrich; 818 mg, 9.28 mmol), as a brown solid (2.5 g, 100%)

$^1$H NMR (399.9 MHz, DMSO-d$_6$) δ 2.24 (6H, s), 2.47-2.49 (2H, m), 3.37-3.41 (2H, m), 4.00 (3H, s), 7.55-7.57 (1H, m), 7.74 (1H, d), 7.96 (1H, d), 8.73 (1H, t); MS m/z 268 [M+H]+.

Intermediate 196

4-amino-N-(3-dimethylaminopropyl)-3-methoxy-benzamide

The title compound was prepared in quantitative yield by an analogous method to the preparation of Intermediate 187, on a 2 g scale utilising N-(2-dimethylaminoethyl)-3-methoxy-4-nitro-benzamide (Intermediate 197).

$^1$H NMR (399.9 MHz, DMSO-d$_6$) δ1.60-1.67 (2H, m), 2.14 (6H, s), 2.25 (2H, t), 3.21-3.26 (2H, m), 3.81 (3H, s), 5.19 (2H, s), 6.61 (1H, d), 7.25-7.30 (2H, m), 8.09 (1H, t); MS m/z 252 [M+H]+.

Intermediate 197

N-(3-dimethylaminopropyl)-3-methoxy-4-nitro-benzamide

The title compound was prepared by an analogous method to the preparation of Intermediate 188, on a 9.28 mmol scale utilising N,N-dimethylpropane-1,3-diamine (Aldrich; 948 mg, 9.28 mmol), as a brown solid (2.33 g, 90%)

$^1$H NMR (399.9 MHz, DMSO-d$_6$) δ1.65-1.72 (2H, m), 2.16 (6H, s), 2.29 (2H, t), 3.34 (2H, m), 4.00 (3H, s), 7.53-7.56 (1H, m), 7.72 (1H, d), 7.96 (1H, d), 8.77 (1H, t); MS m/z 282 [M+H]+.

Intermediate 198

10-chloro-4,4-diethyl-6-methyl-2-propan-2-yl-2,6,9,11-tetrazabicyclo[5.4.0]undeca-7,9,11-trien-5-one To a stirred solution of 10-chloro-4,4-diethyl-2-propan-2-yl-2,6,9,11-tetrazabicyclo[5.4.0]undeca-7,9,11-trien-5-one (Intermediate 197; 2.7 g, 9.1 mmol) in DMA (50 mL) under nitrogen was added methyl iodide (0.627 mL, 10.0 mmol). The mixture was cooled on an ice/water bath to 3° C., and sodium hydride (60% mineral oil dispersion; 0.567 g, 11.8 mmol) added in one portion. The reaction was stirred overnight. The reaction was evaporated to dryness to afford a yellow solid, this was quenched with saturated NH$_4$Cl$_{(aq)}$ (50 mL), extracted with DCM (3×100 mL), dried (MgSO$_4$) and evaporated to yield a yellow solid. This was dissolved in a minimum amount of DCM, diethyl ether was added and the system was sonicated to afford an off white solid. (2.24 g, 80%)

$^1$H NMR (400.132 MHz, CDCl3) δ 0.84 (t, 6H), 1.20 (d, 6H), 1.68-1.50 (m, 4H), 3.27 (s, 3H), 3.41 (s, 2H), 5.31 (septet, 1H), 7.83 (s, 1H); MS m/z 311 [M+H]+.

Intermediate 199

10-chloro-4,4-diethyl-2-propan-2-yl-2,6,9,11-tetrazabicyclo[5.4.0]undeca-7,9,11-trien-5-one To a solution of 2,4-dichloro-5-nitropyrimidine (Aldrich; 5.1 g, 26.4 mmol) and K$_2$CO$_3$ (4.4 g, 31.6 mmol) in acetone (150 mL) was slowly added methyl2-ethyl-2-[(propan-2-ylamino)methyl]butanoate (Intermediate 200; 5.3 g, 26.4 mmol) in acetone (30 mL). The mixture was stirred at room temperature for 18 hours. The reaction was filtered and the solvent evaporated. The residue and iron (4.4 g, 79.2 mmol) were added to acetic acid (175 mL) and heated at 80° C. overnight. The resulting solution was filtered and the solvent evaporated and the residue quenched with 2.0 N NaOH$_{(aq)}$ (75 mL), to the resultant emulsion, was added 10% MeOH/DCM (100 ml) and the suspension filtered through a pad of celite. The obtained filtrate was extracted with 10% MeOH/DCM (3×150 mL, dried and the solvent removed. The resultant material was dissolved in DCM and filtered. Acetonitrile was added to the DCM and the DCM was slowly removed in vacuo to give a precipitate, which was filtered and dried to yield the title compound as a white solid. (3.1 g, 33%)

¹H NMR (400.132 MHz, CDCl3) δ 0.90 (t, 6H), 1.21 (d, 6H), 1.68-1.60 (m, 4H), 3.35 (s, 2H), 5.36 (septet, 1H), 7.83 (s, 1H), 8.65 (brs, 1H); MS m/z 297 [M+H]+.

Intermediate 200 methyl2-ethyl-2-[(propan-2-ylamino)methyl]butanoate

Methyl2-(aminomethyl)-2-ethyl-butanoate (Intermediate 201; 8 g, 50 mmol) and acetone (4.35 g, 75 mmol) were added to methanol (230 mL) and stirred for 10 minutes before the rapid addition of sodium triacetoxyborohydride (15.9 g, 75 mmol). The reaction was stirred overnight before being evaporated to dryness. The residue was quenched with saturated $K_2CO_{3(aq)}$ (100 mL), extracted with DCM (3×150 mL), dried and solvent evaporated to yield a dark liquids. Purification was achieved via distillation (65 oC @ 0.18 mbar) to yield the title compound as clear oil (5.3 g, 53%)
¹H NMR (400.132 MHz, CDCl₃) δ 0.79 (t, 6H), 1.02-0.98 (m, 7H), 1.62 (q, 4H), 2.74-2.67 (m, 3H), 3.67 (s, 3H)

Intermediate 201 methyl2-(aminomethyl)-2-ethyl-butanoate

Methylcyanoacetate (Aldrich; 20 g, 0.201 mol) was dissolved in THF (250 mL), to this was added DBU (75 mL, 0.505 mol) and ethyl bromide (40 mL, 0.606 mol). The reaction was stirred at 50° C. for 2 hours before being cooled and quenched with sat $NH_4Cl_{(aq)}$. The organic layer was separated and the remaining aqueous was extracted with diethyl ether (2×100 mL), dried and solvent removed in vacuo to yield yellow oil. Purification was achieved via distillation at 70° C. at 0.5 mbar to afford methyl2-cyano-2-ethyl-butanoate as a clear oil (20 g, 0.129 mol) which was reduced with hydrogen under pressure using Raney nickel catalyst (2 g). The reaction mixture was filtered and solvent evaporated to the title compound as a slightly dark oil. (16 g, 50%).

Intermediate 202

4-amino-3-methoxy-N-[(1S,5R)-9-methyl-9-azabicyclo[3.3.1]non-3-yl]benzamide

The title compound was prepared in quantitative yield by an analogous method to the preparation of Intermediate 187, on a 2 g scale utilising (Intermediate 203).
¹H NMR (399.9 MHz, DMSO-d₆) δ 0.92 (2H, d), 1.39-1.46 (3H, m), 1.88-1.95 (1H, m), 1.92 (1H, d), 2.06 (1H, s), 2.12-2.20 (2H, m), 2.41 (3H, s), 2.97 (2H, d), 3.82 (3H, s), 4.30 (1H, d), 5.18 (2H, s), 6.61 (1H, d), 7.29-7.31 (2H, m), 7.63 (1H, d); MS m/z 304 [M+H]+.

Intermediate 203

3-methoxy-N-[(1S,5R)-9-methyl-9-azabicyclo[3.3.1]non-3-yl]-4-nitro-benzamide

The title compound was prepared by an analogous method to the preparation of Intermediate 188, on a 9.28 mmol scale utilising Endo-9-methyl-9-azabicyclo[3,3,1]-nonan-3-amine (Chempacific; 1.435 g, 9.28 mmol), as a brown solid (1.6 g, 52%)
¹H NMR (399.9 MHz, DMSO-d₆) δ 0.93 (2H, d), 1.45 (3H, m), 1.89-1.95 (1H, m), 1.94 (1H, d), 2.03 (1H, t), 2.18-2.23 (2H, m), 2.42 (3H, s), 3.00 (2H, d), 4.00 (3H, d), 4.31-4.35 (1H, m), 7.56-7.59 (1H, m), 7.72 (1H, d), 7.96 (1H, d), 8.37 (1H, d); MS m/z 332 [M–H]+.

Intermediate 204

4-amino-2-fluoro-5-methoxy-N-[(1S,5R)-9-methyl-9-azabicyclo[3.3.1]non-7-yl]benzamide 4-amino-2-fluoro-5-methoxybenzoic acid (Intermediate 183; 0.75 g, 4.07 mmol), HATU (1.70 g, 4.48 mmol) and DIPEA (2.1 mL, 12.21 mmol) were stirred together in DMF (10 mL) for 10 minutes. Endo-9-methyl-9-azabicyclo[3,3,1]-nonan-3-amine (Chempacific; 0.69 g, 4.48 mmol) in DMF (1 mL) was added and the brown solution stirred at ambient temperature for 2 hours. The solvent was evaporated and the residue dissolved in MeOH and loaded onto an SCX-2 (20 g) column pre-wet with MeOH. The column was washed with MeOH (2 column volumes) and the product eluted with 2M NH3/MeOH (2 column volumes). Product containing fractions were combined and evaporated and the resultant material purified on a silica column eluting with 0-10% 2M NH3/MeOH/DCM). Product containing fractions were combined and evaporated to yield the title compound as a dark brown gum (897 mg, 69%).
¹H NMR (400.132 MHz, DMSO-d6) δ 0.91 (m, 2H), 1.39 (m, 3H), 2.04 (m, 5H), 2.40 (s, 3H), 2.96 (m, 2H), 3.78 (s, 3H), 4.27 (m, 1H), 5.53 (s, 2H), 6.39 (d, 1H), 7.06 (d, 1H), 7.24 (m, 1H); MS m/z 322 [M+H]+.

Intermediate 205

4-amino-N-(1-ethyl-4-piperidyl)-2-fluoro-5-methoxy-benzamide

The title compound was prepared by an analogous method to the preparation of Intermediate 188, on a 5.43 mmol scale utilising 1-ethylpiperidin-4-amine (Fluorochem; 0.77 g, 5.97 mmol), as a gum (1.21 g, 76%).
¹H NMR (400.132 MHz, DMSO-d6) δ 0.99 (t, 3H), 1.52 (m, 2H), 1.78 (m, 2H), 1.97 (m, 2H), 2.31 (q, 2H), 2.80 (m, 2H), 3.72 (m, 1H), 3.77 (s, 3H), 5.54 (bs, 2H), 6.39 (d, 1H), 7.05 (d, 1H), 7.33 (m, 1H); MS m/z 296 [M+H]+.

Intermediate 206

4-amino-N-(2,2-dimethyl-3-pyrrolidin-1-yl-propyl)-3-methoxy-benzamide

A mixture of the 4-amino-3-methoxy-benzoic acid (Aldrich; 2 g, 12 mmol) and 2,2-dimethyl-3-pyrrolidin-1-yl-propan-1-amine (WO 2004033419; 2.1 g, 13.2 mmol) were dissolved in DMF (50 mL), and to the solution was added DIPEA (3.1 g, 4.2 mL). The reaction was cooled with an ice-bath, and to it was added, portionwise, HATU (5.02 g, 13.2 mmol). The reaction mixture was stirred at ambient temperature for 18 hours. The solvent was evaporated, and the residue was partitioned between Ethyl Acetate (100 mL), and saturated aqueous sodium carbonate solution (3×40 mL), washed with brine (3×40 mL), dried over anhydrous Magnesium sulphate, filtered, and the solvent evaporated. The residue was purified by chromatography on a silica column pre-conditioned with Ethyl acetate and eluted with 10% MeOH-DCM+1% NH3. Those fractions containing the desired product were combined and the solvent was evaporated to yield the title compound as a pale brown gum, which crystallised on standing. (500 mgs; 14%).

¹H NMR (400.132 MHz, CDCl3): δ 1.00 (6H, s), 1.75-1.85 (4H, m), 2.55 (2H, s), 2.63-2.75 (4H, m), 3.35-3.39 (2H, d), 3.90 (3H, s), 6.61-6.65 (1H, d), 7.06-7.11 (1H, d), 7.47 (1H, s), 9.05 (1H, bs). MS m/z 306 [M+H]+.

Intermediate 207

4-amino-5-chloro-2-fluoro-N-[(3R)-1-methylpyrrolidin-3-yl]benzamide 4-amino-5-chloro-2-fluorobenzoic acid (Intermediate 176; 300 mg, 1.58 mmol), HATU (903 mg, 2.37 mmol) and (3R)-1-methylpyrrolidin-3-amine di Hydrochloride (Intermediate 184; 325 mg, 2.37 mmol) were stirred in DMF (5 mL) and diisopropylethylamine (1.2 mL, 7.12 mmol) added. The mixture was stirred for 2 hours at room temperature and then absorbed on to an SCX column, washed with methanol and eluted with ammonia in methanol. Product containing fractions were concentrated and purified by column chromatography (5% ammonia in methanol/DCM) to yield the title compound as a pale orange solid (333 mg, 77%).
¹H NMR (399.9 MHz, DMSO-d6) δ1.63-1.71 (1H, m), 2.09-2.18 (1H, m), 2.25 (3H, s), 2.33-2.41 (2H, m), 2.55-2.61 (1H, m), 2.64-2.69 (1H, m), 4.30-4.35 (1H, m), 6.10 (2H, s), 6.55 (1H, d), 7.50 (1H, d), 7.76-7.79 (1H, m)

Intermediate 208

2'-chloro-9'-isopropyl-5'-methyl-8',9'-dihydrospiro[cyclopropane-1,7'-pyrimido[5,4-b][1,4]diazepin]-6'(5'H)-one To a solution of 2'-chloro-9'-isopropyl-8',9'-dihydrospiro[cyclopropane-1,7'-pyrimido[5,4-b][1,4]diazepin]-6'(5'H)-one (Intermediate 209; 5.055 g, 19 mmol) in DMA (300 mL) was added methyl iodide (1.305 mL, 20.9 mmol), followed by sodium hydride (60% mineral oil dispersion; 814 mg, 20.33 mmol). The mixture was stirred at room temperature for 30 minutes. The DMA was removed in vacuo, then water (50 mL) was added. The product precipitated as a sticky gum, which turned into a solid on sonication. The solid was collected by filtration to give a brown powder. This material was dissolved in DCM and dried over sodium sulfate, then purified by column chromatography, eluting with 25% ethyl acetate in hexane, to yield the title compound as a white solid (3.73 g, 70%)
¹H NMR (400.13 MHz, CDCl₃) δ 0.63-0.66 (2H, m), 1.11-1.16 (8H, m), 3.26 (3H, s), 3.44 (2H, s), 4.91-4.98 (1H, m), 7.84 (1H, s); MS m/z 281 [M+H]+.

Intermediate 209

2'-chloro-9'-isopropyl-8',9'-dihydrospiro[cyclopropane-1,7'-pyrimido[5,4-b][1,4]diazepin]-6'(5'H)-one Ethyl1-[[(2-chloro-5-nitro-pyrimidin-4-yl)-propan-2-yl-amino]methyl]cyclopropane-1-carboxylate (Intermediate 208; 10.26 g, 30 mmol) was dissolved in acetic acid (500 mL) and heated to 70° C. Iron powder (6 g) was added in portions over 10 minutes. The mixture was stirred at 70° C. for 3 hours. The reaction mixture was filtered hot through celite, and the pad washed with DCM. The filtrate was evaporated to dryness then sonicated in saturated aqueous sodium hydrogen carbonate solution to give a brown suspension. This was filtered, and the resulting solid washed with water. The solid was then sucked dry on a filter, and suspended in a small amount of methanol with sonication. The methanol suspension was then diluted with DCM (10× excess), and filtered to give a yellow solution, which was dried over sodium sulphate, then concentrated in vacuo to give a yellow/green solid. The solid was triturated under cold methanol to yield the title compound as a white powder. (5 g, 63%)
MS m/z 267 [M−H]+. Retention time 1.81 minutes.

Intermediate 210 ethyl1-[[(2-chloro-5-nitro-pyrimidin-4-yl)-propan-2-yl-amino]methyl]cyclopropane-1-carboxylate To a solution of ethyl1-[(propan-2-ylamino)methyl]cyclopropane-1-carboxylate (Intermediate 211; 9.55 g, 50 mmol) in acetone (300 mL) was added potassium carbonate (7.05 g, 51 mmol) followed by 2,4-dichloro-5-nitropyrimidine (Aldrich; 10.675 g, 55 mmol). The mixture was stirred overnight at room temperature, concentrated in vacuo and partitioned between EtOAc and water. The EtOAc layer was separated, dried over sodium sulfate, then purified by column chromatography (EtOAc/isohexane 10:90), to yield the title compound as a yellow oil. (11 g, 64%)
¹H NMR (400.13 MHz, CDCl3) δ 0.75-0.78 (2H, m), 0.96 (3H, t), 1.10-1.14 (8H, m), 3.42-3.48 (1H, m), 3.59 (2H, s), 3.87-3.93 (2H, m), 8.48 (1H, s); MS m/z 343 [M+H]+.

Intermediate 211 ethyl1-[(propan-2-ylamino)methyl]cyclopropane-1-carboxylate

To a solution of ethyl1-(aminomethyl)cyclopropane-1-carboxylate (Intermediate 114; 20.65 g, 250 mmol) in DCM (200 mL) was added acetone (3.74 mL, 51 mmol). After stirring at room temperature for 15 minutes, sodium acetate (4.185 g, 51 mmol) was added, followed by sodium triacetoxyborohydride (15.905 g, 75 mmol). The suspension was stirred at room temperature for 2 days then partitioned between DCM and an aqueous solution of saturated sodium hydrogen carbonate. The organic layer was separated, then dried over sodium sulphate evaporated to yield the title compound as a clear oil (9.2 g, 100%).
¹H NMR (400.13 MHz, CDCl3) δ 0.60-0.63 (2H, m), 0.86 (6H, d), 1.02-1.09 (5H, m), 1.69 (1H, br s), 2.50 (2H, s), 2.58-2.64 (1H, m), 3.93 (2H, q).

Intermediate 212

4-amino-3-chloro-N-(1-ethyl-4-piperidyl)benzamide

To a mixture of 4-amino-3-chloro-benzoic acid (Fluorochem; 2.575 g, 15 mmol) and 1-ethylpiperidin-4-amine (Fluorochem; 2.12 g, 16.5 mmol) in DMF (50 mL), was added DIPEA (5.2 mL, 30 mmol). The mixture was cooled with an ice-bath. HATU (6.27 g), added and the reaction mixture stirred at ambient temperature for 18 hours. The solvent was evaporated and the residue partitioned between saturated aqueous sodium bicarbonate solution (100 mL), and Ethyl Acetate (4×50 mL). The organic extracts were washed with brine (2×75 ml), dried over anhydrous Magnesium sulphate, filtered, and the solvent evaporated to give the crude product as a gum, which was triturated with ether to yield the title compound as a tan solid (3.54 g, 84%).
¹H NMR; 400.1 MHz (DMSO-d6) δ 1.20-1.26 (3H, t), 1.65-1.85 (2H, bm), 1.92-2.10 (2H, bm), 2.90-3.20 (4H, m), 3.30 (3H, s), 3.40-3.60 (2H, bm), 3.90-4.05 (1H, m), 5.98

(2H, s), 6.77-6.81 (1H, d), 7.554-7.60 (1H, dd), 7.88 (1H, s), 8.10 (1H, bs); MS m/z 282 [M+H]+.

Intermediate 213

4-amino-3-chloro-N-(2-dimethylaminoethyl)benzamide

The title compound was prepared by an analogous method to the preparation of Intermediate 212, on a 15 mmol scale utilising 2,2-Dimethyaminoethylamine (Aldrich; 1.455 g, 16.5 mmol), as a white solid (1.45 g, 40%).
$^1$H NMR; 400.1 MHz (DMSO-d6) δ 2.83 (6H, s), 3.18-3.24 (2H, t), 3.50-3.58 (2H, quartet), 5.95 (2H, s), 6.80-6.83 (1H, d), 7.55-7.60 (1H, d), 7.76 (1H, s), 8.30-8.38 (1H, t); MS m/z 242 [M+H]+.

Intermediate 214

4-amino-3-chloro-N-(3-dimethylaminopropyl)benzamide

The title compound was prepared by an analogous method to the preparation of Intermediate 212, on a 15 mmol scale utilising 3-Dimethylamino-1-propylamine (Aldrich; 1.685 g, 16.5 mmol), as a tan coloured solid (3.25 g, 85%).
$^1$H NMR 400.1 MHz, (DMSO-d6) δ 1.80-1.90 (2H, m), 2.77 (6H, s), 3.00-3.08 (2H, m), 3.25-3.50 (2H, m), 5.88 (2H, s), 6.78-6.82 (1H, d), 7.53-7.59 (1H, dd), 7.75 (1H, s), 8.24-8.30 (1H, t); MS m/z 256 [M+H]+.

Intermediate 215

4-amino-3-chloro-N-(2-pyrrolidin-1-ylethyl)benzamide

The title compound was prepared by an analogous method to the preparation of Intermediate 212, on a 15 mmol scale utilising 2-pyrrolidin-1-ylethanamine (Aldrich; 1.885 g, 16.5 mmol), as a tan coloured solid (2.67 g, 66%).
$^1$H NMR; 400.1 MHz, (DMSO-d6) δ 1.80-2.05 (4H, m), 3.20-3.45 (6H, m), 3.48-3.58 (2H, q), 5.92 (2H, s), 6.78-6.82 (1H, d), 7.55-7.60 (1H, dd), 7.77 (1H, s), 8.30-8.40 (1H, t); MS m/z 268 [M+H]+.

Intermediate 216

4-amino-2-chloro-5-methoxy-N-(1-methyl-4-piperidyl)benzamide

The title compound was prepared by an analogous method to the preparation of Intermediate 212, on a 3.06 mmol scale utilising 4-amino-2-chloro-5-methoxy-benzoic acid (Intermediate 217; 617 mg, 3.06 mmol) and 1-methylpiperidin-4-amine (Fluorochem; 385 mg, 3.37 mmol), as an off-white solid (845 mg, 93%).
$^1$H NMR (399.902 MHz, CDCl3) δ1.61 (m, 2H), 2.05 (m, 2H), 2.20 (m, 2H), 2.30 (s, 3H), 2.76 (m, 2H), 3.88 (s, 3H), 4.03 (m, 3H), 6.57 (d, 1H), 6.63 (s, 1H), 7.34 (s, 1H); MS m/z 298 [M+H]+.

Intermediate 217

4-amino-2-chloro-5-methoxy-benzoic acid 2-chloro-5-methoxy-4-nitro-benzoic acid (Intermediate 218; 762 mg, 3.8 mmol) was dissolved in EtOH (20 mL) and a catalytic amount of 5% Pt on carbon added under an inert atmosphere. The solution was de-gassed and stirred under an atmosphere of hydrogen at room temperature overnight. The catalyst was filtered off and washed with EtOH and solvent evaporated and the resultant material dried under vacuum to yield the title compound as an off-white solid. (617 mg, 98%)
$^1$H NMR (399.902 MHz, DMSO-d6) δ3.72 (s, 3H), 5.65 (br s, 2H), 6.59 (s, 1H), 7.21 (s, 1H), 12.30 (br s, 1H); MS m/z 201 [M+H]+.

Intermediate 218

2-chloro-5-methoxy-4-nitro-benzoic acid 1-chloro-4-methoxy-2-methyl-5-nitro-benzene (APIN; 1 g, 4.96 mmol) was suspended in water (100 mL), potassium permanganate (3.14 g, 19.84 mmol) was added and the mixture diluted further with water (140 mL). The mixture was very slowed heated up to reflux over a 2 hour period and then stirred at reflux for 4 hours then allowed to cool to room temperature overnight with stirring. After 18 hours the mixture was reheated to 80° C. and filtered hot, the manganese filter cake was washed with boiling water (100 mL), then the aqueous filtrate was treated with a couple of drops of sodium metabisulfite solution and the permanganate colour was removed to give a yellow solution. The solution was acidified to pH 2 with concentrated hydrochloric acid and partially evaporated down to a volume of (200 mL) and extracted with EtOAc (2×100 mL). Combined organic extracts were washed with brine, dried (MgSO4) and evaporated to yield the title compound as a yellow solid. (752 mg, 65%).
$^1$H NMR (399.902 MHz, DMSO-d6) δ3.98 (s, 3H), 7.67 (s, 1H), 8.14 (s, 1H), 14.03 (br s, 1H); MS m/z 229 [M−H]+.

Intermediate 219

5-chloro-4-[(2-cyclopentyl-6-methyl-5-oxo-2,6,9,11-tetrazabicyclo[5.4.0]undeca-7,9,11-trien-10-yl)amino]-2-fluoro-benzoic acid tert-butyl 5-chloro-4-[(2-cyclopentyl-6-methyl-5-oxo-2,6,9,11-tetrazabicyclo[5.4.0]undeca-7,9,11-trien-10-yl)amino]-2-fluoro-benzoate (Intermediate 220; 220 mg, 0.45 mmol) was dissolved in DCM (7.5 mL) and trifluoroacetic acid (2.5 mL) added. The mixture was stirred at room temperature for 2 hours. The refraction mixture was evaporated, the residue dissolved in methanol/DCM and absorbed on to an SCX column, which was subsequently washed with methanol and eluted with ammonia in methanol. Product containing fractions were combined and evaporated to yield the title compound as a white solid (195 mg, 100%).
$^1$H NMR (399.9 MHz, DMSO-d6) δ1.54-1.73 (6H, m), 1.88-1.95 (2H, m), 2.58-2.63 (2H, m), 3.18 (3H, s), 3.61-3.65 (2H, m), 4.74-4.79 (1H, m), 7.70 (2H, brs), 7.70 (1H, d), 8.06-8.11 (2H, m); MS m/z 434 [M+H]+.

Intermediate 220 tert-butyl 5-chloro-4-[(2-cyclopentyl-6-methyl-5-oxo-2,6,9,11-tetrazabicyclo[5.4.0]undeca-7,9,11-trien-10-yl)amino]-2-fluoro-benzoate 4-Amino-5-chloro-2-fluorobenzoic acid tert-butyl ester (Intermediate 177; 123 mg, 0.5 mmol) was dissolved in dioxane (7.5 mL). 10-Chloro-2-cyclopentyl-6-methyl-2,6,9,11-tetrazabicyclo[5.4.0]undeca-8,10,12-trien-5-one (Intermediate 1; 155 mg, 0.55 mmol), XANTPHOS (27 mg, 0.05 mmol) and caesium carbonate (327 mg, 1.0 mmol) were added. The system was purged with a stream of nitrogen for 15 minutes and then tris(dibenzylideneacetone) palladium (II) (28 mg, 0.03 mmol) added. The apparatus was evacuated and backfilled with nitrogen (×3) and then heated at 100° C. for 3 hours. The mixture was cooled, filtered and the filtrate absorbed on to an SCX column, which was subsequently washed with methanol and eluted with ammonia in methanol. Product containing fractions were evaporated and the residue purified by column chromatography (2% MeOH/DCM) to yield the title compound as a pale yellow foam (225 mg, 92%).

$^1$H NMR (399.9 MHz, DMSO-$d_6$) δ1.53-1.74 (15H, m), 1.92-1.95 (2H, m), 2.62 (2H, t), 3.19 (3H, s), 3.65 (2H, t), 4.73-4.84 (1H, m), 7.85 (1H, d), 8.15 (1H, s), 8.24 (1H, s), 8.41 (1H, d); MS m/z 490 [M+H]+.

Intermediate 221

3,5-dichloro-4-[(2-cyclopentyl-6-methyl-5-oxo-2,6,9,11-tetrazabicyclo[5.4.0]undeca-7,9,11-trien-10-yl) amino]-2-fluoro-benzoic acid The title compound was prepared by an analogous method to the preparation of Intermediate 219, utilising tert-butyl 3,5-dichloro-4-[(2-cyclopentyl-6-methyl-5-oxo-2,6,9,11-tetrazabicyclo[5.4.0]undeca-7,9,11-trien-10-yl)amino]-2-fluoro-benzoate (Intermediate 222; 236 mg, 0.45 mmol), as an off-white solid (180 mg, 87%).

$^1$H NMR (399.9 MHz, DMSO-$d_6$+$d_4$ AcOH) 61.30-1.63 (8H, m), 2.55 (2H+DMSO, m), 3.15 (3H, s), 3.51-3.54 (2H, m), 4.31 (1H, m), 7.75 (1H, d), 7.97 (1H, s); MS m/z 468 [M+H]+.

Intermediate 222 tert-butyl 3,5-dichloro-4-[(2-cyclopentyl-6-methyl-5-oxo-2,6,9,11-tetrazabicyclo[5.4.0]undeca-7,9,11-trien-10-yl)amino]-2-fluoro-benzoate The title compound was prepared by an analogous method to the preparation of Intermediate 220, utilising tert-butyl 4-amino-3,5-dichloro-2-fluoro-benzoate (Isolated as a by-product during the preparation of Intermediate 177; 236 mg, 0.45 mmol), as an off-white solid (180 mg, 87%).

$^1$H NMR (399.9 MHz, DMSO-$d_6$) δ1.30-1.63 (17H, m), 2.55 (2H+DMSO-d6, m), 3.16 (3H, s), 3.52-3.54 (2H, m), 4.25 (1H, m), 7.89 (1H, d), 8.00 (1H, s), 9.18 (1H, s); MS m/z 524 [M+H]+.

Intermediate 223

7-amino-N-(1-methyl-4-piperidyl)benzo[1,3]dioxole-4-carboxamide

N-(1-methyl-4-piperidyl)-7-nitro-benzo[1,3]dioxole-4-carboxamide (Intermediate 224; 290 mg, 0.94 mmol) was suspended in methanol (50 mL) and the system purged with nitrogen. 10% Pd/C (30 mg) was added and the mixture stirred under a hydrogen atmosphere for 2 hours. The catalyst was filtered off and the filtrate evaporated to give the title compound as a white solid (249 mg, 96%).

$^1$H NMR (399.9 MHz, DMSO-$d_6$) δ 1.43-1.53 (2H, m), 1.78-1.82 (2H, m), 1.98-2.05 (2H, m), 2.12 (3H, s), 2.67 (2H, d), 3.69-3.73 (1H, m), 5.48 (2H, d), 6.06 (2H, s), 6.32 (1H, d), 6.95 (1H, d), 7.11 (1H, d); MS m/z 278 [M+H]+.

Intermediate 224

N-(1-methyl-4-piperidyl)-7-nitro-benzo[1,3]dioxole-4-carboxamide

4-Amino-1-methylpiperidine (Fluorochem; 325 mg, 2.84 mmol), HATU (1.09 g, 2.84 mmol) and 7-nitrobenzo[1,3]dioxole-4-carboxylic acid (WO 2003082827; 400 mg, 1.89 mmol) were stirred in DMF (5 mL) and diisopropylethylamine (0.99 ml, 5.68 mmol) added. The mixture was stirred for 2 hours at room temperature. The reaction mixture was loaded on to an SCX column, which was subsequently washed with methanol and eluted with ammonia in methanol. Product containing fractions were concentrated and the solid suspended in methanol and filtered off to yield the title compound as a yellow solid (295 mg, 51%).

$^1$H NMR (399.9 MHz, DMSO-$d_6$) δ 1.50-1.60 (2H, m), 1.78-1.82 (2H, m), 1.96-2.03 (2H, m), 2.17 (3H, s), 2.72 (2H, d), 3.72-3.76 (1H, m), 6.42 (2H, s), 7.28 (1H, d), 7.62 (1H, d), 7.94 (1H, d); MS m/z 308 [M+H]+.

Intermediate 225

4-amino-N-(1-ethyl-4-piperidyl)-3-fluoro-benzamide 4-amino-3-fluorobenzoic acid (2.115 g, 13.6 mmol), 4-Amino-1-Ethyl Piperidine (Fluorochem; 1.923 g, 15 mmol), HATU (5.7 g, 15 mmol) and DIPEA (7.1 mL, 40.8 mmol) were combined in DMA (60 mL) and the resulting yellow solution stirred at room temperature for 20 minutes. The reaction was left over the weekend at room temperature, solvent evaporated and the residue dissolved in methanol (10 mL) and loaded onto an SCX-2 column (50 g) which pre-wet with MeOH (40 mL), flushed with MeOH (4×30 ml) and eluted with 7N ammonia in MeOH (4×30 mL). Product containing, ammoniacal fractions were combined to yield the title compound as a brown solid (0.819 g, 22%)

MS m/z 266 [M+H]+. Retention time 1.5 minutes

Intermediate 226

4-(azetidin-1-yl)cyclohexan-1-amine tert-butyl N-[4-(azetidin-1-yl)cyclohexyl]carbamate (Intermediate 227; 260 mg, 1.01 mmol) was taken up in DCM (3 mL) and TFA (2 mL) and stirred at ambient temperature for 3 hours.

The reaction mixture was poured directly onto an SCX-3 cartridge (5 g). The cartridge was washed through with DCM (30 mL), followed by methanol (30 mL) and then eluted with 2M ammonia in methanol (25 mL). Ammoniacal fractions were combined and evaporated to yield the title compound as a colourless oil (124 mg, 80%)

$^1$H NMR (400.132 MHz, CDCl3) δ 1.04 (m, 2H), 1.36-1.56 (m, 4H), 1.80 (m, 2H), 1.87-2.10 (m, 3H), 2.63 & 2.79 (2×m, 1H), 3.16 (m, 4H).

Intermediate 227 tert-butyl N-[4-(azetidin-1-yl)cyclohexyl]carbamate

To a stirred solution of N-4-boc-aminocyclohexanone (500 mg, 2.34 mmol) in DCM (7 mL) was added azetidine (220 ul, 3.26 mmol) and the mixture stirred for 15 minutes. Sodium acetate (193 mg, 2.34 mmol) was added, followed by careful addition of sodium triacetoxyborohydride (746 mg, 3.52 mmol) The reaction mixture was stirred, at ambient temperature, under nitrogen for 3 hours, diluted with DCM to 25 mL total volume and filtered. The filtrate was poured onto and SCX-2 (10 g) cartridge and the cartridge washed with methanol (75 mL) then eluted with 2M ammonia in methanol (75 mL). The ammoniacal solution was evaporated, to give a waxy off white solid (200 mg). The SCX cartridge wash was resubmitted to a second SCX-2 cartridge (10 g) and the cartridge again washed with methanol (75 mL) and eluted with 2M ammonia/methanol (75 mL). The ammoniacal solution was evaporated to a colourless gum. Solid products were combined and triturated with isohexane. The resultant crystalline solid was collected by suction filtration and dried to yield the title compound as a white solid (104 mg). A second crop crystallised from the filtrate. This was again collected and dried to give the title compound as fine white needles (260 mg).

Total yield (364 mg, 61%)

$^1$H NMR (400.132 MHz, DMSO-d6) δ 0.80-0.90 (1H, m), 1.05-1.16 (1H, m), 1.21-1.30 (1H, m), 1.37 (9H, s), 1.41-2.09 (8H, m), 3.01 (4H, q), 3.06-3.26 (1H, m), 6.57-6.66 (1H, m).

Intermediate 228

4-amino-2-fluoro-5-methoxy-N-(2-pyrrolidin-1-yl-ethyl)benzamide 4-amino-2-fluoro-5-methoxybenzoic acid (Intermediate 183; 0.75 g, 4.07 mmol), HATU (1.70 g, 4.48 mmol) and DIPEA (2.1 mL, 12.21 mmol) were stirred together in DMF (10 mL) for 25 mins. N-(2-aminoethyl)pyrrolidine (Aldrich; 0.51 g, 4.48 mmol) in DMF (2 mL) was added and the solution stirred at ambient temp for 2 hours.

The solvent was evaporated and the residue dissolved in MeOH and loaded onto an SCX-2 (20 g) column pre-wet with MeOH. The column was washed with MeOH (2 column volumes) and eluted with 2M NH3/MeOH. Product containing fractions were combined and evaporated to a brown gum, which was purified on a silica column eluting with 0-10% 2M NH3/MeOH/DCM. Product containing fractions were combined and evaporated to yield the title compound as a pale brown solid (948 mg, 83%)

$^1$H NMR (400.132 MHz, DMSO-d6) δ 1.69 (m, 4H), 2.48 (m, 4H), 2.56 (t, 2H), 3.36 (m, 4H), 3.77 (s, 3H), 5.59 (s, 2H), 6.40 (d, 1H), 7.13 (d, 1H), 7.51 (m, 1H); MS m/z 282 [M+H]+.

Intermediate 229

4-amino-2,5-difluoro-N-[(3R)-1-methylpyrrolidin-3-yl]benzamide 4-amino-2,5-difluoro-benzoic acid (Rare Chemicals GmbH; 450 mg, 2.6 mmol), (3R)-1-methylpyrrolidin-3-amine di Hydrochloride (Intermediate 184; 473 mg, 2.73 mmol), HATU (1.08 g 2.86 mmol) and DIPEA (2.25 mL, 13 mmol) were combined in DMF (10 mL) and stirred at room temperature for 4 hours. The solvent was evaporated and the residue dissolved in MeOH and added to an SCX-2 column (20 g), pre-wet with MeOH (2 column volumes). The column was flushed with MeOH (2 column volumes) and eluted with 2M ammonia in MeOH. Product containing fractions were combined and evaporated and the resultant material dissolved in DCM and purified on a silica column eluting with 5% 2M ammonia in MeOH/DCM. Fractions containing product were combined and evaporated to a yellow gum. Diethylether was added and re-evaporated and dried under high vacuum to yield the title compound as a yellow gum, which slowly crystallised to a cream solid (550 mg, 83%)

$^1$H NMR (399.902 MHz, CDCl3) δ1.71 (m, 1H), 2.26-2.42 (m, 5H), 2.64 (m, 2H), 2.86 (m, 1H), 4.13 (s, 2H), 4.62 (m, 1H), 6.43 (m, 1H), 6.87 (m, 1H), 7.70 (m, 1H); MS m/z 256 [M+H]+.

Intermediate 230

4-amino-2,5-difluoro-N-(2-pyrrolidin-1-ylethyl)benzamide

The title compound was prepared by an analogous method to the preparation of Intermediate 229, on a 5.77 mmol scale utilising 2-pyrrolidin-1-ylethanamine (Aldrich; 725 mg, 6.35 mmol), as a beige solid (648 mg, 42%)

$^1$H NMR (399.902 MHz, CDCl3) δ1.78 (m, 4H), 2.56 (m, 4H), 2.69 (m, 2H), 3.55 (m, 2H), 4.12 (s, 2H), 6.43 (m, 1H), 7.16 (m, 1H), 7.72 (m, 1H); MS m/z 270 [M+H]+.

Intermediate 231

2-chloro-4-[(2-cyclopentyl-6-methyl-5-oxo-2,6,9,11-tetrazabicyclo[5.4.0]undeca-7,9,11-trien-10-yl)amino]-5-methoxy-benzoic acid 10-Chloro-2-cyclopentyl-6-methyl-2,6,9,11-tetrazabicyclo[5.4.0]undeca-8,10,12-trien-5-one (Intermediate 1; 1 g, 3.56 mmol) and 2-Chloro-3-Methoxy-4-Amino-benzoic acid (Intermediate 223;) were suspended in a water/EtOH (3:1) mixture (40 mL). Concentrated hydrochloric acid (712 µL, 7.12 mmol) was added and the reaction heated at 80° C. overnight.

The reaction mixture was cooled to room temperature and the resulting solid filtered and dried to give the title compound as a beige solid (951 mg, 60%)

$^1$H NMR (399.902 MHz, DMSO-d6) δ1.61 (m, 6H), 1.91 (m, 2H), 2.63 (m, 2H), 3.10 (s, 3H), 3.66 (m, 2H), 3.88 (s, 3H), 4.86 (m, 1H), 7.42 (s, 1H), 8.12 (s, 1H), 8.35 (s, 1H), 8.91 (br s, 1H), 13.10 (br s, 1H); MS m/z 446 [M+H]+.

Intermediate 232

2-Chloro-3-Methoxy-4-Amino-benzoic acid 2-chloro-5-methoxy-4-nitro-benzoic acid (Intermediate 233; 5.87 g, 26.3 mmol) was dissolved in EtOH (100 mL) and a catalytic amount of 5% Pt on carbon added under an inert atmosphere. The solution was de-gassed and then stirred under an atmosphere of hydrogen at room temperature for 6 hours. The catalyst was filtered off and washed with EtOH and the filtrate evaporated and the residue triturated with diethylether and the solid filtered and dried to yield the title compound as a yellow solid (4.53 g, 89%)

$^1$H NMR (399.902 MHz, DMSO-d6) δ3.80 (s, 3H), 5.73 (s, 2H), 6.67 (s, 1H), 7.29 (s, 1H), 12.42 (s, 1H); MS m/z 201 [M+H]+.

Intermediate 233

2-chloro-5-methoxy-4-nitro-benzoic acid 1-chloro-4-methoxy-2-methyl-5-nitro-benzene (APIN Chemicals; 12.58 g, 62.4 mmol) was suspended in water (600 mL) and heated to 90° C. under nitrogen. Potassium permanganate (2 eq, 19.74 g, 125 mmol) in water (500 mL) was added over a period of 25 minutes and then the mixture was heated at reflux for 2 hours. A further addition of potassium permanganate (19.74 g, 125 mmol) in water (500 mL) was made over 15 minutes with the reaction temperature reduced to 91° C. and then heating continued at reflux for 3 hours and then cooled to room temperature and allowed to stand overnight.

The reaction was re-heated to reflux and further addition of potassium permanganate (9.86 g 62.5 mmol) in water (200 mL) made over 5 minutes and the reaction heated at reflux for 2 hours for a further 2 hours.

The reaction mixture was cooled to 80° C. and filtered hot through a pad of celite. The reactor vessel was washed with water (500 mL) and the Manganese filter cake was washed with boiling water (1200 mL). The combined aqueous washings were cooled to room temperature and any excess permanganate colour was removed by the addition of aqueous sodium metabisulfite solution. The resulting yellow solution was acidified to pH 1 with concentrated aqueous hydrochloric acid and the volume reduced from approximately 4000 mL to 3000 mL in vacuo. The aqueous layer was extracted with EtOAc (2×1000 mL) and the combined organic extracts washed with brine (500 mL), dried over MgSO$_4$ and evaporated to yield the title compound as a yellow solid. (8.45 g, 58%)

$^1$H NMR (399.902 MHz, DMSO-d6) δ 3.98 (s, 3H), 7.67 (s, 1H), 8.14 (s, 1H), 14.02 (br s, 1H); MS m/z 229 [M−H]$^+$.

Intermediate 234 tert-butyl 4-[(4-amino-3-methoxy-benzoyl)amino]piperidine-1-carboxylate

To a solution of 4-amino-3-methoxybenzoic acid (Aldrich; 2.4 g, 14.36 mmol) in DMF (100 mL) was added 4-amino-1-bocpiperidine (Aldrich; 3.15 g, 15.72 mmol) and DIPEA (7.5 mL, 43.06 mmol). The resultant solution was carefully treated portionwise (2-3 portions) with HATU (6.88 g, 18.09 mmol) and the resultant mixture was stirred, under nitrogen, at ambient temperature overnight.

The solvent was removed in vacuo and the residue partitioned between saturated aqueous sodium bicarbonate solution (100 mL) and ethyl acetate (100 mL). The organic phase was separated and washed with water (150 mL) and brine (150 mL), dried over magnesium sulphate, filtered and evaporated. The residue was purified by flash chromatography on a silica cartridge eluting with a rising gradient of 0-10% Methanol in DCM. Product containing fractions were combined and evaporated to yield the title compound as a peach coloured foam (2.88 g, 57%)

1H NMR (400.132 MHz, DMSO) δ 1.35-1.47 (11H, m), 1.72-1.80 (2H, m), 2.76-2.90 (2H, m), 3.81 (3H, s), 3.91-4.00 (3H, m), 5.20 (2H, s), 6.61 (1H, d), 7.28-7.30 (2H, m), 7.80 (1H, d); MS m/z 348 [M−H]$^+$.

Intermediate 235

4-amino-N-(1-ethyl-4-piperidyl)-2,5-difluoro-benzamide

The title compound was prepared by an analogous method to the preparation of Intermediate 229, on a 5.77 mmol scale utilising 4-amino-1-ethylpiperidine (Fluorochem; 815 mg, 6.35 mmol), as an orange solid (1.23 g, 75%)

$^1$H NMR (399.902 MHz, CDCl3) δ1.09 (t, 3H), 1.57 (m, 2H), 2.04 (m, 2H), 2.14 (m, 2H), 2.42 (q, 2H), 2.86 (m, 2H), 4.02 (m, 1H), 4.13 (s, 2H), 6.43 (m, 1H), 6.51 (m, 1H), 7.72 (m, 1H); MS m/z 284 [M+H]$^+$.

Intermediate 236

4-[(2-cyclopentyl-4,4,6-trimethyl-5-oxo-2,6,9,11-tetrazabicyclo[5.4.0]undeca-7,9,11-trien-10-yl)amino]-3-methoxy-benzoic acid 10-chloro-2-cyclopentyl-4,4-dimethyl-2,6,9,11-tetrazabicyclo[5.4.0]undeca-8,10,12-trien-5-one (Intermediate 127; 200 mg, 0.65 mmol) and 4-amino-3-methoxybenzoic acid (Aldrich; 130 mg, 0.78 mmol) were taken up in water/ethanol (3:1 v/v; 4 mL). Concentrated hydrochloric acid (130 ul, 1.30 mmol) was added and reaction heated by microwave irradiation at 120° C. for 30 minutes.

The reaction mixture was drowned into water (20 mL) and a precipitated solid collected by suction filtration and dried in vacuum oven, at 55° C. for 90 minutes, to give a dark pink crystalline solid (180 mg).

The filtrate was evaporated to dryness to give further solid, which was combined with the first batch and triturated with an MeCN/Water mix gave a pink solid which was again collected by suction filtration (160 mg).

The filtrate was evaporated and combined with the solid purified by flash chromatography on a silica cartridge eluting with 0-5% MeOH in DCM. to give the title compound as an off white solid (85 mg, 30%).

$^1$H NMR (400.132 MHz, DMSO-d6) δ 1.16 (s, 6H), 1.56-1.93 (m, 8H), 3.20 (s, 3H), 3.52 (s, 2H), 3.96 (s, 3H), 5.14 (m, 1H), 7.60 (m, 2H), 8.08 (s, 1H), 8.19 (d, 1H), 9.18 (br s, 1H)OH just visible at 12.84 (br s, 1H); MS m/z 440 [M+H]$^+$.

Intermediate 237

4-pyrrolidin-1-ylcyclohexan-1-amine tert-butyl N-(4-pyrrolidin-1-ylcyclohexyl)carbamate (Intermediate 238; 222 mg, 0.83 mmol) was taken up in DCM (1.5 mL) and TFA (1 mL). The reaction mixture was stirred at ambient temperature for 3 hours, poured directly onto an SCX-3 cartridge (2 g), pre-wet with DCM. The cartridge was washed through with DCM (10 mL), followed by methanol (30 mL) and then eluted with 2M ammonia in Methanol (25 mL). Evaporation to dryness of the ammoniacal solution yielded the title compound as an amber coloured oil (103 mg, 74%)

$^1$H NMR (400.132 MHz, DMSO-d6) δ 0.94-1.20 (m, 4H), 1.63 (m, 4H), 1.73 (m, 2H), 1.87 (m, 3H), 2.45 (m, 4H), 3.29 (br m, 1H)

Intermediate 238 tert-butyl N-(4-pyrrolidin-1-ylcyclohexyl)carbamate

The title compound was prepared by an analogous method to the preparation of Intermediate 227, on a 2.34 mmol scale utilising pyrrolidine (Aldrich; 250 μL, 3.04 mmol), as a white solid (175 mg, 44%).

$^1$H NMR (400.132 MHz, DMSO-d6) δ 1.15 (m, 4H), 1.38 (s, 9H), 1.64 (m, 4H), 1.75 (m, 2H), 1.88 (m, 3H), 2.45 (m, 4H), 3.15 (m, 1H), 6.64 (m, 1H).

Intermediate 239

4-amino-N-(4-dimethylaminocyclohexyl)-3-methoxy-benzamide 4-amino-N-(4-dimethylaminocyclohexyl)-3-methoxy-benzamide (Intermediate 240; 500 mg, 1.56 mmol) was reduced with 10% Pd/C (60 mg) and hydrogen to yield the title compound (454 mg, 100%).

$^1$H NMR (399.9 MHz, DMSO-d6) δ1.25-1.30 (2H, m), 1.40-1.44 (2H, m), 1.71-1.74 (1H, m), 1.80 (2H, m), 1.82 (2H, m), 2.19 (6H, d due to racemic mixture), 3.82 (3H, s), 3.65 and 3.85 (0.5H each due to racemic mixture), 5.16 (2H, s), 7.26 (1H, dd), 7.30 (1H, d), 7.71 (1H, t); MS m/z 292 [M+H]$^+$.

Intermediate 240

4-amino-N-(4-dimethylaminocyclohexyl)-3-methoxy-benzamide 3-methoxy-4-nitro-benzoyl chloride (Intermediate 189; 1.0 g, 4.64 mmol) was dissolved in DCM (20 mL) and cooled on an ice bath. DIPEA (970 uL) was added dropwise. 1-amino-4-dimethylaminocyclohexane (ABChem. Inc.; 660 mg, 4.64 mmol) was dissolved in DCM (10 mL) and added to the reaction solution. The reaction mixture was brought back to room temperature and stirred for 2 hours. The reaction mixture was washed with brine and NaOH (aq). The organic layer was extracted by filtering through a PTFE cup and evaporated to yield the title compound as an orange solid (1.54 g, 100%).

$^1$H NMR (399.9 MHz, DMSO-d$_6$) δ1.29-1.35 (2H, m), 1.45-1.48 (1H, m), 1.52-1.56 (1H, m), 1.75 (1H, m), 1.85-1.87 (2H, d), 1.95 (2H, d), 2.20 (6H, d due to N-dimethyl should be singlet but is doublet due to stereoisomers), 3.71 and 3.91 (two×0.5H due to stereoisomers), 3.99 (3H, s), 7.51 (1H, t), 7.60 (1H, d), 7.92 (1H, t), 844 (1H, t); MS m/z 332 [M+H]$^+$.

Intermediate 241

4-amino-2-fluoro-N-[(1S,5R)-9-methyl-9-azabicyclo[3.3.1]non-7-yl]benzamide 2-fluoro-N-[(1S,5R)-9-methyl-9-azabicyclo[3.3.1]non-7-yl]-4-nitro-benzamide (Intermediate 242; 500 mg, 1.56 mmol) was reduced using 10% Pd/C (50 mg) and hydrogen stirring at room temperature for 3 hours. The catalyst was removed by filtration and the filtrate evaporated to yield the title compound (454 mg, 100%).

$^1$H NMR (399.9 MHz, DMSO-d$_6$) δ 0.90 (2H, d), 1.38-1.40 (3H, m), 1.85-1.95 (2H, m), 1.99-2.05 (1H, m), 2.14-2.22 (2H, m), 2.40 (3H, s), 2.96 (2H, d), 4.20-4.28 (1H, m), 5.81-5.85 (2H, s), 6.28-6.32 (1H, d), 6.38-6.43 (1H, m), 7.20-7.24 (1H, t), 7.38-7.41 (1H, t); MS m/z 292 [M+H]$^+$.

Intermediate 242

2-fluoro-N-[(1S,5R)-9-methyl-9-azabicyclo[3.3.1]non-7-yl]-4-nitro-benzamide 2-fluoro-4-nitro-benzoyl chloride (Intermediate 243; 2.40 g, 11.79 mmol) was dissolved in DCM (20 mL) and cooled on an ice bath. DIPEA (2.46 mL, 14.15 mmol) was added dropwise followed by Endo-9-methyl-9-azabicyclo[3,3,1]-nonan-3-amine (Chempacific; 1.82 g, 11.79 mmol) dissolved in DCM (10 mL). The reaction mixture was allowed to return to room temperature and stirred for 2 hours and then washed with brine and NaOH$_{(aq)}$. The organic layer was evaporated to yield the title compound as an orange solid (3 g, 79%)

1H NMR (399.9 MHz, DMSO-d$_6$) δ 0.93 (2H, d), 1.34-1.41 (2H, m), 1.46 (1H, t), 1.90 (1H, t), 1.94 (2H, d), 2.21-2.29 (2H, m), 2.41 (3H, s), 2.98-3.00 (2H, m), 4.23-4.34 (1H, m), 7.79-7.83 (1H, m), 8.08-8.16 (1H, m), 8.18-8.24 (1H, m), 8.41 (1H, d); MS m/z 292 [M+H]$^+$.

Intermediate 243

2-fluoro-4-nitro-benzoyl chloride 2-fluoro-4-nitrobenzoic acid (Fluorochem; 2.5 g, 13.51 mmol) was suspended in toluene (25 mL) and thionyl chloride (2.96 mL, 40.52 mmol) added. The reaction mixture was heated at reflux for 1.5 hours, allowed to cool and evaporated to give the title compound as a yellow liquid which gradually solidified on standing (2.74 g, 100%)

$^1$H NMR (399.9 MHz, DMSO-d$_6$) δ7.90-8.10 (3H, m).

Intermediate 244

4-amino-3-chloro-N-(2,2-dimethyl-3-pyrrolidin-1-yl-propyl)benzamide

A mixture of the 4-amino-3-chloro-benzoic acid (Fluorochem; 2.49 g, 14.5 mmol) and 2,2-dimethyl-3-pyrrolidin-1-yl-propan-1-amine (Chemstep; 2.49 g, 15.95 mmol) were dissolved in DMF (50 mL), and to the solution was added DIPEA (5.1 mL, 29.0 mmol). The reaction mixture was cooled with an ice-bath, and HATU (6.06 g, 15.95 mmol) added, portionwise.

The reaction mixture was stirred at ambient temperature for 18 hours. The solvent was evaporated and the residue partitioned between Ethyl Acetate (100 mL), and saturated aqueous sodium carbonate solution (3×40 mL), washed with brine (3×40 mL), dried over anhydrous Magnesium sulphate, filtered, and the solvent evaporated to give the crude product as an oily semi-solid, which was triturated with diethyl ether and filtered to yield the title compound as a pale yellow crystalline solid (850 mg, 19%) The mother-liquors from the trituration were purified on a silica column, pre-equilibrated ethyl acetate and eluting with 10% MeOH-DCM+1% NH3. Product containing fractions were combined and evaporated to give the title compound as a viscous, yellow oil (1.72 g, 38%)

$^1$H NMR (400.1 MHz, CDCl$_3$) δ 1.00 (6H, s), 1.82-1.88 (4H, m), 2.56 (2H, s), 2.65-2.72 (4H, bs), 3.33-3.36 (2H, d), 4.30 (2H, s), 6.73-6.77 (1H, d), 7.55-7.60 (1H, dd), 7.65 (1H, s), 9.38 (1H, s). MS m/z 310 [M+H]$^+$.

Intermediate 245

4-amino-N-[(3R)-1-ethylpyrrolidin-3-yl]-3-methoxy-benzamide

To a solution of 4-amino-3-methoxybenzoic acid (Aldrich; 424 mg, 2.54 mmol) and (3R)-1-ethylpyrrolidin-3-amine (Intermediate 246; 312 mg, 2.73 mmol) in DMF (10 mL) was added DIPEA (1.4 ml, 8.04 mmol). The resultant solution was treated with HATU (1.21 g, 3.18 mmol) and stirred, under nitrogen, at ambient temperature overnight.

The reaction mixture was evaporated to a brown, viscous oil, which was partitioned between DCM (20 mL) and saturated aqueous sodium bicarbonate solution (20 mL). The organic phase was separated and aqueous phase re-extracted with DCM (20 mL). Combined organic solutions were evaporated to dryness and the residue purified on a silica column, eluting with a gradient of 0-10% methanol in DCM. Product containing fractions were combined and evaporated. The resultant material was dissolved in methanol and loaded onto an SCX-2 (10 g) cartridge. The cartridge was washed with methanol (75 mL) and then eluted with 2M ammonia/methanol. The ammoniacal solution was evaporated to yield the title compound as an orange gum (210 mg, 31%).

Intermediate 246

(3R)-1-ethylpyrrolidin-3-amine tert-butyl N-[(3R)-1-ethylpyrrolidin-3-yl]carbamate (Intermediate 247; 945 mg, 4.41 mmol) was taken up in DCM (8 mL) and TFA (4 mL) and stirred at ambient temperature for 3 hours.

The reaction mixture was loaded onto an SCX-3 cartridge (5 g), pre-wet with DCM. The cartridge was washed with DCM (30 mL), followed by methanol (30 mL), then eluted with 2M ammonia in methanol (30 mL). The ammoniacal solution was evaporated to dryness to yield the title compound as an amber oil (152 mg)

The SCX-cartridge pre-wash, which was highly coloured, was poured onto an SCX-3 (20 g) cartridge and the cartridge flushed with methanol (150 mL) and then eluted with 2M ammonia in methanol (100 mL). Evaporation of the ammoniacal fraction afforded a further batch of the title compound as an amber oil (165 mg)

Combined yield (317 mg, 63%)

$^1$H NMR (400.132 MHz, DMSO-d6) δ 0.99 (3H, t), 1.28-1.36 (1H, m), 1.93-2.02 (1H, m), 2.08 (1H, dd), 2.32-2.42 (3H, m), 2.46-2.49 (1H, m), 2.60-2.65 (1H, m), 3.26-3.33 (1H, m).

Intermediate 247 tert-butyl N-[(3R)-1-ethylpyrrolidin-3-yl]carbamate

To a solution of (3R)-(+)-3-(t-butoxycarbonylamino)pyrrolidine (Fluka; 1.54 g, 8.27 mmol) in DMF (25 mL) was added triethylamine (2.3 mL, 16.50 mmol) and ethyl bromide (Aldrich; 1 mL, 13.40 mmol). The reaction mixture was heated by microwave irradiation at 100° C. in for 1 hour.

The reaction mixture was poured into water (400 mL) and the mixture extracted with diethyl ether (2×300 mL). The combined organic extracts were washed with brine, dried over magnesium sulphate, filtered and evaporated to dryness to yield the title compound as an amber coloured oil (825 mg, 47%).

$^1$H NMR (400.132 MHz, DMSO-d6) δ 0.99 (t, 3H), 1.38 (s, 9H), 1.53 (m, 1H), 1.99 (m, 1H), 2.20 (m, 1H), 2.32-2.48 (m, 4H), 2.67 (m, 1H), 3.88 (m, 1H), 6.87 (m, 1H).

Intermediate 248

4-amino-N-(4-dimethylaminocyclohexyl)-2-fluoro-5-methoxy-benzamide 4-amino-2-fluoro-5-methoxy-benzoic acid (Intermediate 183; 0.75 g, 4.07 mmol), HATU (1.70 g, 4.48 mmol) and DIPEA (2.1 ml, 12.21 mmol) were stirred together in DMF (10 mL) for 10 minutes at ambient temperature. 1-amino-4-dimethylaminocyclohexane (ABChem. Inc.; 0.637 g, 4.48 mmol) in DMF (2 mL) was added and the reaction mixture stirred at ambient temperature overnight.

The solvent was evaporated and the residue dissolved in MeOH and loaded onto an SCX-2 (20 g) column pre-wet with MeOH. The column was washed with MeOH (2 column volumes) and the eluted with 2M NH3/MeOH. Product containing fractions were combined and evaporated to give a brown gum which was purified on a silica column eluting with 0-10% 2M NH3/MeOH/DCM to give a single unassigned isoform of the title compound as a pale brown gum (250 mg, 20%)

$^1$H NMR (400.132 MHz, DMSO-d$_6$) δ 1.63 (m, 8H), 2.08 (m, 1H), 2.18 (s, 6H), 3.77 (s, 3H), 3.91 (m, 1H), 5.54 (bs, 2H), 6.40 (d, 1H), 7.06 (d, 1H), 7.24 (m, 1H); MS m/z 310 [M+H]$^+$.

A second unassigned isoform was also isolated and designated Intermediate 249 (394 mg, 31%)

Intermediate 249

4-amino-N-(4-dimethylaminocyclohexyl)-2-fluoro-5-methoxy-benzamide

The title compound was obtained as a single unassigned isoform described above in the preparation of Intermediate 248 as a white solid (394 mg, 31%).

$^1$H NMR (400.132 MHz, DMSO-d$_6$) δ 1.28 (m, 4H), 1.85 (m, 4H), 2.11 (m, 1H), 2.18 (s, 6H), 3.66 (m, 1H), 3.77 (s, 3H), 5.53 (bs, 2H), 6.38 (d, 1H), 7.04 (d, 1H), 7.26 (m, 1H); MS m/z 310 [M+H]$^+$.

Intermediate 250

10-chloro-2-cyclopentyl-4,4-diethyl-6-methyl-2,6,9,11-tetrazabicyclo[5.4.0]undeca-7,9,11-trien-5-one To a stirred solution of 10-chloro-2-cyclopentyl-4,4-diethyl-2,6,9,11-tetrazabicyclo[5.4.0]undeca-7,9,11-trien-5-one (Intermediate 251; 2.5 g, 7.76 mmol) in DMA (50 mL) under nitrogen was added methyl iodide (0.627 mL, 10.0 mmol). The mixture was cooled on an ice/water bath to 3° C., and sodium hydride (60% mineral oil dispersion; 0.567 g, 11.8 mmol) added in one portion. The reaction mixture was stirred on the ice/water bath for 1 hour before warming to room temperature and the reaction stirred for 4 hours. The reaction mixture was evaporated to dryness to afford a black solid, which was quenched with saturated aqueous NH$_4$Cl solution (50 mL), extracted with DCM (3×100 mL), dried and solvent removed in vacuo to yield a black solid which was purified on a silica column eluting with DCM. The obtained solid was added to a diethyl ether and sonicated and the resultant material filtered and dried to yield the title compound as an off white solid (2.1 g, 80%).

$^1$H NMR (400.132 MHz, CDCl3) δ 0.83 (t, 6H), 1.77-1.48 (m, 10H), 1.99-1.91 (m, 2H), 3.27 (s, 3H), 3.43 (s, 2H), 5.34 (quintet, 1H), 7.82 (s, 1H); MS m/z 337 [M+H]$^+$.

Intermediate 251

10-chloro-2-cyclopentyl-4,4-diethyl-2,6,9,11-tetrazabicyclo[5.4.0]undeca-7,9,11-trien-5-one To a solution of methyl2-[(cyclopentylamino)methyl]-2-ethyl-butanoate (Intermediate 252; 7.1 g, 31.3 mmol) in acetone (150 mL) was added potassium carbonate (5.3 g, 38.0 mmol) followed by 2,4-dichloro-5-nitropyrimidine (Aldrich; 6.1 g, 31.3 mmol). The black mixture was stirred at room temperature for 18 hours. The reaction was filtered and the solvent removed in vacuo to yield a black gum, which was dissolved in acetic acid (175 mL) and iron (7.0 g, 125 mmol) added and the reaction heated at 80° C. overnight. The resulting solution was filtered and the solvent removed in vacuo, the black solid/gum was quenched with water (75 mL) and to this was added sodium carbonate until basic, the resultant black emulsion was filtered through a pad of celite. The obtained mixture was extracted with DCM (3×150 mL), dried and the solvent removed in vacuo to yield a black solid. This was passed through a bond elute column (50 g) eluting with 0-1% MeOH in DCM to afford a brown solid, which was triturated with diethyl ether to yield the title compound as a white solid (3.05 g, 30%)

$^1$H NMR (400.132 MHz, CDCl3) δ 0.90 (t, 6H), 1.57-1.48 (m, 2H), 1.81-1.61 (m, 6H), 1.98-1.91 (m, 2H), 3.36 (s, 2H), 5.31 (quintet, 1H), 7.80 (s, 1H), 8.40 (s, 1H); MS m/z 323 [M+H]$^+$.

Intermediate 252 methyl2-[(cyclopentylamino)methyl]-2-ethyl-butanoate

The title compound was prepared by an analogous method to the preparation of Intermediate 200, on a 50 mmol scale utilising Cyclopentanone (Aldrich; 6.33 g, 75 mmol), and distillation at 50° C. and 0.53 mbar pressure, as a clear oil (7.5 g, 65%)

$^1$H NMR (400.132 MHz, CDCl3) δ 0.79 (t, 6H), 1.32-1.24 (m, 2H), 1.53-1.46 (m, 2H), 1.68-1.57 (m, 6H), 1.83-1.72 (m, 2H), 2.67 (s, 2H), 2.99 (quintet, 1H), 3.66 (s, 3H).

Intermediate 253

4-[(2-cyclopentyl-4,4,6-trimethyl-5-oxo-2,6,9,11-tetrazabicyclo[5.4.0]undeca-7,9,11-trien-10-yl)amino]-3-chloro-benzoic acid 2'-chloro-9'-cyclopentyl-5'-methyl-8',9'-dihydrospiro[cyclopropane-1,7'-pyrimido[5,4-b][1,4]diazepin]-6'(5'H)-one (Intermediate 130; 496 mg, 1.62 mmol) and 4-amino-3-chlorobenzoic acid (Fluorochem; 278 mg, 1.62 mmol) were taken up in water/ethanol (3:1 v/v; 12 mL). Concentrated hydrochloric acid (330 uL, 3.30 mmol) was added and the reaction heated at reflux overnight.

The reaction mixture was cooled and then poured into 1M NaOH$_{(aq)}$ (75 mL), and DCM (50 mL) added. The aqueous phase was separated and washed with DCM (50 mL) then acidified until a precipitate formed (~pH 2-3) which was collected by suction filtration and dried, under vacuum, at 70° C., for 2 hours to afford a pale pink solid. The material was taken up in 10% MeOH in DCM (10 mL) and a fine suspension resulted. The mixture was filtered and the collected solid dried to yield the title compound as a pink solid, (58 mg, 8%)

MS m/z 442 [M+H]$^+$. Retention time 1.26 minutes

Intermediate 254

4-amino-2-fluoro-5-methoxy-N-[[1-(pyrrolidin-1-ylmethyl)cyclopropyl]methyl]benzamide 4-amino-2-fluoro-5-methoxy-benzoic acid (Intermediate 183; 500 mg, 2.70 mmol), [1-(pyrrolidin-1-ylmethyl)cyclopropyl]methanamine (Intermediate 33; 417 mg, 2.70 mmol), HATU (1.545 g, 4.05 mmol) and DIPEA (1.415 mL, 8.10 mmol) were dissolved in DMF (8 mL) and left to stir for 3 hours at room temperature. The reaction mixture was loaded onto an SCX-3 column pre-washed with methanol. The column was washed with methanol eluted with 2% 7N ammonia/methanol. Product containing fractions were combined and evaporated and the residue purified on a silica column (5-12% MeOH ammonia/DCM gradient elution) to yield the title compound as an orange-brown solid (200 mg, 23%).

$^1$H NMR (399.9 MHz, DMSO-d6) δ0.29 (2H, broad s), 0.50 (2H, broad s), 1.70 (4H, broad s), 2.45 (4H, s), 2.50 (2H, s), 3.30 (2H, d), 3.75 (3H, s), 5.60 (2H, s), 6.40 (1H, d), 7.15 (1H, d), 8.05 (1H, t); MS m/z 322 [M+H]$^+$.

Intermediate 255

2'-chloro-9'-cyclopentyl-5'-methyl-8',9'-dihydrospiro[cyclohexane-1,7'-pyrimido[5,4-b][1,4]diazepin]-6'(5'H)-one 2'-chloro-9'-cyclopentyl-8',9'-dihydrospiro[cyclohexane-1,7'-pyrimido[5,4-b][1,4]diazepin]-6'(5'H)-one (Intermediate 256; 300 mg, 0.94 mmol) was dissolved in N,N-dimethylacetamide (10 mL) and methyl iodide (65 mL, 1.03 mmol) added followed by sodium hydride (41 mg of a 60% dispersion in mineral oil, 1.00 mmol). The reaction mixture was stirred for 30 minutes. A drop of water added was added and then the reaction mixture was diluted with water and extracted with ethyl acetate (×2). The combined organic extracts were dried (MgSO$_4$) and concentrated and the residue purified by column chromatography (1% MeOH/DCM) to give a sticky white solid (Note 4) that was suspended in diethyl ether and filtered off to yield the title compound as a white crystalline solid (242 mg, 77%).

$^1$H NMR (399.9 MHz, DMSO-d6) δ1.30-1.37 (2H, m), 1.51-1.62 (8H, m), 1.68-1.74 (2H, m), 1.84-1.91 (2H, m), 1.96-2.04 (2H, m), 3.21 (3H, s), 3.47 (2H, s), 4.88-4.96 (1H, m), 8.09 (1H, s); MS m/z 335 [M+H]$^+$.

Intermediate 256

2'-chloro-9'-cyclopentyl-8',9'-dihydrospiro[cyclohexane-1,7'-pyrimido[5,4-b][1,4]diazepin]-6'(5'H)-one Methyl1-(aminomethyl)cyclopentane-1-carboxylate (Intermediate 257; 940 mg, 2.46 mmol) was dissolved in acetic acid (40 mL) and the mixture heated to 70° C. Iron powder (412 mg, 7.37 mmol) was added and the mixture heated for 4 hours, filtered whilst still warm and concentrated. The residue was suspended between DCM and saturated aqueous sodium hydrogen carbonate solution and the mixture was filtered. The layers were then separated and the organic layer dried (MgSO$_4$) and concentrated to give a green, viscous oil. On addition of methanol a white solid formed which was filtered off to yield the title compound (300 mg, 38%).

$^1$H NMR (399.9 MHz, DMSO-d6) δ1.45-1.63 (10H, m), 1.68-1.75 (2H, m), 1.79-1.86 (2H, m), 1.96-2.01 (2H, m), 3.42 (2H, s), 5.06-5.15 (1H, m), 7.87 (1H, s), 9.70 (1H, s); MS m/z 321 [M+H]$^+$.

Intermediate 257 methyl1-(aminomethyl)cyclopentane-1-carboxylate

Methyl1-[(cyclopentylamino)methyl]cyclopentane-1-carboxylate (Intermediate 258; 1.60 g, 7.10 mmol), 2,4-dichloro-5-nitropyrimidine (Aldrich; 1.66 g, 8.52 mmol) and triethylamine (1.2 mL, 8.52 mmol) were stirred in acetonitrile (50 mL) for 4 hours. The reaction mixture was evaporated and the residue dissolved in DCM, washed with water, dried (MgSO$_4$) and evaporated. The residue was purified on a silica column eluting with 1% methanol/DCM to yield the title compound as a yellow oil that crystallised on standing (945 mg, 35%).

$^1$H NMR (399.9 MHz, DMSO-d6) δ1.43-1.70 (12H, m), 1.80-1.87 (2H, m), 1.97-2.01 (2H, m), 3.46-3.55 (1H, m), 3.58 (3H, s), 3.77 (2H, s), 8.90 (1H, s); MS m/z 383 [M+H]$^+$.

Intermediate 258 methyl1-[(cyclopentylamino)methyl]cyclopentane-1-carboxylate

Methyl1-(aminomethyl)cyclopentane-1-carboxylate (Intermediate 259; 1.5 g, 9.54 mmol) and cyclopentanone (1.0 mL, 11.45 mmol) were stirred in DCM (40 mL). Sodium acetate (940 mg, 11.45 mmol) and sodium triacetoxyborohydride (3.04 g, 14.31 mmol) were added. The mixture was stirred at room temperature for 48 hours. The reaction mixture was filtered and the filtrate concentrated. The residue was dissolved in methanol and absorbed on to an SCX column, which was then washed with methanol and eluted with ammonia in methanol. Product containing fractions were combined and evaporated to yield the title compound as a colourless oil (1.64 g, 81%).
$^1$H NMR (399.9 MHz, DMSO-d6) δ1.21-1.34 (2H, m), 1.39-1.70 (13H, m), 1.88-1.94 (2H, m), 2.63 (2H, s), 2.90-2.96 (1H, m), 3.59 (3H, s).

Intermediate 259 methyl1-(aminomethyl)cyclopentane-1-carboxylate

17328/13 Reaction carried out in RSL (P Walker—No. 009/07, Sep. 1, 2007)
Methyl1-cyanocyclopentane-1-carboxylate (Intermediate 260; 6 g, 39.2 mmol) in acetic acid (70 mL) was hydrogenated using PtO$_2$ (600 mg) as a catalyst at room temperature under 4 Bar pressure for 4 hours. The reaction mixture was filtered and concentrated. The residue was taken up in methanol and absorbed on to an SCX column (3×50 g), which was then washed with methanol and eluted with ammonia in methanol. Concentration of product containing fractions yielded the title compound as a pale yellow liquid (6.18 g, 100%).
$^1$H NMR (399.9 MHz, DMSO-d6) δ1.38 (2H, s), 1.52-1.58 (6H, m), 1.87-1.93 (2H, m), 2.67 (2H, s), 3.61 (3H, s).

Intermediate 260 methyl1-cyanocyclopentane-1-carboxylate

Methyl cyanoacetate (Fluka; 25 g, 252.3 mmol) and potassium carbonate (83.7 g, 605.5 mmol) were stirred in DMF (250 mL). 1,4-Dibromobutane (Aldrich; 30.1 mL, 252.3 mmol) was slowly added. This caused and exotherm that continued after the addition was completed and a water bath was used to prevent the temperature exceeding 90° C. The mixture slowly cooled to ambient temperature and was stirred overnight and then heated at 75° C. for 3 hours.
The reaction mixture was cooled and filtered and the filtrate concentrated to about half volume. The mixture was diluted with water (250 mL) and extracted with diethyl ether (2×65 mL). The combined organic extracts were washed with 1N hydrochloric acid, brine, dried (MgSO$_4$) and evaporated to yield the title compound as a pale yellow liquid (31.73 g, 82%).
$^1$H NMR (399.9 MHz, CDCl3) δ1.86-1.91 (4H, m), 2.25-2.29 (4H, m), 3.83 (3H, s).

Intermediate 261

10-chloro-6-methyl-2-(2-oxocyclopentyl)-2,6,9,11-tetrazabicyclo[5.4.0]undeca-7,9,11-trien-5-one 10-chloro-6-methyl-2,6,9,11-tetrazabicyclo[5.4.0]undeca-7,9,11-trien-5-one (Intermediate 100; 256 mg, 1.20 mmol) was taken up in DMA (10 mL) and cooled on an ice-bath, with stirring, under nitrogen. Sodium hydride (60% in mineral oil; 232 mg, 5.8 mmol) was carefully added portionwise and the reaction mixture left to stir for 5 minutes, before removing cooling bath and stirring for a further 30 minutes. A solution of 2-chlorocyclopentanone (Aldrich; 600 uL, 6.00 mmol) in DMA (5 mL) was then added. The reaction mixture was heated to 100° C. and stirred for 3.5 hours and then allowed to cool, before addition of saturated aqueous ammonium chloride solution (1 mL). The mixture was partitioned between DCM (40 mL) and water (40 mL). Phases were separated and the aqueous phase re-extracted with DCM (40 mL). Combined extracts were washed with brine, dried over magnesium sulphate, filtered and evaporated. The residue was purified on a silica column eluting with ethyl acetate. Product containing fractions were combined and evaporated to yield the title compound as a sticky brown gum (211 mg, 60%)
MS m/z 295 [M+H]$^+$.

Intermediate 262

4-bromo-2-chloro-5-fluoro-N-(1-methyl-4-piperidyl)benzamide 4-bromo-2-chloro-5-fluoro-benzoic acid (Apollo Scientific; 5.0 g, 19.8 mmol) was added to DMF (250 mL), to this was added HBTU (9.8 g, 25.7 mmol), N-methyl-4-aminopiperidine (Fluorochem; 2.5 g, 21.8 mmol) and DIPEA (7.0 mL, 39.5 mmol). The reaction was stirred overnight, evaporated to dryness, quenched with 2.0 N NaOH (100 mL), extracted with DCM (3×100 mL), dried and solvent removed in vacuo. The residue was dissolved in hot acetonitrile, allowed to cool filtered, and the filtrate passed through a SCX column and the residue, after evaporation of product containing fractions, recrystallised from hot acetonitrile to yield the title compound as a white solid (5.0 g, 82%).
$^1$H NMR (400.132 MHz, CDCl$_3$) δ 1.64-1.55 (m, 2H), 2.07-2.03 (m, 2H), 2.19-2.14 (m, 2H), 2.29 (s, 3H), 2.79-2.76 (m, 2H), 4.04-3.95 (m, 1H), 6.13 (brd, 1H), 7.48 (d, 1H), 7.62 (d, 1H); MS m/z 350 [M+H]$^+$.

Intermediate 263

10-amino-2-cyclohexyl-6-methyl-2,6,9,11-tetrazabicyclo[5.4.0]undeca-7,9,11-trien-5-one 10-amino-2-cyclohexyl-2,6,9,11-tetrazabicyclo[5.4.0]undeca-7,9,11-trien-5-one (Intermediate 264; 1.0 g, 3.83 mmol) was dissolved in DMF (65 ml), to this was added sodium hydride
(60% mineral oil dispersion; 0.37 g, 7.66 mmol) in one portion. The reaction was stirred under nitrogen for 30 minutes before being cooling 0° C. Methyl Iodide (0.238 mL, 3.83 mmol) in DMF (10 mL) was slowly added to the reaction and the reaction stirred at 0° C. for 2 hours. The reaction was quenched with MeOH and solvent removed in vacuo. The resultant slurry was quenched with saturated aqueous NH$_4$Cl solution (50 mL), extracted with DCM (3×50 mL), dried and solvent evaporated to yield a yellow gum which was purified on a silica column eluting with 0-5% MeOH in DCM. On evaporation of product containing fractions the residue was dissolved in a small amount of DCM, to this was added diethyl ether (50 mL), and the solution slowly evaporated until a precipitate formed. The solution was then sonicated and the precipitate filtered and dried to yield the title compound as a white solid. (0.55 g, 52%)

$^1$H NMR (400.132 MHz, CDCl3) δ 1.18-1.07 (m, 1H), 1.52-1.34 (m, 4H), 1.74-1.68 (m, 1H), 1.85-1.80 (m, 4H), 2.63-2.61 (m, 2H), 3.24 (s, 3H), 3.64-3.61 (m, 2H), 4.41-4.35 (m, 1H), 4.66 (brs, 2H), 7.77 (s, 1H); MS m/z 276 [M+H]$^+$.

Intermediate 264

10-amino-2-cyclohexyl-2,6,9,11-tetrazabicyclo [5.4.0]undeca-7,9,11-trien-5-one 2,4-dichloro-5-nitropyrimidine (Aldrich; 10 g, 0.052 mol) was dissolved in THF (250 mL). To this was added DIPEA (11 mL, 0.062 mol) and the reaction cooled to 0° C. Methyl3-(cyclohexylamino)propanoate (9.5 g, 0.052 mol) in THF (30 mL) was slowly added. The cooling bath was removed and the reaction was stirred at room temperature for 1 hour. To the reaction mixture was added saturated NH$_4$OH$_{(aq)}$ (100 mL), and the reaction heated at 55° C. for 4 hours using a dry ice condenser. The reaction mixture was extracted with DCM (3×100 ml), and combined organic extracts dried and evaporated. The residue was dissolved in methanol (200 mL). Ammonium formate (33 g, 0.52 mol) and 10% palladium (1.5 g) were added. The reaction was heated at reflux for 5 hours, filtered and the methanol evaporated to yield a dark orange solid, which was quenched with 2.0 N NaOH$_{(aq)}$ (100 mL), extracted with DCM (3×150 mL), and combined extracts dried and evaporated to yield an orange solid. Hot acetonitrile was added, this was stirred and then sonicated to give a precipitate that was filtered and dried to yield the title compound as a yellow solid (7.5 g, 55%).
$^1$H NMR (400.132 MHz, CDCl$_3$) δ 1.18-1.05 (m, 1H), 1.48-1.37 (m, 4H), 1.84-1.68 (m, 5H), 2.68-2.66 (m, 2H), 3.62-3.59 (m, 2H), 4.74-4.65 (m, 1H), 5.34 (brs, 2H), 7.59 (s, 1H), 9.57 (s, 1H); MS m/z 262 [M+H]$^+$.

Intermediate 265 methyl3-(cyclohexylamino)propanoate

Cyclohexylamine (Aldrich; 17 g, 0.174 mol) was dissolved in THF (300 mL). To this was added methyl acrylate (Aldrich; 15 g, 0.174 mol) in one portion. The reaction mixture was stirred over the weekend. The solvent was evaporated with care due to the volatility of the product and the residue distilled at 72° C. at 0.30 mbar to yield the title compound as a clear oil (23.7 g, 74%).
$^1$H NMR (400.132 MHz, CDCl3) δ 1.31-1.01 (m, 6H), 1.63-1.57 (m, 1H), 1.75-1.70 (m, 2H), 1.89-1.85 (m, 2H), 2.46-2.39 (m, 1H), 2.50 (t, 2H), 2.90 (t, 2H), 3.68 (s, 3H).

Intermediate 266

10-chloro-2-cyclohexyl-6-methyl-2,6,9,11-tetrazabicyclo[5.4.0]undeca-7,9,11-trien-5-one 10-chloro-2-cyclohexyl-2,6,9,11-tetrazabicyclo[5.4.0]undeca-7,9,11-trien-5-one (Intermediate 267; 5.87 g, 20.91 mmol) was suspended in DMA (450 mL) under nitrogen. Methyl iodide (3.26 g, 23 mmol) was added and the suspension cooled to 5° C. on an ice-water bath. Sodium hydride (60% mineral oil dispersion; 920 mg, 23 mmol) was added in a single portion and the resulting mixture stirred on the ice-water bath for 30 minutes allowed to warm to room temperature and stirred for 16 hours. The reaction mixture was quenched with saturated aqueous ammonium chloride solution (10 mL) and the solvent evaporated. The residue was partitioned between DCM (200 mL) and water (300 mL) and the aqueous phase re-extracted with DCM (100 mL). The combined organic phases were dried (MgSO$_4$) and the evaporated. The residue was taken up in DCM and purified on a silica column eluting with a gradient of 10-50% EtOAc/isohexane over 10 column volumes. Fractions containing product were combined and evaporated to yield the title compound as a cream solid (5.02 g, 81%)
$^1$H NMR (399.902 MHz, CDCl$_3$) δ1.13 (m, 1H), 1.47 (m, 4H), 1.72 (m, 1H), 1.85 (m, 4H), 2.66 (m, 2H), 3.28 (s, 3H), 3.69 (m, 2H), 4.47 (m, 1H), 7.93 (s, 1H); MS m/z 295 [M+H]$^+$.

Intermediate 267

10-chloro-2-cyclohexyl-2,6,9,11-tetrazabicyclo [5.4.0]undeca-7,9,11-trien-5-one

Methyl3-[(2-chloro-5-nitro-pyrimidin-4-yl)-cyclohexyl-amino]propanoate (Intermediate 238; 19.03 g, 55.52 mmol) was dissolved in acetic acid (440 mL) and heated to 70° C. under a nitrogen atmosphere. Iron powder (8.37 g, 150 mmol) was added cautiously, giving a slow exotherm to 82° C., and the mixture stirred at 70° C. for 2 hours. The reaction mixture was cooled to approximately 60° C. and filtered through a pad of celite. The celite was washed through with DCM (500 mL) and the filtrate evaporated and the residue azeotroped with toluene. The resultant material was dissolved in DCM and diluted with EtOAc to give a precipitate which was filtered off. The filtrate was added to a very short pad of silica and eluted with EtOAc and the eluent evaporated to give an orange solid, which was dissolved in DCM (500 mL) and washed with saturated aqueous sodium bicarbonate solution (300 mL). The organic phase contained some insoluble material which was filtered off to give a cream solid. The filtrate was evaporated to dryness and the resulting dark brown gum triturated with DCM (20 mL) and filtered to give a cream solid. The two solids were combined and washed with a small amount of DCM then dried under high vacuum to yield the title compound as a cream solid (5.87 g, 38%)
$^1$H NMR (399.902 MHz, DMSO-d6) δ1.13 (m, 1H), 1.34 (m, 2H), 1.52 (m, 2H), 1.66 (m, 3H), 1.80 (m, 2H), 2.66 (m, 2H), 3.60 (m, 2H), 4.53 (m, 1H), 7.84 (s, 1H), 9.68 (s, 1H); MS m/z 281 [M+H]$^+$.

Intermediate 268 methyl3-[(2-chloro-5-nitro-pyrimidin-4-yl)-cyclohexyl-amino]propanoate

To methyl3-(cyclohexylamino)propanoate (Intermediate 265; 15 g, 80.96 mmol) in acetone (300 mL) at room temperature was added powdered potassium carbonate (16.8 g, 121 mmol).
2,4-Dichloro-5-nitropyrimidine (Frontier Scientific; 17.27 g, 89.06 mmol) in acetone (100 mL) was added over 10 minutes and the resulting yellow mixture stirred at room temperature for 16 hours. The solvent was evaporated and the residue partitioned between EtOAc (500 mL) and water (500 mL). The aqueous phase was re-extracted with EtOAc (2×200 mL). The combined organic solutions were evaporated to approx half the volume, washed with brine (200 mL) and evaporated. The residue was taken up in DCM and purified on a silica column, eluting with 10% EtOAc/isohexane. Product containing fractions were combined and evaporated to yield the title compound as a yellow solid (19.03 g, 62%)
$^1$H NMR (399.902 MHz, CDCl$_3$) δ1.27 (m, 2H), 1.49-1.68 (m, 4H), 1.85 (m, 4H), 2.70 (m, 2H), 3.20 (m, 1H), 3.71 (s, 3H), 3.82 (m, 2H), 8.63 (s, 1H); MS m/z 343 [M+H]$^+$.

Intermediate 269

4-amino-2,5-difluoro-N-[[1-(pyrrolidin-1-ylmethyl) cyclopropyl]methyl]benzamide 4-amino-2,5-difluoro-benzoic acid (Rare Chemicals GmbH; 700 mg, 4.04 mmol), [1-(pyrrolidin-1-ylmethyl)cyclopropyl]methanamine (Intermediate 33; 655 mg, 4.25 mmol), HATU (1.69 g, 4.44 mmol) and DIPEA (2.1 mL, 12.12 mmol) were combined in DMF (10 mL) and stirred at room temperature for 2 hours. The reaction mixture divided into two portions and each loaded on to an SCX-2 column (20 g) pre-wet with MeOH (2 column volumes), flushed with MeOH (2 column volumes) and eluted with 2M ammonia in MeOH. Product containing fractions were evaporated and the residue taken up in DCM and purified on a silica column eluting with a 0-5% gradient of 2M ammonia in MeOH/DCM then 5% 2M ammonia in MeOH/DCM. Fractions containing product were combined and evaporated to yield the title compound as an orange gum which solidified on standing to an orange solid (472 mg, 38%)

$^1$H NMR (399.902 MHz, CDCl$_3$) δ0.37 (m, 2H), 0.55 (m, 2H), 1.75 (m, 4H), 2.50 (m, 6H), 3.42 (m, 2H), 4.08 (s, 2H), 6.43 (m, 1H), 7.70 (m, 1H), 8.53 (m, 1H); MS m/z 310 [M+H]$^+$.

Intermediate 270

2'-chloro-9'-cyclohexyl-5'-methyl-8',9'-dihydrospiro [cyclopropane-1,7'-pyrimido[5,4-b][1,4]diazepin]-6' (5'H)-one To a stirred solution of 2'-chloro-9'-cyclohexyl-8',9'-dihydrospiro[cyclopropane-1,7'-pyrimido[5,4-b][1,4]diazepin]-6'(5'H)-one (Intermediate 271; 849 mg, 2.767 mmol) in DMA (60 mL) under nitrogen was added methyl iodide (190 μL, 3.044 mmol). The mixture was cooled on an ice/water bath and sodium hydride (60% mineral oil dispersion; 122 mg, 3.044 mmol) added in one portion. The reaction mixture was stirred on the ice/water bath for 1 hour, the cooling bath removed and allowed it to warm to room temperature. After 1.5 hours the solvent was evaporated and the residue treated with an excess of water. This afforded a solid, which was filtered off and washed well with water and then dried by dessication under high vacuum over P$_2$O$_5$ overnight. To yield the title compound as an off-white solid (887 mg, 100%)

$^1$H NMR (400.13 MHz, CDCl$_3$) δ 0.57-0.60 (2H, m), 0.97-1.04 (1H, m), 1.05-1.08 (2H, m), 1.18-1.28 (2H, m), 1.34-1.44 (2H, m), 1.60-1.67 (1H, m), 1.71-1.78 (4H, m), 3.19 (3H, s), 3.40 (2H, s), 4.42-4.50 (1H, m), 7.77 (1H, s); MS m/z 321 [M+H]$^+$.

Intermediate 271

2'-chloro-9'-cyclohexyl-8',9'-dihydrospiro[cyclopropane-1,7'-pyrimido[5,4-b][1,4]diazepin]-6'(5'H)-one Ethyl1-[[(2-chloro-5-nitro-pyrimidin-4-yl)-cyclohexylamino]methyl]cyclopropane-1-carboxylate (Intermediate 272; 3.89 g, 10.16 mmol) was dissolved in the acetic acid (75 mL) and the solution heated with stirring to 72° C. under nitrogen on an oil bath. Iron powder (1.5 g) was added in one portion giving a small exotherm to 75° C. over the subsequent 15 minutes.

The reaction temperature dropped back to 72° C. and the reaction was maintained at this temperature for 3 hours and then allowed to cool to room temperature overnight.

The reaction mixture was reheated and filtered hot through celite, and the pad washed with more acetic acid. The filtrate was concentrated in vacuo, then sonicated in saturated aqueous sodium hydrogen carbonate solution to give a brown suspension. This was filtered, and the resulting solid washed with water. The solid was sucked dry, and suspended in methanol with sonication. The suspension was then diluted with DCM, and sodium sulphate added. This mixture was filtered to give a yellow solution, which was concentrated in vacuo to give a yellow solid, which was triturated under cold methanol to give the product as a white powder. The mother liquors were purified on a silica column, to give more clean product, which was combined with the first batch to yield the title compound as a white solid (850 mg, 27%).

$^1$H NMR (400.13 MHz, DMSO-d$_6$) δ 0.88-0.91 (2H, m), 1.05-1.15 (1H, m), 1.15-1.18 (2H, m), 1.31-1.42 (4H, m), 1.61-1.63 (3H, m), 1.74-1.81 (2H, m), 3.44 (2H, s), 4.44 (1H, s), 7.93 (1H, s), 9.77 (1H, s); MS m/z 307 [M+H]$^+$.

Intermediate 272 ethyl1-[[(2-chloro-5-nitro-pyrimidin-4-yl)-cyclohexyl-amino]methyl]cyclopropane-1-carboxylate To a solution of ethyl1-[(cyclohexylamino)methyl]cyclopropane-1-carboxylate (Intermediate 273; 7.175 g, 34 mmol) in acetone (200 mL) was added potassium carbonate 7.05 g, 51 mmol) followed by 2,4-dichloro-5-nitropyrimidine (Aldrich; 9.235 g, 47.6 mmol). The reaction mixture was stirred at room temperature for 5 hours. A further addition of 2,4-dichloro-5-nitropyrimidine (4.62 g, 23.8 mmol) and potassium carbonate (3.5 g, 25.5 mmol) was made and the reaction stirred overnight at room temperature. The reaction mixture was then concentrated in vacuo and partitioned between EtOAc and water. The EtOAc layer was separated, dried over sodium sulphate and purified on a silica column eluting with EtOAc/isohexane 10:90, to yield the title compound as a yellow oil (12 g, 92%).

$^1$H NMR (400.13 MHz, CDCl$_3$) δ 0.76-0.83 (2H, m), 0.90-0.97 (1H, m), 1.00 (4H, s), 1.04-1.10 (2H, m), 1.13-1.15 (2H, m), 1.56 (6H, m), 2.93-2.99 (1H, m), 3.69 (2H, s), 3.94 (2H, q), 8.49 (1H, s); MS m/z 383 [M+H]$^+$.

Intermediate 273 ethyl1-[(cyclohexylamino)methyl]cyclopropane-1-carboxylate

To a solution of ethyl1-(aminomethyl)cyclopropane-1-carboxylate (Intermediate 114; 20.65 g, 50 mmol) in DCM (200 mL) was added cyclohexanone (Aldrich; 5.28 mL, 51 mmol). After stirring at room temperature for 15 minutes, sodium acetate (4.185 g, 75 mmol) was added, followed by sodium triacetoxyborohydride (15.905 g, 75 mmol). The suspension was stirred at room temperature for 2 days then partitioned between DCM and saturated aqueous sodium hydrogen carbonate solution. The organic solution was dried over sodium sulphate and evaporated to yield the title compound as a colourless oil (7.2 g, 64%).

$^1$H NMR (400.13 MHz, CDCl$_3$) δ 0.55-0.58 (2H, m), 0.81-0.97 (4H, m), 0.99-1.08 (7H, m), 1.34-1.39 (1H, m), 1.47-1.51 (2H, m), 1.57-1.65 (2H, m), 2.14-2.21 (1H, m), 2.49 (2H, s), 3.88 (2H, q).

Intermediate 274

4-amino-2,5-difluoro-N-[(1S,5R)-9-methyl-9-azabi-cyclo[3.3.1]non-7-yl]benzamide

A mixture of the 4-Amino-2,5-Difluorobenzoic Acid (Rarechem; 2.4 g, 13.87 mmol) and Endo-9-methyl-9-azabi-cyclo[3,3,1]-nonan-3-amine (Chempacific; 2.355 g, 15.26 mmol) was dissolved in DMF (150 mL), and to the solution was added DIPEA (5.3 mL, 27.74 mmol).

The reaction was cooled on an ice-bath, and HATU (5.805 g, 15.26 mmol) was added, portionwise. The reaction mixture was then stirred at ambient temperature for 18 hours, solvent evaporated, and the residue partitioned between ethyl acetate (200 mL), and saturated aqueous sodium carbonate solution (3×50 mL), washed with brine (3×50 mL), dried over anhydrous magnesium sulphate, filtered, and the solvent evaporated. The residue was purified on an SCX-2 column (50 g), developing and eluting with 1) water; 2) MeOH; and 3) 3.5M $NH_3$-MeOH. The solvent was evaporated to yield the title compound as a tan crystalline solid (2.58 g, 60%).

$^1$H NMR (400.1 MHz; $CDCl_3$) δ 1.00-1.10 (2H, d), 1.23-1.33 (2 h, dt), 1.48-1.58 (1H, m), 1.85-2.03 (4H, d+m), 2.50 (3H, s), 2.44-2.56 (2H, m), 3.04-3.12 (2H, d), 4.20 (2H, s), 4.42-4.56 (1H, m), 6.33-6.50 (1H, m), 6.42-6.50 (1H, dd), 7.70-7.77 (1H, dd). MS m/z 310 [M+H]$^+$.

Intermediate 275

4-amino-3-methoxy-N-[(1R,5S)-9-methyl-3-oxa-9-azabicyclo[3.3.1]non-7-yl]benzamide N-Ethyldiisopropylamine (0.119 mL, 0.68 mmol) was added to 4-amino-3-methoxybenzoic acid (Aldrich; 114 mg, 0.68 mmol), (1R,5S,7s)-9-methyl-3-oxa-9-azabicyclo[3.3.1]nonan-7-amine (Bioorganic & Medicinal Chemistry Letters (1992), 2(6), 519-22, 107 mg, 0.68 mmol) and HATU (260 mg, 0.68 mmol) in DMF (5 mL) at 25° C. The resulting solution was stirred at ambient temperature for 6 hours. The DMF was evaporated to give a brown gum as residue, which was purified by ion exchange chromatography, using an SCX-2 (5 g) column pre-wet with methanol. The desired product was eluted from the column using 2M NH3/MeOH and purified fractions were evaporated to dryness to afford a brown gum which was purified by flash silica chromatography, elution gradient 0 to 100% 5% MeOH/DCM in DCM. Pure fractions were combined and evaporated to dryness to afford the title compound as a beige coloured gum (205 mg, 98%).

$^1$H NMR (400.132 MHz, $CDCl_3$) δ 1.38 (2H, d), 2.39-2.45 (2H, m), 2.53 (3H, s), 2.58-2.68 (4H, m), 3.64 (2H, d), 3.83 (3H, s), 4.58-4.64 (1H, m), 5.60 (2H, s), 6.59 (1H, d), 7.09 (1H, d), 7.33 (1H, d), 8.80 (1H, d); MS m/z 306 [M+H]$^+$.

Supplier Details
Apin Chemicals Ltd
43d Milton Park
Abingdon
Oxon
OX14RU
UK
ABChem Inc
5785 Chemin St-Francois
VIIIe St-Laurent
Quebec H4S1B6, Canada
ABCR GmbH & Co. KG
Im Schlehert 10
D-76187 Karlsruhe
Germany
Activate Scientific GMBH
Eichenstrasse 36
D-93161 Regensburg
Germany
Sigma-Aldrich Company Ltd.
The Old Brickyard
New Road
Gillingham
Dorset
SP8 4XT
UK
Apollo Scientific Ltd.
Whitefield Rd.
Bredbury,
Stockport,
Cheshire,
SK6 2QR
United Kingdom
ASDI Inc
601 Interchange Blvd.
Newark,
Del., 19711
USA
Asinex Ltd.
6 Schukinskaya Street
Moscow
123182
Russia
CBI Building Blocks
40-144 Leninsky Prospect,
Moscow, 119334
Russia
ChemBridge Corporation
16981 Via Tazon
Suite G
San Diego
Calif. 92127
USA
ChemPacific Corporation
6200 Freeport Center
Baltimore
Md. 21224
USA
Chembasics Pty Ltd
5 Blarney St
Unit 1
O'Connor
WA 6163
Australia
Chemstep
Avenue Victor Hugo
Carbon Blanc
33560
France
Enamine Ltd.
23 Alexandra Matrosova Street Kiev
01103
Ukraine
Maybridge
Treville
Tintagel
Cornwall
PL34 OHW
UK
Fluka Chemie AG
Industriestrasse 25
9471 Buchs
Switzerland
Fluorochem Ltd
Wesley Street
Glossop
Derbyshire
SK13 7RY
UK
Frinton Laboratories, Inc.
P.O. Box 2428
NJ, 08362
United States
Matrix Marketing GMBH
Bahnweg Nord 35
CH-9475 Sevelen
Switzerland
Suzhou ChonTech PharmaChem Technology Company Ltd
77 Jinfeng Rd.
Suzhou
Jiang
China
TimTec LLC
Harmony Business Park Building 301-A
Newark
Del.
USA
19711
Zelinsky Institute of Organic Chemistry
47 Leninsky Prospect
Moscow, 117913
Russia Biological Assays for inhibition of PLK The following assay was used to measure the effects of the compounds of the present invention as Plk kinase inhibitors.

In Vitro Plk1 Enzyme Assay

The assay uses Scintillation Proximity Assay (SPA) technology (Antonsson et al., Analytical Biochemistry, 1999, 267: 294-299) to determine the ability of test compounds to inhibit phosphorylation by recombinant Plk1. The full-length Plk1 protein is expressed in insect cells as an N-terminal 6His tag fusion and purified by standard Nickel chelate purification techniques using the His tag.

The amino terminal fragment of Cdc25C (encoding residues 1-165) is expressed in *E. coli* as a GST fusion and purified using the GST tag by standard purification techniques.

Test compounds were prepared as 10 mM stock solutions in dimethyl sulphoxide (DMSO) and diluted into water as required to give a range of final assay concentrations. Aliquots (5 µl) of each compound dilution were dispensed into a well of a 384-well flat bottom white polystyrene plate (Matrix, Catalogue No. 4316). A 35 µl mixture of recombinant purified Plk1 enzyme (12 ng/well), purified GST-Cdc25C (150 ng/well), adenosine triphosphate (ATP; 64 nM), $^{33}$P-labelled adenosine triphosphate ($^{33}$P-ATP; 60 nCi/well) in a buffer solution [comprising 50 mM HEPES pH7.5 buffer, 10 mM manganese chloride ($MnCl_2$), 1 mM dithiothreitol (DTT), 1 mg/ml bovine serum albumin (BSA), 100 µM sodium vanadate ($Na_3VO_4$), 100 µM sodium fluoride (NaF) and 10 mM sodium glycerophosphate] was added and the reactions incubated at ambient temperature for 90 minutes.

Reactions were stopped by addition of EDTA (110 mM) and the Cdc25C substrate captured via its GST tag to anti-GST antibody (Molecular Probes, Cat No A-5800) coated Protein A PVT SPA beads (Amersham Biosciences, Catalogue No. RPQ0019; 250 µg/well) in 50 mM HEPES pH7.5 buffer containing 0.05% (w/v) sodium azide and incubated for up to 2 hours, followed by the addition of 20 µl of 4M caesium chloride (final assay concentration of 1M). Plates were then left in the dark overnight before counting on a Packard TopCount NXT.

Radiolabelled phosphorylated substrate is formed in situ as a result of Plk1 mediated phosphorylation. The SPA beads contain a scintillant that can be stimulated to emit light. This stimulation only occurs when a radiolabelled phosphorylated substrate is bound to the surface of the coated SPA bead causing the emission of blue light that can be measured on a scintillation counter. Accordingly, the extent of Plk1 mediated Cdc25C phosphorylation was assessed. The raw assay data were then analysed by non-linear regression analysis and Plk1 enzyme inhibition for a given test compound is expressed as an IC50 value.

The following examples were tested in this assay and were measured to have IC50 values less than 100 uM

| | | | | | | | | | | | |
|---|---|---|---|---|---|---|---|---|---|---|---|
| 4, | 50, | 51, | 53, | 54, | 74, | 77, | 88, | 94, | 96, | 99, | 116, |
| 117, | 118, | 120, | 121, | 122, | 123, | 125, | 133, | 134, | 135, | 136, | 137, |
| 140, | 141, | 144, | 145, | 146, | 147, | 148, | 149, | 151, | 153, | 154, | 155, |
| 156, | 157, | 158, | 159, | 160, | 163, | 164, | 166, | 168, | 169, | 172, | 174, |
| 175, | 177, | 180, | 183, | 187, | 199, | 205, | 239, | 247, | 248, | 249, | 251, |
| 253, | 254, | 255, | 256, | 257, | 258, | 260, | 261, | 263, | 264, | 265, | 266, |
| 268, | 273, | 275, | 276, | 277, | 433, | | | | | | | with the following examples having IC50 values less than 1 uM

| | | | | | | | | | | | |
|---|---|---|---|---|---|---|---|---|---|---|---|
| 7, | 8, | 12, | 24, | 31, | 32, | 35, | 36, | 37, | 38, | 52, | 65, |
| 67, | 70, | 76, | 80, | 81, | 89, | 90, | 93, | 95, | 98, | 105, | 107, |
| 109, | 112, | 113, | 115, | 124, | 128, | 129, | 130, | 131, | 132, | 138, | 139, |
| 143, | 150, | 161, | 162, | 165, | 173, | 178, | 179, | 182, | 184, | 191, | 195, |
| 196, | 197, | 200, | 212, | 215, | 216, | 220, | 223, | 225, | 226, | 227, | 228, |
| 230, | 233, | 238, | 243, | 244, | 250, | 259, | 262, | 267, | 272, | 282, | 323, |
| 383, | 410, | | | | | | | | | | | with the following having IC50 values less than 0.3 uM

| | | | | | | | | | | | |
|---|---|---|---|---|---|---|---|---|---|---|---|
| 1, | 2, | 5, | 6, | 9, | 10, | 11, | 13, | 14, | 15, | 16, | 17, |
| 18, | 19, | 20, | 21, | 22, | 23, | 25, | 26, | 27, | 28, | 29, | 30, |
| 33, | 34, | 39, | 40, | 41, | 42, | 43, | 44, | 45, | 46, | 47, | 48, |
| 49, | 55, | 56, | 57, | 58, | 59, | 60, | 61, | 62, | 63, | 64, | 69, |
| 71, | 72, | 73, | 75, | 78, | 82, | 83, | 84, | 85, | 86, | 87, | 91, |
| 92, | 100, | 102, | 104, | 111, | 114, | 119, | 142, | 170, | 176, | 181, | 185, |
| 186, | 188, | 189, | 193, | 194, | 201, | 202, | 203, | 206, | 207, | 208, | 209, |
| 210, | 211, | 212, | 213, | 217, | 218, | 219, | 221, | 222, | 224, | 229, | 231, |
| 232, | 234, | 235, | 236, | 237, | 240, | 241, | 245, | 246, | 269, | 270, | 281, |
| 283, | 314, | 315, | 316, | 317, | 318, | 319, | 320, | 321, | 322, | 325, | 326, |
| 327, | 328, | 382, | 385, | 386, | 387, | 430, | 431, | 432. | | | |

For example, Example 14 was measured to have an IC50 of 110 nM, Cell IC50 92 nM.

Cellular Assay

Chromosome condensation in mitosis is accompanied by phosphorylation of histone H3 on serine 10. Dephosphorylation begins in anaphase and ends at early telophase, thus histone H3 serine 10 phosphorylation acts as an excellent mitotic marker and is used to determine the ability of compounds of the present invention to block cells in mitosis.

Cells of the human colon tumour cell line HT29 were seeded into 96 well black plates (Costar, Catalogue No 3904) in phenol red free Dulbecco's Modified Eagles Medium (DMEM) supplemented with 10% (v/v) FCS and 1% (v/v) L-Glutamine and incubated overnight at 37° C. Test compounds were solubilised in DMSO, diluted to give a range of final assay concentrations, added to cells and incubated for 24 h at 37° C. After 24 hours, cells were fixed in 3.7% (v/v) formaldehyde then permeabilised and blocked for 10 minutes in 100 µl 0.5% (v/v) Triton X-100, 1% (w/v) bovine serum albumin (BSA) in phosphate buffered saline (PBS). After washing with PBS, 50 µl primary antibody (1:500 dilution of rabbit anti-phosphohistone H3 (Upstate Catalogue No 06-570) in 1% BSA, 0.05% Tween 20) was added to the cells that were left for 1 hour at room temperature. Cells were again washed with PBS and incubated with 50 µl secondary antibody (1:1000 Alexa Fluor 488 goat anti-rabbit (Molecular Probes Cat No A-11008) and Hoechst (1:10000) diluted in PBS 0.05% (v/v) Tween 20 and left for 1 hour at room temperature in the dark. Cells were washed with PBS then covered with fresh PBS and stored at 4° C. until analysis. Images are acquired and analysed in an automated manner using the Cellomics ArrayScan II or VTi. In this assay both hoechst and phosphohistone H3 staining are measured. Hoechst staining generates a valid cell count while phosphohistone H3 staining determines the number of mitotic cells. Inhibition of Plk leads to an increase in the population of histone H3 Ser10 positive cells, indicating inhibition of proliferation is brought about primarily by arrest of cells in the mitotic phase of the cell cycle. The raw assay data were analysed by non-linear regression analysis and used to determine an IC50 value for each compound.

The following example compounds when tested in this assay and had an IC50 value of less than 30 uM 5, 23, 24, 40, 42, 89, 103, 105, 107, 112, 115, 122, 123, 124, 125, 126, 127, 128, 129, 131, 132, 133, 138, 143, 159, 165, 167, 170, 171, 173, 177, 178, 179, 180, 186, 187, 192, 195, 212, 215, 218, 220, 221, 223, 224, 228, 229, 230, 231, 232, 233, 248, 253, 256, 257, 263, 264, 265, 270, 271, 272, 275, 277, 284, 286, 287, 296, 297, 332, 410 with the following examples having an IC50 less than 1 uM 4, 7, 26, 27, 47, 51, 53, 56, 77, 97, 99, 101, 104, 106, 108, 110, 113, 114, 135, 176, 182, 184, 191, 197, 202, 219, 234, 238, 239, 242, 269, 278, 279, 281, 282, 285, 289, 290, 293, 294, 295, 301, 302, 309, 310, 311, 330, 331, 390, 405, 411, 413, 416, 419, 429, 451 with the following example have an IC50 of less than 0.3 uM 1, 2, 3, 6, 8, 10, 11, 12, 13, 14, 15, 16, 17, 18, 19, 20, 21, 22, 25, 28, 29, 30, 31, 32, 33, 34, 35, 36, 37, 38, 39, 41, 43, 44, 45, 46, 48, 49, 50, 52, 54, 55, 57, 58, 59, 60, 61, 62, 63, 64, 66, 67, 68, 69, 70, 71, 72, 73, 74, 75, 76, 78, 79, 80, 81, 82, 83, 84, 85, 86, 88, 90, 91, 92, 93, 94, 95, 96, 98, 109, 181, 185, 188, 189, 193, 194, 199, 200, 201, 203, 205, 206, 207, 208, 209, 210, 212, 213, 217, 235, 236, 237, 240, 241, 243, 244, 245, 246, 280, 283, 288, 291, 292, 298, 299, 300, 303, 304, 305, 306, 307, 308, 312, 313, 314, 315, 316, 317, 318, 319, 320, 321, 322, 323, 325, 326, 327, 328, 329, 333, 334, 335, 336, 337, 338, 340, 341, 342, 343, 344, 345, 346, 347, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 382, 383, 384, 385, 386, 387, 388, 389, 391, 392, 393, 394, 395, 396, 397, 398, 399, 400, 401, 402, 403, 404, 406, 407, 408, 409, 412, 414, 415, 417, 418, 420, 421, 422, 423, 424, 425, 426, 427, 428, 430, 431, 432, 433, 434, 435, 436, 437, 438, 440, 441, 442, 443, 444, 445, 446 and 453.

For example, Example 14 was measured to have an IC50 92 nM.
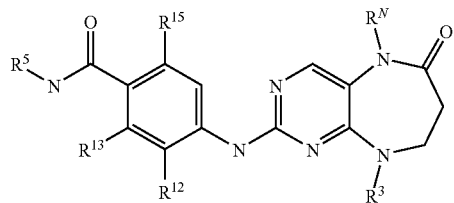
| Example | R³ | Rᴺ | R¹² | R¹³ | R¹⁵ | R⁵ |
|---|---|---|---|---|---|---|
| Example 1: | Cyclopentyl | Me | OMe | H | H | 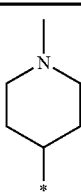 |
| Example 2: | Cyclopentyl | Me | H | H | H | 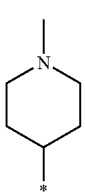 |
| Example 6: | ⁱPr | Me | OMe | H | H | 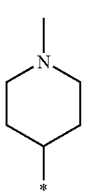 |
| Example 8: | Cyclohexyl | Me | OMe | H | H | 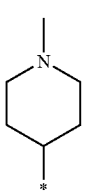 |
| Example 10: | Cyclopentyl | Me | OMe | H | H | 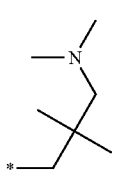 |
| Example 11: | Cyclopentyl | Me | OMe | H | H | 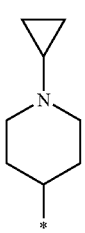 |

-continued

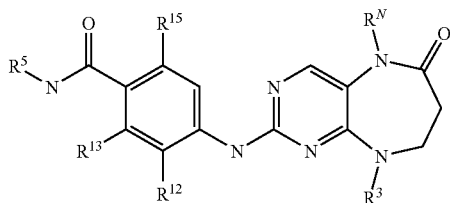

| Example | $R^3$ | $R^N$ | $R^{12}$ | $R^{13}$ | $R^{15}$ | $R^5$ |
|---|---|---|---|---|---|---|
| Example 12: | Cyclopentyl | Me | OMe | H | H | *-CH2CH2-piperidinyl |
| Example 13: | Cyclopentyl | Me | OMe | H | H | morpholinyl-CH2CH2-* |
| Example 14: | Cyclopentyl | Me | OMe | H | H | *-CH2CH2-N(Me)2 |
| Example 15: | Cyclopentyl | Me | OMe | H | H | N-ethyl-2-pyrrolidinyl-CH2-* (Chiral) |
| Example 16: | Cyclopentyl | Me | OMe | H | H | *-CH2CH2-pyrrolidinyl |
| Example 17: | Cyclopentyl | Me | OMe | H | H | *-CH(Me)CH2CH2CH2-N(Et)2 (Chiral) |
| Example 18: | Cyclopentyl | Me | OMe | H | H | *-CH2CH2-N(Et)2 |
| Example 19: | Cyclopentyl | Me | OMe | H | H | *-CH2CH2CH2-N(Me)2 |

-continued
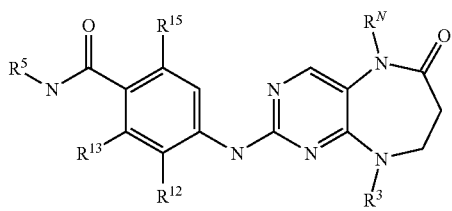
| Example | $R^3$ | $R^N$ | $R^{12}$ | $R^{13}$ | $R^{15}$ | $R^5$ |
|---|---|---|---|---|---|---|
| Example 20: | Cyclopentyl | Me | OMe | H | H | 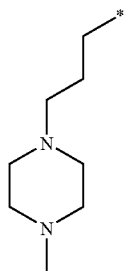 |
| Example 21: | Cyclopentyl | Me | OMe | H | H | 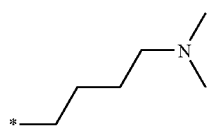 |
| Example 22: | Cyclopentyl | Me | OMe | H | H | 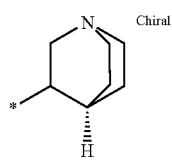 |
| Example 23: | Cyclopentyl | Me | OMe | H | H | 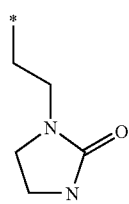 |
| Example 24: | Cyclopentyl | Me | OMe | H | H | 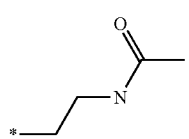 |
| Example 25: | Cyclopentyl | Me | OMe | H | H | 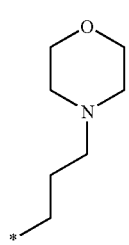 |

-continued
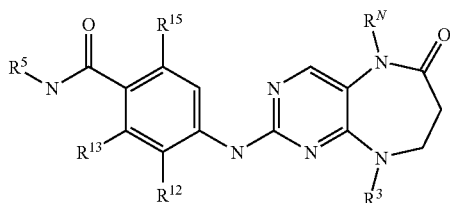
| Example | R³ | R^N | R¹² | R¹³ | R¹⁵ | R⁵ |
|---|---|---|---|---|---|---|
| Example 26: | Cyclopentyl | Me | OMe | H | H | 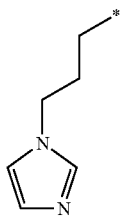 |
| Example 27: | Cyclopentyl | Me | OMe | H | H | 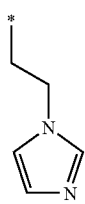 |
| Example 28: | Cyclopentyl | Me | OMe | H | H | 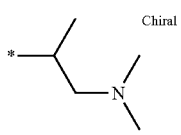 Chiral |
| Example 29: | Cyclopentyl | Me | OMe | H | H | 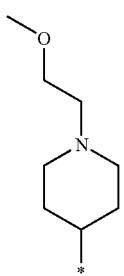 |
| Example 30: | Cyclopentyl | Me | OMe | H | H | 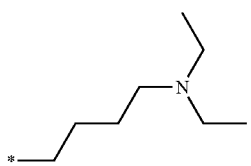 |
| Example 31: | Cyclopentyl | Me | OMe | H | H | 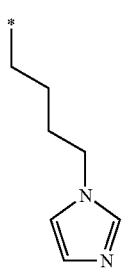 |

-continued
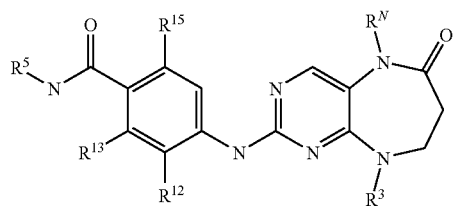
| Example | R³ | Rᴺ | R¹² | R¹³ | R¹⁵ | R⁵ |
|---|---|---|---|---|---|---|
| Example 32: | Cyclopentyl | Me | OMe | H | H | 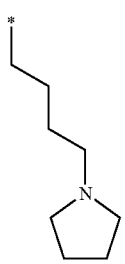 Chiral |
| Example 33: | Cyclopentyl | Me | OMe | H | H | 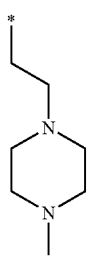 |
| Example 34: | Cyclopentyl | Me | OMe | H | H | 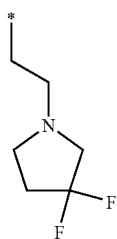 |
| Example 35: | Cyclopentyl | Me | OMe | H | H | 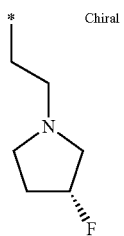 |
| Example 36: | Cyclopentyl | Me | OMe | H | H | Chiral |

-continued
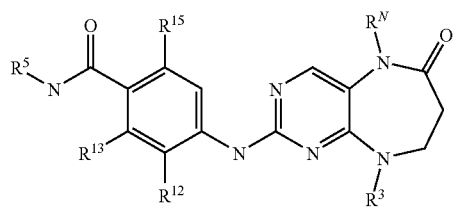
| Example | $R^3$ | $R^N$ | $R^{12}$ | $R^{13}$ | $R^{15}$ | $R^5$ |
|---|---|---|---|---|---|---|
| Example 37: | Cyclopentyl | Me | OMe | H | H | 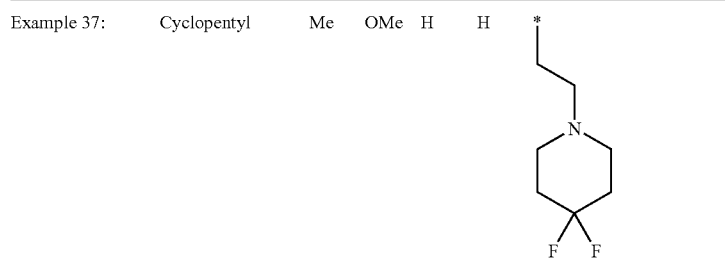 |
| Example 38: | Cyclopentyl | Me | OMe | H | H | 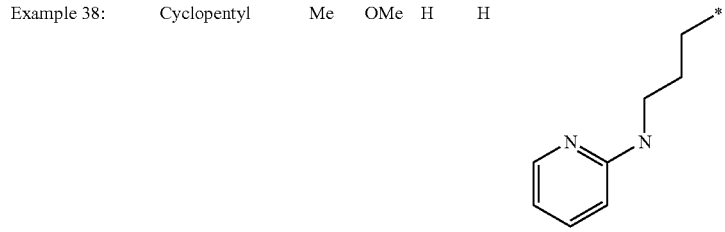 |
| Example 39: | Cyclopentyl | Me | OMe | H | H | 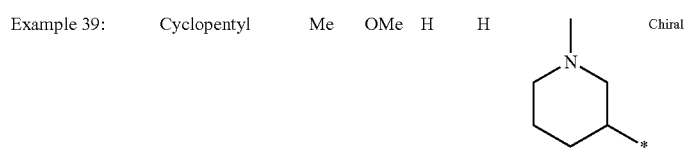 |
| Example 40: | Cyclopentyl | Me | OMe | H | H | 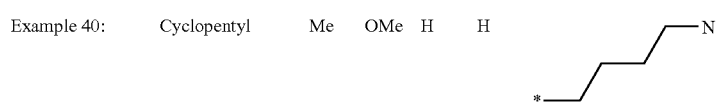 |
| Example 41: | Cyclopentyl | Me | OMe | H | H | 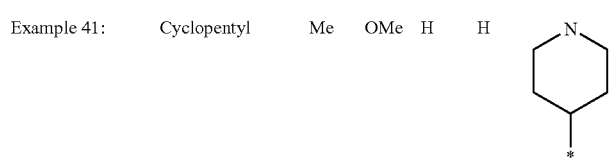 |
| Example 42: | Cyclopentyl | Me | OMe | H | H | 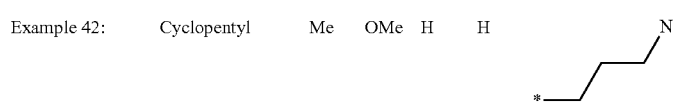 |
| Example 43: | Cyclopentyl | Me | OMe | H | H | 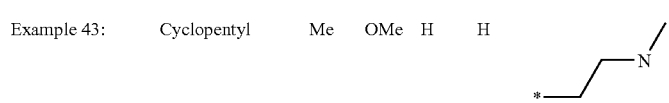 |
| Example 44: | Cyclopentyl | Me | OMe | H | H | 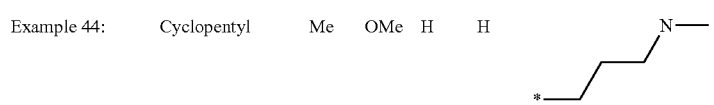 |

-continued
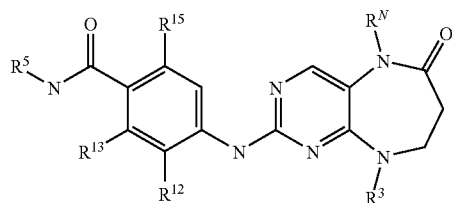
| Example | $R^3$ | $R^N$ | $R^{12}$ | $R^{13}$ | $R^{15}$ | $R^5$ |
|---|---|---|---|---|---|---|
| Example 45: | Cyclopentyl | Me | OMe | H | H |  Chiral |
| Example 46: | Cyclopentyl | Me | OMe | H | H | 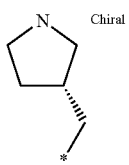 |
| Example 47: | Cyclopentyl | Me | OMe | H | H | 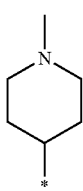 Chiral |
| Example 48: | Cyclopentyl | Me | OMe | H | F | 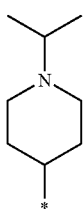 |
| Example 49: | Cyclopentyl | Me | OMe | H | H | 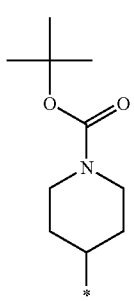 |
| Example 50: | Cyclopentyl | Me | OMe | H | H | 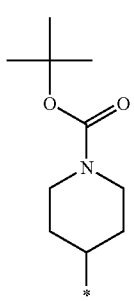 |

-continued
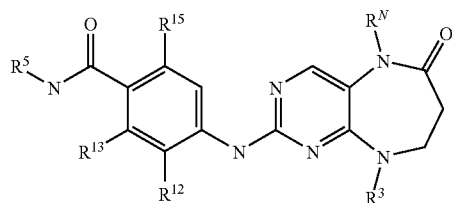
| Example | R³ | R^N | R¹² | R¹³ | R¹⁵ | R⁵ |
|---|---|---|---|---|---|---|
| Example 51: | Cyclopentyl | Me | OMe | H | H | 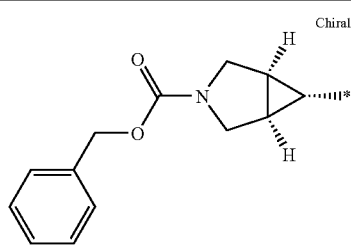 |
| Example 52: | Cyclopentyl | Me | OMe | H | H | 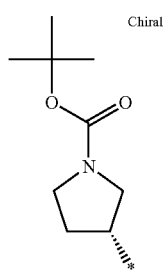 |
| Example 53: | Cyclopentyl | Me | OMe | H | H | 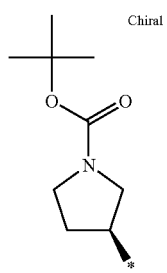 |
| Example 54: | Cyclopentyl | Me | OMe | H | H | 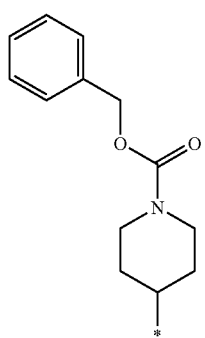 |
| Example 55: | Cyclopentyl | Me | OMe | H | H | 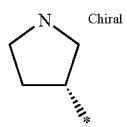 |

-continued

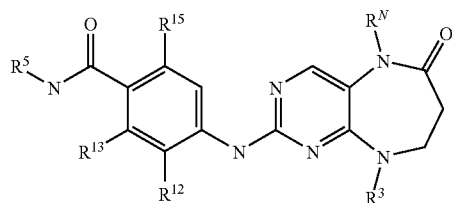

| Example | R³ | Rᴺ | R¹² | R¹³ | R¹⁵ | R⁵ |
|---|---|---|---|---|---|---|
| Example 56: | Cyclopentyl | Me | OMe | H | H | (3-pyrrolidinyl, Chiral) |
| Example 57: | Cyclopentyl | Me | OMe | H | H | (3-azabicyclo[3.1.0]hexyl, Chiral) |
| Example 58: | Cyclopentyl | Me | OMe | H | H | (4-(diethylamino)cyclohexyl) |
| Example 59: | Cyclopentyl | Me | OMe | H | H | (N-methyl-8-azabicyclo[3.2.1]octyl, Chiral) |
| Example 60: | Cyclopentyl | Me | OMe | H | H | (4-(dimethylamino)cyclohexyl) |
| Example 61: | Cyclopentyl | Me | OMe | H | H | (1-ethylpiperidin-4-yl) |
| Example 62: | Cyclopentyl | Me | OMe | H | H | (1-methylpyrrolidin-3-yl, Chiral) |

-continued
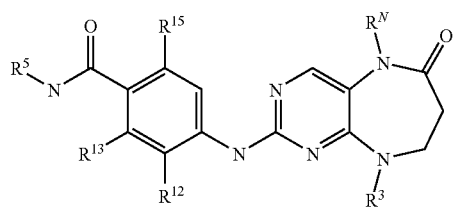
| Example | R³ | Rᴺ | R¹² | R¹³ | R¹⁵ | R⁵ |
|---|---|---|---|---|---|---|
| Example 63: | Cyclopentyl | Me | OMe | H | H | 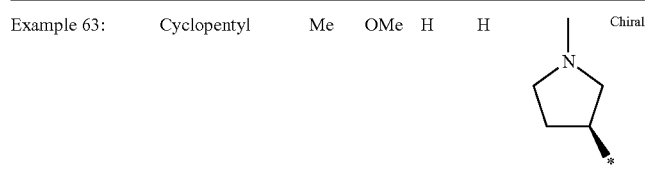 |
| Example 64: | Cyclopentyl | Me | OMe | H | H | 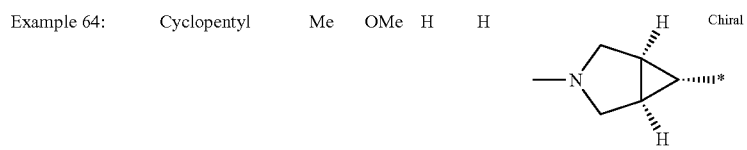 |
| Example 65: | Cyclopentyl | Me | OMe | H | H | 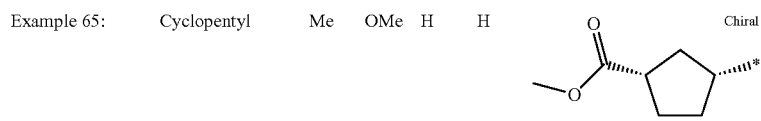 |
| Example 66: | Cyclopentyl | Me | OMe | H | H | 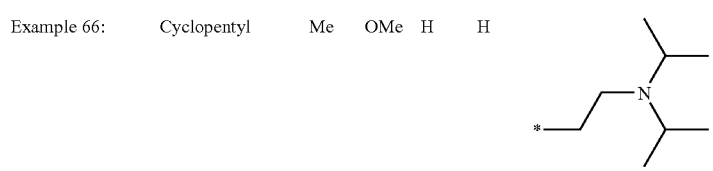 |
| Example 67: | Cyclopentyl | Me | OMe | H | H | 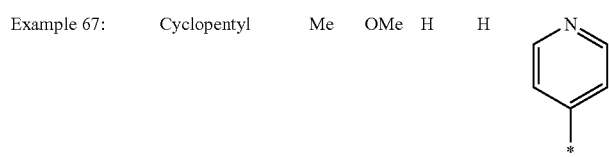 |
| Example 68: | Cyclopentyl | Me | OMe | H | H | 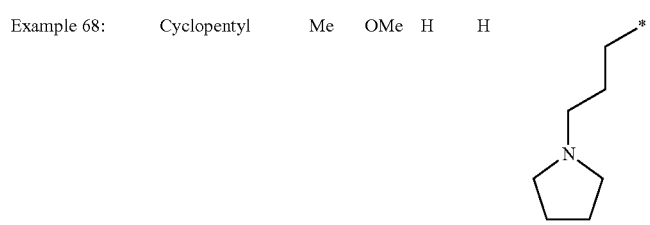 |
| Example 69: | Cyclopentyl | Me | OMe | H | H | 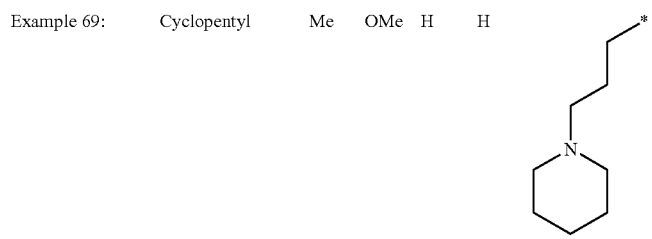 |

-continued
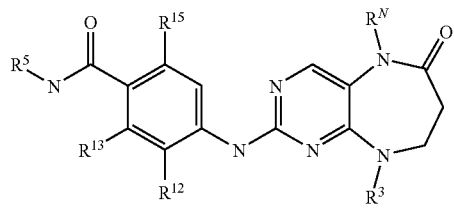
| Example | R³ | R^N | R¹² | R¹³ | R¹⁵ | R⁵ |
|---|---|---|---|---|---|---|
| Example 70: | Cyclopentyl | Me | OMe | H | H | 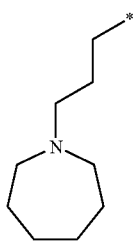 |
| Example 71: | Cyclopentyl | Me | OMe | H | H | 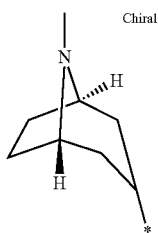 |
| Example 72: | Cyclopentyl | Me | OMe | H | H | 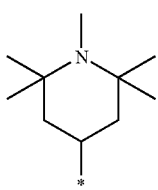 |
| Example 73: | Cyclopentyl | Me | OMe | H | H | 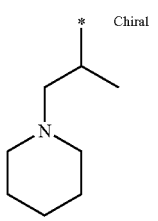 |
| Example 74: | Cyclopentyl | Me | OMe | H | H | 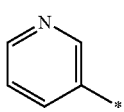 |
| Example 75: | Cyclopentyl | Me | OMe | H | H | 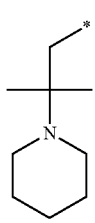 |

-continued
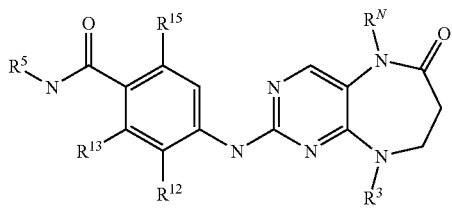
| Example | R³ | Rᴺ | R¹² | R¹³ | R¹⁵ | R⁵ |
|---|---|---|---|---|---|---|
| Example 76: | Cyclopentyl | Me | OMe | H | H | 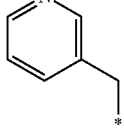 |
| Example 77: | Cyclopentyl | Me | OMe | H | H | 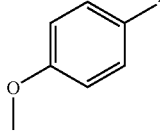 |
| Example 78: | Cyclopentyl | Me | OMe | H | H | 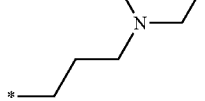 |
| Example 79: | Cyclopentyl | Me | OMe | H | H | 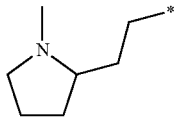 Chiral |
| Example 80: | Cyclopentyl | Me | OMe | H | H | 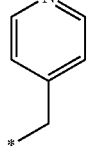 |
| Example 81: | Cyclopentyl | Me | OMe | H | H | 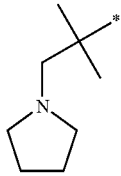 |
| Example 82: | Cyclopentyl | Me | OMe | H | H | 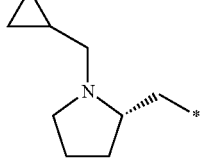 Chiral |
| Example 83: | Cyclopentyl | Me | OMe | H | H | 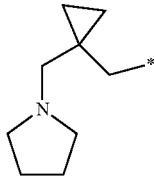 |

-continued
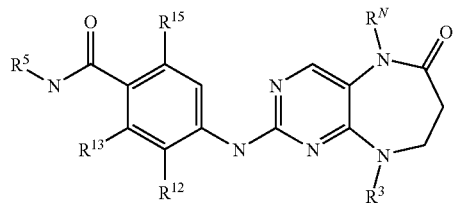
| Example | R³ | R^N | R¹² | R¹³ | R¹⁵ | R⁵ |
|---|---|---|---|---|---|---|
| Example 84: | Cyclopentyl | Me | OMe | H | H | 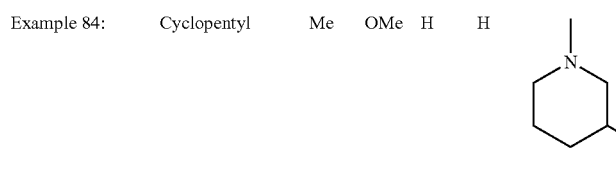 |
| Example 85: | Cyclopentyl | Me | OMe | H | H | 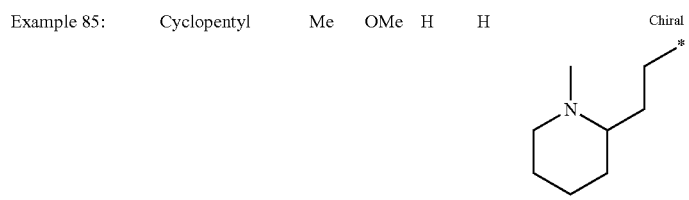 |
| Example 86: | Cyclopentyl | Me | OMe | H | H | 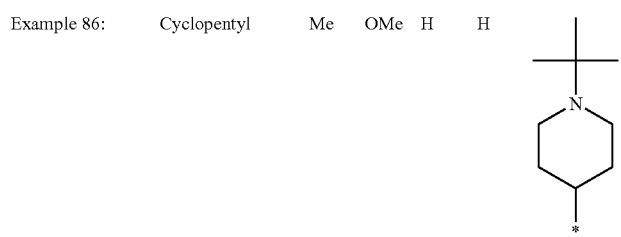 |
| Example 87: | Cyclopentyl | Me | OMe | H | H | 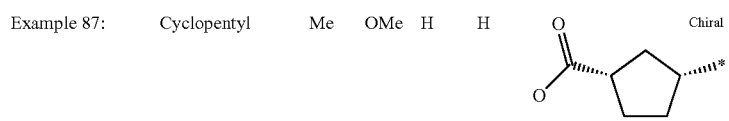 |
| Example 88: | Cyclopentyl | Me | OMe | H | H | 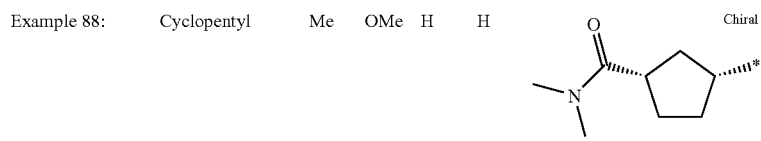 |
| Example 89: | Cyclopentyl | Me | H | H | H | 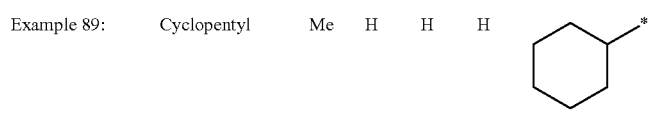 |
| Example 90: | Cyclopentyl | Me | OMe | H | H | 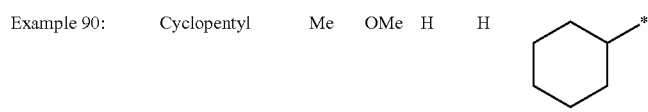 |
| Example 91: | Cyclopentyl | Me | OMe | H | H | *— |
| Example 92: | Cyclopentyl | Me | OMe | H | H | H |
| Example 93: | Cyclopentyl | Me | OMe | H | H |  |

-continued

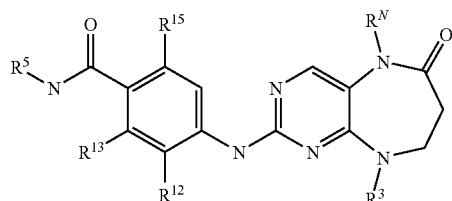

| Example | $R^3$ | $R^N$ | $R^{12}$ | $R^{13}$ | $R^{15}$ | $R^5$ |
|---|---|---|---|---|---|---|
| Example 94: | Cyclopentyl | Me | OMe | H | H | cyclopropylmethyl |
| Example 95: | Cyclopentyl | Me | OMe | H | H | isobutyl |
| Example 96: | Cyclopentyl | Me | OMe | H | H | benzyl |
| Example 97: | Cyclopentyl | Me | H | H | H | H |
| Example 98: | Cyclopentyl | Me | OMe | H | H | cyclobutyl |
| Example 99: | Cyclopentyl | Me | OMe | H | H | phenyl |
| Example 100: | Cyclopentyl | Me | H | H | H | isobutyl |
| Example 101: | Cyclopentyl | Me | H | H | H | phenyl |
| Example 102: | Cyclopentyl | Me | H | H | H | *— |
| Example 184: | Cyclopentyl | Me | Cl | H | H | 2-morpholinoethyl |
| Example 185: | Cyclopentyl | Me | Cl | H | H | 1-methylpiperidin-4-yl |

-continued

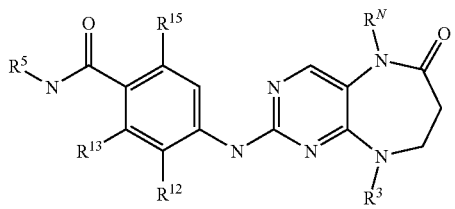

| Example | R³ | R^N | R¹² | R¹³ | R¹⁵ | R⁵ |
|---|---|---|---|---|---|---|
| Example 187: | Cyclopentyl | Me | H | H | F | 1-methylpiperidin-4-yl |
| Example 188: | Cyclopentyl | Me | F | H | F | 1-methylpiperidin-4-yl |
| Example 189: | Cyclopentyl | Me | H | H | H | 1-methylpiperidin-4-yl |
| Example 191: | Cyclopentyl | Me | H | H | H | 2-morpholinoethyl |
| Example 192: | Cyclopentyl | Me | H | H | H | 2-(diethylamino)ethyl |
| Example 193: | Cyclopentyl | Me | Me | H | H | 1-methylpiperidin-4-yl |
| Example 194: | Cyclopentyl | Me | F | H | H | 1-methylpiperidin-4-yl |

-continued
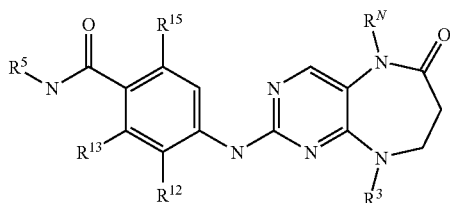
| Example | R³ | R^N | R¹² | R¹³ | R¹⁵ | R⁵ |
|---|---|---|---|---|---|---|
| Example 200: | Cyclopentyl | Me | OEt | H | H | 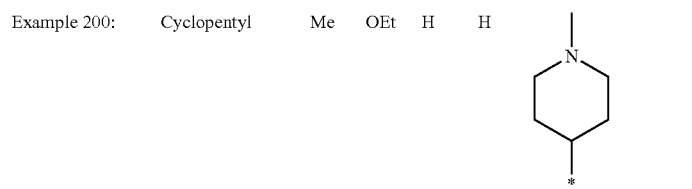 |
| Example 201: | Cyclopentyl | Me | OEt | H | H | 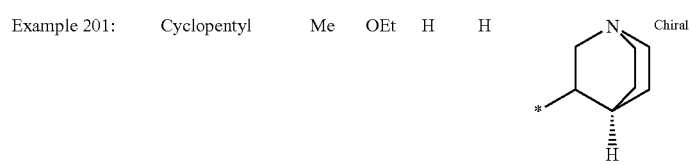 |
| Example 202: | Cyclopentyl | Me | OEt | H | H | 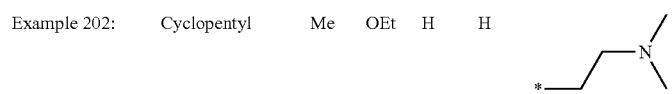 |
| Example 203: | ⁱPr | Me | Cl | H | H | 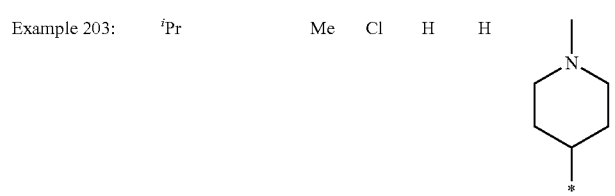 |
| Example 205: | ⁱPr | Me | OMe | H | H | 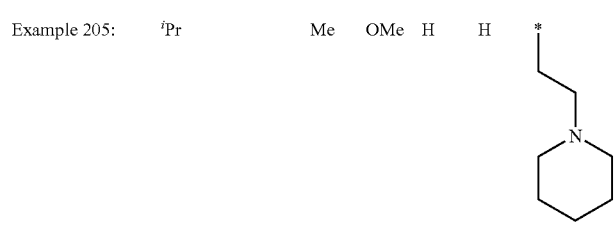 |
| Example 206: | ⁱPr | Me | OMe | H | H | 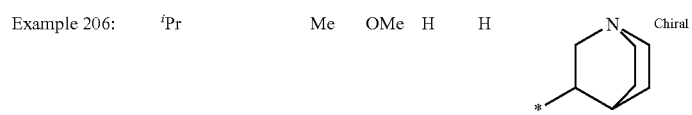 |
| Example 207: | ⁱPr | Me | OMe | H | H | 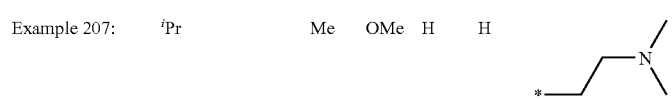 |
| Example 208: | ⁱPr | Me | OMe | H | H | 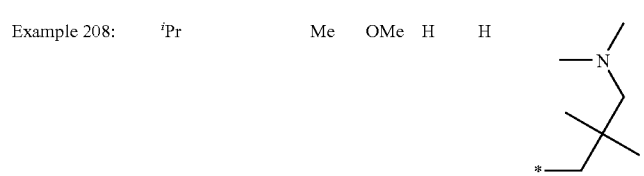 |

-continued
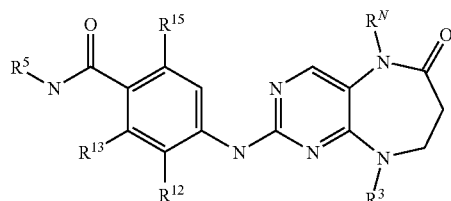
| Example | R³ | Rᴺ | R¹² | R¹³ | R¹⁵ | R⁵ |
|---|---|---|---|---|---|---|
| Example 209: | ⁱPr | Me | OMe | H | H | *-(CH₂)₄-pyrrolidin-1-yl |
| Example 218: | ⁱPr | Me | H | H | H | *-(CH₂)₂-morpholin-4-yl |
| Example 219: | ⁱPr | Me | OMe | H | H | *-(CH₂)₂-morpholin-4-yl |
| Example 222: | ⁱPr | Me | H | H | H | *-CH₂-C(Me)₂-CH₂-NMe₂ |
| Example 228: | ⁱPr | Me | Cl | H | H | *-(CH₂)₂-morpholin-4-yl |
| Example 234: | Cyclopentyl | Me | OMe | H | H | 1-methylpiperidin-4-yl |

-continued
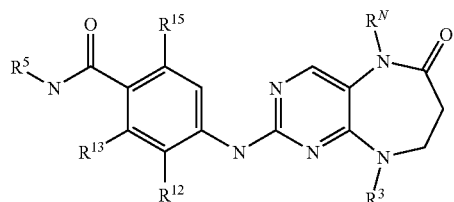
| Example | R³ | R^N | R¹² | R¹³ | R¹⁵ | R⁵ |
|---|---|---|---|---|---|---|
| Example 250: | Cyclopentyl | H | OMe | H | H | 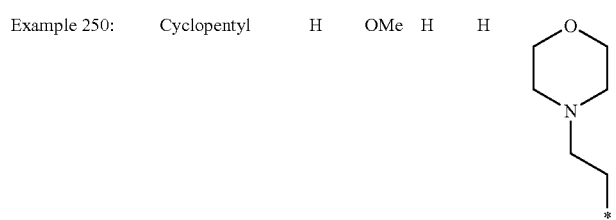 |
| Example 253: | Cyclopentyl | H | H | H | H | 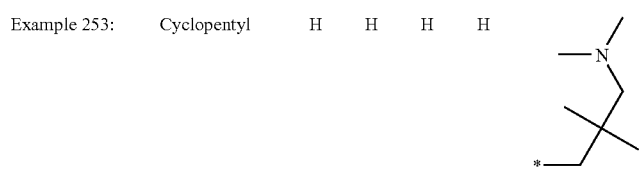 |
| Example 254: | Cyclopentyl | H | H | H | H | 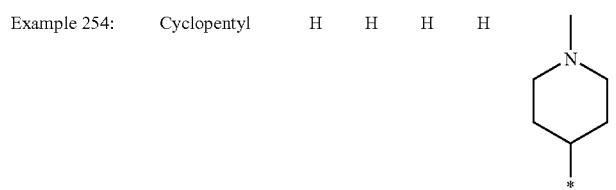 |
| Example 255: | Cyclopentyl | H | Cl | H | H | 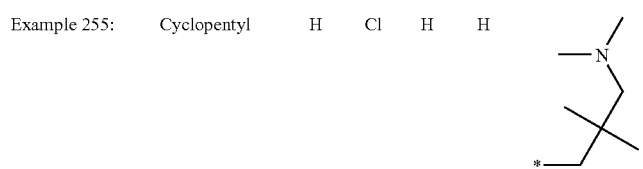 |
| Example 256: | Cyclopentyl | H | H | H | H | 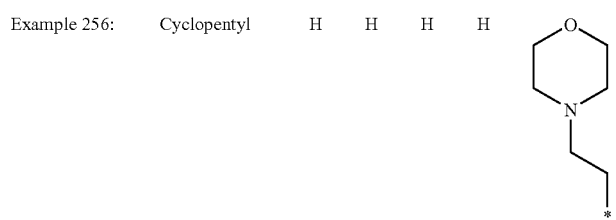 |
| Example 257: | Cyclopentyl | H | Cl | H | H | 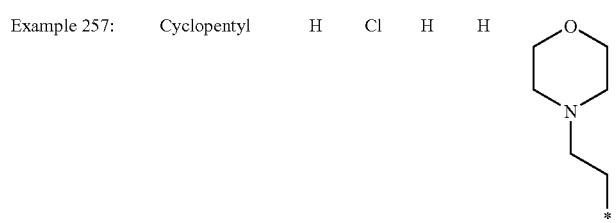 |

-continued
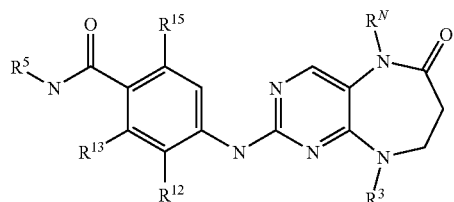
| Example | R³ | Rᴺ | R¹² | R¹³ | R¹⁵ | R⁵ |
|---|---|---|---|---|---|---|
| Example 259: | Cyclopentyl | Me | OMe | H | H | 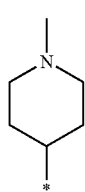 |
| Example 260: | Cyclopentyl | Me | OMe | H | H | 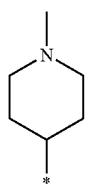 |
| Example 281: | ⁱPr | Me | OEt | H | H | 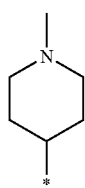 |
| Example 282: | ⁱPr | Me | OEt | H | H | 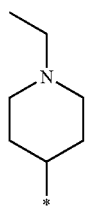 |
| Example 283: | ⁱPr | Me | OEt | H | H | 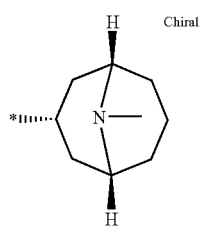 Chiral |
| Example 284: | ⁱPr | Me | OEt | H | H | 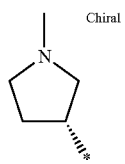 Chiral |

-continued
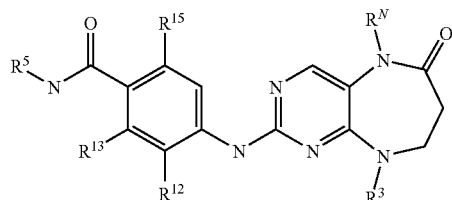
| Example | R³ | Rᴺ | R¹² | R¹³ | R¹⁵ | R⁵ |
|---|---|---|---|---|---|---|
| Example 285: | ⁱPr | Me | OEt | H | H | 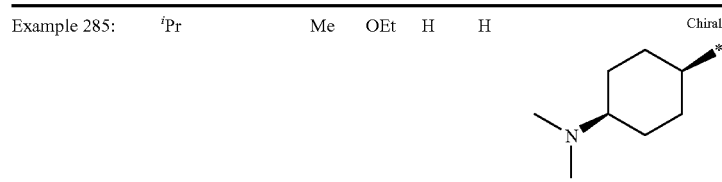 |
| Example 286: | ⁱPr | Me | OEt | H | H | 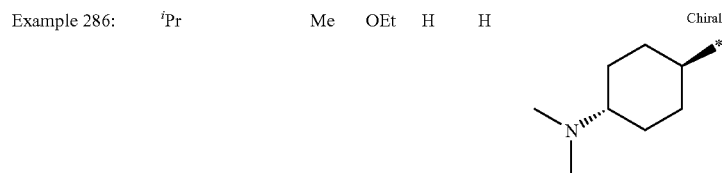 |
| Example 287: | ⁱPr | Me | OEt | H | F | 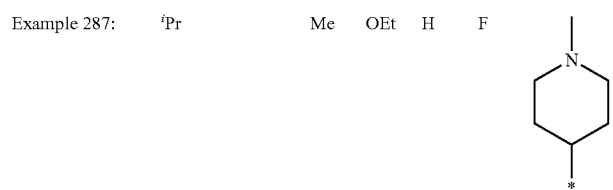 |
| Example 288: | ⁱPr | Me | OEt | H | F | 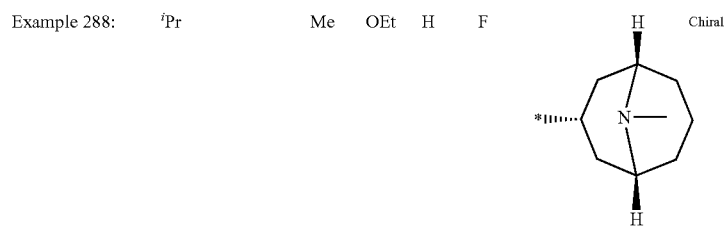 |
| Example 314: | Cyclopentyl | Me | OMe | H | H | 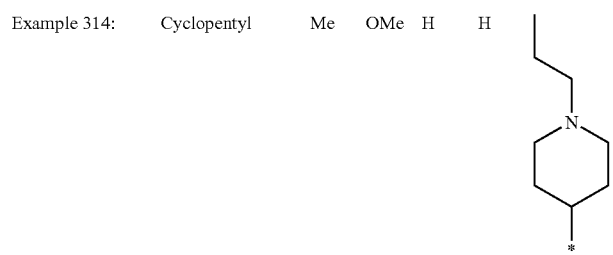 |
| Example 315: | Cyclopentyl | Me | Cl | H | H | 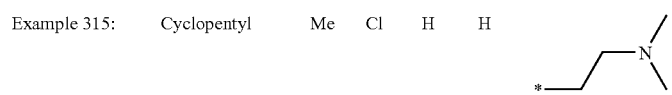 |
| Example 316: | Cyclopentyl | Me | Cl | H | H | 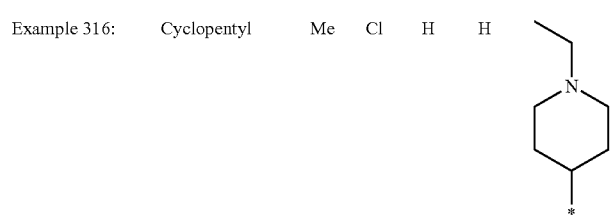 |

-continued
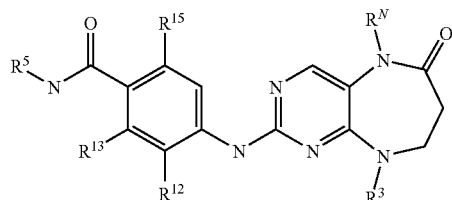
| Example | R³ | Rᴺ | R¹² | R¹³ | R¹⁵ | R⁵ |
|---|---|---|---|---|---|---|
| Example 317: | Cyclopentyl | Me | Cl | H | H | 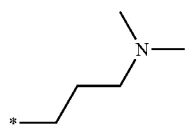 |
| Example 318: | Cyclopentyl | Me | Cl | H | H | 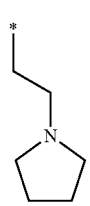 |
| Example 319: | Cyclopentyl | Me | OMe | H | H | 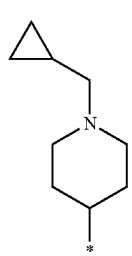 |
| Example 320: | Cyclopentyl | Me | OMe | H | Cl | 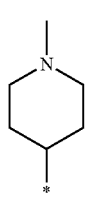 |
| Example 321: | Cyclopentyl | Me | Cl | H | F | 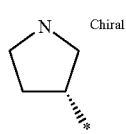 |
| Example 322: | Cyclopentyl | Me | Cl | H | F | 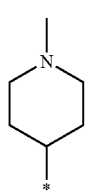 |
| Example 323: | Cyclopentyl | Me | Cl | H | F | 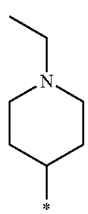 |

-continued
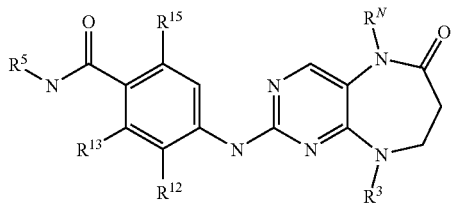
| Example | R³ | R^N | R¹² | R¹³ | R¹⁵ | R⁵ |
|---|---|---|---|---|---|---|
| Example 324: | Cyclopentyl | Me | Cl | H | F | 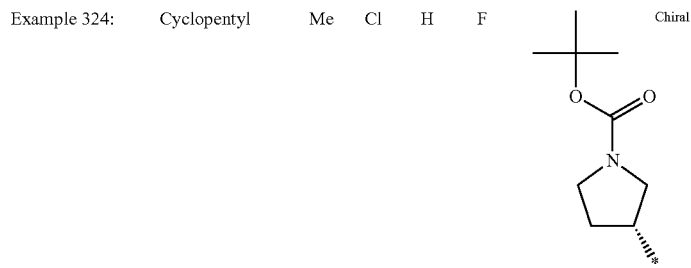 |
| Example 325: | Cyclopentyl | Me | Cl | H | F | 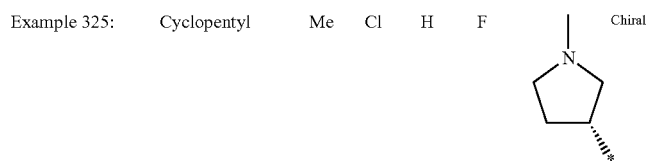 |
| Example 326: | Cyclopentyl | Me | OMe | H | H | 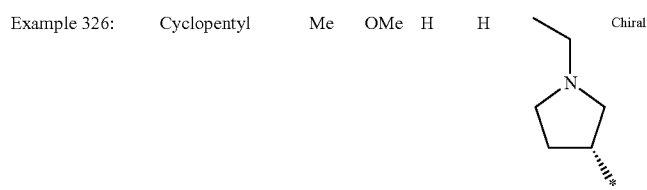 |
| Example 327: | Cyclopentyl | Me | OMe | H | H | 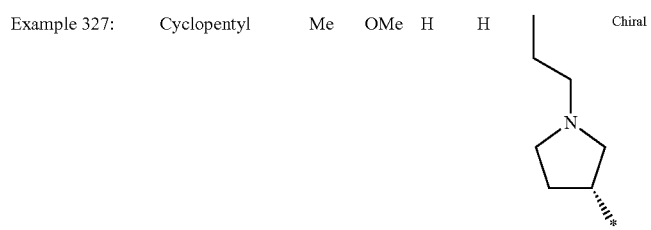 |
| Example 328: | Cyclopentyl | Me | OMe | H | H | 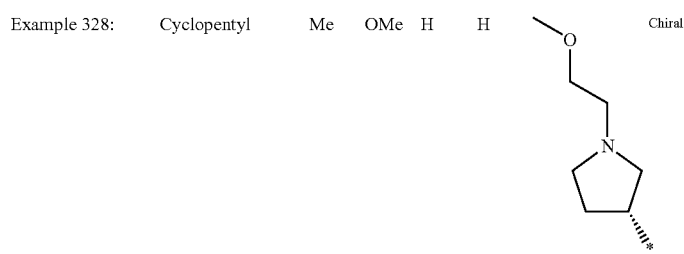 |

-continued
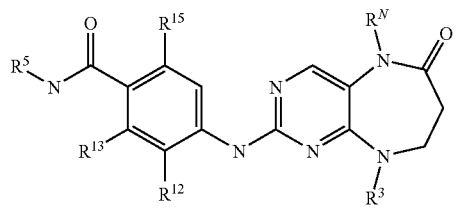
| Example | R³ | Rᴺ | R¹² | R¹³ | R¹⁵ | R⁵ |
|---|---|---|---|---|---|---|
| Example 329: | Cyclopentyl | Me | F | H | H | 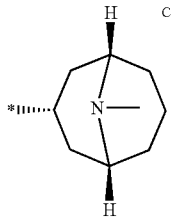 Chiral |
| Example 330: | Cyclopentyl | Me | Cl | H | H | 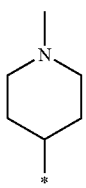 |
| Example 331: | Cyclopentyl | Me | Cl | H | H | 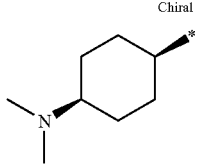 Chiral |
| Example 332: | Cyclopentyl | Me | Cl | H | H | 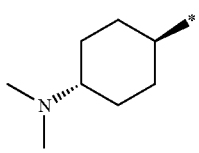 Chiral |
| Example 333: | Cyclopentyl | Me | OMe | H | F | 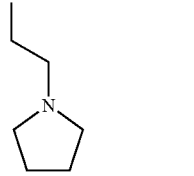 |
| Example 334: | Cyclopentyl | Me | F | H | F | 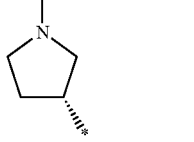 Chiral |
| Example 335: | Cyclopentyl | Me | F | H | F | 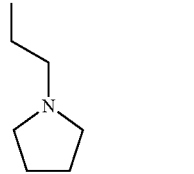 |

-continued
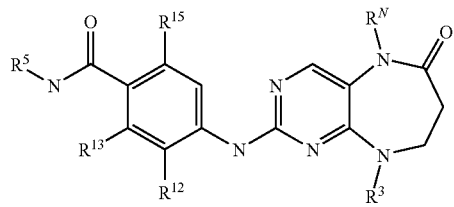
| Example | R³ | R^N | R¹² | R¹³ | R¹⁵ | R⁵ |
|---|---|---|---|---|---|---|
| Example 336: | Cyclopentyl | Me | OMe | H | Cl | 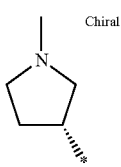 Chiral |
| Example 337: | Cyclopentyl | Me | OMe | H | Cl | 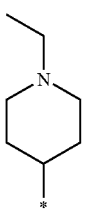 |
| Example 338: | Cyclopentyl | Me | OMe | H | Cl | 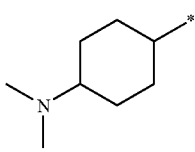 |
| Example 339: | Cyclopentyl | Me | OMe | H | Cl | 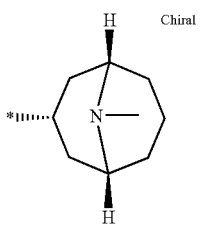 Chiral |
| Example 340: | Cyclopentyl | Me | OMe | H | H | 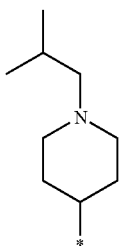 |
| Example 341: | Cyclopentyl | Me | OCH2O | H | | 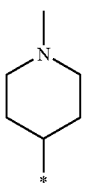 |

-continued
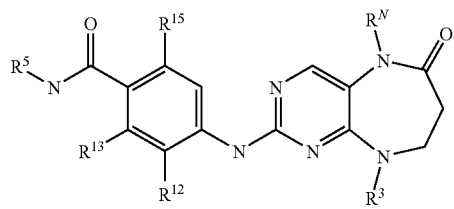
| Example | R³ | R^N | R¹² | R¹³ | R¹⁵ | R⁵ |
|---|---|---|---|---|---|---|
| Example 342: | Cyclopentyl | Me | OMe | H | H | 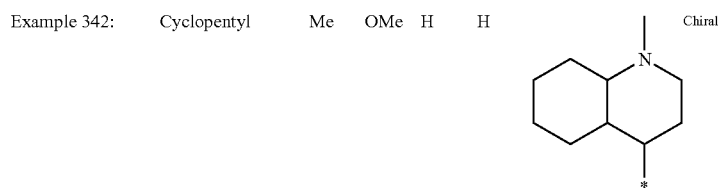 |
| Example 343: | Cyclopentyl | Me | OMe | H | H | 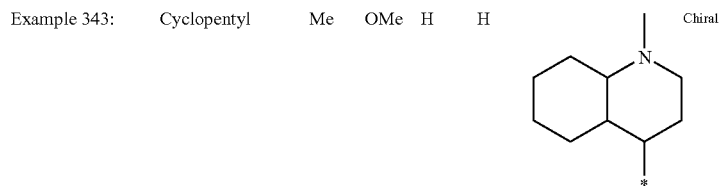 |
| Example 344: | Cyclopentyl | Me | OMe | H | F | 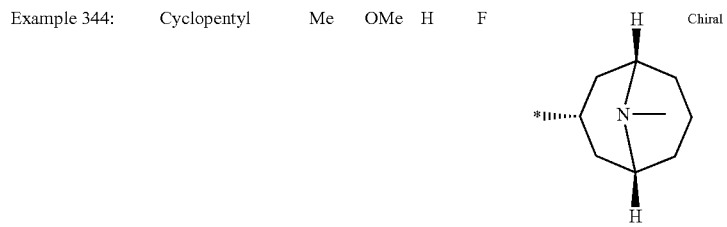 |
| Example 345: | Cyclopentyl | Me | F | H | H | 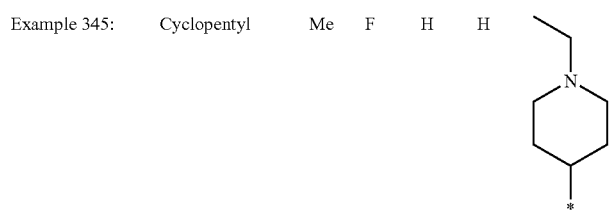 |
| Example 346: | Cyclopentyl | Me | OMe | H | H | 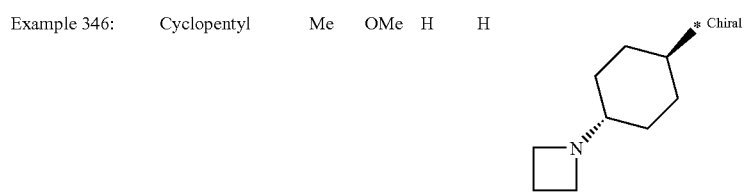 |
| Example 347: | Cyclopentyl | Me | OMe | H | H | 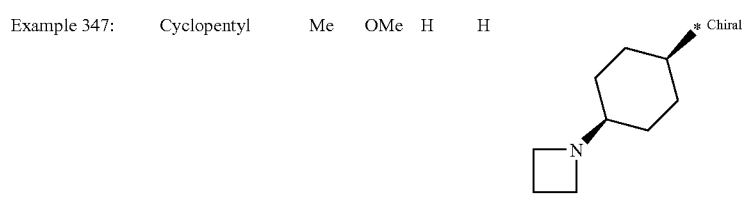 |

-continued
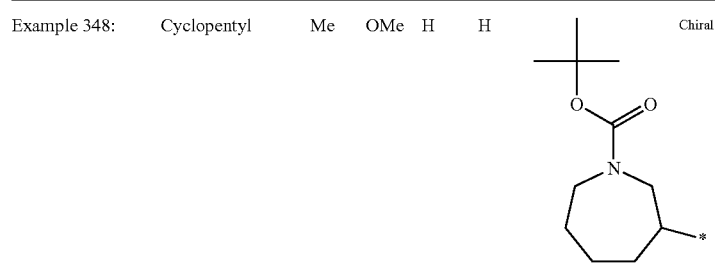
| Example | R³ | Rᴺ | R¹² | R¹³ | R¹⁵ | R⁵ | |
|---|---|---|---|---|---|---|---|
| Example 348: | Cyclopentyl | Me | OMe | H | H | 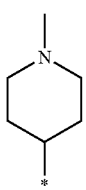 | Chiral |
| Example 411: | Cyclohexyl | Me | F | H | Cl | 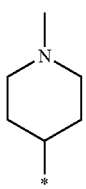 | |
| Example 412: | Cyclohexyl | Me | F | H | F | 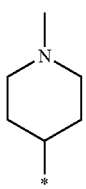 | |
| Example 413: | Cyclohexyl | Me | F | H | F | 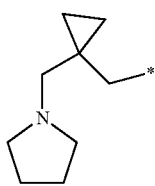 | |
| Example 414: | Cyclohexyl | Me | F | H | F | 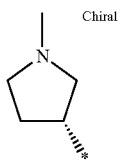 | Chiral |
| Example 415: | Cyclohexyl | Me | F | H | F | 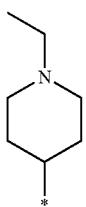 | |

-continued
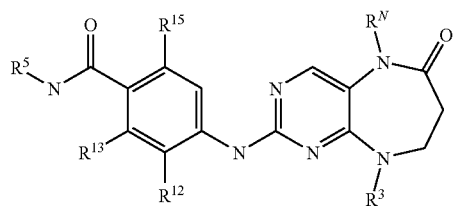
| Example | R³ | R^N | R¹² | R¹³ | R¹⁵ | R⁵ |
|---|---|---|---|---|---|---|
| Example 416: | Cyclohexyl | Me | F | H | F | 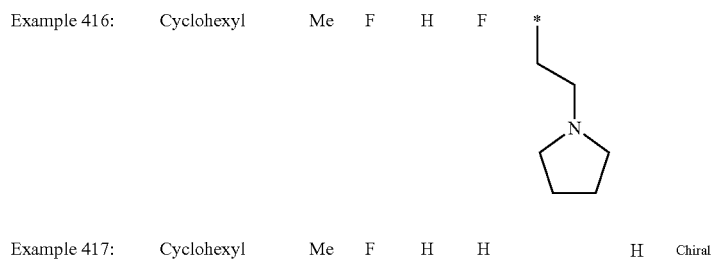 |
| Example 417: | Cyclohexyl | Me | F | H | H | 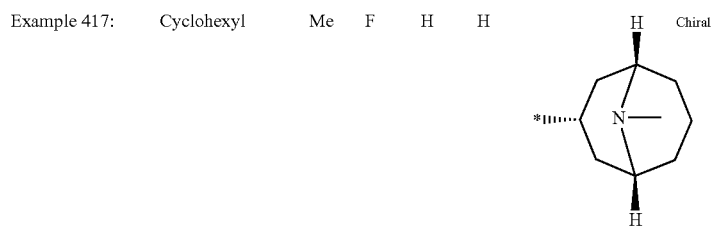 |
| Example 418: | Cyclohexyl | Me | OMe | H | H | 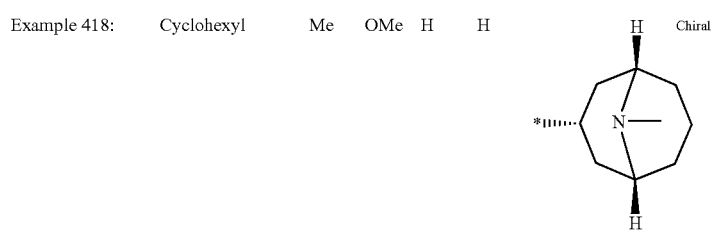 |
| Example 419: | Cyclohexyl | Me | OMe | H | F | 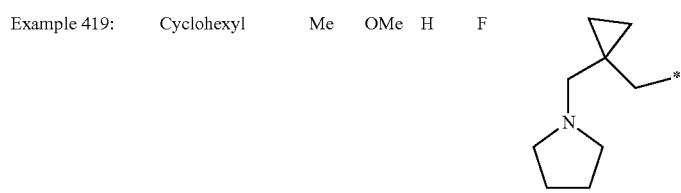 |
| Example 420: | Cyclohexyl | Me | OMe | H | F | 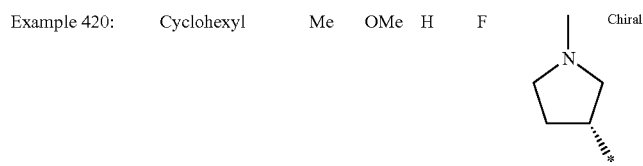 |
| Example 421: | Cyclohexyl | Me | OMe | H | H |  |

-continued
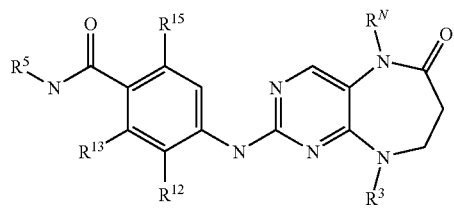
| Example | R³ | Rᴺ | R¹² | R¹³ | R¹⁵ | R⁵ |
|---|---|---|---|---|---|---|
| Example 422: | Cyclohexyl | Me | OMe | H | F | 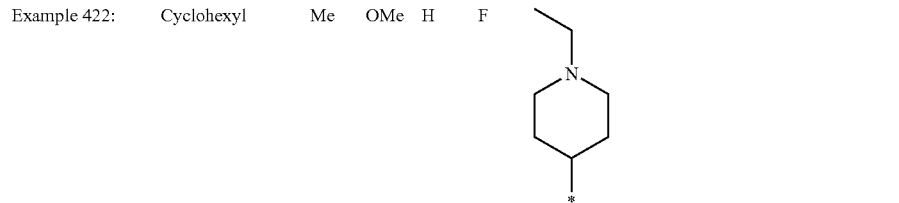 |
| Example 423: | Cyclohexyl | Me | OMe | H | H | 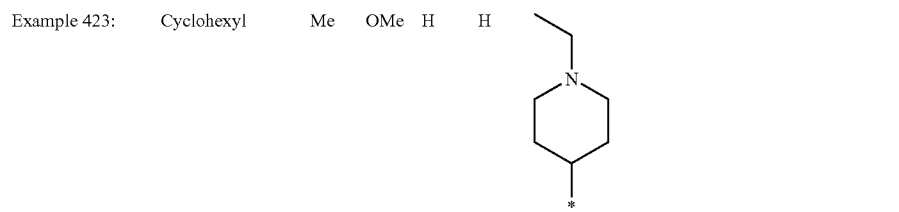 |
| Example 424: | Cyclohexyl | Me | OMe | H | H | 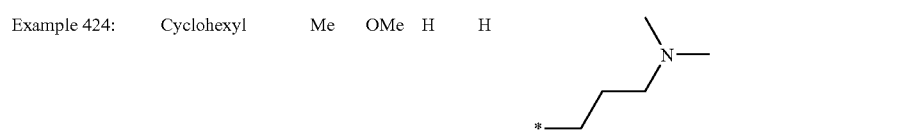 |
| Example 425: | Cyclohexyl | Me | OMe | H | F | 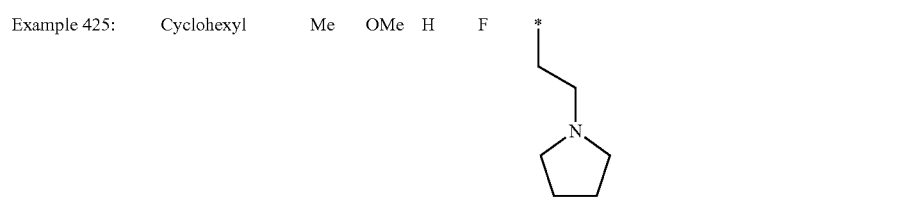 |
| Example 426: | Cyclohexyl | Me | OMe | H | H | 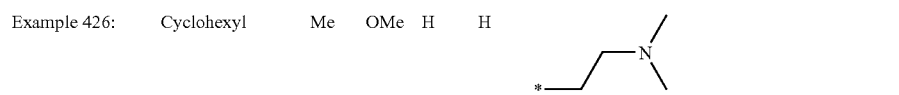 |
| Example 427: | Cyclohexyl | Me | OMe | H | F | 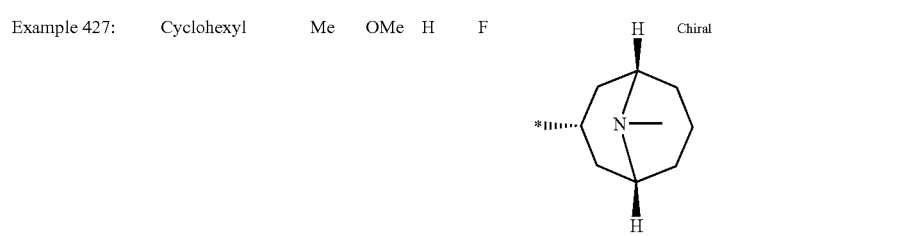 |
| Example 428: | Cyclohexyl | Me | H | H | H | 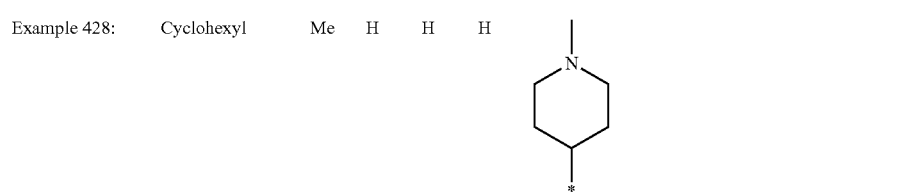 |

-continued
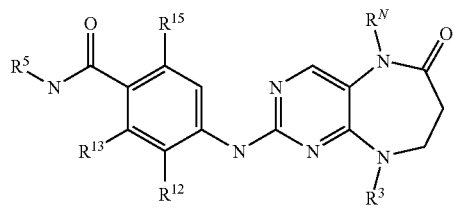
| Example | R³ | Rᴺ | R¹² | R¹³ | R¹⁵ | R⁵ |
|---|---|---|---|---|---|---|
| Example 429: | Cyclohexyl | Me | F | H | H | 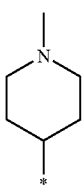 |
| Example 447: | Cyclopentyl | Me | F | H | F | 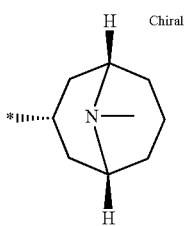 Chiral |
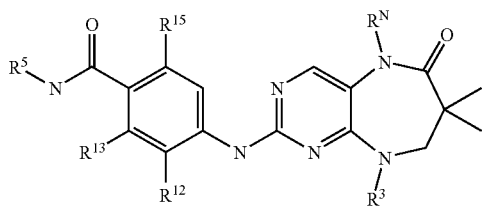
| Example | R³ | Rᴺ | R¹² | R¹³ | R¹⁵ | R⁵ |
|---|---|---|---|---|---|---|
| Example 235: | Cyclopentyl | Me | OMe | H | H | 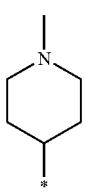 |
| Example 243: | Cyclopentyl | Me | OMe | H | H | 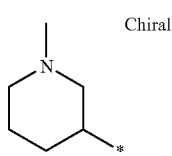 Chiral |

-continued
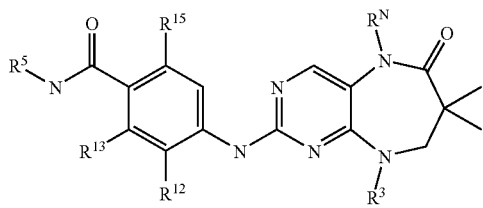
| Example | R³ | R^N | R¹² | R¹³ | R¹⁵ | R⁵ |
|---|---|---|---|---|---|---|
| Example 244: | Cyclopentyl | Me | OMe | H | H | 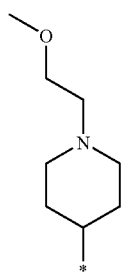 |
| Example 245: | Cyclopentyl | Me | H | H | H | 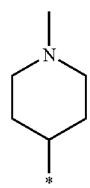 |
| Example 278: | Cyclopentyl | H | OMe | H | H | 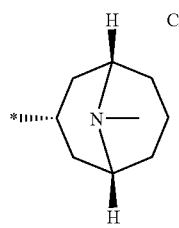 Chiral |
| Example 289: | ⁱPr | Me | Cl | H | F | 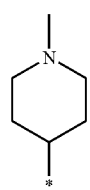 |
| Example 290: | ⁱPr | Me | Cl | H | F | 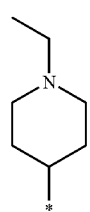 |
| Example 291: | ⁱPr | Me | Cl | H | F | 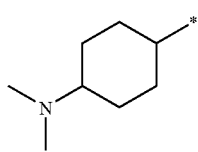 |

-continued

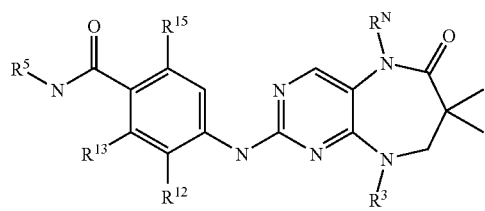

| Example | $R^3$ | $R^N$ | $R^{12}$ | $R^{13}$ | $R^{15}$ | $R^5$ |
|---|---|---|---|---|---|---|
| Example 292: | $^i$Pr | Me | OMe | H | F | (1-methylpyrrolidin-3-yl), Chiral |
| Example 293: | $^i$Pr | Me | OEt | H | H | (1-methylpyrrolidin-3-yl), Chiral |
| Example 294: | $^i$Pr | Me | OEt | H | H | (4-dimethylaminocyclohexyl), Chiral |
| Example 295: | $^i$Pr | Me | OEt | H | H | (4-dimethylaminocyclohexyl), Chiral |
| Example 296: | $^i$Pr | Me | OEt | H | F | (1-methylpiperidin-4-yl) |
| Example 297: | $^i$Pr | Me | OEt | H | F | (1-methylpyrrolidin-3-yl), Chiral |
| Example 298: | $^i$Pr | Me | F | H | H | (N-methyl-tropane derivative), Chiral |

-continued
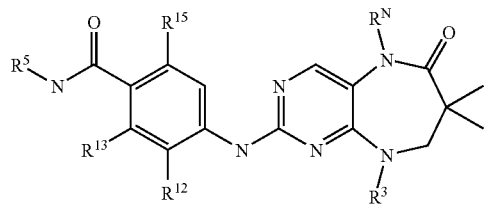
| Example | R³ | Rᴺ | R¹² | R¹³ | R¹⁵ | R⁵ |
|---|---|---|---|---|---|---|
| Example 299: | ⁱPr | Me | OMe | H | H | (S)-1-methylpyrrolidin-3-yl (Chiral) |
| Example 300: | ⁱPr | Me | OMe | H | H | 1-ethylpiperidin-4-yl |
| Example 301: | ⁱPr | Me | OMe | H | H | 2-(pyrrolidin-1-yl)ethyl |
| Example 302: | ⁱPr | Me | OMe | H | H | 2-(dimethylamino)ethyl |
| Example 303: | ⁱPr | Me | OMe | H | H | 3-(dimethylamino)propyl |
| Example 349: | Cyclopentyl | Me | OMe | H | H | piperidin-4-yl |
| Example 350: | Cyclopentyl | Me | OMe | H | H | 1-ethylpiperidin-4-yl |

-continued
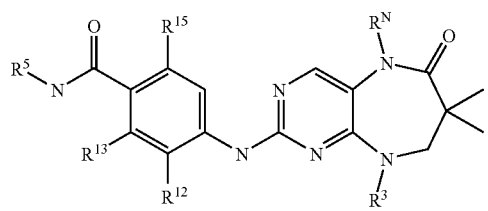
| Example | R³ | Rᴺ | R¹² | R¹³ | R¹⁵ | R⁵ | |
|---|---|---|---|---|---|---|---|
| Example 351: | Cyclopentyl | Me | OMe | H | H | 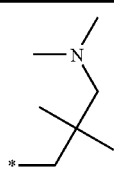 | |
| Example 352: | Cyclopentyl | Me | OMe | H | F | 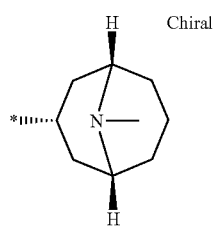 | Chiral |
| Example 353: | Cyclopentyl | Me | F | H | H | 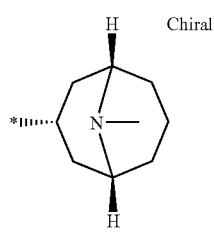 | Chiral |
| Example 354: | Cyclopentyl | Me | OMe | H | H | 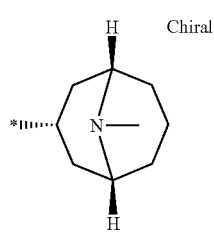 | Chiral |
| Example 355: | Cyclopentyl | Me | F | H | F | 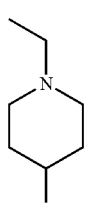 | |
| Example 356: | Cyclopentyl | Me | F | H | F | 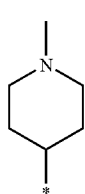 | |

-continued
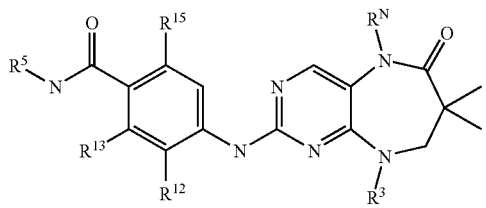
| Example | R³ | Rᴺ | R¹² | R¹³ | R¹⁵ | R⁵ |
|---|---|---|---|---|---|---|
| Example 357: | Cyclopentyl | Me | OMe | H | H | 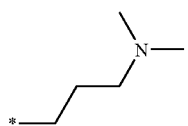 |
| Example 358: | Cyclopentyl | Me | OMe | H | H | 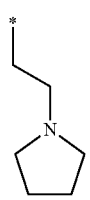 |
| Example 359: | Cyclopentyl | Me | OMe | H | H | 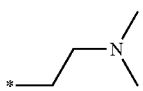 |
| Example 360: | Cyclopentyl | Me | OMe | H | H | 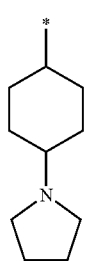 |
| Example 361: | Cyclopentyl | Me | OMe | H | F | 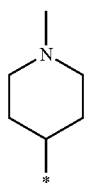 |
| Example 362: | Cyclopentyl | Me | Cl | H | H | 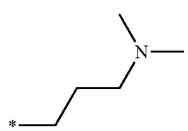 |
| Example 363: | Cyclopentyl | Me | OMe | H | H | 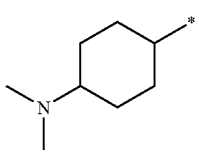 |

-continued
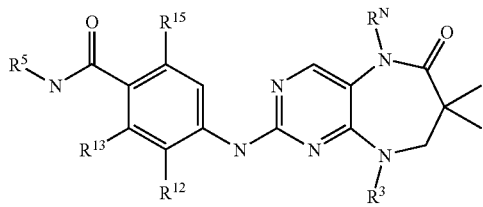
| Example | R³ | Rᴺ | R¹² | R¹³ | R¹⁵ | R⁵ |
|---|---|---|---|---|---|---|
| Example 364: | Cyclopentyl | Me | OMe | H | F | 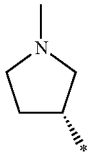 Chiral |
| Example 365: | Cyclopentyl | Me | H | H | H | 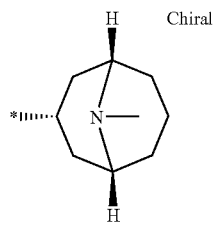 Chiral |
| Example 366: | Cyclopentyl | Me | Cl | H | F | 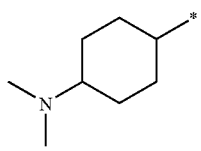 |
| Example 367: | Cyclopentyl | Me | Cl | H | H | 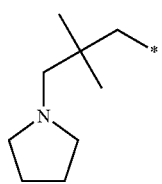 |
| Example 368: | Cyclopentyl | Me | OMe | H | H | 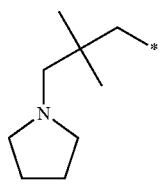 |
| Example 369: | Cyclopentyl | Me | OMe | H | H | 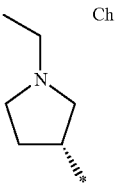 Chiral |
| Example 370: | Cyclopentyl | Me | OMe | H | F | 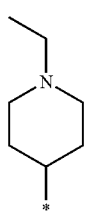 |

-continued
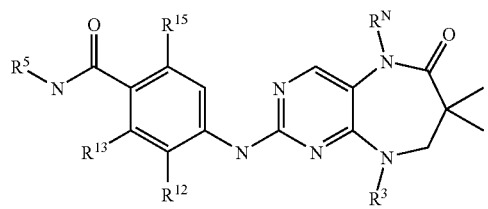
| Example | R³ | R^N | R¹² | R¹³ | R¹⁵ | R⁵ |
|---|---|---|---|---|---|---|
| Example 371: | Cyclopentyl | Me | F | H | H | 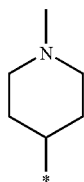 |
| Example 372: | Cyclopentyl | Me | OMe | H | F | 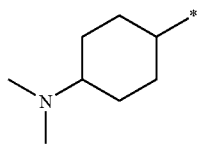 |
| Example 373: | Cyclopentyl | Me | OMe | H | F | 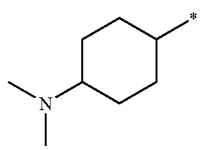 |
| Example 374: | Cyclopentyl | Me | OMe | H | H | 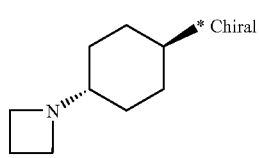 Chiral |
| Example 375: | Cyclopentyl | Me | OMe | H | H | 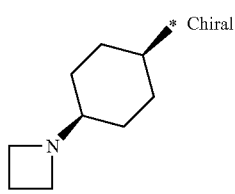 Chiral |

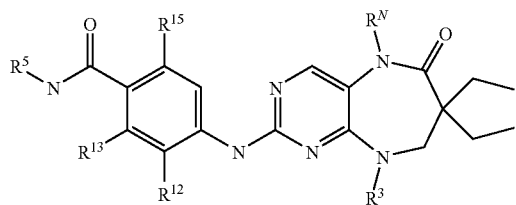
| Example | R³ | Rᴺ | R¹² | R¹³ | R¹⁵ | R⁵ |
|---|---|---|---|---|---|---|
| Example 304: | ᶦPr | Me | OMe | H | H | 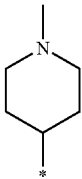 |
| Example 305: | ᶦPr | Me | OMe | H | H | 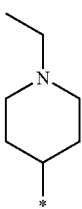 |
| Example 306: | ᶦPr | Me | OMe | H | H | 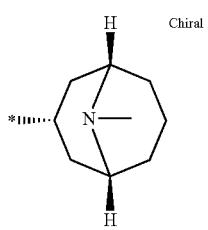 Chiral |
| Example 307: | ᶦPr | Me | OMe | H | F | 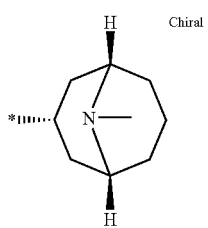 Chiral |
| Example 308: | ᶦPr | Me | OMe | H | F | 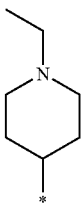 |
| Example 309: | ᶦPr | Me | OMe | H | H | 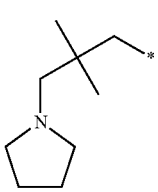 |

-continued
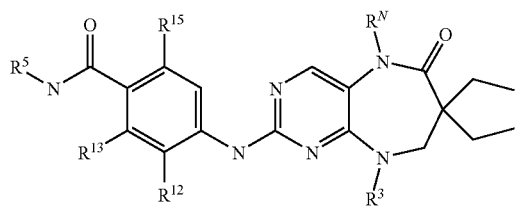
| Example | R³ | Rᴺ | R¹² | R¹³ | R¹⁵ | R⁵ |
|---|---|---|---|---|---|---|
| Example 376: | Cyclopentyl | Me | OMe | H | H | 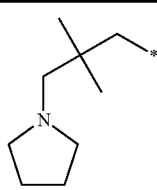 |
| Example 377: | Cyclopentyl | Me | OMe | H | H | 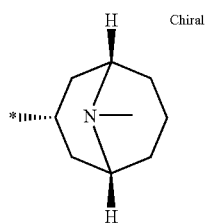 Chiral |
| Example 379: | Cyclopentyl | Me | OMe | H | F | 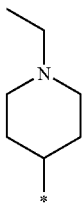 |
| Example 380: | Cyclopentyl | Me | OMe | H | H | 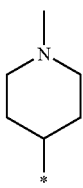 |
| Example 381: | Cyclopentyl | Me | OMe | H | H | 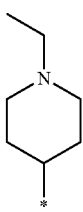 |

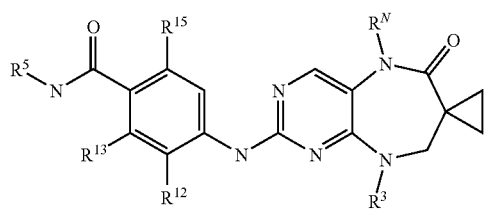
| Example | R³ | R^N | R¹² | R¹³ | R¹⁵ | R⁵ |
|---|---|---|---|---|---|---|
| Example 246: | Cyclopentyl | Me | OMe | H | H | 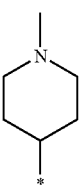 |
| Example 279: | Cyclopentyl | H | F | H | H | 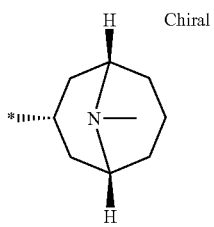 Chiral |
| Example 280: | Cyclopentyl | H | OMe | H | H | 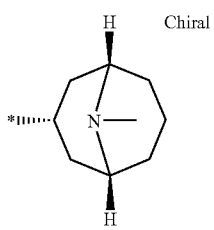 Chiral |
| Example 310: | $^i$Pr | Me | Cl | H | F | 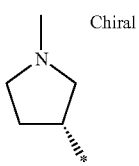 Chiral |
| Example 311: | $^i$Pr | Me | Cl | H | F | 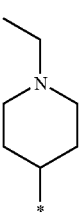 |
| Example 312: | $^i$Pr | Me | OMe | H | H | 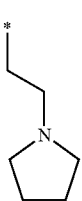 |

-continued
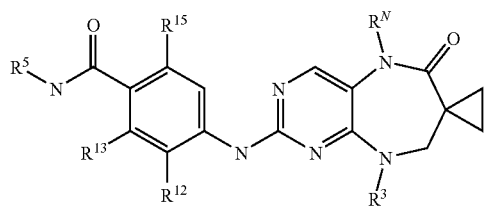
| Example | R³ | Rᴺ | R¹² | R¹³ | R¹⁵ | R⁵ |
|---|---|---|---|---|---|---|
| Example 313: | $^i$Pr | Me | OMe | H | H | 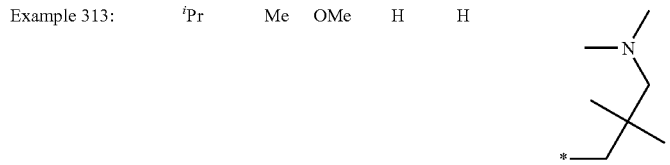 |
| Example 382: | Cyclopentyl | Me | Cl | H | H | 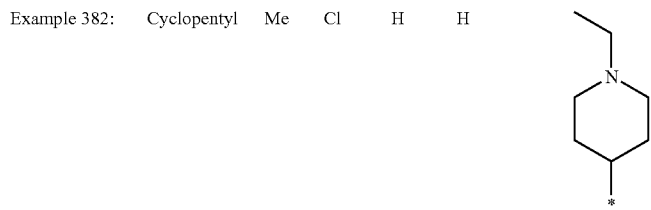 |
| Example 383: | Cyclopentyl | Me | OMe | H | H | 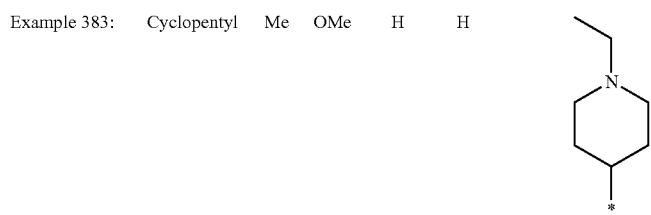 |
| Example 384: | Cyclopentyl | Me | OMe | H | H | 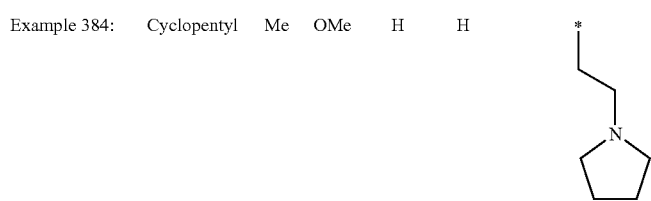 |
| Example 385: | Cyclopentyl | Me | OMe | H | H | 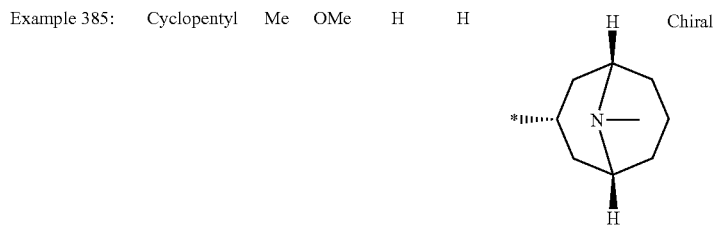 Chiral |
| Example 386: | Cyclopentyl | Me | OMe | H | H | 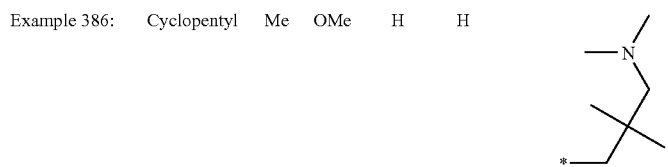 |
| Example 387: | Cyclopentyl | Me | OMe | H | H | 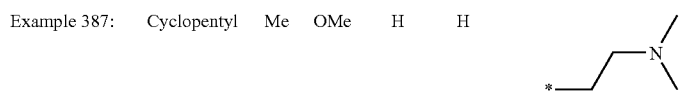 |

-continued
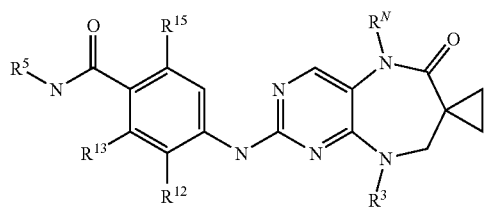
| Example | $R^3$ | $R^N$ | $R^{12}$ | $R^{13}$ | $R^{15}$ | $R^5$ |
|---|---|---|---|---|---|---|
| Example 388: | Cyclopentyl | Me | F | H | H | 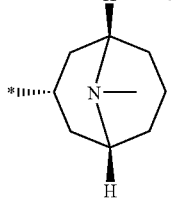 Chiral |
| Example 389: | Cyclopentyl | Me | Cl | H | F | 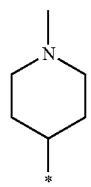 |
| Example 390: | Cyclopentyl | Me | Cl | H | H | 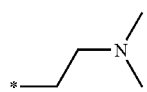 |
| Example 391: | Cyclopentyl | Me | Cl | H | H | 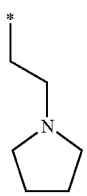 |
| Example 392: | Cyclopentyl | Me | Cl | H | H | 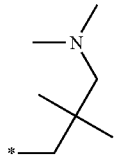 |
| Example 393: | Cyclopentyl | Me | Cl | H | F | 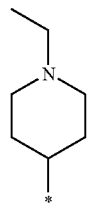 |
| Example 394: | Cyclopentyl | Me | Cl | H | F | 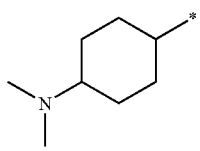 |

-continued
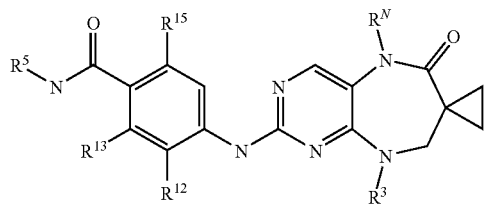
| Example | $R^3$ | $R^N$ | $R^{12}$ | $R^{13}$ | $R^{15}$ | $R^5$ |
|---|---|---|---|---|---|---|
| Example 395: | Cyclopentyl | Me | F | H | F | 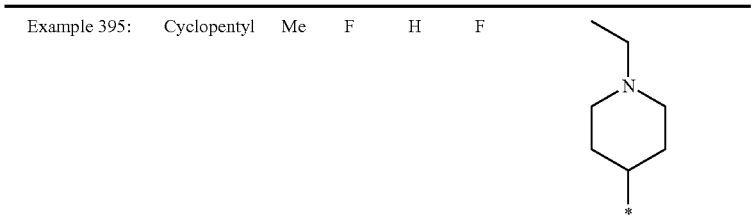 |
| Example 396: | Cyclopentyl | Me | F | H | F | 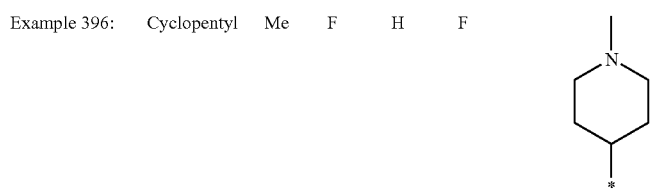 |
| Example 397: | Cyclopentyl | Me | F | H | F | 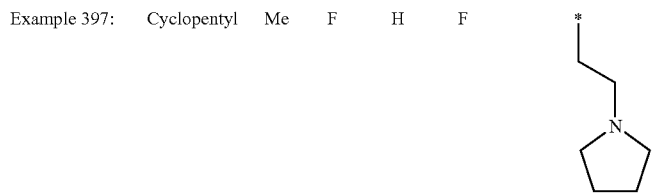 |
| Example 398: | Cyclopentyl | Me | OMe | H | F | 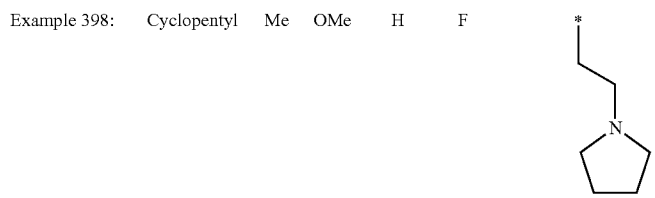 |
| Example 399: | Cyclopentyl | Me | OMe | H | F | Chiral 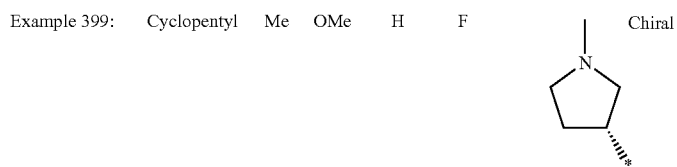 |
| Example 400: | Cyclopentyl | Me | F | H | F | Chiral 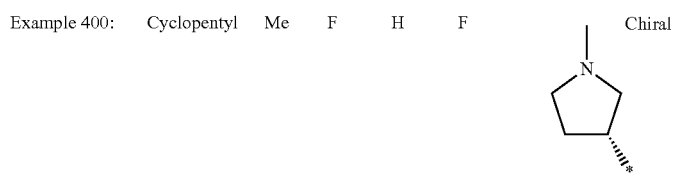 |
| Example 401: | Cyclopentyl | Me | OMe | H | H | 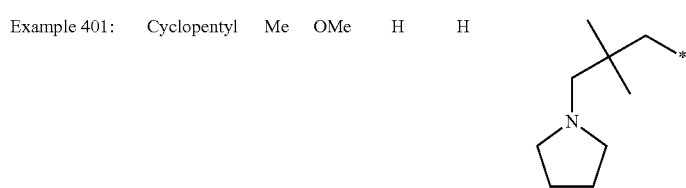 |

-continued
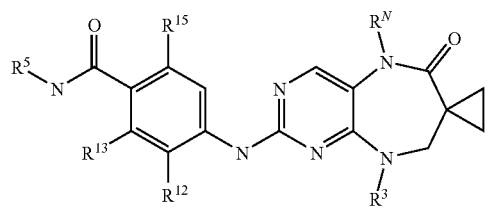
| Example | R³ | Rᴺ | R¹² | R¹³ | R¹⁵ | R⁵ |
|---|---|---|---|---|---|---|
| Example 402: | Cyclopentyl | Me | Cl | H | H | 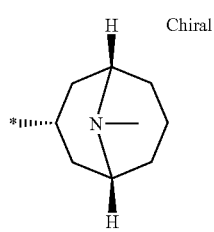 Chiral |
| Example 403: | Cyclopentyl | Me | OMe | H | H | 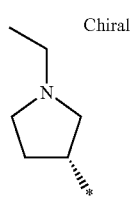 Chiral |
| Example 404: | Cyclopentyl | Me | OMe | H | F | 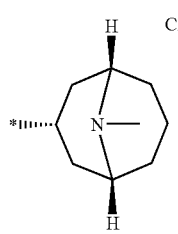 Chiral |
| Example 405: | Cyclopentyl | Me | OMe | H | F | 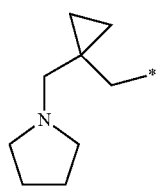 |
| Example 406: | Cyclopentyl | Me | F | H | H | 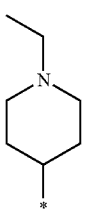 |
| Example 407: | Cyclopentyl | Me | OMe | H | F | 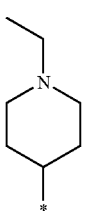 |

-continued
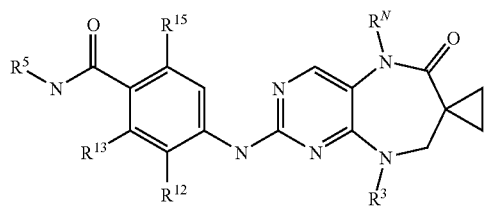
| Example | R³ | Rᴺ | R¹² | R¹³ | R¹⁵ | R⁵ |
|---|---|---|---|---|---|---|
| Example 408: | Cyclopentyl | Me | OCH₂O | | H | 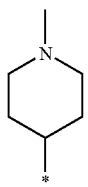 |
| Example 430: | Cyclohexyl | Me | OMe | H | H | 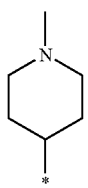 |
| Example 431: | Cyclohexyl | Me | OMe | H | H | 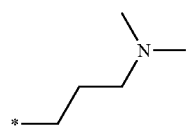 |
| Example 432: | Cyclohexyl | Me | OMe | H | H | 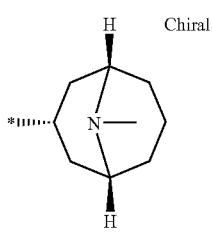 Chiral |
| Example 433: | Cyclohexyl | Me | OMe | H | H | 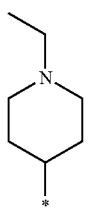 |
| Example 434: | Cyclohexyl | Me | F | H | F | 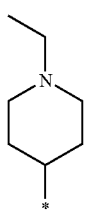 |

-continued
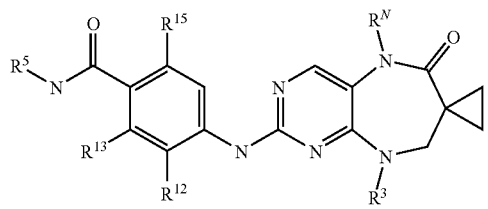
| Example | R³ | Rᴺ | R¹² | R¹³ | R¹⁵ | R⁵ |
|---|---|---|---|---|---|---|
| Example 435: | Cyclohexyl | Me | F | H | H | 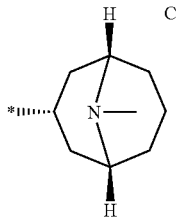 Chiral |
| Example 436: | Cyclohexyl | Me | F | H | F | 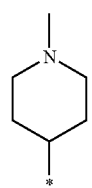 |
| Example 437: | Cyclohexyl | Me | Cl | H | F | 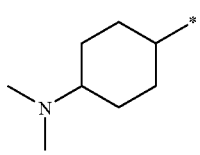 |
| Example 438: | Cyclohexyl | Me | OMe | H | F | 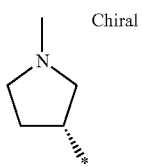 Chiral |
| Example 439: | Cyclohexyl | Me | OMe | H | H | 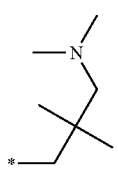 |
| Example 440: | Cyclohexyl | Me | OMe | H | H | 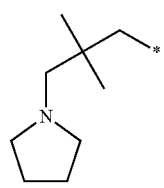 |
| Example 441: | Cyclohexyl | Me | OMe | H | H | 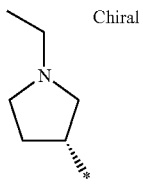 Chiral |

-continued
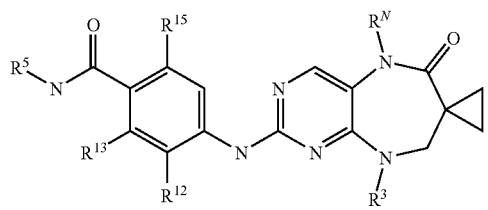
| Example | R³ | R$^N$ | R¹² | R¹³ | R¹⁵ | R⁵ |
|---|---|---|---|---|---|---|
| Example 442: | Cyclohexyl | Me | OMe | H | F | 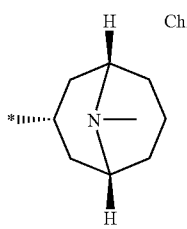 Chiral |
| Example 443: | Cyclohexyl | Me | OMe | H | F | 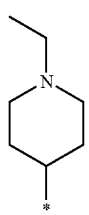 |
| Example 444: | Cyclohexyl | Me | OMe | H | F | 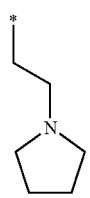 |
| Example 445: | Cyclohexyl | Me | OMe | H | F | 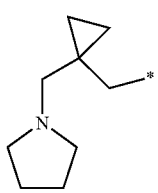 |
| Example 446: | Cyclohexyl | Me | F | H | H | 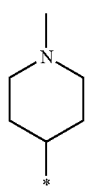 |

-continued

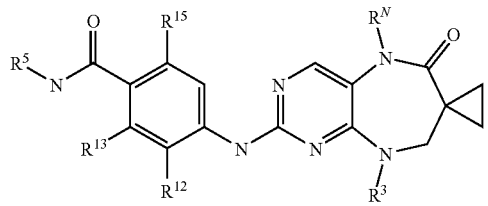

| Example | $R^3$ | $R^N$ | $R^{12}$ | $R^{13}$ | $R^{15}$ | $R^5$ |
|---|---|---|---|---|---|---|
| Example 448: | Cyclopentyl | Me | F | H | F | 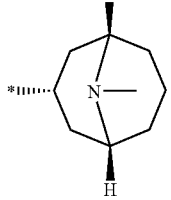 Chiral |
| Example 449: | Cyclohexyl | Me | F | H | F | 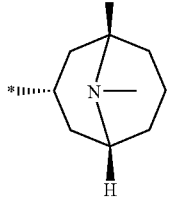 Chiral |
| Example 450: | Cyclohexyl | H | F | H | H | 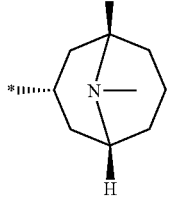 Chiral |

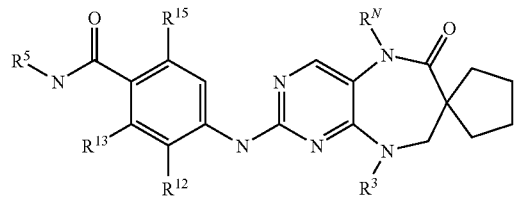

| Example | $R^3$ | $R^N$ | $R^{12}$ | $R^{13}$ | $R^{15}$ | $R^5$ |
|---|---|---|---|---|---|---|
| Example 409: | Cyclopentyl | Me | OMe | H | H | 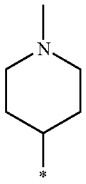 |

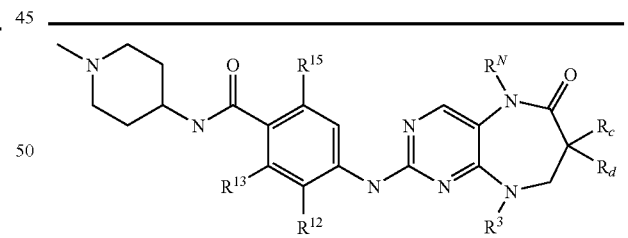

| Example | $R^3$ | $R_c$ | $R_d$ | $R^N$ | $R^{12}$ | $R^{13}$ | $R^{15}$ |
|---|---|---|---|---|---|---|---|
| Example 3: | Cyclopentyl | Me | Me | Me | OMe | H | H |
| | | Racemate | | | | | |
| Example 236: | Cyclopentyl | Et | H | Me | OMe | H | H |
| Example 237: | Cyclopentyl | H | Et | Me | OMe | H | H |
| Example 238: | Cyclopentyl | $^n$Pr | H | Me | OMe | H | H |
| Example 239: | Cyclopentyl | H | $^n$Pr | Me | OMe | H | H |
| Example 240: | Cyclopentyl | Me | H | Me | OMe | H | H |
| Example 241: | Cyclopentyl | H | Me | Me | OMe | H | H |

The invention claimed is:
1. A compound of formula (IIIa)

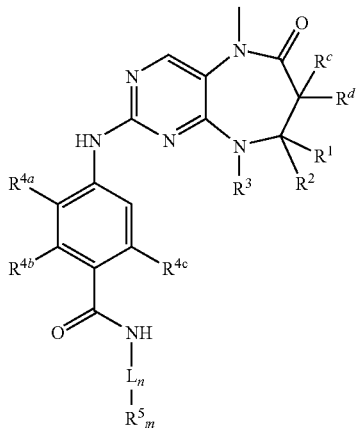

(IIIa)

wherein $R^3$ represents a cyclopentyl group; L represents a linker selected from optionally substituted $C_{2-10}$alkyl; n denotes 0; m denotes 1; $R^5$ denotes a granatanyl group; $R^1$, $R^2$ are hydrogen; $R^C$ and $R^d$ together represent an ethylene bridge; and $R^{4b}$ and $R^{4c}$ are hydrogen and $R^{4a}$ represents fluorine; or a pharmacologically acceptable salt thereof.

2. A compound of Formula (IIIa) according to claim 1 wherein the compound is 4-(9'-cyclopentyl-5'-methyl-6'-oxo-5',6',8',9'-tetrahydrospiro[cyclopropane-1,7'-pyrimido[5,4-b][1,4]diazepine]-2'-ylamino)-3-fluoro-N-[(1 S,5R)-9-methyl-9-azabicyclo[3.3.1]non-7-yl]benzamide or a pharmacologically acceptable salt thereof.

3. A pharmaceutical composition comprising a compound of formula (IIIa), or a pharmacologically acceptable salt thereof, as claimed in claim 1 in association with a pharmaceutically acceptable adjuvant, diluent or carrier.

4. A process for the preparation of a pharmaceutical composition comprising a compound of formula (IIIa), or a pharmacologically acceptable salt thereof, as claimed in claim 1 in association with a pharmaceutically acceptable adjuvant, diluent or carrier which comprises mixing a compound of formula (IIIa) or a pharmacologically acceptable salt thereof, as claimed in claim 1 with a pharmaceutically acceptable adjuvant, diluent or carrier.

5. A pharmaceutical composition comprising a compound of formula (IIIa), or a pharmacologically acceptable salt thereof, as claimed in claim 2 in association with a pharmaceutically acceptable adjuvant, diluent or carrier.

6. A process for the preparation of a pharmaceutical composition comprising a compound of formula (IIIa), or a pharmacologically acceptable salt thereof, as claimed in claim 2 in association with a pharmaceutically acceptable adjuvant, diluent or carrier which comprises mixing a compound of formula (IIIa) or a pharmacologically acceptable salt thereof, as claimed in claim 2 with a pharmaceutically acceptable adjuvant, diluent or carrier.

* * * * *